(12) United States Patent
Collart et al.

(10) Patent No.: US 6,826,488 B1
(45) Date of Patent: Nov. 30, 2004

(54) CRYSTALS, MOLECULAR COMPLEXES, AND METHODS OF DEVELOPING LEAD COMPOUNDS FOR INHIBITORS OF BACTERIAL IMPDH

(75) Inventors: Frank R. Collart, Bolingbrook, IL (US); Eliezer Huberman, LaGrange, IL (US); Andrezej Joachimiak, Bolingbrook, IL (US); Rongguang Zhang, Westmont, IL (US); Edwin M. Westbrook, Lemont, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/533,466

(22) Filed: Mar. 23, 2000

(51) Int. Cl.[7] .................... G06F 19/00; G01N 33/48; G01N 33/53

(52) U.S. Cl. .................... 702/27; 702/19; 435/7.1

(58) Field of Search .............. 702/19, 27; 435/7.1, 435/190; 434/277, 278; 530/350; 514/1

(56) References Cited

U.S. PATENT DOCUMENTS 6,128,582 A * 10/2000 Wilson et al. .............. 702/27

OTHER PUBLICATIONS

Drenth, J., *Principles of Protein X-ray Crystallography* [Published by Springer–Verlag New York Inc., 175 Fifth Ave., New York, NY 10010], pp. 1–19, 1994.*
Fleming et al., Biochemistry, vol. 35, pp. 6990–6997, 1996.*
Geysen et al, Cognitive features of continuous antigenic determinants. J. of Molecular Recognition, vol. 1, pp. 32–40, 1988.*
Russell et al. Structural features can be unconserved in proteins with similar folds. (Journal of Molecular Biology, vol. 244, pp. 332–350, 1994.*
Zhang et al. Characteristics and crystal structure of bacterial inosine–5'–monophosphate dehydrogenase. Biochemistry, vol. 38, pp. 4691–4700, Apr. 13, 1999.*
Allison A. and Eugui E.(1996) "Purine metabolism and immunosuppresive effects of mycophenolate mofetil (MMF)," *Clin Transplantation* 10: 77–84.
Antonino L. et al. (1994) "Probing the active site of human IMP dehydrogenase using halogenated purine riboside 5'–monophosphates and covalent modification reagents," *Biochemistry* 33: 1760–1765.
Antonino L. and Wu J. (1994) "Human IMP Dehydrogenase catalyzes the dehalogenation of 2 fluoro– and 2–chloroinosine 5'–monophosphate in the absence of NAD," *Biochemistry* 33:1753–1759.
Ashbaugh C. and Wessels M.(1995) "Cloning, sequence analysis and expression of the group A steptococcal guaB gene encoding inosine monophosphate dehydrogenase," *Gene* 165: 57–60.

(List continued on next page.)

Primary Examiner—Ardin H. Marschel
(74) Attorney, Agent, or Firm—Alice O. Martin; Barnes & Thornburg LLP

(57) ABSTRACT

The present invention relates to a data storage medium encoded with the structural coordinates of crystallized molecules and molecular complexes which comprise the active site binding pockets of bacterial IMPDH. Such data storage material is capable of displaying such molecules and molecular complexes, or their structural homologues, as a graphical three-dimensional representation on a computer screen. This invention also relates to methods of using the structure coordinates to solve the structure of homologous proteins or protein complexes. In addition, this invention relates to methods of using the structure coordinates to screen and design compounds, including inhibitory compounds, that bind to IMPDH or homologues thereof. This invention also relates to molecules and molecular complexes that comprise the active site binding pockets of IMPDH or close structural homologues of the active site binding pockets. This invention also relates to compounds and pharmaceutical compositions which are inhibitors of bacterial IMPDH.

5 Claims, 8 Drawing Sheets

Catalytic Domain
CBS Dimer Domain

OTHER PUBLICATIONS

Bateman A. (1997) "The structure of a domain common to archaebacteria and the homocystinuria disease protein," TIBS 22, 12–13.

Brunger A. et al. (1998) "Crystallography & NMR system: a new software suite for macromolecular structure determination," Acta Crystal 54: 905–921.

Collart F. and Huberman E. (1990) "Expression of IMP dehydrogenase in differentiating HL–60 cells," Blood 75:570–576.

Collart F. et al. (1996) "Cloning, characterization and sequence comparison of the gene coding for IMP dehydrogenase from pycroccus furiosus," Gene 174:209–216.

Collart F. et al. (1996) "Cloning and characterization of the gene encoding IMP dehydrogenase from Arabidopsis thaliana," Gene 174:217–220.

Hager P. et al. (1994) "Recombinant human inosine monophosphate dehydrogenase type I and type II proteins," Biochemical Pharmacology 49:1323–1329.

Halloran PF. (1996) "Molecular mechanisms of new immunosuppressants," Clin Transplantation 10:118–123.

Hendrickson W. (1991) "Determination of macromolecular structures from anomalous diffraction of synchrotron radiation," Science 254:51–58.

Huete–Perez J. (1995) "Identification of the IMP binding site in the IMP dehydrogenase from Tritichomonas foetus," Biochemistry 34:13889–13894.

Jayaram H. (1992) "Clinical pharmacokinetic study of tiazofurin administered as a 1–hr infusion," Int J. Cancer 51:182–188.

Kabsch W and Sander C. (1983) "Dictionary of protein secondary structure: pattern recognition of hydrogenbonded and geometrical features," Biopolymers 22:2577–2637.

Kerr K. and Hedstron L. (1997) "The roles of conserved carboxylate residues in IMP dehydrogenase and identification of a transition state analog," Biochemistry 36:13365–13373.

Kiguchi et al. (1990) "Induction of cell differentiation in melanoma cells by inhibitors of IMP dehydrogenase: altered patterns of IMP dehydrogenase expression and activity," Cell Growth and Differentiation 1:259–270.

Link J. and Straub K. (1996) "Trapping of an IMP dehydrogenase–substrate covalent intermediate by mycophenolic acid," J. Am. Chem. Soc. 118: 2091–2092.

Navaza J. and Saludjian P. (1997) "AMoRe: an automated molecular replacement program package," Methods in Enzymology 275:581–594.

Nimmesgern et al. (1996) "Conformational changes and stabilization of inosine 5'–monophosphate dehydrogenase associated with ligand binding and inhibition by mycophenolic acid," Journal of Biological Chemistry 271: 19421–19427.

Otwinowski Z. and Minor W. (1997) "Processing of x–ray diffraction data collected in oscillation mode," Methods in Enzymology 276:307–325.

Pannu et al. (1998) "Incorporation of prior phase information strengthens maximum–likelihood structure refinement," Acta Crystl 54: 1285–1294.

Ramakrishnan V. and Biou V. (1997) "Treatment of multiwavelength anomalous diffraction data as a special case of multiple isomorphous replacement," Methods in Enzymology 276: 538–557.

Rice L. and Brunger A. (1994) "Torsion angle dynamics: reduced variable conformational sampling enhances crystallographic structure refinement," PROTEINS: Structure, Function, and Genetics 19: 277–290.

Sintchak et al. (1996) "Structure and mechanism of inosine monophosphate dehydrogenase in complex with the immunosuppressant mycophenolic acid," Cell 85: 921–390.

Smith et al. (1991) "A controlled trial of aerosolized ribavirin in infants receiving mechanical ventilation for severe respiratory syncytial virus infection," The New England Journal of Medicine 325: 24–29.

Wang et al. (1996) "Inactivation of inosine 5'–monophosphate dehydrogenase by the antiviral agent 5–ethynyl–1–beta–D–Ribofuranosylimidazole–4–Carboxamide 5'–monophosphate," Biochemistry 35:95–101.

Westbrook E. and Naday I. (1997) "Charge–coupled device–based area detectors," Methods in Enzymology 276: 244–268.

Whitby F. (1997) "Crystal structure of tritrichomonas foetus inosine–5' monophosphate dehydrogenase and the enzyme-product complex," Biochemistry 36:10666–10674.

Xiang B. and Markham G. (1997) "Probing the mechanism of inosine monophosphate dehydrogenase with kinetic isotope effects and NMR determination of hydride transfer stereospecificity," Archives of Biochemistry and Biophysics 348: 378–382.

Zhou et al. (1997) "Expression, purification, and characterization of inosine 5'–monophosphate dehydrogenase from borrelia burgdorfer," Journal of Biological Chemistry 272:21977–21981.

Zhang, R., et al. (1999) "Characteristics and Crystal Structure of Bacterial Inosine–5'–Monophosphate Dehydrogenase." Biochemistry 38: 4691–4700.

* cited by examiner

CRYSTALS, MOLECULAR COMPLEXES, AND METHODS OF DEVELOPING LEAD COMPOUNDS FOR INHIBITORS OF BACTERIAL IMPDH

The United States Government has rights in this invention pursuant to contract Number W-31-109-ENG-38 between the United States Government and Argonne National Laboratory.

BACKGROUND OF THE INVENTION

The invention relates the crystal structure of IMPDH isolated from bacteria. The structure is different from the structure of mammalian or fungal IMPDH, allowing design of selective inhibitors of bacterial IMPDH.

Inosine monophosphate dehydrogenase (IMPDH; Enzyme Commission (EC) 1.1.1.205) is a rate-limiting enzyme in the synthesis of guanine ribonucleotides. IMPDH has an essential role in providing critical precursors for DNA and RNA biosynthesis and in signal transduction pathways that mediate cell differentiation (Collart et at., 1990; Kiguchi et al., 1990). Because of its central role in purine metabolism, IMPDH is an attractive therapeutic target. Several recent reviews have outlined the utility of mammalian IMPDH inhibitors as anticancer (Pankiewicz, 1997) or antiviral (Andrei et al, 1993) agents or as immunosuppressive drugs (Halloran, 1996) (see Table 1).

TABLE 1

Clinically Useful Inhibitors of IMPDH

| Inhibitor | Clinical Application |
| --- | --- |
| Ribavirin | Antiviral |
| Mycophenolate mofetil | Immunosuppression |
| Mizoribine | Imunosuppression |
| Tiazofurin | Anticancer |

Although there are no reports of selective inhibitors of bacterial IMPDH enzymes, such compounds could have potential application as specific antimicrobial agents.

The active form of IMPDH enzymes (50–55 kDa) is a homotetramer with four active sites per tetramer. A cysteine residue in the active site forms a covalent intermediate with IMP (Wang et al., 1996). A consensus sequence of thirteen amino acid residues that includes cysteine in this active site has been proposed as a signature motif (i.e., an amino acid sequence that can be used as a fingerprint or specific identifier for this class of enzymes) for the IMPDH and guanosine monophosphate (GMP) reductase enzymes (Bairoch, 1995). This IMPDH consensus region is highly conserved in both bacteria and eukaryotes, with 90% and 85% of the respective residues being identical within each kingdom. However, only 40% of these residues remain identical when compared between the two kingdoms. This limited conservation suggests that bacterial and eukaryotic IMPDH enzymes may have distinct characteristics; a suggestion supported by their kinetic differences and differential sensitivity to inhibitors. Enzymes from mammalian sources show distinctly lower values for the $K_m$ for nicotinamide adenine dinucleotide (NAD) than do those enzymes from bacteria. In addition, mammalian IMPDH enzymes are 10–100 times more sensitive to inhibition by mycophenolic acid (MPA) than are bacterial IMPDH enzymes. Sequence analysis of all known IMPDH enzymes supports the distinction between bacterial and eukaryotic enzymes. A deep branching of the bacterial and eukaryotic forms of IMPDH is observed upon phylogenetic analysis of the relationships among the various IMPDH genes (Collart et al, 1996 a and b). This phylogenetic analysis indicates a general functional conservation of amino acid and suggests a unique amino acid sequence signature for these kingdoms.

The elucidation of a kingdom-specific signature for IMPDH enzymes is an important element in the development of specific inhibitors. The two partial structures of IMPDH from Chinese hamster (Sintchak et al., 1996) (85% structure complete with bound transition state analogue and mycophenolic acid, MPA) and Tritrichomonas foetus (Whitby et al., 1997) (68% structure complete with bound xanthosine monophosphate [XMP]) have been reported with only the coordinates of the latter available in the Protein Data Bank (PDB). These structures furnished the initial information about the structure and reaction mechanism of eukaryotic IMPDH enzymes. Inhibitors of IMPDH in bacteria are needed to treat infections, in particular, to overcome the barrier of antibiotic resistance.

BRIEF SUMMARY OF THE INVENTION

The invention relates for the first time a crystal structure of a bacterial IMPDH. This invention relates that bacterial and mammalian IMPDH enzymes provide the same catalytic function, but have a set of unique structural and biochemical characteristics. An embodiment is a crystal structure of IMPDH isolated from Streptococcus pyogenes. S. pyogenes IMP dehydrogenase represents the class of bacterial IMPDH enzymes that show distinct functional differences when compared to mammalian IMPDH enzymes. The bacterial enzymes bind NAD poorly (Zhou et al., 1997; Kerr et al., 1997) ($K_M$>1 mM) and are inhibited by MPA only at very high concentrations (Ki>0.5 mM). Elucidation of the structural basis of these distinct characteristics is useful to aid in design of specific IMPDH inhibitors that will inhibit the infectious agent without harming the host's IMPDH.

The coding sequence of bacterial IMPDH specifies a protein of 493 amino acids that contain only a single cysteine residue at the active site (Ashbaugh et al., 1995). IMPDH from S. pyogenes is a representative bacterial enzyme because the organism is pathogenic, and therefore a good model for the investigation of enzyme inhibitors. Streptococci are the most common cause of worldwide pneumonia and a leading cause of pediatric infections. The structure of the S. pyogenes bacterial IMPDH provides the basis for elucidation of the structural characteristics that distinguish bacterial from eukaryotic IMPDH enzymes. Knowledge of these characteristics permits an understanding of why these enzymes exhibit functionally distinct behavior and therefore provides a foundation for the design of specific inhibitors of IMPDH that have clinical value.

In addition to inhibiting pathogens, the immunosuppressive use of IMPDH inhibitors is applicable to treat chronic inflammatory diseases such as arthritis, diabetes, or systemic lupus erythromotosis. Use of the IMPDH structure from S. pyogenes will facilitate identification of other pathogens that will be inhibited by drugs that inhibit S. pyogenes.

Definitions and Abbreviations

A "binding pocket" is a space in a molecule in which an inhibitor of the molecule is bound.

The following abbreviations are used throughout the application:

A = Ala = Alanine
V = Val = Valine
L = Leu = Leucine
I = Ile = Isoleucine
P = Pro = Proline
F = Phe = Phenylalanine
W = Trp = Trytophan
M = Met = Methionine
G = Gly = Glycine
S = Ser = Serine
T = Thr = Threonine
C = Cys = Cysteine
Y = Tyr = Tyrosine
N = Asn = Asparagine
Q = Gln = Glutamine
D = Asp = Aspartic Acid
E = Glu = Glutamic Acid
K = Lys = Lysine
R = Arg = Arginine
H = His = Histidine
CBS = Cystathionine-β-synthase
GMP = Guanosine monophosphate
IMP = Inosine monophosphate
IMPDH = Inosine monophosphate dehydrogenase
MPA = Mycophenolic acid
NAD = Nicotinamide adenine dinucleotide
PDB = Protein Data Bank
XMP = Xanthosine monophosphate

BRIEF DESCRIPTION OF THE DRAWINGS

FIG. 2 is a representation of the secondary structure of the IMPDH monomer.

FIG. 3 shows an IMPDH active site.

DETAILED DESCRIPTION OF THE INVENTION

Figure 1A:
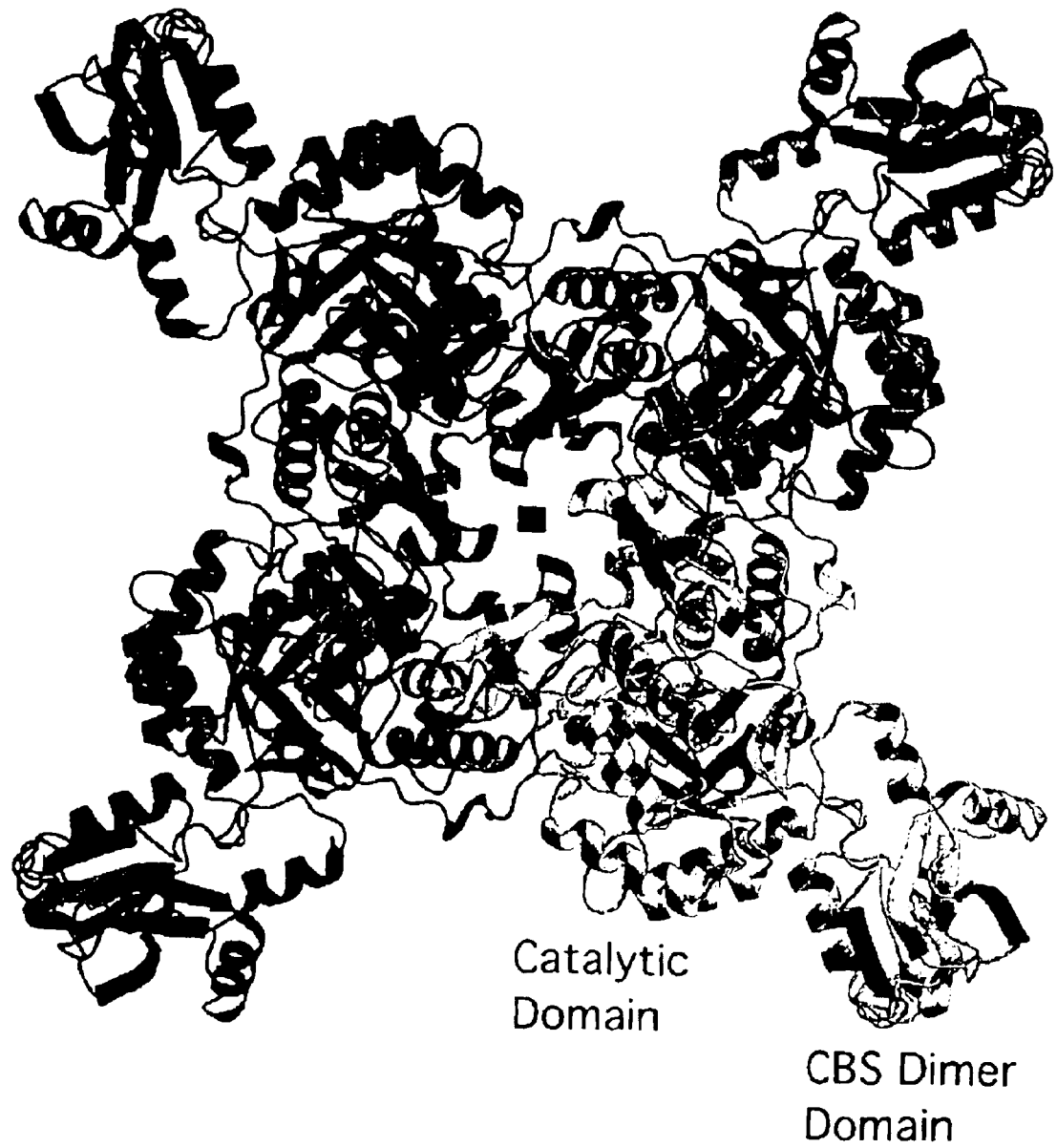
FIG. 1 is a ribbon drawing of the catalytically active IMPDH tetramer; the tetramer is displayed parallel (FIG. 1a) and perpendicular (FIG 1b) to the four-fold axis. Each subunit is shown with a spacefilling model of IMP, the active site of each subunit.

The invention relates the crystal structure of a bacterial IMPDH with substrate bound in the catalytic site. Conditions for producing a crystal from bacterial IMPDH were completely different than for humans. The structure was determined using SeMet-substituted protein and multi-wavelength anomalous diffraction (MAD) (Hendrickson, 1991) analysis of data obtained with synchrotron radiation from the undulator beamline of the Structural Biology Center at the Advanced Photon Source. The high quality of the data allowed determination of the structure of both catalytic and cystathionine-β-synthase (CBS) dimer domains. The α/β barrel domain of IMPDH embodies the catalytic framework. The CBS dimer domain contains two CBS motifs that are known to play a regulatory role in other proteins. However, their function in IMPDH is unknown. This is the first crystal structure reported of a complete CBS dimer domain. Bacterial and mammalian IMPDH enzymes have distinct kinetic and biochemical characteristics. Comparison of this bacterial IMPDH with the known partial structures from eukaryotic organisms provides an explanation of their distinct properties and contributes to the design of specific bacterial inhibitors.

Structure of Bacterial IMPDH

The structure of S. pyogenes IMPDH (FIG. 1) provides a new resource to define the distinct characteristics of bacterial and mammalian IMPDH enzymes. Features such as the catalytic motifs, active site flap region and CBS dimer domain are structurally conserved, but show a different pattern of sequence conservation in bacteria and eukaryotes. Analysis of sequence differences in these regions suggests they could contribute to the differential signature of the bacterial and mammalian enzymes. One of these sequence regions is the αG helix (FIG. 2) that forms part of the catalytic pocket. Analysis of sequence alignments for this region (Table 2) indicates a pattern of catalytic residues conserved in all enzymes and a secondary pattern of amino acid conservation associated with either bacterial or eukaryotic IMPDH enzymes. In this region, the pattern of bacterial sequence conservation is superimposed on a pattern of residues highly conserved in IMPDH enzymes from all organisms. These highly conserved residues are involved in IMP binding; the characteristics of which appear to be similar for bacterial and eukaryotic IMPDH enzymes. The existence of distinct bacterial catalytic pocket is supported by site-specific mutants at positions E421 and Y450 (Numbering corresponds to the amino acid sequence of the S. pyogenes IMPDH enzyme) that appear to differentially alter the activity of the mammalian and bacterial IMPDH enzymes. Residue Y450 in S. pyogenes IMPDH is located at the noncatalytic end of the TIM barrel. However, this region has contacts with another molecule in the tetramer and contributes to the catalytic environment of the adjacent monomer (FIG. 3). Site-specific mutagenesis results show partial retention of activity with an alanine substitution but no activity with an aspartic acid substitution for this residue. Aspartic acid was selected as a replacement on the basis of sequence alignments that show 12 of 13 eucaryotic enzymes contain aspartic acid at the corresponding position (the exception being asparagine in T. foetus). The partial activity observed with the Ala replacement suggests Y450 does not have an essential role in catalysis but does contribute to the environment of the catalytic pocket. Further analysis of this region will provide insight into the differences in the environment of the catalytic pocket in bacterial and eucaryotic enzymes and also the role of the tetrameric form of the active enzyme. The E421 in S. pyogenes IMPDH is conserved in bacteria while eucaryotic IMPDH enzymes contain glutamine in the corresponding position. In hamster IMPDH, the corresponding residue, Q441, is implicated in the binding of MPA. Comparison of the residues involved in MPA binding in the hamster enzyme (D274, Ser276, N303, R322, G326, T333, Q441) with the equivalent residues in *S. pyogenes* IMPDH indicates that these residues are largely conserved. The aspartic acid, asparagine, glycine, and threonine residues are identical, but threonine replaces S276 (although serine is present in other bacterial enzymes), and K301 replaces the hamster R322 residue. The most significant change appears to be replacement of E421 with Q441 (interestingly, this residue is part of the active-site flap). Although this suggests that the NAD binding pockets of hamster and bacterial IMPDH differ, a change in activity was not observed upon substitution of glutamine for glutamic acid at position 421. It is possible that this substitution does not affect the observed activity but may alter the sensitivity to MPA.

The active site flap represents another region that could account for the kinetic and biochemical differences between IMPDH enzymes. This flap is present in all IMPDH enzymes and is disordered in all IMPDH structures but may become ordered to upon NAD binding. Sequence comparisons (Table 2) indicate the loop size is conserved but sequence conservation is limited. A conserved feature of this region is the presence of an Arginine next to one or two aromatic residues. Since IMP and NAD bind sequentially to the active site, these residues may bind to the phosphate or the adenine or nicotinamide ring thereby ordering the active site. The sequence heterogeneity observed in this flap region may also account for the discriminatory features of bacterial and mammalian IMPDH enzymes.

Figures 1B, 2B:
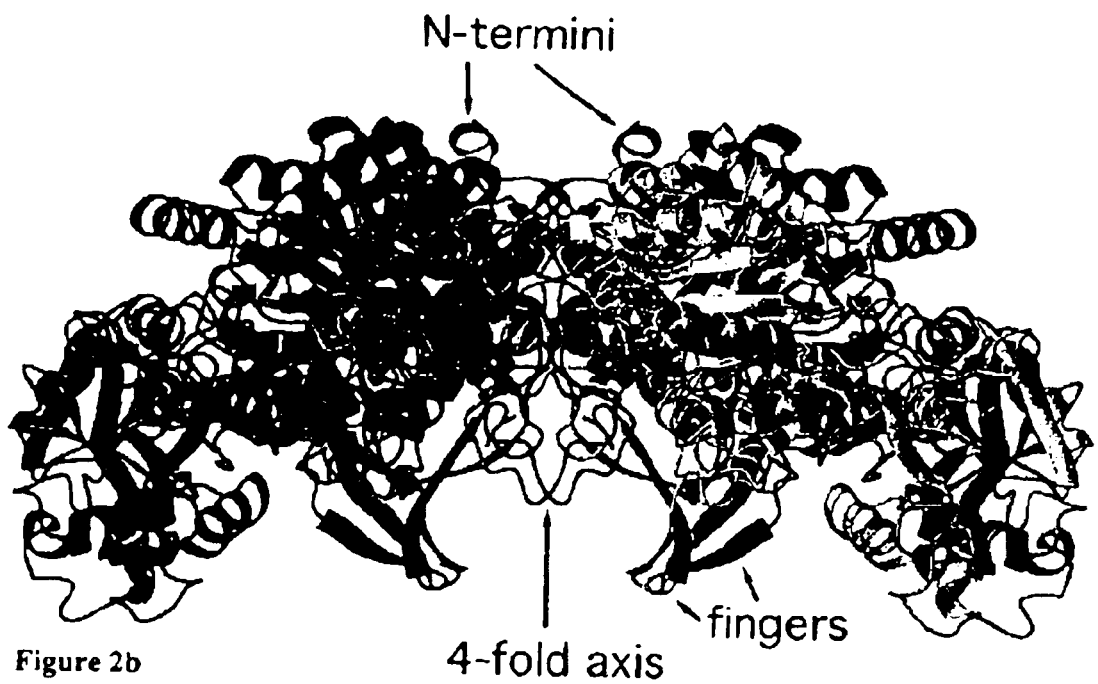
(FIG. 2b) Stereoview ribbon diagram arranged approximately perpendicular to the axis of the TIM barrel fold; IMP is shown as a ball and stick model.
Figure 2A:
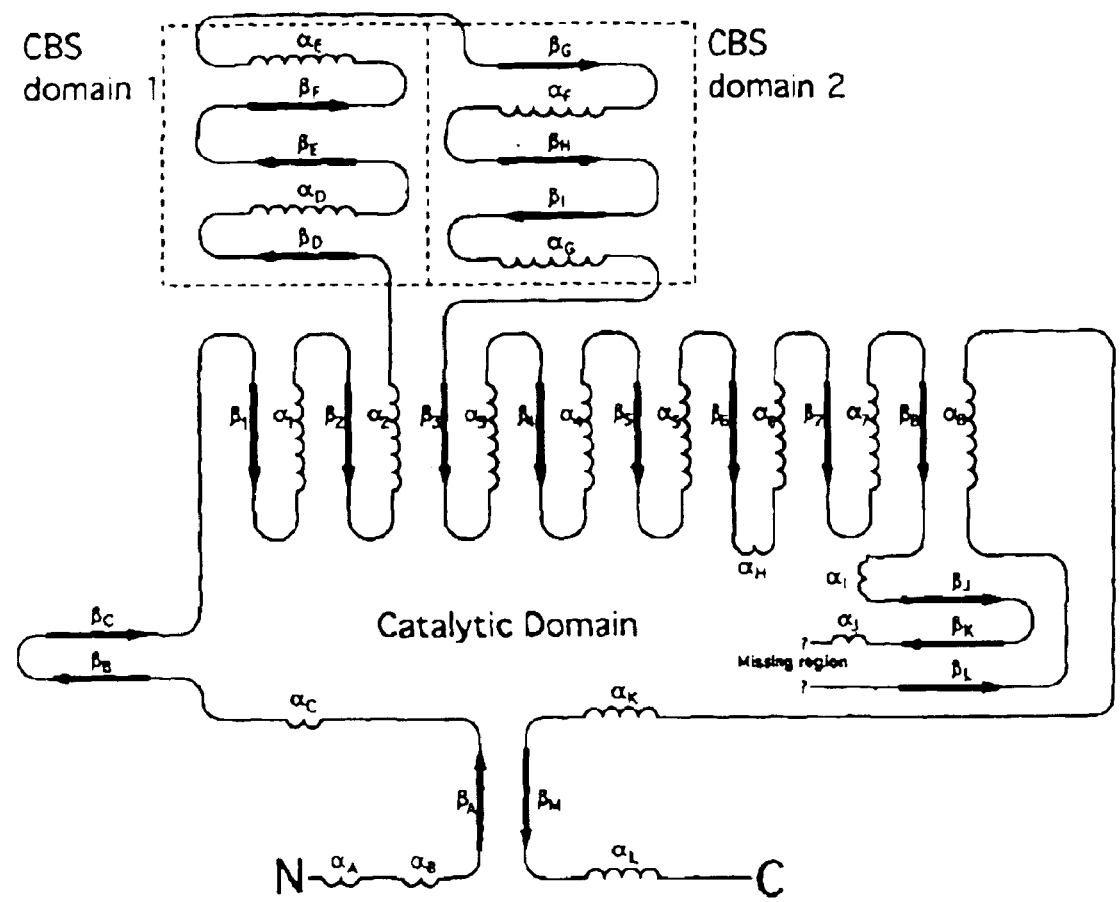
(FIG. 2a) Topology diagram of IMPDH domains. Secondary structure was assigned using the Kabsch and Sander (1983) algorithm along with visual inspection. The α helices and β strands that form the TIM barrel fold are labeled α1–α8 and β1–β8. The remaining strands and helices are designated in alphanumeric order (e.g., $\alpha_A$–$\alpha_L$). The part of the structure not visible in the electron density maps is marked as "?".
Figure 2B:
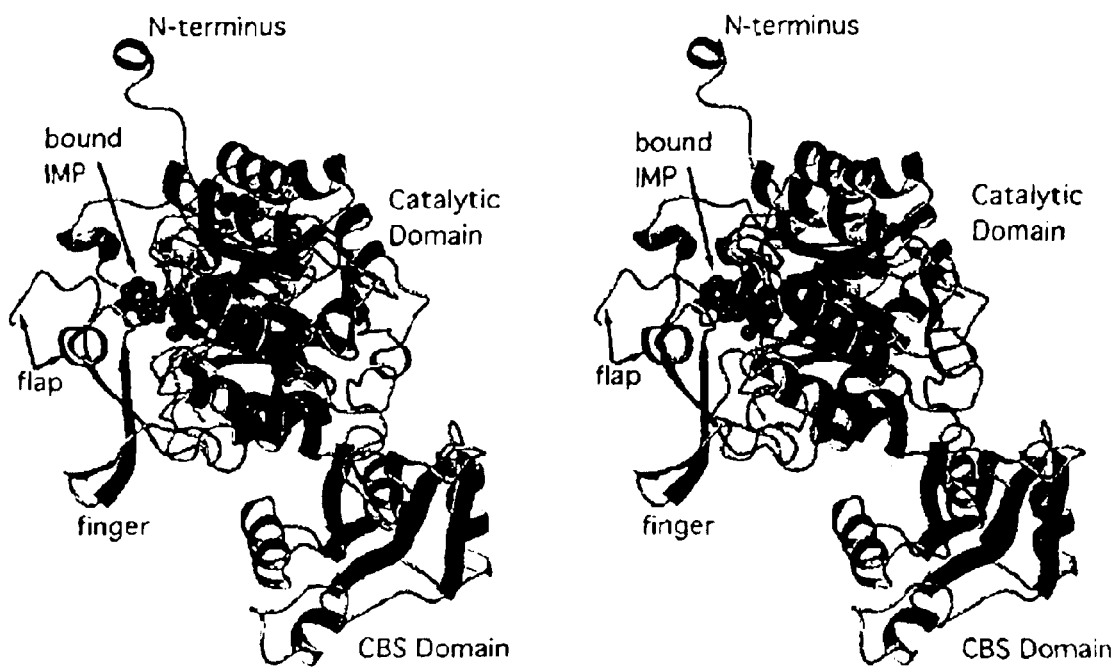

The finger region and the CBS dimer domain are not involved in catalysis but are found in all IMPDH enzymes. These regions show little sequence conservation but have been structurally conserved. The finger structure is composed of two anti-parallel β-strand structures stabilized by hydrogen bonding and interactions with the βL region (FIG. 2). The CBS dimer domain contains two CBS motifs arranged on a pseudo-dyad axis. In other proteins (e.g. cystathionine-beta-synthase and chloride channel proteins), mutations in these domains are associated with pathologic consequences. It has also been suggested (Nimmesgern et al., 1996) that these domains may be involved in cytoplasmic targeting or other regulatory functions. In either case, the metabolic expenditure required for conservation of these structures suggests an underlying functional role.

A unique aspect of the *S. pyogenes* IMPDH structure is that it allows examination of the initial stage of the catalytic cycle. IMP does not form a covalent bond in the absence of NAD. Covalent bond formation requires reorientation of the hypoxanthine ring and nucleophilic attack on C2 by Cys310. This suggests that NAD may have multiple roles as hydride acceptor, substrate activator, and also in contributing to the structure of the active site pocket. NAD binding likely initiates realignment of the hypoxanthine ring and also facilitates the electron shift with the ring required for formation of the thioimidate intermediate.

The structure of *S. pyogenes* IMPDH allows for a detailed comparison of the eukaryotic and bacterial enzymes and provides the basis for an explanation for the unique properties of the bacterial enzymes. This knowledge aids the design of inhibitors that specifically target bacterial IMPDH enzymes.

Determination of Bacterial IMPDH Crystal Structure

Figure 4:
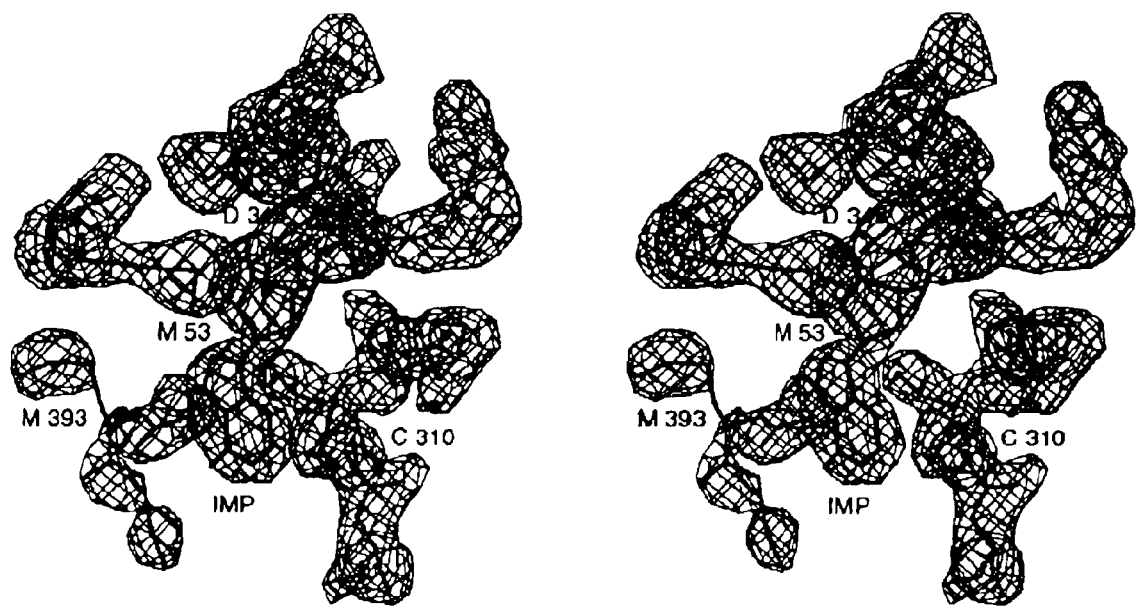
FIG. 4 is a stereoview of the electron density map around the active site; the solvent-flattened MAD map is calculated at 2.5 Å resolution drawn at a contour level of 1.2σ.

The crystal structure of *S. pyogenes* IMPDH was determined at 1.9 Å resolution by replacing all methionine residues in the enzyme with selenomethionine and applying MAD phasing methods (Hendrickson, 1991). The IMPDH crystals were tetragonal (space group I422, a=b=151.49 Å, c=101.67 Å, α=β=γ=90°) and contained one 53 kDa monomer per asymmetric unit. The enzyme contains 13 methionine residues: a potential 13 selenium sites (Table 3). Data were collected at three x-ray energies: at the peak and edge energies of the selenium absorption spectrum, and at a lower energy far from the edge. The initial model of the α/β barrel core (amino acid residues 15–90 and 222–460) was obtained by molecular replacement using a search model derived from the atomic coordinates of IMPDH from *T. foetus* (Whitby et al., 1997). These phases were sufficient to permit location of 6 selenium sites. Four rounds of phase development, in which the selenium sites were refined against the three data sets in program MLPHARE (Otwinowski, 1991), permitted location of the remaining selenium atoms in different Fourier maps. The electron density map used for interpretation of this structure was phased by MLPHARE with all 13 selenium sites. The figure of merit (FOM) for this phasing calculation was 0.64 (Table 4); the phasing power was 2.1 for all data between 10–2.5 Å resolution. Solvent flattening and density modification (Cowtan, 1994) further improved the electron density map (FOM=0.72), which at this point was clear enough to trace almost all of the main peptide chain and most side chains (FIG. 4). Registration of the sequence was made easy because methionine residues could be identified with the known selenium positions. The model was refined with the program CNS (Brünger, et al., 1998), which significantly improved the interpretation of several regions in the model that were initially ambiguous. The model disclosed herein contains 3,992 nonhydrogen atoms, from residues 2–401 and 416–492, in two distinct domains. The crystallographic R-factor is 23.2% (R-free: 26.1%) for all reflections between 6 and 1.9 Å resolution (Table 5). The current model contains 422 water molecules with an average B factor for all nonhydrogen protein atoms of 37.5 Å (Table 5). This structure is significantly more complete (97%) and of higher resolution (1.9 Å) than those reported for IMPDH from Chinese hamster (Sintchak et al., 1996) (85%, 2.3 Å) and *T. foetus* (Whitby et at., 1997) (68%, 2.3 Å). The map also contains clearly defined electron density for the IMP substrate, bound in the catalytic site.

Catalytic Domain of Bacterial IMPDH

The *S. pyogenes* IMPDH tetramer is composed of four identical subunits where each monomer has a two-domain structure (FIG. 1a). The catalytic domain (amino acid residues 2–92 and 224–492) forms the interior core of the active tetrameric enzyme and is approximately 40×40×50 Å. This domain contains the catalytic site that is positioned near the tetramer four-fold at the subunit interface (FIG. 1b). This location places access to the active site on the same face of the tetramer. The CBS dimer domain (residues 93–223, approximately 20×20×30 Å) is on the active site face and projects outward from the core of the tetrameric unit placing this domain in the comer of the square formed by E162.

The core of the catalytic domain (FIG. 2a) is formed by an α/β barrel structure that provides a scaffold for the attachment of additional structural and catalytic moieties and the CBS dimer domain. This core region contains a series of eight parallel α/β motifs with the active site near the C-terminus of the β-strands (FIG 2b). The number and relative location of the barrel structures in *S. pyogenes* IMPDH are similar to that reported for the Chinese hamster (Sintchak et al., 1996) and *T. foetus* (Whitby et al., 1997) IMPDH and for other nicotinamide-dependent oxidoreductases. However, in IMPDH the phosphate-binding site is occupied by IMP rather than by the phosphate of the NAD or NADP cofactors as seen in the other nicotinamide dependent oxidoreductases.

The β-strand structures and the interior residues of the helices are hydrophobic with very few water molecules observed in the interior of the α/β barrel structure. This hydrophobic environment and the network of hydrogen bonds provide a stable scaffold to anchor the functional and catalytic motifs. Examination of the sequence conservation for IMPDH representatives from the three kingdoms suggests a limited sequence conservation of the α/β barrel core structure relative to the high level of conservation observed for residues forming the catalytic site pocket. The sequence conservation of α/β barrel core is restricted to residues adjacent to the active site pocket and to a region representing the junction between the catalytic and CBS dimer domains.

Several large structural and catalytic protrusions connect the β-strands and α-helices of the α/β barrel surface. The distal face of the α/β barrel (furthest from the IMP binding pocket) provides for entry of the N-terminus (strand β1). The CBS dimer domain is attached through helix α2 and strand β3. Connections between the remaining α/β motifs are short (2–5 amino acid residues) and characterized by a preponderance of proline, glycine and hydrophobic residues. The C-terminal region exits from helix α8 and is located on the opposite face of the tetramer from the N-terminus.

The protrusions on the proximal face of the α/β barrel scaffold range in size from 3–67 residues and define the character of the active site. Three of the barrel connections (β1/α1, β6/α6, and β7/α7) show greater than a 50% amino acid sequence conservation for IMPDH proteins representing the three kingdoms. The β8/α8 protrusion is the largest (67 residues) of the proximal face motifs and contains the "finger" structure (βJ and βK, FIGS. 1b, 2a), short helices αI and αJ, strand βM, and regions that have a role in catalysis and that interact with other IMPDH monomers in the tetramer. This protrusion sequence is also highly conserved with regional sequence conservation of 60–80% in three distinct 10-amino acid residue segments. A distinct feature of this region is a "flap" (residues 396–419) on one edge of the active site that apparently projects into the solvent. This flap has been suggested to function by potentially folding over the catalytic pocket controlling access to and ordering the active site. (Whitby et al., 1997) This structure is similar to the active site flap involved in the catalytic mechanism of lactate dehydrogenase (Holbrook t al., 1975). In the S. pyogenes IMPDH 1.9 Å structure, 14 residues in this loop remain disordered in the presence of substrate in the active site and also in IMPDH crystals containing product, transition state analogue complexed with MPA (Sintchak et al., 1996; Whitby et al., 1997. This persistent disorder suggests that NAD binding may be critical for structuring the flap; a suggestion supported by the resistance of this region to proteolysis acquired by NAD binding (Nimmesgem et al., 1996). This also suggests that MPA binding does not involve an interaction with this flap and does not entirely mimic NAD binding. These features suggest this flap may be important in mediating NAD binding specificity in the active site and may be responsible for some of the kinetic differences of IMPDH enzymes from bacteria and eukaryotes.

CBS Dimer Domain

Figure 5:
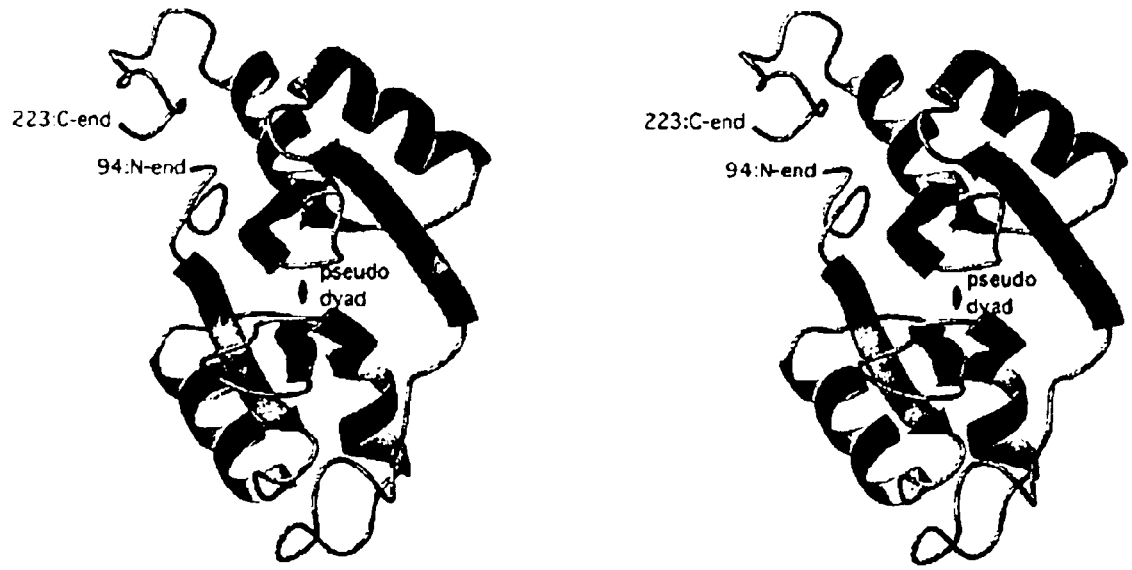
FIG. 5 is a representation of the secondary structure of the CBS dimer domain shown as a stereoview ribbon diagram arranged approximately along the dyad axis of the two CBS motifs.

The CBS dimer domain contains residues 94–223 with an approximate size of 20×20×30 Å. A CBS domain was originally identified in cystathionine-β-synthase and proposed as a regulatory element since mutations lead to the human disease homocystinuria (Bateman, 1997). The CBS dimer domain is composed of two CBS motifs arranged approximately on a two-fold dyad axis (FIG. 5). Each CBS motif has the characteristic sheet/helix/sheet/sheet/helix topology. This is the first reported complete structure for this domain. The CBS dimer domain does not interact with the other subunits in the active tetrameric enzyme and may not be required for activity (Sintchak et al., 1996; Zhou et al., 1997). Although the amino acid sequence of this domain is not as well conserved as that of the catalytic domain, all IMPDH proteins contain this domain.

In S. pyogenes IMPDH, these domains form a minibarrel structure that has a hydrophobic core region with hydrophilic residues on the surface. Among bacteria, the degree of amino acid conservation is highest in the E and F β-strands (FIG. 2a) that span the interior of the CBS dimer domain and provide a resource of hydrophobic residues. The α-helices on the exterior maintain the character of this domain with hydrophilic residues on the exterior surfaces and hydrophobic residues positioned on the interior. There is a well-defined cleft between CBS motifs (approximately 15 Å in length) between the CBS motifs; this cleft may function as a potential binding site for regulatory molecules. There is not a defined role for CBS motifs in bacteria but in eukaryotic organisms they may have a role in cytoplasmic targeting, protein-protein interactions or protein regulation (Bateman, 1997). In view of these unique characteristics, it is possible that, in bacteria, this domain may possess a species-specific regulatory role.

Tetramer Organization

S. pyogenes IMPDH is a perfect tetramer with the four subunits related by a crystallographic four-fold axis. Similarly, the structures reported for Chinese hamster (Sintchak et al., 1996) and T. foetus (Whitby et al., 1997) IMPDH also display four-fold symmetry. The scope of these structures encompass the apo-enzyme and several substrate, product, and inhibitor complexes The tetrameric structure of IMPDH is stabilized by monomeric contacts with each of the adjacent subunits. Many of these contacts originate from interactions of the N- and C-terminal regions of the adjacent monomeric units. The subunit interactions can be arranged into three groups differing in their proximity to the catalytic site and level of amino acid sequence conservation. In one group, the first 14 residues of the N-terminus project approximately 20 Å from the protein core (FIGS. 1a, 2b) and interact with surface residues of an adjacent IMPDH monomer. This regional contact is distal from the catalytic site and involves residues 3–12 of the N-terminus that interact with β-sheet residues 465–468 of an adjacent subunit. The interaction involves hydrogen bonds and salt bridges between amino acid regions that display little sequence conservation. Another loop (residues 22–30), is involved in subunit contacts with the adjacent IMPDH molecule and also forms part of the active site pocket of the adjacent subunit. This region directly contacts the αH helix that is involved in binding IMP and the α4 helix of the α/β motif implicated in the binding of NAD (Sintchak et al., 1996). This region contains amino acid residues that are conserved in IMPDH enzymes from the three kingdoms. The sequence conservation and proximity to the active site suggests these interactions may indirectly mediate catalytic activity and account for the tetrameric character of the active enzyme. Additional subunit contacts originate from β-strand βK and residues 479–484 in an adjacent IMPDH monomer. These regions are on the exterior of the tetramer approximately 20 Å from the IMP binding site and display an amino acid sequence conservation that is restricted to a specific phylogenetic group.

A feature observed in the tetramer structure is the projection of an extended region from the C-terminal face of each monomer subunit (FIG. 1b). These "fingers" are observed in all IMPDH enzymes for which structural information is available. This region of 12 amino acids forms two anti-parallel β-strand structures stabilized by hydrogen bonding and interactions with the βL region (FIG. 2a). Interestingly, in all IMPDH enzymes, this region contains at least two solvent-exposed hydrophobic residues. Other than a predominance of aromatic amino acids, there is little sequence conservation even within the specific phylogenetic domains. However, the β-strand structure of the fingers is preserved and amino acid residues at the base of the fingers are conserved for all phylogenetic groups. The conservation of this structure may have functional consequences for the interaction of the tetramer with other IMPDH complexes or cellular proteins.

Catalytic Site and Implication for the Mechanism of Bacterial IMPDH

IMP dehydrogenase catalyzes the oxidation of inosine 5'-monophosphate to xanthosine 5'-monophosphate with the concomitant reduction of NAD to NADH. IMP is bound at one end of the barrel with the other end blocked by the βB/βC sheet (FIG. 2a). Short helices H, J, and I are structural motifs containing many of the active site residues. During the reaction the hydride is transferred from the C2 carbon of the hypoxanthine ring to NAD and an oxygen atom is substituted in the C2 position resulting in the formation of xanthosine.

Figure 3A:
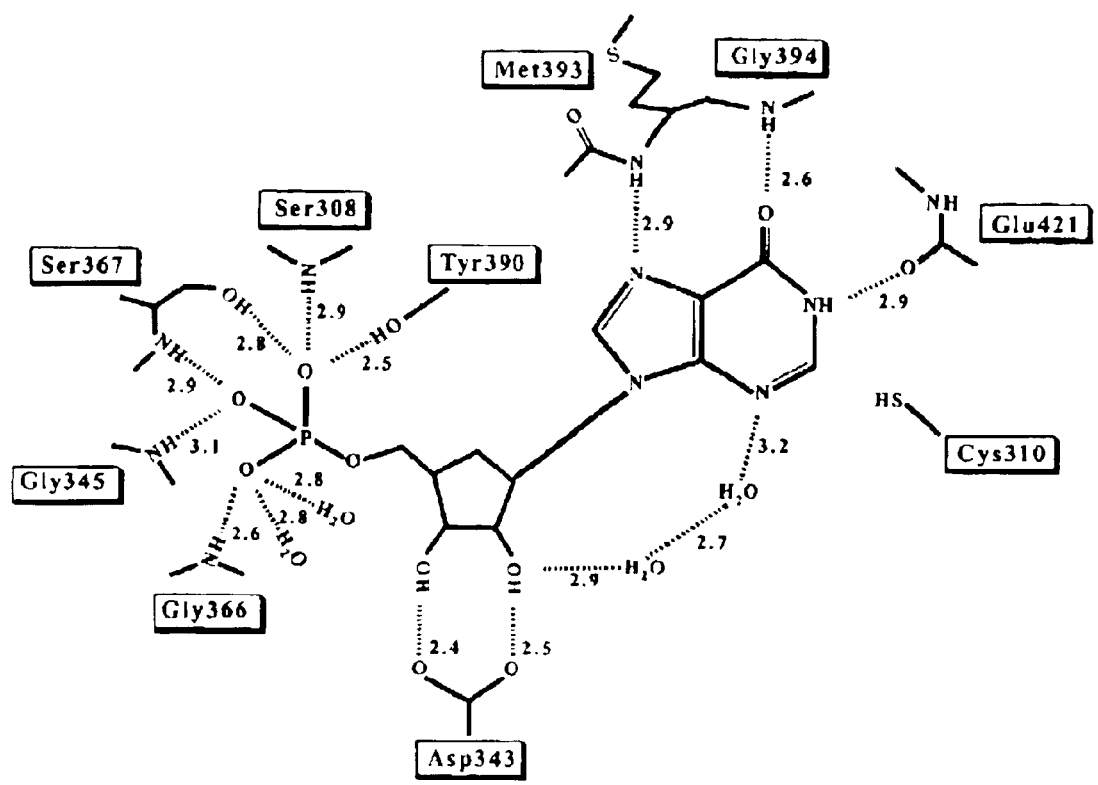
(FIG. 3a) is a cartoon of bound IMP showing side chain interactions and active site residues.

The high-resolution (1.9 Å) crystal structure of S. pyogenes IMP dehydrogenase allows examination of the catalytic site in greater detail than it was possible previously. The enzyme contains the inosine monophosphate substrate bound into the pocket located near the surface of the α/β-barrel structure. The inosine ribose and phosphate moieties are highly coordinated by protein (FIG. 3a). The sugar is in the C2'-endo-conformation and its 2'- and 3'-hydroxyls are hydrogen-bonded with the Asp343 residue as well as with a water molecule that through a water relay system connects with N3 of the hypoxanthine ring (FIG. 3a). The phosphate group is anchored in its site by a number of amino acid side chains (S308, S367 and Y390) and three main chain nitrogens (G345, G366 and S367). The remaining hydrogen-binding potential of the phosphate oxygens is realized with water molecules.

The conformation of the glycosidic torsion angle of the bound nucleotide is anti and the hypoxanthine ring interacts with the ribose and the phosphate moiety only through water mediated interactions and appears to be free to rotate around the glycosidic bond (FIG. 3a). This conformation places H2 of hypoxanthine ring (which is transferred to NAD in the reaction) in a position unobstructed by the rest of the molecule to facilitate the reaction. N1, N7 and O6 of the hypoxanthine ring are hydrogen bonded to the main chain carbonyl of E421 and main chain nitrogen of M393 and G394, respectively. However, N3 is not involved in an interaction with protein and only weakly with solvent. There are van der Waals contacts between the hypoxanthine ring and the Ile309 residue.

Cysteine 310 has been identified previously as a key residue in catalysis (Huete-Pérez et al, 1995; Antonino et al, 1994). The ability of the thiol residue to ionize appears to be critical for the reaction involving nucleophilic attack. The hydroxyl of T312 is in position (3.3 Å) to extract a hydrogen from C310 and therefore ionize the cysteine residue. This is consistent with mutagenesis studies that show that substitution of this residue abolishes enzyme activity (Sintchak et al, 1996). The sulfur atom is located above the plane of the hypoxanthine ring, 3.3 Å from the C2 atom, and is not covalently attached to the ring (FIG. 5c). The C310 is in a position for a nucleophilic attack on C2 carbon once the activation of the CysTEINE residue is accomplished and the orientation of the hypoxanthine ring is adjusted (it can swivel around glycosidic bond). The formation of a tetrahedral intermediate has been proposed (Xiang et at, 1997). However, the present inventions shows that IMPDH does not form a covalent bond with the substrate in the absence of the NAD cofactor. Therefore a cofactor plays not only the role of hydride acceptor but also appears to complete the structure of the catalytic pocket. Initiation of a reaction cycle requires alignment of the hypoxanthine and nicotinamide rings in near parallel fashion and positioning of the C2 of hypoxanthine ring in close contact with C4 on the beta face of nicotinamide ring (Xiang et al., 1997). This places the amide moiety of NAD near the N3 nitrogen of hypoxanthine. Such a configuration may facilitate the electron shift within the hypoxanthine ring required for formation of the thioimidate intermediate. Therefore, it appears that the cofactor may play a role in activation of the substrate. This mechanism is in striking contrast with results obtained with halogenated derivatives of IMP. Human IMPDH catalyses the dehalogenation of 2-fluoro- and 2-chloroinosine 5'-monophosphate in the absence of NAD (Antonino et al., 1994). This suggests that, although the C310 activation system is in place, the reaction does not proceed with IMP because hydride is a much poorer leaving group than chlorine and fluorine and the binding of NAD is required.

Figure 3B:
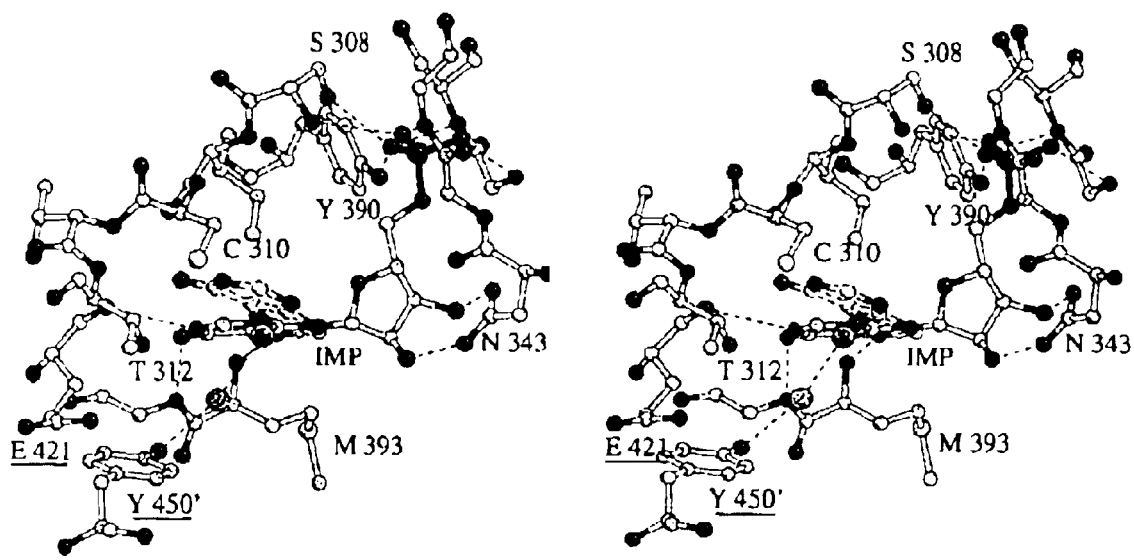
(FIG. 3b) is a stereoview ball and stick diagram of bound IMP illustrating the alignment of the hypoxanthine ring relative to the catalytic Cys310 residue. The dashed ring cartoon indicates the proposed realignment of the hypoxanthine ring initiated by NAD binding. Residues targeted for mutagenesis (E421 and Y450') are underlined. The "'" symbol on Y450 indicates a symmetry related molecule.

The structure of the hamster IMPDH has been reported (Sintchak et al., 1996). This structure contains the hypoxanthine ring covalently bound to C331 (equivalent to C10 in our structure) and an inhibitor MPA bound to the active site. It appears that the hamster IMPDH structure represents the covalent thioimidate intermediate of the reaction in which MPA, an uncompetitive inhibitor, prevents the hydrolysis of the thiopurine covalent intermediate as was suggested previously by Link and Straub (Link et al., 1996) Therefore MPA restricts the access of the solvent molecules and blocks subsequent steps of the reaction. This observation also suggests that the hydrolysis of the thioimidate intermediate is mediated by an activated water molecule originating from the NAD site. In the S. pyogenes IMPDH structure, two water residue were located that are potential candidates for nucleophilic attack on the thioimidate (FIG. 3b). Several residues (E421, T312, and Y450 from and adjacent subunit) in the active site pocket can act as activators of this water molecule. Because MPA can stabilize the thioimidate intermediate in the human enzyme (Sintchak et al., 1996), hydrolysis of thioimidate must be several orders of magnitude slower than the dissociation of NADH. These results are consistent with the mechanism proposed by Wang et al. (1996)

The binding of NAD to IMPDH has not been structurally characterized. However, a structure has been reported for the hamster enzyme complexed with MPA (Sintchak et al., 1996), an uncompetitive inhibitor of mammalian IMPDH enzymes. MPA has been suggested to inhibit the hamster enzyme by mimicking the nicotinamide portion of NAD and blocking access of a catalytic water molecule (Sintchak et al., 1996). Comparison of the residues involved in MPA binding in the hamster enzyme (D274, S276, N303, R322, G1326, T333, Q441) with the equivalent residues in S. pyogenes IMPDH indicates these residues are largely conserved. The Asparagine, Aspartate, Glycine, and Threonine residues are identical, Threonine replaces S276 (although Serine is present in other bacterial enzymes), and Lys301 replaces the hamster R322 residue. The most significant change appears to be replacement of E421 with Q441. Interestingly, this residue is part of the active site flap that is ordered. This suggests that the NAD binding pocket is different in bacterial IMPDH, however the mechanism of If oxidation remains the same.

MATERIALS AND METHODS

Site-specific Mutants.

To validate the role of specific residues in catalysis and to provide a basis for comparing the bacterial and mammalian enzymes, several point mutants were constructed. The sites for mutation were selected on the basis of previous studies suggesting a catalytic role for the region and supported by information derived from the S. pyogenes IMPDH crystal structure. One region targeted for site-specific mutagenesis was the active site flap. This flap is present in all IMPDH enzymes and is disordered in the S. pyogenes IMPDH structures and in the IMPDH structures from hamster and T. foetus. Although this region has not been previously implicated in the catalysis mechanism of IMPDH enzymes, the presence of a conserved RY(FY) motif and the similarities to the flap region in lactate dehydrogenase (Holbrook et al., 1975) suggest a potential role in catalysis. Mutation of R406 to alanine in this flap region results in a complete loss of enzyme activity (Table 6) as might be expected for a residue conserved in all.

TABLE 6

Site-specific mutants of S. pyogenes IMPDH

| Mutant | Corresponding residue in mammalian IMPDH | Region Location | Function | Relative specific activity of purified |
|---|---|---|---|---|
| Arg406 ®Ala | Arg | Active site flap | Catalysis | No activity |
| Tyr450 ®Asp | Asp | Helix 8, TIM barrel | Unknown | No activity |
| Tyr450 ®Ala | Asp | Active site | Unknown | 0.25 |
| Glu421 ®Gln | Gln | $\alpha_J/\beta_L$ Loop | NAD binding region | 1.0 |

IMPDH enzymes. This loss of activity confirms the importance of the active site flap in catalysis. Since there is little sequence conservation of this region, this structure is an attractive target for specific inhibitors.

The catalytic mechanism of S. pyogenes IMPDH involves the hydrolysis of a thioimidate intermediate that we believe is mediated by an activated water molecule originating from the NAD site. In the S. pyogenes IMPDH structure, we have located two water residues that are potential candidates for nucleophilic attack on the thioimidate. Tyrosine 450 originating from an adjacent subunit, is a residue in the active site pocket that can act as an activator of one of these water molecules. This residue is located at the noncatalytic end of a conserved helix (Helix 8) that forms the TIM barrel core. Replacement of Y450 with aspartic acid or alanine (Table 6) results in substantial loss of enzyme activity. Approximately 25% activity is retained for an alanine replacement, but substitution of aspartic acid results in a loss of enzyme activity. This region is conserved in the IMPDH enzymes, but the sequence pattern is different in bacteria and eukaryotes, suggesting this region may contribute to the differential signature of the bacterial and mammalian enzymes.

The NAD binding region (between the $\alpha_J/\beta_L$ loop) was also selected as a target for site-specific mutagenesis. The selection of E421 for mutation was based on an analysis of sequence differences at residues corresponding to or near amino acids identified as MPA binding sites in human IMPDH. The conserved glutamate in bacteria is replaced with a conserved glutamine in eukaryotes. This substitution does not alter the apparent activity of S. pyogenes IMPDH (Table 6). This result was unexpected since replacement of the corresponding residue in the hamster enzyme (Q441) with alanine results in a significant decrease in activity (Sintchak et al., 1996)

Cloning and Expression of S. Pyogenes IMPDH

The coding region of IMPDH was amplified from S. pyogenes genomic DNA (provided by Dr. Michael Boyle, Medical College of Ohio, Toledo, Ohio; Genomic DNA from S. pyogenes is also available from the American Type Culture Collection [ATCC] as catalogue No. 700294D) using coding region-specific primers and a proofreading polymerase (Pfu). The amplified fragment was cloned into a pET23a (Novagen) expression vector and used to transform BL21 (DE3)lysS bacterial cells. DNA sequencing of the expression constructs validated sequence integrity of the initiation and termination regions. Expression of Streptococcal IMPDH was induced by the addition of IPTG to a concentration of 0.5 mM The Streptococcal IMPDH enzyme was purified using a modification of the procedure previously described for the human enzymes (Hager et al., 1995). The modified procedure replaces the Blue Sepharose dye column with a Matrex Green resin (Millipore, Bedford, Mass.). Since the enzyme elutes as a broad peak from the dye column, an additional chromatographic procedure was applied to facilitated enzyme concentration and increase purity. Peak fractions from the dye column are diluted with 20 mM Tris-HCL, pH 7.4 and applied to a MonoQ HR10/10 FPLC column (Pharmacia, Piscataway, N.J.). The column was washed with 20 mM Tris-HCl, pH 7.4, 1 mM DTT and the enzyme eluted with a linear gradient of 0.2–0.7 M NaCl in wash buffer.

Purified IMPDH from S. pyogenes was characterized by N-terminal sequencing and analyzed by mass spectroscopy to validate as much of the internal protein sequence as is possible. An N-terminal sequence was obtained (Yale Biotechnology Resource Center) for 19 residues corresponding to amino acids 2–20 of the predicted sequence and indicated cleavage of the N-terminal methionine as is commonly observed for proteins expressed in E. Coli. Characterization of the purified protein also included matrix-assisted laser desorption ionization mass spectroscopy (MALDI-MS) analysis of the intact and tryptic-digested protein provided by The Biotechnology Resource Laboratory at Yale University. MALDI-MS of the intact protein indicated a molecular weight (MW) of 52,328 similar to the predicted MW of 52,657. In addition to N-terminal sequencing of the intact protein, a tryptic digest of the purified protein was analyzed by MALDI-MS. This analysis provided verification of approximately 60% of the of the internal protein sequence.

Selenomethionyl IMPDH was obtained by growth of the native expression bacterium in M9 medium. Prior to induction of IMPDH expression, de novo methionine synthesis was suppressed by the addition of phenylalanine, valine, threonine, isoleucine, leucine, and lysine to a final concentration of 50 ug/ml. Thirty minutes later, selenomethionine was added to a final concentration of 50 ug/L and IPTG was added 0.25 mM. The induced bacteria were harvested 4–6 h after induction. The purification and crystallization of selenomethionyl IMPDH was as described for the wild-type enzyme and the presence of selenomethionine was verified by amino acid analysis of the purified protein.

Crystallization and Data Collection

Crystals of IMPDH from *S. pyogenes* were grown by the hanging drop method. The reservoir solution was 0.1 M MES (pH 7.2), 1.8 M ammonium sulfate, with 1 mM IMP. The crystals grew in a few days to about 0.1×0.1×0.25 mm (maximum size). Crystals were transferred into a cryoprotectant solvent prepared by the addition of glycerol to the crystallization solution (final glycerol concentration (v/v), 28%). Crystals were flash cooled in liquid nitrogen for all data collections.

Diffraction data were collected on beamline 19ID of the Structural Biology Center at the Advanced Photon Source. The approximate x-ray flux on the sample was 1×10 Ph/sec. Diffraction patterns from IMPDH crystals were collected at 100° K using a 3×3 mosaic CCD area detector (Westbrook et al. 1997) and data were processed by the HKL2000 (Otwinowski et al., 1997) package. Diffraction patterns of the IMPDH crystals exhibited 4/mmm symmetry. Bragg spots with indices other than (h+k+l)=2n were systematically absent. Therefore the space group to which these crystals belong must be I422. The cell dimensions are a=b=151.49 Å, c=101.67 Å, $\alpha=\beta=\gamma=90°$. Each asymmetric unit of this crystal form contains one monomer; the estimated solvent content is 55% and $V_M$=2.79 Å$^3$/Da.

Crystals for the MAD study were of SeMet IMPDH from *S. pyogenes* complexed with IMP. We recorded three data sets for a single crystal, each at a unique x-ray wavelength ($\lambda_1$=1.0781 Å, $\lambda_2$=0.9793 Å, $\lambda_3$=0.9791 Å, Table 3). The entire time to manipulate the sample and acquire data required less than one hour. The crystal was not oriented in any special way prior to data collection. Data quality is summarized in Table 3. The high-resolution data (1.90 Å) were collected from the same crystal at wavelength $\lambda$=1.0332 Å. Details of the experiments and data quality are summarized in Table 3.

Phasing

Phase analysis for the crystal form was initiated by carrying out molecular replacement (MR), using AMORE (Navaza et al., 1997) and the *T. foetus* atomic coordinates (Whitby et al., 1997) from the Protein Data Bank as a search model. The initial molecular replacement solution of this structure produced phases that were not sufficiently close to the correct values for us to interpret the structure further. However this phase set was sufficiently good to identify 6 of the 13 selenium sites in the structure. These selenium sites were refined by the method discussed by Ramakrishnan and Biou (1997), using the program MLPHARE (Otwinowski, 1991), yielding a phase set which permitted identification of two additional selenium atoms. Further MLPHARE refinement with 8 selenium sites produced phases that permitted location of three additional selenium sites by difference Fourier analysis. The next stage of MLPHARE refinement against 11 selenium sites produced phases with which the remaining 2 selenium sites were identified. The final round of MLPHARE phasing with all 13 selenium sites (Table 3) produced a map with which interpretation of the model was completed. Phases were improved during subsequent refinement with CNS (Holbrook et al., 1975) (see below) permitting modeling of 97% of the structure.

Model Building, and Refinement

All model building was carried out with FRODO (Jones, 1968) on an Evans and Sutherland ESV10 graphics workstation. Relative to the map obtained by molecular replacement, the MAD map obtained with six selenium sites allowed localization of IMP in the active site and corrected several errors in the catalytic domain model. The MAD map calculated with 8 selenium sites allowed modeling of the complete N-terminus (except residue 1), the C-terminus to residue 480, and the CBS dimer domain with the exception of residues 114–169. The MAD map obtained with eleven selenium sites allowed assignment of the C-terminus to residue to 490, and decreased the undefined region of the CBS dimer domain to residues 146–162. When all 13 selenium sites were used in the MAD map calculation, it was possible to model the entire molecule, with the exception of residue 1, residues 221–226, the active site flap (residues 402–415) and C-terminal residue 493. CNS refinement improved phases to allow modeling of residues 221–226 in the CBS dimer domain. This model accounts for 97% of the residues predicted from the gene sequence.

Refinement of the initial model against the MAD data was carried out using torsion-angle molecular dynamics (Rice et al., 1994) and the phase restrained MLHL target (Pannu et al., 1998) implemented in CNS (Holbrook et al., 1975). All diffraction data (6.0–1.90 Å) were used throughout the refinement except for a 10% randomly selected test set required for cross-validation of the $\sigma_A$ values used in the maximum likelihood target and free R calculations. A flat bulk solvent model was implemented in density modification of the initial MAD maps, with the program DM (Cowtan, 1994). At the later stages, $\sigma_A$ phase-combined maps (Pannu et al., 1998) were calculated, with model phases calculated from the MLHL refined model combined with experimental phases. Alternate cycles of model rebuilding, positional refinement, restrained B-factor refinement, and water placement followed, decreasing the free R-factor from its initial value of 48% to 26.1% and yielding the current R-factor of 23.2% (Table 5). The model has a correlation coefficient ($F_a$ versus $F_c$) of 95% and an estimated coordinate error of 0.3 Å using the SIGMAA (Read, 1986) sftware suite. Stereochemical and other refinement parameters are given in Table 4. By PROCHECK (Laskowski et al., 1993) criteria, the model has 91.2% of the main chain torsion angles within the "allowed regions" of the Ramachandran plot and 8.8% within the "additional allowed regions".

Coordinates

The coordinates of the crystalline IMPDH molecule (Table 7) have been deposited in the Brookhaven Protein Data Bank under accession number 1ZFJ.

TABLE 2

Catalytic Region

| | | | | | |
|---|---|---|---|---|---|
| Bacteria | PGSIC | TTRVVAGVGV | (SEQ ID NO: 1) | | *Streptococcus pyogenes* |
| | PGSIC | TTRVVAGVGV | (SEQ ID NO: 2) | | *Bacillus subtilis* |
| | PGSIC | TTRIVTGVGV | (SEQ ID NO: 3) | | *Escherichia coli* |
| | PGSIC | TTRVVAGVGV | (SEQ ID NO: 4) | | *Bacillus subtilis* |
| | PGSIC | TTRVVAGVGV | (SEQ ID NO: 5) | | *Mycobacterium tuberculosis* |
| Ecarya | SGSIC | ITQEVLACGR | (SEQ ID NO: 6) | | *Homo sapiens* |
| | SGSIC | ITQEVLACGR | (SEQ ID NO: 7) | | *Mus musculus* |
| | SGSIC | ITQEVLACGR | (SEQ ID NO: 8) | | *Arabidopsis thaliana* |
| | SGSIC | ITQEVLACGR | (SEQ ID NO: 9) | | *Leishmania donovani* |
| | TGSIC | ITQKVMACGR | (SEQ ID NO: 10) | | *Saccharomyces cerevisiae* |
| | SGSIC | ITQEVMACGR | (SEQ ID NO: 11) | | *Drosophila melanogaster* |

Active Site Flap

| | | | | | |
|---|---|---|---|---|---|
| Bacteria | MA......KG | SSDRYFQ.SD | NAADKLVPEG | (SEQ ID NO: 12) | *Streptococcus pyogenes* |
| | MS......KG | SSDRYFQ.SD | NAADKLVPEG | (SEQ ID NO: 13) | *Bacillus subtilis* |
| | MK......KG | SSDRYFQGSV | NEANKLVPEG | (SEQ ID NO: 14) | *Escherichia coli* |
| | ME......KG | SKDRYFQ... | EENKKFVPEG | (SEQ ID NO: 15) | *Bacillus subtilis* |
| | MRGRGGATSY | SKDRYFADDA | LSEDKLVPEG | (SEQ ID NO: 16) | *Mycobacterium tuberculosis* |
| Eucarya | MD....KHLS | SQNRYFSEAD | KIK...VAQG | (SEQ ID NO: 17) | *Homo sapiens* |
| | MD....KHLS | SQNRYFSEAD | KIK...VAQG | (SEQ ID NO: 18) | *Mus musculus* |
| | MERGDAKGAA | MSRYYHNEMD | KMK...VAQG | (SEQ ID NO: 19) | *Arabidopsis thaliana* |
| | MQKTGTKGNA | STSRYFSESD | SVL...VAQG | (SEQ ID NO: 20) | *Leishmania donovani* |
| | MTKG...... | SDQRYLGDQT | KLK...IAQG | (SEQ ID NO: 21) | *Drosophila melanogaster* |
| | M....SQGKE | SGKRYLSENE | AVQ...VAQG | (SEQ ID NO: 22) | *Saccharomyces cerevisiae* |

TABLE 3

Crystal and MAD Data Collection Parameters for IMPDH

Crystal Parameters

| | |
|---|---|
| Unit Cell | a = b = 151.49 Å, c = 101.67 Å, α = β = γ = 90° |
| Space Group | I422 |
| MW | 53,328 |
| Mol/AU | 1 |
| Se-Met/AU | 13 |

MAD Data Collection (SeMet IMPDH)

| | |
|---|---|
| Oscillation Angle | 1° |
| Oscillation Range | 90° |
| Exposure time/degree | 5 sec |

| | Edge ($\lambda_2$) | Peak ($\lambda_3$) | Remote ($\lambda_1$) |
|---|---|---|---|
| Wavelength (Å) | 0.9793 | 0.9791 | 1.0781 |
| Resolution (Å) | 2.5 | 2.5 | 2.5 |
| Total observations | 283910 | 276365 | 272576 |
| Unique reflections | 20633 | 20627 | 20686 |
| Redundancy | 6.9 | 6.7 | 6.6 |
| Completeness | 99.7 | 99.7 | 99.6 |
| $R_{merge}$ (%) | 7.7 | 9.6 | 5.9 |

High Resolution Data Set

| | |
|---|---|
| Oscillation angle | 1° |
| Oscillation range | 90° |
| Exposure time/degree | 8 sec |
| Wavelength (Å) | 1.0332 |
| Resolution (Å) | 30–1.90 |
| Total observations | 263,355 |
| Unique reflections | 44,921 |
| Completeness (%) | 96.5 |
| $R_{merge}$ (%) | 6.8 |

TABLE 4

Summary of MLPHARE Phasing

| Resolution (Å) | Acentric | | | Centric | | | All | |
|---|---|---|---|---|---|---|---|---|
| | No | FOM[a] | Phasing[b] power | No | FOM | Phasing power | No | FOM |
| 7.27 | 631 | 0.56 | 1.71 | 231 | 0.51 | 1.71 | 862 | 0.55 |
| 5.71 | 759 | 0.79 | 3.35 | 167 | 0.71 | 3.03 | 926 | 0.78 |
| 4.71 | 1188 | 0.79 | 3.18 | 208 | 0.68 | 2.40 | 1396 | 0.77 |
| 4.00 | 1719 | 0.77 | 2.86 | 242 | 0.65 | 1.92 | 1961 | 0.76 |
| 3.48 | 2337 | 0.75 | 2.42 | 265 | 0.65 | 1.82 | 2602 | 0.74 |
| 3.08 | 3053 | 0.70 | 2.13 | 283 | 0.60 | 1.49 | 3336 | 0.69 |
| 2.76 | 3860 | 0.62 | 1.78 | 270 | 0.54 | 1.09 | 4130 | 0.61 |
| 2.5 | 4642 | 0.45 | 1.21 | 207 | 0.41 | 0.81 | 4849 | 0.45 |
| Total | 18189 | 0.64 | 2.02 | 1873 | 0.60 | 1.63 | 20062 | 0.64 |

[a]Figure of Merit is a measure of the relative reliability of a phase based on the consistency of the MIR analysis from one derivative to the next. The maximum value is 1.0.
[b]MAD phasing power is defined:
$\{(|F_{hl} - F_{hi}|^2)/\int P_{\lambda 1 \rightarrow \lambda i}(\phi)(||F_{\lambda l}|e^{i\phi} + F_{hi} - F_{hl}| - |F_{\lambda i}|)^2 \, d\phi\}^{1/2}$ computed for individual lack-of-closure expressions between the reflections of the reference wavelength $\lambda_l$, its Friedel mate, and the Bijvoet pairs measured at the other wavelengths ($F_{hi}$). $P_{\lambda 1 \otimes \lambda i}(\phi)$ is the corresponding phase probability distribution.

TABLE 5

Refinement Statistics from CNS and PROCHECK

| | |
|---|---|
| Resolution range (Å) | 6.0–1.90 |
| Reflections | 40,828 |
| σ cutoff | none |
| R-value[1] (%) | 23.2 |
| Free R-value[2] (%) | 26.1 (4095 reflections) |
| Completeness (%) | 88.6 |
| Number of nonhydrogen atoms | 3997 |
| Number of solvent molecules | 422 |
| Number of IMP | 1 |
| Luzzati coordinate error (5.0–1.9 Å) | 0.34 Å |
| $\sigma_A$-coordinate error (5.0–1.9 Å) | 0.30 Å |
| Bond length deviation | 0.0059 Å |
| Bond angle deviation | 1.3029° |
| Improper angle deviation | 0.745° |
| Dihedrals deviation | 21.702° |
| Average B-factor: | |
| Protein atoms | 37.5 Å² |
| Catalytic domain | 34.4 Å² |
| CBS dimer domain | 43.4 Å² |
| Solvent atoms | 50.1 Å² |
| Residues in core phi-psi regions | 91.2% |
| Residues in disallowed regions | 0.0% |

[1] $R\text{-value} = \dfrac{|F_{obs}| - \kappa|F_{calc}|}{|F_{obs}|}$

[2]Free R-value is the R-value obtained for a test set of reflections (10% of the diffraction data) not used during refinement or $\sigma_A$ calculations.

TABLE 7

| | |
|---|---|
| HEADER | DEHYDROGENASE    MAR. 29, 1999    1ZFJ |
| TITLE | INOSINE MONOPHOSPHATE DEHYDROGENASE (IMPDH; EC 1.1.1.205) |
| TITLE | 2 FROM *STREPTOCOCCUS PYOGENES* |
| COMPND | MOL_ID: 1; |
| COMPND | 2 MOLECULE: INOSINE MONOPHOSPHATE DEHYDROGENASE; |
| COMPND | 3 CHAIN: A; |
| COMPND | 4 FRAGMENT: CATALYTIC DOMAIN, CBS DOMAIN; |
| COMPND | 5 EC: 1.1.1.205; |
| COMPND | 6 ENGINEERED: YES; |
| COMPND | 7 BIOLOGICAL_UNIT: TETRAMER |
| SOURCE | MOL_ID: 1; |
| SOURCE | 2 ORGANISM_SCIENTIFIC: *STREPTOCOCCUS PYOGENES*; |
| SOURCE | 3 EXPRESSION_SYSTEM: *STREPTOCOCCUS PYOGENES*; |
| SOURCE | 4 EXPRESSION_SYSTEM_STRAIN: *ESCHERICHIA COLI* |
| KEYWDS | IMPDH, DEHYDROGENASE, CBS DOMAINS |
| EXPDTA | X-RAY DIFFRACTION |
| AUTHOR | R. ZHANG, G. EVANS, F. J. ROTELLA, E. M. WESTBROOK, D. BENO, E. HUBERMAN, |
| AUTHOR | 2 A. JOACHIMIAK, F. R. COLLART |

TABLE 7-continued

| | | |
|---|---|---|
| JRNL | AUTH | R. ZHANG, G. EVANS, F. J. ROTELLA, E. M. WESTBROOK, D. BENO, |
| JRNL | AUTH | 2 E. HUBERMAN, A. JOACHIMIAK, F. R. COLLART |
| JRNL | TITL | CHARACTERISTICS AND CRYSTAL STRUCTURE OF BACTERIAL |
| JRNL | TITL | 2 IMP DEHYDROGENASE |
| JRNL | REF | TO BE PUBLISHED |
| JRNL | REFN | 0353 |
| REMARK | 1 | |
| REMAKK | 2 | |
| REMARK | 2 | RESOLUTION. 1.90 ANGSTROMS. |
| REMARK | 3 | |
| REMARK | 3 | REFINEMENT. |
| REMARK | 3 | PROGRAM : CNS 0.3 |
| REMARK | 3 | AUTHORS : BRUNGER, ADAMS, CLORE, DELANO, GROS, GROSSE- |
| REMARK | 3 | : KUNSTLEVE, JIANG, KUSZEWSKI, NILGES, PANNU, |
| REMARK | 3 | : READ, RICE, SIMONSON, WARREN |
| REMARK | 3 | |
| REMARK | 3 | REFINEMENT TARGET : NULL |
| REMARK | 3 | |
| REMARK | 3 | DATA USED IN REFINEMENT. |
| REMARK | 3 | RESOLUTION RANGE HIGH (ANGSTROMS) : 1.9 |
| REMARK | 3 | RESOLUTION RANGE LOW (ANGSTROMS) : 6.0 |
| REMARK | 3 | DATA CUTOFF (SIGMA(F)) : 0.0 |
| REMARK | 3 | OUTLIER CUTOFF HIGH (RMS(ABS(F))) : 986591.3 |
| REMARK | 3 | COMPLETENESS (WORKING + TEST) (%) : 88.2 |
| REMARK | 3 | NUMBER OF REFLECTIONS : 39729 |
| REMARK | 3 | |
| REMARK | 3 | |
| REMARK | 3 | FIT TO DATA USED IN REFINEMENT. |
| REMARK | 3 | CROSS-VALIDATION METHOD : THROUGHOUT |
| REMARK | 3 | FREE R VALUE TEST SET SELECTION : RANDOM |
| REMARK | 3 | R VALUE (WORKING SET) : 0.232 |
| REMARK | 3 | FREE R VALUE : 0.263 |
| REMARK | 3 | FREE R VALUE TEST SET SIZE (%) : 10.0 |
| REMARK | 3 | FREE R VALUE TEST SET COUNT : 3980 |
| REMARK | 3 | ESTIMATED ERROR OF FREE R VALUE : 0.004 |
| REMARK | 3 | |
| REMARK | 3 | FIT IN THE HIGHEST RESOLUTION BIN. |
| REMARK | 3 | TOTAL NUMBER OF BINS USED : 6 |
| REMARK | 3 | BIN RESOLUTION RANGE HIGH (A) : 1.9 |
| REMARK | 3 | BIN RESOLUTION RANGE LOW (A) : 2.01 |
| REMARK | 3 | BIN COMPLETENESS (WORKING + TEST) (%) : 70.8 |
| REMARK | 3 | REFLECTIONS IN BIN (WORKING SET) : 4706 |
| REMARK | 3 | BIN R VALUE (WORKING SET) : 0.357 |
| REMARK | 3 | BIN FREE R VALUE : 0.368 |
| REMARK | 3 | BIN FREE R VALUE TEST SET SIZE (%) : 10.2 |
| REMARK | 3 | BIN FREE R VALUE TEST SET COUNT : 534 |
| REMARK | 3 | ESTIMATED ERROR OF BIN FREE R VALUE : 0.02 |
| REMARK | 3 | |
| REMARK | 3 | NUMBER OF NON-HYDROGEN ATOMS USED IN REFINEMENT. |
| REMARK | 3 | PROTEIN ATOMS : 3544 |
| REMARK | 3 | NUCLEIC ACID ATOMS : 0 |
| REMARK | 3 | HETEROGEN ATOMS : 23 |
| REMARK | 3 | SOLVENT ATOMS : 499 |
| REMARK | 3 | |
| REMARK | 3 | B VALUES. |
| REMARK | 3 | FROM WILSON PLOT (A**2) : 21.9 |
| REMARK | 3 | MEAN B VALUE (OVERALL, A**2) : NULL |
| REMARK | 3 | OVERALL ANISOTROPIC B VALUE. |
| REMARK | 3 | B11 (A**2) : 9.84 |
| REMARK | 3 | B22 (A**2) : 9.84 |
| REMARK | 3 | B33 (A**2) : −19.7 |
| REMARK | 3 | B12 (A**2) : 0.0 |
| REMARK | 3 | B13 (A**2) : 0.0 |
| REMARK | 3 | B23 (A**2) : 0.0 |
| REMARK | 3 | |
| REMARK | 3 | ESTIMATED COORDINATE ERROR. |
| REMARK | 3 | ESD FROM LUZZATI PLOT (A) : 0.29 |
| REMARK | 3 | ESD FROM SIGMAA (A) : 0.33 |
| REMARK | 3 | LOW RESOLUTION CUTOFF (A) : 5.0 |
| REMARK | 3 | |
| REMARK | 3 | CROSS-VALIDATED ESTIMATED COORDINATE ERROR. |
| REMARK | 3 | ESD FROM C-V LUZZATI PLOT (A) : 0.32 |
| REMARK | 3 | ESD FROM C-V SIGMAA (A) : 0.37 |
| REMARK | 3 | |
| REMARK | 3 | RMS DEVIATIONS FROM IDEAL VALUES. |
| REMARK | 3 | BOND LENGTHS (A) : 0.018 |
| REMARK | 3 | BOND ANGLES (DEGREES) : 2.2 |
| REMARK | 3 | DIHEDRAL ANGLES (DEGREES) : 21.8 |
| REMARK | 3 | IMPROPER ANGLES (DEGREES) : 2.37 |

TABLE 7-continued

| REMARK | 3 | | | | | |
|---|---|---|---|---|---|---|
| REMARK | 3 | ISOTROPIC THERMAL MODEL : RESTRAINED | | | | |
| REMARK | 3 | | | | | |
| REMARK | 3 | ISOTROPIC THERMAL FACTOR RESTRAINTS. | | | RMS | SIGMA |
| REMARK | 3 | MAIN-CHAIN BOND | (A**2) : | 1.21 ; | 1.5 | |
| REMARK | 3 | MAIN-CHAIN ANGLE | (A**2) : | 1.92 ; | 2.0 | |
| REMARK | 3 | SIDE-CHAIN BOND | (A**2) : | 1.98 ; | 2.0 | |
| REMARK | 3 | SIDE-CHAIN ANGLE | (A**2) : | 3.02 ; | 2.5 | |
| REMARK | 3 | | | | | |
| REMARK | 3 | | | | | |
| REMARK | 3 | BULK SOLVENT MODELING. | | | | |
| REMARK | 3 | METHOD USED : NULL | | | | |
| REMARK | 3 | KSOL : NULL | | | | |
| REMARK | 3 | BSOL : NULL | | | | |
| REMARK | 3 | | | | | |
| REMARK | 3 | NCS MODEL : NULL | | | | |
| REMARK | 3 | | | | | |
| REMARK | 3 | NCS RESTRAINTS. | | RMS | SIGMA/WEIGHT | |
| REMARK | 3 | GROUP 1 POSITIONAL | (A) : NULL ; NULL | | | |
| REMARK | 3 | GROUP 1 B-FACTOR | (A**2) : NULL ; NULL | | | |
| REMARK | 3 | | | | | |
| REMARK | 3 | PARAMETER FILE 1 : PROTEIN_REP.PARAM | | | | |
| REMARK | 3 | PARAMETER FILE 2 : WATER_REP.PARAM | | | | |
| REMARK | 3 | PARAMETER FILE 3 : IMP.PAR | | | | |
| REMARK | 3 | TOPOLOGY FILE 1 : PROTEIN.TOP | | | | |
| REMARK | 3 | TOPOLOGY FILE 2 : WATER.TOP | | | | |
| REMARK | 3 | TOPOLOGY FILE 3 : IMP.TOP | | | | |
| REMARK | 3 | | | | | |
| REMARK | 3 | OTHER REFINEMENT REMARKS: BULK SOLVENT MODEL USED | | | | |
| REMARK | 4 | | | | | |
| REMARK | 4 | 1ZFJ COMPLIES WITH FORMAT V. 2.3, JUL. 9, 1998 | | | | |
| REMARK | 7 | | | | | |
| REMARK | 7 | S. PYOGENES IMPDH IS A TETRAMER WITH ITS FOUR SUBUNITS | | | | |
| REMARK | 7 | RELATED BY A CRYSTALLOGRAPHIC FOURFOLD AXIS. EACH MONOMER | | | | |
| REMARK | 7 | HAS A TWO-DOMAIN STRUCTURE: A CATALYTIC DOMAIN | | | | |
| REMARK | 7 | (AMINO ACID RESIDUES 2–92 AND 224–492) FORMING THE INTERIOR | | | | |
| REMARK | 7 | CORE OF THE ACTIVE TETRAMERIC ENZYME AND A CBS DIMER DOMAIN | | | | |
| REMARK | 7 | (RESIDUES 93–223) PROJECTING OUTWARD FROM THE CORNERS OF | | | | |
| REMARK | 7 | THE SQUARE. THE CBS DESIGNATION ARISES FROM THE ORIGINAL | | | | |
| REMARK | 7 | IDENTIFICATION OF THIS FOLDING MOTIF IN THE ENZYME | | | | |
| REMARK | 7 | CYSTATHIONINE-"BETA"-SYNTASE [BATEMAN, A. (1997) TRENDS | | | | |
| REMARK | 7 | BIOCHEM. SCI. 22, 12–13]. THE CBS DIMER DOMAIN, FOUND IN | | | | |
| REMARK | 7 | IMPDH PROTEINS FROM ALL THREE KINGDOMS, IS COMPOSED OF TWO | | | | |
| REMARK | 7 | CBS MOTIFS RELATED BY APPROXIMATE TWOFOLD SYMMETRY (RMS | | | | |
| REMARK | 7 | DEVIATIONS BETWEEN ALPHA CARBON ATOMS: 2.7 ANGSTROMS). | | | | |
| REMARK | 7 | EACH CBS MOTIF HAS THE CHARACTERISTIC | | | | |
| REMARK | 7 | SHEET/HELIX/SHEET/SHEET/HELIX TOPOLOGY. THIS IS THE FIRST | | | | |
| REMARK | 7 | REPORTED COMPLETE STRUCTURE OF A CBS DIMER DOMAIN, A | | | | |
| REMARK | 7 | FOLDING MOTIF PROPOSED TO ACT AS A REGULATORY ELEMENT | | | | |
| REMARK | 7 | SINCE MUTATIONS LEAD TO THE HUMAN DISEASE HOMOCYSTINURIA. | | | | |
| REMARK | 7 | EACH IPMDH MONOMER CONTAINS IMP IN THE CATALYTIC SITE. | | | | |
| REMARK | 7 | THIS SUBSTRATE IS NOT COVALENTLY BOUND TO THE ACTIVE SITE | | | | |
| REMARK | 7 | CYS310 SUGGESTING THAT IMP DOES NOT FORM A COVALENT BOND | | | | |
| REMARK | 7 | IN THE ABSENCE OF NAD. | | | | |
| REMARK | 100 | | | | | |
| REMARK | 100 | THIS ENTRY HAS BEEN PROCESSED BY RCSB ON MAR. 30, 1999. | | | | |
| REMARK | 100 | THE RCSB ID CODE IS RCSB000749. | | | | |
| REMARK | 200 | | | | | |
| REMARK | 200 | EXPERIMENTAL DETAILS | | | | |
| REMARK | 200 | EXPERIMENT TYPE | | : X-RAY DIFFRACTION | | |
| REMARK | 200 | DATE OF DATA COLLECTION | | : NULL | | |
| REMARK | 200 | TEMPERATURE | (KELVIN) | : 110.0 | | |
| REMARK | 200 | PH | | : 7.2 | | |
| REMARK | 200 | NUMBER OF CRYSTALS USED | | : 1 | | |
| REMARK | 200 | | | | | |
| REMARK | 200 | SYNCHROTRON | (Y/N) | : Y | | |
| REMARK | 200 | RADIATION SOURCE | | : APS | | |
| REMARK | 200 | BEAMLINE | | : 19ID | | |
| REMARK | 200 | X-RAY GENERATOR MODEL | | : NULL | | |
| REMARK | 200 | MONOCHROMATIC OR LAUE | (M/L) | : M | | |
| REMARK | 200 | WAVELENGTH OR RANGE | (A) | : 0.9791, 1.0781 | | |
| REMARK | 200 | MONOCHROMATOR | | : SI (111) | | |
| REMARK | 200 | OPTICS | | : MIRROR | | |
| REMARK | 200 | | | | | |
| REMARK | 200 | DETECTOR TYPE | | : CCD | | |
| REMARK | 200 | DETECTOR MANUFACTURER | | : ANL (SBC1) 3X3 MOSAI | | |
| REMARK | 200 | INTENSITY-INTEGRATION SOFTWARE | | : DENZO (HKL2000) | | |
| REMARK | 200 | DATA SCALING SOFTWARE | | : SCALEPACK (HKL2000) | | |
| REMARK | 200 | | | | | |

TABLE 7-continued

| | | | | | | |
|---|---|---|---|---|---|---|
| REMARK | 200 | NUMBER OF UNIQUE REFLECTIONS | | : 44921 | | |
| REMARK | 200 | RESOLUTION RANGE HIGH | (A) | : 1.9 | | |
| REMARK | 200 | RESOLUTION RANGE LOW | (A) | : 40.0 | | |
| REMARK | 200 | REJECTION CRITERIA | (SIGMA(I)) | : 0.0 | | |
| REMARK | 200 | | | | | |
| REMARK | 200 | OVERALL. | | | | |
| REMARK | 200 | COMPLETENESS FOR RANGE | (%) | : 96.5 | | |
| REMARK | 200 | DATA REDUNDANCY | | : 6.2 | | |
| REMARK | 200 | R MERGE | (I) | : 0.068 | | |
| REMARK | 200 | R SYM | (I) | : NULL | | |
| REMARK | 200 | <I/SIGMA(I)> FOR THE DATA SET | | : 6.0 | | |
| REMARK | 200 | | | | | |
| REMARK | 200 | IN THE HIGHEST RESOLUTION SHELL. | | | | |
| REMARK | 200 | HIGHEST RESOLUTION SHELL, RANGE HIGH | (A) | : 1.9 | | |
| REMARK | 200 | HIGHEST RESOLUTION SHELL, RANGE LOW | (A) | : 1.97 | | |
| REMARK | 200 | COMPLETENESS FOR SHELL | (%) | : 87.6 | | |
| REMARK | 200 | DATA REDUNDANCY IN SHELL | | : 3.0 | | |
| REMARK | 200 | R MERGE FOR SHELL | (I) | : 0.319 | | |
| REMARK | 200 | R SYM FOR SHELL | (I) | : NULL | | |
| REMARK | 200 | <I/SIGMA(I)> FOR SHELL | | : 2.5 | | |
| REMARK | 200 | | | | | |
| REMARK | 200 | DIFFRACTION PROTOCOL: MAD | | | | |
| REMARK | 200 | METHOD USED TO DETERMINE THE STRUCTURE: MAD | | | | |
| REMARK | 200 | SOFTWARE USED: CNS, CCP4 | | | | |
| REMARK | 200 | STARTING MODEL: NULL | | | | |
| REMARK | 200 | | | | | |
| REMARK | 200 | REMARK: NULL | | | | |
| REMARK | 280 | | | | | |
| REMARK | 280 | CRYSTAL | | | | |
| REMARK | 280 | SOLVENT CONTENT, VS (%): 49.0 | | | | |
| REMARK | 280 | MATTHEWS COEFFICIENT, VM (ANGSTROMS**3/DA): NULL | | | | |
| REMARK | 280 | | | | | |
| REMARK | 280 | CRYSTALLIZATION CONDITIONS: 0.1 M MES (PH 7.2), 1.8 M | | | | |
| REMARK | 280 | AMMONIUIM SULFATE, 10 MM COCL2 | | | | |
| REMARK | 290 | | | | | |
| REMARK | 290 | CRYSTALLOGRAPHIC SYMMETRY | | | | |
| REMARK | 290 | SYMMETRY OPERATORS FOR SPACE GROUP: I 4 2 2 | | | | |
| REMARK | 290 | | | | | |
| REMARK | 290 | SYMOP | SYMMETRY | | | |
| REMARK | 290 | NNNMMM | OPERATOR | | | |
| REMARK | 290 | 1555 | X, Y, Z | | | |
| REMARK | 290 | 2555 | −X, −Y, Z | | | |
| REMARK | 290 | 3555 | −Y, X, Z | | | |
| REMARK | 290 | 4555 | Y, −X, Z | | | |
| REMARK | 290 | 5555 | −X, Y, −Z | | | |
| REMARK | 290 | 6555 | X, −Y, −Z | | | |
| REMARK | 290 | 7555 | Y, X, −Z | | | |
| REMARK | 290 | 8555 | −Y, −X, −Z | | | |
| REMARK | 290 | 9555 | 1/2+X, 1/2+Y, 1/2+Z | | | |
| REMARK | 290 | 10555 | 1/2−X, 1/2−Y, 1/2+Z | | | |
| REMARK | 290 | 11555 | 1/2−Y, 1/2+X, 1/2+Z | | | |
| REMARK | 290 | 12555 | 1/2+Y, 1/2−X, 1/2+Z | | | |
| REMARK | 290 | 13555 | 1/2−X, 1/2+Y, 1/2−Z | | | |
| REMARK | 290 | 14555 | 1/2+X, 1/2−Y, 1/2−Z | | | |
| REMARK | 290 | 15555 | 1/2+Y, 1/2+X, 1/2−Z | | | |
| REMARK | 290 | 16555 | 1/2−Y, 1/2−X, 1/2−Z | | | |
| REMARK | 290 | | | | | |
| REMARK | 290 | WHERE NNN -> OPERATOR NUMBER | | | | |
| REMARK | 290 | MMM -> TRANSLATION VECTOR | | | | |
| REMARK | 290 | | | | | |
| REMARK | 290 | CRYSTALLOGRAPHIC SYMMETRY TRANSFORMATIONS | | | | |
| REMARK | 290 | THE FOLLOWING TRANSFORMATIONS OPERATE ON THE ATOM/HETATM | | | | |
| REMARK | 290 | RECORDS IN THIS ENTRY TO PRODUCE CRYSTALLOGRAPHICALLY | | | | |
| REMARK | 290 | RELATED MOLECULES. | | | | |
| REMARK | 290 | SMTRY1 | 1 | 1.000000 | 0.000000 | 0.000000 | 0.00000 |
| REMARK | 290 | SMTRY2 | 1 | 0.000000 | 1.000000 | 0.000000 | 0.00000 |
| REMARK | 290 | SMTRY3 | 1 | 0.000000 | 0.000000 | 1.000000 | 0.00000 |
| REMARK | 290 | SMTRY1 | 2 | −1.000000 | 0.000000 | 0.000000 | 0.00000 |
| REMARK | 290 | SMTRY2 | 2 | 0.000000 | −1.000000 | 0.000000 | 0.00000 |
| REMARK | 290 | SMTRY3 | 2 | 0.000000 | 0.000000 | 1.000000 | 0.00000 |
| REMARK | 290 | SMTRY1 | 3 | 0.000000 | −1.000000 | 0.000000 | 0.00000 |
| REMARK | 290 | SMTRY2 | 3 | 1.000000 | 0.000000 | 0.000000 | 0.00000 |
| REMARK | 290 | SMTRY3 | 3 | 0.000000 | 0.000000 | 1.000000 | 0.00000 |
| REMARK | 290 | SMTRY1 | 4 | 0.000000 | 1.000000 | 0.000000 | 0.00000 |
| REMARK | 290 | SMTRY2 | 4 | −1.000000 | 0.000000 | 0.000000 | 0.00000 |
| REMARK | 290 | SMTRY3 | 4 | 0.000000 | 0.000000 | 1.000000 | 0.00000 |
| REMARK | 290 | SMTRY1 | 5 | −1.000000 | 0.000000 | 0.000000 | 0.00000 |
| REMARK | 290 | SMTRY2 | 5 | 0.000000 | 1.000000 | 0.000000 | 0.00000 |
| REMARK | 290 | SMTRY3 | 5 | 0.000000 | 0.000000 | −1.000000 | 0.00000 |

TABLE 7-continued

| | | | | | | | |
|---|---|---|---|---|---|---|---|
| REMARK | 290 | SMTRY1 | 6 | 1.000000 | 0.000000 | 0.000000 | 0.00000 |
| REMARK | 290 | SMTRY2 | 6 | 0.000000 | −1.000000 | 0.000000 | 0.00000 |
| REMARK | 290 | SMTRY3 | 6 | 0.000000 | 0.000000 | −1.000000 | 0.00000 |
| REMARK | 290 | SMTRY1 | 7 | 0.000000 | 1.000000 | 0.000000 | 0.00000 |
| REMARK | 290 | SMTRY2 | 7 | 1.000000 | 0.000000 | 0.000000 | 0.00000 |
| REMARK | 290 | SMTRY3 | 7 | 0.000000 | 0.000000 | −1.000000 | 0.00000 |
| REMARK | 290 | SMTRY1 | 8 | 0.000000 | −1.000000 | 0.000000 | 0.00000 |
| REMARK | 290 | SMTRY2 | 8 | −1.000000 | 0.000000 | 0.000000 | 0.00000 |
| REMARK | 290 | SMTRY3 | 8 | 0.000000 | 0.000000 | −1.000000 | 0.00000 |
| REMARK | 290 | SMTRY1 | 9 | 1.000000 | 0.000000 | 0.000000 | 75.74000 |
| REMARK | 290 | SMTRY2 | 9 | 0.000000 | 1.000000 | 0.000000 | 75.74000 |
| REMARK | 290 | SMTRY3 | 9 | 0.000000 | 0.000000 | 1.000000 | 50.84000 |
| REMARK | 290 | SMTRY1 | 10 | −1.000000 | 0.000000 | 0.000000 | 75.74000 |
| REMARK | 290 | SMTRY2 | 10 | 0.000000 | −1.000000 | 0.000000 | 75.74000 |
| REMARK | 290 | SMTRY3 | 10 | 0.000000 | 0.000000 | 1.000000 | 50.84000 |
| REMARK | 290 | SMTRY1 | 11 | 0.000000 | −1.000000 | 0.000000 | 75.74000 |
| REMARK | 290 | SMTRY2 | 11 | 1.000000 | 0.000000 | 0.000000 | 75.74000 |
| REMARK | 290 | SMTRY3 | 11 | 0.000000 | 0.000000 | 1.000000 | 50.84000 |
| REMARK | 290 | SMTRY1 | 12 | 0.000000 | 1.000000 | 0.000000 | 75.74000 |
| REMARK | 290 | SMTRY2 | 12 | −1.000000 | 0.000000 | 0.000000 | 75.74000 |
| REMARK | 290 | SMTRY3 | 12 | 0.000000 | 0.000000 | 1.000000 | 50.84000 |
| REMARK | 290 | SMTRY1 | 13 | −1.000000 | 0.000000 | 0.000000 | 75.74000 |
| REMARK | 290 | SMTRY2 | 13 | 0.000000 | 1.000000 | 0.000000 | 75.74000 |
| REMARK | 290 | SMTRY3 | 13 | 0.000000 | 0.0DO000 | −1.000000 | 50.84000 |
| REMARK | 290 | SMTRY1 | 14 | 1.000000 | 0.000000 | 0.000000 | 75.74000 |
| REMARK | 290 | SMTRY2 | 14 | 0.000000 | −1.000000 | 0.000000 | 75.74000 |
| REMARK | 290 | SMTRY3 | 14 | 0.000000 | 0.000000 | −1.000000 | 50.84000 |
| REMARK | 290 | SMTRY1 | 15 | 0.000000 | 1.000000 | 0.000000 | 75.74000 |
| REMARK | 290 | SMTRY2 | 15 | 1.000000 | 0.000000 | 0.000000 | 75.74000 |
| REMARK | 290 | SMTRY3 | 15 | 0.000000 | 0.000000 | −1.000000 | 50.84000 |
| REMARK | 290 | SMTRY1 | 16 | 0.000000 | −1.000000 | 0.000000 | 75.74000 |
| REMARK | 290 | SMTRY2 | 16 | −1.000000 | 0.000000 | 0.000000 | 75.74000 |
| REMARK | 290 | SMTRY3 | 16 | 0.000000 | 0.000000 | −1.000000 | 50.84000 |

```
REMARK   290
REMARK   290 REMARK: NULL
REMARK   470
REMARK   470 MISSING ATOM
REMARK   470 THE FOLLOWING RESIDUES HAVE MISSING ATOMS (M = MODEL NUMBER;
REMARK   470 RES = RESIDUE NAME; C = CHAIN IDENTIFIER; SSEQ = SEQUENCE NUMBER;
REMARK   470 I = INSERTION CODE):
REMARK   470   M RES CSSEQI   ATOMS
REMARK   470     LYS A 109  CG    CD    CE    NZ
REMARK   470     GLU A 114  CG    CD    OE1   OE2
REMARK   470     ARG A 121  CG    CD    NE    CZ    NH1   NH2
REMARK   470     ARG A 143  CG    CD    NE    CZ    NH1   NH2
REMARK   470     LYS A 400  CG    CD    CE    NZ
REMARK   470     LYS A 401  CG    CD    CE    NZ
REMARK   470     ASN A 416  CG    OD1   ND2
REMARK   470     LYS A 417  CG    CD    CE    NZ
REMARK   470     LEU A 418  CG    CD1   CD2
REMARK   470     VAL A 492  CA    C     O     CB    CG1   CG2
REMARK   500
REMARK   500 GEOMETRY AND STEREOCHEMISTRY
REMARK   500 SUBTOPIC: CLOSE CONTACTS
REMARK   500
REMARK   500 THE FOLLOWING ATOMS THAT ARE RELATED BY CRYSTALLOGRAPHIC
REMARK   500 SYMMETRY ARE IN CLOSE CONTACT. AN ATOM LOCATED WITHIN 0.15
REMARK   500 ANGSTROMS OF A SYMMETRY RELATED ATOM IS ASSUMED TO BE ON A
REMARK   500 SPECIAL POSITION AND IS, THEREFORE, LISTED IN REMARK 375
REMARK   500 INSTEAD OF REMARK 500. ATOMS WITH NON-BLANK ALTERNATE
REMARK   500 LOCATION INDICATORS ARE NOT INCLUDED IN THE CALCULATIONS.
REMARK   500
REMARK   500 DISTANCE CUTOFF:
REMARK   500 2.2 ANGSTROMS FOR CONTACTS NOT INVOLVING HYDROGEN ATOMS
REMARK   500 1.6 ANGSTROMS FOR CONTACTS INVOLVING HYDROGEN ATOMS
REMARK   500
REMARK   500  ATM1   RES C   SSEQI   ATM2   RES C   SSEQI   SSYMOP   DISTANCE
REMARK   500   O     HOH     866     O      HOH     866     6565     2.10
REMARK   500
REMARK   500 GEOMETRY AND STEREOCHEMISTRY
REMARK   500 SUBTOPIC: CLOSE CONTACTS IN SAME ASYMMETRIC UNIT
REMARK   500
REMARK   500 THE FOLLOWING ATOMS ARE IN CLOSE CONTACT.
REMARK   500
REMARK   500  ATM1   RES C   SSEQI  ATM2    RES C   SSEQI
REMARK   500   O     HOH     676    O       HOH     508    1.73
REMARK   500   O     HOH     641    OD1     ASN A   275    2.10
REMARK   500
REMARK   500 GEOMETRY AND STEREOCHEMISTRY
```

TABLE 7-continued

```
REMARK   500  SUBTOPIC: COVALENT BOND ANGLES
REMARK   500
REMARK   500  THE STEREOCHEMICAL PARAMETERS OF THE FOLLOWING RESIDUES
REMARK   500  HAVE VALUES WHICH DEVIATE FROM EXPECTED VALUES BY MORE
REMARK   500  THAN 4*RMSD (M = MODEL NUMBER; RES = RESIDUE NAME; C = CHAIN
REMARK   500  IDENTIFIER; SSEQ = SEQUENCE NUMBER; I = INSERTION CODE).
REMARK   500
REMARK   500  STANDARD TABLE:
REMARK   500  FORMAT: (10X, I3, 1X, A3, 1X, A1, I4, A1, 3 (1X, A4, 2X), 12X, F5.1)
REMARK   500
REMARK   500  EXPECTED VALUES: ENGH AND HUBER, 1991
REMARK   500
REMARK   500     M RES CSSEQI    ATM1      ATM2      ATM3
REMARK   500       PHE  A      8 N    - CA    - C      ANGL. DEV. =   -6.3 DEGREES
REMARK   500       THR  A     14 N    - CA    - C      ANGL. DEV. =   -7.3 DEGREES
REMARK   500       ASP  A     16 N    - CA    - C      ANGL. DEV. =    5.5 DEGREES
REMARK   500       VAL  A     18 N    - CA    - C      ANGL. DEV. =    6.1 DEGREES
REMARK   500       PRO  A     22 CB   - CG    - CD     ANGL. DEV. =   -6.5 DEGREES
REMARK   500       PRO  A     29 CB   - CG    - CD     ANGL. DEV. =   -7.0 DEGREES
REMARK   500       LEU  A     42 N    - CA    - C      ANGL. DEV. =    6.8 DEGREES
REMARK   500       ILE  A     46 N    - CA    - C      ANGL. DEV. =   -6.8 DEGREES
REMARK   500       PRO  A     47 CB   - CG    - CD     ANGL. DEV. =   -6.7 DEGREES
REMARK   500       THR  A     57 N    - CA    - C      ANGL. DEV. =   10.1 DEGREES
REMARK   500       GLY  A     58 N    - CA    - C      ANGL. DEV. =  -10.6 DEGREES
REMARK   500       GLU  A     86 N    - CA    - C      ANGL. DEV. =   -5.8 DEGREES
REMARK   500       ASN  A     95 N    - CA    - C      ANGL. DEV. =   -6.1 DEGREES
REMARK   500       ILE  A     99 N    - CA    - C      ANGL. DEV. =   -6.4 DEGREES
REMARK   500       PRO  A    101 CB   - CG    - CD     ANGL. DEV. =   -6.8 DEGREES
REMARK   500       PHE  A    102 N    - CA    - C      ANGL. DEV. =   -7.3 DEGREES
REMARK   500       PRO  A    106 CB   - CG    - CD     ANGL. DEV. =   -7.2 DEGREES
REMARK   500       LEU  A    116 CA   - CB    - CG     ANGL. DEV. =    6.4 DEGREES
REMARK   500       PRO  A    126 CB   - CG    - CD     ANGL. DEV. =   -6.9 DEGREES
REMARK   500       LYS  A    135 N    - CA    - C      ANGL. DEV. =   -6.0 DEGREES
REMARK   500       PRO  A    154 CB   - CG    - CD     ANGL. DEV. =   -7.5 DEGREES
REMARK   500       HIS  A    158 N    - CA    - C      ANGL. DEV. =   -7.0 DEGREES
REMARK   500       GLU  A    162 N    - CA    - C      ANGL. DEV. =   -5.6 DEGREES
REMARK   500       HIS  A    163 N    - CA    - C      ANGL. DEV. =   -5.8 DEGREES
REMARK   500       THR  A    171 N    - CA    - C      ANGL. DEV. =   -6.1 DEGREES
REMARK   500       PRO  A    189 CB   - CG    - CD     ANGL. DEV. =   -7.2 DEGREES
REMARK   500       PRO  A    213 N    - CA    - C      ANGL. DEV. =    6.3 DEGREES
REMARK   500       PRO  A    213 CB   - CG    - CD     ANGL. DEV. =   -7.9 DEGREES
REMARK   500       ALA  A    216 N    - CA    - C      ANGL. DEV. =   -6.8 DEGREES
REMARK   500       VAL  A    229 N    - CA    - C      ANGL. DEV. =   -7.0 DEGREES
REMARK   500       ILE  A    252 N    - CA    - C      ANGL. DEV. =   -8.2 DEGREES
REMARK   500       PRO  A    274 N    - CA    - C      ANGL. DEV. =    6.7 DEGREES
REMARK   500       PRO  A    274 CB   - CG    - CD     ANGL. DEV. =   -7.9 DEGREES
REMARK   500       ILE  A    279 N    - CA    - C      ANGL. DEV. =   -9.5 DEGREES
REMARK   500       ALA  A    280 N    - CA    - C      ANGL. DEV. =    7.8 DEGREES
REMARK   500       GLY  A    281 N    - CA    - C      ANGL. DEV. =    6.4 DEGREES
REMARK   500       GLY  A    281 C    - N     - CA     ANGL. DEV. =    6.2 DEGREES
REMARK   500       ASN  A    282 N    - CA    - C      ANGL. DEV. =    6.9 DEGREES
REMARK   500       ILE  A    283 N    - CA    - C      ANGL. DEV. =   -6.3 DEGREES
REMARK   500       GLY  A    305 N    - CA    - C      ANGL. DEV. =    9.1 DEGREES
REMARK   500       PRO  A    306 N    - CA    - C      ANGL. DEV. =    6.5 DEGREES
REMARK   500       PRO  A    306 CB   - CG    - CD     ANGL. DEV. =   -6.4 DEGREES
REMARK   500       PRO  A    321 CB   - CG    - CD     ANGL. DEV. =   -7.5 DEGREES
REMARK   500       GLN  A    322 N    - CA    - C      ANGL. DEV. =    9.4 DEGREES
REMARK   500       THR  A    339 N    - CA    - C      ANGL. DEV. =    8.8 DEGREES
REMARK   500       ILE  A    341 N    - CA    - C      ANGL. DEV. =   -5.8 DEGREES
REMARK   500       ALA  A    342 N    - CA    - C      ANGL. DEV. =   -6.2 DEGREES
REMARK   500       ASP  A    343 N    - CA    - C      ANGL. DEV. =    5.8 DEGREES
REMARK   500       GLY  A    344 N    - CA    - C      ANGL. DEV. =    9.5 DEGREES
REMARK   500       ALA  A    370 N    - CA    - C      ANGL. DEV. =   11.1 DEGREES
REMARK   500       GLU  A    374 N    - CA    - C      ANGL. DEV. =    6.6 DEGREES
REMARK   500       PRO  A    376 CB   - CG    - CD     ANGL. DEV. =   -7.0 DEGREES
REMARK   500       LYS  A    388 N    - CA    - C      ANGL. DEV. =   -5.8 DEGREES
REMARK   500       TYR  A    390 N    - CA    - C      ANGL. DEV. =   -7.0 DEGREES
REMARK   500       PRO  A    420 CB   - CG    - CD     ANGL. DEV. =   -7.1 DEGREES
REMARK   500       GLU  A    461 N    - CA    - C      ANGL. DEV. =    7.6 DEGREES
REMARK   500       ASN  A    462 N    - CA    - C      ANGL. DEV. =    8.8 DEGREES
REMARK   500       VAL  A    466 N    - CA    - C      ANGL. DEV. =   -9.7 DEGREES
REMARK   500       PRO  A    478 N    - CA    - C      ANGL. DEV. =   -5.6 DEGREES
REMARK   500       PRO  A    478 CB   - CG    - CD     ANGL. DEV. =   -7.4 DEGREES
REKARK   500       PRO  A    488 CB   - CG    - CD     ANGL. DEV. =   -7.9 DEGREES
REMARK   500
REMARK   500  GEOMETRY AND STEREOCHEMISTRY
REMARK   500  SUBTOPIC: TORSION ANGLES
REMARK   500
REMARK   500  TORSION ANGLES OUTSIDE THE EXPECTED RAMACHANDRAN REGIONS:
```

TABLE 7-continued

```
REMARK   500 (M = MODEL NUMBER; RES = RESIDUE NAME; C = CHAIN IDENTIFIER;
REMARK   500 SSEQ = SEQUENCE NUMBER; I = INSERTION CODE).
REMARK   500 STANDARD TABLE:
REMARK   500 FORMAT: (10X, I3, 1X, A3, 1X, A1, I4, A1, 4X, F7.2, 3X, F7.2)
REMARK   500
REMARK   500 M RES CSSEQI     PSI      PHI
REMARK   500
REMARK   500     SER A 491    55.58   166.71
REMARK   525
REMARK   525 SOLVENT
REMARK   525 THE FOLLOWING SOLVENT MOLECULES LIE FARTHER THAN EXPECTED
REMARK   525 FROM THE PROTEIN OR NUCLEIC ACID MOLECULE AND MAY BE
REMARK   525 ASSOCIATED WITH A SYMMETRY RELATED MOLECULE (M = MODEL
REMARK   525 NUMBER; RES = RESIDUE NAME; C = CHAIN IDENTIFIER; SSEQ = SEQUENCE
REMARK   525 NUMBER; I = INSERTION CODE):
REMARK   525
REMARK   525 M  RES       CSSEQI
REMARK   525 0  HOH          639      DISTANCE = 8.02 ANGSTROMS
REMARK   525 0  HOH          730      DISTANCE = 6.58 ANGSTROMS
REMARK   525 0  HOH          861      DISTANCE = 5.23 ANGSTROMS
REMARK   525 0  HOH          971      DISTANCE = 5.97 ANGSTROMS
REMARK   525 0  HOH          983      DISTANCE = 6.42 ANGSTROMS
REMARK   525 0  HOH          999      DISTANCE = 6.03 ANGSTROMS
REMARK   525 0  HOH         1021      DISTANCE = 5.20 ANGSTROMS
REMARK   525 0  HOH         1079      DISTANCE = 5.11 ANGSTROMS
REMARK   525 0  HOH         1095      DISTANCE = 5.09 ANGSTROMS
REMARK   525 0  HOH         1136      DISTANCE = 6.40 ANGSTROMS
REMARK   525 0  HOH         1167      DISTANCE = 6.38 ANGSTROMS
REMARK   525 0  HOH         1173      DISTANCE = 5.10 ANGSTROMS
REMARK   525 0  HOH         1181      DISTANCE = 6.76 ANGSTROMS
REMARK   525 0  HOH         1190      DISTANCE = 5.68 ANGSTROMS
REMARK   525 0  HOH         1207      DISTANCE = 8.81 ANGSTROMS
REMARK   525 0  HOH         1216      DISTANCE = 7.22 ANGSTROMS
REMARK   525 0  HOH         1227      DISTANCE = 6.43 ANGSTROMS
REMARK   525 0  HOH         1282      DISTANCE = 7.10 ANGSTROMS
REMARK   525 0  HOH         1302      DISTANCE = 6.33 ANGSTROMS
REMARK   525 0  HOH         1309      DISTANCE = 5.01 ANGSTROMS
REMARK   525 0  HOH         1314      DISTANCE = 5.92 ANGSTROMS
REMARK   525 0  HOH         1316      DISTANCE = 5.40 ANGSTROMS
REMARK   525 0  HOH         1328      DISTANCE = 5.08 ANGSTROMS
REMARK   525 0  HOH         1350      DISTANCE = 6.15 ANGSTROMS
REMARK   525 0  HOH         1351      DISTANCE = 6.96 ANGSTROMS
REMARK   525 0  HOH         1352      DISTANCE = 7.28 ANGSTROMS
REMARK   800
REMARK   800 SITE
REMARK   800 SITE_IDENTIFIER: ASC
REMARK   800 SITE_DESCRIPTION:
REMARK   800 ACTIVE SITE CYSTEINE
REMARK   800
DBREF    1ZFJ A    2      491   SWS  P50099    IMDH_STRPY   2      491
SEQADV   1ZFJ TYR A  387        SWS  1ZFJ_A    PHE   387 CONFLICT
SEQADV   1ZFJ                   SWS  1ZFJ_A    GLY   402 GAP IN THE PDB ENTRY
SEQADV   1ZFJ                   SWS  1ZFJ_A    SER   403 GAP IN THE PDB ENTRY
SEQADV   1ZFJ                   SWS  1ZFJ_A    SER   404 GAP IN THE PDB ENTRY
SEQADV   1ZFJ                   SWS  1ZFJ_A    ASN   405 GAP IN THE PDB ENTRY
SEQADV   1ZFJ                   SWS  1ZFJ_A    ARG   406 GAP IN THE PDB ENTRY
SEQADV   1ZFJ                   SWS  1ZFJ_A    TYR   407 GAP IN THE PDB ENTRY
SEQADV   1ZFJ                   SWS  1ZFJ_A    PHE   408 GAP IN THE PDB ENTRY
SEQADV   1ZFJ                   SWS  1ZFJ_A    GLN   409 GAP IN THE PDB ENTRY
SEQADV   1ZFJ                   SWS  1ZFJ_A    GLY   410 GAP IN THE PDB ENTRY
SEQADV   1ZFJ                   SWS  1ZFJ_A    SER   411 GAP IN THE PDB ENTRY
SEQADV   1ZFJ                   SWS  1ZFJ_A    VAL   412 GAP IN THE PDB ENTRY
SEQADV   1ZFJ                   SWS  1ZFJ_A    ASN   413 GAP IN THE PDB ENTRY
SEQADV   1ZFJ                   SWS  1ZFJ_A    GLU   414 GAP IN THE PDB ENTRY
SEQADV   1ZFJ                   SWS  1ZFJ_A    ALA   415 GAP IN THE PDB ENTRY
SEQADV   1ZFJ MSE A   53        SWS  1ZFJ_A    MET    53 ENGINEERED
SEQADV   1ZFJ MSE A   61        SWS  1ZFJ_A    MET    61 ENGINEERED
SEQADV   1ZFJ MSE A   78        SWS  1ZFJ_A    MET    78 ENGINEERED
SEQADV   1ZFJ MSE A  117        SWS  1ZFJ_A    MET   117 ENGINEERED
SEQADV   1ZFJ MSE A  145        SWS  1ZFJ_A    MET   145 ENGINEERED
SEQADV   1ZFJ MSE A  159        SWS  1ZFJ_A    MET   159 ENGINEERED
SEQADV   1ZFJ MSE A  364        SWS  1ZFJ_A    MET   364 ENGINEERED
SEQADV   1ZFJ MSE A  368        SWS  1ZFJ_A    MET   368 ENGINEERED
SEQADV   1ZFJ MSE A  393        SWS  1ZFJ_A    MET   393 ENGINEERED
SEQADV   1ZFJ MSE A  399        SWS  1ZFJ_A    MET   399 ENGINEERED
SEQADV   1ZFJ MSE A  440        SWS  1ZFJ_A    MET   440 ENGINEERED
SEQADV   1ZFJ MSE A  448        SWS  1ZFJ_A    MET   448 ENGINEERED
SEQADV   1ZFJ MSE A  468        SWS  1ZFJ_A    MET   468 ENGINEERED
SEQRES      1 A  477  SER ASN TRP ASP THR LYS PHE LEU LYS LYS GLY TYR THR
```

TABLE 7-continued

| | | | | | | | | | | | | | | | |
|---|---|---|---|---|---|---|---|---|---|---|---|---|---|---|---|
| SEQRES | 2 | A | 477 | PHE | ASP | ASP | VAL | LEU | LEU | ILE | PRO | ALA | GLU | SER | HIS | VAL |
| SEQRES | 3 | A | 477 | LEU | PRO | ASN | GLU | VAL | ASP | LEU | LYS | THR | LYS | LEU | ALA | ASP |
| SEQRES | 4 | A | 477 | ASN | LEU | THR | LEU | ASN | ILE | PRO | ILE | ILE | THR | ALA | ALA | MSE |
| SEQRES | 5 | A | 477 | ASP | THR | VAL | THR | GLY | SER | LYS | MSE | ALA | ILE | ALA | ILE | ALA |
| SEQRES | 6 | A | 477 | ARG | ALA | GLY | GLY | LEU | GLY | VAL | ILE | HIS | LYS | ASN | MSE | SER |
| SEQRES | 7 | A | 477 | ILE | THR | GLU | GLN | ALA | GLU | GLU | VAL | ARG | LYS | VAL | LYS | ARG |
| SEQRES | 8 | A | 477 | SER | GLU | ASN | GLY | VAL | ILE | ILE | ASP | PRO | PHE | PHE | LEU | THR |
| SEQRES | 9 | A | 477 | PRO | GLU | HIS | LYS | VAL | SER | GLU | ALA | GLU | GLU | LEU | MSE | GLN |
| SEQRES | 10 | A | 477 | ARG | TYR | ARG | ILE | SER | GLY | VAL | PRO | ILE | VAL | GLU | THR | LEU |
| SEQRES | 11 | A | 477 | ALA | ASN | ARG | LYS | LEU | VAL | GLY | ILE | ILE | THR | ASN | ARG | ASP |
| SEQRES | 12 | A | 477 | MSE | ARG | PHE | ILE | SER | ASP | TYR | ASN | ALA | PRO | ILE | SER | GLU |
| SEQRES | 13 | A | 477 | HIS | MSE | THR | SER | GLU | HIS | LEU | VAL | THR | ALA | ALA | VAL | GLY |
| SEQRES | 14 | A | 477 | THR | ASP | LEU | GLU | THR | ALA | GLU | ARG | ILE | LEU | HIS | GLU | HIS |
| SEQRES | 15 | A | 477 | ARG | ILE | GLU | LYS | LEU | PRO | LEU | VAL | ASP | ASN | SER | GLY | ARG |
| SEQRES | 16 | A | 477 | LEU | SER | GLY | LEU | ILE | THR | ILE | LYS | ASP | ILE | GLU | LYS | VAL |
| SEQRES | 17 | A | 477 | ILE | GLU | PHE | PRO | HIS | ALA | ALA | LYS | ASP | GLY | PHE | GLY | ARG |
| SEQRES | 18 | A | 477 | LEU | LEU | VAL | ALA | ALA | ALA | VAL | GLY | VAL | THR | SER | ASP | THR |
| SEQRES | 19 | A | 477 | PHE | GLU | ARG | ALA | GLU | ALA | LEU | PHE | GLU | ALA | GLY | ALA | ASP |
| SEQRES | 20 | A | 477 | ALA | ILE | VAL | ILE | ASP | THR | ALA | HIS | GLY | HIS | SER | ALA | GLY |
| SEQRES | 21 | A | 477 | VAL | LEU | ARG | LYS | ILE | ALA | GLU | ILE | ARG | ALA | HIS | PHE | PRO |
| SEQRES | 22 | A | 477 | ASN | ARG | THR | LEU | ILE | ALA | GLY | ASN | ILE | ALA | THR | ALA | GLU |
| SEQRES | 23 | A | 477 | GLY | ALA | ARG | ALA | LEU | TYR | ASP | ALA | GLY | VAL | ASP | VAL | VAL |
| SEQRES | 24 | A | 477 | LYS | VAL | GLY | ILE | GLY | PRO | GLY | SER | ILE | CYS | THR | THR | ARG |
| SEQRES | 25 | A | 477 | VAL | VAL | ALA | GLY | VAL | GLY | VAL | PRO | GLN | VAL | THR | ALA | ILE |
| SEQRES | 26 | A | 477 | TYR | ASP | ALA | ALA | ALA | VAL | ALA | ARG | GLU | TYR | GLY | LYS | THR |
| SEQRES | 27 | A | 477 | ILE | ILE | ALA | ASP | GLY | GLY | ILE | LYS | TYR | SER | GLY | ASP | ILE |
| SEQRES | 28 | A | 477 | VAL | LYS | ALA | LEU | ALA | ALA | GLY | GLY | ASN | ALA | VAL | MSE | LEU |
| SEQRES | 29 | A | 477 | GLY | SER | MSE | PHE | ALA | GLY | THR | ASP | GLU | ALA | PRO | GLY | GLU |
| SEQRES | 30 | A | 477 | THR | GLU | ILE | TYR | GLN | GLY | ARG | LYS | TYR | LYS | THR | TYR | ARG |
| SEQRES | 31 | A | 477 | GLY | MSE | GLY | SER | ILE | ALA | ALA | MSE | LYS | LYS | ASN | LYS | LEU |
| SEQRES | 32 | A | 477 | VAL | PRO | GLU | GLY | ILE | GLU | GLY | ARG | VAL | ALA | TYR | LYS | GLY |
| SEQRES | 33 | A | 477 | ALA | ALA | SER | ASP | ILE | VAL | PHE | GLN | MSE | LEU | GLY | GLY | ILE |
| SEQRES | 34 | A | 477 | ARG | SER | GLY | MSE | GLY | TYR | VAL | GLY | ALA | GLU | ASP | ILE | GLN |
| SEQRES | 35 | A | 477 | GLU | LEU | HIS | GLU | ASN | ALA | GLN | PHE | VAL | GLU | MSE | SER | GLY |
| SEQRES | 36 | A | 477 | ALA | GLY | LEU | ILE | GLU | SER | HIS | PRO | HIS | ASP | VAL | GLN | ILE |
| SEQRES | 37 | A | 477 | THR | ASN | GLU | ALA | PRO | ASN | TYR | SER | VAL | (SEQ ID NO: 23) | | | |
| MODRES | 1ZFJ | MSE | A | 53 | MET | SELENOMETHIONINE | | | | | | | | | | |
| MODRES | 1ZFJ | MSE | A | 61 | MET | SELENOMETHIONINE | | | | | | | | | | |
| MODRES | 1ZFJ | MSE | A | 78 | MET | SELENOMETHIONINE | | | | | | | | | | |
| MODRES | 1ZFJ | MSE | A | 117 | MET | SELENOMETHIONINE | | | | | | | | | | |
| MODRES | 1ZFJ | MSE | A | 145 | MET | SELENOMETRIONINE | | | | | | | | | | |
| MODRES | 1ZFJ | MSE | A | 159 | MET | SELENOMETHIONINE | | | | | | | | | | |
| MODRES | 1ZFJ | MSE | A | 364 | MET | SELENOMETHIONINE | | | | | | | | | | |
| MODRES | 1ZFJ | MSE | A | 368 | MET | SELENOMETHIONINE | | | | | | | | | | |
| MODRES | 1ZFJ | MSE | A | 393 | MET | SELENOMETHIONINE | | | | | | | | | | |
| MODRES | 1ZFJ | MSE | A | 399 | MET | SELENOMETHIONINE | | | | | | | | | | |
| MODRES | 1ZFJ | MSE | A | 440 | MET | SELENOMETHIONINE | | | | | | | | | | |
| MODRES | 1ZFJ | MSE | A | 448 | MET | SELENOMETHIONINE | | | | | | | | | | |
| MODRES | 1ZFJ | MSE | A | 468 | MET | SELENOMETHIONINE | | | | | | | | | | |
| HET | MSE | A | 53 | 8 | | | | | | | | | | | | |
| HET | MSE | A | 61 | 8 | | | | | | | | | | | | |
| HET | MSE | A | 78 | 8 | | | | | | | | | | | | |
| HET | MSE | A | 117 | 8 | | | | | | | | | | | | |
| HET | MSE | A | 145 | 8 | | | | | | | | | | | | |
| HET | MSE | A | 159 | 8 | | | | | | | | | | | | |
| HET | MSE | A | 364 | 8 | | | | | | | | | | | | |
| HET | MSE | A | 368 | 8 | | | | | | | | | | | | |
| HET | MSE | A | 393 | 8 | | | | | | | | | | | | |
| HET | MSE | A | 399 | 8 | | | | | | | | | | | | |
| HET | MSE | A | 440 | 8 | | | | | | | | | | | | |
| HET | MSE | A | 448 | 8 | | | | | | | | | | | | |
| HET | MSE | A | 468 | 8 | | | | | | | | | | | | |
| HET | IMP | | 500 | 23 | | | | | | | | | | | | |
| HETNAM | | MSE | SELENOMETHIONINE | | | | | | | | | | | | | |
| HETNAM | | IMP | INOSINE-5'-MONOPHOSPHATE | | | | | | | | | | | | | |
| FORMUL | 1 | MSE | 13(C5 H11 N1 O2 SE1) | | | | | | | | | | | | | |
| FORMUL | 2 | IMP | C10 H13 N4 O8 P1 | | | | | | | | | | | | | |
| FORUUL | 3 | HOH | *499(H2 O1) | | | | | | | | | | | | | |
| HELIX | 1 | 1 ASN | A | 3 | THR | A | 6 | 5 | | | | | | | | 4 |
| HELIX | 2 | 2 PHE | A | 15 | ASP | A | 17 | 5 | | | | | | | | 3 |
| HELIX | 3 | 3 PRO | A | 29 | GLU | A | 31 | 5 | | | | | | | | 3 |
| HELIX | 4 | 4 SER | A | 59 | ARG | A | 67 | 5 | | | | | | | | 9 |
| HELIX | 5 | 5 ILE | A | 80 | SER | A | 93 | 1 | | | | | | | | 14 |
| HELIX | 6 | 6 VAL | A | 110 | ARG | A | 119 | 1 | | | | | | | | 10 |
| HELIX | 7 | 7 ASN | A | 142 | PHE | A | 147 | 5 | | | | | | | | 6 |
| HELIX | 8 | 8 LEU | A | 173 | GLU | A | 182 | 1 | | | | | | | | 10 |
| HELIX | 9 | 9 ILE | A | 203 | GLU | A | 211 | 1 | | | | | | | | 9 |
| HELIX | 10 | 10 THR | A | 235 | ALA | A | 245 | 1 | | | | | | | | 11 |
| HELIX | 11 | 11 ALA | A | 260 | HIS | A | 272 | 1 | | | | | | | | 13 |

TABLE 7-continued

| | | | | | | | | | | | | | | | | |
|---|---|---|---|---|---|---|---|---|---|---|---|---|---|---|---|---|
| HELIX | 12 | 12 ALA | A | 286 | ASP | A | 294 | 1 | | | | | | | | 9 |
| HELIX | 13 | 13 THR | A | 312 | VAL | A | 315 | 1 | | | | | | | | 4 |
| HELIX | 14 | 14 GLN | A | 322 | GLU | A | 335 | 1 | | | | | | | | 14 |
| HELIX | 15 | 15 SER | A | 349 | ALA | A | 357 | 1 | | | | | | | | 9 |
| HELIX | 16 | 16 ALA | A | 433 | VAL | A | 451 | 1 | | | | | | | | 19 |
| HELIX | 17 | 17 ILE | A | 456 | ASN | A | 462 | 1 | | | | | | | | 7 |
| HELIX | 18 | 18 GLY | A | 470 | SER | A | 476 | 1 | | | | | | | | 7 |
| SHEET | 1 | A 3 PHE | A | 103 | THR | A | 105 | 0 | | | | | | | | |
| SHEET | 2 | A 3 GLY | A | 124 | VAL | A | 128 | 1 | N | PRO | A | 126 | O | LEU | A | 104 |
| SHEET | 3 | A 3 LEU | A | 136 | THR | A | 141 | -1 | N | ILE | A | 140 | O | VAL | A | 125 |
| SHEET | 1 | B 3 THR | A | 166 | ALA | A | 168 | 0 | | | | | | | | |
| SHEET | 2 | B 3 LYS | A | 187 | VAL | A | 191 | 1 | N | PRO | A | 189 | O | ALA | A | 167 |
| SHEET | 3 | B 3 LEU | A | 197 | THR | A | 202 | -1 | N | ILE | A | 201 | O | LEU | A | 188 |
| SHEET | 1 | C 5 ALA | A | 226 | VAL | A | 229 | 0 | | | | | | | | |
| SHEET | 2 | C 5 ALA | A | 249 | ILE | A | 252 | 1 | N | ALA | A | 249 | O | ALA | A | 227 |
| SHEET | 3 | C 5 LEU | A | 278 | ILE | A | 283 | 1 | N | ILE | A | 279 | O | ILE | A | 250 |
| SHEET | 4 | C 5 VAL | A | 299 | VAL | A | 302 | 1 | N | VAL | A | 299 | O | ALA | A | 280 |
| SHEET | 5 | C 5 THR | A | 339 | ALA | A | 342 | 1 | N | THR | A | 339 | O | VAL | A | 300 |
| SHEET | 1 | D 3 THR | A | 379 | TYR | A | 382 | 0 | | | | | | | | |
| SHEET | 2 | D 3 ARG | A | 385 | ARG | A | 391 | -1 | N | TYR | A | 387 | O | GLU | A | 380 |
| SHEET | 3 | D 3 GLU | A | 424 | ALA | A | 428 | -1 | N | VAL | A | 427 | O | LYS | A | 388 |
| SHEET | 1 | E 2 THR | A | 36 | ALA | A | 39 | 0 | | | | | | | | |
| SHEET | 2 | E 2 LEU | A | 42 | LEU | A | 44 | -1 | N | LEU | A | 44 | O | THR | A | 36 |
| SITE | 1 | ASC 1 CYS A 310 | | | | | | | | | | | | | | |
| CRYST1 | 151.480 | 151.480 | 101.680 | 90.00 | 90.00 | 90.00 | I 4 2 2 | | 16 | | | | | | | |
| ORIGX1 | | 1.000000 | 0.000000 | 0.000000 | | 0.00000 | | | | | | | | | | |
| ORIGX2 | | 0.000000 | 1.000000 | 0.000000 | | 0.00000 | | | | | | | | | | |
| ORIGX3 | | 0.000000 | 0.000000 | 1.000000 | | 0.00000 | | | | | | | | | | |
| SCALE1 | | 0.006601 | 0.000000 | 0.000000 | | 0.00000 | | | | | | | | | | |
| SCALE2 | | 0.000000 | 0.006601 | 0.000000 | | 0.00000 | | | | | | | | | | |
| SCALE3 | | 0.000000 | 0.000000 | 0.009835 | | 0.00000 | | | | | | | | | | |
| ATOM | 1 | N | SER | A | 2 | 82.354 | 51.770 | 46.774 | 1.00 | 44.22 | N | | | | | |
| ATOM | 2 | CA | SER | A | 2 | 81.643 | 51.755 | 45.463 | 1.00 | 42.72 | C | | | | | |
| ATOM | 3 | C | SER | A | 2 | 81.341 | 53.170 | 44.968 | 1.00 | 42.19 | C | | | | | |
| ATOM | 4 | O | SER | A | 2 | 80.656 | 53.941 | 45.653 | 1.00 | 42.81 | O | | | | | |
| ATOM | 5 | CB | SER | A | 2 | 80.340 | 50.980 | 45.597 | 1.00 | 42.36 | C | | | | | |
| ATOM | 6 | OG | SER | A | 2 | 79.625 | 51.016 | 44.380 | 1.00 | 45.23 | O | | | | | |
| ATOM | 7 | N | ASN | A | 3 | 81.847 | 53.515 | 43.782 | 1.00 | 40.04 | N | | | | | |
| ATOM | 8 | CA | ASN | A | 3 | 81.598 | 54.837 | 43.224 | 1.00 | 37.61 | C | | | | | |
| ATOM | 9 | C | ASN | A | 3 | 80.203 | 54.939 | 42.620 | 1.00 | 37.50 | C | | | | | |
| ATOM | 10 | O | ASN | A | 3 | 79.891 | 55.902 | 41.928 | 1.00 | 37.67 | O | | | | | |
| ATOM | 11 | CB | ASN | A | 3 | 82.617 | 55.192 | 42.146 | 1.00 | 36.54 | C | | | | | |
| ATOM | 12 | CG | ASN | A | 3 | 84.019 | 55.274 | 42.674 | 1.00 | 35.28 | C | | | | | |
| ATOM | 13 | OD1 | ASN | A | 3 | 84.244 | 55.741 | 43.787 | 1.00 | 35.10 | O | | | | | |
| ATOM | 14 | ND2 | ASN | A | 3 | 84.984 | 54.853 | 41.861 | 1.00 | 33.91 | N | | | | | |
| ATOM | 15 | N | TRP | A | 4 | 79.364 | 53.940 | 42.857 | 1.00 | 36.95 | N | | | | | |
| ATOM | 16 | CA | TRP | A | 4 | 78.018 | 53.998 | 42.322 | 1.00 | 36.01 | C | | | | | |
| ATOM | 17 | C | TRP | A | 4 | 77.300 | 55.217 | 42.888 | 1.00 | 36.93 | C | | | | | |
| ATOM | 18 | O | TRP | A | 4 | 76.428 | 55.782 | 42.236 | 1.00 | 37.98 | O | | | | | |
| ATOM | 19 | CB | TRP | A | 4 | 77.240 | 52.718 | 42.643 | 1.00 | 33.82 | C | | | | | |
| ATOM | 20 | CG | TRP | A | 4 | 75.814 | 52.835 | 42.261 | 1.00 | 30.69 | C | | | | | |
| ATOM | 21 | CD1 | TRP | A | 4 | 74.805 | 53.326 | 43.029 | 1.00 | 29.45 | C | | | | | |
| ATOM | 22 | CD2 | TRP | A | 4 | 75.257 | 52.614 | 40.956 | 1.00 | 29.97 | C | | | | | |
| ATOM | 23 | NE1 | TRP | A | 4 | 73.652 | 53.434 | 42.286 | 1.00 | 30.83 | N | | | | | |
| ATOM | 24 | CE2 | TRP | A | 4 | 73.902 | 53.007 | 41.010 | 1.00 | 29.48 | C | | | | | |
| ATOM | 25 | CE3 | TRP | A | 4 | 75.775 | 52.129 | 39.747 | 1.00 | 28.30 | C | | | | | |
| ATOM | 26 | CZ2 | TRP | A | 4 | 73.057 | 52.928 | 39.901 | 1.00 | 28.18 | C | | | | | |
| ATOM | 27 | CZ3 | TRP | A | 4 | 74.936 | 52.052 | 38.646 | 1.00 | 27.32 | C | | | | | |
| ATOM | 28 | CH2 | TRP | A | 4 | 73.592 | 52.450 | 38.731 | 1.00 | 28.03 | C | | | | | |
| ATOM | 29 | N | ASP | A | 5 | 77.673 | 55.632 | 44.096 | 1.00 | 37.49 | N | | | | | |
| ATOM | 30 | CA | ASP | A | 5 | 77.054 | 56.804 | 44.705 | 1.00 | 38.18 | C | | | | | |
| ATOM | 31 | C | ASP | A | 5 | 77.778 | 58.093 | 44.327 | 1.00 | 37.52 | C | | | | | |
| ATOM | 32 | O | ASP | A | 5 | 77.324 | 59.189 | 44.643 | 1.00 | 37.71 | O | | | | | |
| ATOM | 33 | CB | ASP | A | 5 | 76.992 | 56.650 | 46.221 | 1.00 | 40.78 | C | | | | | |
| ATOM | 34 | CG | ASP | A | 5 | 76.071 | 55.524 | 46.643 | 1.00 | 44.01 | C | | | | | |
| ATOM | 35 | OD1 | ASP | A | 5 | 74.886 | 55.540 | 46.232 | 1.00 | 43.98 | O | | | | | |
| ATOM | 36 | OD2 | ASP | A | 5 | 76.531 | 54.626 | 47.386 | 1.00 | 46.63 | O | | | | | |
| ATOM | 37 | N | THR | A | 6 | 78.906 | 57.946 | 43.643 | 1.00 | 36.92 | N | | | | | |
| ATOM | 38 | CA | THR | A | 6 | 79.696 | 59.084 | 43.169 | 1.00 | 35.85 | C | | | | | |
| ATOM | 39 | C | THR | A | 6 | 79.911 | 58.884 | 41.662 | 1.00 | 33.68 | C | | | | | |
| ATOM | 40 | O | THR | A | 6 | 80.992 | 59.143 | 41.136 | 1.00 | 33.60 | O | | | | | |
| ATOM | 41 | CB | THR | A | 6 | 81.068 | 59.154 | 43.867 | 1.00 | 36.00 | C | | | | | |
| ATOM | 42 | OG1 | THR | A | 6 | 80.881 | 59.204 | 45.283 | 1.00 | 38.44 | O | | | | | |
| ATOM | 43 | CG2 | THR | A | 6 | 81.810 | 60.400 | 43.444 | 1.00 | 37.48 | C | | | | | |
| ATOM | 44 | N | LYS | A | 7 | 78.863 | 58.404 | 40.992 | 1.00 | 30.86 | N | | | | | |
| ATOM | 45 | CA | LYS | A | 7 | 78.879 | 58.132 | 39.559 | 1.00 | 28.48 | C | | | | | |
| ATOM | 46 | C | LYS | A | 7 | 79.207 | 59.389 | 38.739 | 1.00 | 28.69 | C | | | | | |
| ATOM | 47 | O | LYS | A | 7 | 79.990 | 59.341 | 37.791 | 1.00 | 28.86 | O | | | | | |
| ATOM | 48 | CB | LYS | A | 7 | 77.523 | 57.553 | 39.153 | 1.00 | 25.62 | C | | | | | |

TABLE 7-continued

| ATOM | 49 | CG | LYS | A | 7 | 77.415 | 57.120 | 37.712 | 1.00 | 23.59 | C |
|---|---|---|---|---|---|---|---|---|---|---|---|
| ATOM | 50 | CD | LYS | A | 7 | 78.423 | 56.039 | 37.368 | 1.00 | 23.54 | C |
| ATOM | 51 | CE | LYS | A | 7 | 78.212 | 54.773 | 38.186 | 1.00 | 22.78 | C |
| ATOM | 52 | NZ | LYS | A | 7 | 79.139 | 53.678 | 37.755 | 1.00 | 22.29 | N |
| ATOM | 53 | N | PHE | A | 8 | 78.603 | 60.514 | 39.102 | 1.00 | 29.06 | N |
| ATOM | 54 | CA | PHE | A | 8 | 78.860 | 61.781 | 38.420 | 1.00 | 30.23 | C |
| ATOM | 55 | C | PHE | A | 8 | 79.805 | 62.533 | 39.339 | 1.00 | 31.17 | C |
| ATOM | 56 | O | PHE | A | 8 | 79.392 | 63.206 | 40.278 | 1.00 | 32.04 | O |
| ATOM | 57 | CB | PHE | A | 8 | 77.542 | 62.513 | 38.205 | 1.00 | 29.85 | C |
| ATOM | 58 | CG | PHE | A | 8 | 76.578 | 61.731 | 37.370 | 1.00 | 30.55 | C |
| ATOM | 59 | CD1 | PHE | A | 8 | 76.775 | 61.602 | 36.002 | 1.00 | 29.92 | C |
| ATOM | 60 | CD2 | PHE | A | 8 | 75.544 | 61.019 | 37.963 | 1.00 | 30.12 | C |
| ATOM | 61 | CE1 | PHE | A | 8 | 75.958 | 60.770 | 35.241 | 1.00 | 30.48 | C |
| ATOM | 62 | CE2 | PHE | A | 8 | 74.730 | 60.193 | 37.209 | 1.00 | 28.97 | C |
| ATOM | 63 | CZ | PHE | A | 8 | 74.937 | 60.065 | 35.850 | 1.00 | 29.91 | C |
| ATOM | 64 | N | LEU | A | 9 | 81.090 | 62.394 | 39.049 | 1.00 | 32.70 | N |
| ATOM | 65 | CA | LEU | A | 9 | 82.135 | 62.968 | 39.870 | 1.00 | 34.57 | C |
| ATOM | 66 | C | LEU | A | 9 | 82.222 | 64.485 | 39.903 | 1.00 | 36.07 | C |
| ATOM | 67 | O | LEU | A | 9 | 82.161 | 65.092 | 40.978 | 1.00 | 37.88 | O |
| ATOM | 68 | CB | LEU | A | 9 | 83.482 | 62.380 | 39.451 | 1.00 | 33.71 | C |
| ATOM | 69 | CG | LEU | A | 9 | 84.593 | 62.591 | 40.469 | 1.00 | 32.58 | C |
| ATOM | 70 | CD1 | LEU | A | 9 | 84.139 | 62.012 | 41.789 | 1.00 | 32.56 | C |
| ATOM | 71 | CD2 | LEU | A | 9 | 85.872 | 61.928 | 40.002 | 1.00 | 31.98 | C |
| ATOM | 72 | N | LYS | A | 10 | 82.377 | 65.104 | 38.740 | 1.00 | 35.80 | N |
| ATOM | 73 | CA | LYS | A | 10 | 82.482 | 66.554 | 38.696 | 1.00 | 35.27 | C |
| ATOM | 74 | C | LYS | A | 10 | 82.560 | 67.096 | 37.284 | 1.00 | 34.79 | C |
| ATOM | 75 | O | LYS | A | 10 | 82.440 | 66.341 | 36.321 | 1.00 | 35.02 | O |
| ATOM | 76 | CB | LYS | A | 10 | 83.699 | 67.008 | 39.514 | 1.00 | 35.85 | C |
| ATOM | 77 | CG | LYS | A | 10 | 84.974 | 66.179 | 39.333 | 1.00 | 33.88 | C |
| ATOM | 78 | CD | LYS | A | 10 | 85.554 | 66.275 | 37.947 | 1.00 | 33.98 | C |
| ATOM | 79 | CE | LYS | A | 10 | 86.901 | 65.574 | 37.880 | 1.00 | 35.39 | C |
| ATOM | 80 | NZ | LYS | A | 10 | 87.937 | 66.213 | 38.746 | 1.00 | 35.48 | N |
| ATOM | 81 | N | LYS | A | 11 | 82.742 | 68.407 | 37.167 | 1.00 | 33.79 | N |
| ATOM | 82 | CA | LYS | A | 11 | 82.841 | 69.046 | 35.861 | 1.00 | 33.06 | C |
| ATOM | 83 | C | LYS | A | 11 | 84.280 | 69.274 | 35.431 | 1.00 | 30.80 | C |
| ATOM | 84 | O | LYS | A | 11 | 85.159 | 69.516 | 36.259 | 1.00 | 30.97 | O |
| ATOM | 85 | CB | LYS | A | 11 | 82.072 | 70.365 | 35.858 | 1.00 | 35.00 | C |
| ATOM | 86 | CG | LYS | A | 11 | 80.568 | 70.163 | 35.851 | 1.00 | 40.89 | C |
| ATOM | 87 | CD | LYS | A | 11 | 79.802 | 71.475 | 35.945 | 1.00 | 44.76 | C |
| ATOM | 88 | CE | LYS | A | 11 | 80.018 | 72.131 | 37.301 | 1.00 | 47.54 | C |
| ATOM | 89 | NZ | LYS | A | 11 | 79.596 | 71.236 | 38.419 | 1.00 | 48.72 | N |
| ATOM | 90 | N | GLY | A | 12 | 84.511 | 69.168 | 34.126 | 1.00 | 29.21 | N |
| ATOM | 91 | CA | GLY | A | 12 | 85.837 | 69.370 | 33.576 | 1.00 | 26.68 | C |
| ATOM | 92 | C | GLY | A | 12 | 85.824 | 70.536 | 32.604 | 1.00 | 26.32 | C |
| ATOM | 93 | O | GLY | A | 12 | 84.807 | 70.798 | 31.952 | 1.00 | 25.14 | O |
| ATOM | 94 | N | TYR | A | 13 | 86.949 | 71.241 | 32.522 | 1.00 | 25.87 | N |
| ATOM | 95 | CA | TYR | A | 13 | 87.095 | 72.389 | 31.633 | 1.00 | 27.06 | C |
| ATOM | 96 | C | TYR | A | 13 | 88.044 | 72.084 | 30.500 | 1.00 | 26.35 | C |
| ATOM | 97 | O | TYR | A | 13 | 89.042 | 71.397 | 30.690 | 1.00 | 25.99 | O |
| ATOM | 98 | CB | TYR | A | 13 | 87.659 | 73.604 | 32.376 | 1.00 | 29.47 | C |
| ATOM | 99 | CG | TYR | A | 13 | 86.747 | 74.148 | 33.430 | 1.00 | 34.86 | C |
| ATOM | 100 | CD1 | TYR | A | 13 | 85.471 | 74.600 | 33.098 | 1.00 | 36.83 | C |
| ATOM | 101 | CD2 | TYR | A | 13 | 87.147 | 74.206 | 34.763 | 1.00 | 37.11 | C |
| ATOM | 102 | CE1 | TYR | A | 13 | 84.612 | 75.093 | 34.062 | 1.00 | 39.35 | C |
| ATOM | 103 | CE2 | TYR | A | 13 | 86.294 | 74.700 | 35.739 | 1.00 | 40.44 | C |
| ATOM | 104 | CZ | TYR | A | 13 | 85.027 | 75.140 | 35.379 | 1.00 | 41.53 | c |
| ATOM | 105 | OH | TYR | A | 13 | 84.161 | 75.613 | 36.336 | 1.00 | 45.89 | O |
| ATOM | 106 | N | THR | A | 14 | 87.727 | 72.606 | 29.322 | 1.00 | 25.75 | N |
| ATOM | 107 | CA | THR | A | 14 | 88.585 | 72.448 | 28.159 | 1.00 | 25.34 | C |
| ATOM | 108 | C | THR | A | 14 | 89.024 | 73.877 | 27.830 | 1.00 | 23.61 | C |
| ATOM | 109 | O | THR | A | 14 | 88.469 | 74.832 | 28.367 | 1.00 | 22.92 | O |
| ATOM | 110 | CB | THR | A | 14 | 87.817 | 71.829 | 26.970 | 1.00 | 26.77 | C |
| ATOM | 111 | OG1 | THR | A | 14 | 88.700 | 71.699 | 25.846 | 1.00 | 31.58 | O |
| ATOM | 112 | CG2 | THR | A | 14 | 86.635 | 72.702 | 26.583 | 1.00 | 27.27 | C |
| ATOM | 113 | N | PHE | A | 15 | 90.011 | 74.032 | 26.957 | 1.00 | 22.10 | N |
| ATOM | 114 | CA | PHE | A | 15 | 90.509 | 75.353 | 26.613 | 1.00 | 20.64 | C |
| ATOM | 115 | C | PHE | A | 15 | 89.435 | 76.391 | 26.278 | 1.00 | 20.42 | C |
| ATOM | 116 | O | PHE | A | 15 | 89.579 | 77.555 | 26.641 | 1.00 | 20.85 | O |
| ATOM | 117 | CB | PHE | A | 15 | 91.504 | 75.238 | 25.460 | 1.00 | 20.90 | C |
| ATOM | 118 | CG | PHE | A | 15 | 92.685 | 74.365 | 25.770 | 1.00 | 21.02 | C |
| ATOM | 119 | CD1 | PHE | A | 15 | 93.568 | 74.699 | 26.790 | 1.00 | 20.82 | C |
| ATOM | 120 | CD2 | PHE | A | 15 | 92.897 | 73.189 | 25.070 | 1.00 | 20.78 | C |
| ATOM | 121 | CE1 | PHE | A | 15 | 94.636 | 73.871 | 27.102 | 1.00 | 20.57 | C |
| ATOM | 122 | CE2 | PHE | A | 15 | 93.967 | 72.356 | 25.381 | 1.00 | 20.90 | C |
| ATOM | 123 | CZ | PHE | A | 15 | 94.832 | 72.699 | 26.396 | 1.00 | 19.69 | C |
| ATOM | 124 | N | ASP | A | 16 | 88.362 | 75.987 | 25.601 | 1.00 | 20.30 | N |
| ATOM | 125 | CA | ASP | A | 16 | 87.318 | 76.936 | 25.230 | 1.00 | 21.26 | C |
| ATOM | 126 | C | ASP | A | 16 | 86.312 | 77.314 | 26.320 | 1.00 | 20.86 | C |
| ATOM | 127 | O | ASP | A | 16 | 85.364 | 78.050 | 26.061 | 1.00 | 20.85 | O |

TABLE 7-continued

| | | | | | | | | | | |
|---|---|---|---|---|---|---|---|---|---|---|
| ATOM | 128 | CB | ASP | A | 16 | 86.564 | 76.457 | 23.983 | 1.00 | 23.23 C |
| ATOM | 129 | CG | ASP | A | 16 | 87.418 | 76.509 | 22.721 | 1.00 | 28.01 C |
| ATOM | 130 | OD1 | ASP | A | 16 | 88.319 | 77.374 | 22.636 | 1.00 | 29.29 O |
| ATOM | 131 | OD2 | ASP | A | 16 | 87.167 | 75.713 | 21.789 | 1.00 | 31.34 O |
| ATOM | 132 | N | ASP | A | 17 | 86.511 | 76.824 | 27.538 | 1.00 | 21.11 N |
| ATOM | 133 | CA | ASP | A | 17 | 85.609 | 77.165 | 28.645 | 1.00 | 20.51 C |
| ATOM | 134 | C | ASP | A | 17 | 86.192 | 78.287 | 29.487 | 1.00 | 19.73 C |
| ATOM | 135 | O | ASP | A | 17 | 85.475 | 78.926 | 30.244 | 1.00 | 20.34 O |
| ATOM | 136 | CB | ASP | A | 17 | 85.376 | 75.971 | 29.581 | 1.00 | 20.06 C |
| ATOM | 137 | CG | ASP | A | 17 | 84.651 | 74.827 | 28.913 | 1.00 | 21.90 C |
| ATOM | 138 | OD1 | ASP | A | 17 | 83.571 | 75.067 | 28.330 | 1.00 | 21.40 O |
| ATOM | 139 | OD2 | ASP | A | 17 | 85.151 | 73.680 | 28.985 | 1.00 | 21.34 O |
| ATOM | 140 | N | VAL | A | 18 | 87.491 | 78.530 | 29.343 | 1.00 | 19.47 N |
| ATOM | 141 | CA | VAL | A | 18 | 88.180 | 79.532 | 30.149 | 1.00 | 19.26 C |
| ATOM | 142 | C | VAL | A | 18 | 89.054 | 80.548 | 29.410 | 1.00 | 20.62 C |
| ATOM | 143 | O | VAL | A | 18 | 89.468 | 80.344 | 28.267 | 1.00 | 20.73 O |
| ATOM | 144 | CB | VAL | A | 18 | 89.076 | 78.833 | 31.199 | 1.00 | 18.24 C |
| ATOM | 145 | CG1 | VAL | A | 18 | 88.244 | 77.912 | 32.060 | 1.00 | 17.13 C |
| ATOM | 146 | CG2 | VAL | A | 18 | 90.169 | 78.038 | 30.505 | 1.00 | 17.00 C |
| ATOM | 147 | N | LEU | A | 19 | 89.335 | 81.642 | 30.106 | 1.00 | 20.27 N |
| ATOM | 148 | CA | LEU | A | 19 | 90.186 | 82.723 | 29.627 | 1.00 | 21.23 C |
| ATOM | 149 | C | LEU | A | 19 | 91.101 | 83.118 | 30.785 | 1.00 | 21.23 C |
| ATOM | 150 | O | LEU | A | 19 | 90.700 | 83.040 | 31.946 | 1.00 | 21.35 O |
| ATOM | 151 | CB | LEU | A | 19 | 89.347 | 83.945 | 29.245 | 1.00 | 20.79 C |
| ATOM | 152 | CG | LEU | A | 19 | 88.497 | 83.867 | 27.991 | 1.00 | 20.91 C |
| ATOM | 153 | CD1 | LEU | A | 19 | 87.558 | 85.052 | 27.924 | 1.00 | 19.17 C |
| ATOM | 154 | CD2 | LEU | A | 19 | 89.417 | 83.812 | 26.798 | 1.00 | 19.74 C |
| ATOM | 155 | N | LEU | A | 20 | 92.324 | 83.537 | 30.484 | 1.00 | 20.61 N |
| ATOM | 156 | CA | LEU | A | 20 | 93.222 | 83.979 | 31.541 | 1.00 | 21.37 C |
| ATOM | 157 | C | LEU | A | 20 | 92.857 | 85.421 | 31.868 | 1.00 | 22.07 C |
| ATOM | 158 | O | LEU | A | 20 | 92.623 | 86.234 | 30.972 | 1.00 | 22.23 O |
| ATOM | 159 | CB | LEU | A | 20 | 94.676 | 83.894 | 31.087 | 1.00 | 20.78 C |
| ATOM | 160 | CG | LEU | A | 20 | 95.210 | 82.474 | 30.972 | 1.00 | 21.20 C |
| ATOM | 161 | CD1 | LEU | A | 20 | 96.567 | 82.488 | 30.305 | 1.00 | 22.29 C |
| ATOM | 162 | CD2 | LEU | A | 20 | 95.273 | 81.857 | 32.355 | 1.00 | 20.57 C |
| ATOM | 163 | N | ILE | A | 21 | 92.796 | 85.734 | 33.154 | 1.00 | 22.61 N |
| ATOM | 164 | CA | ILE | A | 21 | 92.442 | 87.075 | 33.591 | 1.00 | 21.81 C |
| ATOM | 165 | C | ILE | A | 21 | 93.657 | 87.998 | 33.597 | 1.00 | 23.02 C |
| ATOM | 166 | O | ILE | A | 21 | 94.720 | 87.649 | 34.121 | 1.00 | 24.26 O |
| ATOM | 167 | CB | ILE | A | 21 | 91.838 | 87.041 | 35.010 | 1.00 | 21.50 C |
| ATOM | 168 | CG1 | ILE | A | 21 | 90.667 | 86.055 | 35.059 | 1.00 | 20.85 C |
| ATOM | 169 | CG2 | ILE | A | 21 | 91.363 | 88.434 | 35.403 | 1.00 | 22.33 C |
| ATOM | 170 | CD1 | ILE | A | 21 | 90.045 | 85.907 | 36.432 | 1.00 | 19.20 C |
| ATOM | 171 | N | PRO | A | 22 | 93.522 | 89.195 | 33.010 | 1.00 | 23.71 N |
| ATOM | 172 | CA | PRO | A | 22 | 94.637 | 90.141 | 32.979 | 1.00 | 23.92 C |
| ATOM | 173 | C | PRO | A | 22 | 95.029 | 90.494 | 34.416 | 1.00 | 24.84 C |
| ATOM | 174 | O | PRO | A | 22 | 94.176 | 90.501 | 35.300 | 1.00 | 26.16 O |
| ATOM | 175 | CB | PRO | A | 22 | 94.033 | 91.330 | 32.240 | 1.00 | 23.95 C |
| ATOM | 176 | CG | PRO | A | 22 | 92.999 | 90.678 | 31.355 | 1.00 | 24.02 C |
| ATOM | 177 | CD | PRO | A | 22 | 92.346 | 89.784 | 32.351 | 1.00 | 23.20 C |
| ATOM | 178 | N | ALA | A | 23 | 96.308 | 90.784 | 34.652 | 1.00 | 25.54 N |
| ATOM | 179 | CA | ALA | A | 23 | 96.780 | 91.131 | 35.995 | 1.00 | 25.69 C |
| ATOM | 180 | C | ALA | A | 23 | 97.898 | 92.164 | 35.919 | 1.00 | 26.22 C |
| ATOM | 181 | O | ALA | A | 23 | 98.405 | 92.446 | 34.840 | 1.00 | 25.70 O |
| ATOM | 182 | CB | ALA | A | 23 | 97.273 | 89.881 | 36.711 | 1.00 | 25.54 C |
| ATOM | 183 | N | GLU | A | 24 | 98.283 | 92.737 | 37.055 | 1.00 | 27.57 N |
| ATOM | 184 | CA | GLU | A | 24 | 99.352 | 93.725 | 37.024 | 1.00 | 30.95 C |
| ATOM | 185 | C | GLU | A | 24 | 100.569 | 93.024 | 36.449 | 1.00 | 30.88 C |
| ATOM | 186 | O | GLU | A | 24 | 100.818 | 91.859 | 36.753 | 1.00 | 30.38 O |
| ATOM | 187 | CB | GLU | A | 24 | 99.658 | 94.276 | 38.425 | 1.00 | 33.75 C |
| ATOM | 188 | CG | GLU | A | 24 | 100.218 | 93.274 | 39.406 | 1.00 | 39.88 C |
| ATOM | 189 | CD | GLU | A | 24 | 100.497 | 93.886 | 40.774 | 1.00 | 43.61 C |
| ATOM | 190 | OE1 | GLU | A | 24 | 101.322 | 94.825 | 40.863 | 1.00 | 44.89 O |
| ATOM | 191 | OE2 | GLU | A | 24 | 99.887 | 93.422 | 41.763 | 1.00 | 46.51 O |
| ATOM | 192 | N | SER | A | 25 | 101.315 | 93.729 | 35.606 | 1.00 | 32.20 N |
| ATOM | 193 | CA | SER | A | 25 | 102.494 | 93.160 | 34.971 | 1.00 | 33.78 C |
| ATOM | 194 | C | SER | A | 25 | 103.714 | 94.082 | 35.000 | 1.00 | 35.09 C |
| ATOM | 195 | O | SER | A | 25 | 103.594 | 95.289 | 34.783 | 1.00 | 35.62 O |
| ATOM | 196 | CB | SER | A | 25 | 102.163 | 92.803 | 33.520 | 1.00 | 32.84 C |
| ATOM | 197 | OG | SER | A | 25 | 103.294 | 92.273 | 32.853 | 1.00 | 32.95 O |
| ATOM | 198 | N | HIS | A | 26 | 104.883 | 93.501 | 35.267 | 1.00 | 36.35 N |
| ATOM | 199 | CA | HIS | A | 26 | 106.136 | 94.252 | 35.293 | 1.00 | 37.85 C |
| ATOM | 200 | C | HIS | A | 26 | 107.125 | 93.640 | 34.315 | 1.00 | 37.72 C |
| ATOM | 201 | O | HIS | A | 26 | 108.333 | 93.814 | 34.457 | 1.00 | 38.42 O |
| ATOM | 202 | CB | HIS | A | 26 | 106.758 | 94.245 | 36.685 | 1.00 | 40.84 C |
| ATOM | 203 | CG | HIS | A | 26 | 105.885 | 94.852 | 37.738 | 1.00 | 45.91 C |
| ATOM | 204 | ND1 | HIS | A | 26 | 104.734 | 94.242 | 38.195 | 1.00 | 48.22 N |
| ATOM | 205 | CD2 | HIS | A | 26 | 105.978 | 96.030 | 38.403 | 1.00 | 47.24 C |
| ATOM | 206 | CE1 | HIS | A | 26 | 104.158 | 95.017 | 39.097 | 1.00 | 48.99 C |

TABLE 7-continued

| | | | | | | | | | | |
|---|---|---|---|---|---|---|---|---|---|---|
| ATOM | 207 | NE2 | HIS | A | 26 | 104.892 | 96.107 | 39.241 | 1.00 48.85 | N |
| ATOM | 208 | N | VAL | A | 27 | 106.611 | 92.922 | 33.323 | 1.00 36.55 | N |
| ATOM | 209 | CA | VAL | A | 27 | 107.462 | 92.284 | 32.333 | 1.00 35.90 | C |
| ATOM | 210 | C | VAL | A | 27 | 106.851 | 92.414 | 30.947 | 1.00 34.96 | C |
| ATOM | 211 | O | VAL | A | 27 | 105.689 | 92.080 | 30.742 | 1.00 35.93 | O |
| ATOM | 212 | CB | VAL | A | 27 | 107.665 | 90.783 | 32.670 | 1.00 37.27 | C |
| ATOM | 213 | CG1 | VAL | A | 27 | 106.315 | 90.069 | 32.733 | 1.00 38.23 | C |
| ATOM | 214 | CG2 | VAL | A | 27 | 108.573 | 90.130 | 31.633 | 1.00 37.72 | C |
| ATOM | 215 | N | LEU | A | 28 | 107.627 | 92.922 | 29.998 | 1.00 33.88 | N |
| ATOM | 216 | CA | LEU | A | 28 | 107.132 | 93.073 | 28.638 | 1.00 33.33 | C |
| ATOM | 217 | C | LEU | A | 28 | 107.190 | 91.714 | 27.960 | 1.00 33.40 | C |
| ATOM | 218 | O | LEU | A | 28 | 107.946 | 90.842 | 28.380 | 1.00 33.65 | O |
| ATOM | 219 | CB | LEU | A | 28 | 107.973 | 94.093 | 27.868 | 1.00 32.03 | C |
| ATOM | 220 | CG | LEU | A | 28 | 107.935 | 95.515 | 28.434 | 1.00 32.97 | C |
| ATOM | 221 | CD1 | LEU | A | 28 | 108.782 | 96.432 | 27.584 | 1.00 31.82 | C |
| ATOM | 222 | CD2 | LEU | A | 28 | 106.516 | 96.014 | 28.468 | 1.00 32.76 | C |
| ATOM | 223 | N | PRO | A | 29 | 106.384 | 91.508 | 26.906 | 1.00 33.27 | N |
| ATOM | 224 | CA | PRO | A | 29 | 106.389 | 90.222 | 26.211 | 1.00 33.55 | C |
| ATOM | 225 | C | PRO | A | 29 | 107.779 | 89.774 | 25.759 | 1.00 34.80 | C |
| ATOM | 226 | O | PRO | A | 29 | 108.142 | 88.608 | 25.909 | 1.00 33.98 | O |
| ATOM | 227 | CB | PRO | A | 29 | 105.446 | 90.480 | 25.036 | 1.00 33.09 | C |
| ATOM | 228 | CG | PRO | A | 29 | 104.465 | 91.448 | 25.633 | 1.00 32.91 | C |
| ATOM | 229 | CD | PRO | A | 29 | 105.435 | 92.423 | 26.248 | 1.00 33.11 | C |
| ATOM | 230 | N | ASN | A | 30 | 108.554 | 90.712 | 25.222 | 1.00 36.70 | N |
| ATOM | 231 | CA | ASN | A | 30 | 109.886 | 90.412 | 24.713 | 1.00 38.86 | C |
| ATOM | 232 | C | ASN | A | 30 | 110.908 | 90.077 | 25.786 | 1.00 39.09 | C |
| ATOM | 233 | O | ASN | A | 30 | 112.034 | 89.703 | 25.468 | 1.00 40.70 | O |
| ATOM | 234 | CB | ASN | A | 30 | 110.405 | 91.574 | 23.869 | 1.00 40.69 | C |
| ATOM | 235 | CG | ASN | A | 30 | 110.444 | 92.872 | 24.644 | 1.00 43.86 | C |
| ATOM | 236 | OD1 | ASN | A | 30 | 109.404 | 93.408 | 25.029 | 1.00 46.68 | O |
| ATOM | 237 | ND2 | ASN | A | 30 | 111.644 | 93.379 | 24.892 | 1.00 44.75 | N |
| ATOM | 238 | N | GLU | A | 31 | 110.539 | 90.205 | 27.052 | 1.00 38.38 | N |
| ATOM | 239 | CA | GLU | A | 31 | 111.483 | 89.876 | 28.108 | 1.00 38.11 | C |
| ATOM | 240 | C | GLU | A | 31 | 111.012 | 88.724 | 28.984 | 1.00 36.56 | C |
| ATOM | 241 | O | GLU | A | 31 | 111.606 | 88.455 | 30.028 | 1.00 36.28 | O |
| ATOM | 242 | CB | GLU | A | 31 | 111.784 | 91.110 | 28.966 | 1.00 41.04 | C |
| ATOM | 243 | CG | GLU | A | 31 | 110.561 | 91.828 | 29.480 | 1.00 44.82 | C |
| ATOM | 244 | CD | GLU | A | 31 | 110.907 | 93.074 | 30.265 | 1.00 47.02 | C |
| ATOM | 245 | OE1 | GLU | A | 31 | 111.466 | 92.948 | 31.376 | 1.00 49.39 | O |
| ATOM | 246 | OE2 | GLU | A | 31 | 110.629 | 94.184 | 29.765 | 1.00 48.56 | O |
| ATOM | 247 | N | VAL | A | 32 | 109.942 | 88.045 | 28.572 | 1.00 34.46 | N |
| ATOM | 248 | CA | VAL | A | 32 | 109.469 | 86.912 | 29.354 | 1.00 32.34 | C |
| ATOM | 249 | C | VAL | A | 32 | 110.435 | 85.761 | 29.082 | 1.00 32.04 | C |
| ATOM | 250 | O | VAL | A | 32 | 110.987 | 85.648 | 27.978 | 1.00 30.35 | O |
| ATOM | 251 | CB | VAL | A | 32 | 108.040 | 86.463 | 28.957 | 1.00 31.69 | C |
| ATOM | 252 | CG1 | VAL | A | 32 | 107.056 | 87.578 | 29.170 | 1.00 31.19 | C |
| ATOM | 253 | CG2 | VAL | A | 32 | 108.023 | 86.034 | 27.535 | 1.00 34.01 | C |
| ATOM | 254 | N | ASP | A | 33 | 110.642 | 84.918 | 30.092 | 1.00 31.28 | N |
| ATOM | 255 | CA | ASP | A | 33 | 111.535 | 83.773 | 29.973 | 1.00 31.91 | C |
| ATOM | 256 | C | ASP | A | 33 | 110.738 | 82.549 | 29.523 | 1.00 31.62 | C |
| ATOM | 257 | O | ASP | A | 33 | 109.861 | 82.079 | 30.247 | 1.00 32.49 | O |
| ATOM | 258 | CB | ASP | A | 33 | 112.191 | 83.491 | 31.326 | 1.00 32.88 | C |
| ATOM | 259 | CG | ASP | A | 33 | 113.233 | 82.397 | 31.252 | 1.00 33.65 | C |
| ATOM | 260 | OD1 | ASP | A | 33 | 113.723 | 81.983 | 32.322 | 1.00 35.11 | O |
| ATOM | 261 | OD2 | ASP | A | 33 | 113.569 | 81.959 | 30.128 | 1.00 34.94 | O |
| ATOM | 262 | N | LEU | A | 34 | 111.038 | 82.037 | 28.332 | 1.00 31.40 | N |
| ATOM | 263 | CA | LEU | A | 34 | 110.334 | 80.871 | 27.806 | 1.00 31.53 | C |
| ATOM | 264 | C | LEU | A | 34 | 110.977 | 79.528 | 28.149 | 1.00 33.19 | C |
| ATOM | 265 | O | LEU | A | 34 | 110.436 | 78.470 | 27.801 | 1.00 33.53 | O |
| ATOM | 266 | CB | LEU | A | 34 | 110.194 | 80.979 | 26.285 | 1.00 30.67 | C |
| ATOM | 267 | CG | LEU | A | 34 | 108.990 | 81.696 | 25.671 | 1.00 29.76 | C |
| ATOM | 268 | CD1 | LEU | A | 34 | 108.758 | 83.013 | 26.322 | 1.00 31.73 | C |
| ATOM | 269 | CD2 | LEU | A | 34 | 109.229 | 81.865 | 24.192 | 1.00 29.76 | C |
| ATOM | 270 | N | LYS | A | 35 | 112.122 | 79.550 | 28.826 | 1.00 33.83 | N |
| ATOM | 271 | CA | LYS | A | 35 | 112.780 | 78.291 | 29.159 | 1.00 34.29 | C |
| ATOM | 272 | C | LYS | A | 35 | 111.974 | 77.434 | 30.114 | 1.00 33.40 | C |
| ATOM | 273 | O | LYS | A | 35 | 111.196 | 77.941 | 30.934 | 1.00 32.21 | O |
| ATOM | 274 | CB | LYS | A | 35 | 114.167 | 78.521 | 29.770 | 1.00 36.57 | C |
| ATOM | 275 | CG | LYS | A | 35 | 115.196 | 79.107 | 28.821 | 1.00 39.86 | C |
| ATOM | 276 | CD | LYS | A | 35 | 116.586 | 79.017 | 29.440 | 1.00 43.11 | C |
| ATOM | 277 | CE | LYS | A | 35 | 116.664 | 79.750 | 30.780 | 1.00 45.95 | C |
| ATOM | 278 | NZ | LYS | A | 35 | 116.444 | 81.232 | 30.640 | 1.00 49.28 | N |
| ATOM | 279 | N | THR | A | 36 | 112.169 | 76.124 | 30.005 | 1.00 31.86 | N |
| ATOM | 280 | CA | THR | A | 36 | 111.484 | 75.190 | 30.886 | 1.00 30.97 | C |
| ATOM | 281 | C | THR | A | 36 | 112.381 | 73.969 | 31.106 | 1.00 31.69 | C |
| ATOM | 282 | O | THR | A | 36 | 112.895 | 73.385 | 30.146 | 1.00 31.07 | O |
| ATOM | 283 | CB | THR | A | 36 | 110.092 | 74.754 | 30.298 | 1.00 28.79 | C |
| ATOM | 284 | OG1 | THR | A | 36 | 109.436 | 73.879 | 31.223 | 1.00 26.65 | O |
| ATOM | 285 | CG2 | THR | A | 36 | 110.257 | 74.036 | 28.956 | 1.00 25.84 | C |

TABLE 7-continued

| | | | | | | | | | | |
|---|---|---|---|---|---|---|---|---|---|---|
| ATOM | 286 | N | LYS | A | 37 | 112.603 | 73.617 | 32.368 | 1.00 32.29 | N |
| ATOM | 287 | CA | LYS | A | 37 | 113.418 | 72.450 | 32.675 | 1.00 34.79 | C |
| ATOM | 288 | C | LYS | A | 37 | 112.456 | 71.305 | 32.920 | 1.00 34.78 | C |
| ATOM | 289 | O | LYS | A | 37 | 111.611 | 71.375 | 33.812 | 1.00 35.62 | O |
| ATOM | 290 | CB | LYS | A | 37 | 114.291 | 72.670 | 33.921 | 1.00 36.21 | C |
| ATOM | 291 | CG | LYS | A | 37 | 115.164 | 71.452 | 34.243 | 1.00 39.26 | C |
| ATOM | 292 | CD | LYS | A | 37 | 116.208 | 71.705 | 35.329 | 1.00 41.30 | C |
| ATOM | 293 | CE | LYS | A | 37 | 115.590 | 71.952 | 36.693 | 1.00 43.41 | C |
| ATOM | 294 | NZ | LYS | A | 37 | 116.654 | 72.208 | 37.723 | 1.00 45.01 | N |
| ATOM | 295 | N | LEU | A | 38 | 112.575 | 70.261 | 32.109 | 1.00 35.03 | N |
| ATOM | 296 | CA | LEU | A | 38 | 111.702 | 69.102 | 32.219 | 1.00 35.59 | C |
| ATOM | 297 | C | LEU | A | 38 | 112.319 | 68.043 | 33.115 | 1.00 36.52 | C |
| ATOM | 298 | O | LEU | A | 38 | 111.614 | 67.298 | 33.796 | 1.00 36.39 | O |
| ATOM | 299 | CB | LEU | A | 38 | 111.423 | 68.533 | 30.825 | 1.00 33.92 | C |
| ATOM | 300 | CG | LEU | A | 38 | 110.683 | 69.502 | 29.893 | 1.00 32.62 | C |
| ATOM | 301 | CD1 | LEU | A | 38 | 110.462 | 68.861 | 28.531 | 1.00 31.57 | C |
| ATOM | 302 | CD2 | LEU | A | 38 | 109.356 | 69.887 | 30.523 | 1.00 31.42 | C |
| ATOM | 303 | N | ALA | A | 39 | 113.644 | 67.995 | 33.106 | 1.00 38.25 | N |
| ATOM | 304 | CA | ALA | A | 39 | 114.403 | 67.056 | 33.915 | 1.00 40.08 | C |
| ATOM | 305 | C | ALA | A | 39 | 115.831 | 67.591 | 34.003 | 1.00 41.95 | C |
| ATOM | 306 | O | ALA | A | 39 | 116.223 | 68.463 | 33.220 | 1.00 42.09 | O |
| ATOM | 307 | CB | ALA | A | 39 | 114.388 | 65.677 | 33.266 | 1.00 39.28 | C |
| ATOM | 308 | N | ASP | A | 40 | 116.602 | 67.073 | 34.954 | 1.00 43.87 | N |
| ATOM | 309 | CA | ASP | A | 40 | 117.993 | 67.486 | 35.146 | 1.00 45.01 | C |
| ATOM | 310 | C | ASP | A | 40 | 118.722 | 67.562 | 33.806 | 1.00 45.03 | C |
| ATOM | 311 | O | ASP | A | 40 | 119.467 | 68.505 | 33.535 | 1.00 45.51 | O |
| ATOM | 312 | CB | ASP | A | 40 | 118.688 | 66.481 | 36.060 | 1.00 46.91 | C |
| ATOM | 313 | CG | ASP | A | 40 | 118.075 | 66.436 | 37.446 | 1.00 49.68 | C |
| ATOM | 314 | OD1 | ASP | A | 40 | 118.340 | 65.458 | 38.180 | 1.00 51.95 | O |
| ATOM | 315 | OD2 | ASP | A | 40 | 117.345 | 67.387 | 37.812 | 1.00 50.80 | O |
| ATOM | 316 | N | ASN | A | 41 | 118.487 | 66.557 | 32.972 | 1.00 44.94 | N |
| ATOM | 317 | CA | ASN | A | 41 | 119.090 | 66.455 | 31.642 | 1.00 44.54 | C |
| ATOM | 318 | C | ASN | A | 41 | 118.289 | 67.153 | 30.545 | 1.00 43.23 | C |
| ATOM | 319 | O | ASN | A | 41 | 118.775 | 67.316 | 29.422 | 1.00 42.49 | O |
| ATOM | 320 | CB | ASN | A | 41 | 119.233 | 64.969 | 31.280 | 1.00 47.24 | C |
| ATOM | 321 | CG | ASN | A | 41 | 118.956 | 64.687 | 29.801 | 1.00 48.33 | C |
| ATOM | 322 | OD1 | ASN | A | 41 | 119.714 | 65.095 | 28.922 | 1.00 50.74 | O |
| ATOM | 323 | ND2 | ASN | A | 41 | 117.852 | 64.001 | 29.530 | 1.00 47.16 | N |
| ATOM | 324 | N | LEU | A | 42 | 117.074 | 67.589 | 30.866 | 1.00 41.33 | N |
| ATOM | 325 | CA | LEU | A | 42 | 116.227 | 68.186 | 29.845 | 1.00 39.00 | C |
| ATOM | 326 | C | LEU | A | 42 | 115.637 | 69.573 | 30.120 | 1.00 37.99 | C |
| ATOM | 327 | O | LEU | A | 42 | 114.653 | 69.716 | 30.848 | 1.00 37.43 | O |
| ATOM | 328 | CB | LEU | A | 42 | 115.102 | 67.200 | 29.532 | 1.00 38.42 | C |
| ATOM | 329 | CG | LEU | A | 42 | 114.599 | 67.104 | 28.099 | 1.00 37.18 | C |
| ATOM | 330 | CD1 | LEU | A | 42 | 115.752 | 66.736 | 27.172 | 1.00 36.38 | C |
| ATOM | 331 | CD2 | LEU | A | 42 | 113.509 | 66.047 | 28.032 | 1.00 36.67 | C |
| ATOM | 332 | N | THR | A | 43 | 116.242 | 70.586 | 29.511 | 1.00 35.65 | N |
| ATOM | 333 | CA | THR | A | 43 | 115.783 | 71.960 | 29.639 | 1.00 34.45 | C |
| ATOM | 334 | C | THR | A | 43 | 115.610 | 72.521 | 28.232 | 1.00 33.69 | C |
| ATOM | 335 | O | THR | A | 43 | 116.539 | 72.482 | 27.421 | 1.00 33.77 | O |
| ATOM | 336 | CB | THR | A | 43 | 116.792 | 72.827 | 30.404 | 1.00 34.76 | C |
| ATOM | 337 | OG1 | THR | A | 43 | 116.874 | 72.372 | 31.755 | 1.00 36.40 | O |
| ATOM | 338 | CG2 | THR | A | 43 | 116.358 | 74.281 | 30.402 | 1.00 35.16 | C |
| ATOM | 339 | N | LEU | A | 44 | 114.421 | 73.039 | 27.936 | 1.00 31.23 | N |
| ATOM | 340 | CA | LEU | A | 44 | 114.157 | 73.578 | 26.614 | 1.00 28.88 | C |
| ATOM | 341 | C | LEU | A | 44 | 114.097 | 75.095 | 26.683 | 1.00 27.97 | C |
| ATOM | 342 | O | LEU | A | 44 | 113.799 | 75.655 | 27.733 | 1.00 29.11 | O |
| ATOM | 343 | CB | LEU | A | 44 | 112.830 | 73.016 | 26.094 | 1.00 28.32 | C |
| ATOM | 344 | CG | LEU | A | 44 | 112.680 | 71.487 | 26.107 | 1.00 27.65 | C |
| ATOM | 345 | CD1 | LEU | A | 44 | 111.299 | 71.107 | 25.598 | 1.00 26.79 | C |
| ATOM | 346 | CD2 | LEU | A | 44 | 113.756 | 70.840 | 25.248 | 1.00 28.11 | C |
| ATOM | 347 | N | ASN | A | 45 | 114.380 | 75.756 | 25.565 | 1.00 26.86 | N |
| ATOM | 348 | CA | ASN | A | 45 | 114.337 | 77.215 | 25.492 | 1.00 27.18 | C |
| ATOM | 349 | C | ASN | A | 45 | 112.933 | 77.752 | 25.191 | 1.00 27.96 | C |
| ATOM | 350 | O | ASN | A | 45 | 112.680 | 78.947 | 25.312 | 1.00 27.92 | O |
| ATOM | 351 | CB | ASN | A | 45 | 115.323 | 77.699 | 24.443 | 1.00 27.75 | C |
| ATOM | 352 | CG | ASN | A | 45 | 116.755 | 77.510 | 24.878 | 1.00 28.46 | C |
| ATOM | 353 | OD1 | ASN | A | 45 | 117.644 | 77.325 | 24.051 | 1.00 30.13 | O |
| ATOM | 354 | ND2 | ASN | A | 45 | 116.993 | 77.579 | 26.184 | 1.00 27.73 | N |
| ATOM | 355 | N | ILE | A | 46 | 112.033 | 76.863 | 24.777 | 1.00 27.88 | N |
| ATOM | 356 | CA | ILE | A | 46 | 110.636 | 77.213 | 24.516 | 1.00 26.86 | C |
| ATOM | 357 | C | ILE | A | 46 | 109.848 | 75.975 | 24.946 | 1.00 27.09 | C |
| ATOM | 358 | O | ILE | A | 46 | 110.282 | 74.843 | 24.701 | 1.00 27.35 | O |
| ATOM | 359 | CB | ILE | A | 46 | 110.375 | 77.537 | 23.028 | 1.00 25.10 | C |
| ATOM | 360 | CG1 | ILE | A | 46 | 110.724 | 76.340 | 22.147 | 1.00 25.03 | C |
| ATOM | 361 | CG2 | ILE | A | 46 | 111.182 | 78.756 | 22.632 | 1.00 26.47 | C |
| ATOM | 362 | CD1 | ILE | A | 46 | 110.468 | 76.573 | 20.657 | 1.00 22.34 | C |
| ATOM | 363 | N | PRO | A | 47 | 108.702 | 76.170 | 25.626 | 1.00 25.80 | N |
| ATOM | 364 | CA | PRO | A | 47 | 107.849 | 75.082 | 26.112 | 1.00 24.42 | C |

TABLE 7-continued

| | | | | | | | | | | |
|---|---|---|---|---|---|---|---|---|---|---|
| ATOM | 365 | C | PRO | A | 47 | 107.077 | 74.339 | 25.024 | 1.00 | 24.61 C |
| ATOM | 366 | O | PRO | A | 47 | 105.912 | 73.988 | 25.223 | 1.00 | 23.97 O |
| ATOM | 367 | CB | PRO | A | 47 | 106.929 | 75.808 | 27.083 | 1.00 | 23.99 C |
| ATOM | 368 | CG | PRO | A | 47 | 106.697 | 77.097 | 26.351 | 1.00 | 23.63 C |
| ATOM | 369 | CD | PRO | A | 47 | 108.135 | 77.467 | 26.036 | 1.00 | 24.98 C |
| ATOM | 370 | N | ILE | A | 48 | 107.735 | 74.063 | 23.901 | 1.00 | 23.91 N |
| ATOM | 371 | CA | ILE | A | 48 | 107.083 | 73.395 | 22.784 | 1.00 | 24.05 C |
| ATOM | 372 | C | ILE | A | 48 | 107.730 | 72.083 | 22.322 | 1.00 | 24.29 C |
| ATOM | 373 | O | ILE | A | 48 | 108.943 | 72.013 | 22.098 | 1.00 | 23.94 O |
| ATOM | 374 | CB | ILE | A | 48 | 106.997 | 74.368 | 21.592 | 1.00 | 25.68 C |
| ATOM | 375 | CG1 | ILE | A | 48 | 106.193 | 75.605 | 22.009 | 1.00 | 25.65 C |
| ATOM | 376 | CG2 | ILE | A | 48 | 106.376 | 73.675 | 20.379 | 1.00 | 25.11 C |
| ATOM | 377 | CD1 | ILE | A | 48 | 106.124 | 76.678 | 20.949 | 1.00 | 26.76 C |
| ATOM | 378 | N | ILE | A | 49 | 106.897 | 71.054 | 22.162 | 1.00 | 23.20 N |
| ATOM | 379 | CA | ILE | A | 49 | 107.343 | 69.732 | 21.725 | 1.00 | 23.13 C |
| ATOM | 380 | C | ILE | A | 49 | 106.454 | 69.215 | 20.588 | 1.00 | 23.01 C |
| ATOM | 381 | O | ILE | A | 49 | 105.241 | 69.397 | 20.623 | 1.00 | 22.62 O |
| ATOM | 382 | CB | ILE | A | 49 | 107.274 | 68.723 | 22.876 | 1.00 | 22.04 C |
| ATOM | 383 | CG1 | ILE | A | 49 | 108.027 | 69.277 | 24.093 | 1.00 | 20.85 C |
| ATOM | 384 | CG2 | ILE | A | 49 | 107.847 | 67.376 | 22.412 | 1.00 | 21.51 C |
| ATOM | 385 | CD1 | ILE | A | 49 | 107.922 | 68.416 | 25.333 | 1.00 | 19.42 C |
| ATOM | 386 | N | THR | A | 50 | 107.059 | 68.573 | 19.587 | 1.00 | 22.84 N |
| ATOM | 387 | CA | THR | A | 50 | 106.303 | 68.049 | 18.449 | 1.00 | 23.78 C |
| ATOM | 388 | C | THR | A | 50 | 105.913 | 66.582 | 18.643 | 1.00 | 24.70 C |
| ATOM | 389 | O | THR | A | 50 | 106.746 | 65.746 | 18.989 | 1.00 | 25.64 O |
| ATOM | 390 | CB | THR | A | 50 | 107.096 | 68.200 | 17.126 | 1.00 | 23.25 C |
| ATOM | 391 | OG1 | THR | A | 50 | 108.344 | 67.503 | 17.219 | 1.00 | 24.27 O |
| ATOM | 392 | CG2 | THR | A | 50 | 107.360 | 69.666 | 16.838 | 1.00 | 23.48 C |
| ATOM | 393 | N | ALA | A | 50 | 104.641 | 66.279 | 18.401 | 1.00 | 24.84 N |
| ATOM | 394 | CA | ALA | A | 51 | 104.100 | 64.937 | 18.576 | 1.00 | 24.13 C |
| ATOM | 395 | C | ALA | A | 51 | 104.842 | 63.813 | 17.849 | 1.00 | 25.28 C |
| ATOM | 396 | O | ALA | A | 51 | 105.385 | 63.997 | 16.760 | 1.00 | 24.45 O |
| ATOM | 397 | CB | ALA | A | 51 | 102.638 | 64.931 | 18.183 | 1.00 | 23.17 C |
| ATOM | 398 | N | ALA | A | 52 | 104.852 | 62.639 | 18.477 | 1.00 | 26.02 N |
| ATOM | 399 | CA | ALA | A | 52 | 105.496 | 61.450 | 17.932 | 1.00 | 26.54 C |
| ATOM | 400 | C | ALA | A | 52 | 104.539 | 60.787 | 16.945 | 1.00 | 26.47 C |
| ATOM | 401 | O | ALA | A | 52 | 104.097 | 59.660 | 17.146 | 1.00 | 26.78 O |
| ATOM | 402 | CB | ALA | A | 52 | 105.833 | 60.484 | 19.063 | 1.00 | 25.79 C |
| HETATM | 403 | N | MSE | A | 53 | 104.221 | 61.496 | 15.871 | 1.00 | 27.09 N |
| HETATM | 404 | CA | MSE | A | 53 | 103.294 | 60.985 | 14.868 | 1.00 | 27.91 C |
| HETATM | 405 | C | MSE | A | 53 | 103.997 | 60.874 | 13.532 | 1.00 | 27.12 C |
| HETATM | 406 | O | MSE | A | 53 | 104.710 | 61.790 | 13.133 | 1.00 | 26.01 O |
| HETATM | 407 | CB | MSE | A | 53 | 102.094 | 61.932 | 14.775 | 1.00 | 29.38 C |
| HETATM | 408 | CG | MSE | A | 53 | 101.381 | 62.108 | 16.124 | 1.00 | 32.60 C |
| HETATM | 409 | SE | MSE | A | 53 | 99.997 | 63.279 | 16.089 | 1.00 | 36.50 SE |
| HETATM | 410 | CE | MSE | A | 53 | 100.826 | 64.714 | 15.572 | 1.00 | 38.59 C |
| ATOM | 411 | N | ASP | A | 54 | 103.790 | 59.757 | 12.837 | 1.00 | 27.85 N |
| ATOM | 412 | CA | ASP | A | 54 | 104.443 | 59.546 | 11.550 | 1.00 | 28.83 C |
| ATOM | 413 | C | ASP | A | 54 | 104.108 | 60.560 | 10.460 | 1.00 | 29.48 C |
| ATOM | 414 | O | ASP | A | 54 | 104.665 | 60.493 | 9.366 | 1.00 | 30.74 O |
| ATOM | 415 | CB | ASP | A | 54 | 104.212 | 58.113 | 11.049 | 1.00 | 29.72 C |
| ATOM | 416 | CG | ASP | A | 54 | 102.754 | 57.784 | 10.826 | 1.00 | 31.41 C |
| ATOM | 417 | OD1 | ASP | A | 54 | 102.474 | 56.604 | 10.539 | 1.00 | 34.67 O |
| ATOM | 418 | OD2 | ASP | A | 54 | 101.888 | 58.674 | 10.925 | 1.00 | 32.27 O |
| ATOM | 419 | N | THR | A | 55 | 103.211 | 61.501 | 10.753 | 1.00 | 29.32 N |
| ATOM | 420 | CA | THR | A | 55 | 102.850 | 62.548 | 9.796 | 1.00 | 27.93 C |
| ATOM | 421 | C | THR | A | 55 | 103.282 | 63.914 | 10.328 | 1.00 | 27.76 C |
| ATOM | 422 | O | THR | A | 55 | 102.985 | 64.945 | 9.728 | 1.00 | 27.97 O |
| ATOM | 423 | CB | THR | A | 55 | 101.328 | 62.574 | 9.497 | 1.00 | 28.66 C |
| ATOM | 424 | OG1 | THR | A | 55 | 100.584 | 62.643 | 10.721 | 1.00 | 28.50 O |
| ATOM | 425 | CG2 | THR | A | 55 | 100.915 | 61.334 | 8.720 | 1.00 | 28.74 C |
| ATOM | 426 | N | VAL | A | 56 | 103.997 | 63.912 | 11.454 | 1.00 | 26.53 N |
| ATOM | 427 | CA | VAL | A | 56 | 104.479 | 65.153 | 12.061 | 1.00 | 25.82 C |
| ATOM | 429 | C | VAL | A | 56 | 105.975 | 65.173 | 12.392 | 1.00 | 25.65 C |
| ATOM | 429 | O | VAL | A | 56 | 106.675 | 66.085 | 11.977 | 1.00 | 27.06 O |
| ATOM | 430 | CB | VAL | A | 56 | 103.700 | 65.500 | 13.361 | 1.00 | 24.87 C |
| ATOM | 431 | CG1 | VAL | A | 56 | 104.243 | 66.781 | 13.975 | 1.00 | 23.59 C |
| ATOM | 432 | CG2 | VAL | A | 56 | 102.230 | 65.679 | 13.052 | 1.00 | 24.94 C |
| ATOM | 433 | N | THR | A | 57 | 106.487 | 64.178 | 13.108 | 1.00 | 25.55 N |
| ATOM | 434 | CA | THR | A | 57 | 107.895 | 64.235 | 13.479 | 1.00 | 24.90 C |
| ATOM | 435 | C | THR | A | 57 | 108.881 | 63.190 | 12.993 | 1.00 | 25.70 C |
| ATOM | 436 | O | THR | A | 57 | 108.933 | 62.077 | 13.510 | 1.00 | 26.76 O |
| ATOM | 437 | CB | THR | A | 57 | 108.070 | 64.304 | 15.022 | 1.00 | 24.37 C |
| ATOM | 438 | OG1 | THR | A | 57 | 107.342 | 65.420 | 15.536 | 1.00 | 24.74 O |
| ATOM | 439 | CG2 | THR | A | 57 | 109.535 | 64.499 | 15.391 | 1.00 | 22.67 C |
| ATOM | 440 | N | GLY | A | 58 | 109.696 | 63.592 | 12.025 | 1.00 | 25.19 N |
| ATOM | 441 | CA | GLY | A | 58 | 110.762 | 62.749 | 11.517 | 1.00 | 24.08 C |
| ATOM | 442 | C | GLY | A | 58 | 112.004 | 63.541 | 11.912 | 1.00 | 23.78 C |
| ATOM | 443 | O | GLY | A | 58 | 111.881 | 64.497 | 12.682 | 1.00 | 21.95 O |

TABLE 7-continued

| | | | | | | | | | | |
|---|---|---|---|---|---|---|---|---|---|---|
| ATOM | 444 | N | SER | A | 59 | 113.180 | 63.179 | 11.399 | 1.00 | 24.38 N |
| ATOM | 445 | CA | SER | A | 59 | 114.417 | 63.901 | 11.723 | 1.00 | 24.47 C |
| ATOM | 446 | C | SER | A | 59 | 114.406 | 65.388 | 11.318 | 1.00 | 24.98 C |
| ATOM | 447 | O | SER | A | 59 | 114.915 | 66.229 | 12.052 | 1.00 | 25.40 O |
| ATOM | 448 | CB | SER | A | 59 | 115.614 | 63.193 | 11.090 | 1.00 | 23.93 C |
| ATOM | 449 | OG | SER | A | 59 | 115.404 | 62.980 | 9.705 | 1.00 | 26.47 O |
| ATOM | 450 | N | LYS | A | 60 | 113.836 | 65.710 | 10.156 | 1.00 | 25.85 N |
| ATOM | 451 | CA | LYS | A | 60 | 113.747 | 67.103 | 9.702 | 1.00 | 26.54 C |
| ATOM | 452 | C | LYS | A | 60 | 112.985 | 67.987 | 10.696 | 1.00 | 25.73 C |
| ATOM | 453 | O | LYS | A | 60 | 113.389 | 69.118 | 10.983 | 1.00 | 25.68 O |
| ATOM | 454 | CB | LYS | A | 60 | 113.029 | 67.190 | 8.358 | 1.00 | 27.44 C |
| ATOM | 455 | CG | LYS | A | 60 | 113.902 | 67.124 | 7.148 | 1.00 | 31.91 C |
| ATOM | 456 | CD | LYS | A | 60 | 113.034 | 67.048 | 5.878 | 1.00 | 35.71 C |
| ATOM | 457 | CE | LYS | A | 60 | 112.071 | 68.237 | 5.710 | 1.00 | 36.50 C |
| ATOM | 458 | NZ | LYS | A | 60 | 112.742 | 69.542 | 5.417 | 1.00 | 38.79 N |
| HETATM | 459 | N | MSE | A | 61 | 111.864 | 67.482 | 11.196 | 1.00 | 25.26 N |
| HETATM | 460 | CA | MSE | A | 61 | 111.060 | 68.242 | 12.140 | 1.00 | 25.61 C |
| HETATM | 461 | C | MSE | A | 61 | 111.773 | 68.317 | 13.482 | 1.00 | 24.55 C |
| HETATM | 462 | O | MSE | A | 61 | 111.805 | 69.373 | 14.115 | 1.00 | 24.99 O |
| HETATM | 463 | CB | MSE | A | 61 | 109.678 | 67.587 | 12.295 | 1.00 | 27.32 C |
| HETATM | 464 | CG | MSE | A | 61 | 108.708 | 68.290 | 13.258 | 1.00 | 29.47 C |
| HETATM | 465 | SE | MSE | A | 61 | 108.189 | 69.988 | 12.808 | 1.00 | 35.03 SE |
| HETATM | 466 | CE | MSE | A | 61 | 109.528 | 70.965 | 13.376 | 1.00 | 35.39 C |
| ATOM | 467 | N | ALA | A | 62 | 112.343 | 67.194 | 13.914 | 1.00 | 23.85 N |
| ATOM | 468 | CA | ALA | A | 62 | 113.065 | 67.144 | 15.184 | 1.00 | 23.20 C |
| ATOM | 469 | C | ALA | A | 62 | 114.223 | 68.124 | 15.141 | 1.00 | 22.77 C |
| ATOM | 470 | O | ALA | A | 62 | 114.588 | 68.717 | 16.147 | 1.00 | 22.10 O |
| ATOM | 471 | CB | ALA | A | 62 | 113.581 | 65.747 | 15.445 | 1.00 | 23.29 C |
| ATOM | 472 | N | ILE | A | 63 | 114.798 | 68.292 | 13.959 | 1.00 | 22.99 N |
| ATOM | 473 | CA | ILE | A | 63 | 115.898 | 69.221 | 13.775 | 1.00 | 23.52 C |
| ATOM | 474 | C | ILE | A | 63 | 115.426 | 70.683 | 13.828 | 1.00 | 24.19 C |
| ATOM | 475 | O | ILE | A | 63 | 116.042 | 71.519 | 14.514 | 1.00 | 23.98 O |
| ATOM | 476 | CB | ILE | A | 63 | 116.606 | 68.934 | 12.442 | 1.00 | 23.78 C |
| ATOM | 477 | CG1 | ILE | A | 63 | 117.400 | 67.627 | 12.569 | 1.00 | 24.18 C |
| ATOM | 478 | CG2 | ILE | A | 63 | 117.476 | 70.110 | 12.047 | 1.00 | 25.35 C |
| ATOM | 479 | CD1 | ILE | A | 63 | 118.130 | 67.209 | 11.319 | 1.00 | 26.14 C |
| ATOM | 480 | N | ALA | A | 64 | 114.326 | 70.981 | 13.129 | 1.00 | 24.07 N |
| ATOM | 481 | CA | ALA | A | 64 | 113.762 | 72.335 | 13.091 | 1.00 | 23.68 C |
| ATOM | 482 | C | ALA | A | 64 | 113.230 | 72.799 | 14.447 | 1.00 | 23.69 C |
| ATOM | 483 | O | ALA | A | 64 | 113.452 | 73.943 | 14.847 | 1.00 | 24.51 O |
| ATOM | 484 | CB | ALA | A | 64 | 112.649 | 72.418 | 12.052 | 1.00 | 22.06 C |
| ATOM | 485 | N | ILE | A | 65 | 112.528 | 71.927 | 15.161 | 1.00 | 23.23 N |
| ATOM | 486 | CA | ILE | A | 65 | 111.993 | 72.336 | 16.456 | 1.00 | 23.60 C |
| ATOM | 487 | C | ILE | A | 65 | 113.100 | 72.513 | 17.500 | 1.00 | 23.66 C |
| ATOM | 488 | O | ILE | A | 65 | 112.983 | 73.332 | 18.416 | 1.00 | 23.86 O |
| ATOM | 489 | CB | ILE | A | 65 | 110.932 | 71.324 | 16.980 | 1.00 | 23.74 C |
| ATOM | 490 | CG1 | ILE | A | 65 | 110.372 | 71.801 | 18.326 | 1.00 | 23.72 C |
| ATOM | 491 | CG2 | ILE | A | 65 | 111.541 | 69.929 | 17.108 | 1.00 | 23.00 C |
| ATOM | 492 | CD1 | ILE | A | 65 | 109.618 | 73.128 | 18.258 | 1.00 | 23.28 C |
| ATOM | 493 | N | ALA | A | 66 | 114.169 | 71.739 | 17.370 | 1.00 | 23.35 N |
| ATOM | 494 | CA | ALA | A | 66 | 115.277 | 71.845 | 18.310 | 1.00 | 24.29 C |
| ATOM | 495 | C | ALA | A | 66 | 116.019 | 73.163 | 18.037 | 1.00 | 23.90 C |
| ATOM | 496 | O | ALA | A | 66 | 116.379 | 73.888 | 18.970 | 1.00 | 23.78 O |
| ATOM | 497 | CB | ALA | A | 66 | 116.222 | 70.639 | 18.164 | 1.00 | 24.32 C |
| ATOM | 498 | N | ARG | A | 67 | 116.236 | 73.480 | 16.762 | 1.00 | 22.77 N |
| ATOM | 499 | CA | ARG | A | 67 | 116.916 | 74.725 | 16.415 | 1.00 | 23.18 C |
| ATOM | 500 | C | ARG | A | 67 | 116.158 | 75.926 | 16.954 | 1.00 | 23.38 C |
| ATOM | 501 | O | ARG | A | 67 | 116.747 | 76.955 | 17.274 | 1.00 | 23.27 O |
| ATOM | 502 | CB | ARG | A | 67 | 117.061 | 74.850 | 14.900 | 1.00 | 23.27 C |
| ATOM | 503 | CG | ARG | A | 67 | 118.069 | 73.896 | 14.321 | 1.00 | 25.02 C |
| ATOM | 504 | CD | ARG | A | 67 | 118.110 | 73.962 | 12.806 | 1.00 | 25.68 C |
| ATOM | 505 | NE | ARG | A | 67 | 119.304 | 73.292 | 12.310 | 1.00 | 27.14 N |
| ATOM | 506 | CZ | ARG | A | 67 | 119.562 | 73.049 | 11.032 | 1.00 | 28.72 C |
| ATOM | 507 | NH1 | ARG | A | 67 | 118.707 | 73.415 | 10.088 | 1.00 | 30.38 N |
| ATOM | 508 | NH2 | ARG | A | 67 | 120.694 | 72.451 | 10.698 | 1.00 | 30.93 N |
| ATOM | 509 | N | ALA | A | 68 | 114.842 | 75.791 | 17.053 | 1.00 | 23.80 N |
| ATOM | 510 | CA | ALA | A | 68 | 114.006 | 76.871 | 17.555 | 1.00 | 24.57 C |
| ATOM | 511 | C | ALA | A | 68 | 114.011 | 76.902 | 19.083 | 1.00 | 24.29 C |
| ATOM | 512 | O | ALA | A | 68 | 113.504 | 77.839 | 19.691 | 1.00 | 25.66 O |
| ATOM | 513 | CB | ALA | A | 68 | 112.582 | 76.714 | 17.032 | 1.00 | 24.39 C |
| ATOM | 514 | N | GLY | A | 69 | 114.582 | 75.876 | 19.704 | 1.00 | 24.27 N |
| ATOM | 515 | CA | GLY | A | 69 | 114.632 | 75.844 | 21.154 | 1.00 | 23.26 C |
| ATOM | 516 | C | GLY | A | 69 | 113.718 | 74.804 | 21.764 | 1.00 | 23.92 C |
| ATOM | 517 | O | GLY | A | 69 | 113.633 | 74.691 | 22.986 | 1.00 | 24.04 O |
| ATOM | 518 | N | GLY | A | 70 | 113.038 | 74.036 | 20.918 | 1.00 | 23.60 N |
| ATOM | 519 | CA | GLY | A | 70 | 112.124 | 73.025 | 21.416 | 1.00 | 23.82 C |
| ATOM | 520 | C | GLY | A | 70 | 112.661 | 71.607 | 21.404 | 1.00 | 24.81 C |
| ATOM | 521 | O | GLY | A | 70 | 113.873 | 71.383 | 21.370 | 1.00 | 24.12 O |
| ATOM | 522 | N | LEU | A | 71 | 111.745 | 70.643 | 21.430 | 1.00 | 24.57 N |

TABLE 7-continued

| | | | | | | | | | | |
|---|---|---|---|---|---|---|---|---|---|---|
| ATOM | 523 | CA | LEU | A | 71 | 112.113 | 69.235 | 21.436 | 1.00 | 24.66 C |
| ATOM | 524 | C | LEU | A | 71 | 111.237 | 68.454 | 20.473 | 1.00 | 25.01 C |
| ATOM | 525 | O | LEU | A | 71 | 110.023 | 68.641 | 20.443 | 1.00 | 26.48 O |
| ATOM | 526 | CB | LEU | A | 71 | 111.945 | 68.653 | 22.842 | 1.00 | 23.51 C |
| ATOM | 527 | CG | LEU | A | 71 | 112.350 | 67.193 | 23.025 | 1.00 | 23.35 C |
| ATOM | 528 | CD1 | LEU | A | 71 | 113.832 | 67.082 | 22.735 | 1.00 | 24.00 C |
| ATOM | 529 | CD2 | LEU | A | 71 | 112.053 | 66.716 | 24.441 | 1.00 | 21.93 C |
| ATOM | 530 | N | GLY | A | 72 | 111.858 | 67.589 | 19.682 | 1.00 | 24.71 N |
| ATOM | 531 | CA | GLY | A | 72 | 111.110 | 66.767 | 18.751 | 1.00 | 24.20 C |
| ATOM | 532 | C | GLY | A | 72 | 111.122 | 65.316 | 19.216 | 1.00 | 23.85 C |
| ATOM | 533 | O | GLY | A | 72 | 112.148 | 64.816 | 19.671 | 1.00 | 24.20 O |
| ATOM | 534 | N | VAL | A | 73 | 109.980 | 64.643 | 19.116 | 1.00 | 23.07 N |
| ATOM | 535 | CA | VAL | A | 73 | 109.874 | 63.247 | 19.519 | 1.00 | 23.30 C |
| ATOM | 536 | C | VAL | A | 73 | 109.683 | 62.388 | 18.269 | 1.00 | 23.74 C |
| ATOM | 537 | O | VAL | A | 73 | 108.610 | 62.387 | 17.664 | 1.00 | 23.75 O |
| ATOM | 538 | CB | VAL | A | 73 | 108.680 | 63.043 | 20.496 | 1.00 | 22.77 C |
| ATOM | 539 | CG1 | VAL | A | 73 | 108.604 | 61.590 | 20.950 | 1.00 | 22.04 C |
| ATOM | 540 | CG2 | VAL | A | 73 | 108.835 | 63.970 | 21.703 | 1.00 | 20.60 C |
| ATOM | 541 | N | ILE | A | 74 | 110.742 | 61.680 | 17.874 | 1.00 | 25.21 N |
| ATOM | 542 | CA | ILE | A | 74 | 110.698 | 60.822 | 16.690 | 1.00 | 26.76 C |
| ATOM | 543 | C | ILE | A | 74 | 109.751 | 59.668 | 16.939 | 1.00 | 28.54 C |
| ATOM | 544 | O | ILE | A | 74 | 109.871 | 58.932 | 17.917 | 1.00 | 28.80 O |
| ATOM | 545 | CB | ILE | A | 74 | 112.070 | 60.216 | 16.332 | 1.00 | 27.10 C |
| ATOM | 546 | CG1 | ILE | A | 74 | 113.127 | 61.317 | 16.167 | 1.00 | 27.28 C |
| ATOM | 547 | CG2 | ILE | A | 74 | 111.934 | 59.376 | 15.058 | 1.00 | 25.49 C |
| ATOM | 548 | CD1 | ILE | A | 74 | 112.841 | 62.293 | 15.058 | 1.00 | 29.69 C |
| ATOM | 549 | N | HIS | A | 75 | 108.808 | 59.517 | 16.029 | 1.00 | 31.17 N |
| ATOM | 550 | CA | HIS | A | 75 | 107.800 | 58.482 | 16.111 | 1.00 | 34.55 C |
| ATOM | 551 | C | HIS | A | 75 | 108.375 | 57.081 | 15.924 | 1.00 | 34.59 C |
| ATOM | 552 | O | HIS | A | 75 | 109.427 | 56.904 | 15.301 | 1.00 | 34.10 O |
| ATOM | 553 | CB | HIS | A | 75 | 106.758 | 58.798 | 15.065 | 1.00 | 39.30 C |
| ATOM | 554 | CG | HIS | A | 75 | 107.336 | 59.466 | 13.861 | 1.00 | 46.72 C |
| ATOM | 555 | ND1 | HIS | A | 75 | 108.504 | 59.030 | 13.267 | 1.00 | 50.41 N |
| ATOM | 556 | CD2 | HIS | A | 75 | 106.850 | 60.439 | 13.055 | 1.00 | 50.89 C |
| ATOM | 557 | CE1 | HIS | A | 75 | 108.706 | 59.698 | 12.143 | 1.00 | 51.89 C |
| ATOM | 558 | NE2 | HIS | A | 75 | 107.716 | 60.561 | 11.990 | 1.00 | 53.11 N |
| ATOM | 559 | N | LYS | A | 76 | 107.666 | 56.086 | 16.458 | 1.00 | 34.75 N |
| ATOM | 560 | CA | LYS | A | 76 | 108.097 | 54.688 | 16.409 | 1.00 | 35.86 C |
| ATOM | 561 | C | LYS | A | 76 | 107.398 | 53.821 | 15.349 | 1.00 | 36.31 C |
| ATOM | 562 | O | LYS | A | 76 | 107.467 | 52.586 | 15.391 | 1.00 | 36.33 O |
| ATOM | 563 | CB | LYS | A | 76 | 107.896 | 54.063 | 17.790 | 1.00 | 35.61 C |
| ATOM | 564 | CG | LYS | A | 76 | 106.439 | 54.013 | 18.235 | 1.00 | 36.48 C |
| ATOM | 565 | CD | LYS | A | 76 | 106.313 | 53.405 | 19.624 | 1.00 | 38.36 C |
| ATOM | 566 | CE | LYS | A | 76 | 104.892 | 52.950 | 19.910 | 1.00 | 38.72 C |
| ATOM | 567 | NZ | LYS | A | 76 | 103.918 | 54.041 | 19.706 | 1.00 | 40.04 N |
| ATOM | 568 | N | ASN | A | 77 | 106.736 | 54.461 | 14.394 | 1.00 | 36.56 N |
| ATOM | 569 | CA | ASN | A | 77 | 106.031 | 53.723 | 13.360 | 1.00 | 36.37 C |
| ATOM | 570 | C | ASN | A | 77 | 107.032 | 53.345 | 12.265 | 1.00 | 36.27 C |
| ATOM | 571 | O | ASN | A | 77 | 106.823 | 53.619 | 11.077 | 1.00 | 36.44 O |
| ATOM | 572 | CB | ASN | A | 77 | 104.904 | 54.587 | 12.784 | 1.00 | 37.00 C |
| ATOM | 573 | CG | ASN | A | 77 | 103.721 | 53.770 | 12.312 | 1.00 | 37.48 C |
| ATOM | 574 | OD1 | ASN | A | 77 | 103.882 | 52.747 | 11.647 | 1.00 | 38.78 O |
| ATOM | 575 | ND2 | ASN | A | 77 | 102.520 | 54.232 | 12.634 | 1.00 | 37.68 N |
| HETATM | 576 | N | MSE | A | 78 | 108.132 | 52.730 | 12.681 | 1.00 | 35.58 N |
| HETATM | 577 | CA | MSE | A | 78 | 109.177 | 52.293 | 11.758 | 1.00 | 36.20 C |
| HETATM | 578 | C | MSE | A | 78 | 110.104 | 51.313 | 12.475 | 1.00 | 35.86 C |
| HETATM | 579 | O | MSE | A | 78 | 110.038 | 51.188 | 13.694 | 1.00 | 36.31 O |
| HETATM | 580 | CB | MSE | A | 78 | 109.956 | 53.500 | 11.207 | 1.00 | 37.66 C |
| HETATM | 581 | CG | MSE | A | 78 | 110.414 | 54.534 | 12.237 | 1.00 | 39.57 C |
| HETATM | 582 | SE | MSE | A | 78 | 111.321 | 55.923 | 11.449 | 1.00 | 43.88 SE |
| HETATM | 583 | CE | MSE | A | 78 | 111.298 | 57.131 | 12.764 | 1.00 | 43.70 C |
| ATOM | 584 | N | SER | A | 79 | 110.956 | 50.606 | 11.739 | 1.00 | 34.43 N |
| ATOM | 585 | CA | SER | A | 79 | 111.828 | 49.639 | 12.391 | 1.00 | 34.01 C |
| ATOM | 586 | C | SER | A | 79 | 112.734 | 50.315 | 13.421 | 1.00 | 34.22 C |
| ATOM | 587 | O | SER | A | 79 | 112.961 | 51.525 | 13.356 | 1.00 | 34.05 O |
| ATOM | 588 | CB | SER | A | 79 | 112.676 | 48.897 | 11.362 | 1.00 | 32.01 C |
| ATOM | 589 | OG | SER | A | 79 | 113.613 | 49.764 | 10.771 | 1.00 | 31.21 O |
| ATOM | 590 | N | ILE | A | 80 | 113.229 | 49.528 | 14.378 | 1.00 | 33.98 N |
| ATOM | 591 | CA | ILE | A | 80 | 114.123 | 50.031 | 15.418 | 1.00 | 34.25 C |
| ATOM | 592 | C | ILE | A | 80 | 115.356 | 50.641 | 14.759 | 1.00 | 34.44 C |
| ATOM | 593 | O | ILE | A | 80 | 115.847 | 51.687 | 15.177 | 1.00 | 34.28 O |
| ATOM | 594 | CB | ILE | A | 80 | 114.574 | 48.895 | 16.369 | 1.00 | 33.95 C |
| ATOM | 595 | CG1 | ILE | A | 80 | 113.366 | 48.322 | 17.105 | 1.00 | 33.91 C |
| ATOM | 596 | CG2 | ILE | A | 80 | 115.594 | 49.416 | 17.369 | 1.00 | 34.09 C |
| ATOM | 597 | CD1 | ILE | A | 80 | 113.714 | 47.217 | 18.090 | 1.00 | 34.10 C |
| ATOM | 598 | N | THR | A | 81 | 115.849 | 49.976 | 13.720 | 1.00 | 34.69 N |
| ATOM | 599 | CA | THR | A | 81 | 117.017 | 50.450 | 12.991 | 1.00 | 34.33 C |
| ATOM | 600 | C | THR | A | 81 | 116.719 | 51.788 | 12.306 | 1.00 | 34.17 C |
| ATOM | 601 | O | THR | A | 81 | 117.533 | 52.708 | 12.365 | 1.00 | 34.07 O |

TABLE 7-continued

| | | | | | | | | | | |
|---|---|---|---|---|---|---|---|---|---|---|
| ATOM | 602 | CB | THR | A | 81 | 117.472 | 49.393 | 11.944 | 1.00 | 33.53 C |
| ATOM | 603 | OG1 | THR | A | 81 | 117.988 | 48.248 | 12.627 | 1.00 | 33.84 O |
| ATOM | 604 | CG2 | THR | A | 81 | 118.542 | 49.942 | 11.036 | 1.00 | 33.63 C |
| ATOM | 605 | N | GLU | A | 82 | 115.550 | 51.895 | 11.674 | 1.00 | 34.36 N |
| ATOM | 606 | CA | GLU | A | 82 | 115.148 | 53.117 | 10.973 | 1.00 | 33.72 C |
| ATOM | 607 | C | GLU | A | 82 | 114.936 | 54.269 | 11.941 | 1.00 | 32.06 C |
| ATOM | 608 | O | GLU | A | 82 | 115.289 | 55.407 | 11.642 | 1.00 | 31.19 O |
| ATOM | 609 | CB | GLU | A | 82 | 113.853 | 52.884 | 10.188 | 1.00 | 37.28 C |
| ATOM | 610 | CG | GLU | A | 82 | 113.953 | 51.828 | 9.093 | 1.00 | 42.63 C |
| ATOM | 611 | CD | GLU | A | 82 | 112.589 | 51.420 | 8.520 | 1.00 | 45.15 C |
| ATOM | 612 | OE1 | GLU | A | 82 | 111.711 | 50.979 | 9.302 | 1.00 | 44.54 O |
| ATOM | 613 | OE2 | GLU | A | 82 | 112.404 | 51.530 | 7.284 | 1.00 | 47.14 O |
| ATOM | 614 | N | GLN | A | 83 | 114.354 | 53.978 | 13.100 | 1.00 | 30.48 N |
| ATOM | 615 | CA | GLN | A | 83 | 114.107 | 55.022 | 14.080 | 1.00 | 29.17 C |
| ATOM | 616 | C | GLN | A | 83 | 115.413 | 55.520 | 14.694 | 1.00 | 29.61 C |
| ATOM | 617 | O | GLN | A | 83 | 115.565 | 56.720 | 14.947 | 1.00 | 30.50 O |
| ATOM | 618 | CB | GLN | A | 83 | 113.178 | 54.526 | 15.186 | 1.00 | 27.78 C |
| ATOM | 619 | CG | GLN | A | 83 | 112.691 | 55.646 | 16.087 | 1.00 | 26.47 C |
| ATOM | 620 | CD | GLN | A | 83 | 111.897 | 55.160 | 17.277 | 1.00 | 25.24 C |
| ATOM | 621 | OE1 | GLN | A | 83 | 111.368 | 55.960 | 18.048 | 1.00 | 27.62 O |
| ATOM | 622 | NE2 | GLN | A | 83 | 111.817 | 53.851 | 17.444 | 1.00 | 25.23 N |
| ATOM | 623 | N | ALA | A | 84 | 116.353 | 54.604 | 14.929 | 1.00 | 29.43 N |
| ATOM | 624 | CA | ALA | A | 84 | 117.654 | 54.955 | 15.501 | 1.00 | 28.41 C |
| ATOM | 625 | C | ALA | A | 84 | 118.472 | 55.837 | 14.559 | 1.00 | 28.88 C |
| ATOM | 626 | O | ALA | A | 84 | 119.146 | 56.766 | 14.998 | 1.00 | 29.24 O |
| ATOM | 627 | CB | ALA | A | 84 | 118.427 | 53.704 | 15.826 | 1.00 | 27.73 C |
| ATOM | 628 | N | GLU | A | 85 | 118.416 | 55.535 | 13.267 | 1.00 | 28.73 N |
| ATOM | 629 | CA | GLU | A | 85 | 119.139 | 56.298 | 12.260 | 1.00 | 31.28 C |
| ATOM | 630 | C | GLU | A | 85 | 118.518 | 57.684 | 12.123 | 1.00 | 31.60 C |
| ATOM | 631 | O | GLU | A | 85 | 119.203 | 58.673 | 11.854 | 1.00 | 30.88 O |
| ATOM | 632 | CB | GLU | A | 85 | 119.072 | 55.557 | 10.922 | 1.00 | 34.79 C |
| ATOM | 633 | CG | GLU | A | 85 | 119.767 | 56.251 | 9.762 | 1.00 | 40.50 C |
| ATOM | 634 | CD | GLU | A | 85 | 121.231 | 56.553 | 10.051 | 1.00 | 43.61 C |
| ATOM | 635 | OE1 | GLU | A | 85 | 121.984 | 55.612 | 10.413 | 1.00 | 44.96 O |
| ATOM | 636 | OE2 | GLU | A | 85 | 121.624 | 57.736 | 9.905 | 1.00 | 44.87 O |
| ATOM | 637 | N | GLU | A | 86 | 117.204 | 57.739 | 12.300 | 1.00 | 31.99 N |
| ATOM | 638 | CA | GLU | A | 86 | 116.452 | 58.983 | 12.232 | 1.00 | 32.20 C |
| ATOM | 639 | C | GLU | A | 86 | 116.996 | 59.854 | 13.382 | 1.00 | 32.56 C |
| ATOM | 640 | O | GLU | A | 86 | 117.257 | 61.053 | 13.218 | 1.00 | 32.08 O |
| ATOM | 641 | CB | GLU | A | 86 | 114.972 | 58.667 | 12.449 | 1.00 | 33.98 C |
| ATOM | 642 | CG | GLU | A | 86 | 114.002 | 59.724 | 11.988 | 1.00 | 38.81 C |
| ATOM | 643 | CD | GLU | A | 86 | 113.971 | 59.856 | 10.480 | 1.00 | 40.86 C |
| ATOM | 644 | OE1 | GLU | A | 86 | 113.133 | 60.628 | 9.969 | 1.00 | 42.44 O |
| ATOM | 645 | OE2 | GLU | A | 86 | 114.785 | 59.190 | 9.807 | 1.00 | 41.41 O |
| ATOM | 646 | N | VAL | A | 87 | 117.176 | 59.225 | 14.543 | 1.00 | 31.45 N |
| ATOM | 647 | CA | VAL | A | 87 | 117.701 | 59.890 | 15.725 | 1.00 | 31.84 C |
| ATOM | 648 | C | VAL | A | 87 | 119.146 | 60.342 | 15.513 | 1.00 | 32.90 C |
| ATOM | 649 | O | VAL | A | 87 | 119.515 | 61.458 | 15.893 | 1.00 | 32.72 O |
| ATOM | 650 | CB | VAL | A | 87 | 117.637 | 58.952 | 16.950 | 1.00 | 31.80 C |
| ATOM | 651 | CG1 | VAL | A | 87 | 118.476 | 59.511 | 18.099 | 1.00 | 31.50 C |
| ATOM | 652 | CG2 | VAL | A | 87 | 116.196 | 58.796 | 17.394 | 1.00 | 30.99 C |
| ATOM | 653 | N | ARG | A | 88 | 119.969 | 59.481 | 14.920 | 1.00 | 32.89 N |
| ATOM | 654 | CA | ARG | A | 88 | 121.353 | 59.860 | 14.679 | 1.00 | 33.91 C |
| ATOM | 655 | C | ARG | A | 88 | 121.385 | 61.104 | 13.813 | 1.00 | 33.69 C |
| ATOM | 656 | O | ARG | A | 88 | 122.176 | 62.007 | 14.060 | 1.00 | 34.42 O |
| ATOM | 657 | CB | ARG | A | 88 | 122.142 | 58.740 | 13.989 | 1.00 | 35.05 C |
| ATOM | 658 | CG | ARG | A | 88 | 122.412 | 57.533 | 14.861 | 1.00 | 38.65 C |
| ATOM | 659 | CD | ARG | A | 88 | 123.375 | 56.540 | 14.195 | 1.00 | 40.90 C |
| ATOM | 660 | NE | ARG | A | 88 | 123.796 | 55.505 | 15.141 | 1.00 | 43.00 N |
| ATOM | 661 | CZ | ARG | A | 88 | 123.038 | 54.493 | 15.550 | 1.00 | 43.55 C |
| ATOM | 662 | NH1 | ARG | A | 88 | 123.515 | 53.610 | 16.421 | 1.00 | 43.61 N |
| ATOM | 663 | NH2 | ARG | A | 88 | 121.819 | 54.340 | 15.060 | 1.00 | 45.10 N |
| ATOM | 664 | N | LYS | A | 89 | 120.519 | 61.167 | 12.805 | 1.00 | 33.67 N |
| ATOM | 665 | CA | LYS | A | 89 | 120.509 | 62.331 | 11.929 | 1.00 | 33.25 C |
| ATOM | 666 | C | LYS | A | 89 | 120.348 | 63.618 | 12.703 | 1.00 | 32.41 C |
| ATOM | 667 | O | LYS | A | 89 | 120.956 | 64.630 | 12.356 | 1.00 | 33.80 O |
| ATOM | 668 | CB | LYS | A | 89 | 119.406 | 62.243 | 10.873 | 1.00 | 33.93 C |
| ATOM | 669 | CG | LYS | A | 89 | 119.689 | 61.251 | 9.758 | 1.00 | 37.76 C |
| ATOM | 670 | CD | LYS | A | 89 | 118.720 | 61.454 | 8.596 | 1.00 | 39.45 C |
| ATOM | 671 | CE | LYS | A | 89 | 118.999 | 60.487 | 7.453 | 1.00 | 39.82 C |
| ATOM | 672 | NZ | LYS | A | 89 | 118.777 | 59.074 | 7.855 | 1.00 | 42.12 N |
| ATOM | 673 | N | VAL | A | 90 | 119.539 | 63.597 | 13.755 | 1.00 | 30.97 N |
| ATOM | 674 | CA | VAL | A | 90 | 119.346 | 64.811 | 14.526 | 1.00 | 29.42 C |
| ATOM | 675 | C | VAL | A | 90 | 120.612 | 65.152 | 15.304 | 1.00 | 29.81 C |
| ATOM | 676 | O | VAL | A | 90 | 120.989 | 66.327 | 15.402 | 1.00 | 29.55 O |
| ATOM | 677 | CB | VAL | A | 90 | 118.145 | 64.690 | 15.494 | 1.00 | 27.62 C |
| ATOM | 678 | CG1 | VAL | A | 90 | 118.020 | 65.958 | 16.335 | 1.00 | 26.39 C |
| ATOM | 679 | CG2 | VAL | A | 90 | 116.863 | 64.484 | 14.697 | 1.00 | 25.45 C |
| ATOM | 680 | N | LYS | A | 91 | 121.280 | 64.132 | 15.839 | 1.00 | 30.20 N |

TABLE 7-continued

| | | | | | | | | | | |
|---|---|---|---|---|---|---|---|---|---|---|
| ATOM | 681 | CA | LYS | A | 91 | 122.502 | 64.372 | 16.607 | 1.00 | 30.65 C |
| ATOM | 682 | C | LYS | A | 91 | 123.646 | 64.827 | 15.701 | 1.00 | 30.99 C |
| ATOM | 683 | O | LYS | A | 91 | 124.487 | 65.625 | 16.105 | 1.00 | 32.06 O |
| ATOM | 684 | CB | LYS | A | 91 | 122.921 | 63.113 | 17.371 | 1.00 | 28.83 C |
| ATOM | 685 | CG | LYS | A | 91 | 121.862 | 62.546 | 18.307 | 1.00 | 28.25 C |
| ATOM | 686 | CD | LYS | A | 91 | 121.288 | 63.582 | 19.281 | 1.00 | 28.84 C |
| ATOM | 687 | CE | LYS | A | 91 | 122.332 | 64.181 | 20.217 | 1.00 | 27.53 C |
| ATOM | 688 | NZ | LYS | A | 91 | 121.726 | 65.148 | 21.203 | 1.00 | 28.66 N |
| ATOM | 689 | N | ARG | A | 92 | 123.664 | 64.329 | 14.470 | 1.00 | 32.03 N |
| ATOM | 690 | CA | ARG | A | 92 | 124.708 | 64.678 | 13.513 | 1.00 | 33.25 C |
| ATOM | 691 | C | ARG | A | 92 | 124.491 | 66.031 | 12.856 | 1.00 | 33.96 C |
| ATOM | 692 | O | ARG | A | 92 | 125.369 | 66.532 | 12.151 | 1.00 | 35.10 O |
| ATOM | 693 | CB | ARG | A | 92 | 124.790 | 63.627 | 12.409 | 1.00 | 34.10 C |
| ATOM | 694 | CG | ARG | A | 92 | 125.206 | 62.236 | 12.834 | 1.00 | 35.26 C |
| ATOM | 695 | CD | ARG | A | 92 | 126.593 | 62.227 | 13.424 | 1.00 | 38.81 C |
| ATOM | 696 | NE | ARG | A | 92 | 127.118 | 60.867 | 13.504 | 1.00 | 40.97 N |
| ATOM | 697 | CZ | ARG | A | 92 | 128.235 | 60.524 | 14.142 | 1.00 | 42.15 C |
| ATOM | 698 | NH1 | ARG | A | 92 | 128.962 | 61.443 | 14.771 | 1.00 | 41.49 N |
| ATOM | 699 | NH2 | ARG | A | 92 | 128.622 | 59.254 | 14.148 | 1.00 | 43.12 N |
| ATOM | 700 | N | SER | A | 93 | 123.325 | 66.625 | 13.075 | 1.00 | 34.14 N |
| ATOM | 701 | CA | SER | A | 93 | 123.016 | 67.910 | 12.461 | 1.00 | 34.71 C |
| ATOM | 702 | C | SER | A | 93 | 124.039 | 69.013 | 12.806 | 1.00 | 35.09 C |
| ATOM | 703 | O | SER | A | 93 | 124.714 | 69.554 | 11.924 | 1.00 | 35.54 O |
| ATOM | 704 | CB | SER | A | 93 | 121.601 | 68.342 | 12.863 | 1.00 | 34.35 C |
| ATOM | 705 | OG | SER | A | 93 | 121.171 | 69.453 | 12.097 | 1.00 | 33.84 O |
| ATOM | 706 | N | GLU | A | 94 | 124.148 | 69.343 | 14.087 | 1.00 | 35.16 N |
| ATOM | 707 | CA | GLU | A | 94 | 125.077 | 70.367 | 14.545 | 1.00 | 35.95 C |
| ATOM | 708 | C | GLU | A | 94 | 126.125 | 69.754 | 15.462 | 1.00 | 34.73 C |
| ATOM | 709 | O | GLU | A | 94 | 125.799 | 68.965 | 16.352 | 1.00 | 34.32 O |
| ATOM | 710 | CB | GLU | A | 94 | 124.290 | 71.494 | 15.221 | 1.00 | 38.41 C |
| ATOM | 711 | CG | GLU | A | 94 | 123.485 | 72.240 | 14.164 | 1.00 | 43.97 C |
| ATOM | 712 | CD | GLU | A | 94 | 122.504 | 73.241 | 14.699 | 1.00 | 46.41 C |
| ATOM | 713 | OE1 | GLU | A | 94 | 122.889 | 74.140 | 15.485 | 1.00 | 49.20 O |
| ATOM | 714 | OE2 | GLU | A | 94 | 121.331 | 73.134 | 14.300 | 1.00 | 49.67 O |
| ATOM | 715 | N | ASN | A | 95 | 127.387 | 70.118 | 15.239 | 1.00 | 33.02 N |
| ATOM | 716 | CA | ASN | A | 95 | 128.479 | 69.543 | 16.012 | 1.00 | 32.01 C |
| ATOM | 717 | C | ASN | A | 95 | 129.343 | 68.043 | 15.831 | 1.00 | 32.61 C |
| ATOM | 718 | O | ASN | A | 95 | 128.609 | 67.259 | 16.747 | 1.00 | 33.70 O |
| ATOM | 719 | CB | ASN | A | 95 | 128.372 | 69.913 | 17.492 | 1.00 | 30.02 C |
| ATOM | 720 | CG | ASN | A | 95 | 128.838 | 71.321 | 17.770 | 1.00 | 29.11 C |
| ATOM | 721 | OD1 | ASN | A | 95 | 128.954 | 71.729 | 18.923 | 1.00 | 29.21 O |
| ATOM | 722 | ND2 | ASN | A | 95 | 129.111 | 72.078 | 16.709 | 1.00 | 29.45 N |
| ATOM | 723 | N | GLY | A | 96 | 127.930 | 67.669 | 14.620 | 1.00 | 32.33 N |
| ATOM | 724 | CA | GLY | A | 96 | 127.697 | 66.283 | 14.265 | 1.00 | 31.72 C |
| ATOM | 725 | C | GLY | A | 96 | 128.798 | 65.309 | 14.592 | 1.00 | 31.80 C |
| ATOM | 726 | O | GLY | A | 96 | 128.522 | 64.157 | 14.919 | 1.00 | 32.70 O |
| ATOM | 727 | N | VAL | A | 97 | 130.044 | 65.759 | 14.494 | 1.00 | 30.80 N |
| ATOM | 728 | CA | VAL | A | 97 | 131.176 | 64.893 | 14.779 | 1.00 | 29.44 C |
| ATOM | 729 | C | VAL | A | 97 | 132.092 | 65.468 | 15.859 | 1.00 | 29.78 C |
| ATOM | 730 | O | VAL | A | 97 | 133.265 | 65.111 | 15.944 | 1.00 | 29.29 O |
| ATOM | 731 | CB | VAL | A | 97 | 131.988 | 64.591 | 13.483 | 1.00 | 29.17 C |
| ATOM | 732 | CG1 | VAL | A | 97 | 131.121 | 63.797 | 12.506 | 1.00 | 27.93 C |
| ATOM | 733 | CG2 | VAL | A | 97 | 132.467 | 65.888 | 12.836 | 1.00 | 27.87 C |
| ATOM | 734 | N | ILE | A | 98 | 131.542 | 66.357 | 16.684 | 1.00 | 29.98 N |
| ATOM | 735 | CA | ILE | A | 98 | 132.288 | 66.962 | 17.789 | 1.00 | 30.43 C |
| ATOM | 736 | C | ILE | A | 98 | 132.855 | 65.806 | 18.637 | 1.00 | 29.83 C |
| ATOM | 737 | O | ILE | A | 98 | 133.873 | 65.950 | 19.309 | 1.00 | 30.21 O |
| ATOM | 738 | CB | ILE | A | 98 | 131.352 | 67.877 | 18.652 | 1.00 | 29.97 C |
| ATOM | 739 | CG1 | ILE | A | 98 | 132.152 | 68.633 | 19.712 | 1.00 | 29.73 C |
| ATOM | 740 | CG2 | ILE | A | 98 | 130.264 | 67.044 | 19.317 | 1.00 | 30.85 C |
| ATOM | 741 | CD1 | ILE | A | 98 | 133.036 | 69.704 | 19.171 | 1.00 | 27.65 C |
| ATOM | 742 | N | ILE | A | 99 | 132.174 | 64.665 | 18.593 | 1.00 | 29.88 N |
| ATOM | 743 | CA | ILE | A | 99 | 132.594 | 63.450 | 19.290 | 1.00 | 31.02 C |
| ATOM | 744 | C | ILE | A | 99 | 132.126 | 62.306 | 18.397 | 1.00 | 32.81 C |
| ATOM | 745 | O | ILE | A | 99 | 131.219 | 62.488 | 17.580 | 1.00 | 34.65 O |
| ATOM | 746 | CB | ILE | A | 99 | 131.937 | 63.285 | 20.675 | 1.00 | 30.36 C |
| ATOM | 747 | CG1 | ILE | A | 99 | 130.431 | 63.074 | 20.522 | 1.00 | 29.67 C |
| ATOM | 748 | CG2 | ILE | A | 99 | 132.225 | 64.503 | 21.530 | 1.00 | 29.88 C |
| ATOM | 749 | CD1 | ILE | A | 99 | 129.736 | 62.684 | 21.811 | 1.00 | 29.26 C |
| ATOM | 750 | N | ASP | A | 100 | 132.724 | 61.130 | 18.544 | 1.00 | 33.17 N |
| ATOM | 751 | CA | ASP | A | 100 | 132.353 | 59.993 | 17.704 | 1.00 | 34.04 C |
| ATOM | 752 | C | ASP | A | 100 | 132.387 | 60.391 | 16.234 | 1.00 | 33.78 C |
| ATOM | 753 | O | ASP | A | 100 | 131.398 | 60.248 | 15.520 | 1.00 | 34.06 O |
| ATOM | 754 | CB | ASP | A | 100 | 130.956 | 59.485 | 18.050 | 1.00 | 35.98 C |
| ATOM | 755 | CG | ASP | A | 100 | 130.844 | 59.045 | 19.490 | 1.00 | 39.21 C |
| ATOM | 756 | OD1 | ASP | A | 100 | 131.737 | 58.305 | 19.952 | 1.00 | 41.93 O |
| ATOM | 757 | OD2 | ASP | A | 100 | 129.861 | 59.425 | 20.159 | 1.00 | 41.57 O |
| ATOM | 758 | N | PRO | A | 101 | 133.532 | 60.909 | 15.767 | 1.00 | 33.06 N |
| ATOM | 759 | CA | PRO | A | 101 | 133.697 | 61.334 | 14.377 | 1.00 | 33.37 C |

TABLE 7-continued

| | | | | | | | | | |
|---|---|---|---|---|---|---|---|---|---|
| ATOM | 760 | C | PRO | A | 101 | 133.763 | 60.179 | 13.382 | 1.00 32.86 C |
| ATOM | 761 | O | PRO | A | 101 | 133.952 | 59.031 | 13.763 | 1.00 33.47 O |
| ATOM | 762 | CB | PRO | A | 101 | 135.007 | 62.112 | 14.438 | 1.00 33.67 C |
| ATOM | 763 | CG | PRO | A | 101 | 135.786 | 61.284 | 15.427 | 1.00 32.82 C |
| ATOM | 764 | CD | PRO | A | 101 | 134.765 | 61.193 | 16.526 | 1.00 32.08 C |
| ATOM | 765 | N | PHE | A | 102 | 133.589 | 60.488 | 12.104 | 1.00 33.11 N |
| ATOM | 766 | CA | PHE | A | 102 | 133.693 | 59.469 | 11.065 | 1.00 33.73 C |
| ATOM | 767 | C | PHE | A | 102 | 135.160 | 59.479 | 10.692 | 1.00 33.47 C |
| ATOM | 768 | O | PHE | A | 102 | 135.813 | 60.506 | 10.805 | 1.00 34.81 O |
| ATOM | 769 | CB | PHE | A | 102 | 132.876 | 59.832 | 9.817 | 1.00 34.53 C |
| ATOM | 770 | CG | PHE | A | 102 | 131.396 | 59.878 | 10.045 | 1.00 35.48 C |
| ATOM | 771 | CD1 | PHE | A | 102 | 130.703 | 58.738 | 10.431 | 1.00 35.76 C |
| ATOM | 772 | CD2 | PHE | A | 102 | 130.691 | 61.069 | 9.880 | 1.00 36.37 C |
| ATOM | 773 | CE1 | PHE | A | 102 | 129.325 | 58.787 | 10.652 | 1.00 37.70 C |
| ATOM | 774 | CE2 | PHE | A | 102 | 129.313 | 61.124 | 10.097 | 1.00 36.90 C |
| ATOM | 775 | CZ | PHE | A | 102 | 128.632 | 59.982 | 10.483 | 1.00 36.80 C |
| ATOM | 776 | N | PHE | A | 103 | 135.684 | 58.346 | 10.252 | 1.00 34.52 N |
| ATOM | 777 | CA | PHE | A | 103 | 137.081 | 58.283 | 9.858 | 1.00 35.62 C |
| ATOM | 778 | C | PHE | A | 103 | 137.394 | 57.001 | 9.104 | 1.00 36.66 C |
| ATOM | 779 | O | PHE | A | 103 | 136.670 | 56.013 | 9.215 | 1.00 37.58 O |
| ATOM | 780 | CB | PHE | A | 103 | 137.989 | 58.453 | 11.094 | 1.00 34.86 C |
| ATOM | 781 | CG | PHE | A | 103 | 137.695 | 57.493 | 12.221 | 1.00 34.87 C |
| ATOM | 782 | CD1 | PHE | A | 103 | 138.125 | 56.168 | 12.167 | 1.00 34.75 C |
| ATOM | 783 | CD2 | PHE | A | 103 | 136.978 | 57.917 | 13.340 | 1.00 34.59 C |
| ATOM | 784 | CE1 | PHE | A | 103 | 137.846 | 55.281 | 13.213 | 1.00 34.04 C |
| ATOM | 785 | CE2 | PHE | A | 103 | 136.696 | 57.037 | 14.387 | 1.00 34.29 C |
| ATOM | 786 | CZ | PHE | A | 103 | 137.130 | 55.720 | 14.322 | 1.00 33.77 C |
| ATOM | 787 | N | LEU | A | 104 | 138.453 | 57.036 | 8.307 | 1.00 37.81 N |
| ATOM | 788 | CA | LEU | A | 104 | 138.872 | 55.879 | 7.532 | 1.00 39.19 C |
| ATOM | 789 | C | LEU | A | 104 | 140.378 | 55.799 | 7.650 | 1.00 40.33 C |
| ATOM | 790 | O | LEU | A | 104 | 141.005 | 56.725 | 8.159 | 1.00 40.69 O |
| ATOM | 791 | CB | LEU | A | 104 | 138.470 | 56.035 | 6.062 | 1.00 39.32 C |
| ATOM | 792 | CG | LEU | A | 104 | 136.970 | 56.076 | 5.745 | 1.00 39.96 C |
| ATOM | 793 | CD1 | LEU | A | 104 | 136.769 | 56.381 | 4.278 | 1.00 40.31 C |
| ATOM | 794 | CD2 | LEU | A | 104 | 136.321 | 54.747 | 6.108 | 1.00 40.67 C |
| ATOM | 795 | N | THR | A | 105 | 140.957 | 54.697 | 7.184 | 1.00 41.82 N |
| ATOM | 796 | CA | THR | A | 105 | 142.402 | 54.502 | 7.249 | 1.00 42.36 C |
| ATOM | 797 | C | THR | A | 105 | 143.017 | 54.739 | 5.880 | 1.00 43.67 C |
| ATOM | 798 | O | THR | A | 105 | 142.305 | 54.885 | 4.892 | 1.00 42.24 O |
| ATOM | 799 | CB | THR | A | 105 | 142.764 | 53.062 | 7.696 | 1.00 42.10 C |
| ATOM | 800 | OG1 | THR | A | 105 | 142.395 | 52.126 | 6.673 | 1.00 41.32 O |
| ATOM | 801 | CG2 | THR | A | 105 | 142.038 | 52.712 | 8.990 | 1.00 40.95 C |
| ATOM | 802 | N | PRO | A | 106 | 144.354 | 54.802 | 5.810 | 1.00 45.85 N |
| ATOM | 803 | CA | PRO | A | 106 | 145.017 | 55.018 | 4.521 | 1.00 48.15 C |
| ATOM | 804 | C | PRO | A | 106 | 144.730 | 53.792 | 3.643 | 1.00 50.24 C |
| ATOM | 805 | O | PRO | A | 106 | 144.611 | 53.881 | 2.419 | 1.00 50.39 O |
| ATOM | 806 | CB | PRO | A | 106 | 146.493 | 55.109 | 4.920 | 1.00 47.46 C |
| ATOM | 807 | CG | PRO | A | 106 | 146.422 | 55.617 | 6.356 | 1.00 46.60 C |
| ATOM | 808 | CD | PRO | A | 106 | 145.364 | 54.693 | 6.876 | 1.00 45.95 C |
| ATOM | 809 | N | GLU | A | 107 | 144.606 | 52.651 | 4.312 | 1.00 51.71 N |
| ATOM | 810 | CA | GLU | A | 107 | 144.347 | 51.375 | 3.670 | 1.00 52.95 C |
| ATOM | 811 | C | GLU | A | 107 | 143.116 | 51.449 | 2.777 | 1.00 52.83 C |
| ATOM | 812 | O | GLU | A | 107 | 143.177 | 51.081 | 1.608 | 1.00 53.42 O |
| ATOM | 813 | CB | GLU | A | 107 | 144.138 | 50.302 | 4.739 | 1.00 55.06 C |
| ATOM | 814 | CG | GLU | A | 107 | 145.023 | 50.465 | 5.974 | 1.00 58.02 C |
| ATOM | 815 | CD | GLU | A | 107 | 146.496 | 50.615 | 5.636 | 1.00 60.20 C |
| ATOM | 816 | OE1 | GLU | A | 107 | 146.863 | 51.634 | 5.009 | 1.00 61.69 O |
| ATOM | 817 | OE2 | GLU | A | 107 | 147.288 | 49.713 | 5.995 | 1.00 62.09 O |
| ATOM | 818 | N | HIS | A | 108 | 142.003 | 51.919 | 3.339 | 1.00 52.97 N |
| ATOM | 819 | CA | HIS | A | 108 | 140.736 | 52.045 | 2.611 | 1.00 52.34 C |
| ATOM | 820 | C | HIS | A | 108 | 140.913 | 52.647 | 1.232 | 1.00 52.01 C |
| ATOM | 821 | O | HIS | A | 108 | 141.923 | 53.284 | 0.942 | 1.00 52.35 O |
| ATOM | 822 | CB | HIS | A | 108 | 139.745 | 52.907 | 3.398 | 1.00 52.32 C |
| ATOM | 823 | CG | HIS | A | 108 | 139.233 | 52.257 | 4.642 | 1.00 52.17 C |
| ATOM | 824 | ND1 | HIS | A | 108 | 138.355 | 51.198 | 4.619 | 1.00 53.21 N |
| ATOM | 825 | CD2 | HIS | A | 108 | 139.495 | 52.498 | 5.947 | 1.00 52.86 C |
| ATOM | 826 | CE1 | HIS | A | 108 | 138.097 | 50.814 | 5.856 | 1.00 52.97 C |
| ATOM | 827 | NE2 | HIS | A | 108 | 138.778 | 51.587 | 6.681 | 1.00 52.99 N |
| ATOM | 828 | N | LYS | A | 109 | 139.915 | 52.443 | 0.387 | 1.00 51.80 N |
| ATOM | 829 | CA | LYS | A | 109 | 139.945 | 52.962 | −0.967 | 1.00 52.18 C |
| ATOM | 830 | C | LYS | A | 109 | 139.137 | 54.260 | −1.038 | 1.00 52.51 C |
| ATOM | 831 | O | LYS | A | 109 | 138.083 | 54.380 | −0.409 | 1.00 52.67 O |
| ATOM | 832 | CB | LYS | A | 109 | 139.370 | 51.922 | −1.929 | 1.00 52.23 C |
| ATOM | 833 | N | VAL | A | 110 | 139.637 | 55.233 | −1.792 | 1.00 52.49 N |
| ATOM | 834 | CA | VAL | A | 110 | 138.942 | 56.509 | −1.938 | 1.00 52.35 C |
| ATOM | 835 | C | VAL | A | 110 | 137.447 | 56.292 | −2.190 | 1.00 52.34 C |
| ATOM | 836 | O | VAL | A | 110 | 136.619 | 57.135 | −1.838 | 1.00 52.26 O |
| ATOM | 837 | CB | VAL | A | 110 | 139.572 | 57.355 | −3.087 | 1.00 52.12 C |
| ATOM | 838 | CG1 | VAL | A | 110 | 139.815 | 56.494 | −4.295 | 1.00 52.21 C |

TABLE 7-continued

| | | | | | | | | | | |
|---|---|---|---|---|---|---|---|---|---|---|
| ATOM | 839 | CG2 | VAL | A | 110 | 138.655 | 58.499 | −3.467 | 1.00 51.75 | C |
| ATOM | 840 | N | SER | A | 111 | 137.111 | 55.151 | −2.785 | 1.00 52.59 | N |
| ATOM | 841 | CA | SER | A | 111 | 135.721 | 54.813 | −3.079 | 1.00 52.79 | C |
| ATOM | 842 | C | SER | A | 111 | 134.908 | 54.753 | −1.799 | 1.00 52.49 | C |
| ATOM | 843 | O | SER | A | 111 | 133.805 | 55.295 | −1.729 | 1.00 52.98 | O |
| ATOM | 844 | CB | SER | A | 111 | 135.630 | 53.457 | −3.785 | 1.00 52.72 | C |
| ATOM | 845 | OG | SER | A | 111 | 136.290 | 53.485 | −5.035 | 1.00 54.78 | O |
| ATOM | 846 | N | GLU | A | 112 | 135.458 | 54.086 | −0.789 | 1.00 51.81 | N |
| ATOM | 847 | CA | GLU | A | 112 | 134.776 | 53.944 | 0.488 | 1.00 51.26 | C |
| ATOM | 848 | C | GLU | A | 112 | 134.617 | 55.315 | 1.135 | 1.00 51.38 | C |
| ATOM | 849 | O | GLU | A | 112 | 133.658 | 55.563 | 1.861 | 1.00 50.07 | O |
| ATOM | 850 | CB | GLU | A | 112 | 135.565 | 52.990 | 1.391 | 1.00 50.74 | C |
| ATOM | 851 | CG | GLU | A | 112 | 135.912 | 51.665 | 0.706 | 1.00 50.40 | C |
| ATOM | 852 | CD | GLU | A | 112 | 136.572 | 50.652 | 1.633 | 1.00 51.24 | C |
| ATOM | 853 | OE1 | GLU | A | 112 | 135.884 | 50.113 | 2.524 | 1.00 51.42 | O |
| ATOM | 854 | OE2 | GLU | A | 112 | 137.786 | 50.399 | 1.476 | 1.00 51.68 | O |
| ATOM | 855 | N | ALA | A | 113 | 135.555 | 56.213 | 0.845 | 1.00 52.48 | N |
| ATOM | 856 | CA | ALA | A | 113 | 135.509 | 57.570 | 1.392 | 1.00 53.74 | C |
| ATOM | 857 | C | ALA | A | 113 | 134.348 | 58.346 | 0.769 | 1.00 53.99 | C |
| ATOM | 858 | O | ALA | A | 113 | 133.653 | 59.108 | 1.450 | 1.00 53.28 | O |
| ATOM | 859 | CB | ALA | A | 113 | 136.834 | 58.294 | 1.129 | 1.00 53.95 | C |
| ATOM | 860 | N | GLU | A | 114 | 134.148 | 58.157 | −0.531 | 1.00 54.68 | N |
| ATOM | 861 | CA | GLU | A | 114 | 133.055 | 58.824 | −1.221 | 1.00 55.97 | C |
| ATOM | 862 | C | GLU | A | 114 | 131.743 | 58.169 | −0.781 | 1.00 56.86 | C |
| ATOM | 863 | O | GLU | A | 114 | 130.685 | 58.799 | −0.811 | 1.00 56.32 | O |
| ATOM | 864 | CB | GLU | A | 114 | 133.228 | 58.705 | −2.732 | 1.00 55.49 | C |
| ATOM | 865 | N | GLU | A | 115 | 131.813 | 56.904 | −0.366 | 1.00 57.91 | N |
| ATOM | 866 | CA | GLU | A | 115 | 130.616 | 56.209 | 0.076 | 1.00 59.80 | C |
| ATOM | 867 | C | GLU | A | 115 | 130.052 | 56.916 | 1.293 | 1.00 60.45 | C |
| ATOM | 868 | O | GLU | A | 115 | 128.866 | 57.239 | 1.326 | 1.00 60.90 | O |
| ATOM | 869 | CB | GLU | A | 115 | 130.905 | 54.747 | 0.444 | 1.00 61.61 | C |
| ATOM | 870 | CG | GLU | A | 115 | 131.454 | 53.877 | −0.683 | 1.00 63.71 | C |
| ATOM | 871 | CD | GLU | A | 115 | 131.451 | 52.391 | −0.333 | 1.00 64.61 | C |
| ATOM | 872 | OE1 | GLU | A | 115 | 131.959 | 52.023 | 0.753 | 1.00 64.98 | O |
| ATOM | 873 | OE2 | GLU | A | 115 | 130.946 | 51.590 | −1.152 | 1.00 65.96 | O |
| ATOM | 874 | N | LEU | A | 116 | 130.898 | 57.161 | 2.294 | 1.00 61.14 | N |
| ATOM | 875 | CA | LEU | A | 116 | 130.433 | 57.830 | 3.504 | 1.00 62.15 | C |
| ATOM | 876 | C | LEU | A | 116 | 130.306 | 59.343 | 3.372 | 1.00 62.60 | C |
| ATOM | 877 | O | LEU | A | 116 | 129.583 | 59.975 | 4.149 | 1.00 62.47 | O |
| ATOM | 878 | CB | LEU | A | 116 | 131.299 | 57.443 | 4.719 | 1.00 62.38 | C |
| ATOM | 879 | CG | LEU | A | 116 | 132.827 | 57.374 | 4.656 | 1.00 62.61 | C |
| ATOM | 880 | CD1 | LEU | A | 116 | 133.375 | 58.712 | 4.232 | 1.00 64.03 | C |
| ATOM | 881 | CD2 | LEU | A | 116 | 133.389 | 56.975 | 6.020 | 1.00 60.86 | C |
| HETATM | 882 | N | MSE | A | 117 | 130.988 | 59.929 | 2.388 | 1.00 63.07 | N |
| HETATM | 883 | CA | MSE | A | 117 | 130.877 | 61.368 | 2.176 | 1.00 63.64 | C |
| HETATM | 884 | C | MSE | A | 117 | 129.512 | 61.672 | 1.578 | 1.00 62.94 | C |
| HETATM | 885 | O | MSE | A | 117 | 128.967 | 62.754 | 1.770 | 1.00 63.05 | O |
| HETATM | 886 | CB | MSE | A | 117 | 131.948 | 61.892 | 1.218 | 1.00 65.51 | C |
| HETATM | 887 | CG | MSE | A | 117 | 133.350 | 61.990 | 1.775 | 1.00 68.03 | C |
| HETATM | 888 | SE | MSE | A | 117 | 134.418 | 62.891 | 0.609 | 1.00 71.39 | SE |
| HETATM | 889 | CE | MSE | A | 117 | 135.980 | 62.908 | 1.489 | 1.00 71.27 | C |
| ATOM | 890 | N | GLN | A | 118 | 128.967 | 60.715 | 0.837 | 1.00 62.33 | N |
| ATOM | 891 | CA | GLN | A | 118 | 127.666 | 60.904 | 0.216 | 1.00 62.54 | C |
| ATOM | 892 | C | GLN | A | 118 | 126.526 | 60.316 | 1.036 | 1.00 61.98 | C |
| ATOM | 893 | O | GLN | A | 118 | 125.375 | 60.725 | 0.884 | 1.00 61.93 | O |
| ATOM | 894 | CB | GLN | A | 118 | 127.664 | 60.341 | −1.215 | 1.00 63.28 | C |
| ATOM | 895 | CG | GLN | A | 118 | 128.093 | 61.366 | −2.289 | 1.00 65.32 | C |
| ATOM | 896 | CD | GLN | A | 118 | 129.504 | 61.938 | −2.088 | 1.00 66.65 | C |
| ATOM | 897 | OE1 | GLN | A | 118 | 129.903 | 62.898 | −2.760 | 1.00 66.36 | O |
| ATOM | 898 | NE2 | GLN | A | 118 | 130.266 | 61.340 | −1.179 | 1.00 67.13 | N |
| ATOM | 899 | N | ARG | A | 119 | 126.843 | 59.371 | 1.915 | 1.00 61.19 | N |
| ATOM | 900 | CA | ARG | A | 119 | 125.819 | 58.770 | 2.762 | 1.00 60.86 | C |
| ATOM | 901 | C | ARG | A | 119 | 125.467 | 59.751 | 3.884 | 1.00 60.07 | C |
| ATOM | 902 | O | ARG | A | 119 | 124.294 | 59.993 | 4.159 | 1.00 60.05 | O |
| ATOM | 903 | CB | ARG | A | 119 | 126.322 | 57.458 | 3.373 | 1.00 61.79 | C |
| ATOM | 904 | CG | ARG | A | 119 | 125.271 | 56.709 | 4.188 | 1.00 63.14 | C |
| ATOM | 905 | CD | ARG | A | 119 | 125.850 | 55.496 | 4.928 | 1.00 64.66 | C |
| ATOM | 906 | NE | ARG | A | 119 | 126.606 | 54.585 | 4.064 | 1.00 66.88 | N |
| ATOM | 907 | CZ | ARG | A | 119 | 126.125 | 53.988 | 2.973 | 1.00 67.98 | C |
| ATOM | 908 | NH1 | ARG | A | 119 | 124.870 | 54.195 | 2.584 | 1.00 68.24 | N |
| ATOM | 909 | NH2 | ARG | A | 119 | 126.902 | 53.171 | 2.269 | 1.00 68.20 | N |
| ATOM | 910 | N | TYR | A | 120 | 126.491 | 60.318 | 4.520 | 1.00 58.88 | N |
| ATOM | 911 | CA | TYR | A | 120 | 126.284 | 61.257 | 5.618 | 1.00 57.61 | C |
| ATOM | 912 | C | TYR | A | 120 | 126.450 | 62.692 | 5.172 | 1.00 57.09 | C |
| ATOM | 913 | O | TYR | A | 120 | 126.409 | 63.612 | 5.989 | 1.00 57.12 | O |
| ATOM | 914 | CB | TYR | A | 120 | 127.257 | 60.974 | 6.766 | 1.00 57.42 | C |
| ATOM | 915 | CG | TYR | A | 120 | 127.192 | 59.552 | 7.269 | 1.00 57.82 | C |
| ATOM | 916 | CD1 | TYR | A | 120 | 127.890 | 58.529 | 6.623 | 1.00 57.64 | C |
| ATOM | 917 | CD2 | TYR | A | 120 | 126.365 | 59.214 | 8.337 | 1.00 57.74 | C |

TABLE 7-continued

| | | | | | | | | | | |
|---|---|---|---|---|---|---|---|---|---|---|
| ATOM | 918 | CE1 | TYR | A | 120 | 127.760 | 57.207 | 7.028 | 1.00 57.96 | C |
| ATOM | 919 | CE2 | TYR | A | 120 | 126.226 | 57.895 | 8.748 | 1.00 58.11 | C |
| ATOM | 920 | CZ | TYR | A | 120 | 126.923 | 56.897 | 8.091 | 1.00 58.31 | C |
| ATOM | 921 | OH | TYR | A | 120 | 126.772 | 55.590 | 8.496 | 1.00 58.89 | O |
| ATOM | 922 | N | ARG | A | 121 | 126.638 | 62.875 | 3.872 | 1.00 56.83 | N |
| ATOM | 923 | CA | ARG | A | 121 | 126.818 | 64.200 | 3.293 | 1.00 56.77 | C |
| ATOM | 924 | C | ARG | A | 121 | 127.838 | 65.035 | 4.069 | 1.00 56.25 | C |
| ATOM | 925 | O | ARG | A | 121 | 127.479 | 65.797 | 4.966 | 1.00 56.28 | O |
| ATOM | 926 | CB | ARG | A | 121 | 125.486 | 64.927 | 3.233 | 1.00 57.20 | C |
| ATOM | 927 | N | ILE | A | 122 | 129.110 | 64.875 | 3.715 | 1.00 56.16 | N |
| ATOM | 928 | CA | ILE | A | 122 | 130.198 | 65.608 | 4.349 | 1.00 55.55 | C |
| ATOM | 929 | C | ILE | A | 122 | 131.305 | 65.938 | 3.339 | 1.00 55.54 | C |
| ATOM | 930 | O | ILE | A | 122 | 131.590 | 65.158 | 2.418 | 1.00 54.76 | O |
| ATOM | 931 | CB | ILE | A | 122 | 130.793 | 64.811 | 5.536 | 1.00 55.74 | C |
| ATOM | 932 | CG1 | ILE | A | 122 | 131.116 | 63.377 | 5.094 | 1.00 55.80 | C |
| ATOM | 933 | CG2 | ILE | A | 122 | 129.830 | 64.836 | 6.717 | 1.00 54.89 | C |
| ATOM | 934 | CD1 | ILE | A | 122 | 131.738 | 62.510 | 6.186 | 1.00 55.41 | C |
| ATOM | 935 | N | SER | A | 123 | 131.915 | 67.106 | 3.535 | 1.00 54.93 | N |
| ATOM | 936 | CA | SER | A | 123 | 132.984 | 67.625 | 2.681 | 1.00 54.06 | C |
| ATOM | 937 | C | SER | A | 123 | 134.342 | 66.963 | 2.907 | 1.00 52.28 | C |
| ATOM | 938 | O | SER | A | 123 | 135.218 | 67.017 | 2.037 | 1.00 51.82 | O |
| ATOM | 939 | CB | SER | A | 123 | 133.121 | 69.139 | 2.902 | 1.00 55.93 | C |
| ATOM | 940 | OG | SER | A | 123 | 134.227 | 69.683 | 2.192 | 1.00 58.65 | O |
| ATOM | 941 | N | GLY | A | 124 | 134.516 | 66.353 | 4.077 | 1.00 50.22 | N |
| ATOM | 942 | CA | GLY | A | 124 | 135.780 | 65.706 | 4.383 | 1.00 47.42 | C |
| ATOM | 943 | C | GLY | A | 124 | 135.668 | 64.500 | 5.297 | 1.00 45.07 | C |
| ATOM | 944 | O | GLY | A | 124 | 134.709 | 64.357 | 6.055 | 1.00 44.24 | O |
| AT0M | 945 | N | VAL | A | 125 | 136.674 | 63.634 | 5.222 | 1.00 43.19 | N |
| ATOM | 946 | CA | VAL | A | 125 | 136.728 | 62.421 | 6.031 | 1.00 40.55 | C |
| ATOM | 947 | C | VAL | A | 125 | 138.068 | 62.319 | 6.761 | 1.00 38.76 | C |
| ATOM | 948 | O | VAL | A | 125 | 139.108 | 62.120 | 6.127 | 1.00 38.57 | O |
| ATOM | 949 | CB | VAL | A | 125 | 136.569 | 61.164 | 5.143 | 1.00 40.66 | C |
| ATOM | 950 | CG1 | VAL | A | 125 | 136.596 | 59.900 | 5.994 | 1.00 38.37 | C |
| ATOM | 951 | CG2 | VAL | A | 125 | 135.287 | 61.260 | 4.349 | 1.00 40.81 | C |
| ATOM | 952 | N | PRO | A | 126 | 138.066 | 62.478 | 8.101 | 1.00 36.88 | N |
| ATOM | 953 | CA | PRO | A | 126 | 139.315 | 62.379 | 8.853 | 1.00 35.19 | C |
| ATOM | 954 | C | PRO | A | 126 | 139.932 | 61.024 | 8.545 | 1.00 35.43 | C |
| ATOM | 955 | O | PRO | A | 126 | 139.225 | 60.021 | 8.465 | 1.00 35.78 | O |
| ATOM | 956 | CB | PRO | A | 126 | 138.837 | 62.486 | 10.296 | 1.00 34.50 | C |
| ATOM | 957 | CG | PRO | A | 126 | 137.674 | 63.417 | 10.171 | 1.00 34.23 | C |
| ATOM | 958 | CD | PRO | A | 126 | 136.951 | 62.747 | 9.026 | 1.00 35.70 | C |
| ATOM | 959 | N | ILE | A | 127 | 141.244 | 60.993 | 8.351 | 1.00 35.94 | N |
| ATOM | 960 | CA | ILE | A | 127 | 141.934 | 59.741 | 8.048 | 1.00 35.44 | C |
| ATOM | 961 | C | ILE | A | 127 | 142.914 | 59.398 | 9.158 | 1.00 34.68 | C |
| ATOM | 962 | O | ILE | A | 127 | 143.803 | 60.183 | 9.481 | 1.00 34.35 | O |
| ATOM | 963 | CB | ILE | A | 127 | 142.673 | 59.831 | 6.687 | 1.00 35.26 | C |
| ATOM | 964 | CG1 | ILE | A | 127 | 141.653 | 60.068 | 5.574 | 1.00 33.84 | C |
| ATOM | 965 | CG2 | ILE | A | 127 | 143.454 | 58.559 | 6.420 | 1.00 34.74 | C |
| ATOM | 966 | CD1 | ILE | A | 127 | 140.587 | 59.008 | 5.506 | 1.00 32.76 | C |
| ATOM | 967 | N | VAL | A | 128 | 142.733 | 58.220 | 9.744 | 1.00 35.29 | N |
| ATOM | 968 | CA | VAL | A | 128 | 143.577 | 57.769 | 10.842 | 1.00 35.15 | C |
| ATOM | 969 | C | VAL | A | 128 | 144.430 | 56.582 | 10.430 | 1.00 36.25 | C |
| ATOM | 970 | O | VAL | A | 128 | 144.079 | 55.831 | 9.522 | 1.00 35.92 | O |
| ATOM | 971 | CB | VAL | A | 128 | 142.721 | 57.391 | 12.065 | 1.00 34.44 | C |
| ATOM | 972 | CG1 | VAL | A | 128 | 141.877 | 58.590 | 12.486 | 1.00 33.76 | C |
| ATOM | 973 | CG2 | VAL | A | 128 | 141.820 | 56.211 | 11.732 | 1.00 34.06 | C |
| ATOM | 974 | N | GLU | A | 129 | 145.556 | 56.416 | 11.106 | 1.00 37.38 | N |
| ATOM | 975 | CA | GLU | A | 129 | 146.467 | 55.332 | 10.798 | 1.00 39.94 | C |
| ATOM | 976 | C | GLU | A | 129 | 145.759 | 53.984 | 10.909 | 1.00 40.56 | C |
| ATOM | 977 | O | GLU | A | 129 | 145.765 | 53.196 | 9.967 | 1.00 41.74 | O |
| ATOM | 978 | CB | GLU | A | 129 | 147.666 | 55.398 | 11.743 | 1.00 42.72 | C |
| ATOM | 979 | CG | GLU | A | 129 | 148.817 | 54.478 | 11.383 | 1.00 46.98 | C |
| ATOM | 980 | CD | GLU | A | 129 | 150.030 | 54.715 | 12.260 | 1.00 48.82 | C |
| ATOM | 981 | OE1 | GLU | A | 129 | 151.062 | 54.051 | 12.044 | 1.00 51.32 | O |
| ATOM | 982 | OE2 | GLU | A | 129 | 149.952 | 55.568 | 13.165 | 1.00 50.14 | O |
| ATOM | 983 | N | THR | A | 130 | 145.138 | 53.733 | 12.057 | 1.00 41.09 | N |
| ATOM | 984 | CA | THR | A | 130 | 144.414 | 52.487 | 12.309 | 1.00 41.55 | C |
| ATOM | 985 | C | THR | A | 130 | 143.047 | 52.806 | 12.908 | 1.00 42.57 | C |
| ATOM | 986 | O | THR | A | 130 | 142.936 | 53.676 | 13.769 | 1.00 42.54 | O |
| ATOM | 987 | CB | THR | A | 130 | 145.185 | 51.596 | 13.311 | 1.00 41.31 | C |
| ATOM | 988 | OG1 | THR | A | 130 | 146.399 | 51.125 | 12.716 | 1.00 42.29 | O |
| ATOM | 989 | CG2 | THR | A | 130 | 144.359 | 50.423 | 13.721 | 1.00 42.50 | C |
| ATOM | 990 | N | LEU | A | 131 | 142.004 | 52.115 | 12.459 | 1.00 43.48 | N |
| ATOM | 991 | CA | LEU | A | 131 | 140.673 | 52.358 | 13.010 | 1.00 44.46 | C |
| ATOM | 992 | C | LEU | A | 131 | 140.687 | 52.246 | 14.537 | 1.00 45.25 | C |
| ATOM | 993 | O | LEU | A | 131 | 139.931 | 52.937 | 15.223 | 1.00 45.86 | O |
| ATOM | 994 | CB | LEU | A | 131 | 139.653 | 51.354 | 12.463 | 1.00 43.91 | C |
| ATOM | 995 | CG | LEU | A | 131 | 139.245 | 51.387 | 10.993 | 1.00 44.06 | C |
| ATOM | 996 | CD1 | LEU | A | 131 | 138.161 | 50.346 | 10.768 | 1.00 43.41 | C |

TABLE 7-continued

| | | | | | | | | | | |
|---|---|---|---|---|---|---|---|---|---|---|
| ATOM | 997 | CD2 | LEU | A | 131 | 138.724 | 52.767 | 10.616 | 1.00 | 43.19 C |
| ATOM | 998 | N | ALA | A | 132 | 141.547 | 51.370 | 15.058 | 1.00 | 45.26 N |
| ATOM | 999 | CA | ALA | A | 132 | 141.662 | 51.144 | 16.497 | 1.00 | 45.23 C |
| ATOM | 1000 | C | ALA | A | 132 | 142.550 | 52.169 | 17.192 | 1.00 | 45.48 C |
| ATOM | 1001 | O | ALA | A | 132 | 142.308 | 52.513 | 18.350 | 1.00 | 45.96 O |
| ATOM | 1002 | CB | ALA | A | 132 | 142.194 | 49.742 | 16.757 | 1.00 | 45.56 C |
| ATOM | 1003 | N | ASN | A | 133 | 143.576 | 52.647 | 16.490 | 1.00 | 45.46 N |
| ATOM | 1004 | CA | ASN | A | 133 | 144.501 | 53.631 | 17.046 | 1.00 | 45.65 C |
| ATOM | 1005 | C | ASN | A | 133 | 143.949 | 55.048 | 16.975 | 1.00 | 43.65 C |
| ATOM | 1006 | O | ASN | A | 133 | 144.187 | 55.858 | 17.869 | 1.00 | 42.55 O |
| ATOM | 1007 | CB | ASN | A | 133 | 145.843 | 53.574 | 16.311 | 1.00 | 49.92 C |
| ATOM | 1008 | CG | ASN | A | 133 | 146.520 | 52.219 | 16.448 | 1.00 | 56.12 C |
| ATOM | 1009 | OD1 | ASN | A | 133 | 146.006 | 51.203 | 15.966 | 1.00 | 58.65 O |
| ATOM | 1010 | ND2 | ASN | A | 133 | 147.675 | 52.191 | 17.123 | 1.00 | 58.07 N |
| ATOM | 1011 | N | ARG | A | 134 | 143.216 | 55.339 | 15.907 | 1.00 | 40.92 N |
| ATOM | 1012 | CA | ARG | A | 134 | 142.625 | 56.658 | 15.695 | 1.00 | 39.45 C |
| ATOM | 1013 | C | ARG | A | 134 | 143.613 | 57.821 | 15.694 | 1.00 | 38.37 C |
| ATOM | 1014 | O | ARG | A | 134 | 143.246 | 58.957 | 15.992 | 1.00 | 36.45 O |
| ATOM | 1015 | CB | ARG | A | 134 | 141.497 | 56.900 | 16.709 | 1.00 | 38.26 C |
| ATOM | 1016 | CG | ARG | A | 134 | 140.300 | 56.027 | 16.404 | 1.00 | 38.05 C |
| ATOM | 1017 | CD | ARG | A | 134 | 139.161 | 56.142 | 17.384 | 1.00 | 38.82 C |
| ATOM | 1018 | NE | ARG | A | 134 | 138.665 | 57.501 | 17.541 | 1.00 | 39.64 N |
| ATOM | 1019 | CZ | ARG | A | 134 | 137.458 | 57.789 | 18.023 | 1.00 | 41.06 C |
| ATOM | 1020 | NH1 | ARG | A | 134 | 136.635 | 56.808 | 18.381 | 1.00 | 41.95 N |
| ATOM | 1021 | NH2 | ARG | A | 134 | 137.079 | 59.052 | 18.177 | 1.00 | 40.31 N |
| ATOM | 1022 | N | LYS | A | 135 | 144.861 | 57.532 | 15.335 | 1.00 | 38.36 N |
| ATOM | 1023 | CA | LYS | A | 135 | 145.888 | 58.562 | 15.277 | 1.00 | 38.55 C |
| ATOM | 1024 | C | LYS | A | 135 | 145.654 | 59.286 | 13.962 | 1.00 | 38.13 C |
| ATOM | 1025 | O | LYS | A | 135 | 145.719 | 58.689 | 12.888 | 1.00 | 38.05 O |
| ATOM | 1026 | CB | LYS | A | 135 | 147.286 | 57.944 | 15.286 | 1.00 | 40.56 C |
| ATOM | 1027 | CG | LYS | A | 135 | 148.357 | 58.915 | 15.766 | 1.00 | 44.66 C |
| ATOM | 1028 | CD | LYS | A | 135 | 149.768 | 58.434 | 15.482 | 1.00 | 46.81 C |
| ATOM | 1029 | CE | LYS | A | 135 | 150.058 | 58.514 | 13.995 | 1.00 | 48.72 C |
| ATOM | 1030 | NZ | LYS | A | 135 | 151.483 | 58.202 | 13.692 | 1.00 | 51.64 N |
| ATOM | 1031 | N | LEU | A | 136 | 145.372 | 60.577 | 14.041 | 1.00 | 37.97 N |
| ATOM | 1032 | CA | LEU | A | 136 | 145.083 | 61.351 | 12.842 | 1.00 | 37.65 C |
| ATOM | 1033 | C | LEU | A | 136 | 146.305 | 61.414 | 11.939 | 1.00 | 37.71 C |
| ATOM | 1034 | O | LEU | A | 136 | 147.377 | 61.816 | 12.375 | 1.00 | 37.36 O |
| ATOM | 1035 | CB | LEU | A | 136 | 144.675 | 62.772 | 13.222 | 1.00 | 36.41 C |
| ATOM | 1036 | CG | LEU | A | 136 | 143.745 | 63.524 | 12.278 | 1.00 | 36.38 C |
| ATOM | 1037 | CD1 | LEU | A | 136 | 143.847 | 64.993 | 12.619 | 1.00 | 37.47 C |
| ATOM | 1038 | CD2 | LEU | A | 136 | 144.126 | 63.310 | 10.839 | 1.00 | 37.55 C |
| ATOM | 1039 | N | VAL | A | 137 | 146.153 | 61.015 | 10.684 | 1.00 | 37.97 N |
| ATOM | 1040 | CA | VAL | A | 137 | 147.270 | 61.082 | 9.755 | 1.00 | 38.94 C |
| ATOM | 1041 | C | VAL | A | 137 | 146.934 | 62.066 | 8.654 | 1.00 | 39.72 C |
| ATOM | 1042 | O | VAL | A | 137 | 147.820 | 62.555 | 7.953 | 1.00 | 41.11 O |
| ATOM | 1043 | CB | VAL | A | 137 | 147.599 | 59.708 | 9.131 | 1.00 | 39.02 C |
| ATOM | 1044 | CG1 | VAL | A | 137 | 148.108 | 58.761 | 10.207 | 1.00 | 39.27 C |
| ATOM | 1045 | CG2 | VAL | A | 137 | 146.369 | 59.134 | 8.452 | 1.00 | 39.34 C |
| ATOM | 1046 | N | GLY | A | 138 | 145.647 | 62.366 | 8.510 | 1.00 | 39.89 N |
| ATOM | 1047 | CA | GLY | A | 138 | 145.225 | 63.305 | 7.487 | 1.00 | 40.00 C |
| ATOM | 1048 | C | GLY | A | 138 | 143.723 | 63.410 | 7.327 | 1.00 | 40.02 C |
| ATOM | 1049 | O | GLY | A | 138 | 142.964 | 62.994 | 8.197 | 1.00 | 39.08 O |
| ATOM | 1050 | N | ILE | A | 139 | 143.292 | 63.972 | 6.208 | 1.00 | 40.37 N |
| ATOM | 1051 | CA | ILE | A | 139 | 141.873 | 64.123 | 5.951 | 1.00 | 42.42 C |
| ATOM | 1052 | C | ILE | A | 139 | 141.619 | 64.260 | 4.462 | 1.00 | 44.67 C |
| ATOM | 1053 | O | ILE | A | 139 | 142.292 | 65.033 | 3.784 | 1.00 | 47.01 O |
| ATOM | 1054 | CB | ILE | A | 139 | 141.318 | 65.358 | 6.674 | 1.00 | 40.67 C |
| ATOM | 1055 | CG1 | ILE | A | 139 | 139.861 | 65.581 | 6.289 | 1.00 | 39.76 C |
| ATOM | 1056 | CG2 | ILE | A | 139 | 142.149 | 66.568 | 6.332 | 1.00 | 41.34 C |
| ATOM | 1057 | CD1 | ILE | A | 139 | 139.218 | 66.707 | 7.054 | 1.00 | 39.54 C |
| ATOM | 1058 | N | ILE | A | 140 | 140.656 | 63.504 | 3.946 | 1.00 | 46.05 N |
| ATOM | 1059 | CA | ILE | A | 140 | 140.339 | 63.579 | 2.524 | 1.00 | 46.92 C |
| ATOM | 1060 | C | ILE | A | 140 | 139.150 | 64.519 | 2.348 | 1.00 | 47.17 C |
| ATOM | 1061 | O | ILE | A | 140 | 138.198 | 64.483 | 3.133 | 1.00 | 46.73 O |
| ATOM | 1062 | CB | ILE | A | 140 | 140.011 | 62.179 | 1.944 | 1.00 | 47.40 C |
| ATOM | 1063 | CG1 | ILE | A | 140 | 139.843 | 62.274 | 0.430 | 1.00 | 48.09 C |
| ATOM | 1064 | CG2 | ILE | A | 140 | 138.739 | 61.622 | 2.572 | 1.00 | 46.23 C |
| ATOM | 1065 | CD1 | ILE | A | 140 | 139.614 | 60.936 | −0.222 | 1.00 | 49.16 C |
| ATOM | 1066 | N | THR | A | 141 | 139.221 | 65.379 | 1.334 | 1.00 | 48.17 N |
| ATOM | 1067 | CA | THR | A | 141 | 138.152 | 66.343 | 1.072 | 1.00 | 49.05 C |
| ATOM | 1068 | C | THR | A | 141 | 137.655 | 66.341 | −0.379 | 1.00 | 50.14 C |
| ATOM | 1069 | O | THR | A | 141 | 138.275 | 65.739 | −1.259 | 1.00 | 49.18 O |
| ATOM | 1070 | CB | THR | A | 141 | 138.606 | 67.774 | 1.423 | 1.00 | 47.83 C |
| ATOM | 1071 | OG1 | THR | A | 141 | 139.757 | 68.119 | 0.640 | 1.00 | 46.02 O |
| ATOM | 1072 | CG2 | THR | A | 141 | 138.942 | 67.872 | 2.899 | 1.00 | 47.21 C |
| ATOM | 1073 | N | ASN | A | 142 | 136.528 | 67.021 | −0.608 | 1.00 | 51.50 N |
| ATOM | 1074 | CA | ASN | A | 142 | 135.933 | 67.126 | −1.939 | 1.00 | 52.02 C |
| ATOM | 1075 | C | ASN | A | 142 | 137.001 | 67.465 | −2.969 | 1.00 | 52.18 C |

TABLE 7-continued

| | | | | | | | | | | |
|---|---|---|---|---|---|---|---|---|---|---|
| ATOM | 1076 | O | ASN | A | 142 | 137.129 | 66.788 | −3.996 | 1.00 | 51.47 O |
| ATOM | 1077 | CB | ASN | A | 142 | 134.855 | 68.212 | −1.971 | 1.00 | 52.46 C |
| ATOM | 1078 | CG | ASN | A | 142 | 133.687 | 67.903 | −1.070 | 1.00 | 53.06 C |
| ATOM | 1079 | OD1 | ASN | A | 142 | 133.150 | 66.803 | −1.098 | 1.00 | 53.57 O |
| ATOM | 1080 | ND2 | ASN | A | 142 | 133.269 | 66.884 | −0.279 | 1.00 | 53.81 N |
| ATOM | 1081 | N | ARG | A | 143 | 137.756 | 68.525 | −2.692 | 1.00 | 52.54 N |
| ATOM | 1082 | CA | ARG | A | 143 | 138.825 | 68.951 | −3.584 | 1.00 | 54.02 C |
| ATOM | 1083 | C | ARG | A | 143 | 139.664 | 67.726 | −3.944 | 1.00 | 54.83 C |
| ATOM | 1084 | O | ARG | A | 143 | 140.061 | 67.543 | −5.096 | 1.00 | 54.60 O |
| ATOM | 1085 | CB | ARG | A | 143 | 139.695 | 70.014 | −2.902 | 1.00 | 53.82 C |
| ATOM | 1086 | N | ASP | A | 144 | 139.915 | 66.883 | −2.949 | 1.00 | 55.80 N |
| ATOM | 1087 | CA | ASP | A | 144 | 140.700 | 65.677 | −3.152 | 1.00 | 56.78 C |
| ATOM | 1088 | C | ASP | A | 144 | 139.969 | 64.713 | −4.074 | 1.00 | 56.65 C |
| ATOM | 1089 | O | ASP | A | 144 | 140.574 | 64.119 | −4.959 | 1.00 | 56.82 O |
| ATOM | 1090 | CB | ASP | A | 144 | 140.969 | 64.991 | −1.812 | 1.00 | 58.80 C |
| ATOM | 1091 | CG | ASP | A | 144 | 141.647 | 65.910 | −0.810 | 1.00 | 61.29 C |
| ATOM | 1092 | OD1 | ASP | A | 144 | 141.895 | 65.471 | 0.337 | 1.00 | 61.86 O |
| ATOM | 1093 | OD2 | ASP | A | 144 | 141.931 | 67.075 | −1.171 | 1.00 | 63.17 O |
| HETATM | 1094 | N | MSE | A | 145 | 138.667 | 64.562 | −3.870 | 1.00 | 56.83 N |
| HETATM | 1095 | CA | MSE | A | 145 | 137.880 | 63.639 | −4.682 | 1.00 | 57.70 C |
| HETATM | 1096 | C | MSE | A | 145 | 137.785 | 64.062 | −6.151 | 1.00 | 57.60 C |
| HETATM | 1097 | O | MSE | A | 145 | 137.748 | 63.206 | −7.041 | 1.00 | 57.31 O |
| HETATM | 1098 | CB | MSE | A | 145 | 136.471 | 63.475 | −4.085 | 1.00 | 59.38 C |
| HETATM | 1099 | CG | MSE | A | 145 | 136.437 | 62.951 | −2.630 | 1.00 | 60.94 C |
| HETATM | 1100 | SE | MSE | A | 145 | 137.129 | 61.269 | −2.351 | 1.00 | 62.97 SE |
| HETATM | 1101 | CE | MSE | A | 145 | 135.969 | 60.258 | −3.296 | 1.00 | 61.65 C |
| ATOM | 1102 | N | ARG | A | 146 | 137.750 | 65.371 | −6.407 | 1.00 | 57.09 N |
| ATOM | 1103 | CA | ARG | A | 146 | 137.664 | 65.877 | −7.782 | 1.00 | 56.31 C |
| ATOM | 1104 | C | ARG | A | 146 | 138.988 | 65.762 | −8.528 | 1.00 | 56.60 C |
| ATOM | 1105 | O | ARG | A | 146 | 139.012 | 65.623 | −9.750 | 1.00 | 56.62 O |
| ATOM | 1106 | CB | ARG | A | 146 | 137.156 | 67.326 | −7.793 | 1.00 | 54.46 C |
| ATOM | 1107 | CG | ARG | A | 146 | 135.700 | 67.413 | −7.370 | 1.00 | 53.47 C |
| ATOM | 1108 | CD | ARG | A | 146 | 135.118 | 68.816 | −7.389 | 1.00 | 52.51 C |
| ATOM | 1109 | NE | ARG | A | 146 | 135.796 | 69.724 | −6.471 | 1.00 | 51.48 N |
| ATOM | 1110 | CZ | ARG | A | 146 | 135.178 | 70.651 | −5.747 | 1.00 | 50.40 C |
| ATOM | 1111 | NH1 | ARG | A | 146 | 135.878 | 71.435 | −4.942 | 1.00 | 50.47 N |
| ATOM | 1112 | NH2 | ARG | A | 146 | 133.858 | 70.774 | −5.804 | 1.00 | 49.06 N |
| ATOM | 1113 | N | PHE | A | 147 | 140.087 | 65.813 | −7.787 | 1.00 | 57.55 N |
| ATOM | 1114 | CA | PHE | A | 147 | 141.414 | 65.682 | −8.375 | 1.00 | 58.70 C |
| ATOM | 1115 | C | PHE | A | 147 | 141.641 | 64.221 | −8.736 | 1.00 | 59.46 C |
| ATOM | 1116 | O | PHE | A | 147 | 142.318 | 63.911 | −9.718 | 1.00 | 58.95 O |
| ATOM | 1117 | CB | PHE | A | 147 | 142.485 | 66.148 | −7.377 | 1.00 | 58.89 C |
| ATOM | 1118 | CG | PHE | A | 147 | 143.894 | 65.843 | −7.807 | 1.00 | 59.83 C |
| ATOM | 1119 | CD1 | PHE | A | 147 | 144.369 | 64.530 | −7.822 | 1.00 | 60.00 C |
| ATOM | 1120 | CD2 | PHE | A | 147 | 144.741 | 66.865 | −8.228 | 1.00 | 60.66 C |
| ATOM | 1121 | CE1 | PHE | A | 147 | 145.662 | 64.238 | −8.252 | 1.00 | 60.08 C |
| ATOM | 1122 | CE2 | PHE | A | 147 | 146.040 | 66.587 | −8.661 | 1.00 | 60.69 C |
| ATOM | 1123 | CZ | PHE | A | 147 | 146.500 | 65.268 | −8.673 | 1.00 | 60.63 C |
| ATOM | 1124 | N | ILE | A | 148 | 141.062 | 63.335 | −7.928 | 1.00 | 60.40 N |
| ATOM | 1125 | CA | ILE | A | 148 | 141.187 | 61.889 | −8.103 | 1.00 | 62.00 C |
| ATOM | 1126 | C | ILE | A | 148 | 140.398 | 61.335 | −9.291 | 1.00 | 63.07 C |
| ATOM | 1127 | O | ILE | A | 148 | 139.203 | 61.593 | −9.441 | 1.00 | 62.54 O |
| ATOM | 1128 | CB | ILE | A | 148 | 140.735 | 61.148 | −6.823 | 1.00 | 61.84 C |
| ATOM | 1129 | CG1 | ILE | A | 148 | 141.583 | 61.602 | −5.640 | 1.00 | 60.88 C |
| ATOM | 1130 | CG2 | ILE | A | 148 | 140.870 | 59.641 | −7.006 | 1.00 | 61.40 C |
| ATOM | 1131 | CD1 | ILE | A | 148 | 141.125 | 61.022 | −4.335 | 1.00 | 61.89 C |
| ATOM | 1132 | N | SER | A | 149 | 141.083 | 60.554 | −10.120 | 1.00 | 65.13 N |
| ATOM | 1133 | CA | SER | A | 149 | 140.476 | 59.958 | −11.299 | 1.00 | 67.10 C |
| ATOM | 1134 | C | SER | A | 149 | 139.843 | 58.606 | −10.999 | 1.00 | 68.06 C |
| ATOM | 1135 | O | SER | A | 149 | 138.637 | 58.434 | −11.177 | 1.00 | 68.25 O |
| ATOM | 1136 | CB | SER | A | 149 | 141.522 | 59.797 | −12.399 | 1.00 | 67.81 C |
| ATOM | 1137 | OG | SER | A | 149 | 140.952 | 59.177 | −13.539 | 1.00 | 70.51 O |
| ATOM | 1138 | N | ASP | A | 150 | 140.655 | 57.649 | −10.552 | 1.00 | 68.94 N |
| ATOM | 1139 | CA | ASP | A | 150 | 140.150 | 56.315 | −10.231 | 1.00 | 70.14 C |
| ATOM | 1140 | C | ASP | A | 150 | 139.976 | 56.065 | −8.731 | 1.00 | 70.46 C |
| ATOM | 1141 | O | ASP | A | 150 | 140.951 | 56.007 | −7.976 | 1.00 | 69.92 O |
| ATOM | 1142 | CB | ASP | A | 150 | 141.060 | 55.240 | −10.832 | 1.00 | 70.63 C |
| ATOM | 1143 | CG | ASP | A | 150 | 140.627 | 53.834 | −10.454 | 1.00 | 71.26 C |
| ATOM | 1144 | OD1 | ASP | A | 150 | 140.813 | 53.447 | −9.281 | 1.00 | 71.97 O |
| ATOM | 1145 | OD2 | ASP | A | 150 | 140.084 | 53.120 | −11.323 | 1.00 | 71.75 O |
| ATOM | 1146 | N | TYR | A | 151 | 138.720 | 55.901 | −8.320 | 1.00 | 71.24 N |
| ATOM | 1147 | CA | TYR | A | 151 | 138.374 | 55.667 | −6.924 | 1.00 | 72.22 C |
| ATOM | 1148 | C | TYR | A | 151 | 138.715 | 54.281 | −6.383 | 1.00 | 73.14 C |
| ATOM | 1149 | O | TYR | A | 151 | 138.725 | 54.073 | −5.173 | 1.00 | 73.06 O |
| ATOM | 1150 | CB | TYR | A | 151 | 136.886 | 55.953 | −6.698 | 1.00 | 71.67 C |
| ATOM | 1151 | CG | TYR | A | 151 | 136.524 | 57.422 | −6.784 | 1.00 | 72.11 C |
| ATOM | 1152 | CD1 | TYR | A | 151 | 135.227 | 57.860 | −6.503 | 1.00 | 71.81 C |
| ATOM | 1153 | CD2 | TYR | A | 151 | 137.484 | 58.383 | −7.117 | 1.00 | 72.04 C |
| ATOM | 1154 | CE1 | TYR | A | 151 | 134.896 | 59.218 | −6.548 | 1.00 | 71.71 C |

TABLE 7-continued

| | | | | | | | | | |
|---|---|---|---|---|---|---|---|---|---|
| ATOM | 1155 | CE2 | TYR | A | 151 | 137.165 | 59.740 | −7.165 | 1.00 71.99 C |
| ATOM | 1156 | CZ | TYR | A | 151 | 135.872 | 60.151 | −6.880 | 1.00 72.05 C |
| ATOM | 1157 | OH | TYR | A | 151 | 135.558 | 61.492 | −6.927 | 1.00 72.25 O |
| ATOM | 1158 | N | ASN | A | 152 | 138.995 | 53.334 | −7.270 | 1.00 74.39 N |
| ATOM | 1159 | CA | ASN | A | 152 | 139.336 | 51.982 | −6.841 | 1.00 75.27 C |
| ATOM | 1160 | C | ASN | A | 152 | 140.814 | 51.937 | −6.437 | 1.00 75.50 C |
| ATOM | 1161 | O | ASN | A | 152 | 141.587 | 51.113 | −6.932 | 1.00 75.85 O |
| ATOM | 1162 | CB | ASN | A | 152 | 139.064 | 50.987 | −7.976 | 1.00 75.63 C |
| ATOM | 1163 | CG | ASN | A | 152 | 139.219 | 49.539 | −7.539 | 1.00 76.28 C |
| ATOM | 1164 | OD1 | ASN | A | 152 | 139.084 | 48.620 | −8.350 | 1.00 77.14 O |
| ATOM | 1165 | ND2 | ASN | A | 152 | 139.497 | 49.329 | −6.254 | 1.00 76.29 N |
| ATOM | 1166 | N | ALA | A | 153 | 141.199 | 52.834 | −5.536 | 1.00 75.52 N |
| ATOM | 1167 | CA | ALA | A | 153 | 142.578 | 52.906 | −5.067 | 1.00 75.70 C |
| ATOM | 1168 | C | ALA | A | 153 | 142.649 | 53.360 | −3.609 | 1.00 76.00 C |
| ATOM | 1169 | O | ALA | A | 153 | 141.778 | 54.093 | −3.133 | 1.00 75.58 O |
| ATOM | 1170 | CB | ALA | A | 153 | 143.375 | 53.864 | −5.951 | 1.00 75.45 C |
| ATOM | 1171 | N | PRO | A | 154 | 143.696 | 52.929 | −2.880 | 1.00 76.38 N |
| ATOM | 1172 | CA | PRO | A | 154 | 143.883 | 53.294 | −1.474 | 1.00 76.60 C |
| ATOM | 1173 | C | PRO | A | 154 | 143.829 | 54.809 | −1.297 | 1.00 76.99 C |
| ATOM | 1174 | O | PRO | A | 154 | 144.532 | 55.552 | −1.984 | 1.00 76.89 O |
| ATOM | 1175 | CB | PRO | A | 154 | 145.258 | 52.707 | −1.164 | 1.00 76.34 C |
| ATOM | 1176 | CG | PRO | A | 154 | 145.247 | 51.457 | −2.012 | 1.00 75.98 C |
| ATOM | 1177 | CD | PRO | A | 154 | 144.813 | 52.076 | −3.321 | 1.00 76.29 C |
| ATOM | 1178 | N | ILE | A | 155 | 142.988 | 55.258 | −0.372 | 1.00 77.55 N |
| ATOM | 1179 | CA | ILE | A | 155 | 142.818 | 56.681 | −0.114 | 1.00 78.03 C |
| ATOM | 1180 | C | ILE | A | 155 | 144.150 | 57.341 | 0.208 | 1.00 78.39 C |
| ATOM | 1181 | O | ILE | A | 155 | 144.232 | 58.559 | 0.337 | 1.00 78.68 O |
| ATOM | 1182 | CB | ILE | A | 155 | 141.834 | 56.914 | 1.050 | 1.00 77.70 C |
| ATOM | 1183 | CG1 | ILE | A | 155 | 141.484 | 58.397 | 1.151 | 1.00 78.19 C |
| ATOM | 1184 | CG2 | ILE | A | 155 | 142.450 | 56.433 | 2.349 | 1.00 77.56 C |
| ATOM | 1185 | CD1 | ILE | A | 155 | 140.407 | 58.690 | 2.160 | 1.00 78.30 C |
| ATOM | 1186 | N | SER | A | 156 | 145.190 | 56.523 | 0.330 | 1.00 79.20 N |
| ATOM | 1187 | CA | SER | A | 156 | 146.534 | 57.002 | 0.631 | 1.00 80.33 C |
| ATOM | 1188 | C | SER | A | 156 | 147.172 | 57.678 | −0.584 | 1.00 81.04 C |
| ATOM | 1189 | O | SER | A | 156 | 147.530 | 58.859 | −0.535 | 1.00 81.05 O |
| ATOM | 1190 | CB | SER | A | 156 | 147.408 | 55.828 | 1.079 | 1.00 80.24 C |
| ATOM | 1191 | OG | SER | A | 156 | 148.735 | 56.249 | 1.337 | 1.00 80.63 O |
| ATOM | 1192 | N | GLU | A | 157 | 147.308 | 56.914 | −1.667 | 1.00 81.98 N |
| ATOM | 1193 | CA | GLU | A | 157 | 147.904 | 57.392 | −2.913 | 1.00 82.66 C |
| ATOM | 1194 | C | GLU | A | 157 | 147.458 | 58.803 | −3.271 | 1.00 83.46 C |
| ATOM | 1195 | O | GLU | A | 157 | 148.228 | 59.588 | −3.821 | 1.00 84.07 O |
| ATOM | 1196 | CB | GLU | A | 157 | 147.556 | 56.426 | −4.047 | 1.00 82.38 C |
| ATOM | 1197 | CG | GLU | A | 157 | 148.089 | 55.022 | −3.808 | 1.00 82.83 C |
| ATOM | 1198 | CD | GLU | A | 157 | 147.657 | 54.028 | −4.865 | 1.00 83.03 C |
| ATOM | 1199 | OE1 | GLU | A | 157 | 148.095 | 52.857 | −4.790 | 1.00 82.84 O |
| ATOM | 1200 | OE2 | GLU | A | 157 | 146.877 | 54.415 | −5.763 | 1.00 83.32 O |
| ATOM | 1201 | N | HIS | A | 158 | 146.209 | 59.117 | −2.952 | 1.00 84.27 N |
| ATOM | 1202 | CA | HIS | A | 158 | 145.643 | 60.434 | −3.219 | 1.00 84.85 C |
| ATOM | 1203 | C | HIS | A | 158 | 145.351 | 60.997 | −1.845 | 1.00 84.86 C |
| ATOM | 1204 | O | HIS | A | 158 | 144.307 | 60.702 | −1.263 | 1.00 84.99 O |
| ATOM | 1205 | CB | HIS | A | 158 | 144.344 | 60.285 | −4.004 | 1.00 85.54 C |
| ATOM | 1206 | CG | HIS | A | 158 | 144.473 | 59.414 | −5.212 | 1.00 86.62 C |
| ATOM | 1207 | ND1 | HIS | A | 158 | 145.274 | 59.744 | −6.284 | 1.00 87.28 N |
| ATOM | 1208 | CD2 | HIS | A | 158 | 143.939 | 58.204 | −5.499 | 1.00 87.21 C |
| ATOM | 1209 | CE1 | HIS | A | 158 | 145.227 | 58.773 | −7.180 | 1.00 87.78 C |
| ATOM | 1210 | NE2 | HIS | A | 158 | 144.424 | 57.828 | −6.727 | 1.00 87.86 N |
| HETATM | 1211 | N | MSE | A | 159 | 146.256 | 61.812 | −1.319 | 1.00 84.93 N |
| HETATM | 1212 | CA | MSE | A | 159 | 146.042 | 62.323 | 0.020 | 1.00 85.49 C |
| HETATM | 1213 | C | MSE | A | 159 | 146.301 | 63.765 | 0.395 | 1.00 84.25 C |
| HETATM | 1214 | O | MSE | A | 159 | 146.445 | 64.646 | −0.450 | 1.00 84.36 O |
| HETATM | 1215 | CB | MSE | A | 159 | 146.789 | 61.430 | 0.998 | 1.00 87.98 C |
| HETATM | 1216 | CG | MSE | A | 159 | 145.862 | 60.499 | 1.708 | 1.00 91.79 C |
| HETATM | 1217 | SE | MSE | A | 159 | 144.854 | 61.381 | 2.951 | 1.00 96.88 SE |
| HETATM | 1218 | CE | MSE | A | 159 | 143.842 | 60.037 | 3.500 | 1.00 95.69 C |
| ATOM | 1219 | N | THR | A | 160 | 146.334 | 63.979 | 1.707 | 1.00 82.42 N |
| ATOM | 1220 | CA | THR | A | 160 | 146.554 | 65.285 | 2.294 | 1.00 80.55 C |
| ATOM | 1221 | C | THR | A | 160 | 147.496 | 65.164 | 3.494 | 1.00 79.27 C |
| ATOM | 1222 | O | THR | A | 160 | 147.094 | 65.408 | 4.636 | 1.00 79.55 O |
| ATOM | 1223 | CB | THR | A | 160 | 145.220 | 65.902 | 2.763 | 1.00 80.73 C |
| ATOM | 1224 | OG1 | THR | A | 160 | 144.314 | 65.984 | 1.655 | 1.00 80.34 O |
| ATOM | 1225 | CG2 | THR | A | 160 | 145.444 | 67.296 | 3.327 | 1.00 80.81 C |
| ATOM | 1226 | N | SER | A | 161 | 148.740 | 64.758 | 3.238 | 1.00 77.07 N |
| ATOM | 1227 | CA | SER | A | 161 | 149.739 | 64.647 | 4.304 | 1.00 74.22 C |
| ATOM | 1228 | C | SER | A | 161 | 150.444 | 65.995 | 4.396 | 1.00 72.09 C |
| ATOM | 1229 | O | SER | A | 161 | 151.661 | 66.101 | 4.203 | 1.00 72.10 O |
| ATOM | 1230 | CB | SER | A | 161 | 150.761 | 63.542 | 4.005 | 1.00 74.18 C |
| ATOM | 1231 | OG | SER | A | 161 | 150.194 | 62.254 | 4.160 | 1.00 73.46 O |
| ATOM | 1232 | N | GLU | A | 162 | 149.649 | 67.023 | 4.678 | 1.00 68.49 N |
| ATOM | 1233 | CA | GLU | A | 162 | 150.138 | 68.386 | 4.802 | 1.00 63.99 C |

TABLE 7-continued

| | | | | | | | | | | |
|---|---|---|---|---|---|---|---|---|---|---|
| ATOM | 1234 | C | GLU | A | 162 | 150.457 | 68.572 | 6.275 | 1.00 | 59.31 C |
| ATOM | 1235 | O | GLU | A | 162 | 150.507 | 67.606 | 7.030 | 1.00 | 59.06 O |
| ATOM | 1236 | CB | GLU | A | 162 | 149.045 | 69.372 | 4.378 | 1.00 | 66.51 C |
| ATOM | 1237 | CG | GLU | A | 162 | 148.309 | 68.983 | 3.088 | 1.00 | 69.52 C |
| ATOM | 1238 | CD | GLU | A | 162 | 149.171 | 69.063 | 1.834 | 1.00 | 71.43 C |
| ATOM | 1239 | OE1 | GLU | A | 162 | 148.736 | 68.542 | 0.781 | 1.00 | 72.92 O |
| ATOM | 1240 | OE2 | GLU | A | 162 | 150.266 | 69.661 | 1.890 | 1.00 | 72.32 O |
| ATOM | 1241 | N | HIS | A | 163 | 150.673 | 69.812 | 6.683 | 1.00 | 53.68 N |
| ATOM | 1242 | CA | HIS | A | 163 | 150.977 | 70.095 | 8.075 | 1.00 | 48.20 C |
| ATOM | 1243 | C | HIS | A | 163 | 149.629 | 70.167 | 8.775 | 1.00 | 45.82 C |
| ATOM | 1244 | O | HIS | A | 163 | 148.922 | 71.167 | 8.680 | 1.00 | 46.57 O |
| ATOM | 1245 | CB | HIS | A | 163 | 151.724 | 71.430 | 8.187 | 1.00 | 45.00 C |
| ATOM | 1246 | CG | HIS | A | 163 | 152.253 | 71.721 | 9.555 | 1.00 | 40.59 C |
| ATOM | 1247 | ND1 | HIS | A | 163 | 153.047 | 70.833 | 10.249 | 1.00 | 38.53 N |
| ATOM | 1248 | CD2 | HIS | A | 163 | 152.151 | 72.822 | 10.335 | 1.00 | 38.60 C |
| ATOM | 1249 | CE1 | HIS | A | 163 | 153.412 | 71.374 | 11.396 | 1.00 | 37.85 C |
| ATOM | 1250 | NE2 | HIS | A | 163 | 152.883 | 72.582 | 11.472 | 1.00 | 38.90 N |
| ATOM | 1251 | N | LEU | A | 164 | 149.271 | 69.096 | 9.467 | 1.00 | 42.78 N |
| ATOM | 1252 | CA | LEU | A | 164 | 147.990 | 69.033 | 10.156 | 1.00 | 39.51 C |
| ATOM | 1253 | C | LEU | A | 164 | 147.812 | 70.110 | 11.218 | 1.00 | 36.83 C |
| ATOM | 1254 | O | LEU | A | 164 | 148.676 | 70.312 | 12.068 | 1.00 | 36.48 O |
| ATOM | 1255 | CB | LEU | A | 164 | 147.800 | 67.641 | 10.781 | 1.00 | 39.26 C |
| ATOM | 1256 | CG | LEU | A | 164 | 147.792 | 66.468 | 9.789 | 1.00 | 39.23 C |
| ATOM | 1257 | CD1 | LEU | A | 164 | 147.637 | 65.153 | 10.537 | 1.00 | 39.06 C |
| ATOM | 1258 | CD2 | LEU | A | 164 | 146.665 | 66.650 | 8.788 | 1.00 | 38.45 C |
| ATOM | 1259 | N | VAL | A | 165 | 146.689 | 70.817 | 11.139 | 1.00 | 33.58 N |
| ATOM | 1260 | CA | VAL | A | 165 | 146.356 | 71.858 | 12.103 | 1.00 | 30.38 C |
| ATOM | 1261 | C | VAL | A | 165 | 145.268 | 71.266 | 12.996 | 1.00 | 29.08 C |
| ATOM | 1262 | O | VAL | A | 165 | 144.223 | 70.841 | 12.514 | 1.00 | 28.47 O |
| ATOM | 1263 | CB | VAL | A | 165 | 145.840 | 73.131 | 11.395 | 1.00 | 29.47 C |
| ATOM | 1264 | CG1 | VAL | A | 165 | 145.440 | 74.176 | 12.417 | 1.00 | 27.78 C |
| ATOM | 1265 | CG2 | VAL | A | 165 | 146.931 | 73.687 | 10.486 | 1.00 | 28.52 C |
| ATOM | 1266 | N | THR | A | 166 | 145.515 | 71.228 | 14.301 | 1.00 | 28.43 N |
| ATOM | 1267 | CA | THR | A | 166 | 144.551 | 70.641 | 15.219 | 1.00 | 27.43 C |
| ATOM | 1268 | C | THR | A | 166 | 144.388 | 71.443 | 16.492 | 1.00 | 27.43 C |
| ATOM | 1269 | O | THR | A | 166 | 145.090 | 72.427 | 16.723 | 1.00 | 27.24 O |
| ATOM | 1270 | CB | THR | A | 166 | 144.978 | 69.212 | 15.652 | 1.00 | 28.78 C |
| ATOM | 1271 | OG1 | THR | A | 166 | 146.169 | 69.289 | 16.447 | 1.00 | 27.74 O |
| ATOM | 1272 | CG2 | THR | A | 166 | 145.251 | 68.333 | 14.437 | 1.00 | 29.11 C |
| ATOM | 1273 | N | ALA | A | 167 | 143.451 | 70.991 | 17.321 | 1.00 | 26.41 N |
| ATOM | 1274 | CA | ALA | A | 167 | 143.164 | 71.612 | 18.608 | 1.00 | 25.08 C |
| ATOM | 1275 | C | ALA | A | 167 | 142.994 | 70.494 | 19.630 | 1.00 | 24.35 C |
| ATOM | 1276 | O | ALA | A | 167 | 142.641 | 69.368 | 19.282 | 1.00 | 23.64 O |
| ATOM | 1277 | CB | ALA | A | 167 | 141.900 | 72.441 | 18.517 | 1.00 | 24.85 C |
| ATOM | 1278 | N | ALA | A | 168 | 143.249 | 70.804 | 20.893 | 1.00 | 24.53 N |
| ATOM | 1279 | CA | ALA | A | 168 | 143.131 | 69.808 | 21.947 | 1.00 | 24.62 C |
| ATOM | 1280 | C | ALA | A | 168 | 141.679 | 69.424 | 22.180 | 1.00 | 25.16 C |
| ATOM | 1281 | O | ALA | A | 168 | 140.770 | 70.186 | 21.873 | 1.00 | 25.69 O |
| ATOM | 1282 | CB | ALA | A | 168 | 143.731 | 70.346 | 23.232 | 1.00 | 24.00 C |
| ATOM | 1283 | N | VAL | A | 169 | 141.461 | 68.234 | 22.722 | 1.00 | 26.41 N |
| ATOM | 1284 | CA | VAL | A | 169 | 140.111 | 67.784 | 23.018 | 1.00 | 27.15 C |
| ATOM | 1285 | C | VAL | A | 169 | 139.504 | 68.792 | 23.993 | 1.00 | 28.21 C |
| ATOM | 1286 | O | VAL | A | 169 | 140.173 | 69.253 | 24.917 | 1.00 | 28.71 O |
| ATOM | 1287 | CB | VAL | A | 169 | 140.133 | 66.394 | 23.670 | 1.00 | 27.41 C |
| ATOM | 1288 | CG1 | VAL | A | 169 | 138.720 | 65.941 | 23.967 | 1.00 | 27.70 C |
| ATOM | 1289 | CG2 | VAL | A | 169 | 140.843 | 65.403 | 22.750 | 1.00 | 26.92 C |
| ATOM | 1290 | N | GLY | A | 170 | 138.247 | 69.157 | 23.770 | 1.00 | 29.34 N |
| ATOM | 1291 | CA | GLY | A | 170 | 137.594 | 70.107 | 24.652 | 1.00 | 29.95 C |
| ATOM | 1292 | C | GLY | A | 170 | 137.638 | 71.578 | 24.268 | 1.00 | 30.17 C |
| ATOM | 1293 | O | GLY | A | 170 | 137.060 | 72.400 | 24.972 | 1.00 | 30.81 O |
| ATOM | 1294 | N | THR | A | 171 | 138.313 | 71.940 | 23.181 | 1.00 | 31.70 N |
| ATOM | 1295 | CA | THR | A | 171 | 138.357 | 73.347 | 22.800 | 1.00 | 32.99 C |
| ATOM | 1296 | C | THR | A | 171 | 136.942 | 73.680 | 22.353 | 1.00 | 32.68 C |
| ATOM | 1297 | O | THR | A | 171 | 136.318 | 72.891 | 21.636 | 1.00 | 33.39 O |
| ATOM | 1298 | CB | THR | A | 171 | 139.329 | 73.610 | 21.632 | 1.00 | 34.57 C |
| ATOM | 1299 | OG1 | THR | A | 171 | 138.728 | 73.204 | 20.402 | 1.00 | 38.21 O |
| ATOM | 1300 | CG2 | THR | A | 171 | 140.606 | 72.818 | 21.823 | 1.00 | 34.01 C |
| ATOM | 1301 | N | ASP | A | 172 | 136.432 | 74.831 | 22.780 | 1.00 | 32.59 N |
| ATOM | 1302 | CA | ASP | A | 172 | 135.074 | 75.242 | 22.441 | 1.00 | 31.82 C |
| ATOM | 1303 | C | ASP | A | 172 | 135.001 | 75.879 | 21.064 | 1.00 | 31.23 C |
| ATOM | 1304 | O | ASP | A | 172 | 136.026 | 76.090 | 20.417 | 1.00 | 30.61 O |
| ATOM | 1305 | CB | ASP | A | 172 | 134.553 | 76.209 | 23.497 | 1.00 | 33.64 C |
| ATOM | 1306 | CG | ASP | A | 172 | 135.373 | 77.478 | 23.574 | 1.00 | 36.95 C |
| ATOM | 1307 | OD1 | ASP | A | 172 | 135.141 | 78.284 | 24.499 | 1.00 | 40.09 O |
| ATOM | 1308 | OD2 | ASP | A | 172 | 136.245 | 77.682 | 22.706 | 1.00 | 38.33 O |
| ATOM | 1309 | N | LEU | A | 173 | 133.785 | 76.183 | 20.618 | 1.00 | 30.04 N |
| ATOM | 1310 | CA | LEU | A | 173 | 133.578 | 76.782 | 19.307 | 1.00 | 30.23 C |
| ATOM | 1311 | C | LEU | A | 173 | 134.226 | 78.152 | 19.168 | 1.00 | 31.09 C |
| ATOM | 1312 | O | LEU | A | 173 | 134.694 | 78.521 | 18.094 | 1.00 | 29.98 O |

TABLE 7-continued

| | | | | | | | | | |
|---|---|---|---|---|---|---|---|---|---|
| ATOM | 1313 | CB | LEU | A | 173 | 132.084 | 76.893 | 19.009 | 1.00 29.27 C |
| ATOM | 1314 | CG | LEU | A | 173 | 131.337 | 75.561 | 18.956 | 1.00 30.61 C |
| ATOM | 1315 | CD1 | LEU | A | 173 | 129.898 | 75.791 | 18.506 | 1.00 31.11 C |
| ATOM | 1316 | CD2 | LEU | A | 173 | 132.036 | 74.623 | 17.988 | 1.00 31.30 C |
| ATOM | 1317 | N | GLU | A | 174 | 134.264 | 78.898 | 20.262 | 1.00 32.92 N |
| ATOM | 1318 | CA | GLU | A | 174 | 134.840 | 80.230 | 20.249 | 1.00 35.64 C |
| ATOM | 1319 | C | GLU | A | 174 | 136.335 | 80.202 | 19.925 | 1.00 36.13 C |
| ATOM | 1320 | O | GLU | A | 174 | 136.824 | 81.034 | 19.157 | 1.00 35.92 O |
| ATOM | 1321 | CB | GLU | A | 174 | 134.617 | 80.896 | 21.604 | 1.00 38.56 C |
| ATOM | 1322 | CG | GLU | A | 174 | 134.920 | 82.379 | 21.627 | 1.00 43.61 C |
| ATOM | 1323 | CD | GLU | A | 174 | 134.812 | 82.960 | 23.025 | 1.00 46.61 C |
| ATOM | 1324 | OE1 | GLU | A | 174 | 133.771 | 82.735 | 23.687 | 1.00 48.37 O |
| ATOM | 1325 | OE2 | GLU | A | 174 | 135.765 | 83.644 | 23.457 | 1.00 48.22 O |
| ATOM | 1326 | N | THR | A | 175 | 137.064 | 79.254 | 20.508 | 1.00 36.59 N |
| ATOM | 1327 | CA | THR | A | 175 | 138.501 | 79.156 | 20.252 | 1.00 37.34 C |
| ATOM | 1328 | C | THR | A | 175 | 138.805 | 78.488 | 18.913 | 1.00 35.61 C |
| ATOM | 1329 | O | THR | A | 175 | 139.771 | 78.853 | 18.231 | 1.00 35.02 O |
| ATOM | 1330 | CB | THR | A | 175 | 139.234 | 78.394 | 21.383 | 1.00 39.60 C |
| ATOM | 1331 | OG1 | THR | A | 175 | 140.618 | 78.248 | 21.031 | 1.00 42.14 O |
| ATOM | 1332 | CG2 | THR | A | 175 | 138.631 | 77.015 | 21.596 | 1.00 42.29 C |
| ATOM | 1333 | N | ALA | A | 176 | 137.969 | 77.519 | 18.537 | 1.00 34.40 N |
| ATOM | 1334 | CA | ALA | A | 176 | 138.122 | 76.803 | 17.271 | 1.00 33.17 C |
| ATOM | 1335 | C | ALA | A | 176 | 137.936 | 77.780 | 16.115 | 1.00 32.96 C |
| ATOM | 1336 | O | ALA | A | 176 | 138.682 | 77.751 | 15.142 | 1.00 32.68 O |
| ATOM | 1337 | CB | ALA | A | 176 | 137.106 | 75.680 | 17.182 | 1.00 31.85 C |
| ATOM | 1338 | N | GLU | A | 177 | 136.937 | 78.649 | 16.234 | 1.00 33.83 N |
| ATOM | 1339 | CA | GLU | A | 177 | 136.655 | 79.657 | 15.217 | 1.00 35.00 C |
| ATOM | 1340 | C | GLU | A | 177 | 137.902 | 80.499 | 15.001 | 1.00 35.49 C |
| ATOM | 1341 | O | GLU | A | 177 | 138.252 | 80.855 | 13.876 | 1.00 36.40 O |
| ATOM | 1342 | CB | GLU | A | 177 | 135.526 | 80.570 | 15.679 | 1.00 35.49 C |
| ATOM | 1343 | CG | GLU | A | 177 | 135.167 | 81.644 | 14.675 | 1.00 38.23 C |
| ATOM | 1344 | CD | GLU | A | 177 | 134.092 | 82.584 | 15.185 | 1.00 40.34 C |
| ATOM | 1345 | OE1 | GLU | A | 177 | 133.594 | 83.395 | 14.378 | 1.00 41.80 O |
| ATOM | 1346 | OE2 | GLU | A | 177 | 133.750 | 82.522 | 16.390 | 1.00 42.06 O |
| ATOM | 1347 | N | ARG | A | 178 | 138.563 | 80.815 | 16.105 | 1.00 35.48 N |
| ATOM | 1348 | CA | ARG | A | 178 | 139.779 | 81.605 | 16.099 | 1.00 35.76 C |
| ATOM | 1349 | C | ARG | A | 178 | 140.891 | 80.849 | 15.372 | 1.00 35.00 C |
| ATOM | 1350 | O | ARG | A | 178 | 141.604 | 81.418 | 14.536 | 1.00 35.81 O |
| ATOM | 1351 | CB | ARG | A | 178 | 140.180 | 81.888 | 17.541 | 1.00 37.77 C |
| ATOM | 1352 | CG | ARG | A | 178 | 141.397 | 82.765 | 17.737 | 1.00 41.57 C |
| ATOM | 1353 | CD | ARG | A | 178 | 141.581 | 82.930 | 19.229 | 1.00 43.96 C |
| ATOM | 1354 | NE | ARG | A | 178 | 140.343 | 83.441 | 19.807 | 1.00 46.74 N |
| ATOM | 1355 | CZ | ARG | A | 178 | 139.911 | 83.163 | 21.031 | 1.00 48.54 C |
| ATOM | 1356 | NH1 | ARG | A | 178 | 140.618 | 82.369 | 21.828 | 1.00 48.33 N |
| ATOM | 1357 | NH2 | ARG | A | 178 | 138.759 | 83.675 | 21.454 | 1.00 49.63 N |
| ATOM | 1358 | N | ILE | A | 179 | 141.034 | 79.564 | 15.680 | 1.00 32.20 N |
| ATOM | 1359 | CA | ILE | A | 179 | 142.070 | 78.763 | 15.046 | 1.00 30.42 C |
| ATOM | 1360 | C | ILE | A | 179 | 141.753 | 78.583 | 13.556 | 1.00 30.40 C |
| ATOM | 1361 | O | ILE | A | 179 | 142.626 | 78.716 | 12.707 | 1.00 30.21 O |
| ATOM | 1362 | CB | ILE | A | 179 | 142.201 | 77.380 | 15.744 | 1.00 29.67 C |
| ATOM | 1363 | CG1 | ILE | A | 179 | 142.477 | 77.585 | 17.239 | 1.00 28.14 C |
| ATOM | 1364 | CG2 | ILE | A | 179 | 143.327 | 76.560 | 15.100 | 1.00 27.22 C |
| ATOM | 1365 | CD1 | ILE | A | 179 | 142.463 | 76.313 | 18.067 | 1.00 26.32 C |
| ATOM | 1366 | N | LEU | A | 180 | 140.499 | 78.292 | 13.240 | 1.00 30.34 N |
| ATOM | 1367 | CA | LEU | A | 180 | 140.102 | 78.107 | 11.849 | 1.00 31.10 C |
| ATOM | 1368 | C | LEU | A | 180 | 140.345 | 79.366 | 11.025 | 1.00 31.52 C |
| ATOM | 1369 | O | LEU | A | 180 | 140.713 | 79.290 | 9.856 | 1.00 30.22 O |
| ATOM | 1370 | CB | LEU | A | 180 | 138.623 | 77.713 | 11.769 | 1.00 31.47 C |
| ATOM | 1371 | CG | LEU | A | 180 | 138.242 | 76.307 | 12.247 | 1.00 30.67 C |
| ATOM | 1372 | CD1 | LEU | A | 180 | 136.735 | 76.209 | 12.402 | 1.00 32.24 C |
| ATOM | 1373 | CD2 | LEU | A | 180 | 138.752 | 75.273 | 11.256 | 1.00 30.35 C |
| ATOM | 1374 | N | HIS | A | 181 | 140.139 | 80.524 | 11.642 | 1.00 33.19 N |
| ATOM | 1375 | CA | HIS | A | 181 | 140.340 | 81.790 | 10.953 | 1.00 35.20 C |
| ATOM | 1376 | C | HIS | A | 181 | 141.806 | 82.126 | 10.694 | 1.00 36.88 C |
| ATOM | 1377 | O | HIS | A | 181 | 142.149 | 82.651 | 9.631 | 1.00 36.71 O |
| ATOM | 1378 | CB | HIS | A | 161 | 139.665 | 82.930 | 11.728 | 1.00 35.30 C |
| ATOM | 1379 | CG | HIS | A | 181 | 138.169 | 82.952 | 11.590 | 1.00 36.21 C |
| ATOM | 1380 | ND1 | HIS | A | 181 | 137.379 | 83.913 | 12.186 | 1.00 35.97 N |
| ATOM | 1381 | CD2 | HIS | A | 181 | 137.323 | 82.143 | 10.906 | 1.00 35.37 C |
| ATOM | 1382 | CE1 | HIS | A | 181 | 136.113 | 83.695 | 11.875 | 1.00 35.54 C |
| ATOM | 1383 | NE2 | HIS | A | 181 | 136.052 | 82.628 | 11.100 | 1.00 35.36 N |
| ATOM | 1384 | N | GLU | A | 182 | 142.677 | 81.827 | 11.650 | 1.00 38.45 N |
| ATOM | 1385 | CA | GLU | A | 182 | 144.092 | 82.123 | 11.476 | 1.00 39.85 C |
| ATOM | 1386 | C | GLU | A | 182 | 144.760 | 81.234 | 10.436 | 1.00 38.65 C |
| ATOM | 1387 | O | GLU | A | 182 | 145.780 | 81.608 | 9.861 | 1.00 38.54 O |
| ATOM | 1388 | CB | GLU | A | 182 | 144.849 | 81.960 | 12.790 | 1.00 43.25 C |
| ATOM | 1389 | CG | GLU | A | 182 | 146.348 | 82.210 | 12.626 | 1.00 49.40 C |
| ATOM | 1390 | CD | GLU | A | 182 | 147.159 | 81.826 | 13.855 | 1.00 53.96 C |
| ATOM | 1391 | OE1 | GLU | A | 182 | 148.394 | 82.037 | 13.826 | 1.00 56.51 O |

TABLE 7-continued

| ATOM | 1392 | OE2 | GLU | A | 182 | 146.570 | 81.310 | 14.840 | 1.00 | 55.87 | O |
|------|------|-----|-----|---|-----|---------|--------|--------|------|-------|---|
| ATOM | 1393 | N | HIS | A | 183 | 144.183 | 80.062 | 10.196 | 1.00 | 37.07 | N |
| ATOM | 1394 | CA | HIS | A | 183 | 144.758 | 79.101 | 9.262 | 1.00 | 36.26 | C |
| ATOM | 1395 | C | HIS | A | 183 | 143.963 | 78.982 | 7.973 | 1.00 | 36.75 | C |
| ATOM | 1396 | O | HIS | A | 183 | 144.223 | 78.101 | 7.146 | 1.00 | 36.54 | O |
| ATOM | 1397 | CB | HIS | A | 183 | 144.846 | 77.743 | 9.955 | 1.00 | 34.77 | C |
| ATOM | 1398 | CG | HIS | A | 183 | 145.625 | 77.778 | 11.235 | 1.00 | 34.78 | C |
| ATOM | 1399 | ND1 | HIS | A | 183 | 147.004 | 77.752 | 11.271 | 1.00 | 35.14 | N |
| ATOM | 1400 | CD2 | HIS | A | 183 | 145.220 | 77.922 | 12.519 | 1.00 | 33.17 | C |
| ATOM | 1401 | CE1 | HIS | A | 183 | 147.412 | 77.878 | 12.521 | 1.00 | 34.52 | C |
| ATOM | 1402 | NE2 | HIS | A | 183 | 146.349 | 77.985 | 13.297 | 1.00 | 34.67 | N |
| ATOM | 1403 | N | ARG | A | 184 | 142.997 | 79.880 | 7.807 | 1.00 | 37.38 | N |
| ATOM | 1404 | CA | ARG | A | 184 | 142.147 | 79.887 | 6.622 | 1.00 | 37.97 | C |
| ATOM | 1405 | C | ARG | A | 184 | 141.668 | 78.485 | 6.287 | 1.00 | 36.24 | C |
| ATOM | 1406 | O | ARG | A | 184 | 141.815 | 78.034 | 5.157 | 1.00 | 34.85 | O |
| ATOM | 1407 | CB | ARG | A | 184 | 142.897 | 80.473 | 5.420 | 1.00 | 40.41 | C |
| ATOM | 1408 | CG | ARG | A | 184 | 143.263 | 81.954 | 5.537 | 1.00 | 44.51 | C |
| ATOM | 1409 | CD | ARG | A | 184 | 144.039 | 82.396 | 4.299 | 1.00 | 49.58 | C |
| ATOM | 1410 | NE | ARG | A | 184 | 143.298 | 82.080 | 3.076 | 1.00 | 54.75 | N |
| ATOM | 1411 | CZ | ARG | A | 184 | 143.764 | 82.247 | 1.839 | 1.00 | 57.24 | C |
| ATOM | 1412 | NH1 | ARG | A | 184 | 144.987 | 82.733 | 1.640 | 1.00 | 58.91 | N |
| ATOM | 1413 | NH2 | ARG | A | 184 | 143.007 | 81.923 | 0.796 | 1.00 | 58.17 | N |
| ATOM | 1414 | N | ILE | A | 185 | 141.107 | 77.797 | 7.279 | 1.00 | 34.80 | N |
| ATOM | 1415 | CA | ILE | A | 185 | 140.589 | 76.447 | 7.079 | 1.00 | 34.18 | C |
| ATOM | 1416 | C | ILE | A | 185 | 139.142 | 76.323 | 7.542 | 1.00 | 34.03 | C |
| ATOM | 1417 | O | ILE | A | 185 | 138.648 | 77.157 | 8.299 | 1.00 | 32.73 | O |
| ATOM | 1418 | CB | ILE | A | 185 | 141.433 | 75.387 | 7.822 | 1.00 | 33.30 | C |
| ATOM | 1419 | CG1 | ILE | A | 185 | 141.606 | 75.789 | 9.286 | 1.00 | 32.78 | C |
| ATOM | 1420 | CG2 | ILE | A | 185 | 142.767 | 75.198 | 7.114 | 1.00 | 33.84 | C |
| ATOM | 1421 | CD1 | ILE | A | 185 | 142.348 | 74.769 | 10.120 | 1.00 | 32.98 | C |
| ATOM | 1422 | N | GLU | A | 186 | 138.467 | 75.273 | 7.086 | 1.00 | 34.75 | N |
| ATOM | 1423 | CA | GLU | A | 186 | 137.075 | 75.057 | 7.450 | 1.00 | 35.67 | C |
| ATOM | 1424 | C | GLU | A | 186 | 136.815 | 73.918 | 8.430 | 1.00 | 34.22 | C |
| ATOM | 1425 | O | GLU | A | 186 | 135.795 | 73.926 | 9.110 | 1.00 | 34.10 | O |
| ATOM | 1426 | CB | GLU | A | 186 | 136.242 | 74.863 | 6.187 | 1.00 | 38.26 | C |
| ATOM | 1427 | CG | GLU | A | 186 | 136.193 | 76.098 | 5.321 | 1.00 | 42.63 | C |
| ATOM | 1428 | CD | GLU | A | 186 | 135.354 | 75.899 | 4.080 | 1.00 | 47.23 | C |
| ATOM | 1429 | OE1 | GLU | A | 186 | 135.168 | 76.884 | 3.328 | 1.00 | 50.49 | O |
| ATOM | 1430 | OE2 | GLU | A | 186 | 134.880 | 74.761 | 3.848 | 1.00 | 48.96 | O |
| ATOM | 1431 | N | LYS | A | 187 | 137.721 | 72.942 | 8.496 | 1.00 | 33.47 | N |
| ATOM | 1432 | CA | LYS | A | 187 | 137.590 | 71.805 | 9.422 | 1.00 | 32.86 | C |
| ATOM | 1433 | C | LYS | A | 187 | 138.755 | 71.785 | 10.411 | 1.00 | 30.96 | C |
| ATOM | 1434 | O | LYS | A | 187 | 139.917 | 71.876 | 10.012 | 1.00 | 30.22 | O |
| ATOM | 1435 | CB | LYS | A | 187 | 137.565 | 70.456 | 8.674 | 1.00 | 34.99 | C |
| ATOM | 1436 | CG | LYS | A | 187 | 136.246 | 70.067 | 8.021 | 1.00 | 38.77 | C |
| ATOM | 1437 | CD | LYS | A | 187 | 135.898 | 70.942 | 6.827 | 1.00 | 43.65 | C |
| ATOM | 1438 | CE | LYS | A | 187 | 136.826 | 70.688 | 5.634 | 1.00 | 47.20 | C |
| ATOM | 1439 | NZ | LYS | A | 187 | 136.695 | 69.309 | 5.064 | 1.00 | 48.81 | N |
| ATOM | 1440 | N | LEU | A | 188 | 138.451 | 71.654 | 11.697 | 1.00 | 28.56 | N |
| ATOM | 1441 | CA | LEU | A | 188 | 139.500 | 71.619 | 12.714 | 1.00 | 26.39 | C |
| ATOM | 1442 | C | LEU | A | 188 | 139.439 | 70.340 | 13.533 | 1.00 | 26.27 | C |
| ATOM | 1443 | O | LEU | A | 188 | 138.629 | 70.228 | 14.448 | 1.00 | 26.83 | O |
| ATOM | 1444 | CB | LEU | A | 188 | 139.364 | 72.812 | 13.658 | 1.00 | 25.30 | C |
| ATOM | 1445 | CG | LEU | A | 188 | 140.373 | 72.899 | 14.804 | 1.00 | 25.12 | C |
| ATOM | 1446 | CD1 | LEU | A | 188 | 141.779 | 73.097 | 14.245 | 1.00 | 24.40 | C |
| ATOM | 1447 | CD2 | LEU | A | 188 | 140.001 | 74.055 | 15.709 | 1.00 | 25.16 | C |
| ATOM | 1448 | N | PRO | A | 189 | 140.299 | 69.360 | 13.222 | 1.00 | 25.63 | N |
| ATOM | 1449 | CA | PRO | A | 189 | 140.327 | 68.088 | 13.949 | 1.00 | 25.71 | C |
| ATOM | 1450 | C | PRO | A | 189 | 140.736 | 68.292 | 15.405 | 1.00 | 25.74 | C |
| ATOM | 1451 | O | PRO | A | 189 | 141.598 | 69.120 | 15.704 | 1.00 | 25.84 | O |
| ATOM | 1452 | CB | PRO | A | 189 | 141.372 | 67.284 | 13.179 | 1.00 | 25.33 | C |
| ATOM | 1453 | CG | PRO | A | 189 | 141.290 | 67.884 | 11.789 | 1.00 | 26.79 | C |
| ATOM | 1454 | CD | PRO | A | 189 | 141.316 | 69.339 | 12.163 | 1.00 | 25.56 | C |
| ATOM | 1455 | N | LEU | A | 190 | 140.104 | 67.546 | 16.306 | 1.00 | 26.25 | N |
| ATOM | 1456 | CA | LEU | A | 190 | 140.414 | 67.623 | 17.729 | 1.00 | 25.59 | C |
| ATOM | 1457 | C | LEU | A | 190 | 141.105 | 66.314 | 18.076 | 1.00 | 26.60 | C |
| ATOM | 1458 | O | LEU | A | 190 | 140.565 | 65.227 | 17.833 | 1.00 | 26.44 | O |
| ATOM | 1459 | CB | LEU | A | 190 | 139.139 | 67.777 | 18.557 | 1.00 | 24.57 | C |
| ATOM | 1460 | CG | LEU | A | 190 | 138.236 | 68.966 | 18.223 | 1.00 | 24.56 | C |
| ATOM | 1461 | CD1 | LEU | A | 190 | 137.073 | 68.992 | 19.206 | 1.00 | 24.55 | C |
| ATOM | 1462 | CD2 | LEU | A | 190 | 139.026 | 70.266 | 18.309 | 1.00 | 24.12 | C |
| ATOM | 1463 | N | VAL | A | 191 | 142.303 | 66.411 | 18.639 | 1.00 | 27.41 | N |
| ATOM | 1464 | CA | VAL | A | 191 | 143.069 | 65.223 | 18.984 | 1.00 | 26.97 | C |
| ATOM | 1465 | C | VAL | A | 191 | 143.589 | 65.339 | 20.403 | 1.00 | 27.90 | C |
| ATOM | 1466 | O | VAL | A | 191 | 143.693 | 66.442 | 20.929 | 1.00 | 27.60 | O |
| ATOM | 1467 | CB | VAL | A | 191 | 144.267 | 65.065 | 18.024 | 1.00 | 26.42 | C |
| ATOM | 1468 | CG1 | VAL | A | 191 | 143.769 | 65.012 | 16.585 | 1.00 | 25.29 | C |
| ATOM | 1469 | CG2 | VAL | A | 191 | 145.236 | 66.225 | 18.196 | 1.00 | 25.51 | C |
| ATOM | 1470 | N | ASP | A | 192 | 143.895 | 64.211 | 21.039 | 1.00 | 29.14 | N |

TABLE 7-continued

| | | | | | | | | | | |
|---|---|---|---|---|---|---|---|---|---|---|
| ATOM | 1471 | CA | ASP | A | 192 | 144.449 | 64.285 | 22.381 | 1.00 | 29.84 C |
| ATOM | 1472 | C | ASP | A | 192 | 145.958 | 64.466 | 22.287 | 1.00 | 29.63 C |
| ATOM | 1473 | O | ASP | A | 192 | 146.528 | 64.519 | 21.190 | 1.00 | 28.08 O |
| ATOM | 1474 | CB | ASP | A | 192 | 144.117 | 63.049 | 23.237 | 1.00 | 29.60 C |
| ATOM | 1475 | CG | ASP | A | 192 | 144.600 | 61.748 | 22.633 | 1.00 | 29.23 C |
| ATOM | 1476 | OD1 | ASP | A | 192 | 145.698 | 61.693 | 22.045 | 1.00 | 29.02 O |
| ATOM | 1477 | OD2 | ASP | A | 192 | 143.880 | 60.751 | 22.791 | 1.00 | 32.38 O |
| ATOM | 1478 | N | ASN | A | 193 | 146.595 | 64.564 | 23.447 | 1.00 | 30.91 N |
| ATOM | 1479 | CA | ASN | A | 193 | 148.033 | 64.774 | 23.525 | 1.00 | 32.71 C |
| ATOM | 1480 | C | ASN | A | 193 | 148.867 | 63.703 | 22.840 | 1.00 | 33.29 C |
| ATOM | 1481 | O | ASN | A | 193 | 150.085 | 63.832 | 22.720 | 1.00 | 33.19 O |
| ATOM | 1482 | CB | ASN | A | 193 | 148.440 | 64.909 | 24.987 | 1.00 | 34.40 C |
| ATOM | 1483 | CG | ASN | A | 193 | 149.093 | 66.230 | 25.272 | 1.00 | 35.62 C |
| ATOM | 1484 | OD1 | ASN | A | 193 | 148.574 | 67.279 | 24.901 | 1.00 | 37.39 O |
| ATOM | 1485 | ND2 | ASN | A | 193 | 150.236 | 66.193 | 25.938 | 1.00 | 38.24 N |
| ATOM | 1486 | N | SER | A | 194 | 148.203 | 62.652 | 22.376 | 1.00 | 33.93 N |
| ATOM | 1487 | CA | SER | A | 194 | 148.879 | 61.564 | 21.691 | 1.00 | 33.58 C |
| ATOM | 1488 | C | SER | A | 194 | 148.552 | 61.538 | 20.209 | 1.00 | 32.89 C |
| ATOM | 1489 | O | SER | A | 194 | 148.921 | 60.592 | 19.522 | 1.00 | 33.82 O |
| ATOM | 1490 | CB | SER | A | 194 | 148.494 | 60.227 | 22.323 | 1.00 | 34.55 C |
| ATOM | 1491 | OG | SER | A | 194 | 149.014 | 60.139 | 23.643 | 1.00 | 37.23 O |
| ATOM | 1492 | N | GLY | A | 195 | 147.861 | 62.566 | 19.717 | 1.00 | 31.61 N |
| ATOM | 1493 | CA | GLY | A | 195 | 147.505 | 62.613 | 18.305 | 1.00 | 29.53 C |
| ATOM | 1494 | C | GLY | A | 195 | 146.314 | 61.738 | 17.930 | 1.00 | 29.01 C |
| ATOM | 1495 | O | GLY | A | 195 | 146.060 | 61.483 | 16.756 | 1.00 | 28.69 O |
| ATOM | 1496 | N | ARG | A | 196 | 145.578 | 61.274 | 18.932 | 1.00 | 28.50 N |
| ATOM | 1497 | CA | ARG | A | 196 | 144.412 | 60.441 | 18.696 | 1.00 | 28.40 C |
| ATOM | 1498 | C | ARG | A | 196 | 143.202 | 61.325 | 18.409 | 1.00 | 27.84 C |
| ATOM | 1499 | O | ARG | A | 196 | 142.906 | 62.253 | 19.161 | 1.00 | 27.44 O |
| ATOM | 1500 | CB | ARG | A | 196 | 144.152 | 59.560 | 19.922 | 1.00 | 30.26 C |
| ATOM | 1501 | CG | ARG | A | 196 | 142.860 | 58.752 | 19.887 | 1.00 | 31.17 C |
| ATOM | 1502 | CD | ARG | A | 196 | 142.663 | 58.063 | 21.216 | 1.00 | 33.36 C |
| ATOM | 1503 | NE | ARG | A | 196 | 141.253 | 57.834 | 21.501 | 1.00 | 38.05 N |
| ATOM | 1504 | CZ | ARG | A | 196 | 140.471 | 57.008 | 20.822 | 1.00 | 39.60 C |
| ATOM | 1505 | NH1 | ARG | A | 196 | 140.966 | 56.321 | 19.808 | 1.00 | 42.65 N |
| ATOM | 1506 | NH2 | ARG | A | 196 | 139.192 | 56.877 | 21.152 | 1.00 | 40.11 N |
| ATOM | 1507 | N | LEU | A | 197 | 142.510 | 61.030 | 17.313 | 1.00 | 27.30 N |
| ATOM | 1508 | CA | LEU | A | 197 | 141.332 | 61.792 | 16.904 | 1.00 | 27.90 C |
| ATOM | 1509 | C | LEU | A | 197 | 140.125 | 61.586 | 17.825 | 1.00 | 27.27 C |
| ATOM | 1510 | O | LEU | A | 197 | 139.661 | 60.460 | 17.997 | 1.00 | 26.44 O |
| ATOM | 1511 | CB | LEU | A | 197 | 140.928 | 61.394 | 15.488 | 1.00 | 26.93 C |
| ATOM | 1512 | CG | LEU | A | 197 | 139.711 | 62.116 | 14.912 | 1.00 | 26.60 C |
| ATOM | 1513 | CD1 | LEU | A | 197 | 140.067 | 63.569 | 14.604 | 1.00 | 24.69 C |
| ATOM | 1514 | CD2 | LEU | A | 197 | 139.268 | 61.396 | 13.637 | 1.00 | 26.73 C |
| ATOM | 1515 | N | SER | A | 198 | 139.610 | 62.674 | 18.393 | 1.00 | 26.75 N |
| ATOM | 1516 | CA | SER | A | 198 | 138.452 | 62.585 | 19.277 | 1.00 | 27.12 C |
| ATOM | 1517 | C | SER | A | 198 | 137.202 | 63.163 | 18.635 | 1.00 | 27.80 C |
| ATOM | 1518 | O | SER | A | 198 | 136.093 | 62.836 | 19.038 | 1.00 | 29.05 O |
| ATOM | 1519 | CB | SER | A | 198 | 138.703 | 63.331 | 20.581 | 1.00 | 27.75 C |
| ATOM | 1520 | OG | SER | A | 198 | 138.836 | 64.720 | 20.352 | 1.00 | 28.75 O |
| ATOM | 1521 | N | GLY | A | 199 | 137.380 | 64.035 | 17.647 | 1.00 | 27.55 N |
| ATOM | 1522 | CA | GLY | A | 199 | 136.240 | 64.641 | 16.990 | 1.00 | 26.57 C |
| ATOM | 1523 | C | GLY | A | 199 | 136.681 | 65.739 | 16.050 | 1.00 | 26.31 C |
| ATOM | 1524 | O | GLY | A | 199 | 137.874 | 65.905 | 15.814 | 1.00 | 26.69 O |
| ATOM | 1525 | N | LEU | A | 200 | 135.727 | 66.502 | 15.534 | 1.00 | 25.94 N |
| ATOM | 1526 | CA | LEU | A | 200 | 136.031 | 67.564 | 14.590 | 1.00 | 26.36 C |
| ATOM | 1527 | C | LEU | A | 200 | 135.040 | 68.719 | 14.635 | 1.00 | 25.73 C |
| ATOM | 1528 | O | LEU | A | 200 | 133.839 | 68.505 | 14.730 | 1.00 | 24.48 O |
| ATOM | 1529 | CB | LEU | A | 200 | 136.102 | 66.966 | 13.173 | 1.00 | 28.24 C |
| ATOM | 1530 | CG | LEU | A | 200 | 136.355 | 67.848 | 11.938 | 1.00 | 30.21 C |
| ATOM | 1531 | CD1 | LEU | A | 200 | 136.938 | 67.013 | 10.809 | 1.00 | 30.99 C |
| ATOM | 1532 | CD2 | LEU | A | 200 | 135.063 | 68.517 | 11.506 | 1.00 | 32.05 C |
| ATOM | 1533 | N | ILE | A | 201 | 135.567 | 69.942 | 14.584 | 1.00 | 26.65 N |
| ATOM | 1534 | CA | ILE | A | 201 | 134.759 | 71.160 | 14.591 | 1.00 | 27.46 C |
| ATOM | 1535 | C | ILE | A | 201 | 134.862 | 71.811 | 13.205 | 1.00 | 29.38 C |
| ATOM | 1536 | O | ILE | A | 201 | 135.944 | 71.871 | 12.604 | 1.00 | 29.46 O |
| ATOM | 1537 | CB | ILE | A | 201 | 135.244 | 72.150 | 15.660 | 1.00 | 26.43 C |
| ATOM | 1538 | CG1 | ILE | A | 201 | 135.132 | 71.508 | 17.047 | 1.00 | 27.07 C |
| ATOM | 1539 | CG2 | ILE | A | 201 | 134.417 | 73.423 | 15.595 | 1.00 | 27.71 C |
| ATOM | 1540 | CD1 | ILE | A | 201 | 135.613 | 72.380 | 18.218 | 1.00 | 24.40 C |
| ATOM | 1541 | N | THR | A | 202 | 133.728 | 72.296 | 12.703 | 1.00 | 30.75 N |
| ATOM | 1542 | CA | THR | A | 202 | 133.660 | 72.906 | 11.379 | 1.00 | 32.31 C |
| ATOM | 1543 | C | THR | A | 202 | 133.207 | 74.358 | 11.414 | 1.00 | 32.21 C |
| ATOM | 1544 | O | THR | A | 202 | 132.650 | 74.825 | 12.405 | 1.00 | 31.14 O |
| ATOM | 1545 | CB | THR | A | 202 | 132.691 | 72.113 | 10.472 | 1.00 | 33.40 C |
| ATOM | 1546 | OG1 | THR | A | 202 | 133.146 | 70.760 | 10.361 | 1.00 | 36.21 O |
| ATOM | 1547 | CG2 | THR | A | 202 | 132.632 | 72.718 | 9.080 | 1.00 | 36.76 C |
| ATOM | 1548 | N | ILE | A | 203 | 133.452 | 75.066 | 10.315 | 1.00 | 33.57 N |
| ATOM | 1549 | CA | ILE | A | 203 | 133.062 | 76.461 | 10.196 | 1.00 | 33.87 C |

TABLE 7-continued

| ATOM | 1550 | C | ILE | A | 203 | 131.531 | 76.544 | 10.244 | 1.00 | 34.10 | C |
|---|---|---|---|---|---|---|---|---|---|---|---|
| ATOM | 1551 | O | ILE | A | 203 | 130.978 | 77.430 | 10.887 | 1.00 | 33.80 | O |
| ATOM | 1552 | CB | ILE | A | 203 | 133.621 | 77.084 | 8.877 | 1.00 | 33.87 | C |
| ATOM | 1553 | CG1 | ILE | A | 203 | 133.384 | 78.589 | 8.869 | 1.00 | 33.89 | C |
| ATOM | 1554 | CG2 | ILE | A | 203 | 132.995 | 76.434 | 7.664 | 1.00 | 34.39 | C |
| ATOM | 1555 | CD1 | ILE | A | 203 | 134.165 | 79.321 | 9.950 | 1.00 | 34.38 | C |
| ATOM | 1556 | N | LYS | A | 204 | 130.852 | 75.605 | 9.587 | 1.00 | 34.73 | N |
| ATOM | 1557 | CA | LYS | A | 204 | 129.388 | 75.578 | 9.588 | 1.00 | 36.17 | C |
| ATOM | 1558 | C | LYS | A | 204 | 128.838 | 75.505 | 11.014 | 1.00 | 36.21 | C |
| ATOM | 1559 | O | LYS | A | 204 | 127.916 | 76.243 | 11.360 | 1.00 | 36.39 | O |
| ATOM | 1560 | CB | LYS | A | 204 | 128.857 | 74.386 | 8.782 | 1.00 | 38.20 | C |
| ATOM | 1561 | CG | LYS | A | 204 | 129.058 | 74.473 | 7.284 | 1.00 | 41.84 | C |
| ATOM | 1562 | CD | LYS | A | 204 | 130.529 | 74.521 | 6.918 | 1.00 | 47.07 | C |
| ATOM | 1563 | CE | LYS | A | 204 | 130.723 | 74.686 | 5.410 | 1.00 | 50.14 | C |
| ATOM | 1564 | NZ | LYS | A | 204 | 132.165 | 74.843 | 5.037 | 1.00 | 52.54 | N |
| ATOM | 1565 | N | ASP | A | 205 | 129.391 | 74.611 | 11.834 | 1.00 | 36.04 | N |
| ATOM | 1566 | CA | ASP | A | 205 | 128.950 | 74.472 | 13.224 | 1.00 | 36.48 | C |
| ATOM | 1567 | C | ASP | A | 205 | 128.922 | 75.830 | 13.886 | 1.00 | 35.58 | C |
| ATOM | 1568 | O | ASP | A | 205 | 127.995 | 76.162 | 14.624 | 1.00 | 36.04 | O |
| ATOM | 1569 | CB | ASP | A | 205 | 129.909 | 73.606 | 14.036 | 1.00 | 38.56 | C |
| ATOM | 1570 | CG | ASP | A | 205 | 129.957 | 72.189 | 13.569 | 1.00 | 40.22 | C |
| ATOM | 1571 | OD1 | ASP | A | 205 | 130.764 | 71.431 | 14.141 | 1.00 | 41.68 | O |
| ATOM | 1572 | OD2 | ASP | A | 205 | 129.196 | 71.833 | 12.644 | 1.00 | 42.07 | O |
| ATOM | 1573 | N | ILE | A | 206 | 129.970 | 76.604 | 13.637 | 1.00 | 34.72 | N |
| ATOM | 1574 | CA | ILE | A | 206 | 130.092 | 77.933 | 14.209 | 1.00 | 34.65 | C |
| ATOM | 1575 | C | ILE | A | 206 | 129.025 | 78.854 | 13.628 | 1.00 | 34.32 | C |
| ATOM | 1576 | O | ILE | A | 206 | 128.466 | 79.693 | 14.326 | 1.00 | 34.37 | O |
| ATOM | 1577 | CB | ILE | A | 206 | 131.494 | 78.485 | 13.933 | 1.00 | 34.36 | C |
| ATOM | 1578 | CG1 | ILE | A | 206 | 132.522 | 77.495 | 14.486 | 1.00 | 35.28 | C |
| ATOM | 1579 | CG2 | ILE | A | 206 | 131.665 | 79.849 | 14.575 | 1.00 | 34.33 | C |
| ATOM | 1580 | CD1 | ILE | A | 206 | 133.948 | 77.829 | 14.164 | 1.00 | 36.11 | C |
| ATOM | 1581 | N | GLU | A | 207 | 128.732 | 78.669 | 12.348 | 1.00 | 34.71 | N |
| ATOM | 1582 | CA | GLU | A | 207 | 127.737 | 79.479 | 11.671 | 1.00 | 35.12 | C |
| ATOM | 1583 | C | GLU | A | 207 | 126.326 | 79.117 | 12.120 | 1.00 | 34.48 | C |
| ATOM | 1584 | O | GLU | A | 207 | 125.462 | 79.991 | 12.222 | 1.00 | 34.41 | O |
| ATOM | 1585 | CB | GLU | A | 207 | 127.864 | 79.302 | 10.160 | 1.00 | 36.78 | C |
| ATOM | 1586 | CG | GLU | A | 207 | 129.266 | 79.555 | 9.649 | 1.00 | 39.03 | C |
| ATOM | 1587 | CD | GLU | A | 207 | 129.353 | 79.532 | 8.139 | 1.00 | 41.21 | C |
| ATOM | 1588 | OE1 | GLU | A | 207 | 128.871 | 78.550 | 7.519 | 1.00 | 41.65 | O |
| ATOM | 1589 | OE2 | GLU | A | 207 | 129.918 | 80.497 | 7.575 | 1.00 | 43.02 | O |
| ATOM | 1590 | N | LYS | A | 208 | 126.090 | 77.835 | 12.392 | 1.00 | 32.85 | N |
| ATOM | 1591 | CA | LYS | A | 208 | 124.770 | 77.396 | 12.838 | 1.00 | 31.74 | C |
| ATOM | 1592 | C | LYS | A | 208 | 124.462 | 77.924 | 14.223 | 1.00 | 30.98 | C |
| ATOM | 1593 | O | LYS | A | 208 | 123.306 | 78.107 | 14.577 | 1.00 | 31.35 | O |
| ATOM | 1594 | CB | LYS | A | 208 | 124.668 | 75.874 | 12.824 | 1.00 | 31.08 | C |
| ATOM | 1595 | CG | LYS | A | 208 | 124.654 | 75.281 | 11.429 | 1.00 | 32.19 | C |
| ATOM | 1596 | CD | LYS | A | 208 | 124.629 | 73.769 | 11.485 | 1.00 | 32.69 | C |
| ATOM | 1597 | CE | LYS | A | 208 | 124.667 | 73.162 | 10.102 | 1.00 | 33.70 | C |
| ATOM | 1598 | NZ | LYS | A | 208 | 124.676 | 71.678 | 10.190 | 1.00 | 35.26 | N |
| ATOM | 1599 | N | VAL | A | 209 | 125.499 | 78.172 | 15.010 | 1.00 | 31.31 | N |
| ATOM | 1600 | CA | VAL | A | 209 | 125.305 | 78.713 | 16.346 | 1.00 | 31.66 | C |
| ATOM | 1601 | C | VAL | A | 209 | 124.770 | 80.136 | 16.169 | 1.00 | 32.91 | C |
| ATOM | 1602 | O | VAL | A | 209 | 123.948 | 80.614 | 16.953 | 1.00 | 33.61 | O |
| ATOM | 1603 | CB | VAL | A | 209 | 126.634 | 78.733 | 17.137 | 1.00 | 30.78 | C |
| ATOM | 1604 | CG1 | VAL | A | 209 | 126.430 | 79.378 | 18.494 | 1.00 | 30.86 | C |
| ATOM | 1605 | CG2 | VAL | A | 209 | 127.151 | 77.323 | 17.307 | 1.00 | 29.89 | C |
| ATOM | 1606 | N | ILE | A | 210 | 125.236 | 80.807 | 15.120 | 1.00 | 33.36 | N |
| ATOM | 1607 | CA | ILE | A | 210 | 124.791 | 82.164 | 14.822 | 1.00 | 34.24 | C |
| ATOM | 1608 | C | ILE | A | 210 | 123.357 | 82.142 | 14.291 | 1.00 | 33.53 | C |
| ATOM | 1609 | O | ILE | A | 210 | 122.480 | 82.843 | 14.798 | 1.00 | 32.71 | O |
| ATOM | 1610 | CB | ILE | A | 210 | 125.712 | 82.834 | 13.766 | 1.00 | 35.30 | C |
| ATOM | 1611 | CG1 | ILE | A | 210 | 127.090 | 83.101 | 14.378 | 1.00 | 36.13 | C |
| ATOM | 1612 | CG2 | ILE | A | 210 | 125.080 | 84.121 | 13.243 | 1.00 | 34.62 | C |
| ATOM | 1613 | CD1 | ILE | A | 210 | 127.040 | 83.976 | 15.620 | 1.00 | 37.62 | C |
| ATOM | 1614 | N | GLU | A | 211 | 123.135 | 81.320 | 13.271 | 1.00 | 33.34 | N |
| ATOM | 1615 | CA | GLU | A | 211 | 121.832 | 81.179 | 12.635 | 1.00 | 33.18 | C |
| ATOM | 1616 | C | GLU | A | 211 | 120.689 | 80.778 | 13.565 | 1.00 | 32.49 | C |
| ATOM | 1617 | O | GLU | A | 211 | 119.572 | 81.266 | 13.405 | 1.00 | 32.64 | O |
| ATOM | 1618 | CB | GLU | A | 211 | 121.943 | 80.186 | 11.482 | 1.00 | 34.14 | C |
| ATOM | 1619 | CG | GLU | A | 211 | 120.657 | 79.924 | 10.751 | 1.00 | 36.42 | C |
| ATOM | 1620 | CD | GLU | A | 211 | 120.868 | 78.997 | 9.582 | 1.00 | 39.42 | C |
| ATOM | 1621 | OE1 | GLU | A | 211 | 121.606 | 78.009 | 9.757 | 1.00 | 42.56 | O |
| ATOM | 1622 | OE2 | GLU | A | 211 | 120.292 | 79.233 | 8.499 | 1.00 | 40.95 | O |
| ATOM | 1623 | N | PHE | A | 212 | 120.952 | 79.893 | 14.526 | 1.00 | 31.88 | N |
| ATOM | 1624 | CA | PHE | A | 212 | 119.912 | 79.465 | 15.466 | 1.00 | 30.57 | C |
| ATOM | 1625 | C | PHE | A | 212 | 120.409 | 79.610 | 16.902 | 1.00 | 30.83 | C |
| ATOM | 1626 | O | PHE | A | 212 | 120.705 | 78.622 | 17.578 | 1.00 | 30.70 | O |
| ATOM | 1627 | CB | PHE | A | 212 | 119.510 | 78.007 | 15.234 | 1.00 | 29.04 | C |
| ATOM | 1628 | CG | PHE | A | 212 | 119.187 | 77.673 | 13.807 | 1.00 | 27.87 | C |

TABLE 7-continued

| | | | | | | | | | |
|---|---|---|---|---|---|---|---|---|---|
| ATOM | 1629 | CD1 | PHE | A | 212 | 120.161 | 77.139 | 12.969 | 1.00 27.41 C |
| ATOM | 1630 | CD2 | PHE | A | 212 | 117.905 | 77.864 | 13.307 | 1.00 27.70 C |
| ATOM | 1631 | CE1 | PHE | A | 212 | 119.863 | 76.792 | 11.651 | 1.00 27.08 C |
| ATOM | 1632 | CE2 | PHE | A | 212 | 117.595 | 77.520 | 11.985 | 1.00 28.23 C |
| ATOM | 1633 | CZ | PHE | A | 212 | 118.578 | 76.982 | 11.159 | 1.00 27.46 C |
| ATOM | 1634 | N | PRO | A | 213 | 120.482 | 80.850 | 17.396 | 1.00 30.79 N |
| ATOM | 1635 | CA | PRO | A | 213 | 120.943 | 81.168 | 18.745 | 1.00 30.59 C |
| ATOM | 1636 | C | PRO | A | 213 | 120.208 | 80.531 | 19.926 | 1.00 30.81 C |
| ATOM | 1637 | O | PRO | A | 213 | 120.792 | 80.375 | 20.991 | 1.00 32.42 O |
| ATOM | 1638 | CB | PRO | A | 213 | 120.853 | 82.693 | 18.766 | 1.00 30.59 C |
| ATOM | 1639 | CG | PRO | A | 213 | 119.680 | 82.949 | 17.850 | 1.00 29.65 C |
| ATOM | 1640 | CD | PRO | A | 213 | 120.117 | 82.091 | 16.697 | 1.00 30.72 C |
| ATOM | 1641 | N | HIS | A | 214 | 118.944 | 80.156 | 19.757 | 1.00 31.01 N |
| ATOM | 1642 | CA | HIS | A | 214 | 118.193 | 79.589 | 20.872 | 1.00 29.81 C |
| ATOM | 1643 | C | HIS | A | 214 | 117.983 | 78.090 | 20.793 | 1.00 28.54 C |
| ATOM | 1644 | O | HIS | A | 214 | 117.133 | 77.549 | 21.499 | 1.00 26.06 O |
| ATOM | 1645 | CB | HIS | A | 214 | 116.825 | 80.258 | 20.990 | 1.00 32.85 C |
| ATOM | 1646 | CG | HIS | A | 214 | 116.876 | 81.752 | 20.955 | 1.00 36.67 C |
| ATOM | 1647 | ND1 | HIS | A | 214 | 116.854 | 82.469 | 19.776 | 1.00 38.33 N |
| ATOM | 1648 | CD2 | HIS | A | 214 | 116.998 | 82.663 | 21.949 | 1.00 37.66 C |
| ATOM | 1649 | CE1 | HIS | A | 214 | 116.960 | 83.758 | 20.047 | 1.00 38.52 C |
| ATOM | 1650 | NE2 | HIS | A | 214 | 117.049 | 83.903 | 21.357 | 1.00 38.92 N |
| ATOM | 1651 | N | ALA | A | 215 | 118.756 | 77.424 | 19.943 | 1.00 27.04 N |
| ATOM | 1652 | CA | ALA | A | 215 | 118.633 | 75.984 | 19.774 | 1.00 26.19 C |
| ATOM | 1653 | C | ALA | A | 215 | 118.800 | 75.263 | 21.100 | 1.00 25.46 C |
| ATOM | 1654 | O | ALA | A | 215 | 119.618 | 75.658 | 21.924 | 1.00 25.60 O |
| ATOM | 1655 | CB | ALA | A | 215 | 119.667 | 75.486 | 18.768 | 1.00 25.12 C |
| ATOM | 1656 | N | ALA | A | 216 | 118.004 | 74.216 | 21.305 | 1.00 25.96 N |
| ATOM | 1657 | CA | ALA | A | 216 | 118.072 | 73.417 | 22.523 | 1.00 25.69 C |
| ATOM | 1658 | C | ALA | A | 216 | 119.095 | 72.341 | 22.211 | 1.00 26.07 C |
| ATOM | 1659 | O | ALA | A | 216 | 118.880 | 71.516 | 21.327 | 1.00 27.31 O |
| ATOM | 1660 | CB | ALA | A | 216 | 116.714 | 72.797 | 22.824 | 1.00 25.56 C |
| ATOM | 1661 | N | LYS | A | 217 | 120.212 | 72.355 | 22.931 | 1.00 26.34 N |
| ATOM | 1662 | CA | LYS | A | 217 | 121.289 | 71.409 | 22.677 | 1.00 25.73 C |
| ATOM | 1663 | C | LYS | A | 217 | 121.786 | 70.689 | 23.918 | 1.00 26.81 C |
| ATOM | 1664 | O | LYS | A | 217 | 121.480 | 71.084 | 25.044 | 1.00 25.57 O |
| ATOM | 1665 | CB | LYS | A | 217 | 122.450 | 72.150 | 22.015 | 1.00 25.06 C |
| ATOM | 1666 | CG | LYS | A | 217 | 122.081 | 72.771 | 20.672 | 1.00 24.94 C |
| ATOM | 1667 | CD | LYS | A | 217 | 123.162 | 73.693 | 20.150 | 1.00 24.62 C |
| ATOM | 1668 | CE | LYS | A | 217 | 122.830 | 74.159 | 18.749 | 1.00 26.52 C |
| ATOM | 1669 | NZ | LYS | A | 217 | 123.873 | 75.063 | 18.196 | 1.00 28.65 N |
| ATOM | 1670 | N | ASP | A | 218 | 122.546 | 69.616 | 23.700 | 1.00 28.28 N |
| ATOM | 1671 | CA | ASP | A | 218 | 123.106 | 68.855 | 24.808 | 1.00 29.53 C |
| ATOM | 1672 | C | ASP | A | 218 | 124.458 | 69.434 | 25.200 | 1.00 29.72 C |
| ATOM | 1673 | O | ASP | A | 218 | 124.864 | 70.494 | 24.715 | 1.00 27.51 O |
| ATOM | 1674 | CB | ASP | A | 218 | 123.270 | 67.363 | 24.458 | 1.00 30.13 C |
| ATOM | 1675 | CG | ASP | A | 218 | 124.142 | 67.130 | 23.231 | 1.00 32.50 C |
| ATOM | 1676 | OD1 | ASP | A | 218 | 125.144 | 67.853 | 23.060 | 1.00 33.09 O |
| ATOM | 1677 | OD2 | ASP | A | 218 | 123.848 | 66.200 | 22.447 | 1.00 32.34 O |
| ATOM | 1678 | N | GLU | A | 219 | 125.143 | 68.718 | 26.082 | 1.00 31.09 N |
| ATOM | 1679 | CA | GLU | A | 219 | 126.445 | 69.117 | 26.586 | 1.00 33.04 C |
| ATOM | 1680 | C | GLU | A | 219 | 127.492 | 69.306 | 25.505 | 1.00 31.97 C |
| ATOM | 1681 | O | GLU | A | 219 | 128.455 | 70.037 | 25.697 | 1.00 33.31 O |
| ATOM | 1682 | CB | GLU | A | 219 | 126.931 | 68.087 | 27.613 | 1.00 36.51 C |
| ATOM | 1683 | CG | GLU | A | 219 | 126.807 | 66.636 | 27.148 | 1.00 43.30 C |
| ATOM | 1684 | CD | GLU | A | 219 | 127.129 | 65.626 | 28.245 | 1.00 46.43 C |
| ATOM | 1685 | OE1 | GLU | A | 219 | 126.570 | 65.740 | 29.358 | 1.00 49.99 O |
| ATOM | 1686 | OE2 | GLU | A | 219 | 127.926 | 64.702 | 27.994 | 1.00 49.56 O |
| ATOM | 1687 | N | PHE | A | 220 | 127.297 | 68.663 | 24.363 | 1.00 31.08 N |
| ATOM | 1688 | CA | PHE | A | 220 | 128.253 | 68.753 | 23.264 | 1.00 30.41 C |
| ATOM | 1689 | C | PHE | A | 220 | 127.863 | 69.773 | 22.205 | 1.00 30.02 C |
| ATOM | 1690 | O | PHE | A | 220 | 128.534 | 69.897 | 21.180 | 1.00 30.29 O |
| ATOM | 1691 | CB | PHE | A | 220 | 128.401 | 67.378 | 22.619 | 1.00 30.42 C |
| ATOM | 1692 | CG | PHE | A | 220 | 128.737 | 66.292 | 23.600 | 1.00 31.61 C |
| ATOM | 1693 | CD1 | PHE | A | 220 | 129.949 | 66.306 | 24.287 | 1.00 31.76 C |
| ATOM | 1694 | CD2 | PHE | A | 220 | 127.831 | 65.267 | 23.855 | 1.00 31.51 C |
| ATOM | 1695 | CE1 | PHE | A | 220 | 130.252 | 65.317 | 25.209 | 1.00 32.04 C |
| ATOM | 1696 | CE2 | PHE | A | 220 | 128.124 | 64.276 | 24.775 | 1.00 31.75 C |
| ATOM | 1697 | CZ | PHE | A | 220 | 129.337 | 64.299 | 25.453 | 1.00 31.56 C |
| ATOM | 1698 | N | GLY | A | 221 | 126.773 | 70.496 | 22.453 | 1.00 30.25 N |
| ATOM | 1699 | CA | GLY | A | 221 | 126.308 | 71.485 | 21.498 | 1.00 29.06 C |
| ATOM | 1700 | C | GLY | A | 221 | 125.573 | 70.852 | 20.325 | 1.00 28.96 C |
| ATOM | 1701 | O | GLY | A | 221 | 125.519 | 71.417 | 19.232 | 1.00 27.40 O |
| ATOM | 1702 | N | ARG | A | 222 | 125.029 | 69.658 | 20.551 | 1.00 28.41 N |
| ATOM | 1703 | CA | ARG | A | 222 | 124.269 | 68.949 | 19.534 | 1.00 27.01 C |
| ATOM | 1704 | C | ARG | A | 222 | 122.797 | 69.105 | 19.909 | 1.00 25.67 C |
| ATOM | 1705 | O | ARG | A | 222 | 122.448 | 69.100 | 21.081 | 1.00 24.90 O |
| ATOM | 1706 | CB | ARG | A | 222 | 124.640 | 67.470 | 19.518 | 1.00 26.66 C |
| ATOM | 1707 | CG | ARG | A | 222 | 126.102 | 67.212 | 19.270 | 1.00 27.12 C |

TABLE 7-continued

| ATOM | 1708 | CD  | ARG | A | 222 | 126.398 | 65.719 | 19.306 | 1.00 | 28.42 | C |
| ATOM | 1709 | NE  | ARG | A | 222 | 125.961 | 65.097 | 20.559 | 1.00 | 30.08 | N |
| ATOM | 1710 | CZ  | ARG | A | 222 | 126.067 | 63.799 | 20.827 | 1.00 | 27.75 | C |
| ATOM | 1711 | NH1 | ARG | A | 222 | 126.599 | 62.973 | 19.934 | 1.00 | 25.60 | N |
| ATOM | 1712 | NH2 | ARG | A | 222 | 125.620 | 63.328 | 21.981 | 1.00 | 27.54 | N |
| ATOM | 1713 | N   | LEU | A | 223 | 121.944 | 69.248 | 18.906 | 1.00 | 25.37 | N |
| ATOM | 1714 | CA  | LEU | A | 223 | 120.506 | 69.417 | 19.129 | 1.00 | 25.09 | C |
| ATOM | 1715 | C   | LEU | A | 223 | 119.943 | 68.277 | 19.967 | 1.00 | 25.23 | C |
| ATOM | 1716 | O   | LEU | A | 223 | 120.390 | 67.128 | 19.853 | 1.00 | 25.90 | O |
| ATOM | 1717 | CB  | LEU | A | 223 | 119.766 | 69.464 | 17.782 | 1.00 | 22.94 | C |
| ATOM | 1718 | CG  | LEU | A | 223 | 120.155 | 70.538 | 16.755 | 1.00 | 23.39 | C |
| ATOM | 1719 | CD1 | LEU | A | 223 | 119.455 | 70.265 | 15.420 | 1.00 | 22.13 | C |
| ATOM | 1720 | CD2 | LEU | A | 223 | 119.802 | 71.917 | 17.288 | 1.00 | 22.20 | C |
| ATOM | 1721 | N   | LEU | A | 224 | 118.963 | 68.595 | 20.811 | 1.00 | 24.72 | N |
| ATOM | 1722 | CA  | LEU | A | 224 | 118.318 | 67.585 | 21.647 | 1.00 | 24.86 | C |
| ATOM | 1723 | C   | LEU | A | 224 | 117.331 | 66.806 | 20.806 | 1.00 | 24.46 | C |
| ATOM | 1724 | O   | LEU | A | 224 | 116.871 | 67.281 | 19.775 | 1.00 | 24.23 | O |
| ATOM | 1725 | CB  | LEU | A | 224 | 117.545 | 68.226 | 22.798 | 1.00 | 23.92 | C |
| ATOM | 1726 | CG  | LEU | A | 224 | 118.313 | 68.961 | 23.888 | 1.00 | 25.09 | C |
| ATOM | 1727 | CD1 | LEU | A | 224 | 117.344 | 69.527 | 24.924 | 1.00 | 21.77 | C |
| ATOM | 1728 | CD2 | LEU | A | 224 | 119.295 | 67.987 | 24.529 | 1.00 | 25.24 | C |
| ATOM | 1729 | N   | VAL | A | 225 | 117.008 | 65.600 | 21.243 | 1.00 | 25.32 | N |
| ATOM | 1730 | CA  | VAL | A | 225 | 116.027 | 64.803 | 20.532 | 1.00 | 25.61 | C |
| ATOM | 1731 | C   | VAL | A | 225 | 115.498 | 63.714 | 21.440 | 1.00 | 25.77 | C |
| ATOM | 1732 | O   | VAL | A | 225 | 116.227 | 63.181 | 22.282 | 1.00 | 25.12 | O |
| ATOM | 1733 | CB  | VAL | A | 225 | 116.601 | 64.151 | 19.237 | 1.00 | 27.42 | C |
| ATOM | 1734 | CG1 | VAL | A | 225 | 117.632 | 63.069 | 19.577 | 1.00 | 26.05 | C |
| ATOM | 1735 | CG2 | VAL | A | 225 | 115.456 | 63.574 | 18.400 | 1.00 | 26.21 | C |
| ATOM | 1736 | N   | ALA | A | 226 | 114.214 | 63.412 | 21.272 | 1.00 | 24.98 | N |
| ATOM | 1737 | CA  | ALA | A | 226 | 113.547 | 62.373 | 22.037 | 1.00 | 23.32 | C |
| ATOM | 1738 | C   | ALA | A | 226 | 112.985 | 61.398 | 21.013 | 1.00 | 23.19 | C |
| ATOM | 1739 | O   | ALA | A | 226 | 112.839 | 61.734 | 19.838 | 1.00 | 22.48 | O |
| ATOM | 1740 | CB  | ALA | A | 226 | 112.426 | 62.966 | 22.876 | 1.00 | 22.70 | C |
| ATOM | 1741 | N   | ALA | A | 227 | 112.692 | 60.184 | 21.452 | 1.00 | 22.90 | N |
| ATOM | 1742 | CA  | ALA | A | 227 | 112.143 | 59.179 | 20.560 | 1.00 | 24.67 | C |
| ATOM | 1743 | C   | ALA | A | 227 | 111.116 | 58.381 | 21.346 | 1.00 | 26.09 | C |
| ATOM | 1744 | O   | ALA | A | 227 | 111.237 | 58.219 | 22.566 | 1.00 | 26.01 | O |
| ATOM | 1745 | CB  | ALA | A | 227 | 113.255 | 58.266 | 20.029 | 1.00 | 22.84 | C |
| ATOM | 1746 | N   | ALA | A | 228 | 110.098 | 57.892 | 20.650 | 1.00 | 26.88 | N |
| ATOM | 1747 | CA  | ALA | A | 228 | 109.053 | 57.130 | 21.306 | 1.00 | 27.92 | C |
| ATOM | 1748 | C   | ALA | A | 228 | 109.201 | 55.630 | 21.125 | 1.00 | 29.27 | C |
| ATOM | 1749 | O   | ALA | A | 228 | 109.788 | 55.149 | 20.153 | 1.00 | 28.65 | O |
| ATOM | 1750 | CB  | ALA | A | 228 | 107.697 | 57.575 | 20.792 | 1.00 | 28.14 | C |
| ATOM | 1751 | N   | VAL | A | 229 | 108.662 | 54.901 | 22.091 | 1.00 | 30.70 | N |
| ATOM | 1752 | CA  | VAL | A | 229 | 108.654 | 53.447 | 22.082 | 1.00 | 31.77 | C |
| ATOM | 1753 | C   | VAL | A | 229 | 107.354 | 53.075 | 22.785 | 1.00 | 33.71 | C |
| ATOM | 1754 | O   | VAL | A | 229 | 106.778 | 53.897 | 23.508 | 1.00 | 34.20 | O |
| ATOM | 1755 | CB  | VAL | A | 229 | 109.847 | 52.850 | 22.876 | 1.00 | 31.31 | C |
| ATOM | 1756 | CG1 | VAL | A | 229 | 111.156 | 53.346 | 22.298 | 1.00 | 31.39 | C |
| ATOM | 1757 | CG2 | VAL | A | 229 | 109.739 | 53.208 | 24.357 | 1.00 | 31.01 | C |
| ATOM | 1758 | N   | GLY | A | 230 | 106.871 | 51.858 | 22.570 | 1.00 | 34.88 | N |
| ATOM | 1759 | CA  | GLY | A | 230 | 105.652 | 51.453 | 23.240 | 1.00 | 35.58 | C |
| ATOM | 1760 | C   | GLY | A | 230 | 105.976 | 50.476 | 24.352 | 1.00 | 36.88 | C |
| ATOM | 1761 | O   | GLY | A | 230 | 107.100 | 50.411 | 24.840 | 1.00 | 36.39 | O |
| ATOM | 1762 | N   | VAL | A | 231 | 104.975 | 49.722 | 24.772 | 1.00 | 39.52 | N |
| ATOM | 1763 | CA  | VAL | A | 231 | 105.176 | 48.719 | 25.801 | 1.00 | 41.92 | C |
| ATOM | 1764 | C   | VAL | A | 231 | 104.905 | 47.363 | 25.140 | 1.00 | 43.78 | C |
| ATOM | 1765 | O   | VAL | A | 231 | 103.779 | 46.858 | 25.143 | 1.00 | 44.73 | O |
| ATOM | 1766 | CB  | VAL | A | 231 | 104.240 | 48.966 | 26.997 | 1.00 | 41.08 | C |
| ATOM | 1767 | CG1 | VAL | A | 231 | 104.639 | 50.257 | 27.691 | 1.00 | 40.96 | C |
| ATOM | 1768 | CG2 | VAL | A | 231 | 102.810 | 49.071 | 26.526 | 1.00 | 40.96 | C |
| ATOM | 1769 | N   | THR | A | 232 | 105.954 | 46.807 | 24.538 | 1.00 | 44.60 | N |
| ATOM | 1770 | CA  | THR | A | 232 | 105.881 | 45.532 | 23.845 | 1.00 | 45.87 | C |
| ATOM | 1771 | C   | THR | A | 232 | 107.106 | 44.710 | 24.200 | 1.00 | 46.68 | C |
| ATOM | 1772 | O   | THR | A | 232 | 107.838 | 45.059 | 25.120 | 1.00 | 47.51 | O |
| ATOM | 1773 | CB  | THR | A | 232 | 105.842 | 45.739 | 22.328 | 1.00 | 46.37 | C |
| ATOM | 1774 | OG1 | THR | A | 232 | 107.038 | 46.404 | 21.906 | 1.00 | 46.75 | O |
| ATOM | 1775 | CG2 | THR | A | 232 | 104.645 | 46.590 | 21.946 | 1.00 | 46.43 | C |
| ATOM | 1776 | N   | SER | A | 233 | 107.342 | 43.626 | 23.468 | 1.00 | 48.35 | N |
| ATOM | 1777 | CA  | SER | A | 233 | 108.491 | 42.768 | 23.755 | 1.00 | 49.99 | C |
| ATOM | 1778 | C   | SER | A | 233 | 109.804 | 43.315 | 23.199 | 1.00 | 50.98 | C |
| ATOM | 1779 | O   | SER | A | 233 | 110.887 | 42.949 | 23.667 | 1.00 | 52.13 | O |
| ATOM | 1780 | CB  | SER | A | 233 | 108.256 | 41.355 | 23.211 | 1.00 | 49.80 | C |
| ATOM | 1781 | OG  | SER | A | 233 | 108.089 | 41.370 | 21.809 | 1.00 | 51.16 | O |
| ATOM | 1782 | N   | ASP | A | 234 | 109.710 | 44.197 | 22.210 | 1.00 | 51.06 | N |
| ATOM | 1783 | CA  | ASP | A | 234 | 110.901 | 44.779 | 21.606 | 1.00 | 51.16 | C |
| ATOM | 1784 | C   | ASP | A | 234 | 111.207 | 46.174 | 22.142 | 1.00 | 50.20 | C |
| ATOM | 1785 | O   | ASP | A | 234 | 112.024 | 46.892 | 21.570 | 1.00 | 50.68 | O |
| ATOM | 1786 | CB  | ASP | A | 234 | 110.733 | 44.835 | 20.092 | 1.00 | 52.65 | C |

TABLE 7-continued

| | | | | | | | | | | |
|---|---|---|---|---|---|---|---|---|---|---|
| ATOM | 1787 | CG | ASP | A | 234 | 109.474 | 45.563 | 19.686 | 1.00 | 55.59 C |
| ATOM | 1788 | OD1 | ASP | A | 234 | 108.388 | 45.134 | 20.138 | 1.00 | 57.24 O |
| ATOM | 1789 | OD2 | ASP | A | 234 | 109.566 | 46.556 | 18.924 | 1.00 | 56.62 O |
| ATOM | 1790 | N | THR | A | 235 | 110.559 | 46.553 | 23.239 | 1.00 | 48.92 N |
| ATOM | 1791 | CA | THR | A | 235 | 110.775 | 47.866 | 23.837 | 1.00 | 48.36 C |
| ATOM | 1792 | C | THR | A | 235 | 112.219 | 48.115 | 24.279 | 1.00 | 48.23 C |
| ATOM | 1793 | O | THR | A | 235 | 112.835 | 49.092 | 23.855 | 1.00 | 48.06 O |
| ATOM | 1794 | CB | THR | A | 235 | 109.844 | 48.080 | 25.035 | 1.00 | 48.22 C |
| ATOM | 1795 | OG1 | THR | A | 235 | 108.492 | 48.121 | 24.572 | 1.00 | 48.44 O |
| ATOM | 1796 | CG2 | THR | A | 235 | 110.164 | 49.382 | 25.740 | 1.00 | 48.44 C |
| ATOM | 1797 | N | PHE | A | 236 | 112.755 | 47.248 | 25.138 | 1.00 | 47.72 N |
| ATOM | 1798 | CA | PHE | A | 236 | 114.133 | 47.403 | 25.594 | 1.00 | 46.43 C |
| ATOM | 1799 | C | PHE | A | 236 | 115.075 | 47.536 | 24.420 | 1.00 | 45.57 C |
| ATOM | 1800 | O | PHE | A | 236 | 115.856 | 48.480 | 24.342 | 1.00 | 45.91 O |
| ATOM | 1801 | CB | PHE | A | 236 | 114.568 | 46.209 | 26.434 | 1.00 | 47.23 C |
| ATOM | 1802 | CG | PHE | A | 236 | 114.351 | 46.394 | 27.892 | 1.00 | 48.55 C |
| ATOM | 1803 | CD1 | PHE | A | 236 | 115.014 | 47.402 | 28.572 | 1.00 | 49.39 C |
| ATOM | 1804 | CD2 | PHE | A | 236 | 113.483 | 45.567 | 28.591 | 1.00 | 50.16 C |
| ATOM | 1805 | CE1 | PHE | A | 236 | 114.817 | 47.588 | 29.931 | 1.00 | 51.05 C |
| ATOM | 1806 | CE2 | PHE | A | 236 | 113.276 | 45.742 | 29.959 | 1.00 | 51.03 C |
| ATOM | 1807 | CZ | PHE | A | 236 | 113.945 | 46.755 | 30.630 | 1.00 | 51.13 C |
| ATOM | 1808 | N | GLU | A | 237 | 114.998 | 46.570 | 23.513 | 1.00 | 44.78 N |
| ATOM | 1809 | CA | GLU | A | 237 | 115.835 | 46.548 | 22.320 | 1.00 | 44.06 C |
| ATOM | 1810 | C | GLU | A | 237 | 115.749 | 47.901 | 21.626 | 1.00 | 41.89 C |
| ATOM | 1811 | O | GLU | A | 237 | 116.756 | 48.466 | 21.210 | 1.00 | 41.21 O |
| ATOM | 1812 | CB | GLU | A | 237 | 115.334 | 45.461 | 21.375 | 1.00 | 46.63 C |
| ATOM | 1813 | CG | GLU | A | 237 | 116.258 | 45.132 | 20.226 | 1.00 | 50.92 C |
| ATOM | 1814 | CD | GLU | A | 237 | 115.598 | 44.192 | 19.233 | 1.00 | 54.10 C |
| ATOM | 1815 | OE1 | GLU | A | 237 | 114.939 | 43.224 | 19.686 | 1.00 | 55.04 O |
| ATOM | 1816 | OE2 | GLU | A | 237 | 115.749 | 44.410 | 18.004 | 1.00 | 55.45 O |
| ATOM | 1817 | N | ARG | A | 238 | 114.524 | 48.410 | 21.521 | 1.00 | 40.47 N |
| ATOM | 1818 | CA | ARG | A | 238 | 114.244 | 49.691 | 20.880 | 1.00 | 39.30 C |
| ATOM | 1819 | C | ARG | A | 238 | 114.820 | 50.864 | 21.667 | 1.00 | 38.27 C |
| ATOM | 1820 | O | ARG | A | 238 | 115.508 | 51.715 | 21.109 | 1.00 | 37.62 O |
| ATOM | 1821 | CB | ARG | A | 238 | 112.738 | 49.888 | 20.743 | 1.00 | 38.03 C |
| ATOM | 1822 | CG | ARG | A | 238 | 112.380 | 50.858 | 19.656 | 1.00 | 38.82 C |
| ATOM | 1823 | CD | ARG | A | 238 | 110.901 | 51.126 | 19.586 | 1.00 | 39.86 C |
| ATOM | 1824 | NE | ARG | A | 238 | 110.555 | 51.547 | 18.236 | 1.00 | 42.82 N |
| ATOM | 1825 | CZ | ARG | A | 238 | 110.332 | 50.707 | 17.233 | 1.00 | 43.08 C |
| ATON | 1826 | NH1 | ARG | A | 238 | 110.410 | 49.402 | 17.430 | 1.00 | 44.36 N |
| ATOM | 1827 | NH2 | ARG | A | 238 | 110.066 | 51.170 | 16.025 | 1.00 | 43.46 N |
| ATOM | 1828 | N | ALA | A | 239 | 114.518 | 50.904 | 22.962 | 1.00 | 38.15 N |
| ATOM | 1829 | CA | ALA | A | 239 | 114.991 | 51.960 | 23.848 | 1.00 | 37.99 C |
| ATOM | 1830 | C | ALA | A | 239 | 116.516 | 52.030 | 23.869 | 1.00 | 39.80 C |
| ATOM | 1831 | O | ALA | A | 239 | 117.093 | 53.121 | 23.815 | 1.00 | 39.71 O |
| ATOM | 1832 | CB | ALA | A | 239 | 114.461 | 51.729 | 25.249 | 1.00 | 36.95 C |
| ATOM | 1833 | N | GLU | A | 240 | 117.174 | 50.873 | 23.944 | 1.00 | 41.10 N |
| ATOM | 1834 | CA | GLU | A | 240 | 118.631 | 50.852 | 23.965 | 1.00 | 41.70 C |
| ATOM | 1835 | C | GLU | A | 240 | 119.239 | 51.237 | 22.621 | 1.00 | 40.70 C |
| ATOM | 1836 | O | GLU | A | 240 | 120.358 | 51.744 | 22.570 | 1.00 | 40.79 O |
| ATOM | 1837 | CB | GLU | A | 240 | 119.157 | 49.486 | 24.428 | 1.00 | 44.05 C |
| ATOM | 1838 | CG | GLU | A | 240 | 118.629 | 48.286 | 23.678 | 1.00 | 48.07 C |
| ATOM | 1839 | CD | GLU | A | 240 | 119.141 | 46.973 | 24.266 | 1.00 | 51.41 C |
| ATOM | 1840 | OE1 | GLU | A | 240 | 119.010 | 46.776 | 25.499 | 1.00 | 51.93 O |
| ATOM | 1841 | OE2 | GLU | A | 240 | 119.664 | 46.135 | 23.496 | 1.00 | 52.53 O |
| ATOM | 1842 | N | ALA | A | 241 | 118.508 | 51.005 | 21.536 | 1.00 | 39.57 N |
| ATOM | 1843 | CA | ALA | A | 241 | 118.999 | 51.373 | 20.208 | 1.00 | 39.09 C |
| ATOM | 1844 | C | ALA | A | 241 | 118.911 | 52.893 | 20.071 | 1.00 | 38.48 C |
| ATOM | 1845 | O | ALA | A | 241 | 119.805 | 53.533 | 19.521 | 1.00 | 38.30 O |
| ATOM | 1846 | CB | ALA | A | 241 | 118.161 | 50.701 | 19.125 | 1.00 | 39.36 C |
| ATOM | 1847 | N | LEU | A | 242 | 117.822 | 53.460 | 20.579 | 1.00 | 37.48 N |
| ATOM | 1848 | CA | LEU | A | 242 | 117.603 | 54.902 | 20.549 | 1.00 | 36.64 C |
| ATOM | 1849 | C | LEU | A | 242 | 118.607 | 55.648 | 21.421 | 1.00 | 36.34 C |
| ATOM | 1850 | O | LEU | A | 242 | 119.217 | 56.620 | 20.973 | 1.00 | 35.49 O |
| ATOM | 1851 | CB | LEU | A | 242 | 116.177 | 55.212 | 20.999 | 1.00 | 36.24 C |
| ATOM | 1852 | CG | LEU | A | 242 | 115.079 | 55.051 | 19.940 | 1.00 | 37.63 C |
| ATOM | 1853 | CD1 | LEU | A | 242 | 115.390 | 53.933 | 18.970 | 1.00 | 37.59 C |
| ATOM | 1854 | CD2 | LEU | A | 242 | 113.748 | 54.825 | 20.654 | 1.00 | 37.84 C |
| ATOM | 1855 | N | PHE | A | 243 | 118.785 | 55.209 | 22.666 | 1.00 | 36.35 N |
| ATOM | 1856 | CA | PHE | A | 243 | 119.749 | 55.879 | 23.534 | 1.00 | 36.90 C |
| ATOM | 1857 | C | PHE | A | 243 | 121.143 | 55.806 | 22.930 | 1.00 | 37.73 C |
| ATOM | 1858 | O | PHE | A | 243 | 121.890 | 56.781 | 22.958 | 1.00 | 38.96 O |
| ATOM | 1859 | CB | PHE | A | 243 | 119.769 | 55.262 | 24.938 | 1.00 | 35.66 C |
| ATOM | 1860 | CG | PHE | A | 243 | 118.619 | 55.683 | 25.803 | 1.00 | 34.47 C |
| ATOM | 1861 | CD1 | PHE | A | 243 | 118.325 | 57.032 | 25.980 | 1.00 | 34.10 C |
| ATOM | 1862 | CD2 | PHE | A | 243 | 117.850 | 54.739 | 26.474 | 1.00 | 33.97 C |
| ATOM | 1863 | CE1 | PHE | A | 243 | 117.280 | 57.432 | 26.818 | 1.00 | 33.89 C |
| ATOM | 1864 | CE2 | PHE | A | 243 | 116.802 | 55.130 | 27.317 | 1.00 | 33.03 C |
| ATOM | 1865 | CZ | PHE | A | 243 | 116.517 | 56.474 | 27.489 | 1.00 | 32.69 C |

TABLE 7-continued

| | | | | | | | | | | |
|---|---|---|---|---|---|---|---|---|---|---|
| ATOM | 1866 | N | GLU | A | 244 | 121.477 | 54.650 | 22.370 | 1.00 | 38.32 N |
| ATOM | 1867 | CA | GLU | A | 244 | 122.779 | 54.431 | 21.763 | 1.00 | 39.15 C |
| ATOM | 1868 | C | GLU | A | 244 | 122.974 | 55.304 | 20.531 | 1.00 | 37.76 C |
| ATOM | 1869 | O | GLU | A | 244 | 124.103 | 55.550 | 20.103 | 1.00 | 37.31 O |
| ATOM | 1870 | CB | GLU | A | 244 | 122.932 | 52.959 | 21.380 | 1.00 | 43.06 C |
| ATOM | 1871 | CG | GLU | A | 244 | 124.297 | 52.595 | 20.823 | 1.00 | 48.69 C |
| ATOM | 1872 | CD | GLU | A | 244 | 124.375 | 51.141 | 20.407 | 1.00 | 53.07 C |
| ATOM | 1873 | OE1 | GLU | A | 244 | 124.097 | 50.272 | 21.266 | 1.00 | 55.43 O |
| ATOM | 1874 | OE2 | GLU | A | 244 | 124.713 | 50.866 | 19.228 | 1.00 | 54.65 O |
| ATOM | 1875 | N | ALA | A | 245 | 121.873 | 55.767 | 19.951 | 1.00 | 36.29 N |
| ATOM | 1876 | CA | ALA | A | 245 | 121.964 | 56.619 | 18.770 | 1.00 | 35.13 C |
| ATOM | 1877 | C | ALA | A | 245 | 122.120 | 58.061 | 19.224 | 1.00 | 33.93 C |
| ATOM | 1878 | O | ALA | A | 245 | 122.455 | 58.935 | 18.437 | 1.00 | 34.56 O |
| ATOM | 1879 | CB | ALA | A | 245 | 120.723 | 56.463 | 17.897 | 1.00 | 35.38 C |
| ATOM | 1880 | N | GLY | A | 246 | 121.873 | 58.301 | 20.506 | 1.00 | 32.96 N |
| ATOM | 1881 | CA | GLY | A | 246 | 122.022 | 59.640 | 21.039 | 1.00 | 32.17 C |
| ATOM | 1882 | C | GLY | A | 246 | 120.812 | 60.256 | 21.720 | 1.00 | 31.72 C |
| ATOM | 1883 | O | GLY | A | 246 | 120.919 | 61.358 | 22.265 | 1.00 | 32.01 O |
| ATOM | 1884 | N | ALA | A | 247 | 119.673 | 59.570 | 21.710 | 1.00 | 30.21 N |
| ATOM | 1885 | CA | ALA | A | 247 | 118.465 | 60.123 | 22.328 | 1.00 | 29.83 C |
| ATOM | 1886 | C | ALA | A | 247 | 118.739 | 60.676 | 23.718 | 1.00 | 29.13 C |
| ATOM | 1887 | O | ALA | A | 247 | 119.392 | 60.038 | 24.529 | 1.00 | 29.36 O |
| ATOM | 1888 | CB | ALA | A | 247 | 117.365 | 59.064 | 22.398 | 1.00 | 29.66 C |
| ATOM | 1889 | N | ASP | A | 248 | 118.231 | 61.874 | 23.976 | 1.00 | 29.42 N |
| ATOM | 1890 | CA | ASP | A | 248 | 118.401 | 62.541 | 25.262 | 1.00 | 29.22 C |
| ATOM | 1891 | C | ASP | A | 248 | 117.283 | 62.141 | 26.218 | 1.00 | 28.93 C |
| ATOM | 1892 | O | ASP | A | 248 | 117.334 | 62.412 | 27.416 | 1.00 | 28.35 O |
| ATOM | 1893 | CB | ASP | A | 248 | 118.400 | 64.049 | 25.032 | 1.00 | 31.00 C |
| ATOM | 1894 | CG | ASP | A | 248 | 119.557 | 64.495 | 24.153 | 1.00 | 33.31 C |
| ATOM | 1895 | OD1 | ASP | A | 248 | 120.674 | 64.660 | 24.689 | 1.00 | 34.76 O |
| ATOM | 1896 | OD2 | ASP | A | 248 | 119.359 | 64.648 | 22.922 | 1.00 | 33.85 O |
| ATOM | 1897 | N | ALA | A | 249 | 116.268 | 61.487 | 25.666 | 1.00 | 28.79 N |
| ATOM | 1898 | CA | ALA | A | 249 | 115.127 | 61.020 | 26.439 | 1.00 | 28.18 C |
| ATOM | 1899 | C | ALA | A | 249 | 114.279 | 60.097 | 25.568 | 1.00 | 28.88 C |
| ATOM | 1900 | O | ALA | A | 249 | 114.314 | 60.181 | 24.341 | 1.00 | 28.79 O |
| ATOM | 1901 | CB | ALA | A | 249 | 114.298 | 62.209 | 26.903 | 1.00 | 27.25 C |
| ATOM | 1902 | N | ILE | A | 250 | 113.543 | 59.189 | 26.192 | 1.00 | 28.48 N |
| ATOM | 1903 | CA | ILE | A | 250 | 112.669 | 58.324 | 25.421 | 1.00 | 29.55 C |
| ATOM | 1904 | C | ILE | A | 250 | 111.260 | 58.577 | 25.916 | 1.00 | 29.65 C |
| ATOM | 1905 | O | ILE | A | 250 | 111.056 | 58.932 | 27.085 | 1.00 | 29.05 O |
| ATOM | 1906 | CB | ILE | A | 250 | 113.000 | 56.813 | 25.587 | 1.00 | 30.94 C |
| ATOM | 1907 | CG1 | ILE | A | 250 | 113.023 | 56.441 | 27.070 | 1.00 | 32.35 C |
| ATOM | 1908 | CG2 | ILE | A | 250 | 114.303 | 56.479 | 24.876 | 1.00 | 30.20 C |
| ATOM | 1909 | CD1 | ILE | A | 250 | 113.296 | 54.968 | 27.328 | 1.00 | 34.16 C |
| ATOM | 1910 | N | VAL | A | 251 | 110.289 | 58.414 | 25.024 | 1.00 | 29.98 N |
| ATOM | 1911 | CA | VAL | A | 251 | 108.894 | 58.615 | 25.385 | 1.00 | 30.11 C |
| ATOM | 1912 | C | VAL | A | 251 | 108.119 | 57.310 | 25.254 | 1.00 | 31.15 C |
| ATOM | 1913 | O | VAL | A | 251 | 107.939 | 56.777 | 24.157 | 1.00 | 31.33 O |
| ATOM | 1914 | CB | VAL | A | 251 | 108.222 | 59.698 | 24.499 | 1.00 | 29.28 C |
| ATOM | 1915 | CG1 | VAL | A | 251 | 106.749 | 59.837 | 24.869 | 1.00 | 28.74 C |
| ATOM | 1916 | CG2 | VAL | A | 251 | 108.924 | 61.032 | 24.689 | 1.00 | 28.73 C |
| ATOM | 1917 | N | ILE | A | 252 | 107.686 | 56.791 | 26.394 | 1.00 | 32.25 N |
| ATOM | 1918 | CA | ILE | A | 252 | 106.907 | 55.567 | 26.445 | 1.00 | 34.36 C |
| ATOM | 1919 | C | ILE | A | 252 | 105.488 | 56.052 | 26.169 | 1.00 | 35.92 C |
| ATOM | 1920 | O | ILE | A | 252 | 104.796 | 56.541 | 27.055 | 1.00 | 35.07 O |
| ATOM | 1921 | CB | ILE | A | 252 | 107.030 | 54.933 | 27.838 | 1.00 | 34.93 C |
| ATOM | 1922 | CG1 | ILE | A | 252 | 108.516 | 54.658 | 28.119 | 1.00 | 34.36 C |
| ATOM | 1923 | CG2 | ILE | A | 252 | 106.190 | 53.662 | 27.918 | 1.00 | 34.35 C |
| ATOM | 1924 | CD1 | ILE | A | 252 | 108.830 | 54.276 | 29.536 | 1.00 | 35.76 C |
| ATOM | 1925 | N | ASP | A | 253 | 105.084 | 55.928 | 24.911 | 1.00 | 37.82 N |
| ATOM | 1926 | CA | ASP | A | 253 | 103.793 | 56.405 | 24.439 | 1.00 | 38.30 C |
| ATOM | 1927 | C | ASP | A | 253 | 102.759 | 55.298 | 24.528 | 1.00 | 36.33 C |
| ATOM | 1928 | O | ASP | A | 253 | 102.900 | 54.256 | 23.897 | 1.00 | 35.52 O |
| ATOM | 1929 | CB | ASP | A | 253 | 103.969 | 56.886 | 22.987 | 1.00 | 42.68 C |
| ATOM | 1930 | CG | ASP | A | 253 | 103.027 | 58.024 | 22.608 | 1.00 | 47.26 C |
| ATOM | 1931 | OD1 | ASP | A | 253 | 103.007 | 59.059 | 23.324 | 1.00 | 49.54 O |
| ATOM | 1932 | OD2 | ASP | A | 253 | 102.326 | 57.895 | 21.574 | 1.00 | 49.50 O |
| ATOM | 1933 | N | THR | A | 254 | 101.720 | 55.535 | 25.319 | 1.00 | 35.67 N |
| ATOM | 1934 | CA | THR | A | 254 | 100.654 | 54.553 | 25.507 | 1.00 | 35.99 C |
| ATOM | 1935 | C | THR | A | 254 | 99.267 | 55.208 | 25.434 | 1.00 | 33.80 C |
| ATOM | 1936 | O | THR | A | 254 | 99.115 | 56.398 | 25.716 | 1.00 | 33.46 O |
| ATOM | 1937 | CB | THR | A | 254 | 100.769 | 53.870 | 26.894 | 1.00 | 37.36 C |
| ATOM | 1938 | OG1 | THR | A | 254 | 102.127 | 53.489 | 27.131 | 1.00 | 40.12 O |
| ATOM | 1939 | CG2 | THR | A | 254 | 99.898 | 52.617 | 26.943 | 1.00 | 39.58 C |
| ATOM | 1940 | N | ALA | A | 255 | 98.257 | 54.424 | 25.076 | 1.00 | 32.56 N |
| ATOM | 1941 | CA | ALA | A | 255 | 96.901 | 54.943 | 25.000 | 1.00 | 31.89 C |
| ATOM | 1942 | C | ALA | A | 255 | 96.381 | 55.122 | 26.419 | 1.00 | 31.60 C |
| ATOM | 1943 | O | ALA | A | 255 | 95.756 | 56.131 | 26.743 | 1.00 | 31.27 O |
| ATOM | 1944 | CB | ALA | A | 255 | 96.021 | 53.983 | 24.239 | 1.00 | 31.75 C |

TABLE 7-continued

| | | | | | | | | | | |
|---|---|---|---|---|---|---|---|---|---|---|
| ATOM | 1945 | N | HIS | A | 256 | 96.646 | 54.133 | 27.266 | 1.00 | 31.05 N |
| ATOM | 1946 | CA | HIS | A | 256 | 96.211 | 54.183 | 28.652 | 1.00 | 30.66 C |
| ATOM | 1947 | C | HIS | A | 256 | 97.423 | 53.961 | 29.541 | 1.00 | 31.22 C |
| ATOM | 1948 | O | HIS | A | 256 | 97.811 | 52.826 | 29.784 | 1.00 | 32.42 O |
| ATOM | 1949 | CB | HIS | A | 256 | 95.183 | 53.092 | 28.932 | 1.00 | 28.92 C |
| ATOM | 1950 | CG | HIS | A | 256 | 94.514 | 53.230 | 30.263 | 1.00 | 28.92 C |
| ATOM | 1951 | ND1 | HIS | A | 256 | 93.767 | 52.223 | 30.832 | 1.00 | 29.33 N |
| ATOM | 1952 | CD2 | HIS | A | 256 | 94.461 | 54.270 | 31.128 | 1.00 | 28.44 C |
| ATOM | 1953 | CB1 | HIS | A | 256 | 93.284 | 52.636 | 31.991 | 1.00 | 29.11 C |
| ATOM | 1954 | NE2 | HIS | A | 256 | 93.690 | 53.875 | 32.194 | 1.00 | 29.27 N |
| ATOM | 1955 | N | GLY | A | 257 | 98.017 | 55.043 | 30.026 | 1.00 | 32.56 N |
| ATOM | 1956 | CA | GLY | A | 257 | 99.196 | 54.927 | 30.871 | 1.00 | 33.03 C |
| ATOM | 1957 | C | GLY | A | 257 | 98.907 | 54.494 | 32.297 | 1.00 | 33.73 C |
| ATOM | 1958 | O | GLY | A | 257 | 99.825 | 54.233 | 33.073 | 1.00 | 34.44 O |
| ATOM | 1959 | N | HIS | A | 258 | 97.633 | 54.407 | 32.655 | 1.00 | 33.24 N |
| ATOM | 1960 | CA | HIS | A | 258 | 97.277 | 54.009 | 34.005 | 1.00 | 32.25 C |
| ATOM | 1961 | C | HIS | A | 258 | 97.016 | 52.500 | 33.995 | 1.00 | 33.33 C |
| ATOM | 1962 | O | HIS | A | 258 | 96.237 | 51.991 | 34.796 | 1.00 | 34.50 O |
| ATOM | 1963 | CB | HIS | A | 258 | 96.025 | 54.768 | 34.447 | 1.00 | 30.67 C |
| ATOM | 1964 | CG | HIS | A | 258 | 95.892 | 54.923 | 35.932 | 1.00 | 28.53 C |
| ATOM | 1965 | ND1 | HIS | A | 258 | 96.576 | 54.135 | 36.831 | 1.00 | 28.44 N |
| ATOM | 1966 | CD2 | HIS | A | 258 | 95.100 | 55.735 | 36.672 | 1.00 | 27.04 C |
| ATOM | 1967 | CE1 | HIS | A | 258 | 96.212 | 54.455 | 38.059 | 1.00 | 27.92 C |
| ATOM | 1968 | NE2 | HIS | A | 258 | 95.316 | 55.422 | 37.991 | 1.00 | 27.43 N |
| ATOM | 1969 | N | SER | A | 259 | 97.664 | 51.790 | 33.076 | 1.00 | 33.64 N |
| ATOM | 1970 | CA | SER | A | 259 | 97.502 | 50.340 | 32.974 | 1.00 | 35.31 C |
| ATOM | 1971 | C | SER | A | 259 | 98.572 | 49.598 | 33.765 | 1.00 | 35.20 C |
| ATOM | 1972 | O | SER | A | 259 | 99.745 | 49.975 | 33.751 | 1.00 | 35.19 O |
| ATOM | 1973 | CB | SER | A | 259 | 97.593 | 49.883 | 31.521 | 1.00 | 36.71 C |
| ATOM | 1974 | OG | SER | A | 259 | 96.600 | 50.498 | 30.734 | 1.00 | 42.41 O |
| ATOM | 1975 | N | ALA | A | 260 | 98.160 | 48.525 | 34.434 | 1.00 | 35.34 N |
| ATOM | 1976 | CA | ALA | A | 260 | 99.075 | 47.718 | 35.228 | 1.00 | 34.81 C |
| ATOM | 1977 | C | ALA | A | 260 | 100.264 | 47.288 | 34.377 | 1.00 | 34.54 C |
| ATOM | 1978 | O | ALA | A | 260 | 101.415 | 47.394 | 34.797 | 1.00 | 34.57 O |
| ATOM | 1979 | CB | ALA | A | 260 | 98.345 | 46.500 | 35.769 | 1.00 | 34.40 C |
| ATOM | 1980 | N | GLY | A | 261 | 99.971 | 46.808 | 33.174 | 1.00 | 34.40 N |
| ATOM | 1981 | CA | GLY | A | 261 | 101.013 | 46.368 | 32.271 | 1.00 | 33.69 C |
| ATOM | 1982 | C | GLY | A | 261 | 102.003 | 47.458 | 31.920 | 1.00 | 33.68 C |
| ATOM | 1983 | O | GLY | A | 261 | 103.211 | 47.220 | 31.923 | 1.00 | 35.39 O |
| ATOM | 1984 | N | VAL | A | 262 | 101.505 | 48.652 | 31.612 | 1.00 | 31.87 N |
| ATOM | 1985 | CA | VAL | A | 262 | 102.372 | 49.769 | 31.260 | 1.00 | 30.22 C |
| ATOM | 1986 | C | VAL | A | 262 | 103.257 | 50.106 | 32.453 | 1.00 | 30.85 C |
| ATOM | 1987 | O | VAL | A | 262 | 104.459 | 50.296 | 32.310 | 1.00 | 29.76 O |
| ATOM | 1988 | CB | VAL | A | 262 | 101.545 | 51.037 | 30.851 | 1.00 | 29.14 C |
| ATOM | 1989 | CG1 | VAL | A | 262 | 102.469 | 52.200 | 30.517 | 1.00 | 25.83 C |
| ATOM | 1990 | CG2 | VAL | A | 262 | 100.668 | 50.723 | 29.653 | 1.00 | 28.66 C |
| ATOM | 1991 | N | LEU | A | 263 | 102.657 | 50.170 | 33.635 | 1.00 | 32.42 N |
| ATOM | 1992 | CA | LEU | A | 263 | 103.404 | 50.504 | 34.842 | 1.00 | 35.12 C |
| ATOM | 1993 | C | LEU | A | 263 | 104.479 | 49.449 | 35.109 | 1.00 | 37.28 C |
| ATOM | 1994 | O | LEU | A | 263 | 105.579 | 49.747 | 35.580 | 1.00 | 37.10 O |
| ATOM | 1995 | CB | LEU | A | 263 | 102.445 | 50.611 | 36.035 | 1.00 | 33.85 C |
| ATOM | 1996 | CG | LEU | A | 263 | 101.288 | 51.607 | 35.876 | 1.00 | 32.67 C |
| ATOM | 1997 | CD1 | LEU | A | 263 | 100.436 | 51.594 | 37.126 | 1.00 | 31.79 C |
| ATOM | 1998 | CD2 | LEU | A | 263 | 101.827 | 53.004 | 35.615 | 1.00 | 31.44 C |
| ATOM | 1999 | N | ARG | A | 264 | 104.148 | 48.208 | 34.792 | 1.00 | 39.38 N |
| ATOM | 2000 | CA | ARG | A | 264 | 105.067 | 47.107 | 34.981 | 1.00 | 41.52 C |
| ATOM | 2001 | C | ARG | A | 264 | 106.272 | 47.304 | 34.064 | 1.00 | 40.90 C |
| ATOM | 2002 | O | ARG | A | 264 | 107.410 | 47.312 | 34.517 | 1.00 | 40.25 O |
| ATOM | 2003 | CB | ARG | A | 264 | 104.329 | 45.804 | 34.674 | 1.00 | 45.25 C |
| ATOM | 2004 | CG | ARG | A | 264 | 105.121 | 44.513 | 34.813 | 1.00 | 50.16 C |
| ATOM | 2005 | CD | ARG | A | 264 | 104.144 | 43.343 | 34.780 | 1.00 | 53.35 C |
| ATOM | 2006 | NE | ARG | A | 264 | 103.248 | 43.420 | 33.626 | 1.00 | 56.71 N |
| ATOM | 2007 | CZ | ARG | A | 264 | 102.152 | 42.681 | 33.479 | 1.00 | 58.23 C |
| ATOM | 2008 | NH1 | ARG | A | 264 | 101.810 | 41.805 | 34.416 | 1.00 | 60.06 N |
| ATOM | 2009 | NH2 | ARG | A | 264 | 101.390 | 42.821 | 32.402 | 1.00 | 58.84 N |
| ATOM | 2010 | N | LYS | A | 265 | 106.010 | 47.486 | 32.776 | 1.00 | 40.84 N |
| ATOM | 2011 | CA | LYS | A | 265 | 107.068 | 47.684 | 31.795 | 1.00 | 41.03 C |
| ATOM | 2012 | C | LYS | A | 265 | 107.915 | 48.928 | 32.068 | 1.00 | 41.03 C |
| ATOM | 2013 | O | LYS | A | 265 | 109.130 | 48.909 | 31.885 | 1.00 | 42.30 O |
| ATOM | 2014 | CB | LYS | A | 265 | 106.461 | 47.762 | 30.390 | 1.00 | 41.68 C |
| ATOM | 2015 | CG | LYS | A | 265 | 107.441 | 48.146 | 29.293 | 1.00 | 43.10 C |
| ATOM | 2016 | CD | LYS | A | 265 | 108.624 | 47.198 | 29.235 | 1.00 | 45.73 C |
| ATOM | 2017 | CE | LYS | A | 265 | 108.175 | 45.761 | 29.019 | 1.00 | 47.46 C |
| ATOM | 2018 | NZ | LYS | A | 265 | 107.382 | 45.593 | 27.771 | 1.00 | 48.86 N |
| ATOM | 2019 | N | ILE | A | 266 | 107.278 | 50.009 | 32.504 | 1.00 | 40.38 N |
| ATOM | 2020 | CA | ILE | A | 266 | 107.999 | 51.244 | 32.783 | 1.00 | 39.51 C |
| ATOM | 2021 | C | ILE | A | 266 | 108.989 | 51.061 | 33.920 | 1.00 | 40.45 C |
| ATOM | 2022 | O | ILE | A | 266 | 110.124 | 51.549 | 33.856 | 1.00 | 40.08 O |
| ATOM | 2023 | CB | ILE | A | 266 | 107.028 | 52.396 | 33.134 | 1.00 | 38.28 C |

TABLE 7-continued

| ATOM | 2024 | CG1 | ILE | A | 266 | 106.249 | 52.809 | 31.887 | 1.00 | 36.55 | C |
| --- | --- | --- | --- | --- | --- | --- | --- | --- | --- | --- | --- |
| ATOM | 2025 | CG2 | ILE | A | 266 | 107.795 | 53.572 | 33.704 | 1.00 | 37.78 | C |
| ATOM | 2026 | CD1 | ILE | A | 266 | 105.333 | 53.963 | 32.111 | 1.00 | 36.83 | C |
| ATOM | 2027 | N | ALA | A | 267 | 108.553 | 50.359 | 34.962 | 1.00 | 41.07 | N |
| ATOM | 2028 | CA | ALA | A | 267 | 109.404 | 50.105 | 36.117 | 1.00 | 41.67 | C |
| ATOM | 2029 | C | ALA | A | 267 | 110.584 | 49.260 | 35.672 | 1.00 | 42.17 | C |
| ATOM | 2030 | O | ALA | A | 267 | 111.704 | 49.453 | 36.141 | 1.00 | 42.01 | O |
| ATOM | 2031 | CB | ALA | A | 267 | 108.621 | 49.386 | 37.200 | 1.00 | 41.62 | C |
| ATOM | 2032 | N | GLU | A | 268 | 110.330 | 48.330 | 34.757 | 1.00 | 42.65 | N |
| ATOM | 2033 | CA | GLU | A | 268 | 111.386 | 47.470 | 34.246 | 1.00 | 44.51 | C |
| ATOM | 2034 | C | GLU | A | 268 | 112.334 | 48.294 | 33.383 | 1.00 | 44.45 | C |
| ATOM | 2035 | O | GLU | A | 268 | 113.548 | 48.064 | 33.382 | 1.00 | 45.38 | O |
| ATOM | 2036 | CB | GLU | A | 268 | 110.790 | 46.321 | 33.429 | 1.00 | 46.13 | C |
| ATOM | 2037 | CG | GLU | A | 268 | 109.741 | 45.530 | 34.195 | 1.00 | 50.26 | C |
| ATOM | 2038 | CD | GLU | A | 268 | 109.164 | 44.377 | 33.394 | 1.00 | 52.59 | C |
| ATOM | 2039 | OE1 | GLU | A | 268 | 108.776 | 44.587 | 32.222 | 1.00 | 53.91 | O |
| ATOM | 2040 | OE2 | GLU | A | 268 | 109.080 | 43.260 | 33.947 | 1.00 | 54.82 | O |
| ATOM | 2041 | N | ILE | A | 269 | 111.780 | 49.256 | 32.649 | 1.00 | 43.95 | N |
| ATOM | 2042 | CA | ILE | A | 269 | 112.591 | 50.117 | 31.799 | 1.00 | 43.12 | C |
| ATOM | 2043 | C | ILE | A | 269 | 113.450 | 51.012 | 32.688 | 1.00 | 42.99 | C |
| ATOM | 2044 | O | ILE | A | 269 | 114.627 | 51.236 | 32.402 | 1.00 | 42.66 | O |
| ATOM | 2045 | CB | ILE | A | 269 | 111.716 | 51.001 | 30.881 | 1.00 | 42.99 | C |
| ATOM | 2046 | CG1 | ILE | A | 269 | 110.944 | 50.122 | 29.896 | 1.00 | 42.46 | C |
| ATOM | 2047 | CG2 | ILE | A | 269 | 112.590 | 51.995 | 30.123 | 1.00 | 42.46 | C |
| ATOM | 2048 | CD1 | ILE | A | 269 | 110.036 | 50.898 | 38.968 | 1.00 | 41.32 | C |
| ATOM | 2049 | N | ARG | A | 270 | 112.859 | 51.519 | 33.768 | 1.00 | 42.35 | N |
| ATOM | 2050 | CA | ARG | A | 270 | 113.592 | 52.372 | 34.696 | 1.00 | 42.43 | C |
| ATOM | 2051 | C | ARG | A | 270 | 114.667 | 51.580 | 35.447 | 1.00 | 43.30 | C |
| ATOM | 2052 | O | ARG | A | 270 | 115.802 | 52.033 | 35.598 | 1.00 | 42.17 | O |
| ATOM | 2053 | CB | ARG | A | 270 | 112.630 | 53.026 | 35.689 | 1.00 | 40.28 | C |
| ATOM | 2054 | CG | ARG | A | 270 | 113.335 | 53.693 | 36.857 | 1.00 | 40.08 | C |
| ATOM | 2055 | CD | ARG | A | 270 | 114.401 | 54.661 | 36.381 | 1.00 | 39.52 | C |
| ATOM | 2056 | NE | ARG | A | 270 | 113.843 | 55.890 | 35.835 | 1.00 | 39.63 | N |
| ATOM | 2057 | CZ | ARG | A | 270 | 114.568 | 56.833 | 35.246 | 1.00 | 40.17 | C |
| ATOM | 2058 | NH1 | ARG | A | 270 | 115.879 | 56.682 | 35.127 | 1.00 | 39.75 | N |
| ATOM | 2059 | NH2 | ARG | A | 270 | 113.991 | 57.941 | 34.803 | 1.00 | 41.04 | N |
| ATOM | 2060 | N | ALA | A | 271 | 114.297 | 50.393 | 35.917 | 1.00 | 44.99 | N |
| ATOM | 2061 | CA | ALA | A | 271 | 115.224 | 49.538 | 36.638 | 1.00 | 46.51 | C |
| ATOM | 2062 | C | ALA | A | 271 | 116.445 | 49.281 | 35.766 | 1.00 | 47.60 | C |
| ATOM | 2063 | O | ALA | A | 271 | 117.550 | 49.086 | 36.272 | 1.00 | 49.90 | O |
| ATOM | 2064 | CB | ALA | A | 271 | 114.555 | 48.222 | 36.998 | 1.00 | 46.57 | C |
| ATOM | 2065 | N | HIS | A | 272 | 116.254 | 49.283 | 34.454 | 1.00 | 47.42 | N |
| ATOM | 2066 | CA | HIS | A | 272 | 117.368 | 49.048 | 33.559 | 1.00 | 47.00 | C |
| ATOM | 2067 | C | HIS | A | 272 | 118.096 | 50.347 | 33.204 | 1.00 | 46.88 | C |
| ATOM | 2068 | O | HIS | A | 272 | 119.308 | 50.339 | 33.009 | 1.00 | 47.71 | O |
| ATOM | 2069 | CB | HIS | A | 272 | 116.889 | 48.341 | 32.295 | 1.00 | 47.98 | C |
| ATOM | 2070 | CG | HIS | A | 272 | 117.999 | 47.783 | 31.461 | 1.00 | 50.44 | C |
| ATOM | 2071 | ND1 | HIS | A | 272 | 117.779 | 47.130 | 30.269 | 1.00 | 51.34 | N |
| ATOM | 2072 | CD2 | HIS | A | 272 | 119.341 | 47.762 | 31.658 | 1.00 | 51.66 | C |
| ATOM | 2073 | CE1 | HIS | A | 272 | 118.935 | 46.730 | 29.767 | 1.00 | 52.07 | C |
| ATOM | 2074 | NE2 | HIS | A | 272 | 119.899 | 47.101 | 30.591 | 1.00 | 51.04 | N |
| ATOM | 2075 | N | PHE | A | 273 | 117.370 | 51.462 | 33.124 | 1.00 | 46.29 | N |
| ATOM | 2076 | CA | PHE | A | 273 | 117.991 | 52.755 | 32.806 | 1.00 | 45.64 | C |
| ATOM | 2077 | C | PHE | A | 273 | 117.810 | 53.752 | 33.954 | 1.00 | 46.32 | C |
| ATOM | 2078 | O | PHE | A | 273 | 117.128 | 54.770 | 33.797 | 1.00 | 47.02 | O |
| ATOM | 2079 | CB | PHE | A | 273 | 117.386 | 53.378 | 31.541 | 1.00 | 43.67 | C |
| ATOM | 2080 | CG | PHE | A | 273 | 117.491 | 52.519 | 30.313 | 1.00 | 42.54 | C |
| ATOM | 2081 | CD1 | PHE | A | 273 | 116.589 | 51.489 | 30.088 | 1.00 | 42.71 | C |
| ATOM | 2082 | CD2 | PHE | A | 273 | 118.485 | 52.755 | 29.370 | 1.00 | 42.26 | C |
| ATOM | 2083 | CE1 | PHE | A | 273 | 116.673 | 50.709 | 28.933 | 1.00 | 43.23 | C |
| ATOM | 2084 | CE2 | PHE | A | 273 | 118.580 | 51.981 | 28.217 | 1.00 | 41.40 | C |
| ATOM | 2085 | CZ | PHE | A | 273 | 117.673 | 50.959 | 27.996 | 1.00 | 42.59 | C |
| ATOM | 2086 | N | PRO | A | 274 | 118.431 | 53.483 | 35.116 | 1.00 | 45.94 | N |
| ATOM | 2087 | CA | PRO | A | 274 | 118.355 | 54.329 | 36.313 | 1.00 | 45.40 | C |
| ATOM | 2088 | C | PRO | A | 274 | 118.763 | 55.799 | 36.194 | 1.00 | 45.24 | C |
| ATOM | 2089 | O | PRO | A | 274 | 118.347 | 56.614 | 37.011 | 1.00 | 45.24 | O |
| ATOM | 2090 | CB | PRO | A | 274 | 119.229 | 53.571 | 37.308 | 1.00 | 44.99 | C |
| ATOM | 2091 | CG | PRO | A | 274 | 120.244 | 52.905 | 36.395 | 1.00 | 44.50 | C |
| ATOM | 2092 | CD | PRO | A | 274 | 119.283 | 52.317 | 35.400 | 1.00 | 45.59 | C |
| ATOM | 2093 | N | ASN | A | 275 | 119.566 | 56.145 | 35.195 | 1.00 | 45.09 | N |
| ATOM | 2094 | CA | ASN | A | 275 | 120.015 | 57.527 | 35.042 | 1.00 | 45.14 | C |
| ATOM | 2095 | C | ASN | A | 275 | 119.229 | 58.295 | 33.977 | 1.00 | 44.49 | C |
| ATOM | 2096 | O | ASN | A | 275 | 118.967 | 59.487 | 34.126 | 1.00 | 45.55 | O |
| ATOM | 2097 | CB | ASN | A | 275 | 121.497 | 57.563 | 34.664 | 1.00 | 47.44 | C |
| ATOM | 2098 | CG | ASN | A | 275 | 122.370 | 56.762 | 35.614 | 1.00 | 49.31 | C |
| ATOM | 2099 | OD1 | ASN | A | 275 | 122.481 | 57.076 | 36.795 | 1.00 | 49.47 | O |
| ATOM | 2100 | ND2 | ASN | A | 275 | 123.000 | 55.713 | 35.090 | 1.00 | 51.15 | N |
| ATOM | 2101 | N | ARG | A | 276 | 118.869 | 57.600 | 32.903 | 1.00 | 41.92 | N |
| ATOM | 2102 | CA | ARG | A | 276 | 118.143 | 58.183 | 31.782 | 1.00 | 39.15 | C |

TABLE 7-continued

| ATOM | 2103 | C | ARG | A | 276 | 116.868 | 58.946 | 32.148 | 1.00 | 37.69 | C |
| --- | --- | --- | --- | --- | --- | --- | --- | --- | --- | --- | --- |
| ATOM | 2104 | O | ARG | A | 276 | 116.276 | 58.729 | 33.206 | 1.00 | 37.58 | O |
| ATOM | 2105 | CB | ARG | A | 276 | 117.793 | 57.080 | 30.791 | 1.00 | 39.18 | C |
| ATOM | 2106 | CG | ARG | A | 276 | 118.985 | 56.271 | 30.302 | 1.00 | 37.60 | C |
| ATOM | 2107 | CD | ARG | A | 276 | 119.955 | 57.089 | 29.463 | 1.00 | 36.19 | C |
| ATOM | 2108 | NE | ARG | A | 276 | 121.019 | 56.235 | 28.938 | 1.00 | 35.76 | N |
| ATOM | 2109 | CZ | ARG | A | 276 | 121.913 | 56.609 | 28.031 | 1.00 | 35.25 | C |
| ATOM | 2110 | NH1 | ARG | A | 276 | 121.887 | 57.836 | 27.531 | 1.00 | 36.02 | N |
| ATOM | 2111 | NH2 | ARG | A | 276 | 122.831 | 55.750 | 27.617 | 1.00 | 36.01 | N |
| ATOM | 2112 | N | THR | A | 277 | 116.461 | 59.846 | 31.254 | 1.00 | 35.95 | N |
| ATOM | 2113 | CA | THR | A | 277 | 115.251 | 60.654 | 31.429 | 1.00 | 33.86 | C |
| ATOM | 2114 | C | THR | A | 277 | 114.086 | 59.917 | 30.790 | 1.00 | 32.47 | C |
| ATOM | 2115 | O | THR | A | 277 | 114.108 | 59.638 | 29.587 | 1.00 | 31.01 | O |
| ATOM | 2116 | CB | THR | A | 277 | 115.369 | 62.023 | 30.728 | 1.00 | 33.80 | C |
| ATOM | 2117 | OG1 | THR | A | 277 | 116.362 | 62.822 | 31.381 | 1.00 | 34.95 | O |
| ATOM | 2118 | CG2 | THR | A | 277 | 114.039 | 62.746 | 30.753 | 1.00 | 33.78 | C |
| ATOM | 2119 | N | LEU | A | 278 | 113.073 | 59.602 | 31.588 | 1.00 | 30.23 | N |
| ATOM | 2120 | CA | LEU | A | 278 | 111.915 | 58.889 | 31.070 | 1.00 | 29.28 | C |
| ATOM | 2121 | C | LEU | A | 278 | 110.663 | 59.754 | 31.048 | 1.00 | 28.27 | C |
| ATOM | 2122 | O | LEU | A | 278 | 110.329 | 60.404 | 32.032 | 1.00 | 27.31 | O |
| ATOM | 2123 | CB | LEU | A | 278 | 111.649 | 57.628 | 31.893 | 1.00 | 28.56 | C |
| ATOM | 2124 | CG | LEU | A | 278 | 112.782 | 56.600 | 31.915 | 1.00 | 29.99 | C |
| ATOM | 2125 | CD1 | LEU | A | 278 | 112.339 | 55.362 | 32.692 | 1.00 | 29.20 | C |
| ATOM | 2126 | CD2 | LEU | A | 278 | 113.159 | 56.217 | 30.486 | 1.00 | 30.32 | C |
| ATOM | 2127 | N | ILE | A | 279 | 109.993 | 59.766 | 29.900 | 1.00 | 26.83 | N |
| ATOM | 2128 | CA | ILE | A | 279 | 108.759 | 60.517 | 29.713 | 1.00 | 25.75 | C |
| ATOM | 2129 | C | ILE | A | 279 | 107.756 | 59.403 | 29.451 | 1.00 | 26.77 | C |
| ATOM | 2130 | O | ILE | A | 279 | 108.035 | 58.499 | 28.649 | 1.00 | 25.38 | O |
| ATOM | 2131 | CB | ILE | A | 279 | 108.847 | 61.448 | 28.485 | 1.00 | 23.44 | C |
| ATOM | 2132 | CG1 | ILE | A | 279 | 110.078 | 62.345 | 28.598 | 1.00 | 23.15 | C |
| ATOM | 2133 | CG2 | ILE | A | 279 | 107.604 | 62.310 | 28.405 | 1.00 | 24.07 | C |
| ATOM | 2134 | CD1 | ILE | A | 279 | 110.295 | 63.233 | 27.412 | 1.00 | 23.91 | C |
| ATOM | 2135 | N | ALA | A | 280 | 106.596 | 59.449 | 30.100 | 1.00 | 27.48 | N |
| ATOM | 2136 | CA | ALA | A | 280 | 105.657 | 58.354 | 29.914 | 1.00 | 30.73 | C |
| ATOM | 2137 | C | ALA | A | 280 | 104.246 | 58.667 | 29.469 | 1.00 | 32.08 | C |
| ATOM | 2138 | O | ALA | A | 280 | 103.726 | 59.745 | 29.725 | 1.00 | 31.46 | O |
| ATOM | 2139 | CB | ALA | A | 280 | 105.608 | 57.495 | 31.182 | 1.00 | 30.65 | C |
| ATOM | 2140 | N | GLY | A | 281 | 103.665 | 57.644 | 28.829 | 1.00 | 35.24 | N |
| ATOM | 2141 | CA | GLY | A | 281 | 102.314 | 57.614 | 28.273 | 1.00 | 35.20 | C |
| ATOM | 2142 | C | GLY | A | 281 | 101.303 | 58.614 | 28.763 | 1.00 | 35.43 | C |
| ATOM | 2143 | O | GLY | A | 281 | 101.623 | 59.501 | 29.552 | 1.00 | 37.45 | O |
| ATOM | 2144 | N | ASN | A | 282 | 100.057 | 58.467 | 28.325 | 1.00 | 32.74 | N |
| ATOM | 2145 | CA | ASN | A | 282 | 99.063 | 59.443 | 28.729 | 1.00 | 29.41 | C |
| ATOM | 2146 | C | ASN | A | 282 | 98.088 | 59.056 | 29.815 | 1.00 | 27.37 | C |
| ATOM | 2147 | O | ASN | A | 282 | 97.590 | 57.933 | 29.882 | 1.00 | 26.60 | O |
| ATOM | 2148 | CB | ASN | A | 282 | 98.318 | 59.939 | 27.491 | 1.00 | 30.24 | C |
| ATOM | 2149 | CG | ASN | A | 282 | 99.200 | 60.807 | 26.595 | 1.00 | 31.84 | C |
| ATOM | 2150 | OD1 | ASN | A | 282 | 100.405 | 60.562 | 26.467 | 1.00 | 32.15 | O |
| ATOM | 2151 | ND2 | ASN | A | 282 | 98.600 | 61.809 | 25.949 | 1.00 | 32.17 | N |
| ATOM | 2152 | N | ILE | A | 283 | 97.845 | 60.019 | 30.690 | 1.00 | 25.51 | N |
| ATOM | 2153 | CA | ILE | A | 283 | 96.907 | 59.873 | 31.790 | 1.00 | 24.37 | C |
| ATOM | 2154 | C | ILE | A | 283 | 96.136 | 61.185 | 31.823 | 1.00 | 23.61 | C |
| ATOM | 2155 | O | ILE | A | 283 | 96.532 | 62.160 | 31.175 | 1.00 | 23.14 | O |
| ATOM | 2156 | CB | ILE | A | 283 | 97.636 | 59.631 | 33.150 | 1.00 | 23.62 | C |
| ATOM | 2157 | CG1 | ILE | A | 283 | 98.677 | 60.727 | 33.421 | 1.00 | 22.08 | C |
| ATOM | 2158 | CG2 | ILE | A | 283 | 98.279 | 58.256 | 33.153 | 1.00 | 23.25 | C |
| ATOM | 2159 | CD1 | ILE | A | 283 | 98.119 | 62.094 | 33.881 | 1.00 | 19.86 | C |
| ATOM | 2160 | N | ALA | A | 284 | 95.039 | 61.216 | 32.561 | 1.00 | 22.29 | N |
| ATOM | 2161 | CA | ALA | A | 284 | 94.254 | 62.426 | 32.639 | 1.00 | 23.16 | C |
| ATOM | 2162 | C | ALA | A | 284 | 93.744 | 62.633 | 34.059 | 1.00 | 24.19 | C |
| ATOM | 2163 | O | ALA | A | 284 | 92.839 | 63.434 | 34.300 | 1.00 | 25.24 | O |
| ATOM | 2164 | CB | ALA | A | 284 | 93.102 | 62.347 | 31.659 | 1.00 | 22.62 | C |
| ATOM | 2165 | N | THR | A | 285 | 94.341 | 61.914 | 35.004 | 1.00 | 25.00 | N |
| ATOM | 2166 | CA | THR | A | 285 | 93.936 | 62.015 | 36.403 | 1.00 | 25.00 | C |
| ATOM | 2167 | C | THR | A | 285 | 95.149 | 62.180 | 37.308 | 1.00 | 24.68 | C |
| ATOM | 2168 | O | THR | A | 285 | 96.282 | 61.956 | 36.889 | 1.00 | 22.17 | O |
| ATOM | 2169 | CB | THR | A | 285 | 93.176 | 60.759 | 36.851 | 1.00 | 24.60 | C |
| ATOM | 2170 | OG1 | THR | A | 285 | 94.056 | 59.636 | 36.784 | 1.00 | 27.11 | O |
| ATOM | 2171 | CG2 | THR | A | 285 | 91.975 | 60.501 | 35.953 | 1.00 | 23.14 | C |
| ATOM | 2172 | N | ALA | A | 286 | 94.893 | 62.576 | 38.555 | 1.00 | 25.97 | N |
| ATOM | 2173 | CA | ALA | A | 286 | 95.951 | 62.766 | 39.536 | 1.00 | 26.48 | C |
| ATOM | 2174 | C | ALA | A | 286 | 96.580 | 61.422 | 39.897 | 1.00 | 28.07 | C |
| ATOM | 2175 | O | ALA | A | 286 | 97.800 | 61.329 | 40.057 | 1.00 | 29.78 | O |
| ATOM | 2176 | CB | ALA | A | 286 | 95.395 | 63.445 | 40.783 | 1.00 | 24.43 | C |
| ATOM | 2177 | N | GLU | A | 287 | 95.763 | 60.378 | 40.022 | 1.00 | 29.47 | N |
| ATOM | 2178 | CA | GLU | A | 287 | 96.295 | 59.058 | 40.354 | 1.00 | 30.99 | C |
| ATOM | 2179 | C | GLU | A | 287 | 97.131 | 58.451 | 39.242 | 1.00 | 29.83 | C |
| ATOM | 2180 | O | GLU | A | 287 | 98.109 | 57.744 | 39.505 | 1.00 | 29.81 | O |
| ATOM | 2181 | CB | GLU | A | 287 | 95.173 | 58.094 | 40.739 | 1.00 | 33.93 | C |

TABLE 7-continued

| ATOM | 2182 | CG | GLU | A | 287 | 95.052 | 57.909 | 42.255 | 1.00 | 41.21 | C |
| --- | --- | --- | --- | --- | --- | --- | --- | --- | --- | --- | --- |
| ATOM | 2183 | CD | GLU | A | 287 | 96.298 | 57.259 | 42.899 | 1.00 | 44.34 | C |
| ATOM | 2184 | OE1 | GLU | A | 287 | 96.319 | 57.141 | 44.147 | 1.00 | 45.00 | O |
| ATOM | 2185 | OE2 | GLU | A | 287 | 97.244 | 56.861 | 42.165 | 1.00 | 44.45 | O |
| ATOM | 2186 | N | GLY | A | 288 | 96.746 | 58.726 | 38.000 | 1.00 | 28.61 | N |
| ATOM | 2187 | CA | GLY | A | 288 | 97.495 | 58.204 | 36.876 | 1.00 | 26.94 | C |
| ATOM | 2188 | C | GLY | A | 288 | 98.879 | 58.818 | 36.848 | 1.00 | 26.38 | C |
| ATOM | 2189 | O | GLY | A | 288 | 99.849 | 58.139 | 36.556 | 1.00 | 26.76 | O |
| ATOM | 2190 | N | ALA | A | 289 | 98.974 | 60.109 | 37.150 | 1.00 | 26.64 | N |
| ATOM | 2191 | CA | ALA | A | 289 | 100.257 | 60.793 | 37.156 | 1.00 | 27.29 | C |
| ATOM | 2192 | C | ALA | A | 289 | 101.087 | 60.229 | 38.296 | 1.00 | 29.11 | C |
| ATOM | 2193 | O | ALA | A | 289 | 102.293 | 60.013 | 38.159 | 1.00 | 30.09 | O |
| ATOM | 2194 | CB | ALA | A | 289 | 100.052 | 62.277 | 37.348 | 1.00 | 27.03 | C |
| ATOM | 2195 | N | ARG | A | 290 | 100.428 | 59.983 | 39.423 | 1.00 | 29.67 | N |
| ATOM | 2196 | CA | ARG | A | 290 | 101.091 | 59.433 | 40.600 | 1.00 | 30.07 | C |
| ATOM | 2197 | C | ARG | A | 290 | 101.598 | 58.009 | 40.327 | 1.00 | 29.70 | C |
| ATOM | 2198 | O | ARG | A | 290 | 102.729 | 57.656 | 40.687 | 1.00 | 30.10 | O |
| ATOM | 2199 | CB | ARG | A | 290 | 100.123 | 59.463 | 41.783 | 1.00 | 29.78 | C |
| ATOM | 2200 | CG | ARG | A | 290 | 100.653 | 58.884 | 43.073 | 1.00 | 31.76 | C |
| ATOM | 2201 | CD | ARG | A | 290 | 99.694 | 59.214 | 44.205 | 1.00 | 34.18 | C |
| ATOM | 2202 | NE | ARG | A | 290 | 99.812 | 60.610 | 44.623 | 1.00 | 37.25 | N |
| ATOM | 2203 | CZ | ARG | A | 290 | 98.786 | 61.440 | 44.789 | 1.00 | 38.76 | C |
| ATOM | 2204 | NH1 | ARG | A | 290 | 97.544 | 61.019 | 44.567 | 1.00 | 41.18 | N |
| ATOM | 2205 | NH2 | ARG | A | 290 | 99.001 | 62.685 | 45.195 | 1.00 | 38.72 | N |
| ATOM | 2206 | N | ALA | A | 291 | 100.774 | 57.194 | 39.673 | 1.00 | 28.72 | N |
| ATOM | 2207 | CA | ALA | A | 291 | 101.176 | 55.829 | 39.356 | 1.00 | 26.94 | C |
| ATOM | 2208 | C | ALA | A | 291 | 102.425 | 55.850 | 38.476 | 1.00 | 26.66 | C |
| ATOM | 2209 | O | ALA | A | 291 | 103.363 | 55.092 | 38.700 | 1.00 | 27.57 | O |
| ATOM | 2210 | CB | ALA | A | 291 | 100.041 | 55.096 | 38.649 | 1.00 | 24.83 | C |
| ATOM | 2211 | N | LEU | A | 292 | 102.437 | 56.723 | 37.473 | 1.00 | 26.41 | N |
| ATOM | 2212 | CA | LEU | A | 292 | 103.579 | 56.823 | 36.570 | 1.00 | 26.25 | C |
| ATOM | 2213 | C | LEU | A | 292 | 104.823 | 57.369 | 37.272 | 1.00 | 26.35 | C |
| ATOM | 2214 | O | LEU | A | 292 | 105.927 | 56.861 | 37.069 | 1.00 | 25.85 | O |
| ATOM | 2215 | CB | LEU | A | 292 | 103.221 | 57.688 | 35.356 | 1.00 | 25.03 | C |
| ATOM | 2216 | CG | LEU | A | 292 | 102.247 | 57.053 | 34.351 | 1.00 | 24.67 | C |
| ATOM | 2217 | CD1 | LEU | A | 292 | 101.748 | 58.098 | 33.353 | 1.00 | 24.62 | C |
| ATOM | 2218 | CD2 | LEU | A | 292 | 102.943 | 55.909 | 33.634 | 1.00 | 21.45 | C |
| ATOM | 2219 | N | TYR | A | 293 | 104.661 | 58.408 | 38.083 | 1.00 | 27.07 | N |
| ATOM | 2220 | CA | TYR | A | 293 | 105.809 | 58.947 | 38.804 | 1.00 | 28.43 | C |
| ATOM | 2221 | C | TYR | A | 293 | 106.353 | 57.853 | 39.710 | 1.00 | 29.43 | C |
| ATOM | 2222 | O | TYR | A | 293 | 107.555 | 57.601 | 39.738 | 1.00 | 29.87 | O |
| ATOM | 2223 | CB | TYR | A | 293 | 105.398 | 60.155 | 39.629 | 1.00 | 28.36 | C |
| ATOM | 2224 | CG | TYR | A | 293 | 105.192 | 61.411 | 38.812 | 1.00 | 29.78 | C |
| ATOM | 2225 | CD1 | TYR | A | 293 | 104.175 | 62.310 | 39.134 | 1.00 | 29.30 | C |
| ATOM | 2226 | CD2 | TYR | A | 293 | 106.038 | 61.725 | 37.744 | 1.00 | 29.08 | C |
| ATOM | 2227 | CE1 | TYR | A | 293 | 104.000 | 63.485 | 38.417 | 1.00 | 28.70 | C |
| ATOM | 2228 | CE2 | TYR | A | 293 | 105.868 | 62.905 | 37.020 | 1.00 | 28.90 | C |
| ATOM | 2229 | CZ | TYR | A | 293 | 104.844 | 63.776 | 37.367 | 1.00 | 28.75 | C |
| ATOM | 2230 | OH | TYR | A | 293 | 104.644 | 64.936 | 36.666 | 1.00 | 29.75 | O |
| ATOM | 2231 | N | ASP | A | 294 | 105.456 | 57.191 | 40.435 | 1.00 | 30.73 | N |
| ATOM | 2232 | CA | ASP | A | 294 | 105.846 | 56.104 | 41.325 | 1.00 | 32.03 | C |
| ATOM | 2233 | C | ASP | A | 294 | 106.533 | 54.961 | 40.573 | 1.00 | 33.10 | C |
| ATOM | 2234 | O | ASP | A | 294 | 107.287 | 54.185 | 41.167 | 1.00 | 34.97 | O |
| ATOM | 2235 | CB | ASP | A | 294 | 104.623 | 55.570 | 42.067 | 1.00 | 31.61 | C |
| ATOM | 2236 | CG | ASP | A | 294 | 104.081 | 56.554 | 43.080 | 1.00 | 32.26 | C |
| ATOM | 2237 | OD1 | ASP | A | 294 | 103.034 | 56.266 | 43.700 | 1.00 | 33.58 | O |
| ATOM | 2238 | OD2 | ASP | A | 294 | 104.704 | 57.615 | 43.267 | 1.00 | 32.44 | O |
| ATOM | 2239 | N | ALA | A | 295 | 106.275 | 54.854 | 39.271 | 1.00 | 32.83 | N |
| ATOM | 2240 | CA | ALA | A | 295 | 106.879 | 53.802 | 38.455 | 1.00 | 31.74 | C |
| ATOM | 2241 | C | ALA | A | 295 | 108.264 | 54.224 | 37.992 | 1.00 | 31.68 | C |
| ATOM | 2242 | O | ALA | A | 295 | 108.985 | 53.436 | 37.380 | 1.00 | 32.56 | O |
| ATOM | 2243 | CB | ALA | A | 295 | 105.997 | 53.482 | 37.251 | 1.00 | 30.93 | C |
| ATOM | 2244 | N | GLY | A | 296 | 108.630 | 55.470 | 38.269 | 1.00 | 30.95 | N |
| ATOM | 2245 | CA | GLY | A | 296 | 109.948 | 55.933 | 37.882 | 1.00 | 31.13 | C |
| ATOM | 2246 | C | GLY | A | 296 | 110.045 | 56.900 | 36.717 | 1.00 | 31.66 | C |
| ATOM | 2247 | O | GLY | A | 296 | 111.149 | 57.204 | 36.265 | 1.00 | 31.91 | O |
| ATOM | 2248 | N | VAL | A | 297 | 108.919 | 57.394 | 36.219 | 1.00 | 31.67 | N |
| ATOM | 2249 | CA | VAL | A | 297 | 108.978 | 58.328 | 35.101 | 1.00 | 31.83 | C |
| ATOM | 2250 | C | VAL | A | 297 | 109.416 | 59.716 | 35.586 | 1.00 | 29.98 | C |
| ATOM | 2251 | O | VAL | A | 297 | 109.171 | 60.092 | 36.730 | 1.00 | 29.21 | O |
| ATOM | 2252 | CB | VAL | A | 297 | 107.606 | 58.445 | 34.382 | 1.00 | 32.91 | C |
| ATOM | 2253 | CG1 | VAL | A | 297 | 106.596 | 59.096 | 35.290 | 1.00 | 35.68 | C |
| ATOM | 2254 | CG2 | VAL | A | 297 | 107.747 | 59.266 | 33.125 | 1.00 | 35.70 | C |
| ATOM | 2255 | N | ASP | A | 298 | 110.074 | 60.463 | 34.707 | 1.00 | 28.22 | N |
| ATOM | 2256 | CA | ASP | A | 298 | 110.545 | 61.801 | 35.022 | 1.00 | 27.00 | C |
| ATOM | 2257 | C | ASP | A | 298 | 109.528 | 62.852 | 34.607 | 1.00 | 27.20 | C |
| ATOM | 2258 | O | ASP | A | 298 | 109.281 | 63.813 | 35.332 | 1.00 | 26.86 | O |
| ATOM | 2259 | CB | ASP | A | 298 | 111.870 | 62.071 | 34.309 | 1.00 | 28.58 | C |
| ATOM | 2260 | CG | ASP | A | 298 | 112.974 | 61.149 | 34.776 | 1.00 | 30.31 | C |

TABLE 7-continued

| ATOM | 2261 | OD1 | ASP | A | 298 | 113.221 | 61.114 | 35.994 | 1.00 | 34.37 O |
|------|------|-----|-----|---|-----|---------|--------|--------|------|---------|
| ATOM | 2262 | OD2 | ASP | A | 298 | 113.600 | 60.462 | 33.943 | 1.00 | 31.52 O |
| ATOM | 2263 | N   | VAL | A | 299 | 108.942 | 62.664 | 33.430 | 1.00 | 26.94 N |
| ATOM | 2264 | CA  | VAL | A | 299 | 107.955 | 63.596 | 32.898 | 1.00 | 25.40 C |
| ATOM | 2265 | C   | VAL | A | 299 | 106.704 | 62.825 | 32.462 | 1.00 | 24.71 C |
| ATOM | 2266 | O   | VAL | A | 299 | 106.792 | 61.831 | 31.736 | 1.00 | 24.19 O |
| ATOM | 2267 | CB  | VAL | A | 299 | 108.526 | 64.371 | 31.667 | 1.00 | 25.18 C |
| ATOM | 2268 | CG1 | VAL | A | 299 | 107.573 | 65.493 | 31.255 | 1.00 | 23.30 C |
| ATOM | 2269 | CG2 | VAL | A | 299 | 109.908 | 64.920 | 31.985 | 1.00 | 24.81 C |
| ATOM | 2270 | N   | VAL | A | 300 | 105.544 | 63.287 | 32.916 | 1.00 | 23.99 N |
| ATOM | 2271 | CA  | VAL | A | 300 | 104.270 | 62.661 | 32.576 | 1.00 | 23.71 C |
| ATOM | 2272 | C   | VAL | A | 300 | 103.499 | 63.493 | 31.555 | 1.00 | 24.32 C |
| ATOM | 2273 | O   | VAL | A | 300 | 103.338 | 64.707 | 31.730 | 1.00 | 24.20 O |
| ATOM | 2274 | CB  | VAL | A | 300 | 103.370 | 62.486 | 33.825 | 1.00 | 23.42 C |
| ATOM | 2275 | CG1 | VAL | A | 300 | 101.967 | 62.116 | 33.407 | 1.00 | 23.29 C |
| ATOM | 2276 | CG2 | VAL | A | 300 | 103.923 | 61.391 | 34.722 | 1.00 | 23.23 C |
| ATOM | 2277 | N   | LYS | A | 301 | 103.033 | 62.854 | 30.484 | 1.00 | 24.40 N |
| ATOM | 2278 | CA  | LYS | A | 301 | 102.258 | 63.588 | 29.503 | 1.00 | 24.04 C |
| ATOM | 2279 | C   | LYS | A | 301 | 100.782 | 63.356 | 29.753 | 1.00 | 22.78 C |
| ATOM | 2280 | O   | LYS | A | 301 | 100.322 | 62.229 | 29.960 | 1.00 | 21.52 O |
| ATOM | 2281 | CB  | LYS | A | 301 | 102.686 | 63.259 | 28.065 | 1.00 | 24.29 C |
| ATOM | 2282 | CG  | LYS | A | 301 | 102.809 | 61.818 | 27.709 | 1.00 | 29.51 C |
| ATOM | 2283 | CD  | LYS | A | 301 | 103.757 | 61.674 | 26.489 | 1.00 | 32.99 C |
| ATOM | 2284 | CE  | LYS | A | 301 | 103.228 | 62.284 | 25.187 | 1.00 | 30.67 C |
| ATOM | 2285 | NZ  | LYS | A | 301 | 102.178 | 61.439 | 24.564 | 1.00 | 30.01 N |
| ATOM | 2286 | N   | VAL | A | 302 | 100.060 | 64.470 | 29.782 | 1.00 | 22.18 N |
| ATOM | 2287 | CA  | VAL | A | 302 | 98.641  | 64.485 | 30.061 | 1.00 | 22.10 C |
| ATOM | 2289 | C   | VAL | A | 302 | 97.793  | 64.628 | 28.807 | 1.00 | 22.59 C |
| ATOM | 2289 | O   | VAL | A | 302 | 98.082  | 65.457 | 27.938 | 1.00 | 22.52 O |
| ATOM | 2290 | CB  | VAL | A | 302 | 98.306  | 65.652 | 31.032 | 1.00 | 21.25 C |
| ATOM | 2291 | CG1 | VAL | A | 302 | 96.815  | 65.677 | 31.335 | 1.00 | 20.58 C |
| ATOM | 2292 | CG2 | VAL | A | 302 | 99.103  | 65.504 | 32.312 | 1.00 | 20.42 C |
| ATOM | 2293 | N   | GLY | A | 303 | 96.745  | 63.812 | 28.722 | 1.00 | 22.97 N |
| ATOM | 2294 | CA  | GLY | A | 303 | 95.854  | 63.892 | 27.582 | 1.00 | 22.25 C |
| ATOM | 2295 | C   | GLY | A | 303 | 95.160  | 62.618 | 27.153 | 1.00 | 22.34 C |
| ATOM | 2296 | O   | GLY | A | 303 | 95.784  | 61.750 | 26.566 | 1.00 | 23.71 O |
| ATOM | 2297 | N   | ILE | A | 304 | 93.873  | 62.493 | 27.453 | 1.00 | 22.67 N |
| ATOM | 2298 | CA  | ILE | A | 304 | 93.107  | 61.329 | 27.011 | 1.00 | 24.68 C |
| ATOM | 2299 | C   | ILE | A | 304 | 91.883  | 61.799 | 26.202 | 1.00 | 26.38 C |
| ATOM | 2300 | O   | ILE | A | 304 | 90.881  | 62.237 | 26.770 | 1.00 | 26.11 O |
| ATOM | 2301 | CB  | ILE | A | 304 | 92.625  | 60.446 | 28.195 | 1.00 | 23.24 C |
| ATOM | 2302 | CG1 | ILE | A | 304 | 93.818  | 59.799 | 28.906 | 1.00 | 22.41 C |
| ATOM | 2303 | CG2 | ILE | A | 304 | 91.711  | 59.346 | 27.680 | 1.00 | 21.36 C |
| ATOM | 2304 | CD1 | ILE | A | 304 | 94.503  | 56.718 | 28.113 | 1.00 | 22.43 C |
| ATOM | 2305 | N   | GLY | A | 305 | 91.996  | 61.747 | 24.872 | 1.00 | 28.56 N |
| ATOM | 2306 | CA  | GLY | A | 305 | 90.895  | 62.138 | 24.011 | 1.00 | 30.63 C |
| ATOM | 2307 | C   | GLY | A | 305 | 90.843  | 63.516 | 23.356 | 1.00 | 33.34 C |
| ATOM | 2308 | O   | GLY | A | 305 | 90.112  | 63.666 | 22.370 | 1.00 | 34.88 O |
| ATOM | 2309 | N   | PRO | A | 306 | 91.588  | 64.534 | 23.836 | 1.00 | 33.14 N |
| ATOM | 2310 | CA  | PRO | A | 306 | 91.541  | 65.875 | 23.226 | 1.00 | 33.01 C |
| ATOM | 2311 | C   | PRO | A | 306 | 92.126  | 66.054 | 21.814 | 1.00 | 33.06 C |
| ATOM | 2312 | O   | PRO | A | 306 | 91.928  | 67.104 | 21.191 | 1.00 | 33.29 O |
| ATO  | 2313 | CB  | PRO | A | 306 | 92.275  | 66.728 | 24.256 | 1.00 | 30.93 C |
| ATOM | 2314 | CG  | PRO | A | 306 | 93.353  | 65.772 | 24.704 | 1.00 | 30.96 C |
| ATOM | 2315 | CD  | PRO | A | 306 | 92.504  | 64.547 | 24.992 | 1.00 | 31.97 C |
| ATOM | 2316 | N   | GLY | A | 307 | 92.833  | 65.044 | 21.313 | 1.00 | 33.26 N |
| ATOM | 2317 | CA  | GLY | A | 307 | 93.446  | 65.148 | 19.994 | 1.00 | 33.13 C |
| ATOM | 2318 | C   | GLY | A | 307 | 92.525  | 65.502 | 18.837 | 1.00 | 33.48 C |
| ATOM | 2319 | O   | GLY | A | 307 | 91.414  | 64.982 | 16.739 | 1.00 | 33.64 O |
| ATOM | 2320 | N   | SER | A | 308 | 92.992  | 66.382 | 17.950 | 1.00 | 32.89 N |
| ATOM | 2321 | CA  | SER | A | 308 | 92.209  | 66.802 | 16.783 | 1.00 | 33.08 C |
| ATOM | 2322 | C   | SER | A | 308 | 91.745  | 65.606 | 15.950 | 1.00 | 32.80 C |
| ATOM | 2323 | O   | SER | A | 308 | 90.623  | 65.577 | 15.452 | 1.00 | 33.12 O |
| ATOM | 2324 | CB  | SER | A | 308 | 93.038  | 67.743 | 15.898 | 1.00 | 32.26 C |
| ATOM | 2325 | OG  | SER | A | 308 | 94.229  | 67.114 | 15.448 | 1.00 | 31.53 O |
| ATOM | 2326 | N   | ILE | A | 309 | 92.625  | 64.625 | 15.809 | 1.00 | 33.27 N |
| ATOM | 2327 | CA  | ILE | A | 309 | 92.346  | 63.416 | 15.045 | 1.00 | 34.38 C |
| ATOM | 2328 | C   | ILE | A | 309 | 91.953  | 62.229 | 15.940 | 1.00 | 34.76 C |
| ATOM | 2329 | O   | ILE | A | 309 | 91.843  | 61.095 | 15.471 | 1.00 | 34.40 O |
| ATOM | 2330 | CB  | ILE | A | 309 | 93.590  | 63.033 | 14.176 | 1.00 | 35.31 C |
| ATOM | 2331 | CG1 | ILE | A | 309 | 94.878  | 63.132 | 15.004 | 1.00 | 35.26 C |
| ATOM | 2332 | CG2 | ILE | A | 309 | 93.709  | 63.974 | 12.980 | 1.00 | 34.04 C |
| ATOM | 2333 | CD1 | ILE | A | 309 | 94.957  | 62.199 | 16.191 | 1.00 | 36.80 C |
| ATOM | 2334 | N   | CYS | A | 310 | 91.743  | 62.506 | 17.227 | 1.00 | 35.32 N |
| ATOM | 2335 | CA  | CYS | A | 310 | 91.380  | 61.483 | 18.209 | 1.00 | 35.11 C |
| ATOM | 2336 | C   | CYS | A | 310 | 89.882  | 61.214 | 18.337 | 1.00 | 34.44 C |
| ATOM | 2337 | O   | CYS | A | 310 | 89.072  | 62.142 | 18.449 | 1.00 | 33.70 O |
| ATOM | 2338 | CB  | CYS | A | 310 | 91.922  | 61.873 | 19.587 | 1.00 | 36.64 C |
| ATOM | 2339 | SG  | CYS | A | 310 | 91.351  | 60.810 | 20.950 | 1.00 | 40.34 S |

TABLE 7-continued

| ATOM | 2340 | N | THR | A | 311 | 89.529 | 59.931 | 18.351 | 1.00 | 33.48 | N |
| --- | --- | --- | --- | --- | --- | --- | --- | --- | --- | --- | --- |
| ATOM | 2341 | CA | THR | A | 311 | 88.143 | 59.500 | 18.487 | 1.00 | 33.03 | C |
| ATOM | 2342 | C | THR | A | 311 | 87.936 | 58.662 | 19.756 | 1.00 | 31.85 | C |
| ATOM | 2343 | O | THR | A | 311 | 86.911 | 58.016 | 19.924 | 1.00 | 32.55 | O |
| ATOM | 2344 | CB | THR | A | 311 | 87.720 | 58.657 | 17.287 | 1.00 | 34.00 | C |
| ATOM | 2345 | OG1 | THR | A | 311 | 88.594 | 57.526 | 17.180 | 1.00 | 36.60 | O |
| ATOM | 2346 | CG2 | THR | A | 311 | 87.797 | 59.474 | 16.004 | 1.00 | 34.76 | C |
| ATOM | 2347 | N | THR | A | 312 | 88.912 | 58.667 | 20.650 | 1.00 | 30.55 | N |
| ATOM | 2348 | CA | THR | A | 312 | 88.794 | 57.905 | 21.884 | 1.00 | 29.18 | C |
| ATOM | 2349 | C | THR | A | 312 | 87.523 | 58.238 | 22.661 | 1.00 | 28.00 | C |
| ATOM | 2350 | O | THR | A | 312 | 86.831 | 57.344 | 23.144 | 1.00 | 27.47 | O |
| ATOM | 2351 | CB | THR | A | 312 | 90.018 | 58.142 | 22.783 | 1.00 | 29.25 | C |
| ATOM | 2352 | OG1 | THR | A | 312 | 91.174 | 57.572 | 22.159 | 1.00 | 31.01 | O |
| ATOM | 2353 | CG2 | THR | A | 312 | 89.821 | 57.509 | 24.150 | 1.00 | 30.17 | C |
| ATOM | 2354 | N | ARG | A | 313 | 87.199 | 59.518 | 22.774 | 1.00 | 26.42 | N |
| ATOM | 2355 | CA | ARG | A | 313 | 86.015 | 59.899 | 23.519 | 1.00 | 26.82 | C |
| ATOM | 2356 | C | ARG | A | 313 | 84.712 | 59.469 | 22.858 | 1.00 | 27.41 | C |
| ATOM | 2357 | O | ARG | A | 313 | 83.699 | 59.237 | 23.531 | 1.00 | 28.22 | O |
| ATOM | 2358 | CB | ARG | A | 313 | 86.025 | 61.407 | 23.765 | 1.00 | 27.23 | C |
| ATOM | 2359 | CG | ARG | A | 313 | 87.207 | 61.837 | 24.616 | 1.00 | 28.90 | C |
| ATOM | 2360 | CD | ARG | A | 313 | 87.183 | 63.318 | 24.904 | 1.00 | 31.11 | C |
| ATOM | 2361 | NE | ARG | A | 313 | 88.414 | 63.773 | 25.552 | 1.00 | 32.48 | N |
| ATOM | 2362 | CZ | ARG | A | 313 | 88.674 | 65.046 | 25.840 | 1.00 | 32.07 | C |
| ATOM | 2363 | NH1 | ARG | A | 313 | 87.790 | 65.996 | 25.540 | 1.00 | 30.54 | N |
| ATOM | 2364 | NH2 | ARG | A | 313 | 89.817 | 65.366 | 26.430 | 1.00 | 31.87 | N |
| ATOM | 2365 | N | VAL | A | 314 | 84.746 | 59.339 | 21.540 | 1.00 | 26.45 | N |
| ATOM | 2366 | CA | VAL | A | 314 | 83.576 | 58.952 | 20.774 | 1.00 | 25.00 | C |
| ATOM | 2367 | C | VAL | A | 314 | 83.364 | 57.446 | 20.698 | 1.00 | 24.59 | C |
| ATOM | 2368 | O | VAL | A | 314 | 82.253 | 56.963 | 20.890 | 1.00 | 24.29 | O |
| ATOM | 2369 | CB | VAL | A | 314 | 83.672 | 59.496 | 19.338 | 1.00 | 26.31 | C |
| ATOM | 2370 | CG1 | VAL | A | 314 | 82.429 | 59.127 | 18.558 | 1.00 | 26.03 | C |
| ATOM | 2371 | CG2 | VAL | A | 314 | 83.866 | 60.998 | 19.371 | 1.00 | 25.74 | C |
| ATOM | 2372 | N | VAL | A | 315 | 84.428 | 56.704 | 20.416 | 1.00 | 24.12 | N |
| ATOM | 2373 | CA | VAL | A | 315 | 84.322 | 55.255 | 20.286 | 1.00 | 24.14 | C |
| ATOM | 2374 | C | VAL | A | 315 | 84.419 | 54.460 | 21.595 | 1.00 | 23.17 | C |
| ATOM | 2375 | O | VAL | A | 315 | 83.837 | 53.387 | 21.713 | 1.00 | 22.34 | O |
| ATOM | 2376 | CB | VAL | A | 315 | 85.351 | 54.737 | 19.266 | 1.00 | 23.99 | C |
| ATOM | 2377 | CG1 | VAL | A | 315 | 85.058 | 55.352 | 17.897 | 1.00 | 24.71 | C |
| ATOM | 2378 | CG2 | VAL | A | 315 | 86.754 | 55.099 | 19.705 | 1.00 | 25.41 | C |
| ATOM | 2379 | N | ALA | A | 316 | 85.137 | 54.992 | 22.577 | 1.00 | 22.80 | N |
| ATOM | 2380 | CA | ALA | A | 316 | 85.273 | 54.322 | 23.864 | 1.00 | 22.89 | C |
| ATOM | 2381 | C | ALA | A | 316 | 84.453 | 55.075 | 24.907 | 1.00 | 23.76 | C |
| ATOM | 2382 | O | ALA | A | 316 | 84.096 | 54.525 | 25.955 | 1.00 | 23.93 | O |
| ATOM | 2383 | CB | ALA | A | 316 | 86.739 | 54.277 | 24.278 | 1.00 | 21.84 | C |
| ATOM | 2384 | N | GLY | A | 317 | 84.154 | 56.337 | 24.607 | 1.00 | 24.54 | N |
| ATOM | 2385 | CA | GLY | A | 317 | 83.378 | 57.167 | 25.511 | 1.00 | 24.66 | C |
| ATOM | 2386 | C | GLY | A | 317 | 84.154 | 57.582 | 26.744 | 1.00 | 25.96 | C |
| ATOM | 2387 | O | GLY | A | 317 | 83.558 | 57.954 | 27.759 | 1.00 | 26.42 | O |
| ATOM | 2388 | N | VAL | A | 318 | 85.482 | 57.545 | 26.646 | 1.00 | 25.51 | N |
| ATOM | 2389 | CA | VAL | A | 318 | 86.369 | 57.879 | 27.760 | 1.00 | 24.79 | C |
| ATOM | 2390 | C | VAL | A | 318 | 87.219 | 59.133 | 27.554 | 1.00 | 25.38 | C |
| ATOM | 2391 | O | VAL | A | 318 | 87.633 | 59.437 | 26.438 | 1.00 | 25.50 | O |
| ATOM | 2392 | CB | VAL | A | 318 | 87.317 | 56.693 | 28.049 | 1.00 | 24.92 | C |
| ATOM | 2393 | CG1 | VAL | A | 318 | 88.363 | 57.081 | 29.090 | 1.00 | 24.67 | C |
| ATOM | 2394 | CG2 | VAL | A | 318 | 86.507 | 55.500 | 28.535 | 1.00 | 23.44 | C |
| ATOM | 2395 | N | GLY | A | 319 | 87.477 | 59.851 | 28.645 | 1.00 | 24.73 | N |
| ATOM | 2396 | CA | GLY | A | 319 | 88.304 | 61.043 | 28.578 | 1.00 | 25.39 | C |
| ATOM | 2397 | C | GLY | A | 319 | 87.980 | 62.097 | 29.620 | 1.00 | 25.66 | C |
| ATOM | 2398 | O | GLY | A | 319 | 87.076 | 61.926 | 30.437 | 1.00 | 25.40 | O |
| ATOM | 2399 | N | VAL | A | 320 | 88.737 | 63.188 | 29.609 | 1.00 | 24.72 | N |
| ATOM | 2400 | CA | VAL | A | 320 | 88.484 | 64.281 | 30.535 | 1.00 | 25.55 | C |
| ATOM | 2401 | C | VAL | A | 320 | 88.944 | 65.581 | 29.903 | 1.00 | 23.92 | C |
| ATOM | 2402 | O | VAL | A | 320 | 90.033 | 65.653 | 29.331 | 1.00 | 22.93 | O |
| ATOM | 2403 | CB | VAL | A | 320 | 89.203 | 64.087 | 31.899 | 1.00 | 27.29 | C |
| ATOM | 2404 | CG1 | VAL | A | 320 | 90.667 | 64.017 | 31.693 | 1.00 | 32.20 | C |
| ATOM | 2405 | CG2 | VAL | A | 320 | 88.884 | 65.241 | 32.838 | 1.00 | 26.56 | C |
| ATOM | 2406 | N | PRO | A | 321 | 88.100 | 66.625 | 29.980 | 1.00 | 23.64 | N |
| ATOM | 2407 | CA | PRO | A | 321 | 88.438 | 67.928 | 29.408 | 1.00 | 22.67 | C |
| ATOM | 2408 | C | PRO | A | 321 | 89.872 | 68.279 | 29.791 | 1.00 | 22.52 | C |
| ATOM | 2409 | O | PRO | A | 321 | 90.232 | 68.263 | 30.961 | 1.00 | 23.18 | O |
| ATOM | 2410 | CB | PRO | A | 321 | 87.381 | 68.823 | 30.028 | 1.00 | 23.67 | C |
| ATOM | 2411 | CG | PRO | A | 321 | 86.164 | 67.896 | 29.986 | 1.00 | 20.93 | C |
| ATOM | 2412 | CD | PRO | A | 321 | 86.780 | 66.686 | 30.640 | 1.00 | 22.53 | C |
| ATOM | 2413 | N | GLN | A | 322 | 90.679 | 68.588 | 28.786 | 1.00 | 22.16 | N |
| ATOM | 2414 | CA | GLN | A | 322 | 92.099 | 68.880 | 28.948 | 1.00 | 21.62 | C |
| ATOM | 2415 | C | GLN | A | 322 | 92.573 | 69.884 | 30.002 | 1.00 | 20.84 | C |
| ATOM | 2416 | O | GLN | A | 322 | 93.551 | 69.609 | 30.679 | 1.00 | 21.63 | O |
| ATOM | 2417 | CB | GLN | A | 322 | 92.684 | 69.245 | 27.578 | 1.00 | 22.97 | C |
| ATOM | 2418 | CG | GLN | A | 322 | 94.217 | 69.292 | 27.491 | 1.00 | 24.38 | C |

TABLE 7-continued

| ATOM | 2419 | CD | GLN | A | 322 | 94.896 | 67.951 | 27.725 | 1.00 | 23.75 | C |
|------|------|-----|-----|---|-----|--------|--------|--------|------|-------|---|
| ATOM | 2420 | OE1 | GLN | A | 322 | 96.067 | 67.776 | 27.390 | 1.00 | 26.82 | O |
| ATOM | 2421 | NE2 | GLN | A | 322 | 94.176 | 67.011 | 28.314 | 1.00 | 23.57 | N |
| ATOM | 2422 | N   | VAL | A | 323 | 91.932 | 71.037 | 30.151 | 1.00 | 19.60 | N |
| ATOM | 2423 | CA  | VAL | A | 323 | 92.401 | 71.970 | 31.175 | 1.00 | 19.52 | C |
| ATOM | 2424 | C   | VAL | A | 323 | 92.280 | 71.357 | 32.572 | 1.00 | 20.46 | C |
| ATOM | 2425 | O   | VAL | A | 323 | 93.144 | 71.556 | 33.420 | 1.00 | 22.03 | O |
| ATOM | 2426 | CB  | VAL | A | 323 | 91.645 | 73.322 | 31.143 | 1.00 | 17.80 | C |
| ATOM | 2427 | CG1 | VAL | A | 323 | 92.026 | 74.177 | 32.359 | 1.00 | 17.57 | C |
| ATOM | 2428 | CG2 | VAL | A | 323 | 92.009 | 74.070 | 29.888 | 1.00 | 18.00 | C |
| ATOM | 2429 | N   | THR | A | 324 | 91.210 | 70.616 | 32.815 | 1.00 | 21.51 | N |
| ATOM | 2430 | CA  | THR | A | 324 | 91.029 | 69.961 | 34.106 | 1.00 | 21.74 | C |
| ATOM | 2431 | C   | THR | A | 324 | 92.056 | 68.845 | 34.307 | 1.00 | 22.09 | C |
| ATOM | 2432 | O   | THR | A | 324 | 92.628 | 68.704 | 35.393 | 1.00 | 22.04 | O |
| ATOM | 2433 | CB  | THR | A | 324 | 89.616 | 69.383 | 34.221 | 1.00 | 21.42 | C |
| ATOM | 2434 | OG1 | THR | A | 324 | 88.696 | 70.448 | 34.469 | 1.00 | 23.37 | O |
| ATOM | 2435 | CG2 | THR | A | 324 | 89.532 | 68.370 | 35.335 | 1.00 | 24.31 | C |
| ATOM | 2436 | N   | ALA | A | 325 | 92.296 | 68.062 | 33.256 | 1.00 | 21.63 | N |
| ATOM | 2437 | CA  | ALA | A | 325 | 93.253 | 66.958 | 33.324 | 1.00 | 23.09 | C |
| ATOM | 2438 | C   | ALA | A | 325 | 94.669 | 67.437 | 33.668 | 1.00 | 23.65 | C |
| ATOM | 2439 | O   | ALA | A | 325 | 95.325 | 66.865 | 34.540 | 1.00 | 23.99 | O |
| ATOM | 2440 | CB  | ALA | A | 325 | 93.262 | 66.192 | 32.006 | 1.00 | 22.44 | C |
| ATOM | 2441 | N   | ILE | A | 326 | 95.134 | 68.472 | 32.967 | 1.00 | 23.50 | N |
| ATOM | 2442 | CA  | ILE | A | 326 | 96.458 | 69.067 | 33.182 | 1.00 | 23.40 | C |
| ATOM | 2443 | C   | ILE | A | 326 | 96.576 | 69.483 | 34.641 | 1.00 | 24.71 | C |
| ATOM | 2444 | O   | ILE | A | 326 | 97.520 | 69.124 | 35.337 | 1.00 | 24.66 | O |
| ATOM | 2445 | CB  | ILE | A | 326 | 96.644 | 70.329 | 32.295 | 1.00 | 22.70 | C |
| ATOM | 2446 | CG1 | ILE | A | 326 | 96.680 | 69.913 | 30.821 | 1.00 | 22.18 | C |
| ATOM | 2447 | CG2 | ILE | A | 326 | 97.900 | 71.096 | 32.699 | 1.00 | 20.32 | C |
| ATOM | 2448 | CD1 | ILE | A | 326 | 96.689 | 71.078 | 29.861 | 1.00 | 22.52 | C |
| ATOM | 2449 | N   | TYR | A | 327 | 95.589 | 70.244 | 35.082 | 1.00 | 25.51 | N |
| ATOM | 2450 | CA  | TYR | A | 327 | 95.512 | 70.739 | 36.439 | 1.00 | 27.53 | C |
| ATOM | 2451 | C   | TYR | A | 327 | 95.493 | 69.644 | 37.506 | 1.00 | 26.67 | C |
| ATOM | 2452 | O   | TYR | A | 327 | 96.234 | 69.706 | 38.470 | 1.00 | 26.34 | O |
| ATOM | 2453 | CB  | TYR | A | 327 | 94.278 | 71.615 | 36.527 | 1.00 | 31.94 | C |
| ATOM | 2454 | CG  | TYR | A | 327 | 93.867 | 72.043 | 37.900 | 1.00 | 36.64 | C |
| ATOM | 2455 | CD1 | TYR | A | 327 | 93.354 | 71.127 | 38.812 | 1.00 | 40.23 | C |
| ATOM | 2456 | CD2 | TYR | A | 327 | 93.868 | 73.375 | 38.243 | 1.00 | 38.78 | C |
| ATOM | 2457 | CE1 | TYR | A | 327 | 92.839 | 71.536 | 40.027 | 1.00 | 42.47 | C |
| ATOM | 2458 | CE2 | TYR | A | 327 | 93.358 | 73.790 | 39.431 | 1.00 | 42.01 | C |
| ATOM | 2459 | CZ  | TYR | A | 327 | 92.838 | 72.873 | 40.329 | 1.00 | 43.22 | C |
| ATOM | 2460 | OH  | TYR | A | 327 | 92.305 | 73.316 | 41.524 | 1.00 | 47.71 | O |
| ATOM | 2461 | N   | ASP | A | 328 | 94.635 | 68.650 | 37.347 | 1.00 | 27.41 | N |
| ATOM | 2462 | CA  | ASP | A | 328 | 94.573 | 67.559 | 38.312 | 1.00 | 28.23 | C |
| ATOM | 2463 | C   | ASP | A | 328 | 95.910 | 66.825 | 38.383 | 1.00 | 28.97 | C |
| ATOM | 2464 | O   | ASP | A | 328 | 96.342 | 66.414 | 39.455 | 1.00 | 30.49 | O |
| ATOM | 2465 | CB  | ASP | A | 328 | 93.469 | 66.570 | 37.925 | 1.00 | 28.63 | C |
| ATOM | 2466 | CG  | ASP | A | 328 | 92.074 | 67.171 | 38.042 | 1.00 | 29.55 | C |
| ATOM | 2467 | OD1 | ASP | A | 328 | 91.096 | 66.496 | 37.643 | 1.00 | 28.91 | O |
| ATOM | 2468 | OD2 | ASP | A | 328 | 91.954 | 68.312 | 38.541 | 1.00 | 30.66 | O |
| ATOM | 2469 | N   | ALA | A | 329 | 96.568 | 66.666 | 37.237 | 1.00 | 28.70 | N |
| ATOM | 2470 | CA  | ALA | A | 329 | 97.848 | 65.969 | 37.185 | 1.00 | 27.96 | C |
| ATOM | 2471 | C   | ALA | A | 329 | 98.993 | 66.816 | 37.713 | 1.00 | 27.90 | C |
| ATOM | 2472 | O   | ALA | A | 329 | 99.898 | 66.303 | 38.368 | 1.00 | 27.58 | O |
| ATOM | 2473 | CB  | ALA | A | 329 | 98.150 | 65.534 | 35.755 | 1.00 | 28.88 | C |
| ATOM | 2474 | N   | ALA | A | 330 | 98.950 | 68.112 | 37.417 | 1.00 | 27.54 | N |
| ATOM | 2475 | CA  | ALA | A | 330 | 99.993 | 69.041 | 37.839 | 1.00 | 27.36 | C |
| ATOM | 2476 | C   | ALA | A | 330 | 100.035| 69.195 | 39.352 | 1.00 | 27.62 | C |
| ATOM | 2477 | O   | ALA | A | 330 | 101.039| 69.631 | 39.909 | 1.00 | 27.21 | O |
| ATOM | 2478 | CB  | ALA | A | 330 | 99.784 | 70.397 | 37.175 | 1.00 | 26.61 | C |
| ATOM | 2479 | N   | ALA | A | 331 | 98.941 | 68.841 | 40.016 | 1.00 | 28.38 | N |
| ATOM | 2480 | CA  | ALA | A | 331 | 98.882 | 68.923 | 41.467 | 1.00 | 29.60 | C |
| ATOM | 2481 | C   | ALA | A | 331 | 99.870 | 67.902 | 42.005 | 1.00 | 30.94 | C |
| ATOM | 2482 | O   | ALA | A | 331 | 100.556| 68.144 | 42.995 | 1.00 | 31.96 | O |
| ATOM | 2483 | CB  | ALA | A | 331 | 97.489 | 68.601 | 41.955 | 1.00 | 29.46 | C |
| ATOM | 2484 | N   | VAL | A | 332 | 99.941 | 66.756 | 41.334 | 1.00 | 31.86 | N |
| ATOM | 2485 | CA  | VAL | A | 332 | 100.851| 65.683 | 41.723 | 1.00 | 31.71 | C |
| ATOM | 2486 | C   | VAL | A | 332 | 102.276| 65.984 | 41.267 | 1.00 | 32.27 | C |
| ATOM | 2487 | O   | VAL | A | 332 | 103.231| 65.700 | 41.981 | 1.00 | 32.86 | O |
| ATOM | 2488 | CB  | VAL | A | 332 | 100.408| 64.328 | 41.122 | 1.00 | 30.47 | C |
| ATOM | 2489 | CG1 | VAL | A | 332 | 101.394| 63.229 | 41.512 | 1.00 | 29.17 | C |
| ATOM | 2490 | CG2 | VAL | A | 332 | 99.009 | 63.989 | 41.602 | 1.00 | 29.70 | C |
| ATOM | 2491 | N   | ALA | A | 333 | 102.412| 66.561 | 40.078 | 1.00 | 32.53 | N |
| ATOM | 2492 | CA  | ALA | A | 333 | 103.723| 66.889 | 39.543 | 1.00 | 33.43 | C |
| ATOM | 2493 | C   | ALA | A | 333 | 104.469| 67.763 | 40.528 | 1.00 | 35.24 | C |
| ATOM | 2494 | O   | ALA | A | 333 | 105.677| 67.623 | 40.701 | 1.00 | 35.30 | O |
| ATOM | 2495 | CB  | ALA | A | 333 | 103.587| 67.607 | 38.218 | 1.00 | 32.68 | C |
| ATOM | 2496 | N   | ARG | A | 334 | 103.757| 68.675 | 41.178 | 1.00 | 36.59 | N |
| ATOM | 2497 | CA  | ARG | A | 334 | 104.422| 69.544 | 42.136 | 1.00 | 38.67 | C |

TABLE 7-continued

| | | | | | | | | | | |
|---|---|---|---|---|---|---|---|---|---|---|
| ATOM | 2498 | C | ARG | A | 334 | 104.682 | 68.857 | 43.458 | 1.00 | 38.64 C |
| ATOM | 2499 | O | ARG | A | 334 | 105.646 | 69.181 | 44.140 | 1.00 | 39.25 O |
| ATOM | 2500 | CB | ARG | A | 334 | 103.650 | 70.853 | 42.343 | 1.00 | 39.27 C |
| ATOM | 2501 | CG | ARG | A | 334 | 102.152 | 70.742 | 42.460 | 1.00 | 41.57 C |
| ATOM | 2502 | CD | ARG | A | 334 | 101.611 | 72.112 | 42.821 | 1.00 | 42.79 C |
| ATOM | 2503 | NE | ARG | A | 334 | 102.174 | 73.143 | 41.953 | 1.00 | 41.68 N |
| ATOM | 2504 | CZ | ARG | A | 334 | 102.177 | 74.441 | 42.245 | 1.00 | 41.25 C |
| ATOM | 2505 | NH1 | ARG | A | 334 | 101.648 | 74.876 | 43.384 | 1.00 | 39.55 N |
| ATOM | 2506 | NH2 | ARG | A | 334 | 102.728 | 75.304 | 41.405 | 1.00 | 40.34 N |
| ATOM | 2507 | N | GLU | A | 335 | 103.833 | 67.902 | 43.814 | 1.00 | 38.96 N |
| ATOM | 2508 | CA | GLU | A | 335 | 104.029 | 67.158 | 45.046 | 1.00 | 39.04 C |
| ATOM | 2509 | C | GLU | A | 335 | 105.352 | 66.414 | 44.911 | 1.00 | 37.56 C |
| ATOM | 2510 | O | GLU | A | 335 | 106.158 | 66.383 | 45.836 | 1.00 | 39.04 O |
| ATOM | 2511 | CB | GLU | A | 335 | 102.895 | 66.157 | 45.258 | 1.00 | 40.81 C |
| ATOM | 2512 | CG | GLU | A | 335 | 103.154 | 65.182 | 46.393 | 1.00 | 45.59 C |
| ATOM | 2513 | CD | GLU | A | 335 | 102.064 | 64.136 | 46.538 | 1.00 | 48.65 C |
| ATOM | 2514 | OE1 | GLU | A | 335 | 102.219 | 63.227 | 47.383 | 1.00 | 49.61 O |
| ATOM | 2515 | OE2 | GLU | A | 335 | 101.048 | 64.224 | 45.812 | 1.00 | 51.22 O |
| ATOM | 2516 | N | TYR | A | 336 | 105.571 | 65.828 | 43.741 | 1.00 | 35.56 N |
| ATOM | 2517 | CA | TYR | A | 336 | 106.786 | 65.075 | 43.458 | 1.00 | 33.65 C |
| ATOM | 2518 | C | TYR | A | 336 | 107.915 | 65.956 | 42.950 | 1.00 | 32.06 C |
| ATOM | 2519 | O | TYR | A | 336 | 109.037 | 65.493 | 42.753 | 1.00 | 31.27 O |
| ATOM | 2520 | CB | TYR | A | 336 | 106.508 | 63.979 | 42.418 | 1.00 | 34.56 C |
| ATOM | 2521 | CG | TYR | A | 336 | 105.700 | 62.806 | 42.928 | 1.00 | 35.16 C |
| ATOM | 2522 | CD1 | TYR | A | 336 | 106.183 | 61.504 | 42.802 | 1.00 | 35.01 C |
| ATOM | 2523 | CD2 | TYR | A | 336 | 104.465 | 62.992 | 43.544 | 1.00 | 35.65 C |
| ATOM | 2524 | CE1 | TYR | A | 336 | 105.460 | 60.418 | 43.278 | 1.00 | 35.67 C |
| ATOM | 2525 | CE2 | TYR | A | 336 | 103.730 | 61.910 | 44.025 | 1.00 | 36.28 C |
| ATOM | 2526 | CZ | TYR | A | 336 | 104.234 | 60.624 | 43.890 | 1.00 | 35.77 C |
| ATOM | 2527 | OH | TYR | A | 336 | 103.516 | 59.548 | 44.372 | 1.00 | 36.21 O |
| ATOM | 2528 | N | GLY | A | 337 | 107.619 | 67.230 | 42.738 | 1.00 | 31.22 N |
| ATOM | 2529 | CA | GLY | A | 337 | 108.635 | 68.122 | 42.229 | 1.00 | 29.58 C |
| ATOM | 2530 | C | GLY | A | 337 | 109.068 | 67.679 | 40.847 | 1.00 | 29.59 C |
| ATOM | 2531 | O | GLY | A | 337 | 110.232 | 67.802 | 40.488 | 1.00 | 30.15 O |
| ATOM | 2532 | N | LYS | A | 338 | 108.128 | 67.142 | 40.073 | 1.00 | 29.98 N |
| ATOM | 2533 | CA | LYS | A | 338 | 108.413 | 66.698 | 38.713 | 1.00 | 29.30 C |
| ATOM | 2534 | C | LYS | A | 338 | 107.596 | 67.477 | 37.683 | 1.00 | 28.77 C |
| ATOM | 2535 | O | LYS | A | 338 | 106.830 | 68.377 | 38.040 | 1.00 | 27.37 O |
| ATOM | 2536 | CB | LYS | A | 338 | 108.180 | 65.191 | 38.585 | 1.00 | 30.27 C |
| ATOM | 2537 | CG | LYS | A | 338 | 109.235 | 64.382 | 39.330 | 1.00 | 32.74 C |
| ATOM | 2538 | CD | LYS | A | 338 | 109.034 | 62.886 | 39.194 | 1.00 | 36.45 C |
| ATOM | 2539 | CE | LYS | A | 338 | 110.170 | 62.116 | 39.867 | 1.00 | 38.61 C |
| ATOM | 2540 | NZ | LYS | A | 338 | 110.001 | 60.628 | 39.761 | 1.00 | 40.61 N |
| ATOM | 2541 | N | THR | A | 339 | 107.749 | 67.131 | 36.407 | 1.00 | 27.82 N |
| ATOM | 2542 | CA | THR | A | 339 | 107.056 | 67.863 | 35.356 | 1.00 | 26.32 C |
| ATOM | 2543 | C | THR | A | 339 | 105.980 | 67.165 | 34.517 | 1.00 | 26.06 C |
| ATOM | 2544 | O | THR | A | 339 | 105.806 | 65.943 | 34.542 | 1.00 | 25.01 O |
| ATOM | 2545 | CB | THR | A | 339 | 108.072 | 68.484 | 34.409 | 1.00 | 26.34 C |
| ATOM | 2546 | OG1 | THR | A | 339 | 108.901 | 67.454 | 33.864 | 1.00 | 25.90 O |
| ATOM | 2547 | CG2 | THR | A | 339 | 108.934 | 69.484 | 35.155 | 1.00 | 26.42 C |
| ATOM | 2548 | N | ILE | A | 340 | 105.267 | 67.988 | 33.757 | 1.00 | 25.60 N |
| ATOM | 2549 | CA | ILE | A | 340 | 104.174 | 67.543 | 32.911 | 1.00 | 24.59 C |
| ATOM | 2550 | C | ILE | A | 340 | 104.152 | 68.189 | 31.525 | 1.00 | 23.54 C |
| ATOM | 2551 | O | ILE | A | 340 | 104.555 | 69.337 | 31.342 | 1.00 | 21.85 O |
| ATOM | 2552 | CB | ILE | A | 340 | 102.842 | 67.794 | 33.644 | 1.00 | 25.00 C |
| ATOM | 2553 | CG1 | ILE | A | 340 | 102.598 | 66.631 | 34.599 | 1.00 | 26.20 C |
| ATOM | 2554 | CG2 | ILE | A | 340 | 101.707 | 68.034 | 32.668 | 1.00 | 25.49 C |
| ATOM | 2555 | CD1 | ILE | A | 340 | 101.382 | 66.774 | 35.436 | 1.00 | 29.56 C |
| ATOM | 2556 | N | ILE | A | 341 | 103.695 | 67.414 | 30.548 | 1.00 | 22.21 N |
| ATOM | 2557 | CA | ILE | A | 341 | 103.573 | 67.873 | 29.176 | 1.00 | 20.48 C |
| ATOM | 2558 | C | ILE | A | 341 | 102.080 | 67.824 | 28.863 | 1.00 | 19.91 C |
| ATOM | 2559 | O | ILE | A | 341 | 101.439 | 66.793 | 29.068 | 1.00 | 18.38 O |
| ATOM | 2560 | CB | ILE | A | 341 | 104.346 | 66.941 | 28.210 | 1.00 | 21.69 C |
| ATOM | 2561 | CG1 | ILE | A | 341 | 105.849 | 67.038 | 28.496 | 1.00 | 23.08 C |
| ATOM | 2562 | CG2 | ILE | A | 341 | 104.043 | 67.290 | 26.755 | 1.00 | 19.22 C |
| ATOM | 2563 | CD1 | ILE | A | 341 | 106.695 | 66.098 | 27.657 | 1.00 | 23.45 C |
| ATOM | 2564 | N | ALA | A | 342 | 101.530 | 68.958 | 28.427 | 1.00 | 19.15 N |
| ATOM | 2565 | CA | ALA | A | 342 | 100.121 | 69.060 | 28.046 | 1.00 | 19.91 C |
| ATOM | 2566 | C | ALA | A | 342 | 100.064 | 68.553 | 26.601 | 1.00 | 20.89 C |
| ATOM | 2567 | O | ALA | A | 342 | 100.556 | 69.205 | 25.680 | 1.00 | 20.43 O |
| ATOM | 2568 | CB | ALA | A | 342 | 99.663 | 70.504 | 28.125 | 1.00 | 19.17 C |
| ATOM | 2569 | N | ASP | A | 343 | 99.451 | 67.388 | 26.418 | 1.00 | 21.90 N |
| ATOM | 2570 | CA | ASP | A | 343 | 99.390 | 66.729 | 25.121 | 1.00 | 22.21 C |
| ATOM | 2571 | C | ASP | A | 343 | 98.038 | 66.728 | 24.406 | 1.00 | 23.22 C |
| ATOM | 2572 | O | ASP | A | 343 | 97.128 | 66.005 | 24.796 | 1.00 | 23.89 O |
| ATOM | 2573 | CB | ASP | A | 343 | 99.863 | 65.283 | 25.318 | 1.00 | 23.79 C |
| ATOM | 2574 | CG | ASP | A | 343 | 99.944 | 64.499 | 24.028 | 1.00 | 26.58 C |
| ATOM | 2575 | OD1 | ASP | A | 343 | 100.061 | 63.251 | 24.106 | 1.00 | 25.81 O |
| ATOM | 2576 | OD2 | ASP | A | 343 | 99.911 | 65.122 | 22.941 | 1.00 | 27.87 O |

TABLE 7-continued

| ATOM | 2577 | N | GLY | A | 344 | 97.917 | 67.541 | 23.359 | 1.00 | 24.09 | N |
|---|---|---|---|---|---|---|---|---|---|---|---|
| ATOM | 2578 | CA | GLY | A | 344 | 96.696 | 67.569 | 22.565 | 1.00 | 24.48 | C |
| ATOM | 2579 | C | GLY | A | 344 | 95.592 | 68.587 | 22.818 | 1.00 | 24.98 | C |
| ATOM | 2580 | O | GLY | A | 344 | 95.510 | 69.210 | 23.888 | 1.00 | 25.91 | O |
| ATOM | 2581 | N | GLY | A | 345 | 94.737 | 68.753 | 21.809 | 1.00 | 23.62 | N |
| ATOM | 2582 | CA | GLY | A | 345 | 93.614 | 69.664 | 21.922 | 1.00 | 22.65 | C |
| ATOM | 2583 | C | GLY | A | 345 | 93.944 | 71.128 | 21.758 | 1.00 | 22.90 | C |
| ATOM | 2584 | O | GLY | A | 345 | 93.060 | 71.969 | 21.869 | 1.00 | 23.02 | O |
| ATOM | 2585 | N | ILE | A | 346 | 95.207 | 71.443 | 21.498 | 1.00 | 22.89 | N |
| ATOM | 2586 | CA | ILE | A | 346 | 95.637 | 72.827 | 21.322 | 1.00 | 23.44 | C |
| ATOM | 2587 | C | ILE | A | 346 | 95.528 | 73.267 | 19.869 | 1.00 | 25.23 | C |
| ATOM | 2588 | O | ILE | A | 346 | 96.157 | 72.681 | 18.992 | 1.00 | 26.62 | O |
| ATOM | 2589 | CB | ILE | A | 346 | 97.090 | 73.005 | 21.774 | 1.00 | 22.40 | C |
| ATOM | 2590 | CG1 | ILE | A | 346 | 97.160 | 72.887 | 23.297 | 1.00 | 23.15 | C |
| ATOM | 2591 | CG2 | ILE | A | 346 | 97.631 | 74.327 | 21.268 | 1.00 | 22.29 | C |
| ATOM | 2592 | CD1 | ILE | A | 346 | 98.558 | 72.897 | 23.857 | 1.00 | 25.18 | C |
| ATOM | 2593 | N | LYS | A | 347 | 94.744 | 74.305 | 19.603 | 1.00 | 25.74 | N |
| ATOM | 2594 | CA | LYS | A | 347 | 94.605 | 74.756 | 18.228 | 1.00 | 26.93 | C |
| ATOM | 2595 | C | LYS | A | 347 | 95.037 | 76.200 | 18.004 | 1.00 | 26.46 | C |
| ATOM | 2596 | O | LYS | A | 347 | 95.310 | 76.602 | 16.874 | 1.00 | 27.31 | O |
| ATOM | 2597 | CB | LYS | A | 347 | 93.169 | 74.501 | 17.744 | 1.00 | 29.47 | C |
| ATOM | 2598 | CG | LYS | A | 347 | 92.093 | 75.047 | 18.644 | 1.00 | 32.60 | C |
| ATOM | 2599 | CD | LYS | A | 347 | 90.778 | 74.293 | 18.454 | 1.00 | 36.26 | C |
| ATOM | 2600 | CE | LYS | A | 347 | 89.680 | 74.859 | 19.374 | 1.00 | 39.81 | C |
| ATOM | 2601 | NZ | LYS | A | 347 | 90.034 | 74.868 | 20.845 | 1.00 | 39.97 | N |
| ATOM | 2602 | N | TYR | A | 348 | 95.136 | 76.968 | 19.081 | 1.00 | 24.97 | N |
| ATOM | 2603 | CA | TYR | A | 348 | 95.552 | 78.357 | 18.982 | 1.00 | 24.76 | C |
| ATOM | 2604 | C | TYR | A | 348 | 96.692 | 78.637 | 19.951 | 1.00 | 25.00 | C |
| ATOM | 2605 | O | TYR | A | 348 | 96.810 | 77.976 | 20.987 | 1.00 | 24.58 | O |
| ATOM | 2606 | CB | TYR | A | 348 | 94.384 | 79.280 | 19.313 | 1.00 | 25.92 | C |
| ATOM | 2607 | CG | TYR | A | 348 | 93.224 | 79.180 | 18.362 | 1.00 | 29.00 | C |
| ATOM | 2608 | CD1 | TYR | A | 348 | 93.363 | 79.544 | 17.014 | 1.00 | 31.01 | C |
| ATOM | 2609 | CD2 | TYR | A | 348 | 91.975 | 78.759 | 18.806 | 1.00 | 30.18 | C |
| ATOM | 2610 | CE1 | TYR | A | 348 | 92.280 | 79.496 | 16.139 | 1.00 | 31.84 | C |
| ATOM | 2611 | CE2 | TYR | A | 348 | 90.886 | 78.706 | 17.940 | 1.00 | 32.70 | C |
| ATOM | 2612 | CZ | TYR | A | 348 | 91.046 | 79.078 | 16.614 | 1.00 | 33.71 | C |
| ATOM | 2613 | OH | TYR | A | 348 | 89.960 | 79.054 | 15.775 | 1.00 | 37.15 | O |
| ATOM | 2614 | N | SER | A | 349 | 97.523 | 79.626 | 19.629 | 1.00 | 23.37 | N |
| ATOM | 2615 | CA | SER | A | 349 | 98.632 | 79.970 | 20.503 | 1.00 | 23.44 | C |
| ATOM | 2616 | C | SER | A | 349 | 98.093 | 80.308 | 21.894 | 1.00 | 23.36 | C |
| ATOM | 2617 | O | SER | A | 349 | 98.747 | 80.049 | 22.900 | 1.00 | 23.98 | O |
| ATOM | 2618 | CB | SER | A | 349 | 99.432 | 81.151 | 19.936 | 1.00 | 23.65 | C |
| ATOM | 2619 | OG | SER | A | 349 | 98.657 | 82.331 | 19.874 | 1.00 | 24.07 | O |
| ATOM | 2620 | N | GLY | A | 350 | 96.896 | 80.880 | 21.950 | 1.00 | 22.72 | N |
| ATOM | 2621 | CA | GLY | A | 350 | 96.310 | 81.212 | 23.234 | 1.00 | 22.54 | C |
| ATOM | 2622 | C | GLY | A | 350 | 96.093 | 79.964 | 24.071 | 1.00 | 23.59 | C |
| ATOM | 2623 | O | GLY | A | 350 | 96.186 | 80.009 | 25.291 | 1.00 | 23.00 | O |
| ATOM | 2624 | N | ASP | A | 351 | 95.798 | 78.847 | 23.407 | 1.00 | 23.75 | N |
| ATOM | 2625 | CA | ASP | A | 351 | 95.573 | 77.573 | 24.085 | 1.00 | 23.84 | C |
| ATOM | 2626 | C | ASP | A | 351 | 96.850 | 77.093 | 24.770 | 1.00 | 23.49 | C |
| ATOM | 2627 | O | ASP | A | 351 | 96.798 | 76.434 | 25.811 | 1.00 | 22.59 | O |
| ATOM | 2628 | CB | ASP | A | 351 | 95.097 | 76.509 | 23.088 | 1.00 | 25.03 | C |
| ATOM | 2629 | CG | ASP | A | 351 | 93.660 | 76.720 | 22.638 | 1.00 | 27.18 | C |
| ATOM | 2630 | OD1 | ASP | A | 351 | 93.215 | 76.016 | 21.707 | 1.00 | 28.04 | O |
| ATOM | 2631 | OD2 | ASP | A | 351 | 92.966 | 77.576 | 23.226 | 1.00 | 30.15 | O |
| ATOM | 2632 | N | ILE | A | 352 | 97.994 | 77.421 | 24.178 | 1.00 | 22.40 | N |
| ATOM | 2633 | CA | ILE | A | 352 | 99.274 | 77.032 | 24.749 | 1.00 | 20.34 | C |
| ATOM | 2634 | C | ILE | A | 352 | 99.452 | 77.716 | 26.102 | 1.00 | 21.36 | C |
| ATOM | 2635 | O | ILE | A | 352 | 99.879 | 77.084 | 27.069 | 1.00 | 22.39 | O |
| ATOM | 2636 | CB | ILE | A | 352 | 100.445 | 77.431 | 23.830 | 1.00 | 18.46 | C |
| ATOM | 2637 | CG1 | ILE | A | 352 | 100.296 | 76.753 | 22.474 | 1.00 | 17.19 | C |
| ATOM | 2638 | CG2 | ILE | A | 352 | 101.756 | 77.042 | 24.462 | 1.00 | 17.65 | C |
| ATOM | 2639 | CD1 | ILE | A | 352 | 101.395 | 77.086 | 21.512 | 1.00 | 17.04 | C |
| ATOM | 2640 | N | VAL | A | 353 | 99.122 | 79.005 | 26.172 | 1.00 | 20.35 | N |
| ATOM | 2641 | CA | VAL | A | 353 | 99.269 | 79.753 | 27.413 | 1.00 | 20.32 | C |
| ATOM | 2642 | C | VAL | A | 353 | 98.328 | 79.228 | 28.496 | 1.00 | 19.94 | C |
| ATOM | 2643 | O | VAL | A | 353 | 98.671 | 79.204 | 29.671 | 1.00 | 20.43 | O |
| ATOM | 2644 | CB | VAL | A | 353 | 98.997 | 81.250 | 27.189 | 1.00 | 21.35 | C |
| ATOM | 2645 | CG1 | VAL | A | 353 | 99.315 | 82.026 | 28.455 | 1.00 | 21.91 | C |
| ATOM | 2646 | CG2 | VAL | A | 353 | 99.826 | 81.765 | 26.024 | 1.00 | 22.51 | C |
| ATOM | 2647 | N | LYS | A | 354 | 97.131 | 78.809 | 28.098 | 1.00 | 21.28 | N |
| ATOM | 2648 | CA | LYS | A | 354 | 96.168 | 78.266 | 29.049 | 1.00 | 20.46 | C |
| ATOM | 2649 | C | LYS | A | 354 | 96.674 | 76.925 | 29.563 | 1.00 | 20.59 | C |
| ATOM | 2650 | O | LYS | A | 354 | 96.587 | 76.640 | 30.758 | 1.00 | 21.00 | O |
| ATOM | 2651 | CB | LYS | A | 354 | 94.797 | 78.067 | 28.388 | 1.00 | 21.23 | C |
| ATOM | 2652 | CG | LYS | A | 354 | 94.090 | 79.344 | 27.951 | 1.00 | 20.48 | C |
| ATOM | 2653 | CD | LYS | A | 354 | 92.766 | 79.032 | 27.264 | 1.00 | 19.71 | C |
| ATOM | 2654 | CE | LYS | A | 354 | 92.118 | 80.297 | 26.720 | 1.00 | 22.52 | C |
| ATOM | 2655 | NZ | LYS | A | 354 | 90.917 | 80.013 | 25.879 | 1.00 | 21.12 | N |

TABLE 7-continued

| | | | | | | | | | | | |
|---|---|---|---|---|---|---|---|---|---|---|---|
| ATOM | 2656 | N | ALA | A | 355 | 97.191 | 76.099 | 28.656 | 1.00 | 19.85 | N |
| ATOM | 2657 | CA | ALA | A | 355 | 97.716 | 74.782 | 29.017 | 1.00 | 20.80 | C |
| ATOM | 2658 | C | ALA | A | 355 | 98.886 | 74.933 | 29.978 | 1.00 | 21.77 | C |
| ATOM | 2659 | O | ALA | A | 355 | 99.037 | 74.146 | 30.908 | 1.00 | 22.61 | O |
| ATOM | 2660 | CB | ALA | A | 355 | 98.163 | 74.022 | 27.773 | 1.00 | 19.41 | C |
| ATOM | 2661 | N | LEU | A | 356 | 99.722 | 75.940 | 29.753 | 1.00 | 21.62 | N |
| ATOM | 2662 | CA | LEU | A | 356 | 100.858 | 76.168 | 30.630 | 1.00 | 22.27 | C |
| ATOM | 2663 | C | LEU | A | 356 | 100.367 | 76.727 | 31.957 | 1.00 | 23.40 | C |
| ATOM | 2664 | O | LEU | A | 356 | 100.846 | 76.342 | 33.015 | 1.00 | 24.73 | O |
| ATOM | 2665 | CB | LEU | A | 356 | 101.843 | 77.145 | 29.986 | 1.00 | 21.42 | C |
| ATOM | 2666 | CG | LEU | A | 356 | 102.518 | 76.717 | 28.684 | 1.00 | 20.49 | C |
| ATOM | 2667 | CD1 | LEU | A | 356 | 103.328 | 77.875 | 28.141 | 1.00 | 21.00 | C |
| ATOM | 2668 | CD2 | LEU | A | 356 | 103.386 | 75.488 | 28.925 | 1.00 | 21.89 | C |
| ATOM | 2669 | N | ALA | A | 357 | 99.396 | 77.629 | 31.900 | 1.00 | 23.83 | N |
| ATOM | 2670 | CA | ALA | A | 357 | 98.858 | 78.243 | 33.109 | 1.00 | 24.49 | C |
| ATOM | 2671 | C | ALA | A | 357 | 98.115 | 77.252 | 34.002 | 1.00 | 24.83 | C |
| ATOM | 2672 | O | ALA | A | 357 | 98.034 | 77.445 | 35.210 | 1.00 | 24.39 | O |
| ATOM | 2673 | CB | ALA | A | 357 | 97.943 | 79.396 | 32.739 | 1.00 | 25.49 | C |
| ATOM | 2674 | N | ALA | A | 358 | 97.577 | 76.191 | 33.412 | 1.00 | 23.94 | N |
| ATOM | 2675 | CA | ALA | A | 358 | 96.856 | 75.192 | 34.189 | 1.00 | 23.85 | C |
| ATOM | 2676 | C | ALA | A | 358 | 97.818 | 74.209 | 34.853 | 1.00 | 24.49 | C |
| ATOM | 2677 | O | ALA | A | 358 | 97.391 | 73.320 | 35.595 | 1.00 | 24.74 | O |
| ATOM | 2678 | CB | ALA | A | 358 | 95.865 | 74.440 | 33.300 | 1.00 | 24.65 | C |
| ATOM | 2679 | N | GLY | A | 359 | 99.113 | 74.349 | 34.579 | 1.00 | 24.04 | N |
| ATOM | 2680 | CA | GLY | A | 359 | 100.074 | 73.460 | 35.206 | 1.00 | 23.58 | C |
| ATOM | 2681 | C | GLY | A | 359 | 101.065 | 72.763 | 34.300 | 1.00 | 23.49 | C |
| ATOM | 2682 | O | GLY | A | 359 | 101.964 | 72.073 | 34.786 | 1.00 | 24.97 | O |
| ATOM | 2683 | N | GLY | A | 360 | 100.924 | 72.929 | 32.990 | 1.00 | 22.19 | N |
| ATOM | 2684 | CA | GLY | A | 360 | 101.847 | 72.279 | 32.083 | 1.00 | 19.65 | C |
| ATOM | 2685 | C | GLY | A | 360 | 103.209 | 72.936 | 32.105 | 1.00 | 20.75 | C |
| ATOM | 2686 | O | GLY | A | 360 | 103.312 | 74.134 | 32.324 | 1.00 | 20.45 | O |
| ATOM | 2687 | N | ASN | A | 361 | 104.258 | 72.148 | 31.887 | 1.00 | 20.92 | N |
| ATOM | 2688 | CA | ASN | A | 361 | 105.630 | 72.655 | 31.855 | 1.00 | 22.23 | C |
| ATOM | 2689 | C | ASN | A | 361 | 106.051 | 72.782 | 30.402 | 1.00 | 22.46 | C |
| ATOM | 2690 | O | ASN | A | 361 | 107.060 | 73.407 | 30.079 | 1.00 | 22.58 | O |
| ATOM | 2691 | CB | ASN | A | 361 | 106.568 | 71.697 | 32.589 | 1.00 | 22.17 | C |
| ATOM | 2692 | CG | ASN | A | 361 | 106.338 | 71.703 | 34.085 | 1.00 | 25.53 | C |
| ATOM | 2693 | OD1 | ASN | A | 361 | 106.646 | 72.688 | 34.763 | 1.00 | 27.16 | O |
| ATOM | 2694 | ND2 | ASN | A | 361 | 105.766 | 70.624 | 34.607 | 1.00 | 25.19 | N |
| ATOM | 2695 | N | ALA | A | 362 | 105.251 | 72.178 | 29.530 | 1.00 | 22.54 | N |
| ATOM | 2696 | CA | ALA | A | 362 | 105.481 | 72.193 | 28.095 | 1.00 | 21.37 | C |
| ATOM | 2697 | C | ALA | A | 362 | 104.229 | 71.625 | 27.432 | 1.00 | 21.05 | C |
| ATOM | 2698 | O | ALA | A | 362 | 103.423 | 70.969 | 28.084 | 1.00 | 18.71 | O |
| ATOM | 2699 | CB | ALA | A | 362 | 106.704 | 71.341 | 27.753 | 1.00 | 20.68 | C |
| ATOM | 2700 | N | VAL | A | 363 | 104.058 | 71.895 | 26.142 | 1.00 | 22.66 | N |
| ATOM | 2701 | CA | VAL | A | 363 | 102.903 | 71.377 | 25.410 | 1.00 | 22.68 | C |
| ATOM | 2702 | C | VAL | A | 363 | 103.389 | 70.579 | 24.210 | 1.00 | 22.35 | C |
| ATOM | 2703 | O | VAL | A | 363 | 104.423 | 70.893 | 23.638 | 1.00 | 23.37 | O |
| ATOM | 2704 | CB | VAL | A | 363 | 101.964 | 72.521 | 24.910 | 1.00 | 22.34 | C |
| ATOM | 2705 | CG1 | VAL | A | 363 | 101.440 | 73.333 | 26.088 | 1.00 | 21.37 | C |
| ATOM | 2706 | CG2 | VAL | A | 363 | 102.702 | 73.418 | 23.929 | 1.00 | 22.84 | C |
| HETATM | 2707 | N | MSE | A | 364 | 102.662 | 69.530 | 23.851 | 1.00 | 21.88 | N |
| HETATM | 2708 | CA | MSE | A | 364 | 103.027 | 68.726 | 22.692 | 1.00 | 22.51 | C |
| HETATM | 2709 | C | MSE | A | 364 | 102.014 | 69.063 | 21.608 | 1.00 | 23.49 | C |
| HETATM | 2710 | O | MSE | A | 364 | 100.794 | 69.022 | 21.832 | 1.00 | 23.44 | O |
| HETATM | 2711 | CB | MSE | A | 364 | 103.011 | 67.231 | 23.028 | 1.00 | 24.05 | C |
| HETATM | 2712 | CG | MSE | A | 364 | 103.223 | 66.330 | 21.821 | 1.00 | 27.31 | C |
| HETATM | 2713 | SE | MSE | A | 364 | 103.374 | 64.556 | 22.241 | 1.00 | 35.51 | SE |
| HETATM | 2714 | CE | MSE | A | 364 | 105.096 | 64.508 | 22.891 | 1.00 | 32.69 | C |
| ATOM | 2715 | N | LEU | A | 365 | 102.531 | 69.420 | 20.436 | 1.00 | 23.87 | N |
| ATOM | 2716 | CA | LEU | A | 365 | 101.704 | 69.831 | 19.315 | 1.00 | 24.27 | C |
| ATOM | 2717 | C | LEU | A | 365 | 101.822 | 68.920 | 18.108 | 1.00 | 25.78 | C |
| ATOM | 2718 | O | LEU | A | 365 | 102.926 | 68.614 | 17.666 | 1.00 | 26.09 | C |
| ATOM | 2719 | CB | LEU | A | 365 | 102.104 | 71.238 | 18.905 | 1.00 | 22.73 | C |
| ATOM | 2720 | CG | LEU | A | 365 | 102.093 | 72.219 | 20.060 | 1.00 | 23.17 | C |
| ATOM | 2721 | CD1 | LEU | A | 365 | 102.705 | 73.527 | 19.616 | 1.00 | 24.46 | C |
| ATOM | 2722 | CD2 | LEU | A | 365 | 100.670 | 72.378 | 20.574 | 1.00 | 22.59 | C |
| ATOM | 2723 | N | GLY | A | 366 | 100.678 | 68.508 | 17.569 | 1.00 | 26.69 | N |
| ATOM | 2724 | CA | GLY | A | 366 | 100.667 | 67.651 | 16.398 | 1.00 | 28.30 | C |
| ATOM | 2725 | C | GLY | A | 366 | 100.045 | 68.365 | 15.213 | 1.00 | 29.57 | C |
| ATOM | 2726 | O | GLY | A | 366 | 100.717 | 68.663 | 14.226 | 1.00 | 29.34 | O |
| ATOM | 2727 | N | SER | A | 367 | 98.753 | 68.644 | 15.327 | 1.00 | 30.92 | N |
| ATOM | 2728 | CA | SER | A | 367 | 97.993 | 69.341 | 14.298 | 1.00 | 33.00 | C |
| ATOM | 2729 | C | SER | A | 367 | 98.648 | 70.637 | 13.803 | 1.00 | 34.00 | C |
| ATOM | 2730 | O | SER | A | 367 | 98.750 | 70.848 | 12.598 | 1.00 | 33.51 | O |
| ATOM | 2731 | CB | SER | A | 367 | 96.590 | 69.646 | 14.832 | 1.00 | 34.28 | C |
| ATOM | 2732 | OG | SER | A | 367 | 95.800 | 70.345 | 13.885 | 1.00 | 34.75 | O |
| HETATM | 2733 | N | MSE | A | 368 | 99.097 | 71.501 | 14.713 | 1.00 | 34.95 | N |
| HETATM | 2734 | CA | MSE | A | 368 | 99.712 | 72.765 | 14.296 | 1.00 | 37.45 | C |

TABLE 7-continued

| | | | | | | | | | | |
|---|---|---|---|---|---|---|---|---|---|---|
| HETATM | 2735 | C | MSE | A | 368 | 100.963 | 72.668 | 13.424 | 1.00 | 36.66 C |
| HETATM | 2736 | O | MSE | A | 368 | 101.316 | 73.635 | 12.748 | 1.00 | 36.99 O |
| HETATM | 2737 | CB | MSE | A | 368 | 100.000 | 73.664 | 15.506 | 1.00 | 40.56 C |
| HETATM | 2738 | CG | MSE | A | 368 | 98.719 | 74.111 | 16.191 | 1.00 | 46.02 C |
| HETATM | 2739 | SE | MSE | A | 368 | 98.916 | 75.343 | 17.492 | 1.00 | 56.80 SE |
| HETATM | 2740 | CE | MSE | A | 368 | 99.964 | 74.527 | 18.572 | 1.00 | 55.31 C |
| ATOM | 2741 | N | PHE | A | 369 | 101.626 | 71.513 | 13.417 | 1.00 | 34.82 N |
| ATOM | 2742 | CA | PHE | A | 369 | 102.830 | 71.339 | 12.603 | 1.00 | 31.76 C |
| ATOM | 2743 | C | PHE | A | 369 | 102.600 | 70.421 | 11.416 | 1.00 | 31.43 C |
| ATOM | 2744 | O | PHE | A | 369 | 103.378 | 70.425 | 10.467 | 1.00 | 30.91 O |
| ATOM | 2745 | CB | PHE | A | 369 | 103.977 | 70.786 | 13.460 | 1.00 | 29.79 C |
| ATOM | 2746 | CG | PHE | A | 369 | 104.507 | 71.765 | 14.473 | 1.00 | 26.59 C |
| ATOM | 2747 | CD1 | PHE | A | 369 | 104.387 | 71.518 | 15.829 | 1.00 | 27.53 C |
| ATOM | 2748 | CD2 | PHE | A | 369 | 105.121 | 72.947 | 14.062 | 1.00 | 27.73 C |
| ATOM | 2749 | CE1 | PHE | A | 369 | 104.872 | 72.444 | 16.771 | 1.00 | 27.77 C |
| ATOM | 2750 | CE2 | PHE | A | 369 | 105.605 | 73.874 | 14.990 | 1.00 | 27.15 C |
| ATOM | 2751 | CZ | PHE | A | 369 | 105.481 | 73.622 | 16.345 | 1.00 | 26.83 C |
| ATOM | 2752 | N | ALA | A | 370 | 101.510 | 69.658 | 11.479 | 1.00 | 32.61 N |
| ATOM | 2753 | CA | ALA | A | 370 | 101.108 | 68.668 | 10.465 | 1.00 | 33.73 C |
| ATOM | 2754 | C | ALA | A | 370 | 101.243 | 68.936 | 8.953 | 1.00 | 34.56 C |
| ATOM | 2755 | O | ALA | A | 370 | 101.405 | 67.982 | 8.173 | 1.00 | 35.53 O |
| ATOM | 2756 | CB | ALA | A | 370 | 99.682 | 68.213 | 10.761 | 1.00 | 33.78 C |
| ATOM | 2757 | N | GLY | A | 371 | 101.165 | 70.191 | 8.518 | 1.00 | 33.99 N |
| ATOM | 2758 | CA | GLY | A | 371 | 101.282 | 70.453 | 7.090 | 1.00 | 33.01 C |
| ATOM | 2759 | C | GLY | A | 371 | 102.500 | 71.252 | 6.666 | 1.00 | 33.01 C |
| ATOM | 2760 | O | GLY | A | 371 | 102.537 | 71.811 | 5.564 | 1.00 | 32.73 O |
| ATOM | 2761 | N | THR | A | 372 | 103.508 | 71.299 | 7.530 | 1.00 | 32.22 N |
| ATOM | 2762 | CA | THR | A | 372 | 104.724 | 72.055 | 7.244 | 1.00 | 32.27 C |
| ATOM | 2763 | C | THR | A | 372 | 105.688 | 71.363 | 6.276 | 1.00 | 33.94 C |
| ATOM | 2764 | O | THR | A | 372 | 105.448 | 70.244 | 5.828 | 1.00 | 35.02 O |
| ATOM | 2765 | CB | THR | A | 372 | 105.479 | 72.426 | 8.567 | 1.00 | 30.26 C |
| ATOM | 2766 | OG1 | THR | A | 372 | 105.828 | 71.242 | 9.298 | 1.00 | 27.73 O |
| ATOM | 2767 | CG2 | THR | A | 372 | 104.601 | 73.299 | 9.440 | 1.00 | 28.61 C |
| ATOM | 2768 | N | ASP | A | 373 | 106.771 | 72.052 | 5.937 | 1.00 | 35.72 N |
| ATOM | 2769 | CA | ASP | A | 373 | 107.775 | 71.506 | 5.040 | 1.00 | 37.55 C |
| ATOM | 2770 | C | ASP | A | 373 | 108.346 | 70.234 | 5.665 | 1.00 | 39.10 C |
| ATOM | 2771 | O | ASP | A | 373 | 108.423 | 69.187 | 5.023 | 1.00 | 39.87 O |
| ATOM | 2772 | CB | ASP | A | 373 | 108.893 | 72.531 | 4.844 | 1.00 | 39.43 C |
| ATOM | 2773 | CG | ASP | A | 373 | 108.394 | 73.826 | 4.223 | 1.00 | 42.12 C |
| ATOM | 2774 | OD1 | ASP | A | 373 | 109.121 | 74.847 | 4.253 | 1.00 | 42.31 O |
| ATOM | 2775 | CD2 | ASP | A | 373 | 107.267 | 73.815 | 3.687 | 1.00 | 45.19 O |
| ATOM | 2776 | N | GLU | A | 374 | 108.720 | 70.334 | 6.937 | 1.00 | 39.77 N |
| ATOM | 2777 | CA | GLU | A | 374 | 109.312 | 69.224 | 7.676 | 1.00 | 40.52 C |
| ATOM | 2778 | C | GLU | A | 374 | 108.430 | 67.991 | 7.949 | 1.00 | 40.61 C |
| ATOM | 2779 | O | GLU | A | 374 | 108.938 | 66.870 | 7.961 | 1.00 | 41.45 O |
| ATOM | 2780 | CB | GLU | A | 374 | 109.859 | 69.740 | 9.003 | 1.00 | 40.97 C |
| ATOM | 2781 | CG | GLU | A | 374 | 110.940 | 70.800 | 8.893 | 1.00 | 43.47 C |
| ATOM | 2782 | CD | GLU | A | 374 | 110.498 | 72.042 | 8.138 | 1.00 | 46.43 C |
| ATOM | 2783 | OE1 | GLU | A | 374 | 109.291 | 72.384 | 8.186 | 1.00 | 46.56 O |
| ATOM | 2784 | OE2 | GLU | A | 374 | 111.365 | 72.704 | 7.520 | 1.00 | 48.05 O |
| ATOM | 2785 | N | ALA | A | 375 | 107.132 | 68.180 | 8.176 | 1.00 | 39.40 N |
| ATOM | 2786 | CA | ALA | A | 375 | 106.237 | 67.053 | 8.467 | 1.00 | 39.33 C |
| ATOM | 2787 | C | ALA | A | 375 | 106.201 | 65.981 | 7.367 | 1.00 | 39.58 C |
| ATOM | 2788 | O | ALA | A | 375 | 105.988 | 66.289 | 6.194 | 1.00 | 40.42 O |
| ATOM | 2789 | CB | ALA | A | 375 | 104.827 | 67.568 | 8.740 | 1.00 | 38.20 C |
| ATOM | 2790 | N | PRO | A | 376 | 106.397 | 64.701 | 7.742 | 1.00 | 39.51 N |
| ATOM | 2791 | CA | PRO | A | 376 | 106.400 | 63.547 | 6.833 | 1.00 | 40.37 C |
| ATOM | 2792 | C | PRO | A | 376 | 105.074 | 63.223 | 6.115 | 1.00 | 42.60 C |
| ATOM | 2793 | O | PRO | A | 376 | 105.034 | 62.339 | 5.257 | 1.00 | 44.07 O |
| ATOM | 2794 | CB | PRO | A | 376 | 106.840 | 62.403 | 7.751 | 1.00 | 38.78 C |
| ATOM | 2795 | CG | PRO | A | 376 | 107.612 | 63.112 | 8.842 | 1.00 | 37.80 C |
| ATOM | 2796 | CD | PRO | A | 376 | 106.665 | 64.236 | 9.111 | 1.00 | 37.56 C |
| ATOM | 2797 | N | GLY | A | 377 | 103.992 | 63.916 | 6.465 | 1.00 | 44.20 N |
| ATOM | 2798 | CA | GLY | A | 377 | 102.704 | 63.657 | 5.829 | 1.00 | 45.51 C |
| ATOM | 2799 | C | GLY | A | 377 | 102.780 | 63.611 | 4.312 | 1.00 | 47.08 C |
| ATOM | 2800 | O | GLY | A | 377 | 103.714 | 64.150 | 3.720 | 1.00 | 47.51 O |
| ATOM | 2801 | N | GLU | A | 378 | 101.801 | 62.968 | 3.681 | 1.00 | 48.24 N |
| ATOM | 2802 | CA | GLU | A | 378 | 101.759 | 62.841 | 2.221 | 1.00 | 48.97 C |
| ATOM | 2803 | C | GLU | A | 378 | 100.987 | 64.015 | 1.627 | 1.00 | 48.92 C |
| ATOM | 2804 | O | GLU | A | 378 | 99.905 | 64.345 | 2.096 | 1.00 | 49.36 O |
| ATOM | 2805 | CB | GLU | A | 378 | 101.082 | 61.523 | 1.828 | 1.00 | 50.65 C |
| ATOM | 2806 | CG | GLU | A | 378 | 101.750 | 60.266 | 2.409 | 1.00 | 56.37 C |
| ATOM | 2807 | CD | GLU | A | 378 | 101.682 | 60.184 | 3.950 | 1.00 | 60.26 C |
| ATOM | 2808 | OE1 | GLU | A | 378 | 100.554 | 60.078 | 4.493 | 1.00 | 61.73 O |
| ATOM | 2809 | OE2 | GLU | A | 378 | 102.752 | 60.225 | 4.619 | 1.00 | 60.95 O |
| ATOM | 2810 | N | THR | A | 379 | 101.538 | 64.648 | 0.598 | 1.00 | 48.86 N |
| ATOM | 2811 | CA | THR | A | 379 | 100.868 | 55.786 | −0.030 | 1.00 | 49.21 C |
| ATOM | 2812 | C | THR | A | 379 | 99.683 | 65.876 | −0.911 | 1.00 | 49.89 C |
| ATOM | 2813 | O | THR | A | 379 | 99.745 | 64.394 | −1.658 | 1.00 | 49.37 O |

TABLE 7-continued

| ATOM | 2814 | CB | THR | A | 379 | 101.845 | 66.617 | −0.903 | 1.00 | 48.77 | C |
| --- | --- | --- | --- | --- | --- | --- | --- | --- | --- | --- | --- |
| ATOM | 2815 | OG1 | THR | A | 379 | 102.921 | 67.089 | −0.087 | 1.00 | 49.52 | O |
| ATOM | 2816 | CG2 | THR | A | 379 | 101.133 | 67.821 | −1.527 | 1.00 | 46.54 | C |
| ATOM | 2817 | N | GLU | A | 380 | 98.604 | 66.147 | −0.814 | 1.00 | 50.46 | N |
| ATOM | 2818 | CA | GLU | A | 380 | 97.407 | 65.905 | −1.601 | 1.00 | 51.12 | C |
| ATOM | 2819 | C | GLU | A | 380 | 96.897 | 67.228 | −2.134 | 1.00 | 50.88 | C |
| ATOM | 2820 | O | GLU | A | 380 | 97.110 | 68.283 | −1.538 | 1.00 | 49.94 | O |
| ATOM | 2821 | CB | GLU | A | 380 | 96.322 | 65.227 | −0.758 | 1.00 | 51.47 | C |
| ATOM | 2822 | CG | GLU | A | 380 | 96.762 | 63.909 | −0.168 | 1.00 | 53.35 | C |
| ATOM | 2823 | CD | GLU | A | 380 | 95.633 | 63.169 | 0.503 | 1.00 | 55.74 | C |
| ATOM | 2824 | OE1 | GLU | A | 380 | 94.962 | 63.764 | 1.373 | 1.00 | 56.99 | O |
| ATOM | 2825 | OE2 | GLU | A | 380 | 95.421 | 61.983 | 0.167 | 1.00 | 57.47 | O |
| ATOM | 2826 | N | ILE | A | 381 | 96.226 | 67.165 | −3.272 | 1.00 | 52.06 | N |
| ATOM | 2827 | CA | ILE | A | 381 | 95.697 | 68.364 | −3.884 | 1.00 | 53.51 | C |
| ATOM | 2828 | C | ILE | A | 381 | 94.196 | 68.250 | −4.113 | 1.00 | 53.54 | C |
| ATOM | 2829 | O | ILE | A | 381 | 93.707 | 67.300 | −4.731 | 1.00 | 53.35 | O |
| ATOM | 2830 | CB | ILE | A | 381 | 96.436 | 68.676 | −5.219 | 1.00 | 54.46 | C |
| ATOM | 2831 | CG1 | ILE | A | 381 | 96.307 | 67.515 | −6.199 | 1.00 | 54.90 | C |
| ATOM | 2832 | CG2 | ILE | A | 381 | 97.919 | 68.895 | −4.947 | 1.00 | 55.14 | C |
| ATOM | 2833 | CD1 | ILE | A | 381 | 97.141 | 67.712 | −7.458 | 1.00 | 55.73 | C |
| ATOM | 2634 | N | TYR | A | 382 | 93.472 | 69.228 | −3.579 | 1.00 | 53.11 | N |
| ATOM | 2835 | CA | TYR | A | 382 | 92.029 | 69.285 | −3.699 | 1.00 | 52.90 | C |
| ATOM | 2836 | C | TYR | A | 382 | 91.669 | 70.747 | −3.928 | 1.00 | 52.45 | C |
| ATOM | 2837 | O | TYR | A | 382 | 92.092 | 71.623 | −3.173 | 1.00 | 51.87 | O |
| ATOM | 2838 | CB | TYR | A | 382 | 91.379 | 68.732 | −2.419 | 1.00 | 53.99 | C |
| ATOM | 2839 | CG | TYR | A | 382 | 89.868 | 68.819 | −2.388 | 1.00 | 55.14 | C |
| ATOM | 2840 | CD1 | TYR | A | 382 | 89.221 | 69.793 | −1.623 | 1.00 | 55.14 | C |
| ATOM | 2841 | CD2 | TYR | A | 382 | 89.084 | 67.957 | −3.161 | 1.00 | 55.70 | C |
| ATOM | 2842 | CE1 | TYR | A | 382 | 87.827 | 69.910 | −1.629 | 1.00 | 56.22 | C |
| ATOM | 2843 | CE2 | TYR | A | 382 | 87.688 | 68.066 | −3.177 | 1.00 | 56.34 | C |
| ATOM | 2844 | CZ | TYR | A | 382 | 87.066 | 69.046 | −2.410 | 1.00 | 56.68 | C |
| ATOM | 2845 | OH | TYR | A | 382 | 85.693 | 69.174 | −2.439 | 1.00 | 57.02 | O |
| ATOM | 2846 | N | GLN | A | 383 | 90.903 | 70.999 | −4.987 | 1.00 | 52.24 | N |
| ATOM | 2847 | CA | GLN | A | 383 | 90.484 | 72.348 | −5.358 | 1.00 | 52.02 | C |
| ATOM | 2848 | C | GLN | A | 383 | 91.687 | 73.210 | −5.721 | 1.00 | 51.03 | C |
| ATOM | 2849 | O | GLN | A | 383 | 91.619 | 74.436 | −5.661 | 1.00 | 50.67 | O |
| ATOM | 2850 | CB | GLN | A | 383 | 89.707 | 73.018 | −4.218 | 1.00 | 53.91 | C |
| ATOM | 2851 | CG | GLN | A | 383 | 88.436 | 72.297 | −3.794 | 1.00 | 56.88 | C |
| ATOM | 2852 | CD | GLN | A | 383 | 87.451 | 72.115 | −4.934 | 1.00 | 59.26 | C |
| ATOM | 2853 | OE1 | GLN | A | 383 | 87.746 | 71.441 | −5.926 | 1.00 | 60.79 | O |
| ATOM | 2854 | NE2 | GLN | A | 383 | 86.270 | 72.718 | −4.800 | 1.00 | 59.95 | N |
| ATOM | 2855 | N | GLY | A | 384 | 92.788 | 72.562 | −6.091 | 1.00 | 50.37 | N |
| ATOM | 2856 | CA | GLY | A | 384 | 93.985 | 73.292 | −6.468 | 1.00 | 50.11 | C |
| ATOM | 2857 | C | GLY | A | 384 | 94.977 | 73.527 | −5.341 | 1.00 | 49.99 | C |
| ATOM | 2858 | O | GLY | A | 384 | 96.185 | 73.637 | −5.586 | 1.00 | 50.26 | O |
| ATOM | 2859 | N | ARG | A | 385 | 94.480 | 73.610 | −4.109 | 1.00 | 49.41 | N |
| ATOM | 2860 | CA | ARG | A | 385 | 95.350 | 73.837 | −2.958 | 1.00 | 48.78 | C |
| ATOM | 2861 | C | ARG | A | 385 | 96.049 | 72.559 | −2.527 | 1.00 | 47.90 | C |
| ATOM | 2862 | O | ARG | A | 385 | 95.536 | 71.456 | −2.727 | 1.00 | 47.68 | O |
| ATOM | 2863 | CB | ARG | A | 385 | 94.563 | 74.379 | −1.761 | 1.00 | 49.61 | C |
| ATOM | 2864 | CG | ARG | A | 385 | 93.830 | 75.696 | −1.980 | 1.00 | 51.31 | C |
| ATOM | 2865 | CD | ARG | A | 385 | 92.522 | 75.518 | −2.727 | 1.00 | 52.37 | C |
| ATOM | 2866 | NE | ARG | A | 385 | 91.851 | 76.801 | −2.898 | 1.00 | 54.89 | N |
| ATOM | 2867 | CZ | ARG | A | 385 | 90.660 | 76.958 | −3.467 | 1.00 | 56.27 | C |
| ATOM | 2868 | NH1 | ARG | A | 385 | 89.996 | 75.905 | −3.925 | 1.00 | 57.58 | N |
| ATOM | 2869 | NH2 | ARG | A | 385 | 90.135 | 78.170 | −3.581 | 1.00 | 55.72 | N |
| ATOM | 2870 | N | LYS | A | 386 | 97.220 | 72.712 | −1.920 | 1.00 | 47.18 | N |
| ATOM | 2871 | CA | LYS | A | 386 | 97.977 | 71.561 | −1.450 | 1.00 | 46.53 | C |
| ATOM | 2872 | C | LYS | A | 386 | 97.702 | 71.259 | 0.022 | 1.00 | 45.66 | C |
| ATOM | 2873 | O | LYS | A | 386 | 97.602 | 72.166 | 0.857 | 1.00 | 45.07 | O |
| ATOM | 2874 | CB | LYS | A | 386 | 99.478 | 71.781 | −1.642 | 1.00 | 46.65 | C |
| ATOM | 2875 | CG | LYS | A | 386 | 99.942 | 71.885 | −3.082 | 1.00 | 48.06 | C |
| ATOM | 2876 | CD | LYS | A | 386 | 101.451 | 72.061 | −3.101 | 1.00 | 50.09 | C |
| ATOM | 2877 | CE | LYS | A | 386 | 102.017 | 72.118 | −4.505 | 1.00 | 51.55 | C |
| ATOM | 2878 | HZ | LYS | A | 386 | 103.505 | 72.226 | −4.438 | 1.00 | 52.03 | N |
| ATOM | 2879 | N | TYR | A | 387 | 97.580 | 69.971 | 0.326 | 1.00 | 45.21 | N |
| ATOM | 2880 | CA | TYR | A | 387 | 97.335 | 69.515 | 1.689 | 1.00 | 45.09 | C |
| ATOM | 2881 | C | TYR | A | 387 | 98.420 | 68.561 | 2.155 | 1.00 | 44.05 | C |
| ATOM | 2882 | O | TYR | A | 387 | 99.270 | 68.119 | 1.380 | 1.00 | 44.31 | C |
| ATOM | 2883 | CB | TYR | A | 387 | 95.978 | 68.807 | 1.787 | 1.00 | 45.22 | C |
| ATOM | 2884 | CG | TYR | A | 387 | 94.799 | 69.725 | 1.580 | 1.00 | 45.09 | C |
| ATOM | 2885 | CD1 | TYR | A | 387 | 94.537 | 70.291 | 0.332 | 1.00 | 45.10 | C |
| ATOM | 2886 | CD2 | TYR | A | 387 | 93.981 | 70.063 | 2.652 | 1.00 | 45.00 | C |
| ATOM | 2887 | CE1 | TYR | A | 387 | 93.492 | 71.194 | 0.160 | 1.00 | 45.13 | C |
| ATOM | 2888 | CE2 | TYR | A | 387 | 92.941 | 70.979 | 2.491 | 1.00 | 45.41 | C |
| ATOM | 2889 | CZ | TYR | A | 387 | 92.707 | 71.531 | 1.246 | 1.00 | 45.60 | C |
| ATOM | 2890 | OH | TYR | A | 387 | 91.701 | 72.444 | 1.104 | 1.00 | 47.56 | O |
| ATOM | 2891 | N | LYS | A | 388 | 98.381 | 68.248 | 3.438 | 1.00 | 43.76 | N |
| ATOM | 2892 | CA | LYS | A | 388 | 99.328 | 67.326 | 4.034 | 1.00 | 43.49 | C |

TABLE 7-continued

| | | | | | | | | | | |
|---|---|---|---|---|---|---|---|---|---|---|
| ATOM | 2893 | C | LYS | A | 388 | 98.501 | 66.389 | 4.865 | 1.00 | 41.84 C |
| ATOM | 2894 | O | LYS | A | 388 | 97.731 | 66.834 | 5.703 | 1.00 | 40.70 O |
| ATOM | 2895 | CB | LYS | A | 388 | 100.317 | 68.067 | 4.932 | 1.00 | 45.64 C |
| ATOM | 2896 | CG | LYS | A | 388 | 101.504 | 68.715 | 4.213 | 1.00 | 48.31 C |
| ATOM | 2897 | CD | LYS | A | 388 | 102.626 | 67.706 | 3.892 | 1.00 | 47.96 C |
| ATOM | 2898 | CE | LYS | A | 388 | 103.901 | 68.437 | 3.466 | 1.00 | 47.56 C |
| ATOM | 2899 | NZ | LYS | A | 388 | 105.097 | 67.563 | 3.426 | 1.00 | 46.67 N |
| ATOM | 2900 | N | THR | A | 389 | 98.647 | 65.092 | 4.617 | 1.00 | 42.01 N |
| ATOM | 2901 | CA | THR | A | 389 | 97.902 | 64.098 | 5.370 | 1.00 | 41.89 C |
| ATOM | 2902 | C | THR | A | 389 | 98.290 | 64.224 | 6.833 | 1.00 | 42.40 C |
| ATOM | 2903 | O | THR | A | 389 | 99.418 | 64.598 | 7.172 | 1.00 | 42.02 O |
| ATOM | 2904 | CB | THR | A | 389 | 98.218 | 62.669 | 4.909 | 1.00 | 41.09 C |
| ATOM | 2905 | CG1 | THR | A | 389 | 99.623 | 62.427 | 5.042 | 1.00 | 41.52 O |
| ATOM | 2906 | CG2 | THR | A | 389 | 97.607 | 62.474 | 2.461 | 1.00 | 41.23 C |
| ATOM | 2907 | N | TYR | A | 390 | 97.330 | 63.930 | 7.693 | 1.00 | 42.51 N |
| ATOM | 2908 | CA | TYR | A | 390 | 97.533 | 63.980 | 9.125 | 1.00 | 42.75 C |
| ATOM | 2909 | C | TYR | A | 390 | 96.624 | 62.882 | 9.670 | 1.00 | 43.43 C |
| ATOM | 2910 | O | TYR | A | 390 | 95.406 | 62.969 | 9.551 | 1.00 | 44.28 O |
| ATOM | 2911 | CB | TYR | A | 390 | 97.098 | 65.332 | 9.679 | 1.00 | 41.44 C |
| ATOM | 2912 | CG | TYR | A | 390 | 97.362 | 65.467 | 11.159 | 1.00 | 40.95 C |
| ATOM | 2913 | CD1 | TYR | A | 390 | 96.609 | 66.343 | 11.944 | 1.00 | 41.25 C |
| ATOM | 2914 | CD2 | TYR | A | 390 | 98.373 | 64.729 | 11.777 | 1.00 | 39.46 C |
| ATOM | 2915 | CE1 | TYR | A | 390 | 96.852 | 66.478 | 13.312 | 1.00 | 40.17 C |
| ATOM | 2916 | CE2 | TYR | A | 390 | 98.623 | 64.856 | 13.136 | 1.00 | 40.26 C |
| ATOM | 2917 | CZ | TYR | A | 390 | 97.857 | 65.732 | 13.896 | 1.00 | 39.92 C |
| ATOM | 2918 | OH | TYR | A | 390 | 98.095 | 65.857 | 15.238 | 1.00 | 40.43 O |
| ATOM | 2919 | N | ARG | A | 391 | 97.206 | 61.846 | 10.258 | 1.00 | 44.01 N |
| ATOM | 2920 | CA | ARG | A | 391 | 96.399 | 60.750 | 10.772 | 1.00 | 44.87 C |
| ATOM | 2921 | C | ARG | A | 391 | 96.778 | 60.387 | 12.202 | 1.00 | 45.41 C |
| ATOM | 2922 | O | ARG | A | 391 | 97.954 | 60.450 | 12.580 | 1.00 | 45.88 O |
| ATOM | 2923 | CB | ARG | A | 391 | 96.589 | 59.529 | 9.883 | 1.00 | 44.93 C |
| ATOM | 2924 | CG | ARG | A | 391 | 97.990 | 58.967 | 9.986 | 1.00 | 46.56 C |
| ATOM | 2925 | CD | ARG | A | 391 | 98.242 | 57.872 | 8.981 | 1.00 | 47.95 C |
| ATOM | 2926 | NE | ARG | A | 391 | 99.535 | 57.232 | 9.200 | 1.00 | 48.70 N |
| ATOM | 2927 | CZ | ARG | A | 391 | 100.072 | 56.357 | 8.363 | 1.00 | 49.29 C |
| ATOM | 2928 | NH1 | ARG | A | 391 | 99.425 | 56.024 | 7.252 | 1.00 | 50.30 N |
| ATOM | 2929 | NH2 | ARG | A | 391 | 101.245 | 55.805 | 8.638 | 1.00 | 49.69 N |
| ATOM | 2930 | N | GLY | A | 392 | 95.782 | 60.009 | 12.999 | 1.00 | 45.56 N |
| ATOM | 2931 | CA | GLY | A | 392 | 96.062 | 59.618 | 14.366 | 1.00 | 45.33 C |
| ATOM | 2932 | C | GLY | A | 392 | 96.803 | 58.291 | 14.343 | 1.00 | 45.81 C |
| ATOM | 2933 | O | GLY | A | 392 | 96.578 | 57.467 | 13.451 | 1.00 | 45.18 O |
| HETATM | 2934 | N | MSE | A | 393 | 97.696 | 58.074 | 15.304 | 1.00 | 46.09 N |
| HETATM | 2935 | CA | MSE | A | 393 | 98.437 | 56.818 | 15.344 | 1.00 | 46.91 C |
| HETATM | 2936 | C | MSE | A | 393 | 97.514 | 55.638 | 15.668 | 1.00 | 45.83 C |
| HETATM | 2937 | O | MSE | A | 393 | 97.905 | 54.474 | 15.553 | 1.00 | 45.29 O |
| HETATM | 2938 | CB | MSE | A | 393 | 99.587 | 56.925 | 16.351 | 1.00 | 48.46 C |
| HETATM | 2939 | CG | MSE | A | 393 | 100.671 | 57.905 | 15.906 | 1.00 | 51.44 C |
| HETATM | 2940 | SE | MSE | A | 393 | 101.600 | 57.363 | 14.403 | 1.00 | 55.48 SE |
| HETATM | 2941 | CE | MSE | A | 393 | 102.496 | 55.927 | 15.071 | 1.00 | 55.49 C |
| ATOM | 2942 | N | GLY | A | 394 | 96.280 | 55.954 | 16.049 | 1.00 | 44.70 N |
| ATOM | 2943 | CA | GLY | A | 394 | 95.307 | 54.926 | 16.364 | 1.00 | 44.19 C |
| ATOM | 2944 | C | GLY | A | 394 | 94.355 | 54.686 | 15.206 | 1.00 | 44.14 C |
| ATOM | 2945 | O | GLY | A | 394 | 93.416 | 53.896 | 15.311 | 1.00 | 43.61 O |
| ATOM | 2946 | N | SER | A | 395 | 94.591 | 55.369 | 14.093 | 1.00 | 44.85 N |
| ATOM | 2947 | CA | SER | A | 395 | 93.740 | 55.204 | 12.921 | 1.00 | 45.69 C |
| ATOM | 2948 | C | SER | A | 395 | 94.061 | 53.866 | 12.265 | 1.00 | 46.80 C |
| ATOM | 2949 | O | SER | A | 395 | 95.002 | 53.175 | 12.663 | 1.00 | 47.02 O |
| ATOM | 2950 | CB | SER | A | 395 | 93.968 | 56.340 | 11.916 | 1.00 | 45.01 C |
| ATOM | 2951 | OG | SER | A | 395 | 95.278 | 56.305 | 11.372 | 1.00 | 44.71 O |
| ATOM | 2952 | N | ILE | A | 396 | 93.276 | 53.501 | 11.261 | 1.00 | 47.68 N |
| ATOM | 2953 | CA | ILE | A | 396 | 93.488 | 52.245 | 10.554 | 1.00 | 49.11 C |
| ATOM | 2954 | C | ILE | A | 396 | 94.830 | 52.246 | 9.797 | 1.00 | 49.53 C |
| ATOM | 2955 | O | ILE | A | 396 | 95.705 | 51.418 | 10.070 | 1.00 | 48.83 O |
| ATOM | 2956 | CB | ILE | A | 396 | 92.320 | 51.974 | 9.558 | 1.00 | 49.53 C |
| ATOM | 2957 | CG1 | ILE | A | 396 | 90.990 | 51.908 | 10.315 | 1.00 | 49.28 C |
| ATOM | 2958 | CG2 | ILE | A | 396 | 92.554 | 50.670 | 8.812 | 1.00 | 49.14 C |
| ATOM | 2959 | CD1 | ILE | A | 396 | 90.932 | 50.820 | 11.363 | 1.00 | 49.48 C |
| ATOM | 2960 | N | ALA | A | 397 | 94.988 | 53.183 | 8.863 | 1.00 | 50.24 N |
| ATOM | 2961 | CA | ALA | A | 397 | 96.206 | 53.291 | 8.062 | 1.00 | 51.94 C |
| ATOM | 2962 | C | ALA | A | 397 | 97.475 | 53.255 | 8.903 | 1.00 | 53.51 C |
| ATOM | 2963 | O | ALA | A | 397 | 98.414 | 52.533 | 8.576 | 1.00 | 53.35 O |
| ATOM | 2964 | CB | ALA | A | 397 | 96.177 | 54.567 | 7.227 | 1.00 | 50.87 C |
| ATOM | 2965 | N | ALA | A | 398 | 97.507 | 54.037 | 9.979 | 1.00 | 55.56 N |
| ATOM | 2966 | CA | ALA | A | 398 | 98.677 | 54.074 | 10.851 | 1.00 | 57.66 C |
| ATOM | 2967 | C | ALA | A | 398 | 98.878 | 52.719 | 11.529 | 1.00 | 59.35 C |
| ATOM | 2968 | O | ALA | A | 398 | 99.988 | 52.181 | 11.541 | 1.00 | 59.25 O |
| ATOM | 2969 | CB | ALA | A | 398 | 98.525 | 55.175 | 11.900 | 1.00 | 56.88 C |
| HETATM | 2970 | N | MSE | A | 399 | 97.803 | 52.162 | 12.084 | 1.00 | 61.57 N |
| HETATM | 2971 | CA | MSE | A | 399 | 97.883 | 50.868 | 12.753 | 1.00 | 63.53 C |

TABLE 7-continued

| | | | | | | | | | | |
|---|---|---|---|---|---|---|---|---|---|---|
| HETATM | 2972 | C | MSE | A | 399 | 98.165 | 49.736 | 11.778 | 1.00 | 64.22 C |
| HETATM | 2973 | O | MSE | A | 399 | 98.294 | 48.586 | 12.181 | 1.00 | 64.45 O |
| HETATM | 2974 | CB | MSE | A | 399 | 96.589 | 50.561 | 13.510 | 1.00 | 64.53 C |
| HETATM | 2975 | CG | MSE | A | 399 | 96.335 | 51.428 | 14.726 | 1.00 | 66.17 C |
| HETATM | 2976 | SE | MSE | A | 399 | 94.927 | 50.801 | 15.688 | 1.00 | 70.47 SE |
| HETATM | 2977 | CE | MSE | A | 399 | 93.579 | 50.893 | 14.454 | 1.00 | 68.03 C |
| ATOM | 2978 | N | LYS | A | 400 | 98.275 | 50.067 | 10.498 | 1.00 | 65.70 N |
| ATOM | 2979 | CA | LYS | A | 400 | 98.535 | 49.076 | 9.461 | 1.00 | 67.25 C |
| ATOM | 2980 | C | LYS | A | 400 | 99.753 | 48.195 | 9.743 | 1.00 | 68.24 C |
| ATOM | 2981 | O | LYS | A | 400 | 100.162 | 48.015 | 10.888 | 1.00 | 68.63 O |
| ATOM | 2982 | CB | LYS | A | 400 | 98.703 | 49.771 | 8.118 | 1.00 | 67.70 C |
| ATOM | 2983 | N | LYS | A | 401 | 100.324 | 47.646 | 8.677 | 1.00 | 69.15 N |
| ATOM | 2984 | CA | LYS | A | 401 | 101.487 | 46.771 | 8.773 | 1.00 | 70.20 C |
| ATOM | 2985 | C | LYS | A | 401 | 102.588 | 47.357 | 9.662 | 1.00 | 71.05 C |
| ATOM | 2986 | O | LYS | A | 401 | 102.394 | 48.471 | 10.197 | 1.00 | 71.27 O |
| ATOM | 2987 | CB | LYS | A | 401 | 102.035 | 46.483 | 7.365 | 1.00 | 69.48 C |
| ATOM | 2988 | N | ASN | A | 416 | 92.074 | 47.487 | 5.186 | 1.00 | 72.24 N |
| ATOM | 2989 | CA | ASN | A | 416 | 91.155 | 46.876 | 6.194 | 1.00 | 72.64 C |
| ATOM | 2990 | C | ASN | A | 416 | 91.165 | 47.666 | 7.501 | 1.00 | 72.60 C |
| ATOM | 2991 | O | ASN | A | 416 | 92.209 | 48.176 | 7.915 | 1.00 | 73.31 O |
| ATOM | 2992 | CB | ASN | A | 416 | 91.563 | 45.422 | 6.465 | 1.00 | 72.21 C |
| ATOM | 2993 | N | LYS | A | 417 | 90.004 | 47.744 | 8.152 | 1.00 | 71.58 N |
| ATOM | 2994 | CA | LYS | A | 417 | 89.858 | 48.463 | 9.419 | 1.00 | 70.32 C |
| ATOM | 2995 | C | LYS | A | 417 | 89.985 | 47.484 | 10.580 | 1.00 | 69.53 C |
| ATOM | 2996 | O | LYS | A | 417 | 89.416 | 46.386 | 10.515 | 1.00 | 70.17 O |
| ATOM | 2997 | CB | LYS | A | 417 | 88.499 | 49.146 | 9.472 | 1.00 | 70.50 C |
| ATOM | 2998 | N | LEU | A | 418 | 90.712 | 47.870 | 11.642 | 1.00 | 67.91 N |
| ATOM | 2999 | CA | LEU | A | 418 | 90.903 | 46.996 | 12.826 | 1.00 | 64.90 C |
| ATOM | 3000 | C | LEU | A | 418 | 90.637 | 47.647 | 14.211 | 1.00 | 62.37 C |
| ATOM | 3001 | O | LEU | A | 418 | 91.478 | 47.559 | 15.111 | 1.00 | 62.60 O |
| ATOM | 3002 | CB | LEU | A | 418 | 92.286 | 46.414 | 12.785 | 1.00 | 64.79 C |
| ATOM | 3003 | N | VAL | A | 419 | 99.455 | 48.260 | 14.362 | 1.00 | 59.18 N |
| ATOM | 3004 | CA | VAL | A | 419 | 88.983 | 48.973 | 15.576 | 1.00 | 56.04 C |
| ATOM | 3005 | C | VAL | A | 419 | 89.820 | 50.195 | 15.995 | 1.00 | 53.39 C |
| ATOM | 3006 | O | VAL | A | 419 | 90.533 | 50.180 | 17.005 | 1.00 | 51.68 O |
| ATOM | 3007 | CB | VAL | A | 419 | 88.825 | 48.027 | 16.790 | 1.00 | 56.09 C |
| ATOM | 3008 | CG1 | VAL | A | 419 | 88.330 | 48.818 | 18.006 | 1.00 | 55.27 C |
| ATOM | 3009 | CG2 | VAL | A | 419 | 87.823 | 46.925 | 16.456 | 1.00 | 56.32 C |
| ATOM | 3010 | N | PRO | A | 420 | 89.728 | 51.280 | 15.207 | 1.00 | 51.10 N |
| ATOM | 3011 | CA | PRO | A | 420 | 90.430 | 52.548 | 15.402 | 1.00 | 49.87 C |
| ATOM | 3012 | C | PRO | A | 420 | 89.937 | 53.428 | 16.559 | 1.00 | 48.67 C |
| ATOM | 3013 | O | PRO | A | 420 | 88.758 | 53.419 | 16.924 | 1.00 | 47.55 O |
| ATOM | 3014 | CB | PRO | A | 420 | 90.238 | 53.225 | 14.052 | 1.00 | 49.97 C |
| ATOM | 3015 | CG | PRO | A | 420 | 88.824 | 52.828 | 13.734 | 1.00 | 49.16 C |
| ATOM | 3016 | CD | PRO | A | 420 | 88.939 | 51.338 | 13.961 | 1.00 | 49.81 C |
| ATOM | 3017 | N | GLU | A | 421 | 90.871 | 54.192 | 17.116 | 1.00 | 48.34 N |
| ATOM | 3018 | CA | GLU | A | 421 | 90.610 | 55.123 | 18.208 | 1.00 | 47.97 C |
| ATOM | 3019 | C | GLU | A | 421 | 90.154 | 56.506 | 17.668 | 1.00 | 46.84 C |
| ATOM | 3020 | O | GLU | A | 421 | 91.005 | 57.481 | 18.409 | 1.00 | 47.51 O |
| ATOM | 3021 | CB | GLU | A | 421 | 91.517 | 54.809 | 19.396 | 1.00 | 49.79 C |
| ATOM | 3022 | CG | GLU | A | 421 | 91.207 | 53.512 | 20.149 | 1.00 | 53.19 C |
| ATOM | 3023 | CD | GLU | A | 421 | 90.329 | 53.739 | 21.372 | 1.00 | 53.99 C |
| ATOM | 3024 | OE1 | GLU | A | 421 | 90.730 | 54.563 | 22.228 | 1.00 | 55.23 O |
| ATOM | 3025 | OE2 | GLU | A | 421 | 89.260 | 53.095 | 21.484 | 1.00 | 53.71 O |
| ATOM | 3026 | N | GLY | A | 422 | 91.200 | 56.576 | 16.366 | 1.00 | 45.35 N |
| ATOM | 3027 | CA | GLY | A | 422 | 91.541 | 57.834 | 15.736 | 1.00 | 44.97 C |
| ATOM | 3028 | C | GLY | A | 422 | 91.214 | 57.813 | 14.253 | 1.00 | 44.86 C |
| ATOM | 3029 | O | GLY | A | 422 | 90.918 | 56.760 | 13.684 | 1.00 | 44.42 O |
| ATOM | 3030 | N | ILE | A | 423 | 91.279 | 58.974 | 13.611 | 1.00 | 44.45 N |
| ATOM | 3031 | CA | ILE | A | 423 | 90.954 | 59.045 | 12.196 | 1.00 | 43.46 C |
| ATOM | 3032 | C | ILE | A | 423 | 92.129 | 59.498 | 11.321 | 1.00 | 42.96 C |
| ATOM | 3033 | O | ILE | A | 423 | 93.178 | 59.916 | 11.821 | 1.00 | 41.95 O |
| ATOM | 3034 | CB | ILE | A | 423 | 89.703 | 59.963 | 11.970 | 1.00 | 43.06 C |
| ATOM | 3035 | CG1 | ILE | A | 423 | 89.978 | 61.412 | 12.403 | 1.00 | 42.83 C |
| ATOM | 3036 | CG2 | ILE | A | 423 | 88.534 | 59.439 | 12.788 | 1.00 | 41.55 0. |
| ATOM | 3037 | CD1 | ILE | A | 423 | 90.868 | 62.208 | 11.461 | 1.00 | 43.42 C |
| ATOM | 3038 | N | GLU | A | 424 | 91.934 | 59.387 | 10.012 | 1.00 | 42.19 N |
| ATOM | 3039 | CA | GLU | A | 424 | 92.931 | 59.775 | 9.024 | 1.00 | 42.21 C |
| ATOM | 3040 | C | GLU | A | 424 | 92.422 | 61.047 | 8.363 | 1.00 | 41.48 C |
| ATOM | 3041 | O | GLU | A | 424 | 91.266 | 61.110 | 7.945 | 1.00 | 41.26 O |
| ATOM | 3042 | CB | GLU | A | 424 | 93.071 | 58.680 | 7.963 | 1.00 | 43.26 C |
| ATOM | 3043 | CG | GLU | A | 424 | 93.518 | 57.325 | 8.492 | 1.00 | 45.35 C |
| ATOM | 3044 | CD | GLU | A | 424 | 93.357 | 56.225 | 7.453 | 1.00 | 46.93 C |
| ATOM | 3045 | OE1 | GLU | A | 424 | 93.818 | 56.423 | 6.305 | 1.00 | 48.20 O |
| ATOM | 3046 | OE2 | GLU | A | 424 | 92.780 | 55.162 | 7.780 | 1.00 | 46.63 O |
| ATOM | 3047 | N | GLY | A | 425 | 93.276 | 62.060 | 8.270 | 1.00 | 41.08 N |
| ATOM | 3048 | CA | GLY | A | 425 | 92.857 | 63.303 | 7.643 | 1.00 | 40.46 C |
| ATOM | 3049 | C | GLY | A | 425 | 93.976 | 64.030 | 6.920 | 1.00 | 40.17 C |
| ATOM | 3050 | O | GLY | A | 425 | 95.017 | 63.446 | 6.609 | 1.00 | 39.82 O |

TABLE 7-continued

| ATOM | 3051 | N | ARG | A | 426 | 93.757 | 65.309 | 6.643 | 1.00 | 39.48 | N |
| --- | --- | --- | --- | --- | --- | --- | --- | --- | --- | --- | --- |
| ATOM | 3052 | CA | ARG | A | 426 | 94.753 | 66.117 | 5.967 | 1.00 | 39.94 | C |
| ATOM | 3053 | C | ARG | A | 426 | 94.571 | 67.562 | 6.375 | 1.00 | 40.26 | C |
| ATOM | 3054 | O | ARG | A | 426 | 93.486 | 67.963 | 6.792 | 1.00 | 41.45 | O |
| ATOM | 3055 | CB | ARG | A | 426 | 94.608 | 65.989 | 4.452 | 1.00 | 39.82 | C |
| ATOM | 3056 | CG | ARG | A | 426 | 93.320 | 66.554 | 3.892 | 1.00 | 41.77 | C |
| ATOM | 3057 | CD | ARG | A | 426 | 93.202 | 66.182 | 2.405 | 1.00 | 43.77 | C |
| ATOM | 3058 | NE | ARG | A | 426 | 92.026 | 66.747 | 1.751 | 1.00 | 45.14 | N |
| ATOM | 3059 | CZ | ARG | A | 426 | 91.654 | 66.455 | 0.506 | 1.00 | 46.18 | C |
| ATOM | 3060 | NH1 | ARG | A | 426 | 92.366 | 65.604 | −0.218 | 1.00 | 46.99 | N |
| ATOM | 3061 | NH2 | ARG | A | 426 | 90.577 | 67.021 | −0.021 | 1.00 | 47.23 | N |
| ATOM | 3062 | N | VAL | A | 427 | 95.640 | 68.342 | 6.267 | 1.00 | 40.61 | N |
| ATOM | 3063 | CA | VAL | A | 427 | 95.592 | 69.759 | 6.613 | 1.00 | 40.23 | C |
| ATOM | 3064 | C | VAL | A | 427 | 96.338 | 70.557 | 5.548 | 1.00 | 40.03 | C |
| ATOM | 3065 | O | VAL | A | 427 | 97.235 | 70.033 | 4.885 | 1.00 | 39.67 | O |
| ATOM | 3066 | CE | VAL | A | 427 | 96.225 | 70.029 | 8.001 | 1.00 | 39.28 | C |
| ATOM | 3067 | CG1 | VAL | A | 427 | 95.457 | 69.280 | 9.079 | 1.00 | 37.97 | C |
| ATOM | 3068 | CG2 | VAL | A | 427 | 97.681 | 69.609 | 7.993 | 1.00 | 39.20 | C |
| ATOM | 3069 | N | ALA | A | 429 | 95.945 | 71.815 | 5.381 | 1.00 | 40.23 | N |
| ATOM | 3070 | CA | ALA | A | 428 | 96.562 | 72.700 | 4.406 | 1.00 | 41.04 | C |
| ATOM | 3071 | C | ALA | A | 428 | 98.079 | 72.829 | 4.595 | 1.00 | 42.53 | C |
| ATOM | 3072 | O | ALA | A | 428 | 98.578 | 72.780 | 5.727 | 1.00 | 42.82 | O |
| ATOM | 3073 | CB | ALA | A | 428 | 95.918 | 74.074 | 4.496 | 1.00 | 39.46 | C |
| ATOM | 3074 | N | TYR | A | 429 | 98.801 | 72.975 | 3.480 | 1.00 | 42.74 | N |
| ATOM | 3075 | CA | TYR | A | 429 | 100.251 | 73.168 | 3.491 | 1.00 | 43.20 | C |
| ATOM | 3076 | C | TYR | A | 429 | 100.546 | 74.452 | 4.284 | 1.00 | 42.09 | C |
| ATOM | 3077 | O | TYR | A | 429 | 99.986 | 75.509 | 3.984 | 1.00 | 41.87 | O |
| ATOM | 3078 | CB | TYR | A | 429 | 100.757 | 73.332 | 2.061 | 1.00 | 44.90 | C |
| ATOM | 3079 | CG | TYR | A | 429 | 102.211 | 73.730 | 1.972 | 1.00 | 48.81 | C |
| ATOM | 3080 | CD1 | TYR | A | 429 | 103.228 | 72.842 | 2.329 | 1.00 | 50.14 | C |
| ATOM | 3081 | CD2 | TYR | A | 429 | 102.574 | 75.005 | 1.541 | 1.00 | 49.88 | C |
| ATOM | 3082 | CE1 | TYR | A | 429 | 104.575 | 73.214 | 2.255 | 1.00 | 50.62 | C |
| ATOM | 3083 | CE2 | TYR | A | 429 | 103.915 | 75.388 | 1.463 | 1.00 | 50.81 | C |
| ATOM | 3084 | CZ | TYR | A | 429 | 104.908 | 74.487 | 1.819 | 1.00 | 50.86 | C |
| ATOM | 3085 | OH | TYR | A | 429 | 106.226 | 74.863 | 1.718 | 1.00 | 50.47 | O |
| ATOM | 3086 | N | LYS | A | 430 | 101.429 | 74.372 | 5.276 | 1.00 | 40.05 | N |
| ATOM | 3087 | CA | LYS | A | 430 | 101.727 | 75.541 | 6.102 | 1.00 | 38.56 | C |
| ATOM | 3088 | C | LYS | A | 430 | 103.086 | 76.198 | 5.889 | 1.00 | 37.11 | C |
| ATOM | 3089 | O | LYS | A | 430 | 103.360 | 77.238 | 6.486 | 1.00 | 37.51 | O |
| ATOM | 3090 | CB | LYS | A | 430 | 101.610 | 75.178 | 7.589 | 1.00 | 38.70 | C |
| ATOM | 3091 | CG | LYS | A | 430 | 100.294 | 74.563 | 7.981 | 1.00 | 38.40 | C |
| ATOM | 3092 | CD | LYS | A | 430 | 100.284 | 74.152 | 9.434 | 1.00 | 38.43 | C |
| ATOM | 3093 | CE | LYS | A | 430 | 98.997 | 73.409 | 9.738 | 1.00 | 39.27 | C |
| ATOM | 3094 | NZ | LYS | A | 430 | 98.927 | 72.970 | 11.149 | 1.00 | 40.88 | N |
| ATOM | 3095 | N | GLY | A | 431 | 103.942 | 75.609 | 5.063 | 1.00 | 35.54 | N |
| ATOM | 3096 | CA | GLY | A | 431 | 105.256 | 76.199 | 4.867 | 1.00 | 32.89 | C |
| ATOM | 3097 | C | GLY | A | 431 | 106.199 | 75.798 | 5.991 | 1.00 | 31.20 | C |
| ATOM | 3098 | O | GLY | A | 431 | 105.927 | 74.847 | 6.710 | 1.00 | 30.24 | C |
| ATOM | 3099 | N | ALA | A | 432 | 107.296 | 76.528 | 6.157 | 1.00 | 30.60 | N |
| ATOM | 3100 | CA | ALA | A | 432 | 108.290 | 76.214 | 7.189 | 1.00 | 29.98 | C |
| ATOM | 3101 | C | ALA | A | 432 | 107.759 | 76.197 | 8.618 | 1.00 | 29.06 | C |
| ATOM | 3102 | O | ALA | A | 432 | 106.981 | 77.057 | 9.018 | 1.00 | 30.18 | O |
| ATOM | 3103 | CB | ALA | A | 432 | 109.462 | 77.188 | 7.097 | 1.00 | 29.00 | C |
| ATOM | 3104 | N | ALA | A | 433 | 108.206 | 75.216 | 9.390 | 1.00 | 27.87 | N |
| ATOM | 3105 | CA | ALA | A | 433 | 107.798 | 75.077 | 10.777 | 1.00 | 27.30 | C |
| ATOM | 3106 | C | ALA | A | 433 | 108.341 | 76.225 | 11.624 | 1.00 | 27.35 | C |
| ATOM | 3107 | O | ALA | A | 433 | 107.727 | 76.611 | 12.620 | 1.00 | 27.15 | O |
| ATOM | 3108 | CB | ALA | A | 433 | 108.289 | 73.739 | 11.333 | 1.00 | 28.08 | C |
| ATOM | 3109 | N | SER | A | 434 | 109.493 | 76.766 | 11.238 | 1.00 | 26.71 | N |
| ATOM | 3110 | CA | SER | A | 434 | 110.085 | 77.875 | 11.983 | 1.00 | 27.06 | C |
| ATOM | 3111 | C | SER | A | 434 | 109.131 | 79.070 | 12.036 | 1.00 | 26.79 | C |
| ATOM | 3112 | O | SER | A | 434 | 109.120 | 79.821 | 13.014 | 1.00 | 25.57 | O |
| ATOM | 3113 | CB | SER | A | 434 | 111.419 | 76.306 | 11.357 | 1.00 | 27.17 | C |
| ATOM | 3114 | OG | SER | A | 434 | 111.252 | 78.778 | 10.031 | 1.00 | 28.63 | O |
| ATOM | 3115 | N | ASP | A | 435 | 108.333 | 79.243 | 10.986 | 1.00 | 27.24 | N |
| ATOM | 3116 | CA | ASP | A | 435 | 107.363 | 80.333 | 10.928 | 1.00 | 28.29 | C |
| ATOM | 3117 | C | ASP | A | 435 | 106.188 | 80.060 | 11.868 | 1.00 | 27.92 | C |
| ATOM | 3118 | O | ASP | A | 435 | 105.714 | 80.959 | 12.565 | 1.00 | 28.07 | O |
| ATOM | 3119 | CB | ASP | A | 435 | 106.876 | 80.517 | 9.491 | 1.00 | 31.68 | C |
| ATOM | 3120 | CG | ASP | A | 435 | 107.949 | 81.120 | 8.579 | 1.00 | 35.77 | C |
| ATOM | 3121 | OD1 | ASP | A | 435 | 107.761 | 81.087 | 7.341 | 1.00 | 38.23 | O |
| ATOM | 3122 | OD2 | ASP | A | 435 | 108.968 | 81.643 | 9.096 | 1.00 | 36.12 | O |
| ATOM | 3123 | N | ILE | A | 436 | 105.726 | 78.815 | 11.886 | 1.00 | 26.54 | N |
| ATOM | 3124 | CA | ILE | A | 436 | 104.637 | 78.398 | 12.763 | 1.00 | 25.99 | C |
| ATOM | 3125 | C | ILE | A | 436 | 105.085 | 78.679 | 14.199 | 1.00 | 24.91 | C |
| ATOM | 3126 | O | ILE | A | 436 | 104.388 | 79.320 | 14.977 | 1.00 | 23.37 | O |
| ATOM | 3127 | CB | ILE | A | 436 | 104.357 | 76.867 | 12.617 | 1.00 | 26.46 | C |
| ATOM | 3128 | CG1 | ILE | A | 436 | 104.016 | 76.524 | 11.166 | 1.00 | 28.02 | C |
| ATOM | 3129 | CG2 | ILE | A | 436 | 103.236 | 76.437 | 13.536 | 1.00 | 26.46 | C |

TABLE 7-continued

| | | | | | | | | | | |
|---|---|---|---|---|---|---|---|---|---|---|
| ATOM | 3130 | CD1 | ILE | A | 436 | 102.860 | 77.292 | 10.604 | 1.00 | 30.24 C |
| ATOM | 3131 | N | VAL | A | 437 | 106.268 | 76.191 | 14.539 | 1.00 | 25.92 N |
| ATOM | 3132 | CA | VAL | A | 437 | 106.804 | 78.383 | 15.877 | 1.00 | 27.27 C |
| ATOM | 3133 | C | VAL | A | 437 | 106.902 | 79.853 | 16.244 | 1.00 | 28.27 C |
| ATOM | 3134 | O | VAL | A | 437 | 106.560 | 80.238 | 17.367 | 1.00 | 29.71 O |
| ATOM | 3135 | CB | VAL | A | 437 | 108.200 | 77.747 | 16.022 | 1.00 | 26.18 C |
| ATOM | 3136 | CG1 | VAL | A | 437 | 108.770 | 78.055 | 17.395 | 1.00 | 25.87 C |
| ATOM | 3137 | CG2 | VAL | A | 437 | 108.105 | 76.244 | 15.821 | 1.00 | 26.99 C |
| ATOM | 3138 | N | PHE | A | 438 | 107.367 | 80.678 | 15.307 | 1.00 | 29.44 N |
| ATOM | 3139 | CA | PHE | A | 438 | 107.513 | 82.104 | 15.564 | 1.00 | 29.34 C |
| ATOM | 3140 | C | PHE | A | 438 | 106.182 | 82.759 | 15.872 | 1.00 | 29.77 C |
| ATOM | 3141 | O | PHE | A | 438 | 106.110 | 83.647 | 16.721 | 1.00 | 29.60 O |
| ATOM | 3142 | CE | PHE | A | 438 | 108.183 | 82.799 | 14.382 | 1.00 | 30.41 C |
| ATOM | 3143 | CG | PHE | A | 436 | 108.391 | 84.262 | 14.589 | 1.00 | 32.43 C |
| ATOM | 3144 | CD1 | PHE | A | 438 | 107.342 | 85.160 | 14.424 | 1.00 | 34.66 C |
| ATOM | 3145 | CD2 | PHE | A | 438 | 109.625 | 84.742 | 15.012 | 1.00 | 34.35 C |
| ATOM | 3146 | CE1 | PHE | A | 438 | 107.514 | 86.522 | 14.678 | 1.00 | 35.25 C |
| ATOM | 3147 | CE2 | PHE | A | 438 | 109.816 | 86.100 | 15.273 | 1.00 | 35.59 C |
| ATOM | 3148 | CZ | PHE | A | 438 | 108.752 | 86.994 | 15.105 | 1.00 | 36.08 C |
| ATOM | 3149 | N | GLN | A | 439 | 105.125 | 82.325 | 15.189 | 1.00 | 31.03 N |
| ATOM | 3150 | CA | GLN | A | 439 | 103.801 | 82.885 | 15.440 | 1.00 | 31.99 C |
| ATOM | 3151 | C | GLN | A | 439 | 103.280 | 82.473 | 16.803 | 1.00 | 32.50 C |
| ATOM | 3152 | O | GLN | A | 439 | 102.669 | 83.282 | 17.502 | 1.00 | 33.67 O |
| ATOM | 3153 | CB | GLN | A | 439 | 102.801 | 82.454 | 14.369 | 1.00 | 33.33 C |
| ATOM | 3154 | CG | GLN | A | 439 | 102.962 | 83.175 | 13.052 | 1.00 | 36.37 C |
| ATOM | 3155 | CD | GLN | A | 439 | 102.863 | 84.685 | 13.204 | 1.00 | 38.29 C |
| ATOM | 3156 | NE1 | GLN | A | 439 | 101.882 | 85.212 | 13.746 | 1.00 | 39.62 O |
| ATOM | 3157 | NE2 | GLN | A | 439 | 103.880 | 85.393 | 12.720 | 1.00 | 39.30 N |
| HETATM | 3158 | N | MSE | A | 440 | 103.519 | 81.225 | 17.199 | 1.00 | 31.91 N |
| HETATM | 3159 | CA | MSE | A | 440 | 103.036 | 80.797 | 18.498 | 1.00 | 32.48 C |
| HETATM | 3160 | C | MSE | A | 440 | 103.802 | 81.394 | 19.682 | 1.00 | 30.42 C |
| HETATM | 3161 | O | MSE | A | 440 | 103.199 | 81.680 | 20.718 | 1.00 | 29.98 O |
| HETATM | 3162 | CB | MSE | A | 440 | 102.958 | 79.261 | 18.577 | 1.00 | 36.61 C |
| HETATM | 3163 | CG | MSE | A | 440 | 104.200 | 78.483 | 18.205 | 1.00 | 44.35 C |
| HETATM | 3164 | SE | MSE | A | 440 | 103.911 | 76.661 | 18.242 | 1.00 | 53.13 SE |
| HETATM | 3165 | CE | MSE | A | 440 | 102.652 | 76.462 | 16.958 | 1.00 | 51.30 C |
| ATOM | 3166 | N | LEU | A | 441 | 105.107 | 81.620 | 19.543 | 1.00 | 27.53 N |
| ATOM | 3167 | CA | LEU | A | 441 | 105.867 | 82.206 | 20.648 | 1.00 | 25.82 C |
| ATOM | 3168 | C | LEU | A | 441 | 105.407 | 83.644 | 20.911 | 1.00 | 25.88 C |
| ATOM | 3169 | O | LEU | A | 441 | 105.348 | 84.092 | 22.053 | 1.00 | 26.91 O |
| ATOM | 3170 | CB | LEU | A | 441 | 107.370 | 82.194 | 20.353 | 1.00 | 25.33 C |
| ATOM | 3171 | CG | LEU | A | 441 | 108.062 | 80.839 | 20.155 | 1.00 | 25.97 C |
| ATOM | 3172 | CD1 | LEU | A | 441 | 109.552 | 81.080 | 19.937 | 1.00 | 25.09 C |
| ATOM | 3173 | CD2 | LEU | A | 441 | 107.849 | 79.940 | 21.362 | 1.00 | 25.75 C |
| ATOM | 3174 | N | GLY | A | 442 | 105.076 | 84.366 | 19.850 | 1.00 | 24.13 N |
| ATOM | 3175 | CA | GLY | A | 442 | 104.621 | 85.731 | 20.019 | 1.00 | 23.31 C |
| ATOM | 3176 | C | GLY | A | 442 | 103.358 | 85.780 | 20.849 | 1.00 | 23.82 C |
| ATOM | 3177 | O | GLY | A | 442 | 103.200 | 86.656 | 21.693 | 1.00 | 22.98 O |
| ATOM | 3178 | N | GLY | A | 443 | 102.456 | 84.834 | 20.605 | 1.00 | 24.50 N |
| ATOM | 3179 | CA | GLY | A | 443 | 101.207 | 84.775 | 21.347 | 1.00 | 24.02 C |
| ATOM | 3180 | C | GLY | A | 443 | 101.449 | 84.354 | 22.781 | 1.00 | 24.08 C |
| ATOM | 3181 | O | GLY | A | 443 | 100.773 | 84.822 | 23.696 | 1.00 | 23.64 O |
| ATOM | 3182 | N | ILE | A | 444 | 102.419 | 83.465 | 22.970 | 1.00 | 24.21 N |
| ATOM | 3183 | CA | ILE | A | 444 | 102.780 | 82.979 | 24.300 | 1.00 | 24.08 C |
| ATOM | 3184 | C | ILE | A | 444 | 103.376 | 84.135 | 25.106 | 1.00 | 24.11 C |
| ATOM | 3185 | O | ILE | A | 444 | 103.005 | 84.346 | 26.261 | 1.00 | 23.54 O |
| ATOM | 3186 | CB | ILE | A | 444 | 103.798 | 81.801 | 24.209 | 1.00 | 23.72 C |
| ATOM | 3187 | CG1 | ILE | A | 444 | 103.152 | 80.622 | 23.466 | 1.00 | 22.82 C |
| ATOM | 3188 | CG2 | ILE | A | 444 | 104.241 | 81.360 | 25.612 | 1.00 | 22.84 C |
| ATOM | 3189 | CD1 | ILE | A | 444 | 104.110 | 79.479 | 23.146 | 1.00 | 22.36 C |
| ATOM | 3190 | N | ARG | A | 445 | 104.289 | 84.890 | 24.500 | 1.00 | 23.72 N |
| ATOM | 3191 | CA | ARG | A | 445 | 104.883 | 86.030 | 25.195 | 1.00 | 24.00 C |
| ATOM | 3192 | C | ARG | A | 445 | 103.837 | 87.106 | 25.514 | 1.00 | 23.44 C |
| ATOM | 3193 | O | ARG | A | 445 | 103.891 | 87.721 | 26.576 | 1.00 | 24.01 O |
| ATOM | 3194 | CB | ARG | A | 445 | 106.026 | 86.625 | 24.372 | 1.00 | 22.89 C |
| ATOM | 3195 | CG | ARG | A | 445 | 107.275 | 85.752 | 24.332 | 1.00 | 24.88 C |
| ATOM | 3196 | CD | ARG | A | 445 | 105.356 | 86.373 | 23.456 | 1.00 | 26.53 C |
| ATOM | 3197 | NE | ARG | A | 445 | 109.592 | 85.596 | 23.462 | 1.00 | 27.53 N |
| ATOM | 3198 | CZ | ARG | A | 445 | 110.470 | 85.579 | 24.464 | 1.00 | 30.01 C |
| ATOM | 3199 | NH1 | ARG | A | 445 | 110.262 | 86.303 | 25.561 | 1.00 | 28.96 N |
| ATOM | 3200 | NH2 | ARG | A | 445 | 111.559 | 84.823 | 24.372 | 1.00 | 29.00 N |
| ATOM | 3201 | N | SER | A | 446 | 102.882 | 87.333 | 24.615 | 1.00 | 23.77 N |
| ATOM | 3202 | CA | SER | A | 446 | 101.835 | 88.322 | 24.878 | 1.00 | 24.75 C |
| ATOM | 3203 | C | SER | A | 446 | 100.953 | 87.831 | 26.004 | 1.00 | 23.48 C |
| ATOM | 3204 | O | SER | A | 446 | 100.605 | 88.585 | 26.902 | 1.00 | 24.41 O |
| ATOM | 3205 | CB | SER | A | 446 | 100.953 | 88.558 | 23.656 | 1.00 | 25.42 C |
| ATOM | 3206 | OG | SER | A | 44E | 101.715 | 89.056 | 22.574 | 1.00 | 34.14 O |
| ATOM | 3207 | N | GLY | A | 447 | 100.587 | 86.559 | 25.946 | 1.00 | 22.70 N |
| ATOM | 3208 | CA | GLY | A | 447 | 99.740 | 85.996 | 26.974 | 1.00 | 23.15 C |

TABLE 7-continued

| | | | | | | | | | | |
|---|---|---|---|---|---|---|---|---|---|---|
| ATOM | 3209 | C | GLY | A | 447 | 100.366 | 86.119 | 28.338 | 1.00 | 23.47 C |
| ATOM | 3210 | O | GLY | A | 447 | 99.707 | 86.531 | 29.288 | 1.00 | 24.01 O |
| HETATM | 3211 | N | MSE | A | 448 | 101.641 | 85.754 | 28.435 | 1.00 | 24.62 N |
| HETATM | 3212 | CA | MSE | A | 448 | 102.369 | 85.834 | 29.693 | 1.00 | 25.24 C |
| HETATM | 3213 | C | MSE | A | 448 | 102.566 | 87.302 | 30.112 | 1.00 | 24.99 C |
| HETATM | 3214 | O | MSE | A | 448 | 102.632 | 87.613 | 31.300 | 1.00 | 25.75 O |
| HETATM | 3215 | CB | MSE | A | 448 | 103.704 | 85.090 | 29.569 | 1.00 | 27.58 C |
| HETATM | 3216 | CG | MSE | A | 448 | 103.522 | 83.600 | 29.220 | 1.00 | 31.58 C |
| HETATM | 3217 | SE | MSE | A | 448 | 105.040 | 82.559 | 29.094 | 1.00 | 37.58 SE |
| HETATM | 3218 | CE | MSE | A | 448 | 105.621 | 82.613 | 30.821 | 1.00 | 34.91 C |
| ATOM | 3219 | N | GLY | A | 449 | 102.639 | 88.208 | 29.145 | 1.00 | 24.08 N |
| ATOM | 3220 | CA | GLY | A | 449 | 102.770 | 89.613 | 29.487 | 1.00 | 24.66 C |
| ATOM | 3221 | C | GLY | A | 449 | 101.497 | 90.132 | 20.154 | 1.00 | 25.65 C |
| ATOM | 3222 | O | GLY | A | 449 | 101.550 | 90.876 | 31.131 | 1.00 | 25.66 C |
| ATOM | 3223 | N | TYR | A | 450 | 100.341 | 89.739 | 29.626 | 1.00 | 25.60 N |
| ATOM | 3224 | CA | TYR | A | 450 | 99.059 | 90.166 | 30.178 | 1.00 | 25.77 C |
| ATOM | 3225 | C | TYR | A | 450 | 98.831 | 89.753 | 31.623 | 1.00 | 24.83 C |
| ATOM | 3226 | O | TYR | A | 450 | 98.211 | 90.485 | 32.375 | 1.00 | 25.34 O |
| ATOM | 3227 | CB | TYR | A | 450 | 97.899 | 89.622 | 29.344 | 1.00 | 26.05 C |
| ATOM | 3228 | CG | TYR | A | 450 | 97.590 | 90.402 | 28.096 | 1.00 | 27.41 C |
| ATOM | 3229 | CD1 | TYR | A | 450 | 97.111 | 91.706 | 28.167 | 1.00 | 28.14 C |
| ATOM | 3230 | CD2 | TYR | A | 450 | 97.749 | 89.826 | 26.839 | 1.00 | 28.61 C |
| ATOM | 3231 | CE1 | TYR | A | 450 | 96.793 | 92.419 | 27.007 | 1.00 | 29.06 C |
| ATOM | 3232 | CE2 | TYR | A | 450 | 97.436 | 90.530 | 25.678 | 1.00 | 29.51 C |
| ATOM | 3233 | CZ | TYR | A | 450 | 96.959 | 91.822 | 25.770 | 1.00 | 29.28 C |
| ATOM | 3234 | OH | TYR | A | 450 | 96.640 | 92.501 | 24.618 | 1.00 | 30.87 O |
| ATOM | 3235 | N | VAL | A | 451 | 99.305 | 88.576 | 32.010 | 1.00 | 24.89 N |
| ATOM | 3236 | CA | VAL | A | 451 | 99.098 | 88.121 | 33.376 | 1.00 | 25.62 C |
| ATOM | 3237 | C | VAL | A | 451 | 100.316 | 88.418 | 34.251 | 1.00 | 26.97 C |
| ATOM | 3238 | O | VAL | A | 451 | 100.343 | 88.080 | 35.434 | 1.00 | 27.47 O |
| ATOM | 3239 | CB | VAL | A | 451 | 98.758 | 86.605 | 33.417 | 1.00 | 24.80 C |
| ATOM | 3240 | CG1 | VAL | A | 451 | 97.465 | 86.346 | 32.657 | 1.00 | 22.49 C |
| ATOM | 3241 | CG2 | VAL | A | 451 | 99.884 | 85.787 | 32.822 | 1.00 | 24.04 C |
| ATOM | 3242 | N | GLY | A | 452 | 101.318 | 89.061 | 33.655 | 1.00 | 28.11 N |
| ATOM | 3243 | CA | GLY | A | 452 | 102.518 | 89.425 | 34.384 | 1.00 | 28.84 C |
| ATOM | 3244 | C | GLY | A | 452 | 103.396 | 88.273 | 34.816 | 1.00 | 30.29 C |
| ATOM | 3245 | O | GLY | A | 452 | 104.016 | 88.325 | 35.873 | 1.00 | 30.53 O |
| ATOM | 3246 | N | ALA | A | 453 | 103.461 | 87.231 | 33.998 | 1.00 | 30.98 N |
| ATOM | 3247 | CA | ALA | A | 453 | 104.278 | 86.065 | 34.312 | 1.00 | 31.22 C |
| ATOM | 3248 | C | ALA | A | 453 | 105.623 | 86.177 | 33.612 | 1.00 | 31.80 C |
| ATOM | 3249 | O | ALA | A | 453 | 105.694 | 86.079 | 32.386 | 1.00 | 32.94 O |
| ATOM | 3250 | CB | ALA | A | 453 | 103.567 | 84.800 | 33.862 | 1.00 | 30.42 C |
| ATOM | 3251 | N | GLY | A | 454 | 106.686 | 86.380 | 4.387 | 1.00 | 31.10 N |
| ATOM | 3252 | CA | GLY | A | 454 | 108.015 | 86.497 | 33.806 | 1.00 | 30.70 C |
| ATOM | 3253 | C | GLY | A | 454 | 108.595 | 85.166 | 33.359 | 1.00 | 30.23 C |
| ATOM | 3254 | O | GLY | A | 454 | 109.509 | 85.117 | 32.534 | 1.00 | 29.71 O |
| ATOM | 3255 | N | ASP | A | 455 | 108.076 | 84.086 | 33.930 | 1.00 | 30.07 N |
| ATOM | 3256 | CA | ASP | A | 455 | 108.504 | 82.742 | 33.583 | 1.00 | 30.58 C |
| ATOM | 3257 | C | ASP | A | 455 | 107.326 | 81.825 | 33.830 | 1.00 | 30.31 C |
| ATOM | 3258 | O | ASP | A | 455 | 106.353 | 82.228 | 34.463 | 1.00 | 30.69 O |
| ATOM | 3259 | CB | ASP | A | 455 | 109.701 | 82.290 | 34.426 | 1.00 | 32.56 C |
| ATOM | 3260 | CG | ASP | A | 455 | 109.415 | 82.301 | 35.919 | 1.00 | 34.66 C |
| ATOM | 3261 | OD1 | ASP | A | 455 | 108.311 | 81.896 | 36.331 | 1.00 | 36.16 O |
| ATOM | 3262 | OD2 | ASP | A | 455 | 110.313 | 82.688 | 36.694 | 1.00 | 38.54 O |
| ATOM | 3263 | N | ILE | A | 456 | 107.412 | 80.593 | 33.343 | 1.00 | 29.95 N |
| ATOM | 3264 | CA | ILE | A | 456 | 106.326 | 79.634 | 33.502 | 1.00 | 30.50 C |
| ATOM | 3265 | C | ILE | A | 456 | 105.976 | 79.367 | 34.957 | 1.00 | 31.87 C |
| ATOM | 3266 | O | ILE | A | 456 | 104.820 | 79.103 | 35.274 | 1.00 | 32.52 O |
| ATOM | 3267 | CB | ILE | A | 456 | 106.657 | 78.302 | 32.791 | 1.00 | 29.40 C |
| ATOM | 3268 | CG1 | ILE | A | 456 | 106.775 | 78.555 | 31.287 | 1.00 | 29.89 C |
| ATOM | 3269 | CG2 | ILE | A | 456 | 105.589 | 77.259 | 33.082 | 1.00 | 28.25 C |
| ATOM | 3270 | CD1 | ILE | A | 456 | 107.179 | 77.342 | 30.477 | 1.00 | 31.58 C |
| ATOM | 3271 | N | GLN | A | 457 | 106.964 | 79.445 | 35.844 | 1.00 | 32.73 N |
| ATOM | 3272 | CA | GLN | A | 457 | 106.718 | 79.207 | 37.264 | 1.00 | 33.99 C |
| ATOM | 3273 | C | GLN | A | 457 | 105.672 | 80.193 | 37.801 | 1.00 | 33.89 C |
| ATOM | 3274 | O | GLN | A | 457 | 104.718 | 79.800 | 38.477 | 1.00 | 33.85 C |
| ATOM | 3275 | CB | GLN | A | 457 | 108.021 | 79.349 | 38.049 | 1.00 | 36.03 C |
| ATOM | 3276 | CG | GLN | A | 457 | 107.883 | 79.030 | 39.528 | 1.00 | 41.19 C |
| ATOM | 3277 | CD | GLN | A | 457 | 109.173 | 79.257 | 40.300 | 1.00 | 44.64 C |
| ATOM | 3278 | OE1 | GLN | A | 457 | 110.235 | 78.745 | 39.930 | 1.00 | 46.35 O |
| ATOM | 3279 | NE2 | GLN | A | 457 | 109.084 | 80.019 | 41.386 | 1.00 | 46.46 N |
| ATOM | 3280 | N | GLU | A | 458 | 105.860 | 81.475 | 37.494 | 1.00 | 33.67 N |
| ATOM | 3281 | CA | GLU | A | 458 | 104.937 | 82.523 | 37.925 | 1.00 | 32.88 C |
| ATOM | 3282 | C | GLU | A | 458 | 103.574 | 82.270 | 37.315 | 1.00 | 30.94 C |
| ATOM | 3283 | O | GLU | A | 458 | 102.542 | 82.607 | 37.889 | 1.00 | 30.37 O |
| ATOM | 3284 | CB | GLU | A | 458 | 105.436 | 83.899 | 37.478 | 1.00 | 33.84 C |
| ATOM | 3285 | CG | GLU | A | 458 | 106.617 | 84.441 | 38.255 | 1.00 | 36.71 C |
| ATOM | 3286 | CD | GLU | A | 458 | 107.151 | 85.736 | 37.661 | 1.00 | 39.24 C |
| ATOM | 3287 | OE1 | GLU | A | 458 | 106.336 | 86.630 | 37.337 | 1.00 | 39.29 O |

TABLE 7-continued

| | | | | | | | | | | |
|---|---|---|---|---|---|---|---|---|---|---|
| ATOM | 3288 | OE2 | GLU | A | 458 | 108.390 | 85.867 | 37.532 | 1.00 | 41.42 O |
| ATOM | 3289 | N | LEU | A | 459 | 103.587 | 81.673 | 36.137 | 1.00 | 30.11 N |
| ATOM | 3290 | CA | LEU | A | 459 | 102.365 | 81.363 | 35.424 | 1.00 | 29.90 C |
| ATOM | 3291 | C | LEU | A | 459 | 101.543 | 80.371 | 36.251 | 1.00 | 30.10 C |
| ATOM | 3292 | O | LEU | A | 459 | 100.340 | 80.560 | 36.446 | 1.00 | 30.22 O |
| ATOM | 3293 | CB | LEU | A | 459 | 102.725 | 80.779 | 34.056 | 1.00 | 29.44 C |
| ATOM | 3294 | CG | LEU | A | 459 | 101.699 | 80.716 | 32.938 | 1.00 | 28.07 C |
| ATOM | 3295 | CD1 | LEU | A | 459 | 101.087 | 82.092 | 32.708 | 1.00 | 27.42 C |
| ATOM | 3296 | CD2 | LEU | A | 459 | 102.404 | 80.226 | 31.689 | 1.00 | 26.36 C |
| ATOM | 3297 | N | HIS | A | 460 | 102.190 | 79.322 | 36.754 | 1.00 | 30.22 N |
| ATOM | 3298 | CA | HIS | A | 460 | 101.483 | 78.337 | 37.561 | 1.00 | 30.19 C |
| ATOM | 3299 | C | HIS | A | 460 | 100.980 | 78.973 | 38.850 | 1.00 | 30.56 C |
| ATOM | 3300 | O | MIS | A | 460 | 99.824 | 78.792 | 39.228 | 1.00 | 30.63 O |
| ATOM | 3301 | CB | HIS | A | 460 | 102.378 | 77.138 | 37.927 | 1.00 | 30.63 C |
| ATOM | 3302 | CC | MIS | A | 460 | 102.860 | 76.337 | 36.753 | 1.00 | 31.06 C |
| ATOM | 3303 | ND1 | HIS | A | 460 | 102.178 | 76.270 | 35.558 | 1.00 | 31.79 N |
| ATOM | 3304 | CD2 | HIS | A | 460 | 103.925 | 75.507 | 36.620 | 1.00 | 31.34 C |
| ATOM | 3305 | CE1 | HIS | A | 460 | 102.802 | 75.437 | 34.742 | 1.00 | 31.58 C |
| ATOM | 3306 | NE2 | HIS | A | 460 | 103.865 | 74.959 | 35.361 | 1.00 | 30.54 N |
| ATOM | 3307 | N | GLU | A | 461 | 101.853 | 79.733 | 39.509 | 1.00 | 31.26 N |
| ATOM | 3308 | CA | GLU | A | 461 | 101.538 | 80.387 | 40.789 | 1.00 | 32.15 C |
| ATOM | 3309 | C | GLU | A | 461 | 100.548 | 81.562 | 40.795 | 1.00 | 30.88 C |
| ATOM | 3310 | O | GLU | A | 461 | 99.740 | 81.687 | 41.715 | 1.00 | 29.77 O |
| ATOM | 3311 | CB | GLU | A | 461 | 102.833 | 80.887 | 41.457 | 1.00 | 33.27 C |
| ATOM | 3312 | CG | GLU | A | 461 | 103.899 | 79.832 | 41.728 | 1.00 | 35.31 C |
| ATOM | 3313 | CD | GLU | A | 461 | 103.422 | 78.711 | 42.633 | 1.00 | 36.84 C |
| ATOM | 3314 | OE1 | GLU | A | 461 | 102.952 | 78.986 | 43.758 | 1.00 | 37.87 O |
| ATOM | 3315 | OE2 | GLU | A | 461 | 103.533 | 77.543 | 42.214 | 1.00 | 40.15 O |
| ATOM | 3316 | N | ASN | A | 462 | 100.616 | 82.417 | 39.779 | 1.00 | 29.95 N |
| ATOM | 3317 | CA | ASN | A | 462 | 99.779 | 83.611 | 39.733 | 1.00 | 30.16 C |
| ATOM | 3318 | C | ASN | A | 462 | 98.589 | 83.674 | 38.774 | 1.00 | 29.60 C |
| ATOM | 3319 | O | ASN | A | 462 | 97.568 | 84.282 | 39.107 | 1.00 | 30.16 O |
| ATOM | 3320 | CB | ASN | A | 462 | 100.683 | 84.817 | 39.484 | 1.00 | 31.63 C |
| ATOM | 3321 | CG | ASN | A | 462 | 101.759 | 84.960 | 40.543 | 1.00 | 32.75 C |
| ATOM | 3322 | OD1 | ASN | A | 462 | 102.725 | 85.696 | 40.367 | 1.00 | 35.69 O |
| ATOM | 3323 | ND2 | ASN | A | 462 | 101.588 | 84.262 | 41.656 | 1.00 | 31.98 N |
| ATOM | 3324 | N | ALA | A | 463 | 98.711 | 83.066 | 37.598 | 1.00 | 27.52 N |
| ATOM | 3325 | CA | ALA | A | 463 | 97.634 | 83.103 | 36.610 | 1.00 | 26.51 C |
| ATOM | 3326 | C | ALA | A | 463 | 96.338 | 82.451 | 37.076 | 1.00 | 25.73 C |
| ATOM | 3327 | O | ALA | A | 463 | 96.348 | 81.386 | 37.679 | 1.00 | 25.89 O |
| ATOM | 3328 | CB | ALA | A | 463 | 98.096 | 82.465 | 35.313 | 1.00 | 24.91 C |
| ATOM | 3329 | N | GLN | A | 464 | 95.222 | 83.113 | 36.785 | 1.00 | 25.80 N |
| ATOM | 3330 | CA | GLN | A | 464 | 93.888 | 82.619 | 37.136 | 1.00 | 25.60 C |
| ATOM | 3331 | C | GLN | A | 464 | 92.959 | 82.601 | 35.923 | 1.00 | 24.30 C |
| ATOM | 3332 | C | GLN | A | 464 | 93.147 | 83.369 | 34.977 | 1.00 | 23.88 O |
| ATOM | 3333 | CB | GLN | A | 464 | 93.270 | 83.492 | 38.214 | 1.00 | 25.18 C |
| ATOM | 3334 | CG | GLN | A | 464 | 93.996 | 83.413 | 39.517 | 1.00 | 28.22 C |
| ATOM | 3335 | CD | GLN | A | 464 | 93.378 | 84.314 | 40.545 | 1.00 | 29.41 C |
| ATOM | 3336 | OE1 | GLN | A | 464 | 93.378 | 85.539 | 40.395 | 1.00 | 30.21 O |
| ATOM | 3337 | NE2 | GLN | A | 464 | 92.829 | 83.716 | 41.596 | 1.00 | 30.03 N |
| ATOM | 3338 | N | PHE | A | 465 | 91.962 | 81.721 | 35.959 | 1.00 | 22.93 N |
| ATOM | 3339 | CA | PHE | A | 465 | 91.009 | 81.614 | 34.868 | 1.00 | 22.72 C |
| ATOM | 3340 | C | PHE | A | 465 | 89.627 | 82.121 | 35.246 | 1.00 | 23.14 C |
| ATOM | 3341 | O | PHE | A | 465 | 89.199 | 82.035 | 36.404 | 1.00 | 23.64 O |
| ATOM | 3342 | CB | PHE | A | 465 | 90.820 | 80.162 | 34.415 | 1.00 | 22.18 C |
| ATOM | 3343 | CG | PHE | A | 465 | 92.042 | 79.513 | 33.836 | 1.00 | 23.68 C |
| ATOM | 3344 | CD1 | PHE | A | 465 | 92.775 | 78.594 | 34.577 | 1.00 | 25.25 C |
| ATOM | 3345 | CD2 | PHE | A | 465 | 92.437 | 79.780 | 32.533 | 1.00 | 23.42 C |
| ATOM | 3346 | CE1 | PHE | A | 465 | 93.884 | 77.947 | 34.025 | 1.00 | 24.49 C |
| ATOM | 3347 | CE2 | PHE | A | 465 | 93.544 | 79.138 | 31.974 | 1.00 | 23.33 C |
| ATOM | 3348 | CZ | PHE | A | 465 | 94.265 | 78.220 | 32.724 | 1.00 | 24.38 C |
| ATOM | 3349 | N | VAL | A | 466 | 88.932 | 82.656 | 34.251 | 1.00 | 22.63 N |
| ATOM | 3350 | CA | VAL | A | 466 | 87.556 | 83.094 | 34.415 | 1.00 | 21.20 C |
| ATOM | 3351 | C | VAL | A | 466 | 86.828 | 82.188 | 33.423 | 1.00 | 21.50 C |
| ATOM | 3352 | O | VAL | A | 466 | 87.281 | 81.994 | 32.300 | 1.00 | 19.95 O |
| ATOM | 3353 | CB | VAL | A | 466 | 87.352 | 84.586 | 34.061 | 1.00 | 19.34 C |
| ATOM | 3354 | CG1 | VAL | A | 466 | 87.897 | 84.887 | 32.698 | 1.00 | 18.84 C |
| ATOM | 3355 | CG2 | VAL | A | 466 | 85.872 | 84.924 | 34.123 | 1.00 | 18.58 C |
| ATOM | 3356 | N | GLU | A | 467 | 85.726 | 81.601 | 33.854 | 1.00 | 22.06 N |
| ATOM | 3357 | CA | GLU | A | 467 | 84.979 | 80.698 | 33.005 | 1.00 | 24.06 C |
| ATOM | 3358 | C | GLU | A | 467 | 84.050 | 81.439 | 32.068 | 1.00 | 24.75 C |
| ATOM | 3359 | O | GLU | A | 467 | 83.415 | 82.413 | 32.465 | 1.00 | 25.25 O |
| ATOM | 3360 | CB | GLU | A | 467 | 84.151 | 79.763 | 33.858 | 1.00 | 24.21 C |
| ATOM | 3361 | CG | GLU | A | 467 | 83.546 | 78.653 | 33.077 | 1.00 | 28.44 C |
| ATOM | 3362 | CD | GLU | A | 467 | 82.524 | 77.934 | 33.879 | 1.00 | 32.19 C |
| ATOM | 3363 | OE1 | GLU | A | 467 | 82.756 | 77.771 | 35.093 | 1.00 | 34.37 O |
| ATOM | 3364 | OE2 | GLU | A | 467 | 81.502 | 77.521 | 33.298 | 1.00 | 35.05 O |
| HETATM | 3365 | N | MSE | A | 468 | 83.956 | 80.981 | 30.826 | 1.00 | 24.94 N |
| HETATM | 3366 | CA | MSE | A | 468 | 83.066 | 81.631 | 29.878 | 1.00 | 26.54 C |

TABLE 7-continued

| | | | | | | | | | | |
|---|---|---|---|---|---|---|---|---|---|---|
| HETATM | 3367 | C | MSE | A | 468 | 82.086 | 80.645 | 29.274 | 1.00 | 26.74 C |
| HETATM | 3368 | O | MSE | A | 468 | 82.353 | 79.444 | 29.218 | 1.00 | 26.45 O |
| HETATM | 3369 | CB | MSE | A | 468 | 83.858 | 82.322 | 28.763 | 1.00 | 28.88 C |
| HETATM | 3370 | CG | MSE | A | 468 | 84.730 | 81.421 | 27.918 | 1.00 | 31.63 C |
| HETATM | 3371 | SE | MSE | A | 468 | 85.425 | 82.387 | 26.542 | 1.00 | 39.89 SE |
| HETATM | 3372 | CE | MSE | A | 468 | 86.595 | 81.206 | 25.795 | 1.00 | 34.18 C |
| ATOM | 3373 | N | SER | A | 469 | 80.945 | 81.156 | 28.827 | 1.00 | 27.65 N |
| ATOM | 3374 | CA | SER | A | 469 | 79.919 | 80.314 | 28.212 | 1.00 | 28.52 C |
| ATOM | 3375 | C | SER | A | 469 | 80.148 | 80.275 | 26.705 | 1.00 | 29.26 C |
| ATOM | 3376 | O | SER | A | 469 | 81.093 | 80.886 | 26.197 | 1.00 | 28.60 O |
| ATOM | 3377 | CB | SER | A | 469 | 78.532 | 80.888 | 28.488 | 1.00 | 27.30 C |
| ATOM | 3378 | OG | SER | A | 469 | 78.385 | 82.148 | 27.847 | 1.00 | 27.56 O |
| ATOM | 3379 | N | GLY | A | 470 | 79.271 | 79.566 | 25.996 | 1.00 | 31.42 N |
| ATOM | 3380 | CA | GLY | A | 470 | 79.384 | 79.479 | 24.549 | 1.00 | 33.33 C |
| ATOM | 3381 | C | GLY | A | 470 | 79.362 | 80.860 | 23.920 | 1.00 | 35.22 |
| ATOM | 3382 | O | GLY | A | 470 | 80.083 | 81.131 | 22.956 | 1.00 | 36.54 O |
| ATOM | 3383 | N | ALA | A | 471 | 78.530 | 81.738 | 24.477 | 1.00 | 35.45 N |
| ATOM | 3384 | CA | ALA | A | 471 | 78.408 | 83.106 | 23.992 | 1.00 | 36.13 C |
| ATOM | 3385 | C | ALA | A | 471 | 79.720 | 83.867 | 24.206 | 1.00 | 36.97 C |
| ATOM | 3386 | O | ALA | A | 471 | 80.182 | 84.595 | 23.321 | 1.00 | 37.26 O |
| ATOM | 3387 | CB | ALA | A | 471 | 77.268 | 83.809 | 24.722 | 1.00 | 35.98 C |
| ATOM | 3388 | N | GLY | A | 472 | 80.311 | 83.701 | 25.388 | 1.00 | 37.72 N |
| ATOM | 3389 | CA | GLY | A | 472 | 81.565 | 84.369 | 25.691 | 1.00 | 38.01 C |
| ATOM | 3390 | C | GLY | A | 472 | 82.656 | 83.924 | 24.730 | 1.00 | 38.54 C |
| ATOM | 3391 | O | GLY | A | 472 | 83.558 | 84.695 | 24.385 | 1.00 | 38.01 O |
| ATOM | 3392 | N | LEU | A | 473 | 82.573 | 82.667 | 24.296 | 1.00 | 38.34 N |
| ATOM | 3393 | CA | LEU | A | 473 | 83.550 | 82.125 | 23.363 | 1.00 | 37.79 C |
| ATOM | 3394 | C | LEU | A | 473 | 83.349 | 82.890 | 22.050 | 1.00 | 37.07 C |
| ATOM | 3395 | O | LEU | A | 473 | 84.316 | 83.285 | 21.395 | 1.00 | 36.58 O |
| ATOM | 3396 | CB | LEU | A | 473 | 83.306 | 80.624 | 23.152 | 1.00 | 38.74 C |
| ATOM | 3397 | CG | LEU | A | 473 | 84.497 | 79.733 | 22.761 | 1.00 | 39.23 C |
| ATOM | 3398 | CD1 | LEU | A | 473 | 83.986 | 78.347 | 22.459 | 1.00 | 38.60 C |
| ATOM | 3399 | CD2 | LEU | A | 473 | 85.229 | 80.274 | 21.558 | 1.00 | 40.46 C |
| ATOM | 3400 | N | ILE | A | 474 | 82.084 | 83.108 | 21.687 | 1.00 | 36.82 N |
| ATOM | 3401 | CA | ILE | A | 474 | 81.737 | 83.841 | 20.463 | 1.00 | 36.70 C |
| ATOM | 3402 | C | ILE | A | 474 | 82.348 | 85.238 | 20.536 | 1.00 | 36.56 C |
| ATOM | 3403 | O | ILE | A | 474 | 82.968 | 85.707 | 19.582 | 1.00 | 36.03 O |
| ATOM | 3404 | CB | ILE | A | 474 | 80.198 | 84.001 | 20.294 | 1.00 | 36.35 C |
| ATOM | 3405 | CG1 | ILE | A | 474 | 79.516 | 82.630 | 20.276 | 1.00 | 36.33 C |
| ATOM | 3406 | CG2 | ILE | A | 474 | 79.889 | 84.760 | 19.006 | 1.00 | 35.09 C |
| ATOM | 3407 | CD1 | ILE | A | 474 | 79.989 | 81.719 | 19.171 | 1.00 | 35.80 C |
| ATOM | 3408 | N | GLU | A | 475 | 82.159 | 85.899 | 21.674 | 1.00 | 35.95 & |
| ATOM | 3409 | CA | GLU | A | 475 | 82.700 | 87.233 | 21.880 | 1.00 | 36.17 C |
| ATOM | 3410 | C | GLU | A | 475 | 84.216 | 87.235 | 21.791 | 1.00 | 36.53 C |
| ATOM | 3411 | O | GLU | A | 475 | 84.807 | 88.209 | 21.327 | 1.00 | 36.42 O |
| ATOM | 3412 | CB | GLU | A | 475 | 82.263 | 87.776 | 23.254 | 1.00 | 37.61 C |
| ATOM | 3413 | CG | GLU | A | 475 | 83.143 | 88.914 | 23.827 | 1.00 | 37.08 C |
| ATOM | 3414 | CD | GLU | A | 475 | 82.626 | 89.458 | 25.164 | 1.00 | 37.58 C |
| ATOM | 3415 | OE1 | GLU | A | 475 | 81.614 | 90.188 | 25.161 | 1.00 | 38.57 O |
| ATOM | 2416 | OE2 | GLU | A | 475 | 83.216 | 89.146 | 26.221 | 1.00 | 33.85 O |
| ATOM | 2417 | N | SER | A | 476 | 84.841 | 86.145 | 22.237 | 1.00 | 37.04 N |
| ATOM | 2418 | CA | SER | A | 476 | 86.300 | 86.039 | 22.242 | 1.00 | 37.27 C |
| ATOM | 2419 | C | SER | A | 476 | 86.924 | 85.973 | 20.851 | 1.00 | 37.06 C |
| ATOM | 2420 | O | SER | A | 476 | 88.046 | 86.442 | 20.638 | 1.00 | 37.30 O |
| ATOM | 3421 | CB | SER | A | 476 | 86.728 | 84.830 | 23.068 | 1.00 | 36.80 C |
| ATOM | 3422 | OG | SER | A | 476 | 86.251 | 84.963 | 24.391 | 1.00 | 36.30 O |
| ATOM | 3423 | N | HIS | A | 477 | 86.197 | 85.391 | 19.908 | 1.00 | 36.25 N |
| ATOM | 3424 | CA | HIS | A | 477 | 86.667 | 85.288 | 18.533 | 1.00 | 36.22 C |
| ATOM | 3425 | C | HIS | A | 477 | 86.181 | 86.477 | 17.724 | 1.00 | 36.09 C |
| ATOM | 3426 | O | HIS | A | 477 | 85.207 | 87.141 | 18.100 | 1.00 | 34.72 O |
| ATOM | 3427 | CB | HIS | A | 477 | 86.132 | 84.008 | 17.897 | 1.00 | 36.36 C |
| ATOM | 3428 | CG | HIS | A | 477 | 86.901 | 82.789 | 18.267 | 1.00 | 36.15 C |
| ATOM | 3429 | ND1 | HIS | A | 477 | 88.077 | 82.440 | 17.644 | 1.00 | 37.86 N |
| ATOM | 3430 | CD2 | HIS | A | 477 | 86.690 | 81.858 | 19.224 | 1.00 | 37.82 C |
| ATOM | 3431 | CE1 | HIS | A | 477 | 88.559 | 81.343 | 18.200 | 1.00 | 38.68 C |
| ATOM | 3432 | NE2 | HIS | A | 477 | 87.736 | 80.969 | 19.162 | 1.00 | 38.42 N |
| ATOM | 3433 | N | PRO | A | 478 | 86.865 | 86.778 | 16.606 | 1.00 | 36.62 N |
| ATOM | 3434 | CA | PRO | A | 478 | 86.409 | 87.910 | 15.801 | 1.00 | 37.52 C |
| ATOM | 3435 | C | PRO | A | 478 | 84.974 | 87.589 | 15.387 | 1.00 | 38.47 C |
| ATOM | 3436 | O | PRO | A | 478 | 84.626 | 86.417 | 15.192 | 1.00 | 37.19 O |
| ATOM | 3437 | CB | PRO | A | 478 | 87.391 | 87.901 | 14.624 | 1.00 | 36.75 C |
| ATOM | 3438 | CG | PRO | A | 478 | 88.651 | 87.370 | 15.266 | 1.00 | 36.00 C |
| ATOM | 3439 | CD | PRO | A | 478 | 88.056 | 86.173 | 15.987 | 1.00 | 36.59 C |
| ATOM | 3440 | N | RIS | A | 479 | 84.141 | 88.617 | 15.271 | 1.00 | 40.10 N |
| ATOM | 3441 | CA | HIS | A | 479 | 82.749 | 88.409 | 14.898 | 1.00 | 41.71 C |
| ATOM | 3442 | C | HIS | A | 479 | 82.163 | 89.607 | 14.178 | 1.00 | 43.00 C |
| ATOM | 3443 | O | HIS | A | 479 | 82.691 | 90.723 | 14.263 | 1.00 | 42.96 O |
| ATOM | 3444 | CB | HIS | A | 479 | 81.906 | 88.138 | 16.142 | 1.00 | 42.19 C |
| ATOM | 3445 | CG | HIS | A | 479 | 82.004 | 89.217 | 17.175 | 1.00 | 42.96 C |

TABLE 7-continued

| ATOM | 3446 | ND1 | HIS | A | 479 | 83.105 | 89.373 | 17.989 | 1.00 | 44.02 N |
| --- | --- | --- | --- | --- | --- | --- | --- | --- | --- | --- |
| ATOM | 3447 | CD2 | HIS | A | 479 | 81.154 | 90.221 | 17.499 | 1.00 | 44.12 C |
| ATOM | 3448 | CE1 | HIS | A | 479 | 82.929 | 90.423 | 18.773 | 1.00 | 43.65 C |
| ATOM | 3449 | NE2 | HIS | A | 479 | 81.753 | 90.956 | 18.495 | 1.00 | 44.04 N |
| ATOM | 3450 | N | ASP | A | 480 | 81.055 | 89.355 | 13.482 | 1.00 | 44.35 N |
| ATOM | 3451 | CA | ASP | A | 480 | 80.321 | 90.373 | 12.741 | 1.00 | 45.86 C |
| ATOM | 3452 | C | ASP | A | 480 | 81.196 | 91.161 | 11.787 | 1.00 | 45.95 C |
| ATOM | 3453 | O | ASP | A | 480 | 81.074 | 92.381 | 11.676 | 1.00 | 46.64 O |
| ATOM | 3454 | CB | ASP | A | 480 | 79.631 | 91.326 | 13.716 | 1.00 | 47.55 C |
| ATOM | 3455 | CG | ASP | A | 480 | 78.698 | 90.601 | 14.672 | 1.00 | 50.07 C |
| ATOM | 3456 | OD1 | ASP | A | 480 | 77.750 | 89.935 | 14.191 | 1.00 | 50.68 O |
| ATOM | 3457 | OD2 | ASP | A | 480 | 78.912 | 90.698 | 15.904 | 1.00 | 52.11 O |
| ATOM | 3458 | N | VAL | A | 481 | 82.083 | 90.457 | 11.099 | 1.00 | 46.00 N |
| ATOM | 3459 | CA | VAL | A | 481 | 82.975 | 91.093 | 10.141 | 1.00 | 45.97 C |
| ATOM | 3460 | C | VAL | A | 481 | 83.437 | 90.069 | 9.105 | 1.00 | 45.58 C |
| ATOM | 3461 | O | VAL | A | 481 | 83.781 | 88.934 | 9.438 | 1.00 | 44.87 O |
| ATOM | 3462 | CB | VAL | A | 481 | 84.199 | 91.748 | 10.861 | 1.00 | 46.24 C |
| ATOM | 3463 | CG1 | VAL | A | 481 | 84.888 | 90.733 | 11.769 | 1.00 | 46.53 C |
| ATOM | 3464 | CG2 | VAL | A | 481 | 85.177 | 92.301 | 9.834 | 1.00 | 45.43 C |
| ATOM | 3465 | N | GLN | A | 482 | 83.416 | 90.475 | 7.842 | 1.00 | 45.62 N |
| ATOM | 3466 | CA | GLN | A | 482 | 83.822 | 89.600 | 6.756 | 1.00 | 45.66 C |
| ATOM | 3467 | C | GLN | A | 482 | 85.331 | 89.650 | 6.600 | 1.00 | 45.00 C |
| ATOM | 3468 | O | GLN | A | 482 | 85.898 | 90.706 | 6.353 | 1.00 | 44.56 O |
| ATOM | 3469 | CB | GLN | A | 482 | 83.129 | 90.035 | 5.466 | 1.00 | 46.54 C |
| ATOM | 3470 | CG | GLN | A | 482 | 83.384 | 89.130 | 4.279 | 1.00 | 49.29 C |
| ATOM | 3471 | CD | GLN | A | 482 | 82.506 | 89.489 | 3.095 | 1.00 | 51.02 C |
| ATOM | 3472 | OE1 | GLN | A | 482 | 81.280 | 89.447 | 3.190 | 1.00 | 53.04 O |
| ATOM | 3473 | NE2 | GLN | A | 482 | 83.126 | 89.847 | 1.976 | 1.00 | 50.81 N |
| ATOM | 3474 | N | ILE | A | 483 | 85.977 | 88.500 | 6.760 | 1.00 | 45.70 N |
| ATOM | 3475 | CA | ILE | A | 483 | 87.431 | 88.406 | 6.643 | 1.00 | 46.40 C |
| ATOM | 3476 | C | ILE | A | 483 | 87.797 | 87.626 | 5.378 | 1.00 | 46.80 C |
| ATOM | 3477 | O | ILE | A | 483 | 87.378 | 86.479 | 5.209 | 1.00 | 47.10 O |
| ATOM | 3478 | CB | ILE | A | 483 | 88.045 | 87.668 | 7.870 | 1.00 | 46.86 C |
| ATOM | 3479 | CG1 | ILE | A | 483 | 87.565 | 88.314 | 9.172 | 1.00 | 47.22 C |
| ATOM | 3480 | CG2 | ILE | A | 483 | 89.566 | 87.721 | 7.804 | 1.00 | 46.15 C |
| ATOM | 3481 | CD1 | ILE | A | 483 | 88.107 | 87.641 | 10.430 | 1.00 | 47.26 C |
| ATOM | 3482 | N | THR | A | 484 | 88.573 | 88.240 | 4.491 | 1.00 | 47.02 N |
| ATOM | 3483 | CA | THR | A | 484 | 88.970 | 87.565 | 3.258 | 1.00 | 47.69 C |
| ATOM | 3484 | C | THR | A | 484 | 90.448 | 87.182 | 3.316 | 1.00 | 47.46 C |
| ATOM | 3485 | O | THR | A | 484 | 90.908 | 86.296 | 2.599 | 1.00 | 46.97 O |
| ATOM | 3486 | CB | THR | A | 484 | 88.710 | 98.453 | 2.002 | 1.00 | 48.12 C |
| ATOM | 3487 | CG1 | THR | A | 484 | 89.451 | 89.676 | 2.114 | 1.00 | 49.12 O |
| ATOM | 3488 | CG2 | THR | A | 484 | 87.219 | 88.767 | 1.861 | 1.00 | 47.18 C |
| ATOM | 3489 | N | ASN | A | 485 | 91.184 | 87.894 | 4.171 | 1.00 | 47.14 N |
| ATOM | 3490 | CA | ASN | A | 485 | 92.605 | 87.644 | 4.356 | 1.00 | 47.75 C |
| ATOM | 3491 | C | ASN | A | 485 | 92.864 | 87.515 | 5.854 | 1.00 | 47.58 C |
| ATOM | 3492 | 0 | ASN | A | 485 | 92.851 | 88.507 | 6.594 | 1.00 | 47.74 O |
| ATOM | 3493 | CB | ASN | A | 485 | 93.436 | 88.785 | 3.767 | 1.00 | 48.75 C |
| ATOM | 3494 | CG | ASN | A | 485 | 94.934 | 88.540 | 3.890 | 1.00 | 50.65 C |
| ATOM | 3495 | OD1 | ASN | A | 485 | 95.453 | 87.518 | 3.429 | 1.00 | 50.94 O |
| ATOM | 3496 | ND2 | ASN | A | 485 | 95.636 | 89.483 | 4.508 | 1.00 | 51.72 N |
| ATOM | 3497 | N | GLU | A | 486 | 93.099 | 86.276 | 6.281 | 1.00 | 46.65 N |
| ATOM | 3498 | CA | GLU | A | 486 | 93.332 | 85.930 | 7.680 | 1.00 | 45.73 C |
| ATOM | 3499 | C | GLU | A | 486 | 94.720 | 86.252 | 8.207 | 1.00 | 45.11 C |
| ATOM | 3500 | 0 | GLU | A | 486 | 95.660 | 86.465 | 7.443 | 1.00 | 45.20 O |
| ATOM | 3501 | CB | GLU | A | 486 | 93.057 | 84.441 | 7.867 | 1.00 | 46.18 C |
| ATOM | 3502 | CG | GLU | A | 486 | 91.649 | 84.047 | 7.462 | 1.00 | 46.84 C |
| ATOM | 3503 | CD | GLU | A | 486 | 91.503 | 82.556 | 7.259 | 1.00 | 47.48 C |
| ATOM | 3504 | OE1 | GLU | A | 486 | 90.380 | 82.105 | 6.946 | 1.00 | 47.47 O |
| ATOM | 3505 | OE2 | GLU | A | 486 | 92.518 | 81.838 | 7.402 | 1.00 | 47.64 O |
| ATOM | 3506 | N | ALA | A | 487 | 94.835 | 86.284 | 9.530 | 1.00 | 44.77 N |
| ATOM | 3507 | CA | ALA | A | 487 | 96.106 | 86.563 | 10.187 | 1.00 | 44.41 C |
| ATOM | 3508 | C | ALA | A | 487 | 96.892 | 85.264 | 10.290 | 1.00 | 44.54 C |
| ATOM | 3509 | 0 | ALA | A | 487 | 96.314 | 84.184 | 10.407 | 1.00 | 43.71 O |
| ATOM | 3510 | CB | ALA | A | 487 | 95.867 | 87.143 | 11.563 | 1.00 | 44.17 C |
| ATOM | 3511 | N | PRO | A | 488 | 98.227 | 85.350 | 10.227 | 1.00 | 45.67 N |
| ATOM | 3512 | CA | PRO | A | 488 | 99.083 | 84.168 | 10.317 | 1.00 | 46.18 C |
| ATOM | 3513 | C | PRO | A | 488 | 98.978 | 83.485 | 11.675 | 1.00 | 46.38 C |
| ATOM | 3514 | O | PRO | A | 488 | 99.572 | 82.434 | 11.892 | 1.00 | 47.49 O |
| ATOM | 3515 | CB | PRO | A | 488 | 100.474 | 84.751 | 10.064 | 1.00 | 46.01 C |
| ATOM | 3516 | CG | PRO | A | 488 | 100.351 | 66.122 | 10.696 | 1.00 | 46.03 C |
| ATOM | 3517 | CD | PRO | A | 488 | 99.059 | 86.551 | 10.034 | 1.00 | 46.59 C |
| ATOM | 3518 | N | ASN | A | 489 | 98.218 | 84.075 | 12.587 | 1.00 | 46.12 N |
| ATOM | 3519 | CA | ASN | A | 489 | 98.073 | 83.499 | 13.918 | 1.00 | 46.19 C |
| ATOM | 3520 | C | ASN | A | 489 | 96.604 | 83.237 | 14.261 | 1.00 | 45.99 C |
| ATOM | 3521 | O | ASN | A | 489 | 96.258 | 82.970 | 15.415 | 1.00 | 45.30 O |
| ATOM | 3522 | CB | ASN | A | 489 | 98.712 | 84.433 | 14.948 | 1.00 | 45.82 C |
| ATOM | 3523 | CG | ASN | A | 489 | 97.953 | 85.736 | 15.101 | 1.00 | 47.05 C |
| ATOM | 3524 | OD1 | ASN | A | 489 | 97.335 | 86.229 | 14.152 | 1.00 | 47.80 O |

TABLE 7-continued

| | | | | | | | | | | |
|---|---|---|---|---|---|---|---|---|---|---|
| ATOM | 3525 | ND2 | ASN | A | 489 | 98.019 | 86.320 | 16.293 | 1.00 | 47.88 N |
| ATOM | 3526 | N | TYR | A | 490 | 95.741 | 83.327 | 13.253 | 1.00 | 45.80 N |
| ATOM | 3527 | CA | TYR | A | 490 | 94.319 | 83.069 | 13.447 | 1.00 | 45.86 C |
| ATOM | 3528 | C | TYR | A | 490 | 93.669 | 82.536 | 12.168 | 1.00 | 46.13 C |
| ATOM | 3529 | C | TYR | A | 490 | 93.361 | 83.295 | 11.246 | 1.00 | 45.86 O |
| ATOM | 3530 | CB | TYR | A | 490 | 93.576 | 84.328 | 13.916 | 1.00 | 44.08 C |
| ATOM | 3531 | CG | TYR | A | 490 | 92.148 | 84.013 | 14.302 | 1.00 | 42.82 C |
| ATOM | 3532 | CD1 | TYR | A | 490 | 91.871 | 83.222 | 15.419 | 1.00 | 41.48 C |
| ATOM | 3533 | CD2 | TYR | A | 490 | 91.080 | 84.402 | 13.489 | 1.00 | 42.13 C |
| ATOM | 3534 | CE1 | TYR | A | 490 | 90.570 | 82.816 | 15.709 | 1.00 | 41.83 C |
| ATOM | 3535 | CE2 | TYR | A | 490 | 89.776 | 84.001 | 13.772 | 1.00 | 41.77 C |
| ATOM | 3536 | CZ | TYR | A | 490 | 89.529 | 83.204 | 14.881 | 1.00 | 41.35 C |
| ATOM | 3537 | OH | TYR | A | 490 | 88.248 | 82.771 | 15.141 | 1.00 | 40.05 O |
| ATOM | 3536 | N | SER | A | 491 | 93.475 | 81.220 | 12.135 | 1.00 | 47.86 N |
| ATOM | 3539 | CA | SER | A | 491 | 92.880 | 80.512 | 11.005 | 1.00 | 49.91 C |
| ATOM | 3540 | C | SER | A | 491 | 93.583 | 80.739 | 9.661 | 1.00 | 51.25 C |
| ATOM | 3541 | O | SER | A | 491 | 94.408 | 81.674 | 9.551 | 1.00 | 53.12 O |
| ATOM | 3542 | CB | SER | A | 491 | 91.402 | 80.881 | 10.887 | 1.00 | 50.03 C |
| ATOM | 3543 | OG | SER | A | 491 | 90.700 | 80.462 | 12.043 | 1.00 | 51.19 O |
| ATOM | 3544 | N | VAL | A | 492 | 93.288 | 79.975 | 8.714 | 1.00 | 52.00 N |
| TER | 3545 | | VAL | A | 492 | | | | | |
| HETATM | 3546 | P | IMP | | 500 | 96.855 | 67.484 | 18.145 | 1.00 | 36.20 P |
| HETATM | 3547 | O1P | IMP | | 500 | 96.567 | 66.958 | 16.764 | 1.00 | 35.78 O |
| HETATM | 3548 | O2P | IMP | | 500 | 97.831 | 68.643 | 18.107 | 1.00 | 37.27 O |
| HETATM | 3549 | O3P | IMP | | 500 | 95.630 | 67.848 | 18.926 | 1.00 | 37.73 O |
| HETATM | 3550 | O5* | IMP | | 500 | 97.576 | 66.348 | 19.098 | 1.00 | 39.55 C |
| HETATM | 3551 | C5* | IMP | | 500 | 96.906 | 65.102 | 19.379 | 1.00 | 43.52 C |
| HETATM | 3552 | C4* | IMP | | 500 | 97.725 | 64.188 | 20.314 | 1.00 | 46.38 C |
| HETATM | 3553 | O4* | IMP | | 500 | 96.849 | 63.056 | 20.510 | 1.00 | 47.93 O |
| HETATM | 3554 | C3* | IMP | | 500 | 99.128 | 63.615 | 19.896 | 1.00 | 47.80 C |
| HETATM | 3555 | O3* | IMP | | 500 | 100.283 | 64.165 | 20.566 | 1.00 | 48.27 O |
| HETATM | 3556 | C2* | IMP | | 500 | 99.063 | 62.138 | 20.401 | 1.00 | 48.14 C |
| HETATM | 3557 | O2* | IMP | | 500 | 99.459 | 61.962 | 21.777 | 1.00 | 47.86 O |
| HETATM | 3558 | C1* | IMP | | 500 | 97.568 | 61.820 | 20.391 | 1.00 | 48.84 C |
| HETATM | 3559 | N9 | IMP | | 500 | 97.172 | 60.952 | 19.187 | 1.00 | 49.35 N |
| HETATM | 3560 | C8 | IMP | | 500 | 97.769 | 60.762 | 17.934 | 1.00 | 49.94 C |
| HETATM | 3561 | N7 | IMP | | 500 | 96.960 | 59.811 | 17.195 | 1.00 | 49.47 N |
| HETATM | 3562 | C5 | IMP | | 500 | 95.903 | 59.489 | 18.092 | 1.00 | 49.72 C |
| HETATM | 3563 | C6 | IMP | | 500 | 94.774 | 58.548 | 17.851 | 1.00 | 49.49 C |
| HETATM | 3564 | O6 | IMP | | 500 | 94.520 | 57.868 | 16.852 | 1.00 | 49.17 O |
| HETATM | 3565 | N1 | IMP | | 500 | 93.959 | 58.521 | 15.994 | 1.00 | 50.36 N |
| HETATM | 3566 | C2 | IMP | | 500 | 94.155 | 59.256 | 20.190 | 1.00 | 50.39 C |
| HETATM | 3567 | N3 | IMP | | 500 | 95.182 | 60.067 | 20.313 | 1.00 | 49.12 N |
| HETATM | 3568 | C4 | IMP | | 500 | 96.016 | 60.150 | 19.259 | 1.00 | 49.43 C |
| HETATM | 3569 | O | HOH | | 501 | 100.576 | 78.275 | 17.774 | 1.00 | 32.86 O |
| HETATM | 3570 | O | HOH | | 503 | 91.095 | 64.490 | 36.206 | 1.00 | 28.90 O |
| HETATM | 3571 | O | HOH | | 504 | 94.498 | 58.629 | 33.377 | 1.00 | 29.01 O |
| HETATM | 3572 | O | HOH | | 505 | 121.994 | 54.382 | 32.283 | 1.00 | 29.34 O |
| HETATM | 3573 | O | HOH | | 506 | 103.325 | 52.600 | 39.850 | 1.00 | 30.92 O |
| HETATM | 3574 | O | HOH | | 506 | 114.082 | 79.200 | 14.020 | 1.00 | 31.09 O |
| HETATM | 3575 | O | HOH | | 509 | 111.782 | 75.357 | 9.474 | 1.00 | 41.74 O |
| HETATM | 3576 | O | HOH | | 510 | 130.431 | 69.550 | 6.520 | 1.00 | 33.07 O |
| HETATM | 3577 | O | HOH | | 511 | 139.704 | 72.872 | 5.502 | 1.00 | 28.29 O |
| HETATM | 3578 | O | HOH | | 512 | 138.165 | 79.843 | 7.558 | 1.00 | 37.74 O |
| HETATM | 3579 | O | HOH | | 513 | 110.012 | 65.496 | 9.942 | 1.00 | 27.19 O |
| HETATM | 3580 | O | HOH | | 514 | 95.709 | 85.791 | 36.220 | 1.00 | 26.84 O |
| HETATM | 3581 | O | HOH | | 515 | 97.359 | 70.230 | 25.703 | 1.00 | 26.44 O |
| HETATM | 3582 | O | HOH | | 516 | 111.343 | 65.984 | 36.009 | 1.00 | 27.68 O |
| HETATM | 3583 | O | HOH | | 517 | 92.610 | 64.734 | 28.562 | 1.00 | 25.19 O |
| HETATM | 3584 | O | HOH | | 518 | 136.337 | 83.402 | 18.230 | 1.00 | 44.74 O |
| HETATM | 3585 | O | HOH | | 519 | 125.872 | 72.828 | 24.786 | 1.00 | 56.58 O |
| HETATM | 3586 | O | HOH | | 520 | 123.394 | 85.143 | 17.982 | 1.00 | 44.83 O |
| HETATM | 3587 | O | HOH | | 521 | 114.051 | 75.607 | 10.822 | 1.00 | 28.33 O |
| HETATM | 3588 | O | HOH | | 522 | 95.439 | 56.751 | 21.398 | 1.00 | 35.18 O |
| HETATM | 3589 | O | HOH | | 523 | 126.131 | 73.771 | 18.625 | 1.00 | 28.52 O |
| HETATM | 3590 | O | HOH | | 524 | 88.573 | 61.550 | 21.356 | 1.00 | 35.43 O |
| HETATM | 3591 | O | HOH | | 525 | 84.159 | 71.151 | 29.206 | 1.00 | 24.40 O |
| HETATM | 3592 | O | HOH | | 526 | 133.284 | 55.863 | 10.735 | 1.00 | 36.12 O |
| HETATM | 3593 | O | HOH | | 527 | 127.221 | 75.361 | 20.788 | 1.00 | 31.12 O |
| HETATM | 3594 | O | HOH | | 528 | 144.500 | 73.437 | 21.138 | 1.00 | 37.89 O |
| HETATM | 3595 | O | HOH | | 529 | 104.651 | 89.119 | 21.108 | 1.00 | 45.21 O |
| HETATM | 3596 | O | HOH | | 530 | 97.113 | 80.827 | 16.767 | 1.00 | 29.31 O |
| HETATM | 3597 | O | HOH | | 531 | 115.587 | 76.287 | 34.279 | 1.00 | 41.57 O |
| HETATM | 3598 | O | HOH | | 532 | 110.085 | 78.952 | 34.960 | 1.00 | 36.98 O |
| HETATM | 3599 | O | HOH | | 533 | 113.576 | 64.235 | 37.324 | 1.00 | 44.04 O |
| HETATM | 3600 | O | HOH | | 536 | 113.308 | 82.910 | 26.870 | 1.00 | 35.47 O |
| HETATM | 3601 | O | HOH | | 537 | 135.913 | 65.420 | 20.988 | 1.00 | 42.04 O |
| HETATM | 3602 | O | HOH | | 538 | 81.878 | 61.168 | 23.889 | 1.00 | 37.18 O |
| HETATM | 3603 | O | HOH | | 539 | 112.973 | 80.799 | 18.829 | 1.00 | 46.80 O |

TABLE 7-continued

| | | | | | | | | | | |
|---|---|---|---|---|---|---|---|---|---|---|
| HETATM | 3604 | O | HOH | 540 | 114.422 | 67.736 | 18.471 | 1.00 | 21.38 | O |
| HETATM | 3605 | O | HOH | 541 | 149.015 | 73.669 | 7.625 | 1.00 | 31.27 | O |
| HETATM | 3606 | O | HOH | 542 | 94.881 | 66.686 | 41.661 | 1.00 | 28.69 | O |
| HETATM | 3607 | O | HOH | 544 | 100.410 | 54.930 | 42.976 | 1.00 | 40.88 | O |
| HETATM | 3608 | O | HOH | 546 | 123.513 | 59.702 | 10.409 | 1.00 | 32.15 | O |
| HETATM | 3609 | O | HOH | 547 | 146.434 | 72.633 | 24.076 | 1.00 | 36.35 | O |
| HETATM | 3610 | O | HOH | 548 | 88.886 | 71.737 | 36.970 | 1.00 | 30.08 | O |
| HETATM | 3611 | O | HOH | 549 | 107.710 | 87.920 | 18.571 | 1.00 | 46.77 | O |
| HETATM | 3612 | O | HOH | 550 | 89.670 | 63.104 | 37.776 | 1.00 | 47.36 | O |
| HETATM | 3613 | O | HOH | 552 | 122.692 | 77.602 | 19.074 | 1.00 | 36.80 | O |
| HETATM | 3614 | O | HOH | 553 | 98.993 | 52.226 | 5.651 | 1.00 | 57.87 | O |
| HETATM | 3615 | O | HOH | 554 | 113.536 | 82.903 | 22.647 | 1.00 | 41.61 | O |
| HETATM | 3616 | O | HOH | 555 | 115.587 | 74.041 | 10.297 | 1.00 | 38.20 | O |
| HETATM | 3617 | O | HOH | 557 | 98.458 | 49.507 | 39.120 | 1.00 | 62.44 | O |
| HETATM | 3618 | O | HOH | 558 | 112.138 | 63.863 | 8.254 | 1.00 | 24.96 | O |
| HETATM | 3619 | O | HOH | 560 | 118.847 | 70.191 | 28.617 | 1.00 | 45.38 | O |
| HETATM | 3620 | O | HOH | 561 | 146.469 | 68.284 | 24.114 | 1.00 | 37.59 | O |
| HETATM | 3621 | O | HOH | 562 | 128.262 | 63.501 | 17.485 | 1.00 | 38.06 | O |
| HETATM | 3622 | O | HOH | 563 | 119.639 | 64.695 | 7.607 | 1.00 | 46.90 | O |
| HETATM | 3623 | O | HOH | 564 | 103.490 | 70.881 | 36.574 | 1.00 | 31.68 | O |
| HETATM | 3624 | O | HOH | 565 | 98.314 | 86.799 | 37.005 | 1.00 | 30.76 | O |
| HETATM | 3625 | O | HOH | 567 | 131.484 | 71.418 | 23.548 | 1.00 | 36.31 | O |
| HETATM | 3626 | O | HOH | 568 | 76.343 | 60.795 | 41.874 | 1.00 | 35.52 | O |
| HETATM | 3627 | O | HOH | 569 | 126.027 | 59.075 | 12.269 | 1.00 | 43.45 | O |
| HETATM | 3628 | O | HOH | 570 | 109.042 | 74.363 | 33.675 | 1.00 | 39.31 | O |
| HETATM | 3629 | O | HOM | 573 | 80.409 | 90.280 | 22.579 | 1.00 | 34.21 | O |
| HETATM | 3630 | O | HOH | 574 | 132.441 | 66.786 | 9.212 | 1.00 | 43.87 | O |
| HETATM | 3631 | O | HOH | 575 | 109.944 | 79.697 | 32.230 | 1.00 | 32.32 | O |
| HETATM | 3632 | O | HOH | 577 | 144.216 | 66.858 | 24.156 | 1.00 | 40.46 | O |
| HETATM | 3633 | O | HOH | 578 | 129.414 | 81.484 | 16.530 | 1.00 | 61.51 | O |
| HETATM | 3634 | O | HOH | 579 | 96.972 | 92.020 | 39.467 | 1.00 | 39.03 | O |
| HETATM | 3635 | O | HOH | 580 | 94.372 | 70.562 | 18.189 | 1.00 | 26.74 | O |
| HETATM | 3636 | O | HOH | 581 | 88.506 | 73.637 | 23.695 | 1.00 | 31.00 | O |
| HETATM | 3637 | O | HOH | 584 | 100.007 | 84.003 | 17.987 | 1.00 | 28.74 | O |
| HETATM | 3638 | O | HOH | 585 | 121.405 | 52.600 | 17.537 | 1.00 | 40.20 | O |
| HETATM | 3639 | O | HOH | 588 | 119.167 | 48.434 | 16.339 | 1.00 | 65.21 | O |
| HETATM | 3640 | O | HOH | 589 | 102.348 | 55.052 | 4.902 | 1.00 | 39.64 | O |
| HETATM | 3641 | O | HOH | 595 | 97.908 | 70.027 | 21.031 | 1.00 | 34.06 | O |
| HETATM | 3642 | O | HOH | 596 | 146.572 | 53.248 | 20.725 | 1.00 | 45.62 | O |
| HETATM | 3643 | O | HOH | 598 | 90.443 | 55.094 | 8.608 | 1.00 | 49.49 | O |
| HETATM | 3644 | O | HOH | 599 | 109.411 | 77.677 | 2.747 | 1.00 | 53.11 | O |
| HETATM | 3645 | O | HOH | 600 | 107.764 | 45.882 | 37.351 | 1.00 | 45.02 | O |
| HETATM | 3646 | O | HOH | 601 | 87.454 | 73.205 | 28.703 | 1.00 | 45.44 | O |
| HETATM | 3647 | O | HOH | 602 | 80.069 | 88.678 | 20.249 | 1.00 | 42.72 | O |
| HETATM | 3648 | O | HOH | 603 | 117.159 | 79.599 | 17.309 | 1.00 | 30.98 | O |
| HETATM | 3649 | O | HOH | 604 | 84.446 | 85.847 | 6.609 | 1.00 | 66.35 | O |
| HETATM | 3650 | O | HOH | 605 | 142.262 | 74.880 | 21.888 | 1.00 | 42.69 | O |
| HETATM | 3651 | O | HOH | 606 | 133.945 | 64.662 | 5.678 | 1.00 | 39.03 | O |
| HETATM | 3652 | O | HOH | 607 | 110.322 | 88.556 | 20.860 | 1.00 | 51.80 | O |
| HETATM | 3653 | O | HOH | 608 | 118.514 | 60.464 | 29.384 | 1.00 | 33.39 | O |
| HETATM | 3654 | O | HOH | 609 | 82.950 | 78.301 | 25.302 | 1.00 | 33.55 | O |
| HETATM | 3655 | O | HOH | 610 | 111.407 | 75.421 | 34.632 | 1.00 | 44.58 | O |
| HETATM | 3656 | O | HOH | 612 | 96.558 | 63.438 | 23.644 | 1.00 | 34.09 | O |
| HETATM | 3657 | O | HOH | 613 | 122.627 | 63.063 | 23.597 | 1.00 | 26.90 | O |
| HETATM | 3658 | O | HOH | 614 | 131.169 | 69.077 | 14.358 | 1.00 | 34.02 | O |
| HETATM | 3659 | O | HOH | 618 | 96.690 | 54.179 | 40.860 | 1.00 | 32.89 | O |
| HETATM | 3660 | O | HOH | 619 | 126.711 | 73.763 | 15.905 | 1.00 | 32.41 | O |
| HETATM | 3661 | O | HOH | 621 | 92.253 | 63.599 | 39.103 | 1.00 | 25.94 | O |
| HETATM | 3662 | O | HOH | 622 | 97.813 | 87.700 | 39.424 | 1.00 | 55.96 | O |
| HETATM | 3663 | O | HOH | 623 | 95.535 | 56.002 | 20.767 | 1.00 | 65.87 | O |
| HETATM | 3664 | O | HOH | 624 | 129.489 | 78.975 | 20.616 | 1.00 | 46.43 | O |
| HETATM | 3665 | O | HOH | 625 | 119.866 | 48.017 | 8.457 | 1.00 | 69.76 | O |
| HETATM | 3666 | O | HOH | 627 | 134.345 | 53.135 | 10.168 | 1.00 | 47.96 | O |
| HETATM | 3667 | O | HOH | 628 | 96.130 | 73.007 | 12.133 | 1.00 | 65.41 | O |
| HETATM | 3668 | O | HOH | 629 | 87.800 | 55.819 | 15.251 | 1.00 | 45.94 | O |
| HETATM | 3669 | O | HOH | 630 | 112.422 | 70.233 | 37.715 | 1.00 | 55.93 | O |
| HETATM | 3670 | O | HOH | 632 | 121.366 | 74.739 | 24.939 | 1.00 | 57.43 | O |
| HETATM | 3671 | O | HOH | 633 | 101.115 | 80.540 | 12.424 | 1.00 | 53.67 | O |
| HETATM | 3672 | O | HOH | 634 | 124.882 | 64.152 | 26.715 | 1.00 | 65.56 | O |
| HETATM | 3673 | O | HOH | 635 | 97.480 | 87.029 | 5.748 | 1.00 | 41.53 | O |
| HETATM | 3674 | O | HOH | 636 | 98.153 | 71.085 | 17.480 | 1.00 | 23.05 | O |
| HETATM | 3675 | O | HOH | 638 | 109.916 | 53.593 | 7.340 | 1.00 | 60.03 | O |
| HETATM | 3676 | O | HOH | 639 | 109.356 | 46.219 | 43.098 | 1.00 | 74.41 | O |
| HETATM | 3677 | O | HOH | 640 | 123.090 | 65.562 | 2.087 | 1.00 | 64.16 | O |
| HETATM | 3678 | O | HOH | 641 | 121.091 | 58.113 | 37.981 | 1.00 | 53.09 | O |
| HETATM | 3679 | O | HOH | 642 | 106.879 | 71.024 | 39.823 | 1.00 | 49.73 | O |
| HETATM | 3680 | O | HOH | 644 | 125.842 | 60.086 | 22.102 | 1.00 | 57.75 | O |
| HETATM | 3681 | O | HOH | 645 | 89.792 | 80.261 | 21.919 | 1.00 | 65.49 | O |
| HETATM | 3682 | O | HOH | 646 | 127.581 | 71.494 | 10.877 | 1.00 | 41.56 | O |

TABLE 7-continued

| | | | | | | | | | | |
|---|---|---|---|---|---|---|---|---|---|---|
| HETATM | 3683 | O | HOH | 647 | 116.711 | 52.692 | 38.666 | 1.00 | 55.88 | O |
| HETATM | 3684 | O | HOH | 648 | 137.352 | 49.806 | 16.559 | 1.00 | 67.37 | O |
| HETATM | 3685 | O | HOH | 649 | 93.707 | 89.594 | 38.028 | 1.00 | 28.70 | O |
| HETATM | 3686 | O | HOH | 650 | 102.722 | 58.313 | 7.082 | 1.00 | 52.26 | O |
| HETATM | 3687 | O | HOH | 651 | 99.494 | 73.756 | −9.807 | 1.00 | 57.10 | O |
| HETATM | 3688 | O | HOH | 652 | 100.369 | 60.404 | 12.181 | 1.00 | 24.56 | O |
| HETATM | 3689 | O | HOH | 653 | 86.387 | 73.114 | 22.271 | 1.00 | 36.14 | O |
| HETATM | 3690 | O | HOH | 655 | 82.774 | 85.056 | 16.980 | 1.00 | 29.50 | O |
| HETATM | 3691 | O | HOH | 656 | 138.719 | 75.750 | 24.731 | 1.00 | 43.44 | O |
| HETATM | 3692 | O | HOH | 657 | 135.443 | 63.373 | 23.553 | 1.00 | 62.79 | O |
| HETATM | 3693 | O | HOH | 658 | 136.532 | 59.341 | 22.164 | 1.00 | 61.51 | O |
| HETATM | 3694 | O | HOH | 659 | 112.228 | 46.754 | 14.166 | 1.00 | 44.56 | O |
| HETATM | 3695 | O | HOH | 661 | 85.056 | 77.737 | 37.011 | 1.00 | 51.97 | O |
| HETATM | 3696 | O | HOH | 664 | 93.862 | 94.123 | 24.058 | 1.00 | 44.59 | O |
| HETATM | 3697 | O | HOH | 665 | 125.115 | 50.268 | 16.057 | 1.00 | 50.48 | O |
| HETATM | 3698 | O | HOH | 666 | 109.792 | 82.218 | 39.304 | 1.00 | 41.41 | O |
| HETATM | 3699 | O | HOH | 667 | 81.419 | 71.538 | 32.800 | 1.00 | 43.84 | O |
| HETATM | 3700 | O | HOH | 671 | 100.872 | 91.979 | 23.613 | 1.00 | 64.05 | O |
| HETATM | 3701 | O | HOH | 672 | 121.924 | 64.730 | 9.693 | 1.00 | 40.99 | O |
| HETATM | 3702 | O | HOH | 673 | 103.164 | 53.450 | 45.794 | 1.00 | 46.76 | O |
| HETATM | 3703 | O | HOH | 674 | 112.887 | 44.758 | 35.892 | 1.00 | 60.15 | O |
| HETATM | 3704 | O | HOH | 675 | 121.226 | 52.298 | 40.410 | 1.00 | 59.96 | O |
| HETATM | 3705 | O | HOH | 676 | 114.778 | 79.883 | 12.588 | 1.00 | 53.72 | O |
| HETATM | 3706 | O | HOH | 677 | 111.493 | 44.375 | 26.336 | 1.00 | 44.91 | O |
| HETATM | 3707 | O | HOH | 680 | 125.672 | 77.196 | 7.641 | 1.00 | 62.63 | O |
| HETATM | 3708 | O | HOH | 681 | 149.427 | 68.734 | 21.594 | 1.00 | 69.45 | O |
| HETATM | 3709 | O | HOH | 682 | 130.498 | 68.890 | 11.409 | 1.00 | 43.07 | O |
| HETATM | 3710 | O | HOH | 684 | 97.027 | 74.301 | −8.091 | 1.00 | 51.74 | O |
| HETATM | 3711 | O | HOH | 685 | 93.468 | 57.644 | 35.310 | 1.00 | 25.70 | O |
| HETATM | 3712 | O | HOH | 687 | 120.082 | 63.118 | 33.794 | 1.00 | 66.97 | O |
| HETATM | 3713 | O | HOH | 688 | 91.794 | 50.180 | 5.365 | 1.00 | 61.88 | O |
| HETATM | 3714 | O | HOH | 691 | 120.955 | 66.509 | 26.956 | 1.00 | 57.92 | O |
| HETATM | 3715 | O | HOH | 692 | 147.976 | 65.172 | 14.279 | 1.00 | 58.48 | O |
| HETATM | 3716 | O | HOH | 693 | 90.415 | 78.310 | 23.880 | 1.00 | 38.31 | O |
| HETATM | 3717 | O | HOH | 694 | 113.372 | 43.333 | 17.881 | 1.00 | 68.93 | O |
| HETATM | 3718 | O | HOH | 695 | 101.223 | 90.113 | 38.606 | 1.00 | 45.49 | O |
| HETATM | 3719 | O | HOH | 696 | 108.151 | 50.895 | 41.168 | 1.00 | 59.49 | O |
| HETATM | 3720 | O | HOH | 697 | 90.431 | 44.244 | 14.620 | 1.00 | 43.55 | O |
| HETATM | 3721 | O | HOH | 698 | 146.554 | 70.443 | 18.977 | 1.00 | 32.63 | O |
| HETATM | 3722 | O | HOH | 702 | 107.324 | 89.479 | 37.117 | 1.00 | 65.35 | O |
| HETATM | 3723 | O | HOH | 706 | 181.406 | 55.047 | 15.937 | 1.00 | 56.70 | C |
| HETATM | 3724 | O | HOH | 707 | 101.778 | 67.697 | −5.655 | 1.00 | 34.92 | O |
| HETATM | 3725 | O | HOH | 709 | 136.699 | 62.881 | −10.241 | 1.00 | 53.86 | O |
| HETATM | 3726 | O | HOH | 710 | 115.523 | 70.686 | 9.393 | 1.00 | 35.01 | O |
| HETATM | 3727 | O | HOH | 714 | 140.987 | 80.163 | 24.272 | 1.00 | 65.37 | O |
| HETATM | 3728 | O | HOH | 715 | 144.845 | 70.181 | 8.359 | 1.00 | 45.96 | O |
| HETATM | 3729 | O | HOH | 716 | 127.420 | 64.712 | 10.814 | 1.00 | 50.93 | O |
| HETATM | 3730 | O | HbH | 717 | 112.586 | 85.955 | 35.733 | 1.00 | 63.37 | O |
| HETATM | 3731 | O | HOH | 718 | 96.397 | 65.225 | 43.866 | 1.00 | 54.78 | O |
| HETATM | 3732 | O | HOH | 719 | 149.381 | 55.765 | 8.190 | 1.00 | 46.95 | O |
| HETATM | 3733 | O | HOH | 723 | 115.502 | 77.990 | 9.376 | 1.00 | 46.76 | O |
| HETATM | 3734 | O | HOH | 725 | 76.437 | 79.568 | 26.459 | 1.00 | 59.19 | O |
| HETATM | 3735 | O | HOH | 726 | 95.324 | 49.183 | 27.259 | 1.00 | 51.94 | O |
| HETATM | 3736 | O | HOH | 727 | 111.936 | 82.375 | 12.461 | 1.00 | 38.86 | O |
| HETATM | 3737 | O | HOH | 728 | 133.312 | 81.928 | 11.453 | 1.00 | 51.26 | O |
| HETATM | 3738 | O | HOH | 729 | 107.996 | 85.280 | 18.442 | 1.00 | 39.71 | O |
| HETATM | 3739 | O | HOH | 730 | 148.848 | 63.651 | −10.490 | 1.00 | 48.09 | O |
| HETATM | 3740 | O | HOH | 733 | 134.306 | 63.018 | 10.766 | 1.00 | 31.65 | O |
| HETATM | 3741 | O | HOH | 735 | 124.671 | 60.360 | 17.610 | 1.00 | 52.69 | O |
| HETATM | 3742 | O | HOH | 736 | 111.727 | 60.489 | 42.963 | 1.00 | 62.15 | O |
| HETATM | 3743 | O | HOH | 737 | 134.980 | 50.157 | 7.477 | 1.00 | 60.92 | O |
| HETATM | 3744 | O | HOH | 738 | 146.654 | 76.277 | 6.833 | 1.00 | 40.87 | O |
| HETATM | 3745 | O | HOH | 739 | 89.251 | 64.149 | 19.814 | 1.00 | 33.88 | O |
| HETATM | 3746 | O | HOH | 741 | 105.433 | 55.341 | 8.828 | 1.00 | 58.55 | O |
| HETATM | 3747 | O | HOH | 749 | 88.458 | 78.199 | 19.817 | 1.00 | 66.31 | O |
| HETATM | 3748 | O | HOH | 750 | 106.898 | 44.639 | 18.376 | 1.00 | 56.87 | O |
| HETATM | 3749 | O | HOH | 751 | 105.309 | 68.078 | 49.132 | 1.00 | 66.24 | O |
| HETATM | 3750 | O | HOH | 752 | 92.980 | 48.934 | 17.873 | 1.00 | 42.58 | O |
| HETATM | 3751 | O | HOH | 753 | 100.420 | 53.758 | 15.446 | 1.00 | 60.31 | O |
| HETATM | 3752 | O | HOH | 754 | 120.798 | 66.196 | 40.717 | 1.00 | 66.93 | O |
| HETATM | 3753 | O | HOH | 755 | 108.406 | 89.679 | 12.448 | 1.00 | 61.48 | O |
| HETATM | 3754 | O | HOH | 757 | 132.463 | 72.528 | 4.509 | 1.00 | 59.31 | O |
| HETATM | 3755 | O | HOH | 761 | 127.038 | 77.545 | 21.661 | 1.00 | 47.91 | O |
| HETATM | 3756 | O | HOH | 762 | 106.459 | 50.413 | 17.617 | 1.00 | 59.90 | O |
| HETATM | 3757 | O | HOH | 765 | 119.622 | 72.534 | 26.691 | 1.00 | 51.38 | O |
| HETATM | 3758 | O | HOH | 766 | 11s.174 | 72.450 | 5.241 | 1.00 | 68.42 | O |
| HETATM | 3759 | O | HOH | 768 | 105.322 | 87.067 | 41.471 | 1.00 | 68.21 | O |
| HETATM | 3760 | O | HOH | 770 | 105.218 | 41.445 | 29.836 | 1.00 | 63.03 | O |
| HETATM | 3761 | O | HOH | 771 | 83.989 | 78.004 | 39.580 | 1.00 | 67.38 | O |

TABLE 7-continued

| | | | | | | | | | | |
|---|---|---|---|---|---|---|---|---|---|---|
| HETATM | 3762 | O | HOH | 772 | 148.829 | 67.245 | 20.069 | 1.00 | 44.56 | O |
| HETATM | 3763 | O | HOH | 773 | 106.544 | 84.270 | 11.229 | 1.00 | 40.15 | O |
| HETATM | 3764 | O | HOH | 775 | 105.699 | 39.006 | 23.992 | 1.00 | 68.38 | O |
| HETATM | 3765 | O | HOH | 778 | 114.007 | 85.900 | 33.916 | 1.00 | 42.88 | O |
| HETATM | 3766 | O | HOH | 780 | 93.889 | 60.095 | 23.291 | 1.00 | 62.44 | O |
| HETATM | 3767 | O | HOH | 781 | 129.215 | 73.681 | 21.887 | 1.00 | 37.93 | O |
| HETATM | 3768 | O | HOH | 787 | 81.781 | 76.779 | 28.784 | 1.00 | 61.15 | O |
| HETATN | 3769 | O | HOH | 788 | 147.918 | 62.639 | 14.966 | 1.00 | 39.80 | O |
| HETATM | 3770 | O | HOH | 789 | 79.084 | 63.731 | 35.792 | 1.00 | 60.46 | O |
| HETATM | 3771 | O | HOH | 791 | 106.162 | 72.361 | 37.935 | 1.00 | 51.27 | O |
| HETATM | 3772 | O | HOH | 793 | 113.985 | 72.209 | 7.836 | 1.00 | 54.33 | O |
| HETATM | 3773 | O | HOH | 794 | 147.561 | 84.941 | 11.984 | 1.00 | 59.95 | O |
| HETATM | 3774 | O | HOH | 796 | 117.356 | 86.976 | 18.333 | 1.00 | 57.65 | O |
| HETATM | 3775 | O | HOH | 797 | 96.398 | 58.891 | 24.526 | 1.00 | 48.25 | O |
| HETATM | 3776 | O | HOH | 799 | 113.947 | 81.311 | 24.929 | 1.00 | 48.99 | O |
| HETATM | 3777 | O | HOH | 800 | 130.861 | 56.862 | 14.557 | 1.00 | 67.81 | O |
| HETATM | 3778 | O | HOH | 803 | 136.966 | 56.000 | −10.559 | 1.00 | 66.93 | O |
| HETATM | 3779 | O | HOH | 807 | 120.744 | 54.584 | 40.505 | 1.00 | 65.23 | O |
| HETATM | 3780 | O | HOH | 809 | 111.191 | 79.767 | 14.798 | 1.00 | 39.00 | O |
| HETATM | 3781 | O | HOH | 810 | 100.504 | 80.761 | 16.287 | 1.00 | 40.40 | O |
| HETATM | 3782 | O | HOH | 812 | 119.309 | 46.953 | 19.630 | 1.00 | 58.74 | O |
| HETATM | 3783 | O | HOH | 817 | 79.924 | 78.741 | 21.466 | 1.00 | 62.43 | O |
| HETATM | 3784 | O | HOH | 819 | 114.995 | 48.374 | 8.804 | 1.00 | 68.51 | O |
| HETATM | 3785 | O | HOH | 823 | 121.219 | 69.376 | 9.088 | 1.00 | 61.14 | O |
| HETATM | 3786 | O | HOH | 824 | 83.259 | 52.990 | 49.620 | 1.00 | 42.61 | O |
| HETATM | 3787 | O | HOH | 826 | 73.121 | 53.007 | 46.366 | 1.00 | 51.95 | O |
| HETATM | 3788 | O | HOH | 829 | 125.131 | 57.072 | 24.888 | 1.00 | 43.39 | O |
| HETATM | 3789 | O | HOH | 830 | 117.478 | 81.142 | 25.399 | 1.00 | 63.97 | O |
| HETATM | 3790 | O | HOH | 832 | 118.060 | 80.843 | 9.442 | 1.00 | 68.90 | O |
| HETATM | 3791 | O | HOH | 833 | 125.309 | 81.768 | 10.259 | 1.00 | 36.71 | O |
| HETATM | 3792 | O | HOH | 834 | 106.669 | 69.383 | 1.728 | 1.00 | 62.38 | O |
| HETATM | 3793 | O | HOH | 836 | 134.415 | 57.557 | 20.513 | 1.00 | 51.26 | O |
| HETATM | 3794 | O | HOH | 837 | 138.774 | 48.063 | 14.052 | 1.00 | 62.75 | O |
| HETATM | 3795 | O | HOH | 838 | 105.034 | 90.698 | 36.793 | 1.00 | 43.22 | O |
| HETATM | 3796 | O | HOH | 839 | 94.179 | 62.599 | 22.253 | 1.00 | 39.73 | O |
| HETATM | 3797 | O | HOH | 840 | 102.012 | 56.721 | 46.229 | 1.00 | 49.59 | O |
| HETATM | 3798 | O | HOH | 842 | 129.445 | 55.023 | 4.305 | 1.00 | 44.96 | O |
| HETATM | 3799 | O | HOH | 843 | 95.363 | 50.937 | 5.969 | 1.00 | 60.45 | O |
| HETATM | 3800 | O | HOH | 847 | 148.499 | 52.780 | 8.080 | 1.00 | 60.01 | O |
| HETATM | 3801 | O | HOH | 852 | 90.466 | 70.795 | 38.792 | 1.00 | 60.50 | O |
| HETATM | 3802 | O | HOH | 853 | 138.576 | 76.612 | 2.592 | 1.00 | 62.24 | O |
| HETATM | 3803 | O | HOH | 855 | 116.588 | 74.760 | 7.223 | 1.00 | 60.72 | O |
| HETATM | 3804 | O | HOH | 860 | 113.703 | 91.874 | 24.531 | 1.00 | 68.47 | O |
| HETATM | 3805 | O | HOH | 861 | 130.923 | 52.830 | 6.921 | 1.00 | 62.84 | O |
| HETATM | 3806 | O | HOH | 862 | 142.316 | 48.653 | 13.579 | 1.00 | 50.41 | O |
| HETATM | 3807 | O | HOH | 863 | 132.567 | 53.947 | 3.095 | 1.00 | 68.97 | O |
| HETATM | 3808 | O | HOH | 865 | 100.473 | 47.680 | 26.060 | 1.00 | 65.28 | O |
| HETATM | 3809 | O | HOH | 866 | 133.655 | 75.864 | 1.041 | 1.00 | 69.12 | O |
| HETATM | 3810 | O | HOH | 867 | 122.519 | 76.254 | 7.931 | 1.00 | 61.12 | O |
| HETATM | 3811 | O | HOH | 868 | 84.905 | 74.842 | 20.730 | 1.00 | 46.62 | O |
| HETATM | 3812 | O | HOH | 869 | 148.011 | 52.884 | 0.797 | 1.00 | 66.79 | O |
| HETATM | 3813 | O | HOH | 872 | 94.647 | 87.503 | 38.810 | 1.00 | 38.25 | O |
| HETATM | 3814 | O | HOH | 873 | 101.350 | 92.083 | 26.520 | 1.00 | 62.62 | O |
| HETATM | 3815 | O | HOH | 875 | 126.984 | 55.912 | −0.651 | 1.00 | 69.71 | O |
| HETATM | 3816 | O | HOH | 878 | 127.346 | 68.643 | 12.063 | 1.00 | 33.35 | O |
| HETATM | 3817 | O | HOH | 879 | 117.590 | 70.113 | 8.367 | 1.00 | 32.01 | O |
| HETATM | 3818 | O | HOH | 884 | 94.685 | 91.830 | 3.118 | 1.00 | 53.98 | O |
| HETATM | 3819 | O | HOM | 886 | 94.421 | 91.554 | 39.231 | 1.00 | 35.13 | O |
| HETATM | 3820 | O | HOH | 887 | 90.370 | 90.226 | 5.222 | 1.00 | 36.45 | O |
| HETATM | 3821 | O | HOH | 888 | 138.171 | 82.094 | 23.696 | 1.00 | 43.62 | O |
| HETATM | 3822 | O | HOH | 890 | 145.344 | 74.873 | 18.144 | 1.00 | 52.45 | O |
| HETATM | 3823 | C | HOH | 891 | 86.699 | 56.553 | 44.193 | 1.00 | 59.80 | O |
| HETATM | 3824 | O | HOH | 895 | 110.253 | 51.388 | 39.073 | 1.00 | 64.37 | O |
| HETATM | 3825 | O | HOH | 899 | 142.548 | 59.418 | 25.624 | 1.00 | 68.03 | O |
| HETATM | 3826 | O | HOH | 902 | 96.309 | 63.463 | 47.551 | 1.00 | 68.27 | O |
| HETATM | 3827 | O | HOH | 904 | 103.052 | 43.719 | 26.788 | 1.00 | 64.56 | O |
| HETATM | 3828 | O | HOH | 905 | 148.314 | 72.538 | 19.514 | 1.00 | 53.02 | O |
| HETATM | 3829 | O | HOH | 906 | 115.081 | 80.764 | 15.768 | 1.00 | 37.40 | O |
| HETATM | 3830 | O | HOH | 907 | 111.660 | 74.882 | 5.430 | 1.00 | 36.15 | O |
| HETATM | 3831 | O | HOH | 908 | 91.410 | 88.940 | 39.058 | 1.00 | 40.21 | O |
| HETATM | 3832 | O | HOH | 909 | 92.100 | 65.397 | 41.837 | 1.00 | 42.61 | O |
| HETATM | 3833 | O | HOH | 910 | 135.015 | 70.210 | 22.164 | 1.00 | 32.10 | O |
| HETATM | 3834 | O | HOH | 911 | 124.196 | 60.165 | 24.502 | 1.00 | 68.95 | O |
| HETATM | 3835 | O | HOH | 912 | 104.972 | 48.595 | 38.399 | 1.00 | 50.34 | O |
| HETATM | 3836 | O | HOH | 913 | 143.458 | 60.042 | 28.053 | 1.00 | 36.04 | O |
| HETATM | 3837 | O | HOH | 916 | 101.435 | 59.347 | 18.933 | 1.00 | 50.24 | O |
| HETATM | 3838 | O | HOH | 917 | 112.207 | 49.761 | 38.732 | 1.00 | 26.79 | O |
| HETATM | 3839 | O | HOH | 918 | 129.684 | 70.406 | 8.637 | 1.00 | 46.40 | O |
| HETATM | 3840 | O | HOH | 921 | 80.125 | 93.172 | 15.865 | 1.00 | 52.80 | O |

TABLE 7-continued

| | | | | | | | | | | |
|---|---|---|---|---|---|---|---|---|---|---|
| HETATM | 3841 | O | HOH | 922 | 149.474 | 69.335 | 14.961 | 1.00 | 54.64 | O |
| HETATM | 3842 | O | HOH | 926 | 102.735 | 61.951 | 20.408 | 1.00 | 35.26 | O |
| HETATM | 3843 | O | HOH | 927 | 70.905 | 53.569 | 44.583 | 1.00 | 70.52 | O |
| HETATM | 3844 | O | HOH | 929 | 114.913 | 79.874 | 33.698 | 1.00 | 57.49 | O |
| HETATM | 3845 | O | HOH | 930 | 150.193 | 75.660 | 8.945 | 1.00 | 35.94 | O |
| HETATM | 3846 | O | HOH | 931 | 108.648 | 54.745 | 43.966 | 1.00 | 62.03 | O |
| HETATM | 3847 | O | HOH | 936 | 121.915 | 58.864 | 24.758 | 1.00 | 55.08 | O |
| HETATM | 3848 | O | HOH | 937 | 79.417 | 58.337 | 48.896 | 1.00 | 68.62 | O |
| HETATM | 3849 | O | HOH | 938 | 113.378 | 43.843 | 23.780 | 1.00 | 41.09 | O |
| HETATM | 3850 | O | HOH | 939 | 120.219 | 59.743 | 27.131 | 1.00 | 44.37 | O |
| HETATM | 3851 | O | HOH | 941 | 105.234 | 64.396 | −0.669 | 1.00 | 73.28 | O |
| HETATM | 3852 | O | HOH | 942 | 141.057 | 80.868 | −0.762 | 1.00 | 67.90 | O |
| HETATM | 3853 | O | HOH | 944 | 119.413 | 75.184 | 6.755 | 1.00 | 98.67 | O |
| HETATM | 3854 | O | HOH | 945 | 95.626 | 74.384 | 14.294 | 1.00 | 63.69 | O |
| HETATM | 3855 | O | HOH | 946 | 95.387 | 53.160 | 20.326 | 1.00 | 59.76 | O |
| HETATM | 3856 | O | HOH | 947 | 112.354 | 72.038 | 3.479 | 1.00 | 55.13 | O |
| HETATM | 3857 | O | HOH | 961 | 116.417 | 63.126 | 34.645 | 1.00 | 53.04 | O |
| HETATM | 3858 | O | HOH | 962 | 91.960 | 70.760 | 43.791 | 1.00 | 62.09 | O |
| HETATM | 3859 | O | HOH | 964 | 80.831 | 84.466 | 14.233 | 1.00 | 66.83 | O |
| HETATM | 3860 | O | HOH | 966 | 111.313 | 64.422 | 5.416 | 1.00 | 43.56 | O |
| HETATM | 3861 | O | HOH | 968 | 133.045 | 80.261 | 24.904 | 1.00 | 59.86 | O |
| HETATM | 3862 | O | HOH | 971 | 113.856 | 45.592 | 40.153 | 1.00 | 68.81 | O |
| HETATM | 3863 | O | HOH | 973 | 149.882 | 57.333 | 6.661 | 1.00 | 61.17 | O |
| HETATM | 3864 | O | HOH | 974 | 114.479 | 45.337 | 23.893 | 1.00 | 48.82 | O |
| HETATM | 3865 | O | HOH | 976 | 122.683 | 49.979 | 23.699 | 1.00 | 54.50 | O |
| HETATM | 3866 | O | HOH | 977 | 107.449 | 93.037 | 22.262 | 1.00 | 67.52 | O |
| HETATM | 3867 | O | HOH | 980 | 71.623 | 55.665 | 43.963 | 1.00 | 50.43 | O |
| HETATM | 3868 | O | HOH | 983 | 81.115 | 79.690 | 16.340 | 1.00 | 68.34 | O |
| HETATM | 3869 | O | HOH | 984 | 146.095 | 68.641 | 21.063 | 1.00 | 40.33 | O |
| HETATM | 3870 | O | HOH | 989 | 84.591 | 87.656 | 11.809 | 1.00 | 61.62 | O |
| HETATM | 3871 | O | HOH | 990 | 101.284 | 84.890 | 35.573 | 1.00 | 66.53 | O |
| HETATM | 3872 | O | HOH | 991 | 132.290 | 57.405 | 16.338 | 1.00 | 66.86 | O |
| HETATM | 3873 | O | HOH | 992 | 107.181 | 71.461 | 43.131 | 1.00 | 68.43 | O |
| HETATM | 3874 | O | HOH | 996 | 121.732 | 77.353 | 22.459 | 1.00 | 56.10 | O |
| HETATM | 3875 | O | HOH | 997 | 123.339 | 62.223 | 9.181 | 1.00 | 53.79 | O |
| HETATM | 3876 | O | HOH | 999 | 118.564 | 57.129 | 2.150 | 1.00 | 64.38 | O |
| HETATM | 3877 | O | HOH | 1002 | 113.406 | 85.261 | 25.792 | 1.00 | 54.44 | O |
| HETATM | 3876 | O | HOH | 1003 | 132.676 | 51.930 | 17.206 | 1.00 | 68.65 | O |
| HETATM | 3879 | O | HOH | 1006 | 82.100 | 75.518 | 31.280 | 1.00 | 51.37 | O |
| HETATM | 3880 | O | HOH | 1007 | 91.217 | 86.172 | 10.703 | 1.00 | 68.50 | O |
| HETATM | 3881 | O | HOH | 1011 | 148.150 | 63.664 | −4.949 | 1.00 | 66.39 | O |
| HETATM | 3882 | O | HOH | 1012 | 108.584 | 47.618 | 13.690 | 1.00 | 63.35 | O |
| HETATM | 3883 | O | HOH | 1014 | 104.916 | 54.259 | 6.694 | 1.00 | 66.63 | O |
| HETATM | 3884 | O | HOH | 1021 | 127.338 | 67.350 | −0.507 | 1.00 | 68.51 | O |
| HETATM | 3885 | O | HOH | 1024 | 100.255 | 43.755 | 35.224 | 1.00 | 49.55 | O |
| HETATM | 3886 | O | HOH | 1026 | 113.002 | 85.034 | 18.817 | 1.00 | 68.03 | O |
| HETATM | 3887 | O | HOH | 1027 | 74.446 | 56.955 | 41.184 | 1.00 | 34.26 | O |
| HETATM | 3888 | O | HOH | 1032 | 123.923 | 66.490 | 27.749 | 1.00 | 51.93 | O |
| HETATM | 3889 | O | HOH | 1037 | 105.661 | 94.018 | 14.310 | 1.00 | 48.05 | O |
| HETATM | 3890 | O | HOH | 1045 | 85.110 | 67.600 | 42.845 | 1.00 | 61.60 | O |
| HETATM | 3891 | O | HOH | 1049 | 72.485 | 57.802 | 45.989 | 1.00 | 68.63 | O |
| HETATM | 3892 | O | HOH | 1051 | 104.785 | 74.784 | 39.154 | 1.00 | 60.69 | C |
| HETATM | 3893 | O | HOH | 1053 | 104.639 | 40.347 | 24.518 | 1.00 | 61.31 | O |
| HETATM | 3894 | O | HOH | 1054 | 142.840 | 80.523 | 20.021 | 1.00 | 68.20 | O |
| HETATM | 3895 | O | HOH | 1056 | 123.658 | 55.426 | 39.072 | 1.00 | 68.01 | O |
| HETATM | 3896 | O | HOH | 1057 | 122.409 | 54.809 | 6.777 | 1.00 | 68.72 | O |
| HETATM | 3897 | O | HOH | 1060 | 148.405 | 75.478 | 20.015 | 1.00 | 68.99 | O |
| HETATM | 3898 | O | HOH | 1066 | 101.285 | 46.434 | 21.329 | 1.00 | 69.66 | O |
| HETATM | 3899 | O | HOH | 1068 | 101.265 | 47.738 | 38.183 | 1.00 | 52.34 | O |
| HETATM | 3900 | O | HOH | 1072 | 116.191 | 83.171 | 15.683 | 1.00 | 63.11 | O |
| HETATM | 3901 | O | HOH | 1076 | 124.162 | 83.118 | 19.379 | 1.00 | 65.19 | O |
| HETATM | 3902 | O | HOH | 1077 | 114.649 | 91.913 | 27.612 | 1.00 | 63.68 | O |
| HETATM | 3903 | O | HOH | 1078 | 131.138 | 72.022 | 1.639 | 1.00 | 65.80 | O |
| HETATM | 3904 | O | HOH | 1079 | 104.565 | 95.248 | 23.931 | 1.00 | 67.66 | O |
| HETATM | 3905 | O | HOH | 1080 | 130.600 | 83.061 | 14.460 | 1.00 | 68.73 | O |
| HETATM | 3906 | O | HOH | 1081 | 108.024 | 57.385 | 44.494 | 1.00 | 68.47 | O |
| HETATM | 3907 | O | HOH | 1089 | 98.180 | 52.040 | 22.425 | 1.00 | 57.82 | O |
| HETATM | 3908 | O | HOH | 1095 | 123.035 | 48.662 | 12.121 | 1.00 | 49.75 | O |
| HETATM | 3909 | O | HOH | 1100 | 116.951 | 82.153 | 13.434 | 1.00 | 47.33 | O |
| HETATM | 3910 | O | HOH | 1109 | 93.000 | 74.011 | 11.563 | 1.00 | 65.00 | O |
| HETATM | 3911 | O | HOH | 1110 | 84.826 | 60.423 | 43.980 | 1.00 | 68.47 | O |
| HETATM | 3912 | O | HOH | 1114 | 95.995 | 48.302 | 8.024 | 1.00 | 46.89 | O |
| HETATM | 3913 | O | HOH | 1115 | 146.331 | 50.245 | −5.119 | 1.00 | 55.03 | O |
| HETATM | 3914 | O | HOH | 1117 | 93.037 | 80.264 | 22.271 | 1.00 | 36.08 | O |
| HETATM | 3915 | O | HOH | 1118 | 127.120 | 59.841 | 19.240 | 1.00 | 36.51 | O |
| HETATM | 3916 | O | HOH | 1123 | 130.326 | 80.122 | 18.283 | 1.00 | 54.14 | O |
| HETATM | 3917 | O | HOH | 1127 | 122.797 | 71.467 | 7.444 | 1.00 | 61.33 | O |
| HETATM | 3918 | O | HOH | 1128 | 86.326 | 63.775 | 40.835 | 1.00 | 65.83 | O |
| HETATM | 3919 | O | HOH | 1129 | 129.934 | 60.674 | 26.265 | 1.00 | 67.06 | O |

TABLE 7-continued

| | | | | | | | | | | |
|---|---|---|---|---|---|---|---|---|---|---|
| HETATM | 3920 | O | HOH | 1132 | 91.126 | 55.593 | 11.580 | 1.00 | 55.91 | O |
| HETATM | 3921 | O | HOH | 1136 | 131.604 | 57.222 | −9.584 | 1.00 | 62.55 | O |
| HETATM | 3922 | O | HOH | 1137 | 122.963 | 68.163 | 16.106 | 1.00 | 33.32 | O |
| HETATM | 3923 | O | HOH | 1140 | 107.890 | 88.486 | 9.887 | 1.00 | 61.56 | C |
| HETATM | 3924 | O | HOH | 1142 | 143.969 | 58.642 | −10.289 | 1.00 | 69.08 | O |
| HETATM | 3925 | O | HOH | 1143 | 88.527 | 78.564 | −1.195 | 1.00 | 66.36 | O |
| HETATM | 3926 | O | HOH | 1146 | 109.850 | 50.598 | 43.199 | 1.00 | 64.27 | O |
| HETATM | 3927 | O | HOH | 1151 | 112.701 | 76.952 | 6.277 | 1.00 | 55.30 | O |
| HETATM | 3928 | O | HOH | 1154 | 102.564 | 50.394 | 12.484 | 1.00 | 59.53 | O |
| HETATM | 3929 | O | HOH | 1161 | 95.856 | 79.770 | 13.615 | 1.00 | 60.09 | O |
| HETATM | 3930 | O | HOH | 1162 | 149.220 | 72.694 | 15.463 | 1.00 | 36.11 | O |
| HETATM | 3931 | O | HOH | 1167 | 134.026 | 86.608 | 28.831 | 1.00 | 55.75 | O |
| HETATM | 3932 | O | HOH | 1168 | 137.288 | 47.676 | −0.383 | 1.00 | 58.53 | O |
| HETATM | 3933 | O | HOH | 1169 | 96.461 | 76.369 | −1.039 | 1.00 | 40.84 | O |
| HETATM | 3934 | O | HOH | 1170 | 146.839 | 76.924 | 18.226 | 1.00 | 62.40 | O |
| HETATM | 3935 | O | HOH | 1173 | 84.778 | 62.413 | 46.009 | 1.00 | 56.40 | O |
| HETATM | 3936 | O | HOH | 1174 | 104.665 | 61.328 | −0.147 | 1.00 | 68.18 | O |
| HETATM | 3937 | O | HOH | 1176 | 148.238 | 49.557 | 15.253 | 1.00 | 68.84 | O |
| HETATM | 3938 | O | HOH | 1180 | 96.826 | 57.686 | 5.466 | 1.00 | 68.82 | O |
| HETATM | 3939 | O | HOH | 1181 | 97.848 | 45.596 | 18.230 | 1.00 | 68.53 | O |
| HETATM | 3940 | O | HOH | 1183 | 105.561 | 78.152 | 46.280 | 1.00 | 55.13 | O |
| HETATM | 3941 | O | HOH | 1184 | 148.363 | 55.663 | 18.453 | 1.00 | 67.78 | O |
| HETATM | 3942 | O | HOH | 1188 | 117.761 | 72.763 | 3.201 | 1.00 | 49.39 | O |
| HETATM | 3943 | O | HOH | 1190 | 129.206 | 55.861 | −5.442 | 1.00 | 69.86 | O |
| HETATM | 3944 | O | HOH | 1195 | 107.481 | 76.284 | 39.087 | 1.00 | 57.19 | O |
| HETATM | 3945 | O | HOH | 1206 | 122.685 | 66.549 | 4.934 | 1.00 | 62.97 | O |
| HETATM | 3946 | O | HOH | 1207 | 150.879 | 41.867 | 5.427 | 1.00 | 67.80 | O |
| HETATM | 3947 | O | HOH | 1216 | 134.077 | 45.934 | 8.123 | 1.00 | 68.54 | O |
| HETATM | 3948 | O | HOH | 1217 | 92.702 | 54.498 | 4.335 | 1.00 | 68.29 | O |
| HETATM | 3949 | O | HOH | 1227 | 133.307 | 89.606 | 16.031 | 1.00 | 55.60 | O |
| HETATM | 3950 | O | HOH | 1228 | 145.314 | 58.907 | 23.524 | 1.00 | 57.48 | O |
| HETATM | 3951 | O | HOH | 1231 | 121.333 | 47.473 | 28.343 | 1.00 | 42.57 | O |
| HETATM | 3952 | O | HOH | 1237 | 80.672 | 64.102 | 43.307 | 1.00 | 62.67 | O |
| HETATM | 3953 | O | HOH | 1239 | 79.197 | 76.085 | 29.202 | 1.00 | 42.02 | O |
| HETATM | 3954 | O | HOH | 1240 | 147.532 | 79.940 | 6.435 | 1.00 | 49.20 | O |
| HETATM | 3955 | O | HOH | 1241 | 105.341 | 73.622 | 43.925 | 1.00 | 46.80 | O |
| HETATM | 3956 | O | HOH | 1242 | 108.748 | 84.315 | 11.317 | 1.00 | 43.50 | O |
| HETATM | 3957 | O | HOH | 1243 | 113.748 | 76.205 | 13.481 | 1.00 | 31.05 | O |
| HETATM | 3958 | O | HOH | 1244 | 106.486 | 82.249 | 41.211 | 1.00 | S3.73 | O |
| HETATM | 3959 | O | HOH | 1245 | 123.229 | 67.990 | 30.863 | 1.00 | 67.62 | O |
| HETATM | 3960 | O | HOH | 1246 | 97.244 | 56.293 | 3.245 | 1.00 | 59.53 | O |
| HETATM | 3961 | O | HOH | 1247 | 84.115 | 75.748 | 18.158 | 1.00 | 47.44 | O |
| HETATM | 3962 | O | HOH | 1248 | 92.641 | 62.480 | 43.494 | 1.00 | 56.54 | O |
| HETATM | 3963 | O | HOH | 1249 | 126.850 | 67.707 | 7.524 | 1.00 | 63.22 | O |
| HETATM | 3964 | O | HOH | 1250 | 116.737 | 46.525 | 9.414 | 1.00 | 60.31 | O |
| HETATM | 3965 | O | HOH | 1251 | 99.435 | 55.524 | 20.442 | 1.00 | 68.76 | O |
| HETATM | 3966 | O | HOH | 1252 | 93.533 | 48.432 | 11.284 | 1.00 | 64.31 | O |
| HETATM | 3967 | O | HOH | 1253 | 115.458 | 55.820 | 8.527 | 1.00 | 68.91 | O |
| HETATM | 3968 | O | HOH | 1254 | 94.383 | 48.132 | 30.166 | 1.00 | 55.54 | O |
| HETATM | 3969 | O | HOH | 1255 | 136.004 | 53.964 | 17.602 | 1.00 | 50.55 | O |
| HETATM | 3970 | O | HOH | 1256 | 97.765 | 60.337 | 0.278 | 1.00 | 67.66 | O |
| HETATM | 3971 | O | HOH | 1257 | 81.887 | 70.128 | 40.015 | 1.00 | 60.06 | O |
| HETATM | 3972 | O | HOH | 1258 | 98.568 | 43.853 | 36.969 | 1.00 | 60.96 | O |
| HETATM | 3973 | O | HOH | 1259 | 102.312 | 50.226 | 23.207 | 1.00 | 69.15 | O |
| HETATM | 3974 | O | HOH | 1260 | 93.845 | 73.542 | 7.463 | 1.00 | 62.17 | O |
| HETATM | 3975 | O | HOH | 1261 | 122.247 | 50.835 | 30.996 | 1.00 | 66.32 | O |
| HETATM | 3976 | O | HOH | 1262 | 137.839 | 46.740 | 1.638 | 1.00 | 44.22 | O |
| HETATM | 3977 | O | HOH | 1263 | 107.295 | 79.492 | 3.520 | 1.00 | 56.86 | O |
| HETATM | 3978 | O | HOH | 1264 | 108.339 | 49.640 | 21.504 | 1.00 | 48.82 | O |
| HETATM | 3979 | O | HOH | 1265 | 105.132 | 63.518 | 48.797 | 1.00 | 62.13 | O |
| HETATM | 3960 | O | HOH | 1266 | 139.420 | 62.113 | 23.787 | 1.00 | 50.94 | O |
| HETATM | 3981 | O | HOH | 1267 | 144.043 | 77.286 | 3.516 | 1.00 | 68.14 | O |
| HETATM | 3982 | O | HOH | 1268 | 149.733 | 53.900 | 4.381 | 1.00 | 56.17 | O |
| HETATM | 3983 | O | HOH | 1269 | 103.004 | 91.675 | 22.454 | 1.00 | 51.28 | O |
| HETATM | 3984 | O | HOH | 1270 | 102.342 | 79.977 | 8.282 | 1.00 | 60.86 | O |
| HETATM | 3985 | O | HOH | 1271 | 104.432 | 79.198 | 8.137 | 1.00 | 49.45 | O |
| HETATM | 3986 | O | HOH | 1272 | 96.642 | 78.325 | 15.154 | 1.00 | 49.69 | O |
| HETATM | 3987 | O | HOH | 1273 | 123.113 | 83.532 | 10.129 | 1.00 | 46.69 | O |
| HETATM | 3988 | O | HOH | 1274 | 108.924 | 75.712 | 35.457 | 1.00 | 44.24 | O |
| HETATM | 3989 | O | HOH | 1275 | 120.284 | 52.133 | 13.839 | 1.00 | 49.42 | O |
| HETATM | 3990 | O | HOH | 1276 | 153.804 | 67.675 | 3.008 | 1.00 | 68.53 | C |
| HETATM | 3991 | O | HOH | 1277 | 132.756 | 49.791 | 2.618 | 1.00 | 54.77 | O |
| HETATM | 3992 | O | HOH | 1278 | 123.687 | 61.097 | −1.686 | 1.00 | 66.47 | O |
| HETATM | 3993 | O | HOH | 1279 | 79.098 | 85.995 | 16.502 | 1.00 | 68.34 | O |
| HETATM | 3994 | O | HOH | 1280 | 81.604 | 77.273 | 22.663 | 1.00 | 51.85 | O |
| HETATM | 3995 | O | HOH | 1281 | 97.665 | 46.523 | 21.377 | 1.00 | 66.98 | O |
| HETATM | 3996 | O | HOH | 1282 | 124.226 | 53.393 | 42.604 | 1.00 | 56.65 | O |
| HETATM | 3997 | O | HOH | 1283 | 70.053 | 51.433 | 45.374 | 1.00 | 31.76 | O |
| HETATM | 3998 | O | HOH | 1284 | 133.004 | 59.283 | 22.298 | 1.00 | 51.14 | O |

TABLE 7-continued

| | | | | | | | | | | |
|---|---|---|---|---|---|---|---|---|---|---|
| HETATM | 3999 | O | HOH | 1285 | 110.435 | 58.745 | 9.141 | 1.00 | 66.24 | O |
| HETATM | 4000 | O | M0H | 1286 | 131.690 | 83.699 | 10.424 | 1.00 | 50.89 | O |
| HETATM | 4001 | O | HOH | 1287 | 87.121 | 83.954 | 6.897 | 1.00 | 61.10 | O |
| HETATM | 4002 | O | HOH | 1289 | 103.343 | 70.654 | 47.251 | 1.00 | 59.87 | O |
| HETATM | 4003 | O | HOH | 1290 | 151.878 | 57.545 | 4.368 | 1.00 | 68.93 | O |
| HETATM | 4004 | O | HOH | 1291 | 109.757 | 52.533 | 5.140 | 1.00 | 68.61 | O |
| HETATM | 4005 | O | HOH | 1292 | 137.500 | 85.244 | 14.713 | 1.00 | 48.53 | O |
| HETATM | 4006 | O | HOH | 1293 | 99.481 | 43.592 | 30.277 | 1.00 | 56.76 | O |
| HETATM | 4007 | O | HOH | 1294 | 79.393 | 66.499 | 44.205 | 1.00 | 51.03 | O |
| HETATM | 4008 | O | HOH | 1295 | 93.025 | 76.731 | 12.952 | 1.00 | 68.06 | O |
| HETATM | 4009 | O | HOH | 1296 | 104.177 | 39.636 | 37.064 | 1.00 | 66.28 | O |
| HETATM | 4010 | C | HOH | 1297 | 131.482 | 71.092 | 26.769 | 1.00 | 63.53 | O |
| HETATM | 4011 | O | HOH | 1299 | 108.732 | 64.733 | 46.862 | 1.00 | 59.61 | O |
| HETATM | 4012 | O | HOH | 1300 | 85.693 | 84.234 | 8.773 | 1.00 | 61.29 | O |
| HETATM | 4013 | O | HOH | 1301 | 130.439 | 55.137 | 19.928 | 1.00 | 68.52 | O |
| HETATM | 4014 | O | HOH | 1302 | 126.942 | 81.225 | 22.497 | 1.00 | 68.12 | O |
| HETATM | 4015 | O | HOH | 1303 | 85.867 | 53.208 | 45.199 | 1.00 | 54.32 | O |
| HETATM | 4016 | O | HOH | 1304 | 104.487 | 89.634 | 40.115 | 1.00 | 64.91 | O |
| HETATM | 4017 | O | HOH | 1305 | 106.217 | 68.163 | −1.625 | 1.00 | 55.54 | O |
| HETATM | 4018 | O | HOH | 1306 | 105.015 | 51.028 | 40.376 | 1.00 | 45.33 | O |
| HETATM | 4019 | O | HOH | 1307 | 120.170 | 70.835 | 39.052 | 1.00 | 58.73 | O |
| HETATM | 4020 | O | HOH | 1308 | 121.326 | 61.115 | 30.539 | 1.00 | 67.23 | O |
| HETATM | 4021 | O | HOH | 1309 | 107.923 | 60.643 | 46.488 | 1.00 | 69.06 | O |
| HETATM | 4022 | O | HOH | 1310 | 78.786 | 53.486 | 48.325 | 1.00 | 55.45 | O |
| HETATM | 4023 | O | HOH | 1311 | 130.804 | 55.401 | 22.465 | 1.00 | 59.73 | O |
| HETATM | 4024 | O | HOH | 1312 | 150.487 | 50.345 | 12.892 | 1.00 | 61.66 | O |
| HETATM | 4025 | O | HOH | 1313 | 100.834 | 38.834 | 32.531 | 1.00 | 62.67 | O |
| HETATM | 4026 | O | HOH | 1314 | 111.244 | 65.102 | 1.801 | 1.00 | 68.69 | O |
| HETATM | 4027 | O | HOH | 1315 | 132.117 | 79.062 | 22.385 | 1.00 | 40.28 | O |
| HETATM | 4025 | O | HOH | 1316 | 91.048 | 57.371 | 42.981 | 1.00 | 57.35 | O |
| HETATM | 4029 | O | HOH | 1317 | 144.712 | 49.327 | 0.134 | 1.00 | 49.54 | O |
| HETATM | 4030 | O | HOH | 1318 | 147.789 | 61.584 | −9.156 | 1.00 | 68.51 | C |
| HETATM | 4031 | O | HOH | 1319 | 123.090 | 61.674 | 6.437 | 1.00 | 69.05 | C |
| HETATM | 4032 | O | HOH | 1320 | 116.358 | 60.623 | 35.690 | 1.00 | 69.30 | O |
| HETATM | 4033 | O | HOH | 1321 | 113.530 | 91.177 | 21.954 | 1.00 | 52.62 | O |
| HETATM | 4034 | O | HOH | 1322 | 110.177 | 74.769 | 14.221 | 1.00 | 65.83 | O |
| HETATM | 4035 | O | HOH | 1323 | 135.219 | 50.902 | −6.112 | 1.00 | 68.00 | O |
| HETATM | 4036 | O | HOH | 1324 | 121.026 | 52.096 | 9.382 | 1.00 | 68.04 | O |
| HETATM | 4037 | O | HOH | 1325 | 86.410 | 84.214 | 10.939 | 1.00 | 54.69 | O |
| HETATM | 4036 | O | HOH | 1326 | 92.066 | 62.207 | −0.340 | 1.00 | 62.69 | O |
| HETATM | 4039 | O | HOH | 1327 | 108.159 | 72.272 | 1.047 | 1.00 | 69.41 | C |
| HETATM | 4040 | O | HOH | 1328 | 136.575 | 47.899 | 9.387 | 1.00 | 67.46 | O |
| HETATM | 4041 | O | HOH | 1329 | 112.693 | 55.745 | 39.945 | 1.00 | 50.31 | O |
| HETATM | 4042 | O | HOH | 1330 | 142.437 | 65.379 | −12.250 | 1.00 | 63.99 | O |
| HETATM | 4043 | O | HOH | 1331 | 97.845 | 53.121 | 3.695 | 1.00 | 68.33 | O |
| HETATM | 4044 | O | HOH | 1332 | 135.048 | 60.985 | 20.232 | 1.00 | 43.95 | O |
| HETATM | 4045 | O | HOH | 1334 | 131.683 | 75.485 | 22.258 | 1.00 | 35.53 | O |
| HETATM | 4046 | O | HOH | 1335 | 105.140 | 83.991 | 8.520 | 1.00 | 63.09 | O |
| HETATM | 4047 | C | HOH | 1336 | 119.421 | 70.763 | 31.673 | 1.00 | 42.24 | O |
| HETATM | 4048 | O | HOH | 1337 | 100.568 | 48.021 | 23.330 | 1.00 | 49.89 | O |
| HETATM | 4049 | O | HOH | 1338 | 133.982 | 54.355 | 16.339 | 1.00 | 62.13 | O |
| HETATM | 4050 | O | HOH | 1339 | 139.885 | 47.835 | 4.658 | 1.00 | 63.64 | O |
| HETATM | 4051 | O | HOH | 1340 | 150.581 | 62.937 | 15.908 | 1.00 | 63.60 | O |
| HETATM | 4052 | O | HOH | 1341 | 152.210 | 51.862 | 8.757 | 1.00 | 61.88 | O |
| HETATM | 4053 | C | HOH | 1342 | 92.864 | 62.277 | 3.434 | 1.00 | 57.80 | O |
| HETATM | 4054 | O | HOH | 1343 | 111.310 | 79.489 | 44.276 | 1.00 | 67.97 | O |
| HETATM | 4055 | O | HOH | 1344 | 149.427 | 48.324 | 7.299 | 1.00 | 59.90 | O |
| HETATM | 4056 | O | HOH | 1345 | 111.003 | 79.259 | 3.914 | 1.00 | 66.53 | O |
| HETATM | 4057 | O | HOH | 1346 | 116.893 | 54.202 | 7.477 | 1.00 | 47.23 | O |
| HETATM | 4058 | O | HOH | 1347 | 86.047 | 83.848 | 13.378 | 1.00 | 53.04 | O |
| HETATM | 4059 | O | HOH | 1348 | 117.820 | 76.586 | 7.356 | 1.00 | 57.31 | O |
| HETATM | 4060 | O | HOH | 1349 | 111.270 | 97.127 | 33.425 | 1.00 | 48.23 | O |
| HETATM | 4061 | O | HOH | 1350 | 129.000 | 77.928 | 24.673 | 1.00 | 44.60 | O |
| HETATM | 4062 | O | HOH | 1351 | 124.726 | 89.092 | 16.877 | 1.00 | 59.34 | O |
| HETATM | 4063 | O | HOH | 1352 | 93.181 | 64.700 | 49.080 | 1.00 | 52.82 | O |
| HETATM | 4064 | O | HOH | 1353 | 79.571 | 72.862 | 32.787 | 1.00 | 68.35 | O |
| HETATM | 4065 | O | HOH | 1354 | 115.741 | 90.948 | 32.009 | 1.00 | 48.04 | O |
| HETATM | 4066 | C | HOH | 1356 | 85.780 | 75.697 | 15.005 | 1.00 | 50.57 | O |
| HETATM | 4067 | O | HOH | 1357 | 112.933 | 95.254 | 27.038 | 1.00 | 44.69 | O |
| CONECT | 403 | 404 | | | | | | | | |
| CONECT | 404 | 403 | 405 | 407 | | | | | | |
| CONECT | 405 | 404 | 406 | | | | | | | |
| CONECT | 406 | 405 | | | | | | | | |
| CONECT | 407 | 404 | 408 | | | | | | | |
| CONECT | 408 | 407 | 409 | | | | | | | |
| CONECT | 409 | 408 | 410 | | | | | | | |
| CONECT | 410 | 409 | | | | | | | | |
| CONECT | 459 | 460 | | | | | | | | |
| CONECT | 460 | 459 | 461 | 463 | | | | | | |

TABLE 7-continued

| | | | | |
|---|---|---|---|---|
| CCNECT | 461 | 460 | 462 | |
| CONECT | 462 | 461 | | |
| CONECT | 463 | 460 | 464 | |
| CONECT | 464 | 463 | 465 | |
| CONECT | 465 | 464 | 466 | |
| CONECT | 466 | 465 | | |
| CONECT | 576 | 577 | | |
| CONECT | 577 | 576 | 578 | 580 |
| CONECT | 578 | 577 | 579 | |
| CONECT | 579 | 578 | | |
| CONECT | 580 | 577 | 581 | |
| CONECT | 581 | 580 | 582 | |
| CONECT | 582 | 581 | 583 | |
| CONECT | 583 | 582 | | |
| CONECT | 882 | 883 | | |
| CONECT | 883 | 882 | 884 | 886 |
| CONECT | 884 | 883 | 885 | |
| CONECT | 885 | 884 | | |
| CONECT | 886 | 883 | 887 | |
| CONECT | 887 | 886 | 888 | |
| CONECT | 888 | 887 | 889 | |
| CONECT | 889 | 888 | | |
| CONECT | 1094 | 1095 | | |
| CONECT | 1095 | 1094 | 1096 | 1098 |
| CONECT | 1096 | 1095 | 1097 | |
| CONECT | 1097 | 1096 | | |
| CONECT | 1098 | 1095 | 1099 | |
| CONECT | 1099 | 1010 | 1100 | |
| CONECT | 1100 | 1099 | 1101 | |
| CONECT | 1101 | 1100 | | |
| CONECT | 1211 | 1212 | | |
| CONECT | 1212 | 1211 | 1213 | 1215 |
| CONECT | 1213 | 1212 | 1214 | |
| CONECT | 1214 | 1213 | | |
| CONECT | 1215 | 1212 | 1216 | |
| CONECT | 1216 | 1215 | 1217 | |
| CONECT | 1217 | 1216 | 1218 | |
| CONECT | 1218 | 1217 | | |
| CONECT | 2707 | 2708 | | |
| CONECT | 2708 | 2707 | 2709 | 2711 |
| CONECT | 2709 | 2708 | 2710 | |
| CONECT | 2710 | 2709 | | |
| CONECT | 2711 | 2708 | 2712 | |
| CONECT | 2712 | 2711 | 2713 | |
| CONECT | 2713 | 2712 | 2714 | |
| CONECT | 2714 | 2713 | | |
| CONECT | 2733 | 2734 | | |
| CONECT | 2734 | 2733 | 2735 | 2737 |
| CONECT | 2735 | 2734 | 2736 | |
| CONECT | 2736 | 2735 | | |
| CONECT | 2737 | 2734 | 2738 | |
| CONECT | 2738 | 2737 | 2739 | |
| CONECT | 2739 | 2738 | 2740 | |
| CONECT | 2740 | 2739 | | |
| CONECT | 2934 | 2935 | | |
| CONECT | 2935 | 2934 | 2936 | 2938 |
| CONECT | 2936 | 2935 | 2937 | |
| CONECT | 2937 | 2936 | | |
| CONECT | 2938 | 2935 | 2939 | |
| CONECT | 2939 | 2938 | 2940 | |
| CONECT | 2940 | 2939 | 2941 | |
| CONECT | 2941 | 2940 | | |
| CONECT | 2970 | 2971 | | |
| CONECT | 2971 | 2970 | 2972 | 2974 |
| CONECT | 2972 | 2971 | 2973 | |
| CONECT | 2973 | 2972 | | |
| CONECT | 2974 | 2971 | 2975 | |
| CONECT | 2975 | 2974 | 2976 | |
| CONECT | 2976 | 2975 | 2977 | |
| CONECT | 2977 | 2976 | | |
| CONECT | 3158 | 3159 | | |
| CONECT | 3159 | 3158 | 3160 | 3162 |
| CONECT | 3160 | 3159 | 3161 | |
| CONECT | 3161 | 3160 | | |
| CONECT | 3162 | 3159 | 3163 | |
| CONECT | 3163 | 3162 | 3164 | |
| CONECT | 3164 | 3163 | 3165 | |
| CONECT | 3165 | 3164 | | |
| CONECT | 3211 | 3212 | | |

TABLE 7-continued

| | | | | |
|---|---|---|---|---|
| CONECT | 3212 | 3211 | 3213 | 3215 |
| CONECT | 3213 | 3212 | 3214 | |
| CONECT | 3214 | 3213 | | |
| CONECT | 3215 | 3212 | 3216 | |
| CONECT | 3216 | 3215 | 3217 | |
| CONECT | 3217 | 3216 | 3218 | |
| CONECT | 3218 | 3217 | | |
| CONECT | 3365 | 3366 | | |
| CONECT | 3366 | 3365 | 3367 | 3369 |
| CONECT | 3367 | 3366 | 3368 | |
| CONECT | 3368 | 3367 | | |
| CONECT | 3369 | 3366 | 3370 | |
| CONECT | 3370 | 3369 | 3371 | |
| CONECT | 3371 | 3370 | 3372 | |
| CONECT | 3372 | 3371 | | |
| CONECT | 3546 | 3547 | 3548 | 3549 3550 |
| CONECT | 3547 | 3546 | | |
| CONECT | 3548 | 3546 | | |
| CONECT | 3549 | 3546 | | |
| CONECT | 3550 | 3546 | 3551 | |
| CONECT | 3551 | 3550 | 3552 | |
| CONECT | 3552 | 3551 | 3553 | 3554 |
| CONECT | 3553 | 3552 | 3558 | |
| CONECT | 3554 | 3552 | 3555 | 3556 |
| CONECT | 3555 | 3554 | | |
| CONECT | 3556 | 3554 | 3557 | 3558 |
| CONECT | 3557 | 3556 | | |
| CONECT | 3558 | 3553 | 3556 | 3559 |
| CONECT | 3559 | 3558 | 3560 | 3568 |
| CONECT | 3560 | 3559 | 3561 | |
| CONECT | 3561 | 3560 | 3562 | |
| CONECT | 3562 | 3561 | 3563 | 3568 |
| CONECT | 3563 | 3562 | 3564 | 3565 |
| CONECT | 3564 | 3563 | | |
| CONECT | 3565 | 3563 | 3566 | |
| CONECT | 3566 | 3565 | 3567 | |
| CONECT | 3567 | 3566 | 3568 | |
| CONECT | 3568 | 3559 | 3562 | 3567 |
| MASTER | 437 | 0 | 14 | 18 16 0 1 64066 1 127 37 |
| END | | | | |

| | | | | | | | | | | |
|---|---|---|---|---|---|---|---|---|---|---|
| ATOM | 1749 | O | ALA | A | 228 | 109.788 | 55.149 | 20.153 | 1.00 | 28.65 O |
| ATOM | 1750 | CB | ALA | A | 228 | 107.697 | 57.575 | 20.792 | 1.00 | 28.14 C |
| ATOM | 1751 | N | VAL | A | 229 | 108.662 | 54.901 | 22.091 | 1.00 | 30.70 N |
| ATOM | 1752 | CA | VAL | A | 229 | 108.654 | 53.447 | 22.082 | 1.00 | 31.77 C |
| ATOM | 1753 | C | VAL | A | 229 | 107.354 | 53.075 | 22.785 | 1.00 | 33.71 C |
| ATOM | 1754 | O | VAL | A | 229 | 106.778 | 53.897 | 23.508 | 1.00 | 34.20 O |
| ATOM | 1755 | CB | VAL | A | 229 | 109.847 | 52.850 | 22.876 | 1.00 | 31.31 C |
| ATOM | 1756 | CG1 | VAL | A | 229 | 111.156 | 53.346 | 22.298 | 1.00 | 31.39 C |
| ATOM | 1757 | CG2 | VAL | A | 229 | 109.739 | 53.208 | 24.357 | 1.00 | 31.01 C |
| ATOM | 1758 | N | GLY | A | 230 | 106.871 | 51.858 | 22.570 | 1.00 | 34.88 N |
| ATOM | 1759 | CA | GLY | A | 230 | 105.652 | 51.453 | 23.240 | 1.00 | 35.58 C |
| ATOM | 1760 | C | GLY | A | 230 | 105.976 | 50.476 | 24.352 | 1.00 | 36.88 C |
| ATOM | 1761 | O | GLY | A | 230 | 107.100 | 50.411 | 24.840 | 1.00 | 36.39 O |
| ATOM | 1762 | N | VAL | A | 231 | 104.975 | 49.722 | 24.772 | 1.00 | 39.52 N |
| ATOM | 1763 | CA | VAL | A | 231 | 105.176 | 48.719 | 25.801 | 1.00 | 41.92 C |
| ATOM | 1764 | C | VAL | A | 231 | 104.905 | 47.363 | 25.140 | 1.00 | 43.78 C |
| ATOM | 1765 | O | VAL | A | 231 | 103.779 | 46.858 | 25.143 | 1.00 | 44.73 O |
| ATOM | 1766 | CB | VAL | A | 231 | 104.240 | 48.966 | 26.997 | 1.00 | 41.08 C |
| ATOM | 1767 | CG1 | VAL | A | 231 | 104.639 | 50.257 | 27.691 | 1.00 | 40.96 C |
| ATOM | 1768 | CG2 | VAL | A | 231 | 102.810 | 49.071 | 26.526 | 1.00 | 40.96 C |
| ATOM | 1769 | N | THR | A | 232 | 105.954 | 46.807 | 24.538 | 1.00 | 44.60 N |
| ATOM | 1770 | CA | THR | A | 232 | 105.881 | 45.532 | 23.845 | 1.00 | 45.87 C |
| ATOM | 1771 | C | THR | A | 232 | 107.106 | 44.710 | 24.200 | 1.00 | 46.68 C |
| ATOM | 1772 | O | THR | A | 232 | 107.838 | 45.059 | 25.120 | 1.00 | 47.51 O |
| ATOM | 1773 | CB | THR | A | 232 | 105.842 | 45.739 | 22.328 | 1.00 | 46.37 C |
| ATOM | 1774 | OG1 | THR | A | 232 | 107.038 | 46.404 | 21.906 | 1.00 | 46.75 O |
| ATOM | 1775 | CG2 | THR | A | 232 | 104.645 | 46.590 | 21.946 | 1.00 | 46.43 C |
| ATOM | 1776 | N | SER | A | 233 | 107.342 | 43.626 | 23.468 | 1.00 | 48.35 N |
| ATOM | 1777 | CA | SER | A | 233 | 108.491 | 42.768 | 23.755 | 1.00 | 49.99 C |
| ATOM | 1778 | C | SER | A | 233 | 109.804 | 43.315 | 23.199 | 1.00 | 50.98 C |
| ATOM | 1779 | O | SER | A | 233 | 110.887 | 42.949 | 23.667 | 1.00 | 52.13 O |
| ATOM | 1780 | CB | SER | A | 233 | 108.256 | 41.355 | 23.211 | 1.00 | 49.80 C |
| ATOM | 1781 | OG | SER | A | 233 | 108.089 | 41.370 | 21.809 | 1.00 | 51.16 O |

-continued

| | | | | | | | | | | |
|---|---|---|---|---|---|---|---|---|---|---|
| ATOM | 1782 | N | ASP | A | 234 | 109.710 | 44.197 | 22.210 | 1.00 | 51.06 N |
| ATOM | 1783 | CA | ASP | A | 234 | 110.901 | 44.779 | 21.606 | 1.00 | 51.16 C |
| ATOM | 1784 | C | ASP | A | 234 | 111.207 | 46.174 | 22.142 | 1.00 | 50.20 C |
| ATOM | 1785 | O | ASP | A | 234 | 112.024 | 46.892 | 21.570 | 1.00 | 50.68 O |
| ATOM | 1786 | CB | ASP | A | 234 | 110.733 | 44.835 | 20.092 | 1.00 | 52.65 C |
| ATOM | 1787 | CG | ASP | A | 234 | 109.474 | 45.563 | 19.686 | 1.00 | 55.59 C |
| ATOM | 1788 | OD1 | ASP | A | 234 | 108.388 | 45.134 | 20.138 | 1.00 | 57.24 O |
| ATOM | 1789 | OD2 | ASP | A | 234 | 109.566 | 46.556 | 18.924 | 1.00 | 56.62 O |
| ATOM | 1790 | N | THR | A | 235 | 110.559 | 46.553 | 23.239 | 1.00 | 48.92 N |
| ATOM | 1791 | CA | THR | A | 235 | 110.775 | 47.866 | 23.837 | 1.00 | 48.36 C |
| ATOM | 1792 | C | THR | A | 235 | 112.219 | 48.115 | 24.279 | 1.00 | 48.23 C |
| ATOM | 1793 | O | THR | A | 235 | 112.835 | 49.092 | 23.855 | 1.00 | 48.06 O |
| ATOM | 1794 | CB | THR | A | 235 | 109.844 | 48.080 | 25.035 | 1.00 | 48.22 C |
| ATOM | 1795 | OG1 | THR | A | 235 | 108.492 | 48.121 | 24.572 | 1.00 | 48.44 O |
| ATOM | 1796 | CG2 | THR | A | 235 | 110.164 | 49.382 | 25.740 | 1.00 | 48.44 C |
| ATOM | 1797 | N | PHE | A | 236 | 112.755 | 47.248 | 25.138 | 1.00 | 47.72 N |
| ATOM | 1798 | CA | PHE | A | 236 | 114.133 | 47.403 | 25.594 | 1.00 | 46.43 C |
| ATOM | 1799 | C | PHE | A | 236 | 115.075 | 47.536 | 24.420 | 1.00 | 45.57 C |
| ATOM | 1800 | O | PHE | A | 236 | 115.856 | 48.480 | 24.342 | 1.00 | 45.91 O |
| ATOM | 1801 | CB | PHE | A | 236 | 114.568 | 46.209 | 26.434 | 1.00 | 47.23 C |
| ATOM | 1802 | CG | PHE | A | 236 | 114.351 | 46.394 | 27.892 | 1.00 | 48.55 C |
| ATOM | 1803 | CD1 | PHE | A | 236 | 115.014 | 47.402 | 28.572 | 1.00 | 49.39 C |
| ATOM | 1804 | CD2 | PHE | A | 236 | 113.483 | 45.567 | 28.591 | 1.00 | 50.16 C |
| ATOM | 1805 | CE1 | PHE | A | 236 | 114.817 | 47.588 | 29.931 | 1.00 | 51.05 C |
| ATOM | 1806 | CE2 | PHE | A | 236 | 113.276 | 45.742 | 29.959 | 1.00 | 51.03 C |
| ATOM | 1807 | CZ | PHE | A | 236 | 113.945 | 46.755 | 30.630 | 1.00 | 51.13 C |
| ATOM | 1808 | N | GLU | A | 237 | 114.998 | 46.570 | 23.513 | 1.00 | 44.78 N |
| ATOM | 1809 | CA | GLU | A | 237 | 115.835 | 46.548 | 22.320 | 1.00 | 44.06 C |
| ATOM | 1810 | C | GLU | A | 237 | 115.749 | 47.901 | 21.626 | 1.00 | 41.89 C |
| ATOM | 1811 | O | GLU | A | 237 | 116.756 | 48.466 | 21.210 | 1.00 | 41.21 O |
| ATOM | 1812 | CB | GLU | A | 237 | 115.334 | 45.461 | 21.375 | 1.00 | 46.63 C |
| ATOM | 1813 | CG | GLU | A | 237 | 116.258 | 45.132 | 20.226 | 1.00 | 50.92 C |
| ATOM | 1814 | CD | GLU | A | 237 | 115.598 | 44.192 | 19.233 | 1.00 | 54.10 C |
| ATOM | 1815 | OE1 | GLU | A | 237 | 114.939 | 43.224 | 19.686 | 1.00 | 55.04 O |
| ATOM | 1816 | OE2 | GLU | A | 237 | 115.749 | 44.410 | 18.004 | 1.00 | 55.45 O |
| ATOM | 1817 | N | ARG | A | 238 | 114.524 | 48.410 | 21.521 | 1.00 | 40.47 N |
| ATOM | 1818 | CA | ARG | A | 238 | 114.244 | 49.691 | 20.880 | 1.00 | 39.30 C |
| ATOM | 1819 | C | ARG | A | 238 | 114.820 | 50.864 | 21.667 | 1.00 | 38.27 C |
| ATOM | 1820 | O | ARG | A | 238 | 115.508 | 51.715 | 21.109 | 1.00 | 37.62 O |
| ATOM | 1821 | CB | ARG | A | 238 | 112.738 | 49.888 | 20.743 | 1.00 | 38.03 C |
| ATOM | 1822 | CG | ARG | A | 238 | 112.380 | 50.858 | 19.656 | 1.00 | 38.82 C |
| ATOM | 1823 | CD | ARG | A | 238 | 110.901 | 51.126 | 19.586 | 1.00 | 39.86 C |
| ATOM | 1824 | NE | ARG | A | 238 | 110.555 | 51.547 | 18.236 | 1.00 | 42.82 N |
| ATOM | 1825 | CZ | ARG | A | 238 | 110.332 | 50.707 | 17.233 | 1.00 | 43.08 C |
| ATON | 1826 | NH1 | ARG | A | 238 | 110.410 | 49.402 | 17.430 | 1.00 | 44.36 N |
| ATOM | 1827 | NH2 | ARG | A | 238 | 110.066 | 51.170 | 16.025 | 1.00 | 43.46 N |
| ATOM | 1828 | N | ALA | A | 239 | 114.518 | 50.904 | 22.962 | 1.00 | 38.15 N |
| ATOM | 1829 | CA | ALA | A | 239 | 114.991 | 51.960 | 23.848 | 1.00 | 37.99 C |
| ATOM | 1830 | C | ALA | A | 239 | 116.516 | 52.030 | 23.869 | 1.00 | 39.80 C |
| ATOM | 1831 | O | ALA | A | 239 | 117.093 | 53.121 | 23.815 | 1.00 | 39.71 O |
| ATOM | 1832 | CB | ALA | A | 239 | 114.461 | 51.729 | 25.249 | 1.00 | 36.95 C |
| ATOM | 1833 | N | GLU | A | 240 | 117.174 | 50.873 | 23.944 | 1.00 | 41.10 N |
| ATOM | 1834 | CA | GLU | A | 240 | 118.631 | 50.852 | 23.965 | 1.00 | 41.70 C |
| ATOM | 1835 | C | GLU | A | 240 | 119.239 | 51.237 | 22.621 | 1.00 | 40.70 C |
| ATOM | 1836 | O | GLU | A | 240 | 120.358 | 51.744 | 22.570 | 1.00 | 40.79 O |
| ATOM | 1837 | CB | GLU | A | 240 | 119.157 | 49.486 | 24.428 | 1.00 | 44.05 C |
| ATOM | 1838 | CG | GLU | A | 240 | 118.629 | 48.286 | 23.678 | 1.00 | 48.07 C |
| ATOM | 1839 | CD | GLU | A | 240 | 119.141 | 46.973 | 24.266 | 1.00 | 51.41 C |
| ATOM | 1840 | OE1 | GLU | A | 240 | 119.010 | 46.776 | 25.499 | 1.00 | 51.93 O |
| ATOM | 1841 | OE2 | GLU | A | 240 | 119.664 | 46.135 | 23.496 | 1.00 | 52.53 O |
| ATOM | 1842 | N | ALA | A | 241 | 118.508 | 51.005 | 21.536 | 1.00 | 39.57 N |
| ATOM | 1843 | CA | ALA | A | 241 | 118.999 | 51.373 | 20.208 | 1.00 | 39.09 C |
| ATOM | 1844 | C | ALA | A | 241 | 118.911 | 52.893 | 20.071 | 1.00 | 38.48 C |
| ATOM | 1845 | O | ALA | A | 241 | 119.805 | 53.533 | 19.521 | 1.00 | 38.30 O |
| ATOM | 1846 | CB | ALA | A | 241 | 118.161 | 50.701 | 19.125 | 1.00 | 39.36 C |
| ATOM | 1847 | N | LEU | A | 242 | 117.822 | 53.460 | 20.579 | 1.00 | 37.48 N |
| ATOM | 1848 | CA | LEU | A | 242 | 117.603 | 54.902 | 20.549 | 1.00 | 36.64 C |
| ATOM | 1849 | C | LEU | A | 242 | 118.607 | 55.648 | 21.421 | 1.00 | 36.34 C |
| ATOM | 1850 | O | LEU | A | 242 | 119.217 | 56.620 | 20.973 | 1.00 | 35.49 O |
| ATOM | 1851 | CB | LEU | A | 242 | 116.177 | 55.212 | 20.999 | 1.00 | 36.24 C |
| ATOM | 1852 | CG | LEU | A | 242 | 115.079 | 55.051 | 19.940 | 1.00 | 37.63 C |
| ATOM | 1853 | CD1 | LEU | A | 242 | 115.390 | 53.933 | 18.970 | 1.00 | 37.59 C |
| ATOM | 1854 | CD2 | LEU | A | 242 | 113.748 | 54.825 | 20.654 | 1.00 | 37.84 C |
| ATOM | 1855 | N | PHE | A | 243 | 118.785 | 55.209 | 22.666 | 1.00 | 36.35 N |
| ATOM | 1856 | CA | PHE | A | 243 | 119.749 | 55.879 | 23.534 | 1.00 | 36.90 C |
| ATOM | 1857 | C | PHE | A | 243 | 121.143 | 55.806 | 22.930 | 1.00 | 37.73 C |
| ATOM | 1858 | O | PHE | A | 243 | 121.890 | 56.781 | 22.958 | 1.00 | 38.96 O |
| ATOM | 1859 | CB | PHE | A | 243 | 119.769 | 55.262 | 24.938 | 1.00 | 35.66 C |
| ATOM | 1860 | CG | PHE | A | 243 | 118.619 | 55.683 | 25.803 | 1.00 | 34.47 C |

-continued

| | | | | | | | | | | |
|---|---|---|---|---|---|---|---|---|---|---|
| ATOM | 1861 | CD1 | PHE | A | 243 | 118.325 | 57.032 | 25.980 | 1.00 | 34.10 C |
| ATOM | 1862 | CD2 | PHE | A | 243 | 117.850 | 54.739 | 26.474 | 1.00 | 33.97 C |
| ATOM | 1863 | CE1 | PHE | A | 243 | 117.280 | 57.432 | 26.818 | 1.00 | 33.89 C |
| ATOM | 1864 | CE2 | PHE | A | 243 | 116.802 | 55.130 | 27.317 | 1.00 | 33.03 C |
| ATOM | 1865 | CZ | PHE | A | 243 | 116.517 | 56.474 | 27.489 | 1.00 | 32.69 C |
| ATOM | 1866 | N | GLU | A | 244 | 121.477 | 54.650 | 22.370 | 1.00 | 38.32 N |
| ATOM | 1867 | CA | GLU | A | 244 | 122.779 | 54.431 | 21.763 | 1.00 | 39.15 C |
| ATOM | 1868 | C | GLU | A | 244 | 122.974 | 55.304 | 20.531 | 1.00 | 37.76 C |
| ATOM | 1869 | O | GLU | A | 244 | 124.103 | 55.550 | 20.103 | 1.00 | 37.31 O |
| ATOM | 1870 | CB | GLU | A | 244 | 122.932 | 52.959 | 21.380 | 1.00 | 43.06 C |
| ATOM | 1871 | CG | GLU | A | 244 | 124.297 | 52.595 | 20.823 | 1.00 | 48.69 C |
| ATOM | 1872 | CD | GLU | A | 244 | 124.375 | 51.141 | 20.407 | 1.00 | 53.07 C |
| ATOM | 1873 | OE1 | GLU | A | 244 | 124.097 | 50.272 | 21.266 | 1.00 | 55.43 O |
| ATOM | 1874 | OE2 | GLU | A | 244 | 124.713 | 50.866 | 19.228 | 1.00 | 54.65 O |
| ATOM | 1875 | N | ALA | A | 245 | 121.873 | 55.767 | 19.951 | 1.00 | 36.29 N |
| ATOM | 1876 | CA | ALA | A | 245 | 121.964 | 56.619 | 18.770 | 1.00 | 35.13 C |
| ATOM | 1877 | C | ALA | A | 245 | 122.120 | 58.061 | 19.224 | 1.00 | 33.93 C |
| ATOM | 1878 | O | ALA | A | 245 | 122.455 | 58.935 | 18.437 | 1.00 | 34.56 O |
| ATOM | 1879 | CB | ALA | A | 245 | 120.723 | 56.463 | 17.897 | 1.00 | 35.38 C |
| ATOM | 1880 | N | GLY | A | 246 | 121.873 | 58.301 | 20.506 | 1.00 | 32.96 N |
| ATOM | 1881 | CA | GLY | A | 246 | 122.022 | 59.640 | 21.039 | 1.00 | 32.17 C |
| ATOM | 1882 | C | GLY | A | 246 | 120.812 | 60.256 | 21.720 | 1.00 | 31.72 C |
| ATOM | 1883 | O | GLY | A | 246 | 120.919 | 61.358 | 22.265 | 1.00 | 32.01 O |
| ATOM | 1884 | N | ALA | A | 247 | 119.673 | 59.570 | 21.710 | 1.00 | 30.21 N |
| ATOM | 1885 | CA | ALA | A | 247 | 118.465 | 60.123 | 22.328 | 1.00 | 29.83 C |
| ATOM | 1886 | C | ALA | A | 247 | 118.739 | 60.676 | 23.718 | 1.00 | 29.13 C |
| ATOM | 1887 | O | ALA | A | 247 | 119.392 | 60.038 | 24.529 | 1.00 | 29.36 O |
| ATOM | 1888 | CB | ALA | A | 247 | 117.365 | 59.064 | 22.398 | 1.00 | 29.66 C |
| ATOM | 1889 | N | ASP | A | 248 | 118.231 | 61.874 | 23.976 | 1.00 | 29.42 N |
| ATOM | 1890 | CA | ASP | A | 248 | 118.401 | 62.541 | 25.262 | 1.00 | 29.22 C |
| ATOM | 1891 | C | ASP | A | 248 | 117.283 | 62.141 | 26.218 | 1.00 | 28.93 C |
| ATOM | 1892 | O | ASP | A | 248 | 117.334 | 62.412 | 27.416 | 1.00 | 28.35 O |
| ATOM | 1893 | CB | ASP | A | 248 | 118.400 | 64.049 | 25.032 | 1.00 | 31.00 C |
| ATOM | 1894 | CG | ASP | A | 248 | 119.557 | 64.495 | 24.153 | 1.00 | 33.31 C |
| ATOM | 1895 | OD1 | ASP | A | 248 | 120.674 | 64.660 | 24.689 | 1.00 | 34.76 O |
| ATOM | 1896 | OD2 | ASP | A | 248 | 119.359 | 64.648 | 22.922 | 1.00 | 33.85 O |
| ATOM | 1897 | N | ALA | A | 249 | 116.268 | 61.487 | 25.666 | 1.00 | 28.79 N |
| ATOM | 1898 | CA | ALA | A | 249 | 115.127 | 61.020 | 26.439 | 1.00 | 28.18 C |
| ATOM | 1899 | C | ALA | A | 249 | 114.279 | 60.097 | 25.568 | 1.00 | 28.88 C |
| ATOM | 1900 | O | ALA | A | 249 | 114.314 | 60.181 | 24.341 | 1.00 | 28.79 O |
| ATOM | 1901 | CB | ALA | A | 249 | 114.298 | 62.209 | 26.903 | 1.00 | 27.25 C |
| ATOM | 1902 | N | ILE | A | 250 | 113.543 | 59.189 | 26.192 | 1.00 | 28.48 N |
| ATOM | 1903 | CA | ILE | A | 250 | 112.669 | 58.324 | 25.421 | 1.00 | 29.55 C |
| ATOM | 1904 | C | ILE | A | 250 | 111.260 | 58.577 | 25.916 | 1.00 | 29.65 C |
| ATOM | 1905 | O | ILE | A | 250 | 111.056 | 58.932 | 27.085 | 1.00 | 29.05 O |
| ATOM | 1906 | CB | ILE | A | 250 | 113.000 | 56.813 | 25.587 | 1.00 | 30.94 C |
| ATOM | 1907 | CG1 | ILE | A | 250 | 113.023 | 56.441 | 27.070 | 1.00 | 32.35 C |
| ATOM | 1908 | CG2 | ILE | A | 250 | 114.303 | 56.479 | 24.876 | 1.00 | 30.20 C |
| ATOM | 1909 | CD1 | ILE | A | 250 | 113.296 | 54.968 | 27.328 | 1.00 | 34.16 C |
| ATOM | 1910 | N | VAL | A | 251 | 110.289 | 58.414 | 25.024 | 1.00 | 29.98 N |
| ATOM | 1911 | CA | VAL | A | 251 | 108.894 | 58.615 | 25.385 | 1.00 | 30.11 C |
| ATOM | 1912 | C | VAL | A | 251 | 108.119 | 57.310 | 25.254 | 1.00 | 31.15 C |
| ATOM | 1913 | O | VAL | A | 251 | 107.939 | 56.777 | 24.157 | 1.00 | 31.33 O |
| ATOM | 1914 | CB | VAL | A | 251 | 108.222 | 59.698 | 24.499 | 1.00 | 29.28 C |
| ATOM | 1915 | CG1 | VAL | A | 251 | 106.749 | 59.837 | 24.869 | 1.00 | 28.74 C |
| ATOM | 1916 | CG2 | VAL | A | 251 | 108.924 | 61.032 | 24.689 | 1.00 | 28.73 C |
| ATOM | 1917 | N | ILE | A | 252 | 107.686 | 56.791 | 26.394 | 1.00 | 32.25 N |
| ATOM | 1918 | CA | ILE | A | 252 | 106.907 | 55.567 | 26.445 | 1.00 | 34.36 C |
| ATOM | 1919 | C | ILE | A | 252 | 105.488 | 56.052 | 26.169 | 1.00 | 35.92 C |
| ATOM | 1920 | O | ILE | A | 252 | 104.796 | 56.541 | 27.055 | 1.00 | 35.07 O |
| ATOM | 1921 | CB | ILE | A | 252 | 107.030 | 54.933 | 27.838 | 1.00 | 34.93 C |
| ATOM | 1922 | CG1 | ILE | A | 252 | 108.516 | 54.658 | 28.119 | 1.00 | 34.36 C |
| ATOM | 1923 | CG2 | ILE | A | 252 | 106.190 | 53.662 | 27.918 | 1.00 | 34.35 C |
| ATOM | 1924 | CD1 | ILE | A | 252 | 108.830 | 54.276 | 29.536 | 1.00 | 35.76 C |
| ATOM | 1925 | N | ASP | A | 253 | 105.084 | 55.928 | 24.911 | 1.00 | 37.82 N |
| ATOM | 1926 | CA | ASP | A | 253 | 103.793 | 56.405 | 24.439 | 1.00 | 38.30 C |
| ATOM | 1927 | C | ASP | A | 253 | 102.759 | 55.298 | 24.528 | 1.00 | 36.33 C |
| ATOM | 1928 | O | ASP | A | 253 | 102.900 | 54.256 | 23.897 | 1.00 | 35.52 O |
| ATOM | 1929 | CB | ASP | A | 253 | 103.969 | 56.886 | 22.987 | 1.00 | 42.68 C |
| ATOM | 1930 | CG | ASP | A | 253 | 103.027 | 58.024 | 22.608 | 1.00 | 47.26 C |
| ATOM | 1931 | OD1 | ASP | A | 253 | 103.007 | 59.059 | 23.324 | 1.00 | 49.54 O |
| ATOM | 1932 | OD2 | ASP | A | 253 | 102.326 | 57.895 | 21.574 | 1.00 | 49.50 O |
| ATOM | 1933 | N | THR | A | 254 | 101.720 | 55.535 | 25.319 | 1.00 | 35.67 N |
| ATOM | 1934 | CA | THR | A | 254 | 100.654 | 54.553 | 25.507 | 1.00 | 35.99 C |
| ATOM | 1935 | C | THR | A | 254 | 99.267 | 55.208 | 25.434 | 1.00 | 33.80 C |
| ATOM | 1936 | O | THR | A | 254 | 99.115 | 56.398 | 25.716 | 1.00 | 33.46 O |
| ATOM | 1937 | CB | THR | A | 254 | 100.769 | 53.870 | 26.894 | 1.00 | 37.36 C |
| ATOM | 1938 | OG1 | THR | A | 254 | 102.127 | 53.489 | 27.131 | 1.00 | 40.12 O |
| ATOM | 1939 | CG2 | THR | A | 254 | 99.898 | 52.617 | 26.943 | 1.00 | 39.58 C |

-continued

| | | | | | | | | | | |
|---|---|---|---|---|---|---|---|---|---|---|
| ATOM | 1940 | N | ALA | A | 255 | 98.257 | 54.424 | 25.076 | 1.00 | 32.56 N |
| ATOM | 1941 | CA | ALA | A | 255 | 96.901 | 54.943 | 25.000 | 1.00 | 31.89 C |
| ATOM | 1942 | C | ALA | A | 255 | 96.381 | 55.122 | 26.419 | 1.00 | 31.60 C |
| ATOM | 1943 | O | ALA | A | 255 | 95.756 | 56.131 | 26.743 | 1.00 | 31.27 O |
| ATOM | 1944 | CB | ALA | A | 255 | 96.021 | 53.983 | 24.239 | 1.00 | 31.75 C |
| ATOM | 1945 | N | HIS | A | 256 | 96.646 | 54.133 | 27.266 | 1.00 | 31.05 N |
| ATOM | 1946 | CA | HIS | A | 256 | 96.211 | 54.183 | 28.652 | 1.00 | 30.66 C |
| ATOM | 1947 | C | HIS | A | 256 | 97.423 | 53.961 | 29.541 | 1.00 | 31.22 C |
| ATOM | 1948 | O | HIS | A | 256 | 97.811 | 52.826 | 29.784 | 1.00 | 32.42 O |
| ATOM | 1949 | CB | HIS | A | 256 | 95.183 | 53.092 | 28.932 | 1.00 | 28.92 C |
| ATOM | 1950 | CG | HIS | A | 256 | 94.514 | 53.230 | 30.263 | 1.00 | 28.92 C |
| ATOM | 1951 | ND1 | HIS | A | 256 | 93.767 | 52.223 | 30.832 | 1.00 | 29.33 N |
| ATOM | 1952 | CD2 | HIS | A | 256 | 94.461 | 54.270 | 31.128 | 1.00 | 28.44 C |
| ATOM | 1953 | CB1 | HIS | A | 256 | 93.284 | 52.636 | 31.991 | 1.00 | 29.11 C |
| ATOM | 1954 | NE2 | HIS | A | 256 | 93.690 | 53.875 | 32.194 | 1.00 | 29.27 N |
| ATOM | 1955 | N | GLY | A | 257 | 98.017 | 55.043 | 30.026 | 1.00 | 32.56 N |
| ATOM | 1956 | CA | GLY | A | 257 | 99.196 | 54.927 | 30.871 | 1.00 | 33.03 C |
| ATOM | 1957 | C | GLY | A | 257 | 98.907 | 54.494 | 32.297 | 1.00 | 33.73 C |
| ATOM | 1958 | O | GLY | A | 257 | 99.825 | 54.233 | 33.073 | 1.00 | 34.44 O |
| ATOM | 1959 | N | HIS | A | 258 | 97.633 | 54.407 | 32.655 | 1.00 | 33.24 N |
| ATOM | 1960 | CA | HIS | A | 258 | 97.277 | 54.009 | 34.005 | 1.00 | 32.25 C |
| ATOM | 1961 | C | HIS | A | 258 | 97.016 | 52.500 | 33.995 | 1.00 | 33.33 C |
| ATOM | 1962 | O | HIS | A | 258 | 96.237 | 51.991 | 34.796 | 1.00 | 34.50 O |
| ATOM | 1963 | CB | HIS | A | 258 | 96.025 | 54.768 | 34.447 | 1.00 | 30.67 C |
| ATOM | 1964 | CG | HIS | A | 258 | 95.892 | 54.923 | 35.932 | 1.00 | 28.53 C |
| ATOM | 1965 | ND1 | HIS | A | 258 | 96.576 | 54.135 | 36.831 | 1.00 | 28.44 N |
| ATOM | 1966 | CD2 | HIS | A | 258 | 95.100 | 55.735 | 36.672 | 1.00 | 27.04 C |
| ATOM | 1967 | CE1 | HIS | A | 258 | 96.212 | 54.455 | 38.059 | 1.00 | 27.92 C |
| ATOM | 1968 | NE2 | HIS | A | 258 | 95.316 | 55.422 | 37.991 | 1.00 | 27.43 N |
| ATOM | 1969 | N | SER | A | 259 | 97.664 | 51.790 | 33.076 | 1.00 | 33.64 N |
| ATOM | 1970 | CA | SER | A | 259 | 97.502 | 50.340 | 32.974 | 1.00 | 35.31 C |
| ATOM | 1971 | C | SER | A | 259 | 98.572 | 49.598 | 33.765 | 1.00 | 35.20 C |
| ATOM | 1972 | O | SER | A | 259 | 99.745 | 49.975 | 33.751 | 1.00 | 35.19 O |
| ATOM | 1973 | CB | SER | A | 259 | 97.593 | 49.883 | 31.521 | 1.00 | 36.71 C |
| ATOM | 1974 | OG | SER | A | 259 | 96.600 | 50.498 | 30.734 | 1.00 | 42.41 O |
| ATOM | 1975 | N | ALA | A | 260 | 98.160 | 48.525 | 34.434 | 1.00 | 35.34 N |
| ATOM | 1976 | CA | ALA | A | 260 | 99.075 | 47.718 | 35.228 | 1.00 | 34.81 C |
| ATOM | 1977 | C | ALA | A | 260 | 100.264 | 47.288 | 34.377 | 1.00 | 34.54 C |
| ATOM | 1978 | O | ALA | A | 260 | 101.415 | 47.394 | 34.797 | 1.00 | 34.57 O |
| ATOM | 1979 | CB | ALA | A | 260 | 98.345 | 46.500 | 35.769 | 1.00 | 34.40 C |
| ATOM | 1980 | N | GLY | A | 261 | 99.971 | 46.808 | 33.174 | 1.00 | 34.40 N |
| ATOM | 1981 | CA | GLY | A | 261 | 101.013 | 46.368 | 32.271 | 1.00 | 33.69 C |
| ATOM | 1982 | C | GLY | A | 261 | 102.003 | 47.458 | 31.920 | 1.00 | 33.68 C |
| ATOM | 1983 | O | GLY | A | 261 | 103.211 | 47.220 | 31.923 | 1.00 | 35.39 O |
| ATOM | 1984 | N | VAL | A | 262 | 101.505 | 48.652 | 31.612 | 1.00 | 31.87 N |
| ATOM | 1985 | CA | VAL | A | 262 | 102.372 | 49.769 | 31.260 | 1.00 | 30.22 C |
| ATOM | 1986 | C | VAL | A | 262 | 103.257 | 50.106 | 32.453 | 1.00 | 30.85 C |
| ATOM | 1987 | O | VAL | A | 262 | 104.459 | 50.296 | 32.310 | 1.00 | 29.76 O |
| ATOM | 1988 | CB | VAL | A | 262 | 101.545 | 51.037 | 30.851 | 1.00 | 29.14 C |
| ATOM | 1989 | CG1 | VAL | A | 262 | 102.469 | 52.200 | 30.517 | 1.00 | 25.83 C |
| ATOM | 1990 | CG2 | VAL | A | 262 | 100.668 | 50.723 | 29.653 | 1.00 | 28.66 C |
| ATOM | 1991 | N | LEU | A | 263 | 102.657 | 50.170 | 33.635 | 1.00 | 32.42 N |
| ATOM | 1992 | CA | LEU | A | 263 | 103.404 | 50.504 | 34.842 | 1.00 | 35.12 C |
| ATOM | 1993 | C | LEU | A | 263 | 104.479 | 49.449 | 35.109 | 1.00 | 37.28 C |
| ATOM | 1994 | O | LEU | A | 263 | 105.579 | 49.747 | 35.580 | 1.00 | 37.10 O |
| ATOM | 1995 | CB | LEU | A | 263 | 102.445 | 50.611 | 36.035 | 1.00 | 33.85 C |
| ATOM | 1996 | CG | LEU | A | 263 | 101.288 | 51.607 | 35.876 | 1.00 | 32.67 C |
| ATOM | 1997 | CD1 | LEU | A | 263 | 100.436 | 51.594 | 37.126 | 1.00 | 31.79 C |
| ATOM | 1998 | CD2 | LEU | A | 263 | 101.827 | 53.004 | 35.615 | 1.00 | 31.44 C |
| ATOM | 1999 | N | ARG | A | 264 | 104.148 | 48.208 | 34.792 | 1.00 | 39.38 N |
| ATOM | 2000 | CA | ARG | A | 264 | 105.067 | 47.107 | 34.981 | 1.00 | 41.52 C |
| ATOM | 2001 | C | ARG | A | 264 | 106.272 | 47.304 | 34.064 | 1.00 | 40.90 C |
| ATOM | 2002 | O | ARG | A | 264 | 107.410 | 47.312 | 34.517 | 1.00 | 40.25 O |
| ATOM | 2003 | CB | ARG | A | 264 | 104.329 | 45.804 | 34.674 | 1.00 | 45.25 C |
| ATOM | 2004 | CG | ARG | A | 264 | 105.121 | 44.513 | 34.813 | 1.00 | 50.16 C |
| ATOM | 2005 | CD | ARG | A | 264 | 104.144 | 43.343 | 34.780 | 1.00 | 53.35 C |
| ATOM | 2006 | NE | ARG | A | 264 | 103.248 | 43.420 | 33.626 | 1.00 | 56.71 N |
| ATOM | 2007 | CZ | ARG | A | 264 | 102.152 | 42.681 | 33.479 | 1.00 | 58.23 C |
| ATOM | 2008 | NH1 | ARG | A | 264 | 101.810 | 41.805 | 34.416 | 1.00 | 60.06 N |
| ATOM | 2009 | NH2 | ARG | A | 264 | 101.390 | 42.821 | 32.402 | 1.00 | 58.84 N |
| ATOM | 2010 | N | LYS | A | 265 | 106.010 | 47.486 | 32.776 | 1.00 | 40.84 N |
| ATOM | 2011 | CA | LYS | A | 265 | 107.068 | 47.684 | 31.795 | 1.00 | 41.03 C |
| ATOM | 2012 | C | LYS | A | 265 | 107.915 | 48.928 | 32.068 | 1.00 | 41.03 C |
| ATOM | 2013 | O | LYS | A | 265 | 109.130 | 48.909 | 31.885 | 1.00 | 42.30 O |
| ATOM | 2014 | CB | LYS | A | 265 | 106.461 | 47.762 | 30.390 | 1.00 | 41.68 C |
| ATOM | 2015 | CG | LYS | A | 265 | 107.441 | 48.146 | 29.293 | 1.00 | 43.10 C |
| ATOM | 2016 | CD | LYS | A | 265 | 108.624 | 47.198 | 29.235 | 1.00 | 45.73 C |
| ATOM | 2017 | CE | LYS | A | 265 | 108.175 | 45.761 | 29.019 | 1.00 | 47.46 C |
| ATOM | 2018 | NZ | LYS | A | 265 | 107.382 | 45.593 | 27.771 | 1.00 | 48.86 N |

-continued

| ATOM | 2019 | N | ILE | A | 266 | 107.278 | 50.009 | 32.504 | 1.00 | 40.38 | N |
| --- | --- | --- | --- | --- | --- | --- | --- | --- | --- | --- | --- |
| ATOM | 2020 | CA | ILE | A | 266 | 107.999 | 51.244 | 32.783 | 1.00 | 39.51 | C |
| ATOM | 2021 | C | ILE | A | 266 | 108.989 | 51.061 | 33.920 | 1.00 | 40.45 | C |
| ATOM | 2022 | O | ILE | A | 266 | 110.124 | 51.549 | 33.856 | 1.00 | 40.08 | O |
| ATOM | 2023 | CB | ILE | A | 266 | 107.028 | 52.396 | 33.134 | 1.00 | 38.28 | C |
| ATOM | 2024 | CG1 | ILE | A | 266 | 106.249 | 52.809 | 31.887 | 1.00 | 36.55 | C |
| ATOM | 2025 | CG2 | ILE | A | 266 | 107.795 | 53.572 | 33.704 | 1.00 | 37.78 | C |
| ATOM | 2026 | CD1 | ILE | A | 266 | 105.333 | 53.963 | 32.111 | 1.00 | 36.83 | C |
| ATOM | 2027 | N | ALA | A | 267 | 108.553 | 50.359 | 34.962 | 1.00 | 41.07 | N |
| ATOM | 2028 | CA | ALA | A | 267 | 109.404 | 50.105 | 36.117 | 1.00 | 41.67 | C |
| ATOM | 2029 | C | ALA | A | 267 | 110.584 | 49.260 | 35.672 | 1.00 | 42.17 | C |
| ATOM | 2030 | O | ALA | A | 267 | 111.704 | 49.453 | 36.141 | 1.00 | 42.01 | O |
| ATOM | 2031 | CB | ALA | A | 267 | 108.621 | 49.386 | 37.200 | 1.00 | 41.62 | C |
| ATOM | 2032 | N | GLU | A | 268 | 110.330 | 48.330 | 34.757 | 1.00 | 42.65 | N |
| ATOM | 2033 | CA | GLU | A | 268 | 111.386 | 47.470 | 34.246 | 1.00 | 44.51 | C |
| ATOM | 2034 | C | GLU | A | 268 | 112.334 | 48.294 | 33.383 | 1.00 | 44.45 | C |
| ATOM | 2035 | O | GLU | A | 268 | 113.548 | 48.064 | 33.382 | 1.00 | 45.38 | O |
| ATOM | 2036 | CB | GLU | A | 268 | 110.790 | 46.321 | 33.429 | 1.00 | 46.13 | C |
| ATOM | 2037 | CG | GLU | A | 268 | 109.741 | 45.530 | 34.195 | 1.00 | 50.26 | C |
| ATOM | 2038 | CD | GLU | A | 268 | 109.164 | 44.377 | 33.394 | 1.00 | 52.59 | C |
| ATOM | 2039 | OE1 | GLU | A | 268 | 108.776 | 44.587 | 32.222 | 1.00 | 53.91 | O |
| ATOM | 2040 | OE2 | GLU | A | 268 | 109.080 | 43.260 | 33.947 | 1.00 | 54.82 | O |
| ATOM | 2041 | N | ILE | A | 269 | 111.780 | 49.256 | 32.649 | 1.00 | 43.95 | N |
| ATOM | 2042 | CA | ILE | A | 269 | 112.591 | 50.117 | 31.799 | 1.00 | 43.12 | C |
| ATOM | 2043 | C | ILE | A | 269 | 113.450 | 51.012 | 32.688 | 1.00 | 42.99 | C |
| ATOM | 2044 | O | ILE | A | 269 | 114.627 | 51.236 | 32.402 | 1.00 | 42.66 | O |
| ATOM | 2045 | CB | ILE | A | 269 | 111.716 | 51.001 | 30.881 | 1.00 | 42.99 | C |
| ATOM | 2046 | CG1 | ILE | A | 269 | 110.944 | 50.122 | 29.896 | 1.00 | 42.46 | C |
| ATOM | 2047 | CG2 | ILE | A | 269 | 112.590 | 51.995 | 30.123 | 1.00 | 42.46 | C |
| ATOM | 2048 | CD1 | ILE | A | 269 | 110.036 | 50.898 | 38.968 | 1.00 | 41.32 | C |
| ATOM | 2049 | N | ARG | A | 270 | 112.859 | 51.519 | 33.768 | 1.00 | 42.35 | N |
| ATOM | 2050 | CA | ARG | A | 270 | 113.592 | 52.372 | 34.696 | 1.00 | 42.43 | C |
| ATOM | 2051 | C | ARG | A | 270 | 114.667 | 51.580 | 35.447 | 1.00 | 43.30 | C |
| ATOM | 2052 | O | ARG | A | 270 | 115.802 | 52.033 | 35.598 | 1.00 | 42.17 | O |
| ATOM | 2053 | CB | ARG | A | 270 | 112.630 | 53.026 | 35.689 | 1.00 | 40.28 | C |
| ATOM | 2054 | CG | ARG | A | 270 | 113.335 | 53.693 | 36.857 | 1.00 | 40.08 | C |
| ATOM | 2055 | CD | ARG | A | 270 | 114.401 | 54.661 | 36.381 | 1.00 | 39.52 | C |
| ATOM | 2056 | NE | ARG | A | 270 | 113.843 | 55.890 | 35.835 | 1.00 | 39.63 | N |
| ATOM | 2057 | CZ | ARG | A | 270 | 114.568 | 56.833 | 35.246 | 1.00 | 40.17 | C |
| ATOM | 2058 | NH1 | ARG | A | 270 | 115.879 | 56.682 | 35.127 | 1.00 | 39.75 | N |
| ATOM | 2059 | NH2 | ARG | A | 270 | 113.991 | 57.941 | 34.803 | 1.00 | 41.04 | N |
| ATOM | 2060 | N | ALA | A | 271 | 114.297 | 50.393 | 35.917 | 1.00 | 44.99 | N |
| ATOM | 2061 | CA | ALA | A | 271 | 115.224 | 49.538 | 36.638 | 1.00 | 46.51 | C |
| ATOM | 2062 | C | ALA | A | 271 | 116.445 | 49.281 | 35.766 | 1.00 | 47.60 | C |
| ATOM | 2063 | O | ALA | A | 271 | 117.550 | 49.086 | 36.272 | 1.00 | 49.90 | O |
| ATOM | 2064 | CB | ALA | A | 271 | 114.555 | 48.222 | 36.998 | 1.00 | 46.57 | C |
| ATOM | 2065 | N | HIS | A | 272 | 116.254 | 49.283 | 34.454 | 1.00 | 47.42 | N |
| ATOM | 2066 | CA | HIS | A | 272 | 117.368 | 49.048 | 33.559 | 1.00 | 47.00 | C |
| ATOM | 2067 | C | HIS | A | 272 | 118.096 | 50.347 | 33.204 | 1.00 | 46.88 | C |
| ATOM | 2068 | O | HIS | A | 272 | 119.308 | 50.339 | 33.009 | 1.00 | 47.71 | O |
| ATOM | 2069 | CB | HIS | A | 272 | 116.889 | 48.341 | 32.295 | 1.00 | 47.98 | C |
| ATOM | 2070 | CG | HIS | A | 272 | 117.999 | 47.783 | 31.461 | 1.00 | 50.44 | C |
| ATOM | 2071 | ND1 | HIS | A | 272 | 117.779 | 47.130 | 30.269 | 1.00 | 51.34 | N |
| ATOM | 2072 | CD2 | HIS | A | 272 | 119.341 | 47.762 | 31.658 | 1.00 | 51.66 | C |
| ATOM | 2073 | CE1 | HIS | A | 272 | 118.935 | 46.730 | 29.767 | 1.00 | 52.07 | C |
| ATOM | 2074 | NE2 | HIS | A | 272 | 119.899 | 47.101 | 30.591 | 1.00 | 51.04 | N |
| ATOM | 2075 | N | PHE | A | 273 | 117.370 | 51.462 | 33.124 | 1.00 | 46.29 | N |
| ATOM | 2076 | CA | PHE | A | 273 | 117.991 | 52.755 | 32.806 | 1.00 | 45.64 | C |
| ATOM | 2077 | C | PHE | A | 273 | 117.810 | 53.752 | 33.954 | 1.00 | 46.32 | C |
| ATOM | 2078 | O | PHE | A | 273 | 117.128 | 54.770 | 33.797 | 1.00 | 47.02 | O |
| ATOM | 2079 | CB | PHE | A | 273 | 117.386 | 53.378 | 31.541 | 1.00 | 43.67 | C |
| ATOM | 2080 | CG | PHE | A | 273 | 117.491 | 52.519 | 30.313 | 1.00 | 42.54 | C |
| ATOM | 2081 | CD1 | PHE | A | 273 | 116.589 | 51.489 | 30.088 | 1.00 | 42.71 | C |
| ATOM | 2082 | CD2 | PHE | A | 273 | 118.485 | 52.755 | 29.370 | 1.00 | 42.26 | C |
| ATOM | 2083 | CE1 | PHE | A | 273 | 116.673 | 50.709 | 28.933 | 1.00 | 43.23 | C |
| ATOM | 2084 | CE2 | PHE | A | 273 | 118.580 | 51.981 | 28.217 | 1.00 | 41.40 | C |
| ATOM | 2085 | CZ | PHE | A | 273 | 117.673 | 50.959 | 27.996 | 1.00 | 42.59 | C |
| ATOM | 2086 | N | PRO | A | 274 | 118.431 | 53.483 | 35.116 | 1.00 | 45.94 | N |
| ATOM | 2087 | CA | PRO | A | 274 | 118.355 | 54.329 | 36.313 | 1.00 | 45.40 | C |
| ATOM | 2088 | C | PRO | A | 274 | 118.763 | 55.799 | 36.194 | 1.00 | 45.24 | C |
| ATOM | 2089 | O | PRO | A | 274 | 118.347 | 56.614 | 37.011 | 1.00 | 45.24 | O |
| ATOM | 2090 | CB | PRO | A | 274 | 119.229 | 53.571 | 37.308 | 1.00 | 44.99 | C |
| ATOM | 2091 | CG | PRO | A | 274 | 120.244 | 52.905 | 36.395 | 1.00 | 44.50 | C |
| ATOM | 2092 | CD | PRO | A | 274 | 119.283 | 52.317 | 35.400 | 1.00 | 45.59 | C |
| ATOM | 2093 | N | ASN | A | 275 | 119.566 | 56.145 | 35.195 | 1.00 | 45.09 | N |
| ATOM | 2094 | CA | ASN | A | 275 | 120.015 | 57.527 | 35.042 | 1.00 | 45.14 | C |
| ATOM | 2095 | C | ASN | A | 275 | 119.229 | 58.295 | 33.977 | 1.00 | 44.49 | C |
| ATOM | 2096 | O | ASN | A | 275 | 118.967 | 59.487 | 34.126 | 1.00 | 45.55 | O |
| ATOM | 2097 | CB | ASN | A | 275 | 121.497 | 57.563 | 34.664 | 1.00 | 47.44 | C |

-continued

| | | | | | | | | | | |
|---|---|---|---|---|---|---|---|---|---|---|
| ATOM | 2098 | CG | ASN | A | 275 | 122.370 | 56.762 | 35.614 | 1.00 | 49.31 C |
| ATOM | 2099 | OD1 | ASN | A | 275 | 122.481 | 57.076 | 36.795 | 1.00 | 49.47 O |
| ATOM | 2100 | ND2 | ASN | A | 275 | 123.000 | 55.713 | 35.090 | 1.00 | 51.15 N |
| ATOM | 2101 | N | ARG | A | 276 | 118.869 | 57.600 | 32.903 | 1.00 | 41.92 N |
| ATOM | 2102 | CA | ARG | A | 276 | 118.143 | 58.183 | 31.782 | 1.00 | 39.15 C |
| ATOM | 2103 | C | ARG | A | 276 | 116.868 | 58.946 | 32.148 | 1.00 | 37.69 C |
| ATOM | 2104 | O | ARG | A | 276 | 116.276 | 58.729 | 33.206 | 1.00 | 37.58 O |
| ATOM | 2105 | CB | ARG | A | 276 | 117.793 | 57.080 | 30.791 | 1.00 | 39.18 C |
| ATOM | 2106 | CG | ARG | A | 276 | 118.985 | 56.271 | 30.302 | 1.00 | 37.60 C |
| ATOM | 2107 | CD | ARG | A | 276 | 119.955 | 57.089 | 29.463 | 1.00 | 36.19 C |
| ATOM | 2108 | NE | ARG | A | 276 | 121.019 | 56.235 | 28.938 | 1.00 | 35.76 N |
| ATOM | 2109 | CZ | ARG | A | 276 | 121.913 | 56.609 | 28.031 | 1.00 | 35.25 C |
| ATOM | 2110 | NH1 | ARG | A | 276 | 121.887 | 57.836 | 27.531 | 1.00 | 36.02 N |
| ATOM | 2111 | NH2 | ARG | A | 276 | 122.831 | 55.750 | 27.617 | 1.00 | 36.01 N |
| ATOM | 2112 | N | THR | A | 277 | 116.461 | 59.846 | 31.254 | 1.00 | 35.95 N |
| ATOM | 2113 | CA | THR | A | 277 | 115.251 | 60.654 | 31.429 | 1.00 | 33.86 C |
| ATOM | 2114 | C | THR | A | 277 | 114.086 | 59.917 | 30.790 | 1.00 | 32.47 C |
| ATOM | 2115 | O | THR | A | 277 | 114.108 | 59.638 | 29.587 | 1.00 | 31.01 O |
| ATOM | 2116 | CB | THR | A | 277 | 115.369 | 62.023 | 30.728 | 1.00 | 33.80 C |
| ATOM | 2117 | OG1 | THR | A | 277 | 116.362 | 62.822 | 31.381 | 1.00 | 34.95 O |
| ATOM | 2118 | CG2 | THR | A | 277 | 114.039 | 62.746 | 30.753 | 1.00 | 33.78 C |
| ATOM | 2119 | N | LEU | A | 278 | 113.073 | 59.602 | 31.588 | 1.00 | 30.23 N |
| ATOM | 2120 | CA | LEU | A | 278 | 111.915 | 58.889 | 31.070 | 1.00 | 29.28 C |
| ATOM | 2121 | C | LEU | A | 278 | 110.663 | 59.754 | 31.048 | 1.00 | 28.27 C |
| ATOM | 2122 | O | LEU | A | 278 | 110.329 | 60.404 | 32.032 | 1.00 | 27.31 O |
| ATOM | 2123 | CB | LEU | A | 278 | 111.649 | 57.628 | 31.893 | 1.00 | 28.56 C |
| ATOM | 2124 | CG | LEU | A | 278 | 112.782 | 56.600 | 31.915 | 1.00 | 29.99 C |
| ATOM | 2125 | CD1 | LEU | A | 278 | 112.339 | 55.362 | 32.692 | 1.00 | 29.20 C |
| ATOM | 2126 | CD2 | LEU | A | 278 | 113.159 | 56.217 | 30.486 | 1.00 | 30.32 C |
| ATOM | 2127 | N | ILE | A | 279 | 109.993 | 59.766 | 29.900 | 1.00 | 26.83 N |
| ATOM | 2128 | CA | ILE | A | 279 | 108.759 | 60.517 | 29.713 | 1.00 | 25.75 C |
| ATOM | 2129 | C | ILE | A | 279 | 107.756 | 59.403 | 29.451 | 1.00 | 26.77 C |
| ATOM | 2130 | O | ILE | A | 279 | 108.035 | 58.499 | 28.649 | 1.00 | 25.38 O |
| ATOM | 2131 | CB | ILE | A | 279 | 108.847 | 61.448 | 28.485 | 1.00 | 23.44 C |
| ATOM | 2132 | CG1 | ILE | A | 279 | 110.078 | 62.345 | 28.598 | 1.00 | 23.15 C |
| ATOM | 2133 | CG2 | ILE | A | 279 | 107.604 | 62.310 | 28.405 | 1.00 | 24.07 C |
| ATOM | 2134 | CD1 | ILE | A | 279 | 110.295 | 63.233 | 27.412 | 1.00 | 23.91 C |
| ATOM | 2135 | N | ALA | A | 280 | 106.596 | 59.449 | 30.100 | 1.00 | 27.48 N |
| ATOM | 2136 | CA | ALA | A | 280 | 105.657 | 58.354 | 29.914 | 1.00 | 30.73 C |
| ATOM | 2137 | C | ALA | A | 280 | 104.246 | 58.667 | 29.469 | 1.00 | 32.08 C |
| ATOM | 2138 | O | ALA | A | 280 | 103.726 | 59.745 | 29.725 | 1.00 | 31.46 O |
| ATOM | 2139 | CB | ALA | A | 280 | 105.608 | 57.495 | 31.182 | 1.00 | 30.65 C |
| ATOM | 2140 | N | GLY | A | 281 | 103.665 | 57.644 | 28.829 | 1.00 | 35.24 N |
| ATOM | 2141 | CA | GLY | A | 281 | 102.314 | 57.614 | 28.273 | 1.00 | 35.20 C |
| ATOM | 2142 | C | GLY | A | 281 | 101.303 | 58.614 | 28.763 | 1.00 | 35.43 C |
| ATOM | 2143 | O | GLY | A | 281 | 101.623 | 59.501 | 29.552 | 1.00 | 37.45 O |
| ATOM | 2144 | N | ASN | A | 282 | 100.057 | 58.467 | 28.325 | 1.00 | 32.74 N |
| ATOM | 2145 | CA | ASN | A | 282 | 99.063 | 59.443 | 28.729 | 1.00 | 29.41 C |
| ATOM | 2146 | C | ASN | A | 282 | 98.088 | 59.056 | 29.815 | 1.00 | 27.37 C |
| ATOM | 2147 | O | ASN | A | 282 | 97.590 | 57.933 | 29.882 | 1.00 | 26.60 O |
| ATOM | 2148 | CB | ASN | A | 282 | 98.318 | 59.939 | 27.491 | 1.00 | 30.24 C |
| ATOM | 2149 | CG | ASN | A | 282 | 99.200 | 60.807 | 26.595 | 1.00 | 31.84 C |
| ATOM | 2150 | OD1 | ASN | A | 282 | 100.405 | 60.562 | 26.467 | 1.00 | 32.15 O |
| ATOM | 2151 | ND2 | ASN | A | 282 | 98.600 | 61.809 | 25.949 | 1.00 | 32.17 N |
| ATOM | 2152 | N | ILE | A | 283 | 97.845 | 60.019 | 30.690 | 1.00 | 25.51 N |
| ATOM | 2153 | CA | ILE | A | 283 | 96.907 | 59.873 | 31.790 | 1.00 | 24.37 C |
| ATOM | 2154 | C | ILE | A | 283 | 96.136 | 61.185 | 31.823 | 1.00 | 23.61 C |
| ATOM | 2155 | O | ILE | A | 283 | 96.532 | 62.160 | 31.175 | 1.00 | 23.14 O |
| ATOM | 2156 | CB | ILE | A | 283 | 97.636 | 59.631 | 33.150 | 1.00 | 23.62 C |
| ATOM | 2157 | CG1 | ILE | A | 283 | 98.677 | 60.727 | 33.421 | 1.00 | 22.08 C |
| ATOM | 2158 | CG2 | ILE | A | 283 | 98.279 | 58.256 | 33.153 | 1.00 | 23.25 C |
| ATOM | 2159 | CD1 | ILE | A | 283 | 98.119 | 62.094 | 33.881 | 1.00 | 19.86 C |
| ATOM | 2160 | N | ALA | A | 284 | 95.039 | 61.216 | 32.561 | 1.00 | 22.29 N |
| ATOM | 2161 | CA | ALA | A | 284 | 94.254 | 62.426 | 32.639 | 1.00 | 23.16 C |
| ATOM | 2162 | C | ALA | A | 284 | 93.744 | 62.633 | 34.059 | 1.00 | 24.19 C |
| ATOM | 2163 | O | ALA | A | 284 | 92.839 | 63.434 | 34.300 | 1.00 | 25.24 O |
| ATOM | 2164 | CB | ALA | A | 284 | 93.102 | 62.347 | 31.659 | 1.00 | 22.62 C |
| ATOM | 2165 | N | THR | A | 285 | 94.341 | 61.914 | 35.004 | 1.00 | 25.00 N |
| ATOM | 2166 | CA | THR | A | 285 | 93.936 | 62.015 | 36.403 | 1.00 | 25.00 C |
| ATOM | 2167 | C | THR | A | 285 | 95.149 | 62.180 | 37.308 | 1.00 | 24.68 C |
| ATOM | 2168 | O | THR | A | 285 | 96.282 | 61.956 | 36.889 | 1.00 | 22.17 O |
| ATOM | 2169 | CB | THR | A | 285 | 93.176 | 60.759 | 36.851 | 1.00 | 24.60 C |
| ATOM | 2170 | OG1 | THR | A | 285 | 94.056 | 59.636 | 36.784 | 1.00 | 27.11 O |
| ATOM | 2171 | CG2 | THR | A | 285 | 91.975 | 60.501 | 35.953 | 1.00 | 23.14 C |
| ATOM | 2172 | N | ALA | A | 286 | 94.893 | 62.576 | 38.555 | 1.00 | 25.97 N |
| ATOM | 2173 | CA | ALA | A | 286 | 95.951 | 62.766 | 39.536 | 1.00 | 26.48 C |
| ATOM | 2174 | C | ALA | A | 286 | 96.580 | 61.422 | 39.897 | 1.00 | 28.07 C |
| ATOM | 2175 | O | ALA | A | 286 | 97.800 | 61.329 | 40.057 | 1.00 | 29.78 O |
| ATOM | 2176 | CB | ALA | A | 286 | 95.395 | 63.445 | 40.783 | 1.00 | 24.43 C |

-continued

| | | | | | | | | | | |
|---|---|---|---|---|---|---|---|---|---|---|
| ATOM | 2177 | N | GLU | A | 287 | 95.763 | 60.378 | 40.022 | 1.00 | 29.47 N |
| ATOM | 2178 | CA | GLU | A | 287 | 96.295 | 59.058 | 40.354 | 1.00 | 30.99 C |
| ATOM | 2179 | C | GLU | A | 287 | 97.131 | 58.451 | 39.242 | 1.00 | 29.83 C |
| ATOM | 2180 | O | GLU | A | 287 | 98.109 | 57.744 | 39.505 | 1.00 | 29.81 O |
| ATOM | 2181 | CB | GLU | A | 287 | 95.173 | 58.094 | 40.739 | 1.00 | 33.93 C |
| ATOM | 2182 | CG | GLU | A | 287 | 95.052 | 57.909 | 42.255 | 1.00 | 41.21 C |
| ATOM | 2183 | CD | GLU | A | 287 | 96.298 | 57.259 | 42.899 | 1.00 | 44.34 C |
| ATOM | 2184 | OE1 | GLU | A | 287 | 96.319 | 57.141 | 44.147 | 1.00 | 45.00 O |
| ATOM | 2185 | OE2 | GLU | A | 287 | 97.244 | 56.861 | 42.165 | 1.00 | 44.45 O |
| ATOM | 2186 | N | GLY | A | 288 | 96.746 | 58.726 | 38.000 | 1.00 | 28.61 N |
| ATOM | 2187 | CA | GLY | A | 288 | 97.495 | 58.204 | 36.876 | 1.00 | 26.94 C |
| ATOM | 2188 | C | GLY | A | 288 | 98.879 | 58.818 | 36.848 | 1.00 | 26.38 C |
| ATOM | 2189 | O | GLY | A | 288 | 99.849 | 58.139 | 36.556 | 1.00 | 26.76 O |
| ATOM | 2190 | N | ALA | A | 289 | 98.974 | 60.109 | 37.150 | 1.00 | 26.64 N |
| ATOM | 2191 | CA | ALA | A | 289 | 100.257 | 60.793 | 37.156 | 1.00 | 27.29 C |
| ATOM | 2192 | C | ALA | A | 289 | 101.087 | 60.229 | 38.296 | 1.00 | 29.11 C |
| ATOM | 2193 | O | ALA | A | 289 | 102.293 | 60.013 | 38.159 | 1.00 | 30.09 O |
| ATOM | 2194 | CB | ALA | A | 289 | 100.052 | 62.277 | 37.348 | 1.00 | 27.03 C |
| ATOM | 2195 | N | ARG | A | 290 | 100.428 | 59.983 | 39.423 | 1.00 | 29.67 N |
| ATOM | 2196 | CA | ARG | A | 290 | 101.091 | 59.433 | 40.600 | 1.00 | 30.07 C |
| ATOM | 2197 | C | ARG | A | 290 | 101.598 | 58.009 | 40.327 | 1.00 | 29.70 C |
| ATOM | 2198 | O | ARG | A | 290 | 102.729 | 57.656 | 40.687 | 1.00 | 30.10 O |
| ATOM | 2199 | CB | ARG | A | 290 | 100.123 | 59.463 | 41.783 | 1.00 | 29.78 C |
| ATOM | 2200 | CG | ARG | A | 290 | 100.653 | 58.884 | 43.073 | 1.00 | 31.76 C |
| ATOM | 2201 | CD | ARG | A | 290 | 99.694 | 59.214 | 44.205 | 1.00 | 34.18 C |
| ATOM | 2202 | NE | ARG | A | 290 | 99.812 | 60.610 | 44.623 | 1.00 | 37.25 N |
| ATOM | 2203 | CZ | ARG | A | 290 | 98.786 | 61.440 | 44.789 | 1.00 | 38.76 C |
| ATOM | 2204 | NH1 | ARG | A | 290 | 97.544 | 61.019 | 44.567 | 1.00 | 41.18 N |
| ATOM | 2205 | NH2 | ARG | A | 290 | 99.001 | 62.685 | 45.195 | 1.00 | 38.72 N |
| ATOM | 2206 | N | ALA | A | 291 | 100.774 | 57.194 | 39.673 | 1.00 | 28.72 N |
| ATOM | 2207 | CA | ALA | A | 291 | 101.176 | 55.829 | 39.356 | 1.00 | 26.94 C |
| ATOM | 2208 | C | ALA | A | 291 | 102.425 | 55.850 | 38.476 | 1.00 | 26.66 C |
| ATOM | 2209 | O | ALA | A | 291 | 103.363 | 55.092 | 38.700 | 1.00 | 27.57 O |
| ATOM | 2210 | CB | ALA | A | 291 | 100.041 | 55.096 | 38.649 | 1.00 | 24.83 C |
| ATOM | 2211 | N | LEU | A | 292 | 102.437 | 56.723 | 37.473 | 1.00 | 26.41 N |
| ATOM | 2212 | CA | LEU | A | 292 | 103.579 | 56.823 | 36.570 | 1.00 | 26.25 C |
| ATOM | 2213 | C | LEU | A | 292 | 104.823 | 57.369 | 37.272 | 1.00 | 26.35 C |
| ATOM | 2214 | O | LEU | A | 292 | 105.927 | 56.861 | 37.069 | 1.00 | 25.85 O |
| ATOM | 2215 | CB | LEU | A | 292 | 103.221 | 57.688 | 35.356 | 1.00 | 25.03 C |
| ATOM | 2216 | CG | LEU | A | 292 | 102.247 | 57.053 | 34.351 | 1.00 | 24.67 C |
| ATOM | 2217 | CD1 | LEU | A | 292 | 101.748 | 58.098 | 33.353 | 1.00 | 24.62 C |
| ATOM | 2218 | CD2 | LEU | A | 292 | 102.943 | 55.909 | 33.634 | 1.00 | 21.45 C |
| ATOM | 2219 | N | TYR | A | 293 | 104.661 | 58.408 | 38.083 | 1.00 | 27.07 N |
| ATOM | 2220 | CA | TYR | A | 293 | 105.809 | 58.947 | 38.804 | 1.00 | 28.43 C |
| ATOM | 2221 | C | TYR | A | 293 | 106.353 | 57.853 | 39.710 | 1.00 | 29.43 C |
| ATOM | 2222 | O | TYR | A | 293 | 107.555 | 57.601 | 39.738 | 1.00 | 29.87 O |
| ATOM | 2223 | CB | TYR | A | 293 | 105.398 | 60.155 | 39.629 | 1.00 | 28.36 C |
| ATOM | 2224 | CG | TYR | A | 293 | 105.192 | 61.411 | 38.812 | 1.00 | 29.78 C |
| ATOM | 2225 | CD1 | TYR | A | 293 | 104.175 | 62.310 | 39.134 | 1.00 | 29.30 C |
| ATOM | 2226 | CD2 | TYR | A | 293 | 106.038 | 61.725 | 37.744 | 1.00 | 29.08 C |
| ATOM | 2227 | CE1 | TYR | A | 293 | 104.000 | 63.485 | 38.417 | 1.00 | 28.70 C |
| ATOM | 2228 | CE2 | TYR | A | 293 | 105.868 | 62.905 | 37.020 | 1.00 | 28.90 C |
| ATOM | 2229 | CZ | TYR | A | 293 | 104.844 | 63.776 | 37.367 | 1.00 | 28.75 C |
| ATOM | 2230 | OH | TYR | A | 293 | 104.644 | 64.936 | 36.666 | 1.00 | 29.75 O |
| ATOM | 2231 | N | ASP | A | 294 | 105.456 | 57.191 | 40.435 | 1.00 | 30.73 N |
| ATOM | 2232 | CA | ASP | A | 294 | 105.846 | 56.104 | 41.325 | 1.00 | 32.03 C |
| ATOM | 2233 | C | ASP | A | 294 | 106.533 | 54.961 | 40.573 | 1.00 | 33.10 C |
| ATOM | 2234 | O | ASP | A | 294 | 107.287 | 54.185 | 41.167 | 1.00 | 34.97 O |
| ATOM | 2235 | CB | ASP | A | 294 | 104.623 | 55.570 | 42.067 | 1.00 | 31.61 C |
| ATOM | 2236 | CG | ASP | A | 294 | 104.081 | 56.554 | 43.080 | 1.00 | 32.26 C |
| ATOM | 2237 | OD1 | ASP | A | 294 | 103.034 | 56.266 | 43.700 | 1.00 | 33.58 O |
| ATOM | 2238 | OD2 | ASP | A | 294 | 104.704 | 57.615 | 43.267 | 1.00 | 32.44 O |
| ATOM | 2239 | N | ALA | A | 295 | 106.275 | 54.854 | 39.271 | 1.00 | 32.83 N |
| ATOM | 2240 | CA | ALA | A | 295 | 106.879 | 53.802 | 38.455 | 1.00 | 31.74 C |
| ATOM | 2241 | C | ALA | A | 295 | 108.264 | 54.224 | 37.992 | 1.00 | 31.68 C |
| ATOM | 2242 | O | ALA | A | 295 | 108.985 | 53.436 | 37.380 | 1.00 | 32.56 O |
| ATOM | 2243 | CB | ALA | A | 295 | 105.997 | 53.482 | 37.251 | 1.00 | 30.93 C |
| ATOM | 2244 | N | GLY | A | 296 | 108.630 | 55.470 | 38.269 | 1.00 | 30.95 N |
| ATOM | 2245 | CA | GLY | A | 296 | 109.948 | 55.933 | 37.882 | 1.00 | 31.13 C |
| ATOM | 2246 | C | GLY | A | 296 | 110.045 | 56.900 | 36.717 | 1.00 | 31.66 C |
| ATOM | 2247 | O | GLY | A | 296 | 111.149 | 57.204 | 36.265 | 1.00 | 31.91 O |
| ATOM | 2248 | N | VAL | A | 297 | 108.919 | 57.394 | 36.219 | 1.00 | 31.67 N |
| ATOM | 2249 | CA | VAL | A | 297 | 108.978 | 58.328 | 35.101 | 1.00 | 31.83 C |
| ATOM | 2250 | C | VAL | A | 297 | 109.416 | 59.716 | 35.586 | 1.00 | 29.98 C |
| ATOM | 2251 | O | VAL | A | 297 | 109.171 | 60.092 | 36.730 | 1.00 | 29.21 O |
| ATOM | 2252 | CB | VAL | A | 297 | 107.606 | 58.445 | 34.382 | 1.00 | 32.91 C |
| ATOM | 2253 | CG1 | VAL | A | 297 | 106.596 | 59.096 | 35.290 | 1.00 | 35.68 C |
| ATOM | 2254 | CG2 | VAL | A | 297 | 107.747 | 59.266 | 33.125 | 1.00 | 35.70 C |
| ATOM | 2255 | N | ASP | A | 298 | 110.074 | 60.463 | 34.707 | 1.00 | 28.22 N |

-continued

| | | | | | | | | | | |
|---|---|---|---|---|---|---|---|---|---|---|
| ATOM | 2256 | CA | ASP | A | 298 | 110.545 | 61.801 | 35.022 | 1.00 | 27.00 C |
| ATOM | 2257 | C | ASP | A | 298 | 109.528 | 62.852 | 34.607 | 1.00 | 27.20 C |
| ATOM | 2258 | O | ASP | A | 298 | 109.281 | 63.813 | 35.332 | 1.00 | 26.86 O |
| ATOM | 2259 | CB | ASP | A | 298 | 111.870 | 62.071 | 34.309 | 1.00 | 28.58 C |
| ATOM | 2260 | CG | ASP | A | 298 | 112.974 | 61.149 | 34.776 | 1.00 | 30.31 C |
| ATOM | 2261 | OD1 | ASP | A | 298 | 113.221 | 61.114 | 35.994 | 1.00 | 34.37 O |
| ATOM | 2262 | OD2 | ASP | A | 298 | 113.600 | 60.462 | 33.943 | 1.00 | 31.52 O |
| ATOM | 2263 | N | VAL | A | 299 | 108.942 | 62.664 | 33.430 | 1.00 | 26.94 N |
| ATOM | 2264 | CA | VAL | A | 299 | 107.955 | 63.596 | 32.898 | 1.00 | 25.40 C |
| ATOM | 2265 | C | VAL | A | 299 | 106.704 | 62.825 | 32.462 | 1.00 | 24.71 C |
| ATOM | 2266 | O | VAL | A | 299 | 106.792 | 61.831 | 31.736 | 1.00 | 24.19 O |
| ATOM | 2267 | CB | VAL | A | 299 | 108.526 | 64.371 | 31.667 | 1.00 | 25.18 C |
| ATOM | 2268 | CG1 | VAL | A | 299 | 107.573 | 65.493 | 31.255 | 1.00 | 23.30 C |
| ATOM | 2269 | CG2 | VAL | A | 299 | 109.908 | 64.920 | 31.985 | 1.00 | 24.81 C |
| ATOM | 2270 | N | VAL | A | 300 | 105.544 | 63.287 | 32.916 | 1.00 | 23.99 N |
| ATOM | 2271 | CA | VAL | A | 300 | 104.270 | 62.661 | 32.576 | 1.00 | 23.71 C |
| ATOM | 2272 | C | VAL | A | 300 | 103.499 | 63.493 | 31.555 | 1.00 | 24.32 C |
| ATOM | 2273 | O | VAL | A | 300 | 103.338 | 64.707 | 31.730 | 1.00 | 24.20 O |
| ATOM | 2274 | CB | VAL | A | 300 | 103.370 | 62.486 | 33.825 | 1.00 | 23.42 C |
| ATOM | 2275 | CG1 | VAL | A | 300 | 101.967 | 62.116 | 33.407 | 1.00 | 23.29 C |
| ATOM | 2276 | CG2 | VAL | A | 300 | 103.923 | 61.391 | 34.722 | 1.00 | 23.23 C |
| ATOM | 2277 | N | LYS | A | 301 | 103.033 | 62.854 | 30.484 | 1.00 | 24.40 N |
| ATOM | 2278 | CA | LYS | A | 301 | 102.258 | 63.588 | 29.503 | 1.00 | 24.04 C |
| ATOM | 2279 | C | LYS | A | 301 | 100.782 | 63.356 | 29.753 | 1.00 | 22.78 C |
| ATOM | 2280 | O | LYS | A | 301 | 100.322 | 62.229 | 29.960 | 1.00 | 21.52 O |
| ATOM | 2281 | CB | LYS | A | 301 | 102.686 | 63.259 | 28.065 | 1.00 | 24.29 C |
| ATOM | 2282 | CG | LYS | A | 301 | 102.809 | 61.818 | 27.709 | 1.00 | 29.51 C |
| ATOM | 2283 | CD | LYS | A | 301 | 103.757 | 61.674 | 26.489 | 1.00 | 32.99 C |
| ATOM | 2284 | CE | LYS | A | 301 | 103.228 | 62.284 | 25.187 | 1.00 | 30.67 C |
| ATOM | 2285 | NZ | LYS | A | 301 | 102.178 | 61.439 | 24.564 | 1.00 | 30.01 N |
| ATOM | 2286 | N | VAL | A | 302 | 100.060 | 64.470 | 29.782 | 1.00 | 22.18 N |
| ATOM | 2287 | CA | VAL | A | 302 | 98.641 | 64.485 | 30.061 | 1.00 | 22.10 C |
| ATOM | 2289 | C | VAL | A | 302 | 97.793 | 64.628 | 28.807 | 1.00 | 22.59 C |
| ATOM | 2289 | O | VAL | A | 302 | 98.082 | 65.457 | 27.938 | 1.00 | 22.52 O |
| ATOM | 2290 | CB | VAL | A | 302 | 98.306 | 65.652 | 31.032 | 1.00 | 21.25 C |
| ATOM | 2291 | CG1 | VAL | A | 302 | 96.815 | 65.677 | 31.335 | 1.00 | 20.58 C |
| ATOM | 2292 | CG2 | VAL | A | 302 | 99.103 | 65.504 | 32.312 | 1.00 | 20.42 C |
| ATOM | 2293 | N | GLY | A | 303 | 96.745 | 63.812 | 28.722 | 1.00 | 22.97 N |
| ATOM | 2294 | CA | GLY | A | 303 | 95.854 | 63.892 | 27.582 | 1.00 | 22.25 C |
| ATOM | 2295 | C | GLY | A | 303 | 95.160 | 62.618 | 27.153 | 1.00 | 22.34 C |
| ATOM | 2296 | O | GLY | A | 303 | 95.784 | 61.750 | 26.566 | 1.00 | 23.71 O |
| ATOM | 2297 | N | ILE | A | 304 | 93.873 | 62.493 | 27.453 | 1.00 | 22.67 N |
| ATOM | 2298 | CA | ILE | A | 304 | 93.107 | 61.329 | 27.011 | 1.00 | 24.68 C |
| ATOM | 2299 | C | ILE | A | 304 | 91.883 | 61.799 | 26.202 | 1.00 | 26.38 C |
| ATOM | 2300 | O | ILE | A | 304 | 90.881 | 62.237 | 26.770 | 1.00 | 26.11 O |
| ATOM | 2301 | CB | ILE | A | 304 | 92.625 | 60.446 | 28.195 | 1.00 | 23.24 C |
| ATOM | 2302 | CG1 | ILE | A | 304 | 93.818 | 59.799 | 28.906 | 1.00 | 22.41 C |
| ATOM | 2303 | CG2 | ILE | A | 304 | 91.711 | 59.346 | 27.680 | 1.00 | 21.36 C |
| ATOM | 2304 | CD1 | ILE | A | 304 | 94.503 | 56.718 | 28.113 | 1.00 | 22.43 C |
| ATOM | 2305 | N | GLY | A | 305 | 91.996 | 61.747 | 24.872 | 1.00 | 28.56 N |
| ATOM | 2306 | CA | GLY | A | 305 | 90.895 | 62.138 | 24.011 | 1.00 | 30.63 C |
| ATOM | 2307 | C | GLY | A | 305 | 90.843 | 63.516 | 23.356 | 1.00 | 33.34 C |
| ATOM | 2308 | O | GLY | A | 305 | 90.112 | 63.666 | 22.370 | 1.00 | 34.88 O |
| ATOM | 2309 | N | PRO | A | 306 | 91.588 | 64.534 | 23.836 | 1.00 | 33.14 N |
| ATOM | 2310 | CA | PRO | A | 306 | 91.541 | 65.875 | 23.226 | 1.00 | 33.01 C |
| ATOM | 2311 | C | PRO | A | 306 | 92.126 | 66.054 | 21.814 | 1.00 | 33.06 C |
| ATOM | 2312 | O | PRO | A | 306 | 91.928 | 67.104 | 21.191 | 1.00 | 33.29 O |
| ATO | 2313 | CB | PRO | A | 306 | 92.275 | 66.728 | 24.256 | 1.00 | 30.93 C |
| ATOM | 2314 | CG | PRO | A | 306 | 93.353 | 65.772 | 24.704 | 1.00 | 30.96 C |
| ATOM | 2315 | CD | PRO | A | 306 | 92.504 | 64.547 | 24.992 | 1.00 | 31.97 C |
| ATOM | 2316 | N | GLY | A | 307 | 92.833 | 65.044 | 21.313 | 1.00 | 33.26 N |
| ATOM | 2317 | CA | GLY | A | 307 | 93.446 | 65.148 | 19.994 | 1.00 | 33.13 C |
| ATOM | 2318 | C | GLY | A | 307 | 92.525 | 65.502 | 18.837 | 1.00 | 33.48 C |
| ATOM | 2319 | O | GLY | A | 307 | 91.414 | 64.982 | 16.739 | 1.00 | 33.64 O |
| ATOM | 2320 | N | SER | A | 308 | 92.992 | 66.382 | 17.950 | 1.00 | 32.89 N |
| ATOM | 2321 | CA | SER | A | 308 | 92.209 | 66.802 | 16.783 | 1.00 | 33.08 C |
| ATOM | 2322 | C | SER | A | 308 | 91.745 | 65.606 | 15.950 | 1.00 | 32.80 C |
| ATOM | 2323 | O | SER | A | 308 | 90.623 | 65.577 | 15.452 | 1.00 | 33.12 O |
| ATOM | 2324 | CB | SER | A | 308 | 93.038 | 67.743 | 15.898 | 1.00 | 32.26 C |
| ATOM | 2325 | OG | SER | A | 308 | 94.229 | 67.114 | 15.448 | 1.00 | 31.53 O |
| ATOM | 2326 | N | ILE | A | 309 | 92.625 | 64.625 | 15.809 | 1.00 | 33.27 N |
| ATOM | 2327 | CA | ILE | A | 309 | 92.346 | 63.416 | 15.045 | 1.00 | 34.38 C |
| ATOM | 2328 | C | ILE | A | 309 | 91.953 | 62.229 | 15.940 | 1.00 | 34.76 C |
| ATOM | 2329 | O | ILE | A | 309 | 91.843 | 61.095 | 15.471 | 1.00 | 34.40 O |
| ATOM | 2330 | CB | ILE | A | 309 | 93.590 | 63.033 | 14.176 | 1.00 | 35.31 C |
| ATOM | 2331 | CG1 | ILE | A | 309 | 94.878 | 63.132 | 15.004 | 1.00 | 35.26 C |
| ATOM | 2332 | CG2 | ILE | A | 309 | 93.709 | 63.974 | 12.980 | 1.00 | 34.04 C |
| ATOM | 2333 | CD1 | ILE | A | 309 | 94.957 | 62.199 | 16.191 | 1.00 | 36.80 C |
| ATOM | 2334 | N | CYS | A | 310 | 91.743 | 62.506 | 17.227 | 1.00 | 35.32 N |

-continued

| | | | | | | | | | |
|---|---|---|---|---|---|---|---|---|---|
| ATOM | 2335 | CA | CYS | A | 310 | 91.380 | 61.483 | 18.209 | 1.00 35.11 C |
| ATOM | 2336 | C | CYS | A | 310 | 89.882 | 61.214 | 18.337 | 1.00 34.44 C |
| ATOM | 2337 | O | CYS | A | 310 | 89.072 | 62.142 | 18.449 | 1.00 33.70 O |
| ATOM | 2338 | CB | CYS | A | 310 | 91.922 | 61.873 | 19.587 | 1.00 36.64 C |
| ATOM | 2339 | SG | CYS | A | 310 | 91.351 | 60.810 | 20.950 | 1.00 40.34 S |
| ATOM | 2340 | N | THR | A | 311 | 89.529 | 59.931 | 18.351 | 1.00 33.48 N |
| ATOM | 2341 | CA | THR | A | 311 | 88.143 | 59.500 | 18.487 | 1.00 33.03 C |
| ATOM | 2342 | C | THR | A | 311 | 87.936 | 58.662 | 19.756 | 1.00 31.85 C |
| ATOM | 2343 | O | THR | A | 311 | 86.911 | 58.016 | 19.924 | 1.00 32.55 O |
| ATOM | 2344 | CB | THR | A | 311 | 87.720 | 58.657 | 17.287 | 1.00 34.00 C |
| ATOM | 2345 | OG1 | THR | A | 311 | 88.594 | 57.526 | 17.180 | 1.00 36.60 O |
| ATOM | 2346 | CG2 | THR | A | 311 | 87.797 | 59.474 | 16.004 | 1.00 34.76 C |
| ATOM | 2347 | N | THR | A | 312 | 88.912 | 58.667 | 20.650 | 1.00 30.55 N |
| ATOM | 2348 | CA | THR | A | 312 | 88.794 | 57.905 | 21.884 | 1.00 29.18 C |
| ATOM | 2349 | C | THR | A | 312 | 87.523 | 58.238 | 22.661 | 1.00 28.00 C |
| ATOM | 2350 | O | THR | A | 312 | 86.831 | 57.344 | 23.144 | 1.00 27.47 O |
| ATOM | 2351 | CB | THR | A | 312 | 90.018 | 58.142 | 22.783 | 1.00 29.25 C |
| ATOM | 2352 | OG1 | THR | A | 312 | 91.174 | 57.572 | 22.159 | 1.00 31.01 O |
| ATOM | 2353 | CG2 | THR | A | 312 | 89.821 | 57.509 | 24.150 | 1.00 30.17 C |
| ATOM | 2354 | N | ARG | A | 313 | 87.199 | 59.518 | 22.774 | 1.00 26.42 N |
| ATOM | 2355 | CA | ARG | A | 313 | 86.015 | 59.899 | 23.519 | 1.00 26.82 C |
| ATOM | 2356 | C | ARG | A | 313 | 84.712 | 59.469 | 22.858 | 1.00 27.41 C |
| ATOM | 2357 | O | ARG | A | 313 | 83.699 | 59.237 | 23.531 | 1.00 28.22 O |
| ATOM | 2358 | CB | ARG | A | 313 | 86.025 | 61.407 | 23.765 | 1.00 27.23 C |
| ATOM | 2359 | CG | ARG | A | 313 | 87.207 | 61.837 | 24.616 | 1.00 28.90 C |
| ATOM | 2360 | CD | ARG | A | 313 | 87.183 | 63.318 | 24.904 | 1.00 31.11 C |
| ATOM | 2361 | NE | ARG | A | 313 | 88.414 | 63.773 | 25.552 | 1.00 32.48 N |
| ATOM | 2362 | CZ | ARG | A | 313 | 88.674 | 65.046 | 25.840 | 1.00 32.07 C |
| ATOM | 2363 | NH1 | ARG | A | 313 | 87.790 | 65.996 | 25.540 | 1.00 30.54 N |
| ATOM | 2364 | NH2 | ARG | A | 313 | 89.817 | 65.366 | 26.430 | 1.00 31.87 N |
| ATOM | 2365 | N | VAL | A | 314 | 84.746 | 59.339 | 21.540 | 1.00 26.45 N |
| ATOM | 2366 | CA | VAL | A | 314 | 83.576 | 58.952 | 20.774 | 1.00 25.00 C |
| ATOM | 2367 | C | VAL | A | 314 | 83.364 | 57.446 | 20.698 | 1.00 24.59 C |
| ATOM | 2368 | O | VAL | A | 314 | 82.253 | 56.963 | 20.890 | 1.00 24.29 O |
| ATOM | 2369 | CB | VAL | A | 314 | 83.672 | 59.496 | 19.338 | 1.00 26.31 C |
| ATOM | 2370 | CG1 | VAL | A | 314 | 82.429 | 59.127 | 18.558 | 1.00 26.03 C |
| ATOM | 2371 | CG2 | VAL | A | 314 | 83.866 | 60.998 | 19.371 | 1.00 25.74 C |
| ATOM | 2372 | N | VAL | A | 315 | 84.428 | 56.704 | 20.416 | 1.00 24.12 N |
| ATOM | 2373 | CA | VAL | A | 315 | 84.322 | 55.255 | 20.286 | 1.00 24.14 C |
| ATOM | 2374 | C | VAL | A | 315 | 84.419 | 54.460 | 21.595 | 1.00 23.17 C |
| ATOM | 2375 | O | VAL | A | 315 | 83.837 | 53.387 | 21.713 | 1.00 22.34 O |
| ATOM | 2376 | CB | VAL | A | 315 | 85.351 | 54.737 | 19.266 | 1.00 23.99 C |
| ATOM | 2377 | CG1 | VAL | A | 315 | 85.058 | 55.352 | 17.897 | 1.00 24.71 C |
| ATOM | 2378 | CG2 | VAL | A | 315 | 86.754 | 55.099 | 19.705 | 1.00 25.41 C |
| ATOM | 2379 | N | ALA | A | 316 | 85.137 | 54.992 | 22.577 | 1.00 22.80 N |
| ATOM | 2380 | CA | ALA | A | 316 | 85.273 | 54.322 | 23.864 | 1.00 22.89 C |
| ATOM | 2381 | C | ALA | A | 316 | 84.453 | 55.075 | 24.907 | 1.00 23.76 C |
| ATOM | 2382 | O | ALA | A | 316 | 84.096 | 54.525 | 25.955 | 1.00 23.93 O |
| ATOM | 2383 | CB | ALA | A | 316 | 86.739 | 54.277 | 24.278 | 1.00 21.84 C |
| ATOM | 2384 | N | GLY | A | 317 | 84.154 | 56.337 | 24.607 | 1.00 24.54 N |
| ATOM | 2385 | CA | GLY | A | 317 | 83.378 | 57.167 | 25.511 | 1.00 24.66 C |
| ATOM | 2386 | C | GLY | A | 317 | 84.154 | 57.582 | 26.744 | 1.00 25.96 C |
| ATOM | 2387 | O | GLY | A | 317 | 83.558 | 57.954 | 27.759 | 1.00 26.42 O |
| ATOM | 2388 | N | VAL | A | 318 | 85.482 | 57.545 | 26.646 | 1.00 25.51 N |
| ATOM | 2389 | CA | VAL | A | 318 | 86.369 | 57.879 | 27.760 | 1.00 24.79 C |
| ATOM | 2390 | C | VAL | A | 318 | 87.219 | 59.133 | 27.554 | 1.00 25.38 C |
| ATOM | 2391 | O | VAL | A | 318 | 87.633 | 59.437 | 26.438 | 1.00 25.50 O |
| ATOM | 2392 | CB | VAL | A | 318 | 87.317 | 56.693 | 28.049 | 1.00 24.92 C |
| ATOM | 2393 | CG1 | VAL | A | 318 | 88.363 | 57.081 | 29.090 | 1.00 24.67 C |
| ATOM | 2394 | CG2 | VAL | A | 318 | 86.507 | 55.500 | 28.535 | 1.00 23.44 C |
| ATOM | 2395 | N | GLY | A | 319 | 87.477 | 59.851 | 28.645 | 1.00 24.73 N |
| ATOM | 2396 | CA | GLY | A | 319 | 88.304 | 61.043 | 28.578 | 1.00 25.39 C |
| ATOM | 2397 | C | GLY | A | 319 | 87.980 | 62.097 | 29.620 | 1.00 25.66 C |
| ATOM | 2398 | O | GLY | A | 319 | 87.076 | 61.926 | 30.437 | 1.00 25.40 O |
| ATOM | 2399 | N | VAL | A | 320 | 88.737 | 63.188 | 29.609 | 1.00 24.72 N |
| ATOM | 2400 | CA | VAL | A | 320 | 88.484 | 64.281 | 30.535 | 1.00 25.55 C |
| ATOM | 2401 | C | VAL | A | 320 | 88.944 | 65.581 | 29.903 | 1.00 23.92 C |
| ATOM | 2402 | O | VAL | A | 320 | 90.033 | 65.653 | 29.331 | 1.00 22.93 O |
| ATOM | 2403 | CB | VAL | A | 320 | 89.203 | 64.087 | 31.899 | 1.00 27.29 C |
| ATOM | 2404 | CG1 | VAL | A | 320 | 90.667 | 64.017 | 31.693 | 1.00 32.20 C |
| ATOM | 2405 | CG2 | VAL | A | 320 | 88.884 | 65.241 | 32.838 | 1.00 26.56 C |
| ATOM | 2406 | N | PRO | A | 321 | 88.100 | 66.625 | 29.980 | 1.00 23.64 N |
| ATOM | 2407 | CA | PRO | A | 321 | 88.438 | 67.928 | 29.408 | 1.00 22.67 C |
| ATOM | 2408 | C | PRO | A | 321 | 89.872 | 68.279 | 29.791 | 1.00 22.52 C |
| ATOM | 2409 | O | PRO | A | 321 | 90.232 | 68.263 | 30.961 | 1.00 23.18 O |
| ATOM | 2410 | CB | PRO | A | 321 | 87.381 | 68.823 | 30.028 | 1.00 23.67 C |
| ATOM | 2411 | CG | PRO | A | 321 | 86.164 | 67.896 | 29.986 | 1.00 20.93 C |
| ATOM | 2412 | CD | PRO | A | 321 | 86.780 | 66.686 | 30.640 | 1.00 22.53 C |
| ATOM | 2413 | N | GLN | A | 322 | 90.679 | 68.588 | 28.786 | 1.00 22.16 N |

-continued

| | | | | | | | | | | |
|---|---|---|---|---|---|---|---|---|---|---|
| ATOM | 2414 | CA | GLN | A | 322 | 92.099 | 68.880 | 28.948 | 1.00 | 21.62 C |
| ATOM | 2415 | C | GLN | A | 322 | 92.573 | 69.884 | 30.002 | 1.00 | 20.84 C |
| ATOM | 2416 | O | GLN | A | 322 | 93.551 | 69.609 | 30.679 | 1.00 | 21.63 O |
| ATOM | 2417 | CB | GLN | A | 322 | 92.684 | 69.245 | 27.578 | 1.00 | 22.97 C |
| ATOM | 2418 | CG | GLN | A | 322 | 94.217 | 69.292 | 27.491 | 1.00 | 24.38 C |
| ATOM | 2419 | CD | GLN | A | 322 | 94.896 | 67.951 | 27.725 | 1.00 | 23.75 C |
| ATOM | 2420 | OE1 | GLN | A | 322 | 96.067 | 67.776 | 27.390 | 1.00 | 26.82 O |
| ATOM | 2421 | NE2 | GLN | A | 322 | 94.176 | 67.011 | 28.314 | 1.00 | 23.57 N |
| ATOM | 2422 | N | VAL | A | 323 | 91.932 | 71.037 | 30.151 | 1.00 | 19.60 N |
| ATOM | 2423 | CA | VAL | A | 323 | 92.401 | 71.970 | 31.175 | 1.00 | 19.52 C |
| ATOM | 2424 | C | VAL | A | 323 | 92.280 | 71.357 | 32.572 | 1.00 | 20.46 C |
| ATOM | 2425 | O | VAL | A | 323 | 93.144 | 71.556 | 33.420 | 1.00 | 22.03 O |
| ATOM | 2426 | CB | VAL | A | 323 | 91.645 | 73.322 | 31.143 | 1.00 | 17.80 C |
| ATOM | 2427 | CG1 | VAL | A | 323 | 92.026 | 74.177 | 32.359 | 1.00 | 17.57 C |
| ATOM | 2428 | CG2 | VAL | A | 323 | 92.009 | 74.070 | 29.888 | 1.00 | 18.00 C |
| ATOM | 2429 | N | THR | A | 324 | 91.210 | 70.616 | 32.815 | 1.00 | 21.51 N |
| ATOM | 2430 | CA | THR | A | 324 | 91.029 | 69.961 | 34.106 | 1.00 | 21.74 C |
| ATOM | 2431 | C | THR | A | 324 | 92.056 | 68.845 | 34.307 | 1.00 | 22.09 C |
| ATOM | 2432 | O | THR | A | 324 | 92.628 | 68.704 | 35.393 | 1.00 | 22.04 O |
| ATOM | 2433 | CB | THR | A | 324 | 89.616 | 69.383 | 34.221 | 1.00 | 21.42 C |
| ATOM | 2434 | OG1 | THR | A | 324 | 88.696 | 70.448 | 34.469 | 1.00 | 23.37 O |
| ATOM | 2435 | CG2 | THR | A | 324 | 89.532 | 68.370 | 35.335 | 1.00 | 24.31 C |
| ATOM | 2436 | N | ALA | A | 325 | 92.296 | 68.062 | 33.256 | 1.00 | 21.63 N |
| ATOM | 2437 | CA | ALA | A | 325 | 93.253 | 66.958 | 33.324 | 1.00 | 23.09 C |
| ATOM | 2438 | C | ALA | A | 325 | 94.669 | 67.437 | 33.668 | 1.00 | 23.65 C |
| ATOM | 2439 | O | ALA | A | 325 | 95.325 | 66.865 | 34.540 | 1.00 | 23.99 O |
| ATOM | 2440 | CB | ALA | A | 325 | 93.262 | 66.192 | 32.006 | 1.00 | 22.44 C |
| ATOM | 2441 | N | ILE | A | 326 | 95.134 | 68.472 | 32.967 | 1.00 | 23.50 N |
| ATOM | 2442 | CA | ILE | A | 326 | 96.458 | 69.067 | 33.182 | 1.00 | 23.40 C |
| ATOM | 2443 | C | ILE | A | 326 | 96.576 | 69.483 | 34.641 | 1.00 | 24.71 C |
| ATOM | 2444 | O | ILE | A | 326 | 97.520 | 69.124 | 35.337 | 1.00 | 24.66 O |
| ATOM | 2445 | CB | ILE | A | 326 | 96.644 | 70.329 | 32.295 | 1.00 | 22.70 C |
| ATOM | 2446 | CG1 | ILE | A | 326 | 96.680 | 69.913 | 30.821 | 1.00 | 22.18 C |
| ATOM | 2447 | CG2 | ILE | A | 326 | 97.900 | 71.096 | 32.699 | 1.00 | 20.32 C |
| ATOM | 2448 | CD1 | ILE | A | 326 | 96.689 | 71.078 | 29.861 | 1.00 | 22.52 C |
| ATOM | 2449 | N | TYR | A | 327 | 95.589 | 70.244 | 35.082 | 1.00 | 25.51 N |
| ATOM | 2450 | CA | TYR | A | 327 | 95.512 | 70.739 | 36.439 | 1.00 | 27.53 C |
| ATOM | 2451 | C | TYR | A | 327 | 95.493 | 69.644 | 37.506 | 1.00 | 26.67 C |
| ATOM | 2452 | O | TYR | A | 327 | 96.234 | 69.706 | 38.470 | 1.00 | 26.34 O |
| ATOM | 2453 | CB | TYR | A | 327 | 94.278 | 71.615 | 36.527 | 1.00 | 31.94 C |
| ATOM | 2454 | CG | TYR | A | 327 | 93.867 | 72.043 | 37.900 | 1.00 | 36.64 C |
| ATOM | 2455 | CD1 | TYR | A | 327 | 93.354 | 71.127 | 38.812 | 1.00 | 40.23 C |
| ATOM | 2456 | CD2 | TYR | A | 327 | 93.868 | 73.375 | 38.243 | 1.00 | 38.78 C |
| ATOM | 2457 | CE1 | TYR | A | 327 | 92.839 | 71.536 | 40.027 | 1.00 | 42.47 C |
| ATOM | 2458 | CE2 | TYR | A | 327 | 93.358 | 73.790 | 39.431 | 1.00 | 42.01 C |
| ATOM | 2459 | CZ | TYR | A | 327 | 92.838 | 72.873 | 40.329 | 1.00 | 43.22 C |
| ATOM | 2460 | OH | TYR | A | 327 | 92.305 | 73.316 | 41.524 | 1.00 | 47.71 O |
| ATOM | 2461 | N | ASP | A | 328 | 94.635 | 68.650 | 37.347 | 1.00 | 27.41 N |
| ATOM | 2462 | CA | ASP | A | 328 | 94.573 | 67.559 | 38.312 | 1.00 | 28.23 C |
| ATOM | 2463 | C | ASP | A | 328 | 95.910 | 66.825 | 38.383 | 1.00 | 28.97 C |
| ATOM | 2464 | O | ASP | A | 328 | 96.342 | 66.414 | 39.455 | 1.00 | 30.49 O |
| ATOM | 2465 | CB | ASP | A | 328 | 93.469 | 66.570 | 37.925 | 1.00 | 28.63 C |
| ATOM | 2466 | CG | ASP | A | 328 | 92.074 | 67.171 | 38.042 | 1.00 | 29.55 C |
| ATOM | 2467 | OD1 | ASP | A | 328 | 91.096 | 66.496 | 37.643 | 1.00 | 28.91 O |
| ATOM | 2468 | OD2 | ASP | A | 328 | 91.954 | 68.312 | 38.541 | 1.00 | 30.66 O |
| ATOM | 2469 | N | ALA | A | 329 | 96.568 | 66.666 | 37.237 | 1.00 | 28.70 N |
| ATOM | 2470 | CA | ALA | A | 329 | 97.848 | 65.969 | 37.185 | 1.00 | 27.96 C |
| ATOM | 2471 | C | ALA | A | 329 | 98.993 | 66.816 | 37.713 | 1.00 | 27.90 C |
| ATOM | 2472 | O | ALA | A | 329 | 99.898 | 66.303 | 38.368 | 1.00 | 27.58 O |
| ATOM | 2473 | CB | ALA | A | 329 | 98.150 | 65.534 | 35.755 | 1.00 | 28.88 C |
| ATOM | 2474 | N | ALA | A | 330 | 98.950 | 68.112 | 37.417 | 1.00 | 27.54 N |
| ATOM | 2475 | CA | ALA | A | 330 | 99.993 | 69.041 | 37.839 | 1.00 | 27.36 C |
| ATOM | 2476 | C | ALA | A | 330 | 100.035 | 69.195 | 39.352 | 1.00 | 27.62 C |
| ATOM | 2477 | O | ALA | A | 330 | 101.039 | 69.631 | 39.909 | 1.00 | 27.21 O |
| ATOM | 2478 | CB | ALA | A | 330 | 99.784 | 70.397 | 37.175 | 1.00 | 26.61 C |
| ATOM | 2479 | N | ALA | A | 331 | 98.941 | 68.841 | 40.016 | 1.00 | 28.38 N |
| ATOM | 2480 | CA | ALA | A | 331 | 98.882 | 68.923 | 41.467 | 1.00 | 29.60 C |
| ATOM | 2481 | C | ALA | A | 331 | 99.870 | 67.902 | 42.005 | 1.00 | 30.94 C |
| ATOM | 2482 | O | ALA | A | 331 | 100.556 | 68.144 | 42.995 | 1.00 | 31.96 O |
| ATOM | 2483 | CB | ALA | A | 331 | 97.489 | 68.601 | 41.955 | 1.00 | 29.46 C |
| ATOM | 2484 | N | VAL | A | 332 | 99.941 | 66.756 | 41.334 | 1.00 | 31.86 N |
| ATOM | 2485 | CA | VAL | A | 332 | 100.851 | 65.683 | 41.723 | 1.00 | 31.71 C |
| ATOM | 2486 | C | VAL | A | 332 | 102.276 | 65.984 | 41.267 | 1.00 | 32.27 C |
| ATOM | 2487 | O | VAL | A | 332 | 103.231 | 65.700 | 41.981 | 1.00 | 32.86 O |
| ATOM | 2488 | CB | VAL | A | 332 | 100.408 | 64.328 | 41.122 | 1.00 | 30.47 C |
| ATOM | 2489 | CG1 | VAL | A | 332 | 101.394 | 63.229 | 41.512 | 1.00 | 29.17 C |
| ATOM | 2490 | CG2 | VAL | A | 332 | 99.009 | 63.989 | 41.602 | 1.00 | 29.70 C |
| ATOM | 2491 | N | ALA | A | 333 | 102.412 | 66.561 | 40.078 | 1.00 | 32.53 N |
| ATOM | 2492 | CA | ALA | A | 333 | 103.723 | 66.889 | 39.543 | 1.00 | 33.43 C |

-continued

| | | | | | | | | | | |
|---|---|---|---|---|---|---|---|---|---|---|
| ATOM | 2493 | C | ALA | A | 333 | 104.469 | 67.763 | 40.528 | 1.00 | 35.24 C |
| ATOM | 2494 | O | ALA | A | 333 | 105.677 | 67.623 | 40.701 | 1.00 | 35.30 O |
| ATOM | 2495 | CB | ALA | A | 333 | 103.587 | 67.607 | 38.218 | 1.00 | 32.68 C |
| ATOM | 2496 | N | ARG | A | 334 | 103.757 | 68.675 | 41.178 | 1.00 | 36.59 N |
| ATOM | 2497 | CA | ARG | A | 334 | 104.422 | 69.544 | 42.136 | 1.00 | 38.67 C |
| ATOM | 2498 | C | ARG | A | 334 | 104.682 | 68.857 | 43.458 | 1.00 | 38.64 C |
| ATOM | 2499 | O | ARG | A | 334 | 105.646 | 69.181 | 44.140 | 1.00 | 39.25 O |
| ATOM | 2500 | CB | ARG | A | 334 | 103.650 | 70.853 | 42.343 | 1.00 | 39.27 C |
| ATOM | 2501 | CG | ARG | A | 334 | 102.152 | 70.742 | 42.460 | 1.00 | 41.57 C |
| ATOM | 2502 | CD | ARG | A | 334 | 101.611 | 72.112 | 42.821 | 1.00 | 42.79 C |
| ATOM | 2503 | NE | ARG | A | 334 | 102.174 | 73.143 | 41.953 | 1.00 | 41.68 N |
| ATOM | 2504 | CZ | ARG | A | 334 | 102.177 | 74.441 | 42.245 | 1.00 | 41.25 C |
| ATOM | 2505 | NH1 | ARG | A | 334 | 101.648 | 74.876 | 43.384 | 1.00 | 39.55 N |
| ATOM | 2506 | NH2 | ARG | A | 334 | 102.728 | 75.304 | 41.405 | 1.00 | 40.34 N |
| ATOM | 2507 | N | GLU | A | 335 | 103.833 | 67.902 | 43.814 | 1.00 | 38.96 N |
| ATOM | 2508 | CA | GLU | A | 335 | 104.029 | 67.158 | 45.046 | 1.00 | 39.04 C |
| ATOM | 2509 | C | GLU | A | 335 | 105.352 | 66.414 | 44.911 | 1.00 | 37.56 C |
| ATOM | 2510 | O | GLU | A | 335 | 106.158 | 66.383 | 45.836 | 1.00 | 39.04 O |
| ATOM | 2511 | CB | GLU | A | 335 | 102.895 | 66.157 | 45.258 | 1.00 | 40.81 C |
| ATOM | 2512 | CG | GLU | A | 335 | 103.154 | 65.182 | 46.393 | 1.00 | 45.59 C |
| ATOM | 2513 | CD | GLU | A | 335 | 102.064 | 64.136 | 46.538 | 1.00 | 48.65 C |
| ATOM | 2514 | OE1 | GLU | A | 335 | 102.219 | 63.227 | 47.383 | 1.00 | 49.61 O |
| ATOM | 2515 | OE2 | GLU | A | 335 | 101.048 | 64.224 | 45.812 | 1.00 | 51.22 O |
| ATOM | 2516 | N | TYR | A | 336 | 105.571 | 65.828 | 43.741 | 1.00 | 35.56 N |
| ATOM | 2517 | CA | TYR | A | 336 | 106.786 | 65.075 | 43.458 | 1.00 | 33.65 C |
| ATOM | 2518 | C | TYR | A | 336 | 107.915 | 65.956 | 42.950 | 1.00 | 32.06 C |
| ATOM | 2519 | O | TYR | A | 336 | 109.037 | 65.493 | 42.753 | 1.00 | 31.27 O |
| ATOM | 2520 | CB | TYR | A | 336 | 106.508 | 63.979 | 42.418 | 1.00 | 34.56 C |
| ATOM | 2521 | CG | TYR | A | 336 | 105.700 | 62.806 | 42.928 | 1.00 | 35.16 C |
| ATOM | 2522 | CD1 | TYR | A | 336 | 106.183 | 61.504 | 42.802 | 1.00 | 35.01 C |
| ATOM | 2523 | CD2 | TYR | A | 336 | 104.465 | 62.992 | 43.544 | 1.00 | 35.65 C |
| ATOM | 2524 | CE1 | TYR | A | 336 | 105.460 | 60.418 | 43.278 | 1.00 | 35.67 C |
| ATOM | 2525 | CE2 | TYR | A | 336 | 103.730 | 61.910 | 44.025 | 1.00 | 36.28 C |
| ATOM | 2526 | CZ | TYR | A | 336 | 104.234 | 60.624 | 43.890 | 1.00 | 35.77 C |
| ATOM | 2527 | OH | TYR | A | 336 | 103.516 | 59.548 | 44.372 | 1.00 | 36.21 O |
| ATOM | 2528 | N | GLY | A | 337 | 107.619 | 67.230 | 42.738 | 1.00 | 31.22 N |
| ATOM | 2529 | CA | GLY | A | 337 | 108.635 | 68.122 | 42.229 | 1.00 | 29.58 C |
| ATOM | 2530 | C | GLY | A | 337 | 109.068 | 67.679 | 40.847 | 1.00 | 29.59 C |
| ATOM | 2531 | O | GLY | A | 337 | 110.232 | 67.802 | 40.488 | 1.00 | 30.15 O |
| ATOM | 2532 | N | LYS | A | 338 | 108.128 | 67.142 | 40.073 | 1.00 | 29.98 N |
| ATOM | 2533 | CA | LYS | A | 338 | 108.413 | 66.698 | 38.713 | 1.00 | 29.30 C |
| ATOM | 2534 | C | LYS | A | 338 | 107.596 | 67.477 | 37.683 | 1.00 | 28.77 C |
| ATOM | 2535 | O | LYS | A | 338 | 106.830 | 68.377 | 38.040 | 1.00 | 27.37 O |
| ATOM | 2536 | CB | LYS | A | 338 | 108.180 | 65.191 | 38.585 | 1.00 | 30.27 C |
| ATOM | 2537 | CG | LYS | A | 338 | 109.235 | 64.382 | 39.330 | 1.00 | 32.74 C |
| ATOM | 2538 | CD | LYS | A | 338 | 109.034 | 62.886 | 39.194 | 1.00 | 36.45 C |
| ATOM | 2539 | CE | LYS | A | 338 | 110.170 | 62.116 | 39.867 | 1.00 | 38.61 C |
| ATOM | 2540 | NZ | LYS | A | 338 | 110.001 | 60.628 | 39.761 | 1.00 | 40.61 N |
| ATOM | 2541 | N | THR | A | 339 | 107.749 | 67.131 | 36.407 | 1.00 | 27.82 N |
| ATOM | 2542 | CA | THR | A | 339 | 107.056 | 67.863 | 35.356 | 1.00 | 26.32 C |
| ATOM | 2543 | C | THR | A | 339 | 105.980 | 67.165 | 34.517 | 1.00 | 26.06 C |
| ATOM | 2544 | O | THR | A | 339 | 105.806 | 65.943 | 34.542 | 1.00 | 25.01 O |
| ATOM | 2545 | CB | THR | A | 339 | 108.072 | 68.484 | 34.409 | 1.00 | 26.34 C |
| ATOM | 2546 | OG1 | THR | A | 339 | 108.901 | 67.454 | 33.864 | 1.00 | 25.90 O |
| ATOM | 2547 | CG2 | THR | A | 339 | 108.934 | 69.484 | 35.155 | 1.00 | 26.42 C |
| ATOM | 2548 | N | ILE | A | 340 | 105.267 | 67.988 | 33.757 | 1.00 | 25.60 N |
| ATOM | 2549 | CA | ILE | A | 340 | 104.174 | 67.543 | 32.911 | 1.00 | 24.59 C |
| ATOM | 2550 | C | ILE | A | 340 | 104.152 | 68.189 | 31.525 | 1.00 | 23.54 C |
| ATOM | 2551 | O | ILE | A | 340 | 104.555 | 69.337 | 31.342 | 1.00 | 21.85 O |
| ATOM | 2552 | CB | ILE | A | 340 | 102.842 | 67.794 | 33.644 | 1.00 | 25.00 C |
| ATOM | 2553 | CG1 | ILE | A | 340 | 102.598 | 66.631 | 34.599 | 1.00 | 26.20 C |
| ATOM | 2554 | CG2 | ILE | A | 340 | 101.707 | 68.034 | 32.668 | 1.00 | 25.49 C |
| ATOM | 2555 | CD1 | ILE | A | 340 | 101.382 | 66.774 | 35.436 | 1.00 | 29.56 C |
| ATOM | 2556 | N | ILE | A | 341 | 103.695 | 67.414 | 30.548 | 1.00 | 22.21 N |
| ATOM | 2557 | CA | ILE | A | 341 | 103.573 | 67.873 | 29.176 | 1.00 | 20.48 C |
| ATOM | 2558 | C | ILE | A | 341 | 102.080 | 67.824 | 28.863 | 1.00 | 19.91 C |
| ATOM | 2559 | O | ILE | A | 341 | 101.439 | 66.793 | 29.068 | 1.00 | 18.38 O |
| ATOM | 2560 | CB | ILE | A | 341 | 104.346 | 66.941 | 28.210 | 1.00 | 21.69 C |
| ATOM | 2561 | CG1 | ILE | A | 341 | 105.849 | 67.038 | 28.496 | 1.00 | 23.08 C |
| ATOM | 2562 | CG2 | ILE | A | 341 | 104.043 | 67.290 | 26.755 | 1.00 | 19.22 C |
| ATOM | 2563 | CD1 | ILE | A | 341 | 106.695 | 66.098 | 27.657 | 1.00 | 23.45 C |
| ATOM | 2564 | N | ALA | A | 342 | 101.530 | 68.958 | 28.427 | 1.00 | 19.15 N |
| ATOM | 2565 | CA | ALA | A | 342 | 100.121 | 69.060 | 28.046 | 1.00 | 19.91 C |
| ATOM | 2566 | C | ALA | A | 342 | 100.064 | 68.553 | 26.601 | 1.00 | 20.89 C |
| ATOM | 2567 | O | ALA | A | 342 | 100.556 | 69.205 | 25.680 | 1.00 | 20.43 O |
| ATOM | 2568 | CB | ALA | A | 342 | 99.663 | 70.504 | 28.125 | 1.00 | 19.17 C |
| ATOM | 2569 | N | ASP | A | 343 | 99.451 | 67.388 | 26.418 | 1.00 | 21.90 N |
| ATOM | 2570 | CA | ASP | A | 343 | 99.390 | 66.729 | 25.121 | 1.00 | 22.21 C |
| ATOM | 2571 | C | ASP | A | 343 | 98.038 | 66.728 | 24.406 | 1.00 | 23.22 C |

-continued

| | | | | | | | | | | |
|---|---|---|---|---|---|---|---|---|---|---|
| ATOM | 2572 | O | ASP | A | 343 | 97.128 | 66.005 | 24.796 | 1.00 | 23.89 O |
| ATOM | 2573 | CB | ASP | A | 343 | 99.863 | 65.283 | 25.318 | 1.00 | 23.79 C |
| ATOM | 2574 | CG | ASP | A | 343 | 99.944 | 64.499 | 24.028 | 1.00 | 26.58 C |
| ATOM | 2575 | OD1 | ASP | A | 343 | 100.061 | 63.251 | 24.106 | 1.00 | 25.81 O |
| ATOM | 2576 | OD2 | ASP | A | 343 | 99.911 | 65.122 | 22.941 | 1.00 | 27.87 O |
| ATOM | 2577 | N | GLY | A | 344 | 97.917 | 67.541 | 23.359 | 1.00 | 24.09 N |
| ATOM | 2578 | CA | GLY | A | 344 | 96.696 | 67.569 | 22.565 | 1.00 | 24.48 C |
| ATOM | 2579 | C | GLY | A | 344 | 95.592 | 68.587 | 22.818 | 1.00 | 24.98 C |
| ATOM | 2580 | O | GLY | A | 344 | 95.510 | 69.210 | 23.888 | 1.00 | 25.91 O |
| ATOM | 2581 | N | GLY | A | 345 | 94.737 | 68.753 | 21.809 | 1.00 | 23.62 N |
| ATOM | 2582 | CA | GLY | A | 345 | 93.614 | 69.664 | 21.922 | 1.00 | 22.65 C |
| ATOM | 2583 | C | GLY | A | 345 | 93.944 | 71.128 | 21.758 | 1.00 | 22.90 C |
| ATOM | 2584 | O | GLY | A | 345 | 93.060 | 71.969 | 21.869 | 1.00 | 23.02 O |
| ATOM | 2585 | N | ILE | A | 346 | 95.207 | 71.443 | 21.498 | 1.00 | 22.89 N |
| ATOM | 2586 | CA | ILE | A | 346 | 95.637 | 72.827 | 21.322 | 1.00 | 23.44 C |
| ATOM | 2587 | C | ILE | A | 346 | 95.528 | 73.267 | 19.869 | 1.00 | 25.23 C |
| ATOM | 2588 | O | ILE | A | 346 | 96.157 | 72.681 | 18.992 | 1.00 | 26.62 O |
| ATOM | 2589 | CB | ILE | A | 346 | 97.090 | 73.005 | 21.774 | 1.00 | 22.40 C |
| ATOM | 2590 | CG1 | ILE | A | 346 | 97.160 | 72.887 | 23.297 | 1.00 | 23.15 C |
| ATOM | 2591 | CG2 | ILE | A | 346 | 97.631 | 74.327 | 21.268 | 1.00 | 22.29 C |
| ATOM | 2592 | CD1 | ILE | A | 346 | 98.558 | 72.897 | 23.857 | 1.00 | 25.18 C |
| ATOM | 2593 | N | LYS | A | 347 | 94.744 | 74.305 | 19.603 | 1.00 | 25.74 N |
| ATOM | 2594 | CA | LYS | A | 347 | 94.605 | 74.756 | 18.228 | 1.00 | 26.93 C |
| ATOM | 2595 | C | LYS | A | 347 | 95.037 | 76.200 | 18.004 | 1.00 | 26.46 C |
| ATOM | 2596 | O | LYS | A | 347 | 95.310 | 76.602 | 16.874 | 1.00 | 27.31 O |
| ATOM | 2597 | CB | LYS | A | 347 | 93.169 | 74.501 | 17.744 | 1.00 | 29.47 C |
| ATOM | 2598 | CG | LYS | A | 347 | 92.093 | 75.047 | 18.644 | 1.00 | 32.60 C |
| ATOM | 2599 | CD | LYS | A | 347 | 90.778 | 74.293 | 18.454 | 1.00 | 36.26 C |
| ATOM | 2600 | CE | LYS | A | 347 | 89.680 | 74.859 | 19.374 | 1.00 | 39.81 C |
| ATOM | 2601 | NZ | LYS | A | 347 | 90.034 | 74.868 | 20.845 | 1.00 | 39.97 N |
| ATOM | 2602 | N | TYR | A | 348 | 95.136 | 76.968 | 19.081 | 1.00 | 24.97 N |
| ATOM | 2603 | CA | TYR | A | 348 | 95.552 | 78.357 | 18.982 | 1.00 | 24.76 C |
| ATOM | 2604 | C | TYR | A | 348 | 96.692 | 78.637 | 19.951 | 1.00 | 25.00 C |
| ATOM | 2605 | O | TYR | A | 348 | 96.810 | 77.976 | 20.987 | 1.00 | 24.58 O |
| ATOM | 2606 | CB | TYR | A | 348 | 94.384 | 79.280 | 19.313 | 1.00 | 25.92 C |
| ATOM | 2607 | CG | TYR | A | 348 | 93.224 | 79.180 | 18.362 | 1.00 | 29.00 C |
| ATOM | 2608 | CD1 | TYR | A | 348 | 93.363 | 79.544 | 17.014 | 1.00 | 31.01 C |
| ATOM | 2609 | CD2 | TYR | A | 348 | 91.975 | 78.759 | 18.806 | 1.00 | 30.18 C |
| ATOM | 2610 | CE1 | TYR | A | 348 | 92.280 | 79.496 | 16.139 | 1.00 | 31.84 C |
| ATOM | 2611 | CE2 | TYR | A | 348 | 90.886 | 78.706 | 17.940 | 1.00 | 32.70 C |
| ATOM | 2612 | CZ | TYR | A | 348 | 91.046 | 79.078 | 16.614 | 1.00 | 33.71 C |
| ATOM | 2613 | OH | TYR | A | 348 | 89.960 | 79.054 | 15.775 | 1.00 | 37.15 O |
| ATOM | 2614 | N | SER | A | 349 | 97.523 | 79.626 | 19.629 | 1.00 | 23.37 N |
| ATOM | 2615 | CA | SER | A | 349 | 98.632 | 79.970 | 20.503 | 1.00 | 23.44 C |
| ATOM | 2616 | C | SER | A | 349 | 98.093 | 80.308 | 21.894 | 1.00 | 23.36 C |
| ATOM | 2617 | O | SER | A | 349 | 98.747 | 80.049 | 22.900 | 1.00 | 23.98 O |
| ATOM | 2618 | CB | SER | A | 349 | 99.432 | 81.151 | 19.936 | 1.00 | 23.65 C |
| ATOM | 2619 | OG | SER | A | 349 | 98.657 | 82.331 | 19.874 | 1.00 | 24.07 O |
| ATOM | 2620 | N | GLY | A | 350 | 96.896 | 80.880 | 21.950 | 1.00 | 22.72 N |
| ATOM | 2621 | CA | GLY | A | 350 | 96.310 | 81.212 | 23.234 | 1.00 | 22.54 C |
| ATOM | 2622 | C | GLY | A | 350 | 96.093 | 79.964 | 24.071 | 1.00 | 23.59 C |
| ATOM | 2623 | O | GLY | A | 350 | 96.186 | 80.009 | 25.291 | 1.00 | 23.00 O |
| ATOM | 2624 | N | ASP | A | 351 | 95.798 | 78.847 | 23.407 | 1.00 | 23.75 N |
| ATOM | 2625 | CA | ASP | A | 351 | 95.573 | 77.573 | 24.085 | 1.00 | 23.84 C |
| ATOM | 2626 | C | ASP | A | 351 | 96.850 | 77.093 | 24.770 | 1.00 | 23.49 C |
| ATOM | 2627 | O | ASP | A | 351 | 96.798 | 76.434 | 25.811 | 1.00 | 22.59 O |
| ATOM | 2628 | CB | ASP | A | 351 | 95.097 | 76.509 | 23.088 | 1.00 | 25.03 C |
| ATOM | 2629 | CG | ASP | A | 351 | 93.660 | 76.720 | 22.638 | 1.00 | 27.18 C |
| ATOM | 2630 | OD1 | ASP | A | 351 | 93.215 | 76.016 | 21.707 | 1.00 | 28.04 O |
| ATOM | 2631 | OD2 | ASP | A | 351 | 92.966 | 77.576 | 23.226 | 1.00 | 30.15 O |
| ATOM | 2632 | N | ILE | A | 352 | 97.994 | 77.421 | 24.178 | 1.00 | 22.40 N |
| ATOM | 2633 | CA | ILE | A | 352 | 99.274 | 77.032 | 24.749 | 1.00 | 20.34 C |
| ATOM | 2634 | C | ILE | A | 352 | 99.452 | 77.716 | 26.102 | 1.00 | 21.36 C |
| ATOM | 2635 | O | ILE | A | 352 | 99.879 | 77.084 | 27.069 | 1.00 | 22.39 O |
| ATOM | 2636 | CB | ILE | A | 352 | 100.445 | 77.431 | 23.830 | 1.00 | 18.46 C |
| ATOM | 2637 | CG1 | ILE | A | 352 | 100.296 | 76.753 | 22.474 | 1.00 | 17.19 C |
| ATOM | 2638 | CG2 | ILE | A | 352 | 101.756 | 77.042 | 24.462 | 1.00 | 17.65 C |
| ATOM | 2639 | CD1 | ILE | A | 352 | 101.395 | 77.086 | 21.512 | 1.00 | 17.04 C |
| ATOM | 2640 | N | VAL | A | 353 | 99.122 | 79.005 | 26.172 | 1.00 | 20.35 N |
| ATOM | 2641 | CA | VAL | A | 353 | 99.269 | 79.753 | 27.413 | 1.00 | 20.32 C |
| ATOM | 2642 | C | VAL | A | 353 | 98.328 | 79.228 | 28.496 | 1.00 | 19.94 C |
| ATOM | 2643 | O | VAL | A | 353 | 98.671 | 79.204 | 29.671 | 1.00 | 20.43 O |
| ATOM | 2644 | CB | VAL | A | 353 | 98.997 | 81.250 | 27.189 | 1.00 | 21.35 C |
| ATOM | 2645 | CG1 | VAL | A | 353 | 99.315 | 82.026 | 28.455 | 1.00 | 21.91 C |
| ATOM | 2646 | CG2 | VAL | A | 353 | 99.826 | 81.765 | 26.024 | 1.00 | 22.51 C |
| ATOM | 2647 | N | LYS | A | 354 | 97.131 | 78.809 | 28.098 | 1.00 | 21.28 N |
| ATOM | 2648 | CA | LYS | A | 354 | 96.168 | 78.266 | 29.049 | 1.00 | 20.46 C |
| ATOM | 2649 | C | LYS | A | 354 | 96.674 | 76.925 | 29.563 | 1.00 | 20.59 C |
| ATOM | 2650 | O | LYS | A | 354 | 96.587 | 76.640 | 30.758 | 1.00 | 21.00 O |

-continued

| | | | | | | | | | | |
|---|---|---|---|---|---|---|---|---|---|---|
| ATOM | 2651 | CB | LYS | A | 354 | 94.797 | 78.067 | 28.388 | 1.00 | 21.23 C |
| ATOM | 2652 | CG | LYS | A | 354 | 94.090 | 79.344 | 27.951 | 1.00 | 20.48 C |
| ATOM | 2653 | CD | LYS | A | 354 | 92.766 | 79.032 | 27.264 | 1.00 | 19.71 C |
| ATOM | 2654 | CE | LYS | A | 354 | 92.118 | 80.297 | 26.720 | 1.00 | 22.52 C |
| ATOM | 2655 | NZ | LYS | A | 354 | 90.917 | 80.013 | 25.879 | 1.00 | 21.12 N |
| ATOM | 2656 | N | ALA | A | 355 | 97.191 | 76.099 | 28.656 | 1.00 | 19.85 N |
| ATOM | 2657 | CA | ALA | A | 355 | 97.716 | 74.782 | 29.017 | 1.00 | 20.80 C |
| ATOM | 2658 | C | ALA | A | 355 | 98.886 | 74.933 | 29.978 | 1.00 | 21.77 C |
| ATOM | 2659 | O | ALA | A | 355 | 99.037 | 74.146 | 30.908 | 1.00 | 22.61 O |
| ATOM | 2660 | CB | ALA | A | 355 | 98.163 | 74.022 | 27.773 | 1.00 | 19.41 C |
| ATOM | 2661 | N | LEU | A | 356 | 99.722 | 75.940 | 29.753 | 1.00 | 21.62 N |
| ATOM | 2662 | CA | LEU | A | 356 | 100.858 | 76.168 | 30.630 | 1.00 | 22.27 C |
| ATOM | 2663 | C | LEU | A | 356 | 100.367 | 76.727 | 31.957 | 1.00 | 23.40 C |
| ATOM | 2664 | O | LEU | A | 356 | 100.846 | 76.342 | 33.015 | 1.00 | 24.73 O |
| ATOM | 2665 | CB | LEU | A | 356 | 101.843 | 77.145 | 29.986 | 1.00 | 21.42 C |
| ATOM | 2666 | CG | LEU | A | 356 | 102.518 | 76.717 | 28.684 | 1.00 | 20.49 C |
| ATOM | 2667 | CD1 | LEU | A | 356 | 103.328 | 77.875 | 28.141 | 1.00 | 21.00 C |
| ATOM | 2668 | CD2 | LEU | A | 356 | 103.386 | 75.488 | 28.925 | 1.00 | 21.89 C |
| ATOM | 2669 | N | ALA | A | 357 | 99.396 | 77.629 | 31.900 | 1.00 | 23.83 N |
| ATOM | 2670 | CA | ALA | A | 357 | 98.858 | 78.243 | 33.109 | 1.00 | 24.49 C |
| ATOM | 2671 | C | ALA | A | 357 | 98.115 | 77.252 | 34.002 | 1.00 | 24.83 C |
| ATOM | 2672 | O | ALA | A | 357 | 98.034 | 77.445 | 35.210 | 1.00 | 24.39 O |
| ATOM | 2673 | CB | ALA | A | 357 | 97.943 | 79.396 | 32.739 | 1.00 | 25.49 C |
| ATOM | 2674 | N | ALA | A | 358 | 97.577 | 76.191 | 33.412 | 1.00 | 23.94 N |
| ATOM | 2675 | CA | ALA | A | 358 | 96.856 | 75.192 | 34.189 | 1.00 | 23.85 C |
| ATOM | 2676 | C | ALA | A | 358 | 97.818 | 74.209 | 34.853 | 1.00 | 24.49 C |
| ATOM | 2677 | O | ALA | A | 358 | 97.391 | 73.320 | 35.595 | 1.00 | 24.74 O |
| ATOM | 2678 | CB | ALA | A | 358 | 95.865 | 74.440 | 33.300 | 1.00 | 24.65 C |
| ATOM | 2679 | N | GLY | A | 359 | 99.113 | 74.349 | 34.579 | 1.00 | 24.04 N |
| ATOM | 2680 | CA | GLY | A | 359 | 100.074 | 73.460 | 35.206 | 1.00 | 23.58 C |
| ATOM | 2681 | C | GLY | A | 359 | 101.065 | 72.763 | 34.300 | 1.00 | 23.49 C |
| ATOM | 2682 | O | GLY | A | 359 | 101.964 | 72.073 | 34.786 | 1.00 | 24.97 O |
| ATOM | 2683 | N | GLY | A | 360 | 100.924 | 72.929 | 32.990 | 1.00 | 22.19 N |
| ATOM | 2684 | CA | GLY | A | 360 | 101.847 | 72.279 | 32.083 | 1.00 | 19.65 C |
| ATOM | 2685 | C | GLY | A | 360 | 103.209 | 72.936 | 32.105 | 1.00 | 20.75 C |
| ATOM | 2686 | O | GLY | A | 360 | 103.312 | 74.134 | 32.324 | 1.00 | 20.45 O |
| ATOM | 2687 | N | ASN | A | 361 | 104.258 | 72.148 | 31.887 | 1.00 | 20.92 N |
| ATOM | 2688 | CA | ASN | A | 361 | 105.630 | 72.655 | 31.855 | 1.00 | 22.23 C |
| ATOM | 2689 | C | ASN | A | 361 | 106.051 | 72.782 | 30.402 | 1.00 | 22.46 C |
| ATOM | 2690 | O | ASN | A | 361 | 107.060 | 73.407 | 30.079 | 1.00 | 22.58 O |
| ATOM | 2691 | CB | ASN | A | 361 | 106.568 | 71.697 | 32.589 | 1.00 | 22.17 C |
| ATOM | 2692 | CG | ASN | A | 361 | 106.338 | 71.703 | 34.085 | 1.00 | 25.53 C |
| ATOM | 2693 | OD1 | ASN | A | 361 | 106.646 | 72.688 | 34.763 | 1.00 | 27.16 O |
| ATOM | 2694 | ND2 | ASN | A | 361 | 105.766 | 70.624 | 34.607 | 1.00 | 25.19 N |
| ATOM | 2695 | N | ALA | A | 362 | 105.251 | 72.178 | 29.530 | 1.00 | 22.54 N |
| ATOM | 2696 | CA | ALA | A | 362 | 105.481 | 72.193 | 28.095 | 1.00 | 21.37 C |
| ATOM | 2697 | C | ALA | A | 362 | 104.229 | 71.625 | 27.432 | 1.00 | 21.05 C |
| ATOM | 2698 | O | ALA | A | 362 | 103.423 | 70.969 | 28.084 | 1.00 | 18.71 O |
| ATOM | 2699 | CB | ALA | A | 362 | 106.704 | 71.341 | 27.753 | 1.00 | 20.68 C |
| ATOM | 2700 | N | VAL | A | 363 | 104.058 | 71.895 | 26.142 | 1.00 | 22.66 N |
| ATOM | 2701 | CA | VAL | A | 363 | 102.903 | 71.377 | 25.410 | 1.00 | 22.68 C |
| ATOM | 2702 | C | VAL | A | 363 | 103.389 | 70.579 | 24.210 | 1.00 | 22.35 C |
| ATOM | 2703 | O | VAL | A | 363 | 104.423 | 70.893 | 23.638 | 1.00 | 23.37 O |
| ATOM | 2704 | CB | VAL | A | 363 | 101.964 | 72.521 | 24.910 | 1.00 | 22.34 C |
| ATOM | 2705 | CG1 | VAL | A | 363 | 101.440 | 73.333 | 26.088 | 1.00 | 21.37 C |
| ATOM | 2706 | CG2 | VAL | A | 363 | 102.702 | 73.418 | 23.929 | 1.00 | 22.84 C |
| HETATM | 2707 | N | MSE | A | 364 | 102.662 | 69.530 | 23.851 | 1.00 | 21.88 N |
| HETATM | 2708 | CA | MSE | A | 364 | 103.027 | 68.726 | 22.692 | 1.00 | 22.51 C |
| HETATM | 2709 | C | MSE | A | 364 | 102.014 | 69.063 | 21.608 | 1.00 | 23.49 C |
| HETATM | 2710 | O | MSE | A | 364 | 100.794 | 69.022 | 21.832 | 1.00 | 23.44 O |
| HETATM | 2711 | CB | MSE | A | 364 | 103.011 | 67.231 | 23.028 | 1.00 | 24.05 C |
| HETATM | 2712 | CG | MSE | A | 364 | 103.223 | 66.330 | 21.821 | 1.00 | 27.31 C |
| HETATM | 2713 | SE | MSE | A | 364 | 103.374 | 64.556 | 22.241 | 1.00 | 35.51 SE |
| HETATM | 2714 | CE | MSE | A | 364 | 105.096 | 64.508 | 22.891 | 1.00 | 32.69 C |
| ATOM | 2715 | N | LEU | A | 365 | 102.531 | 69.420 | 20.436 | 1.00 | 23.87 N |
| ATOM | 2716 | CA | LEU | A | 365 | 101.704 | 69.831 | 19.315 | 1.00 | 24.27 C |
| ATOM | 2717 | C | LEU | A | 365 | 101.822 | 68.920 | 18.108 | 1.00 | 25.78 C |
| ATOM | 2718 | O | LEU | A | 365 | 102.926 | 68.614 | 17.666 | 1.00 | 26.09 C |
| ATOM | 2719 | CB | LEU | A | 365 | 102.104 | 71.238 | 18.905 | 1.00 | 22.73 C |
| ATOM | 2720 | CG | LEU | A | 365 | 102.093 | 72.219 | 20.060 | 1.00 | 23.17 C |
| ATOM | 2721 | CD1 | LEU | A | 365 | 102.705 | 73.527 | 19.616 | 1.00 | 24.46 C |
| ATOM | 2722 | CD2 | LEU | A | 365 | 100.670 | 72.378 | 20.574 | 1.00 | 22.59 C |
| ATOM | 2723 | N | GLY | A | 366 | 100.678 | 68.508 | 17.569 | 1.00 | 26.69 N |
| ATOM | 2724 | CA | GLY | A | 366 | 100.667 | 67.651 | 16.398 | 1.00 | 28.30 C |
| ATOM | 2725 | C | GLY | A | 366 | 100.045 | 68.365 | 15.213 | 1.00 | 29.57 C |
| ATOM | 2726 | O | GLY | A | 366 | 100.717 | 68.663 | 14.226 | 1.00 | 29.34 O |
| ATOM | 2727 | N | SER | A | 367 | 98.753 | 68.644 | 15.327 | 1.00 | 30.92 N |
| ATOM | 2728 | CA | SER | A | 367 | 97.993 | 69.341 | 14.298 | 1.00 | 33.00 C |
| ATOM | 2729 | C | SER | A | 367 | 98.648 | 70.637 | 13.803 | 1.00 | 34.00 C |

-continued

| | | | | | | | | | | |
|---|---|---|---|---|---|---|---|---|---|---|
| ATOM | 2730 | O | SER | A | 367 | 98.750 | 70.848 | 12.598 | 1.00 | 33.51 O |
| ATOM | 2731 | CB | SER | A | 367 | 96.590 | 69.646 | 14.832 | 1.00 | 34.28 C |
| ATOM | 2732 | OG | SER | A | 367 | 95.800 | 70.345 | 13.885 | 1.00 | 34.75 O |
| HETATM | 2733 | N | MSE | A | 368 | 99.097 | 71.501 | 14.713 | 1.00 | 34.95 N |
| HETATM | 2734 | CA | MSE | A | 368 | 99.712 | 72.765 | 14.296 | 1.00 | 37.45 C |
| HETATM | 2735 | C | MSE | A | 368 | 100.963 | 72.668 | 13.424 | 1.00 | 36.66 C |
| HETATM | 2736 | O | MSE | A | 368 | 101.316 | 73.635 | 12.748 | 1.00 | 36.99 O |
| HETATM | 2737 | CB | MSE | A | 368 | 100.000 | 73.664 | 15.506 | 1.00 | 40.56 C |
| HETATM | 2738 | CG | MSE | A | 368 | 98.719 | 74.111 | 16.191 | 1.00 | 46.02 C |
| HETATM | 2739 | SE | MSE | A | 368 | 98.916 | 75.343 | 17.492 | 1.00 | 56.80 SE |
| HETATM | 2740 | CE | MSE | A | 368 | 99.964 | 74.527 | 18.572 | 1.00 | 55.31 C |
| ATOM | 2741 | N | PHE | A | 369 | 101.626 | 71.513 | 13.417 | 1.00 | 34.82 N |
| ATOM | 2742 | CA | PHE | A | 369 | 102.830 | 71.339 | 12.603 | 1.00 | 31.76 C |
| ATOM | 2743 | C | PHE | A | 369 | 102.600 | 70.421 | 11.416 | 1.00 | 31.43 C |
| ATOM | 2744 | O | PHE | A | 369 | 103.378 | 70.425 | 10.467 | 1.00 | 30.91 O |
| ATOM | 2745 | CB | PHE | A | 369 | 103.977 | 70.786 | 13.460 | 1.00 | 29.79 C |
| ATOM | 2746 | CG | PHE | A | 369 | 104.507 | 71.765 | 14.473 | 1.00 | 26.59 C |
| ATOM | 2747 | CD1 | PHE | A | 369 | 104.387 | 71.518 | 15.829 | 1.00 | 27.53 C |
| ATOM | 2748 | CD2 | PHE | A | 369 | 105.121 | 72.947 | 14.062 | 1.00 | 27.73 C |
| ATOM | 2749 | CE1 | PHE | A | 369 | 104.872 | 72.444 | 16.771 | 1.00 | 27.77 C |
| ATOM | 2750 | CE2 | PHE | A | 369 | 105.605 | 73.874 | 14.990 | 1.00 | 27.15 C |
| ATOM | 2751 | CZ | PHE | A | 369 | 105.481 | 73.622 | 16.345 | 1.00 | 26.83 C |
| ATOM | 2752 | N | ALA | A | 370 | 101.510 | 69.658 | 11.479 | 1.00 | 32.61 N |
| ATOM | 2753 | CA | ALA | A | 370 | 101.108 | 68.668 | 10.465 | 1.00 | 33.73 C |
| ATOM | 2754 | C | ALA | A | 370 | 101.243 | 68.936 | 8.953 | 1.00 | 34.56 C |
| ATOM | 2755 | O | ALA | A | 370 | 101.405 | 67.982 | 8.173 | 1.00 | 35.53 O |
| ATOM | 2756 | CB | ALA | A | 370 | 99.682 | 68.213 | 10.761 | 1.00 | 33.78 C |
| ATOM | 2757 | N | GLY | A | 371 | 101.165 | 70.191 | 8.518 | 1.00 | 33.99 N |
| ATOM | 2758 | CA | GLY | A | 371 | 101.282 | 70.453 | 7.090 | 1.00 | 33.01 C |
| ATOM | 2759 | C | GLY | A | 371 | 102.500 | 71.252 | 6.666 | 1.00 | 33.01 C |
| ATOM | 2760 | O | GLY | A | 371 | 102.537 | 71.811 | 5.564 | 1.00 | 32.73 O |
| ATOM | 2761 | N | THR | A | 372 | 103.508 | 71.299 | 7.530 | 1.00 | 32.22 N |
| ATOM | 2762 | CA | THR | A | 372 | 104.724 | 72.055 | 7.244 | 1.00 | 32.27 C |
| ATOM | 2763 | C | THR | A | 372 | 105.688 | 71.363 | 6.276 | 1.00 | 33.94 C |
| ATOM | 2764 | O | THR | A | 372 | 105.448 | 70.244 | 5.828 | 1.00 | 35.02 O |
| ATOM | 2765 | CB | THR | A | 372 | 105.479 | 72.426 | 8.567 | 1.00 | 30.26 C |
| ATOM | 2766 | OG1 | THR | A | 372 | 105.828 | 71.242 | 9.298 | 1.00 | 27.73 O |
| ATOM | 2767 | CG2 | THR | A | 372 | 104.601 | 73.299 | 9.440 | 1.00 | 28.61 C |
| ATOM | 2768 | N | ASP | A | 373 | 106.771 | 72.052 | 5.937 | 1.00 | 35.72 N |
| ATOM | 2769 | CA | ASP | A | 373 | 107.775 | 71.506 | 5.040 | 1.00 | 37.55 C |
| ATOM | 2770 | C | ASP | A | 373 | 108.346 | 70.234 | 5.665 | 1.00 | 39.10 C |
| ATOM | 2771 | O | ASP | A | 373 | 108.423 | 69.187 | 5.023 | 1.00 | 39.87 O |
| ATOM | 2772 | CB | ASP | A | 373 | 108.893 | 72.531 | 4.844 | 1.00 | 39.43 C |
| ATOM | 2773 | CG | ASP | A | 373 | 108.394 | 73.826 | 4.223 | 1.00 | 42.12 C |
| ATOM | 2774 | OD1 | ASP | A | 373 | 109.121 | 74.847 | 4.253 | 1.00 | 42.31 O |
| ATOM | 2775 | CD2 | ASP | A | 373 | 107.267 | 73.815 | 3.687 | 1.00 | 45.19 O |
| ATOM | 2776 | N | GLU | A | 374 | 108.720 | 70.334 | 6.937 | 1.00 | 39.77 N |
| ATOM | 2777 | CA | GLU | A | 374 | 109.312 | 69.224 | 7.676 | 1.00 | 40.52 C |
| ATOM | 2778 | C | GLU | A | 374 | 108.430 | 67.991 | 7.949 | 1.00 | 40.61 C |
| ATOM | 2779 | O | GLU | A | 374 | 108.938 | 66.870 | 7.961 | 1.00 | 41.45 O |
| ATOM | 2780 | CB | GLU | A | 374 | 109.859 | 69.740 | 9.003 | 1.00 | 40.97 C |
| ATOM | 2781 | CG | GLU | A | 374 | 110.940 | 70.800 | 8.893 | 1.00 | 43.47 C |
| ATOM | 2782 | CD | GLU | A | 374 | 110.498 | 72.042 | 8.138 | 1.00 | 46.43 C |
| ATOM | 2783 | OE1 | GLU | A | 374 | 109.291 | 72.384 | 8.186 | 1.00 | 46.56 O |
| ATOM | 2784 | OE2 | GLU | A | 374 | 111.365 | 72.704 | 7.520 | 1.00 | 48.05 O |
| ATOM | 2785 | N | ALA | A | 375 | 107.132 | 68.180 | 8.176 | 1.00 | 39.40 N |
| ATOM | 2786 | CA | ALA | A | 375 | 106.237 | 67.053 | 8.467 | 1.00 | 39.33 C |
| ATOM | 2787 | C | ALA | A | 375 | 106.201 | 65.981 | 7.367 | 1.00 | 39.58 C |
| ATOM | 2788 | O | ALA | A | 375 | 105.988 | 66.289 | 6.194 | 1.00 | 40.42 O |
| ATOM | 2789 | CB | ALA | A | 375 | 104.827 | 67.568 | 8.740 | 1.00 | 38.20 C |
| ATOM | 2790 | N | PRO | A | 376 | 106.397 | 64.701 | 7.742 | 1.00 | 39.51 N |
| ATOM | 2791 | CA | PRO | A | 376 | 106.400 | 63.547 | 6.833 | 1.00 | 40.37 C |
| ATOM | 2792 | C | PRO | A | 376 | 105.074 | 63.223 | 6.115 | 1.00 | 42.60 C |
| ATOM | 2793 | O | PRO | A | 376 | 105.034 | 62.339 | 5.257 | 1.00 | 44.07 O |
| ATOM | 2794 | CB | PRO | A | 376 | 106.840 | 62.403 | 7.751 | 1.00 | 38.78 C |
| ATOM | 2795 | CG | PRO | A | 376 | 107.612 | 63.112 | 8.842 | 1.00 | 37.80 C |
| ATOM | 2796 | CD | PRO | A | 376 | 106.665 | 64.236 | 9.111 | 1.00 | 37.56 C |
| ATOM | 2797 | N | GLY | A | 377 | 103.992 | 63.916 | 6.465 | 1.00 | 44.20 N |
| ATOM | 2798 | CA | GLY | A | 377 | 102.704 | 63.657 | 5.829 | 1.00 | 45.51 C |
| ATOM | 2799 | C | GLY | A | 377 | 102.780 | 63.611 | 4.312 | 1.00 | 47.08 C |
| ATOM | 2800 | O | GLY | A | 377 | 103.714 | 64.150 | 3.720 | 1.00 | 47.51 O |
| ATOM | 2801 | N | GLU | A | 378 | 101.801 | 62.968 | 3.681 | 1.00 | 48.24 N |
| ATOM | 2802 | CA | GLU | A | 378 | 101.759 | 62.841 | 2.221 | 1.00 | 48.97 C |
| ATOM | 2803 | C | GLU | A | 378 | 100.987 | 64.015 | 1.627 | 1.00 | 48.92 C |
| ATOM | 2804 | O | GLU | A | 378 | 99.905 | 64.345 | 2.096 | 1.00 | 49.36 O |
| ATOM | 2805 | CB | GLU | A | 378 | 101.082 | 61.523 | 1.828 | 1.00 | 50.65 C |
| ATOM | 2806 | CG | GLU | A | 378 | 101.750 | 60.266 | 2.409 | 1.00 | 56.37 C |
| ATOM | 2807 | CD | GLU | A | 378 | 101.682 | 60.184 | 3.950 | 1.00 | 60.26 C |
| ATOM | 2808 | OE1 | GLU | A | 378 | 100.554 | 60.078 | 4.493 | 1.00 | 61.73 O |

-continued

| | | | | | | | | | | |
|---|---|---|---|---|---|---|---|---|---|---|
| ATOM | 2809 | OE2 | GLU | A | 378 | 102.752 | 60.225 | 4.619 | 1.00 | 60.95 O |
| ATOM | 2810 | N | THR | A | 379 | 101.538 | 64.648 | 0.598 | 1.00 | 48.86 N |
| ATOM | 2811 | CA | THR | A | 379 | 100.868 | 55.786 | −0.030 | 1.00 | 49.21 C |
| ATOM | 2812 | C | THR | A | 379 | 99.683 | 65.876 | −0.911 | 1.00 | 49.89 C |
| ATOM | 2813 | O | THR | A | 379 | 99.745 | 64.394 | −1.658 | 1.00 | 49.37 O |
| ATOM | 2814 | CB | THR | A | 379 | 101.845 | 66.617 | −0.903 | 1.00 | 48.77 C |
| ATOM | 2815 | OG1 | THR | A | 379 | 102.921 | 67.089 | −0.087 | 1.00 | 49.52 O |
| ATOM | 2816 | CG2 | THR | A | 379 | 101.133 | 67.821 | −1.527 | 1.00 | 46.54 C |
| ATOM | 2817 | N | GLU | A | 380 | 98.604 | 66.147 | −0.814 | 1.00 | 50.46 N |
| ATOM | 2818 | CA | GLU | A | 380 | 97.407 | 65.905 | −1.601 | 1.00 | 51.12 C |
| ATOM | 2819 | C | GLU | A | 380 | 96.897 | 67.228 | −2.134 | 1.00 | 50.88 C |
| ATOM | 2820 | O | GLU | A | 380 | 97.110 | 68.283 | −1.538 | 1.00 | 49.94 O |
| ATOM | 2821 | CB | GLU | A | 380 | 96.322 | 65.227 | −0.758 | 1.00 | 51.47 C |
| ATOM | 2822 | CG | GLU | A | 380 | 96.762 | 63.909 | −0.168 | 1.00 | 53.35 C |
| ATOM | 2823 | CD | GLU | A | 380 | 95.633 | 63.169 | 0.503 | 1.00 | 55.74 C |
| ATOM | 2824 | OE1 | GLU | A | 380 | 94.962 | 63.764 | 1.373 | 1.00 | 56.99 O |
| ATOM | 2825 | OE2 | GLU | A | 380 | 95.421 | 61.983 | 0.167 | 1.00 | 57.47 O |
| ATOM | 2826 | N | ILE | A | 381 | 96.226 | 67.165 | −3.272 | 1.00 | 52.06 N |
| ATOM | 2827 | CA | ILE | A | 381 | 95.697 | 68.364 | −3.884 | 1.00 | 53.51 C |
| ATOM | 2828 | C | ILE | A | 381 | 94.196 | 68.250 | −4.113 | 1.00 | 53.54 C |
| ATOM | 2829 | O | ILE | A | 381 | 93.707 | 67.300 | −4.731 | 1.00 | 53.35 O |
| ATOM | 2830 | CB | ILE | A | 381 | 96.436 | 68.676 | −5.219 | 1.00 | 54.46 C |
| ATOM | 2831 | CG1 | ILE | A | 381 | 96.307 | 67.515 | −6.199 | 1.00 | 54.90 C |
| ATOM | 2832 | CG2 | ILE | A | 381 | 97.919 | 68.895 | −4.947 | 1.00 | 55.14 C |
| ATOM | 2833 | CD1 | ILE | A | 381 | 97.141 | 67.712 | −7.458 | 1.00 | 55.73 C |
| ATOM | 2634 | N | TYR | A | 382 | 93.472 | 69.228 | −3.579 | 1.00 | 53.11 N |
| ATOM | 2835 | CA | TYR | A | 382 | 92.029 | 69.285 | −3.699 | 1.00 | 52.90 C |
| ATOM | 2836 | C | TYR | A | 382 | 91.669 | 70.747 | −3.928 | 1.00 | 52.45 C |
| ATOM | 2837 | O | TYR | A | 382 | 92.092 | 71.623 | −3.173 | 1.00 | 51.87 O |
| ATOM | 2838 | CB | TYR | A | 382 | 91.379 | 68.732 | −2.419 | 1.00 | 53.99 C |
| ATOM | 2839 | CG | TYR | A | 382 | 89.868 | 68.819 | −2.388 | 1.00 | 55.14 C |
| ATOM | 2840 | CD1 | TYR | A | 382 | 89.221 | 69.793 | −1.623 | 1.00 | 55.14 C |
| ATOM | 2841 | CD2 | TYR | A | 382 | 89.084 | 67.957 | −3.161 | 1.00 | 55.70 C |
| ATOM | 2842 | CE1 | TYR | A | 382 | 87.827 | 69.910 | −1.629 | 1.00 | 56.22 C |
| ATOM | 2843 | CE2 | TYR | A | 382 | 87.688 | 68.066 | −3.177 | 1.00 | 56.34 C |
| ATOM | 2844 | CZ | TYR | A | 382 | 87.066 | 69.046 | −2.410 | 1.00 | 56.68 C |
| ATOM | 2845 | OH | TYR | A | 382 | 85.693 | 69.174 | −2.439 | 1.00 | 57.02 O |
| ATOM | 2846 | N | GLN | A | 383 | 90.903 | 70.999 | −4.987 | 1.00 | 52.24 N |
| ATOM | 2847 | CA | GLN | A | 383 | 90.484 | 72.348 | −5.358 | 1.00 | 52.02 C |
| ATOM | 2848 | C | GLN | A | 383 | 91.687 | 73.210 | −5.721 | 1.00 | 51.03 C |
| ATOM | 2849 | O | GLN | A | 383 | 91.619 | 74.436 | −5.661 | 1.00 | 50.67 O |
| ATOM | 2850 | CB | GLN | A | 383 | 89.707 | 73.018 | −4.218 | 1.00 | 53.91 C |
| ATOM | 2851 | CG | GLN | A | 383 | 88.436 | 72.297 | −3.794 | 1.00 | 56.88 C |
| ATOM | 2852 | CD | GLN | A | 383 | 87.451 | 72.115 | −4.934 | 1.00 | 59.26 C |
| ATOM | 2853 | OE1 | GLN | A | 383 | 87.746 | 71.441 | −5.926 | 1.00 | 60.79 O |
| ATOM | 2854 | NE2 | GLN | A | 383 | 86.270 | 72.718 | −4.800 | 1.00 | 59.95 N |
| ATOM | 2855 | N | GLY | A | 384 | 92.788 | 72.562 | −6.091 | 1.00 | 50.37 N |
| ATOM | 2856 | CA | GLY | A | 384 | 93.985 | 73.292 | −6.468 | 1.00 | 50.11 C |
| ATOM | 2857 | C | GLY | A | 384 | 94.977 | 73.527 | −5.341 | 1.00 | 49.99 C |
| ATOM | 2858 | O | GLY | A | 384 | 96.185 | 73.637 | −5.586 | 1.00 | 50.26 O |
| ATOM | 2859 | N | ARG | A | 385 | 94.480 | 73.610 | −4.109 | 1.00 | 49.41 N |
| ATOM | 2860 | CA | ARG | A | 385 | 95.350 | 73.837 | −2.958 | 1.00 | 48.78 C |
| ATOM | 2861 | C | ARG | A | 385 | 96.049 | 72.559 | −2.527 | 1.00 | 47.90 C |
| ATOM | 2862 | O | ARG | A | 385 | 95.536 | 71.456 | −2.727 | 1.00 | 47.68 O |
| ATOM | 2863 | CB | ARG | A | 385 | 94.563 | 74.379 | −1.761 | 1.00 | 49.61 C |
| ATOM | 2864 | CG | ARG | A | 385 | 93.830 | 75.696 | −1.980 | 1.00 | 51.31 C |
| ATOM | 2865 | CD | ARG | A | 385 | 92.522 | 75.518 | −2.727 | 1.00 | 52.37 C |
| ATOM | 2866 | NE | ARG | A | 385 | 91.851 | 76.801 | −2.898 | 1.00 | 54.89 N |
| ATOM | 2867 | CZ | ARG | A | 385 | 90.660 | 76.958 | −3.467 | 1.00 | 56.27 C |
| ATOM | 2868 | NH1 | ARG | A | 385 | 89.996 | 75.905 | −3.925 | 1.00 | 57.58 N |
| ATOM | 2869 | NH2 | ARG | A | 385 | 90.135 | 78.170 | −3.581 | 1.00 | 55.72 N |
| ATOM | 2870 | N | LYS | A | 386 | 97.220 | 72.712 | −1.920 | 1.00 | 47.18 N |
| ATOM | 2871 | CA | LYS | A | 386 | 97.977 | 71.561 | −1.450 | 1.00 | 46.53 C |
| ATOM | 2872 | C | LYS | A | 386 | 97.702 | 71.259 | 0.022 | 1.00 | 45.66 C |
| ATOM | 2873 | O | LYS | A | 386 | 97.602 | 72.166 | 0.857 | 1.00 | 45.07 O |
| ATOM | 2874 | CB | LYS | A | 386 | 99.478 | 71.781 | −1.642 | 1.00 | 46.65 C |
| ATOM | 2875 | CG | LYS | A | 386 | 99.942 | 71.885 | −3.082 | 1.00 | 48.06 C |
| ATOM | 2876 | CD | LYS | A | 386 | 101.451 | 72.061 | −3.101 | 1.00 | 50.09 C |
| ATOM | 2877 | CE | LYS | A | 386 | 102.017 | 72.118 | −4.505 | 1.00 | 51.55 C |
| ATOM | 2878 | HZ | LYS | A | 386 | 103.505 | 72.226 | −4.438 | 1.00 | 52.03 N |
| ATOM | 2879 | N | TYR | A | 387 | 97.580 | 69.971 | 0.326 | 1.00 | 45.21 N |
| ATOM | 2880 | CA | TYR | A | 387 | 97.335 | 69.515 | 1.689 | 1.00 | 45.09 C |
| ATOM | 2881 | C | TYR | A | 387 | 98.420 | 68.561 | 2.155 | 1.00 | 44.05 C |
| ATOM | 2882 | O | TYR | A | 387 | 99.270 | 68.119 | 1.380 | 1.00 | 44.31 C |
| ATOM | 2883 | CB | TYR | A | 387 | 95.978 | 68.807 | 1.787 | 1.00 | 45.22 C |
| ATOM | 2884 | CG | TYR | A | 387 | 94.799 | 69.725 | 1.580 | 1.00 | 45.09 C |
| ATOM | 2885 | CD1 | TYR | A | 387 | 94.537 | 70.291 | 0.332 | 1.00 | 45.10 C |
| ATOM | 2886 | CD2 | TYR | A | 387 | 93.981 | 70.063 | 2.652 | 1.00 | 45.00 C |
| ATOM | 2887 | CE1 | TYR | A | 387 | 93.492 | 71.194 | 0.160 | 1.00 | 45.13 C |

-continued

| | | | | | | | | | | |
|---|---|---|---|---|---|---|---|---|---|---|
| ATOM | 2888 | CE2 | TYR | A | 387 | 92.941 | 70.979 | 2.491 | 1.00 | 45.41 C |
| ATOM | 2889 | CZ | TYR | A | 387 | 92.707 | 71.531 | 1.246 | 1.00 | 45.60 C |
| ATOM | 2890 | OH | TYR | A | 387 | 91.701 | 72.444 | 1.104 | 1.00 | 47.56 O |
| ATOM | 2891 | N | LYS | A | 388 | 98.381 | 68.248 | 3.438 | 1.00 | 43.76 N |
| ATOM | 2892 | CA | LYS | A | 388 | 99.328 | 67.326 | 4.034 | 1.00 | 43.49 C |
| ATOM | 2893 | C | LYS | A | 388 | 98.501 | 66.389 | 4.865 | 1.00 | 41.84 C |
| ATOM | 2894 | O | LYS | A | 388 | 97.731 | 66.834 | 5.703 | 1.00 | 40.70 O |
| ATOM | 2895 | CB | LYS | A | 388 | 100.317 | 68.067 | 4.932 | 1.00 | 45.64 C |
| ATOM | 2896 | CG | LYS | A | 388 | 101.504 | 68.715 | 4.213 | 1.00 | 48.31 C |
| ATOM | 2897 | CD | LYS | A | 388 | 102.626 | 67.706 | 3.892 | 1.00 | 47.96 C |
| ATOM | 2898 | CE | LYS | A | 388 | 103.901 | 68.437 | 3.466 | 1.00 | 47.56 C |
| ATOM | 2899 | NZ | LYS | A | 388 | 105.097 | 67.563 | 3.426 | 1.00 | 46.67 N |
| ATOM | 2900 | N | THR | A | 389 | 98.647 | 65.092 | 4.617 | 1.00 | 42.01 N |
| ATOM | 2901 | CA | THR | A | 389 | 97.902 | 64.098 | 5.370 | 1.00 | 41.89 C |
| ATOM | 2902 | C | THR | A | 389 | 98.290 | 64.224 | 6.833 | 1.00 | 42.40 C |
| ATOM | 2903 | O | THR | A | 389 | 99.418 | 64.598 | 7.172 | 1.00 | 42.02 O |
| ATOM | 2904 | CB | THR | A | 389 | 98.218 | 62.669 | 4.909 | 1.00 | 41.09 C |
| ATOM | 2905 | CG1 | THR | A | 389 | 99.623 | 62.427 | 5.042 | 1.00 | 41.52 O |
| ATOM | 2906 | CG2 | THR | A | 389 | 97.607 | 62.474 | 2.461 | 1.00 | 41.23 C |
| ATOM | 2907 | N | TYR | A | 390 | 97.330 | 63.930 | 7.693 | 1.00 | 42.51 N |
| ATOM | 2908 | CA | TYR | A | 390 | 97.533 | 63.980 | 9.125 | 1.00 | 42.75 C |
| ATOM | 2909 | C | TYR | A | 390 | 96.624 | 62.882 | 9.670 | 1.00 | 43.43 C |
| ATOM | 2910 | O | TYR | A | 390 | 95.406 | 62.969 | 9.551 | 1.00 | 44.28 O |
| ATOM | 2911 | CB | TYR | A | 390 | 97.098 | 65.332 | 9.679 | 1.00 | 41.44 C |
| ATOM | 2912 | CG | TYR | A | 390 | 97.362 | 65.467 | 11.159 | 1.00 | 40.95 C |
| ATOM | 2913 | CD1 | TYR | A | 390 | 96.609 | 66.343 | 11.944 | 1.00 | 41.25 C |
| ATOM | 2914 | CD2 | TYR | A | 390 | 98.373 | 64.729 | 11.777 | 1.00 | 39.46 C |
| ATOM | 2915 | CE1 | TYR | A | 390 | 96.852 | 66.478 | 13.312 | 1.00 | 40.17 C |
| ATOM | 2916 | CE2 | TYR | A | 390 | 98.623 | 64.856 | 13.136 | 1.00 | 40.26 C |
| ATOM | 2917 | CZ | TYR | A | 390 | 97.857 | 65.732 | 13.896 | 1.00 | 39.92 C |
| ATOM | 2918 | OH | TYR | A | 390 | 98.095 | 65.857 | 15.238 | 1.00 | 40.43 O |
| ATOM | 2919 | N | ARG | A | 391 | 97.206 | 61.846 | 10.258 | 1.00 | 44.01 N |
| ATOM | 2920 | CA | ARG | A | 391 | 96.399 | 60.750 | 10.772 | 1.00 | 44.87 C |
| ATOM | 2921 | C | ARG | A | 391 | 96.778 | 60.387 | 12.202 | 1.00 | 45.41 C |
| ATOM | 2922 | O | ARG | A | 391 | 97.954 | 60.450 | 12.580 | 1.00 | 45.88 O |
| ATOM | 2923 | CB | ARG | A | 391 | 96.589 | 59.529 | 9.883 | 1.00 | 44.93 C |
| ATOM | 2924 | CG | ARG | A | 391 | 97.990 | 58.967 | 9.986 | 1.00 | 46.56 C |
| ATOM | 2925 | CD | ARG | A | 391 | 98.242 | 57.872 | 8.981 | 1.00 | 47.95 C |
| ATOM | 2926 | NE | ARG | A | 391 | 99.535 | 57.232 | 9.200 | 1.00 | 48.70 N |
| ATOM | 2927 | CZ | ARG | A | 391 | 100.072 | 56.357 | 8.363 | 1.00 | 49.29 C |
| ATOM | 2928 | NH1 | ARG | A | 391 | 99.425 | 56.024 | 7.252 | 1.00 | 50.30 N |
| ATOM | 2929 | NH2 | ARG | A | 391 | 101.245 | 55.805 | 8.638 | 1.00 | 49.69 N |
| ATOM | 2930 | N | GLY | A | 392 | 95.782 | 60.009 | 12.999 | 1.00 | 45.56 N |
| ATOM | 2931 | CA | GLY | A | 392 | 96.062 | 59.618 | 14.366 | 1.00 | 45.33 C |
| ATOM | 2932 | C | GLY | A | 392 | 96.803 | 58.291 | 14.343 | 1.00 | 45.81 C |
| ATOM | 2933 | O | GLY | A | 392 | 96.578 | 57.467 | 13.451 | 1.00 | 45.18 O |
| HETATM | 2934 | N | MSE | A | 393 | 97.696 | 58.074 | 15.304 | 1.00 | 46.09 N |
| HETATM | 2935 | CA | MSE | A | 393 | 98.437 | 56.818 | 15.344 | 1.00 | 46.91 C |
| HETATM | 2936 | C | MSE | A | 393 | 97.514 | 55.638 | 15.668 | 1.00 | 45.83 C |
| HETATM | 2937 | O | MSE | A | 393 | 97.905 | 54.474 | 15.553 | 1.00 | 45.29 O |
| HETATM | 2938 | CB | MSE | A | 393 | 99.587 | 56.925 | 16.351 | 1.00 | 48.46 C |
| HETATM | 2939 | CG | MSE | A | 393 | 100.671 | 57.905 | 15.906 | 1.00 | 51.44 C |
| HETATM | 2940 | SE | MSE | A | 393 | 101.600 | 57.363 | 14.403 | 1.00 | 55.48 SE |
| HETATM | 2941 | CE | MSE | A | 393 | 102.496 | 55.927 | 15.071 | 1.00 | 55.49 C |
| ATOM | 2942 | N | GLY | A | 394 | 96.280 | 55.954 | 16.049 | 1.00 | 44.70 N |
| ATOM | 2943 | CA | GLY | A | 394 | 95.307 | 54.926 | 16.364 | 1.00 | 44.19 C |
| ATOM | 2944 | C | GLY | A | 394 | 94.355 | 54.686 | 15.206 | 1.00 | 44.14 C |
| ATOM | 2945 | O | GLY | A | 394 | 93.416 | 53.896 | 15.311 | 1.00 | 43.61 O |
| ATOM | 2946 | N | SER | A | 395 | 94.591 | 55.369 | 14.093 | 1.00 | 44.85 N |
| ATOM | 2947 | CA | SER | A | 395 | 93.740 | 55.204 | 12.921 | 1.00 | 45.69 C |
| ATOM | 2948 | C | SER | A | 395 | 94.061 | 53.866 | 12.265 | 1.00 | 46.80 C |
| ATOM | 2949 | O | SER | A | 395 | 95.002 | 53.175 | 12.663 | 1.00 | 47.02 O |
| ATOM | 2950 | CB | SER | A | 395 | 93.968 | 56.340 | 11.916 | 1.00 | 45.01 C |
| ATOM | 2951 | OG | SER | A | 395 | 95.278 | 56.305 | 11.372 | 1.00 | 44.71 O |
| ATOM | 2952 | N | ILE | A | 396 | 93.276 | 53.501 | 11.261 | 1.00 | 47.68 N |
| ATOM | 2953 | CA | ILE | A | 396 | 93.488 | 52.245 | 10.554 | 1.00 | 49.11 C |
| ATOM | 2954 | C | ILE | A | 396 | 94.830 | 52.246 | 9.797 | 1.00 | 49.53 C |
| ATOM | 2955 | O | ILE | A | 396 | 95.705 | 51.418 | 10.070 | 1.00 | 48.83 O |
| ATOM | 2956 | CB | ILE | A | 396 | 92.320 | 51.974 | 9.558 | 1.00 | 49.53 C |
| ATOM | 2957 | CG1 | ILE | A | 396 | 90.990 | 51.908 | 10.315 | 1.00 | 49.28 C |
| ATOM | 2958 | CG2 | ILE | A | 396 | 92.554 | 50.670 | 8.812 | 1.00 | 49.14 C |
| ATOM | 2959 | CD1 | ILE | A | 396 | 90.932 | 50.820 | 11.363 | 1.00 | 49.48 C |
| ATOM | 2960 | N | ALA | A | 397 | 94.988 | 53.183 | 8.863 | 1.00 | 50.24 N |
| ATOM | 2961 | CA | ALA | A | 397 | 96.206 | 53.291 | 8.062 | 1.00 | 51.94 C |
| ATOM | 2962 | C | ALA | A | 397 | 97.475 | 53.255 | 8.903 | 1.00 | 53.51 C |
| ATOM | 2963 | O | ALA | A | 397 | 98.414 | 52.533 | 8.576 | 1.00 | 53.35 O |
| ATOM | 2964 | CB | ALA | A | 397 | 96.177 | 54.567 | 7.227 | 1.00 | 50.87 C |
| ATOM | 2965 | N | ALA | A | 398 | 97.507 | 54.037 | 9.979 | 1.00 | 55.56 N |
| ATOM | 2966 | CA | ALA | A | 398 | 98.677 | 54.074 | 10.851 | 1.00 | 57.66 C |

-continued

| | | | | | | | | | | |
|---|---|---|---|---|---|---|---|---|---|---|
| ATOM | 2967 | C | ALA | A | 398 | 98.878 | 52.719 | 11.529 | 1.00 | 59.35 C |
| ATOM | 2968 | O | ALA | A | 398 | 99.988 | 52.181 | 11.541 | 1.00 | 59.25 O |
| ATOM | 2969 | CB | ALA | A | 398 | 98.525 | 55.175 | 11.900 | 1.00 | 56.88 C |
| HETATM | 2970 | N | MSE | A | 399 | 97.803 | 52.162 | 12.084 | 1.00 | 61.57 N |
| HETATM | 2971 | CA | MSE | A | 399 | 97.883 | 50.868 | 12.753 | 1.00 | 63.53 C |
| HETATM | 2972 | C | MSE | A | 399 | 98.165 | 49.736 | 11.778 | 1.00 | 64.22 C |
| HETATM | 2973 | O | MSE | A | 399 | 98.294 | 48.586 | 12.181 | 1.00 | 64.45 O |
| HETATM | 2974 | CB | MSE | A | 399 | 96.589 | 50.561 | 13.510 | 1.00 | 64.53 C |
| HETATM | 2975 | CG | MSE | A | 399 | 96.335 | 51.428 | 14.726 | 1.00 | 66.17 C |
| HETATM | 2976 | SE | MSE | A | 399 | 94.927 | 50.801 | 15.688 | 1.00 | 70.47 SE |
| HETATM | 2977 | CE | MSE | A | 399 | 93.579 | 50.893 | 14.454 | 1.00 | 68.03 C |
| ATOM | 2978 | N | LYS | A | 400 | 98.275 | 50.067 | 10.498 | 1.00 | 65.70 N |
| ATOM | 2979 | CA | LYS | A | 400 | 98.535 | 49.076 | 9.461 | 1.00 | 67.25 C |
| ATOM | 2980 | C | LYS | A | 400 | 99.753 | 48.195 | 9.743 | 1.00 | 68.24 C |
| ATOM | 2981 | O | LYS | A | 400 | 100.162 | 48.015 | 10.888 | 1.00 | 68.63 O |
| ATOM | 2982 | CB | LYS | A | 400 | 98.703 | 49.771 | 8.118 | 1.00 | 67.70 C |
| ATOM | 2983 | N | LYS | A | 401 | 100.324 | 47.646 | 8.677 | 1.00 | 69.15 N |
| ATOM | 2984 | CA | LYS | A | 401 | 101.487 | 46.771 | 8.773 | 1.00 | 70.20 C |
| ATOM | 2985 | C | LYS | A | 401 | 102.588 | 47.357 | 9.662 | 1.00 | 71.05 C |
| ATOM | 2986 | O | LYS | A | 401 | 102.394 | 48.471 | 10.197 | 1.00 | 71.27 O |
| ATOM | 2987 | CB | LYS | A | 401 | 102.035 | 46.483 | 7.365 | 1.00 | 69.48 C |
| ATOM | 2988 | N | ASN | A | 416 | 92.074 | 47.487 | 5.186 | 1.00 | 72.24 N |
| ATOM | 2989 | CA | ASN | A | 416 | 91.155 | 46.876 | 6.194 | 1.00 | 72.64 C |
| ATOM | 2990 | C | ASN | A | 416 | 91.165 | 47.666 | 7.501 | 1.00 | 72.60 C |
| ATOM | 2991 | O | ASN | A | 416 | 92.209 | 48.176 | 7.915 | 1.00 | 73.31 O |
| ATOM | 2992 | CB | ASN | A | 416 | 91.563 | 45.422 | 6.465 | 1.00 | 72.21 C |
| ATOM | 2993 | N | LYS | A | 417 | 90.004 | 47.744 | 8.152 | 1.00 | 71.58 N |
| ATOM | 2994 | CA | LYS | A | 417 | 89.858 | 48.463 | 9.419 | 1.00 | 70.32 C |
| ATOM | 2995 | C | LYS | A | 417 | 89.985 | 47.484 | 10.580 | 1.00 | 69.53 C |
| ATOM | 2996 | O | LYS | A | 417 | 89.416 | 46.386 | 10.515 | 1.00 | 70.17 O |
| ATOM | 2997 | CB | LYS | A | 417 | 88.499 | 49.146 | 9.472 | 1.00 | 70.50 C |
| ATOM | 2998 | N | LEU | A | 418 | 90.712 | 47.870 | 11.642 | 1.00 | 67.91 N |
| ATOM | 2999 | CA | LEU | A | 418 | 90.903 | 46.996 | 12.826 | 1.00 | 64.90 C |
| ATOM | 3000 | C | LEU | A | 418 | 90.637 | 47.647 | 14.211 | 1.00 | 62.37 C |
| ATOM | 3001 | O | LEU | A | 418 | 91.478 | 47.559 | 15.111 | 1.00 | 62.60 O |
| ATOM | 3002 | CB | LEU | A | 418 | 92.286 | 46.414 | 12.785 | 1.00 | 64.79 C |
| ATOM | 3003 | N | VAL | A | 419 | 99.455 | 48.260 | 14.362 | 1.00 | 59.18 N |
| ATOM | 3004 | CA | VAL | A | 419 | 88.983 | 48.973 | 15.576 | 1.00 | 56.04 C |
| ATOM | 3005 | C | VAL | A | 419 | 89.820 | 50.195 | 15.995 | 1.00 | 53.39 C |
| ATOM | 3006 | O | VAL | A | 419 | 90.533 | 50.180 | 17.005 | 1.00 | 51.68 O |
| ATOM | 3007 | CB | VAL | A | 419 | 88.825 | 48.027 | 16.790 | 1.00 | 56.09 C |
| ATOM | 3008 | CG1 | VAL | A | 419 | 88.330 | 48.818 | 18.006 | 1.00 | 55.27 C |
| ATOM | 3009 | CG2 | VAL | A | 419 | 87.823 | 46.925 | 16.456 | 1.00 | 56.32 C |
| ATOM | 3010 | N | PRO | A | 420 | 89.728 | 51.280 | 15.207 | 1.00 | 51.10 N |
| ATOM | 3011 | CA | PRO | A | 420 | 90.430 | 52.548 | 15.402 | 1.00 | 49.87 C |
| ATOM | 3012 | C | PRO | A | 420 | 89.937 | 53.428 | 16.559 | 1.00 | 48.67 C |
| ATOM | 3013 | O | PRO | A | 420 | 88.758 | 53.419 | 16.924 | 1.00 | 47.55 O |
| ATOM | 3014 | CB | PRO | A | 420 | 90.238 | 53.225 | 14.052 | 1.00 | 49.97 C |
| ATOM | 3015 | CG | PRO | A | 420 | 88.824 | 52.828 | 13.734 | 1.00 | 49.16 C |
| ATOM | 3016 | CD | PRO | A | 420 | 88.939 | 51.338 | 13.961 | 1.00 | 49.81 C |
| ATOM | 3017 | N | GLU | A | 421 | 90.871 | 54.192 | 17.116 | 1.00 | 48.34 N |
| ATOM | 3018 | CA | GLU | A | 421 | 90.610 | 55.123 | 18.208 | 1.00 | 47.97 C |
| ATOM | 3019 | C | GLU | A | 421 | 90.154 | 56.506 | 17.668 | 1.00 | 46.84 C |
| ATOM | 3020 | O | GLU | A | 421 | 91.005 | 57.481 | 18.409 | 1.00 | 47.51 O |
| ATOM | 3021 | CB | GLU | A | 421 | 91.517 | 54.809 | 19.396 | 1.00 | 49.79 C |
| ATOM | 3022 | CG | GLU | A | 421 | 91.207 | 53.512 | 20.149 | 1.00 | 53.19 C |
| ATOM | 3023 | CD | GLU | A | 421 | 90.329 | 53.739 | 21.372 | 1.00 | 53.99 C |
| ATOM | 3024 | OE1 | GLU | A | 421 | 90.730 | 54.563 | 22.228 | 1.00 | 55.23 O |
| ATOM | 3025 | OE2 | GLU | A | 421 | 89.260 | 53.095 | 21.484 | 1.00 | 53.71 O |
| ATOM | 3026 | N | GLY | A | 422 | 91.200 | 56.576 | 16.366 | 1.00 | 45.35 N |
| ATOM | 3027 | CA | GLY | A | 422 | 91.541 | 57.834 | 15.736 | 1.00 | 44.97 C |
| ATOM | 3028 | C | GLY | A | 422 | 91.214 | 57.813 | 14.253 | 1.00 | 44.86 C |
| ATOM | 3029 | O | GLY | A | 422 | 90.918 | 56.760 | 13.684 | 1.00 | 44.42 O |
| ATOM | 3030 | N | ILE | A | 423 | 91.279 | 58.974 | 13.611 | 1.00 | 44.45 N |
| ATOM | 3031 | CA | ILE | A | 423 | 90.954 | 59.045 | 12.196 | 1.00 | 43.46 C |
| ATOM | 3032 | C | ILE | A | 423 | 92.129 | 59.498 | 11.321 | 1.00 | 42.96 C |
| ATOM | 3033 | O | ILE | A | 423 | 93.178 | 59.916 | 11.821 | 1.00 | 41.95 O |
| ATOM | 3034 | CB | ILE | A | 423 | 89.703 | 59.963 | 11.970 | 1.00 | 43.06 C |
| ATOM | 3035 | CG1 | ILE | A | 423 | 89.978 | 61.412 | 12.403 | 1.00 | 42.83 C |
| ATOM | 3036 | CG2 | ILE | A | 423 | 88.534 | 59.439 | 12.788 | 1.00 | 41.55 0. |
| ATOM | 3037 | CD1 | ILE | A | 423 | 90.868 | 62.208 | 11.461 | 1.00 | 43.42 C |
| ATOM | 3038 | N | GLU | A | 424 | 91.934 | 59.387 | 10.012 | 1.00 | 42.19 N |
| ATOM | 3039 | CA | GLU | A | 424 | 92.931 | 59.775 | 9.024 | 1.00 | 42.21 C |
| ATOM | 3040 | C | GLU | A | 424 | 92.422 | 61.047 | 8.363 | 1.00 | 41.48 C |
| ATOM | 3041 | O | GLU | A | 424 | 91.266 | 61.110 | 7.945 | 1.00 | 41.26 O |
| ATOM | 3042 | CB | GLU | A | 424 | 93.071 | 58.680 | 7.963 | 1.00 | 43.26 C |
| ATOM | 3043 | CG | GLU | A | 424 | 93.518 | 57.325 | 8.492 | 1.00 | 45.35 C |
| ATOM | 3044 | CD | GLU | A | 424 | 93.357 | 56.225 | 7.453 | 1.00 | 46.93 C |
| ATOM | 3045 | OE1 | GLU | A | 424 | 93.818 | 56.423 | 6.305 | 1.00 | 48.20 O |

-continued

| | | | | | | | | | |
|---|---|---|---|---|---|---|---|---|---|
| ATOM | 3046 | OE2 | GLU | A | 424 | 92.780 | 55.162 | 7.780 | 1.00 46.63 O |
| ATOM | 3047 | N | GLY | A | 425 | 93.276 | 62.060 | 8.270 | 1.00 41.08 N |
| ATOM | 3048 | CA | GLY | A | 425 | 92.857 | 63.303 | 7.643 | 1.00 40.46 C |
| ATOM | 3049 | C | GLY | A | 425 | 93.976 | 64.030 | 6.920 | 1.00 40.17 C |
| ATOM | 3050 | O | GLY | A | 425 | 95.017 | 63.446 | 6.609 | 1.00 39.82 O |
| ATOM | 3051 | N | ARG | A | 426 | 93.757 | 65.309 | 6.643 | 1.00 39.48 N |
| ATOM | 3052 | CA | ARG | A | 426 | 94.753 | 66.117 | 5.967 | 1.00 39.94 C |
| ATOM | 3053 | C | ARG | A | 426 | 94.571 | 67.562 | 6.375 | 1.00 40.26 C |
| ATOM | 3054 | O | ARG | A | 426 | 93.486 | 67.963 | 6.792 | 1.00 41.45 O |
| ATOM | 3055 | CB | ARG | A | 426 | 94.608 | 65.989 | 4.452 | 1.00 39.82 C |
| ATOM | 3056 | CG | ARG | A | 426 | 93.320 | 66.554 | 3.892 | 1.00 41.77 C |
| ATOM | 3057 | CD | ARG | A | 426 | 93.202 | 66.182 | 2.405 | 1.00 43.77 C |
| ATOM | 3058 | NE | ARG | A | 426 | 92.026 | 66.747 | 1.751 | 1.00 45.14 N |
| ATOM | 3059 | CZ | ARG | A | 426 | 91.654 | 66.455 | 0.506 | 1.00 46.18 C |
| ATOM | 3060 | NH1 | ARG | A | 426 | 92.366 | 65.604 | −0.218 | 1.00 46.99 N |
| ATOM | 3061 | NH2 | ARG | A | 426 | 90.577 | 67.021 | −0.021 | 1.00 47.23 N |
| ATOM | 3062 | N | VAL | A | 427 | 95.640 | 68.342 | 6.267 | 1.00 40.61 N |
| ATOM | 3063 | CA | VAL | A | 427 | 95.592 | 69.759 | 6.613 | 1.00 40.23 C |
| ATOM | 3064 | C | VAL | A | 427 | 96.338 | 70.557 | 5.548 | 1.00 40.03 C |
| ATOM | 3065 | O | VAL | A | 427 | 97.235 | 70.033 | 4.885 | 1.00 39.67 O |
| ATOM | 3066 | CE | VAL | A | 427 | 96.225 | 70.029 | 8.001 | 1.00 39.28 C |
| ATOM | 3067 | CG1 | VAL | A | 427 | 95.457 | 69.280 | 9.079 | 1.00 37.97 C |
| ATOM | 3068 | CG2 | VAL | A | 427 | 97.681 | 69.609 | 7.993 | 1.00 39.20 C |
| ATOM | 3069 | N | ALA | A | 429 | 95.945 | 71.815 | 5.381 | 1.00 40.23 N |
| ATOM | 3070 | CA | ALA | A | 428 | 96.562 | 72.700 | 4.406 | 1.00 41.04 C |
| ATOM | 3071 | C | ALA | A | 428 | 98.079 | 72.829 | 4.595 | 1.00 42.53 C |
| ATOM | 3072 | O | ALA | A | 428 | 98.578 | 72.780 | 5.727 | 1.00 42.82 O |
| ATOM | 3073 | CB | ALA | A | 428 | 95.918 | 74.074 | 4.496 | 1.00 39.46 C |
| ATOM | 3074 | N | TYR | A | 429 | 98.801 | 72.975 | 3.480 | 1.00 42.74 N |
| ATOM | 3075 | CA | TYR | A | 429 | 100.251 | 73.168 | 3.491 | 1.00 43.20 C |
| ATOM | 3076 | C | TYR | A | 429 | 100.546 | 74.452 | 4.284 | 1.00 42.09 C |
| ATOM | 3077 | O | TYR | A | 429 | 99.986 | 75.509 | 3.984 | 1.00 41.87 O |
| ATOM | 3078 | CB | TYR | A | 429 | 100.757 | 73.332 | 2.061 | 1.00 44.90 C |
| ATOM | 3079 | CG | TYR | A | 429 | 102.211 | 73.730 | 1.972 | 1.00 48.81 C |
| ATOM | 3080 | CD1 | TYR | A | 429 | 103.228 | 72.842 | 2.329 | 1.00 50.14 C |
| ATOM | 3081 | CD2 | TYR | A | 429 | 102.574 | 75.005 | 1.541 | 1.00 49.88 C |
| ATOM | 3082 | CE1 | TYR | A | 429 | 104.575 | 73.214 | 2.255 | 1.00 50.62 C |
| ATOM | 3083 | CE2 | TYR | A | 429 | 103.915 | 75.388 | 1.463 | 1.00 50.81 C |
| ATOM | 3084 | CZ | TYR | A | 429 | 104.908 | 74.487 | 1.819 | 1.00 50.86 C |
| ATOM | 3085 | OH | TYR | A | 429 | 106.226 | 74.863 | 1.718 | 1.00 50.47 O |
| ATOM | 3086 | N | LYS | A | 430 | 101.429 | 74.372 | 5.276 | 1.00 40.05 N |
| ATOM | 3087 | CA | LYS | A | 430 | 101.727 | 75.541 | 6.102 | 1.00 38.56 C |
| ATOM | 3088 | C | LYS | A | 430 | 103.086 | 76.198 | 5.889 | 1.00 37.11 C |
| ATOM | 3089 | O | LYS | A | 430 | 103.360 | 77.238 | 6.486 | 1.00 37.51 O |
| ATOM | 3090 | CB | LYS | A | 430 | 101.610 | 75.178 | 7.589 | 1.00 38.70 C |
| ATOM | 3091 | CG | LYS | A | 430 | 100.294 | 74.563 | 7.981 | 1.00 38.40 C |
| ATOM | 3092 | CD | LYS | A | 430 | 100.284 | 74.152 | 9.434 | 1.00 38.43 C |
| ATOM | 3093 | CE | LYS | A | 430 | 98.997 | 73.409 | 9.738 | 1.00 39.27 C |
| ATOM | 3094 | NZ | LYS | A | 430 | 98.927 | 72.970 | 11.149 | 1.00 40.88 N |
| ATOM | 3095 | N | GLY | A | 431 | 103.942 | 75.609 | 5.063 | 1.00 35.54 N |
| ATOM | 3096 | CA | GLY | A | 431 | 105.256 | 76.199 | 4.867 | 1.00 32.89 C |
| ATOM | 3097 | C | GLY | A | 431 | 106.199 | 75.798 | 5.991 | 1.00 31.20 C |
| ATOM | 3098 | O | GLY | A | 431 | 105.927 | 74.847 | 6.710 | 1.00 30.24 O |
| ATOM | 3099 | N | ALA | A | 432 | 107.296 | 76.528 | 6.157 | 1.00 30.60 N |
| ATOM | 3100 | CA | ALA | A | 432 | 108.290 | 76.214 | 7.189 | 1.00 29.98 C |
| ATOM | 3101 | C | ALA | A | 432 | 107.759 | 76.197 | 8.618 | 1.00 29.06 C |
| ATOM | 3102 | O | ALA | A | 432 | 106.981 | 77.057 | 9.018 | 1.00 30.18 O |
| ATOM | 3103 | CB | ALA | A | 432 | 109.462 | 77.188 | 7.097 | 1.00 29.00 C |
| ATOM | 3104 | N | ALA | A | 433 | 108.206 | 75.216 | 9.390 | 1.00 27.87 N |
| ATOM | 3105 | CA | ALA | A | 433 | 107.798 | 75.077 | 10.777 | 1.00 27.30 C |
| ATOM | 3106 | C | ALA | A | 433 | 108.341 | 76.225 | 11.624 | 1.00 27.35 C |
| ATOM | 3107 | O | ALA | A | 433 | 107.727 | 76.611 | 12.620 | 1.00 27.15 O |
| ATOM | 3108 | CB | ALA | A | 433 | 108.289 | 73.739 | 11.333 | 1.00 28.08 C |
| ATOM | 3109 | N | SER | A | 434 | 109.493 | 76.766 | 11.238 | 1.00 26.71 N |
| ATOM | 3110 | CA | SER | A | 434 | 110.085 | 77.875 | 11.983 | 1.00 27.06 C |
| ATOM | 3111 | C | SER | A | 434 | 109.131 | 79.070 | 12.036 | 1.00 26.79 C |
| ATOM | 3112 | O | SER | A | 434 | 109.120 | 79.821 | 13.014 | 1.00 25.57 O |
| ATOM | 3113 | CB | SER | A | 434 | 111.419 | 76.306 | 11.357 | 1.00 27.17 C |
| ATOM | 3114 | OG | SER | A | 434 | 111.252 | 78.778 | 10.031 | 1.00 28.63 O |
| ATOM | 3115 | N | ASP | A | 435 | 108.333 | 79.243 | 10.986 | 1.00 27.24 N |
| ATOM | 3116 | CA | ASP | A | 435 | 107.363 | 80.333 | 10.928 | 1.00 28.29 C |
| ATOM | 3117 | C | ASP | A | 435 | 106.188 | 80.060 | 11.868 | 1.00 27.92 C |
| ATOM | 3118 | O | ASP | A | 435 | 105.714 | 80.959 | 12.565 | 1.00 28.07 O |
| ATOM | 3119 | CB | ASP | A | 435 | 106.876 | 80.517 | 9.491 | 1.00 31.68 C |
| ATOM | 3120 | CG | ASP | A | 435 | 107.949 | 81.120 | 8.579 | 1.00 35.77 C |
| ATOM | 3121 | OD1 | ASP | A | 435 | 107.761 | 81.087 | 7.341 | 1.00 38.23 O |
| ATOM | 3122 | OD2 | ASP | A | 435 | 108.968 | 81.643 | 9.096 | 1.00 36.12 O |
| ATOM | 3123 | N | ILE | A | 436 | 105.726 | 78.815 | 11.886 | 1.00 26.54 N |
| ATOM | 3124 | CA | ILE | A | 436 | 104.637 | 78.398 | 12.763 | 1.00 25.99 C |

-continued

| | | | | | | | | | | |
|---|---|---|---|---|---|---|---|---|---|---|
| ATOM | 3125 | C | ILE | A | 436 | 105.085 | 78.679 | 14.199 | 1.00 | 24.91 C |
| ATOM | 3126 | O | ILE | A | 436 | 104.388 | 79.320 | 14.977 | 1.00 | 23.37 O |
| ATOM | 3127 | CB | ILE | A | 436 | 104.357 | 76.867 | 12.617 | 1.00 | 26.46 C |
| ATOM | 3128 | CG1 | ILE | A | 436 | 104.016 | 76.524 | 11.166 | 1.00 | 28.02 C |
| ATOM | 3129 | CG2 | ILE | A | 436 | 103.236 | 76.437 | 13.536 | 1.00 | 26.46 C |
| ATOM | 3130 | CD1 | ILE | A | 436 | 102.860 | 77.292 | 10.604 | 1.00 | 30.24 C |
| ATOM | 3131 | N | VAL | A | 437 | 106.268 | 76.191 | 14.539 | 1.00 | 25.92 N |
| ATOM | 3132 | CA | VAL | A | 437 | 106.804 | 78.383 | 15.877 | 1.00 | 27.27 C |
| ATOM | 3133 | C | VAL | A | 437 | 106.902 | 79.853 | 16.244 | 1.00 | 28.27 C |
| ATOM | 3134 | O | VAL | A | 437 | 106.560 | 80.238 | 17.367 | 1.00 | 29.71 O |
| ATOM | 3135 | CB | VAL | A | 437 | 108.200 | 77.747 | 16.022 | 1.00 | 26.18 C |
| ATOM | 3136 | CG1 | VAL | A | 437 | 108.770 | 78.055 | 17.395 | 1.00 | 25.87 C |
| ATOM | 3137 | CG2 | VAL | A | 437 | 108.105 | 76.244 | 15.821 | 1.00 | 26.99 C |
| ATOM | 3138 | N | PHE | A | 438 | 107.367 | 80.678 | 15.307 | 1.00 | 29.44 N |
| ATOM | 3139 | CA | PHE | A | 438 | 107.513 | 82.104 | 15.564 | 1.00 | 29.34 C |
| ATOM | 3140 | C | PHE | A | 438 | 106.182 | 82.759 | 15.872 | 1.00 | 29.77 C |
| ATOM | 3141 | O | PHE | A | 438 | 106.110 | 83.647 | 16.721 | 1.00 | 29.60 O |
| ATOM | 3142 | CE | PHE | A | 438 | 108.183 | 82.799 | 14.382 | 1.00 | 30.41 C |
| ATOM | 3143 | CG | PHE | A | 436 | 108.391 | 84.262 | 14.589 | 1.00 | 32.43 C |
| ATOM | 3144 | CD1 | PHE | A | 438 | 107.342 | 85.160 | 14.424 | 1.00 | 34.66 C |
| ATOM | 3145 | CD2 | PHE | A | 438 | 109.625 | 84.742 | 15.012 | 1.00 | 34.35 C |
| ATOM | 3146 | CE1 | PHE | A | 438 | 107.514 | 86.522 | 14.678 | 1.00 | 35.25 C |
| ATOM | 3147 | CE2 | PHE | A | 438 | 109.816 | 86.100 | 15.273 | 1.00 | 35.59 C |
| ATOM | 3148 | CZ | PHE | A | 438 | 108.752 | 86.994 | 15.105 | 1.00 | 36.08 C |
| ATOM | 3149 | N | GLN | A | 439 | 105.125 | 82.325 | 15.189 | 1.00 | 31.03 N |
| ATOM | 3150 | CA | GLN | A | 439 | 103.801 | 82.885 | 15.440 | 1.00 | 31.99 C |
| ATOM | 3151 | C | GLN | A | 439 | 103.280 | 82.473 | 16.803 | 1.00 | 32.50 C |
| ATOM | 3152 | O | GLN | A | 439 | 102.669 | 83.282 | 17.502 | 1.00 | 33.67 O |
| ATOM | 3153 | CB | GLN | A | 439 | 102.801 | 82.454 | 14.369 | 1.00 | 33.33 C |
| ATOM | 3154 | CG | GLN | A | 439 | 102.962 | 83.175 | 13.052 | 1.00 | 36.37 C |
| ATOM | 3155 | CD | GLN | A | 439 | 102.863 | 84.685 | 13.204 | 1.00 | 38.29 C |
| ATOM | 3156 | NE1 | GLN | A | 439 | 101.882 | 85.212 | 13.746 | 1.00 | 39.62 O |
| ATOM | 3157 | NE2 | GLN | A | 439 | 103.880 | 85.393 | 12.720 | 1.00 | 39.30 N |
| HETATM | 3158 | N | MSE | A | 440 | 103.519 | 81.225 | 17.199 | 1.00 | 31.91 N |
| HETATM | 3159 | CA | MSE | A | 440 | 103.036 | 80.797 | 18.498 | 1.00 | 32.48 C |
| HETATM | 3160 | C | MSE | A | 440 | 103.802 | 81.394 | 19.682 | 1.00 | 30.42 C |
| HETATM | 3161 | O | MSE | A | 440 | 103.199 | 81.680 | 20.718 | 1.00 | 29.98 O |
| HETATM | 3162 | CB | MSE | A | 440 | 102.958 | 79.261 | 18.577 | 1.00 | 36.61 C |
| HETATM | 3163 | CG | MSE | A | 440 | 104.200 | 78.483 | 18.205 | 1.00 | 44.35 C |
| HETATM | 3164 | SE | MSE | A | 440 | 103.911 | 76.661 | 18.242 | 1.00 | 53.13 SE |
| HETATM | 3165 | CE | MSE | A | 440 | 102.652 | 76.462 | 16.958 | 1.00 | 51.30 C |
| ATOM | 3166 | N | LEU | A | 441 | 105.107 | 81.620 | 19.543 | 1.00 | 27.53 N |
| ATOM | 3167 | CA | LEU | A | 441 | 105.867 | 82.206 | 20.648 | 1.00 | 25.82 C |
| ATOM | 3168 | C | LEU | A | 441 | 105.407 | 83.644 | 20.911 | 1.00 | 25.88 C |
| ATOM | 3169 | O | LEU | A | 441 | 105.348 | 84.092 | 22.053 | 1.00 | 26.91 O |
| ATOM | 3170 | CB | LEU | A | 441 | 107.370 | 82.194 | 20.353 | 1.00 | 25.33 C |
| ATOM | 3171 | CG | LEU | A | 441 | 108.062 | 80.839 | 20.155 | 1.00 | 25.97 C |
| ATOM | 3172 | CD1 | LEU | A | 441 | 109.552 | 81.080 | 19.937 | 1.00 | 25.09 C |
| ATOM | 3173 | CD2 | LEU | A | 441 | 107.849 | 79.940 | 21.362 | 1.00 | 25.75 C |
| ATOM | 3174 | N | GLY | A | 442 | 105.076 | 84.366 | 19.850 | 1.00 | 24.13 N |
| ATOM | 3175 | CA | GLY | A | 442 | 104.621 | 85.731 | 20.019 | 1.00 | 23.31 C |
| ATOM | 3176 | C | GLY | A | 442 | 103.358 | 85.780 | 20.849 | 1.00 | 23.82 C |
| ATOM | 3177 | O | GLY | A | 442 | 103.200 | 86.656 | 21.693 | 1.00 | 22.98 O |
| ATOM | 3178 | N | GLY | A | 443 | 102.456 | 84.834 | 20.605 | 1.00 | 24.50 N |
| ATOM | 3179 | CA | GLY | A | 443 | 101.207 | 84.775 | 21.347 | 1.00 | 24.02 C |
| ATOM | 3180 | C | GLY | A | 443 | 101.449 | 84.354 | 22.781 | 1.00 | 24.08 C |
| ATOM | 3181 | O | GLY | A | 443 | 100.773 | 84.822 | 23.696 | 1.00 | 23.64 O |
| ATOM | 3182 | N | ILE | A | 444 | 102.419 | 83.465 | 22.970 | 1.00 | 24.21 N |
| ATOM | 3183 | CA | ILE | A | 444 | 102.780 | 82.979 | 24.300 | 1.00 | 24.08 C |
| ATOM | 3184 | C | ILE | A | 444 | 103.376 | 84.135 | 25.106 | 1.00 | 24.11 C |
| ATOM | 3185 | O | ILE | A | 444 | 103.005 | 84.346 | 26.261 | 1.00 | 23.54 O |
| ATOM | 3186 | CB | ILE | A | 444 | 103.798 | 81.801 | 24.209 | 1.00 | 23.72 C |
| ATOM | 3187 | CG1 | ILE | A | 444 | 103.152 | 80.622 | 23.466 | 1.00 | 22.82 C |
| ATOM | 3188 | CG2 | ILE | A | 444 | 104.241 | 81.360 | 25.612 | 1.00 | 22.84 C |
| ATOM | 3189 | CD1 | ILE | A | 444 | 104.110 | 79.479 | 23.146 | 1.00 | 22.36 C |
| ATOM | 3190 | N | ARG | A | 445 | 104.289 | 84.890 | 24.500 | 1.00 | 23.72 N |
| ATOM | 3191 | CA | ARG | A | 445 | 104.883 | 86.030 | 25.195 | 1.00 | 24.00 C |
| ATOM | 3192 | C | ARG | A | 445 | 103.837 | 87.106 | 25.514 | 1.00 | 23.44 C |
| ATOM | 3193 | O | ARG | A | 445 | 103.891 | 87.721 | 26.576 | 1.00 | 24.01 O |
| ATOM | 3194 | CB | ARG | A | 445 | 106.026 | 86.625 | 24.372 | 1.00 | 22.89 C |
| ATOM | 3195 | CG | ARG | A | 445 | 107.275 | 85.752 | 24.332 | 1.00 | 24.88 C |
| ATOM | 3196 | CD | ARG | A | 445 | 105.356 | 86.373 | 23.456 | 1.00 | 26.53 C |
| ATOM | 3197 | NE | ARG | A | 445 | 109.592 | 85.596 | 23.462 | 1.00 | 27.53 N |
| ATOM | 3198 | CZ | ARG | A | 445 | 110.470 | 85.579 | 24.464 | 1.00 | 30.01 C |
| ATOM | 3199 | NH1 | ARG | A | 445 | 110.262 | 86.303 | 25.561 | 1.00 | 28.96 N |
| ATOM | 3200 | NH2 | ARG | A | 445 | 111.559 | 84.823 | 24.372 | 1.00 | 29.00 N |
| ATOM | 3201 | N | SER | A | 446 | 102.882 | 87.333 | 24.615 | 1.00 | 23.77 N |
| ATOM | 3202 | CA | SER | A | 446 | 101.835 | 88.322 | 24.878 | 1.00 | 24.75 C |
| ATOM | 3203 | C | SER | A | 446 | 100.953 | 87.831 | 26.004 | 1.00 | 23.48 C |

-continued

| | | | | | | | | | | |
|---|---|---|---|---|---|---|---|---|---|---|
| ATOM | 3204 | O | SER | A | 446 | 100.605 | 88.585 | 26.902 | 1.00 | 24.41 C |
| ATOM | 3205 | CB | SER | A | 446 | 100.953 | 88.558 | 23.656 | 1.00 | 25.42 C |
| ATOM | 3206 | OG | SER | A | 44E | 101.715 | 89.056 | 22.574 | 1.00 | 34.14 O |
| ATOM | 3207 | N | GLY | A | 447 | 100.587 | 86.559 | 25.946 | 1.00 | 22.70 N |
| ATOM | 3208 | CA | GLY | A | 447 | 99.740 | 85.996 | 26.974 | 1.00 | 23.15 C |
| ATOM | 3209 | C | GLY | A | 447 | 100.366 | 86.119 | 28.338 | 1.00 | 23.47 C |
| ATOM | 3210 | O | GLY | A | 447 | 99.707 | 86.531 | 29.288 | 1.00 | 24.01 O |
| HETATM | 3211 | N | MSE | A | 448 | 101.641 | 85.754 | 28.435 | 1.00 | 24.62 N |
| HETATM | 3212 | CA | MSE | A | 448 | 102.369 | 85.834 | 29.693 | 1.00 | 25.24 C |
| HETATM | 3213 | C | MSE | A | 448 | 102.566 | 87.302 | 30.112 | 1.00 | 24.99 C |
| HETATM | 3214 | O | MSE | A | 448 | 102.632 | 87.613 | 31.300 | 1.00 | 25.75 O |
| HETATM | 3215 | CB | MSE | A | 448 | 103.704 | 85.090 | 29.569 | 1.00 | 27.58 C |
| HETATM | 3216 | CG | MSE | A | 448 | 103.522 | 83.600 | 29.220 | 1.00 | 31.58 C |
| HETATM | 3217 | SE | MSE | A | 448 | 105.040 | 82.559 | 29.094 | 1.00 | 37.58 SE |
| HETATM | 3218 | CE | MSE | A | 448 | 105.621 | 82.613 | 30.821 | 1.00 | 34.91 C |
| ATOM | 3219 | N | GLY | A | 449 | 102.639 | 88.208 | 29.145 | 1.00 | 24.08 N |
| ATOM | 3220 | CA | GLY | A | 449 | 102.770 | 89.613 | 29.487 | 1.00 | 24.66 C |
| ATOM | 3221 | C | GLY | A | 449 | 101.497 | 90.132 | 20.154 | 1.00 | 25.65 C |
| ATOM | 3222 | O | GLY | A | 449 | 101.550 | 90.876 | 31.131 | 1.00 | 25.66 C |
| ATOM | 3223 | N | TYR | A | 450 | 100.341 | 89.739 | 29.626 | 1.00 | 25.60 N |
| ATOM | 3224 | CA | TYR | A | 450 | 99.059 | 90.166 | 30.178 | 1.00 | 25.77 C |
| ATOM | 3225 | C | TYR | A | 450 | 98.831 | 89.753 | 31.623 | 1.00 | 24.83 C |
| ATOM | 3226 | O | TYR | A | 450 | 98.211 | 90.485 | 32.375 | 1.00 | 25.34 O |
| ATOM | 3227 | CB | TYR | A | 450 | 97.899 | 89.622 | 29.344 | 1.00 | 26.05 C |
| ATOM | 3228 | CG | TYR | A | 450 | 97.590 | 90.402 | 28.096 | 1.00 | 27.41 C |
| ATOM | 3229 | CD1 | TYR | A | 450 | 97.111 | 91.706 | 28.167 | 1.00 | 28.14 C |
| ATOM | 3230 | CD2 | TYR | A | 450 | 97.749 | 89.826 | 26.839 | 1.00 | 28.61 C |
| ATOM | 3231 | CE1 | TYR | A | 450 | 96.793 | 92.419 | 27.007 | 1.00 | 29.06 C |
| ATOM | 3232 | CE2 | TYR | A | 450 | 97.436 | 90.530 | 25.678 | 1.00 | 29.51 C |
| ATOM | 3233 | CZ | TYR | A | 450 | 96.959 | 91.822 | 25.770 | 1.00 | 29.28 C |
| ATOM | 3234 | OH | TYR | A | 450 | 96.640 | 92.501 | 24.618 | 1.00 | 30.87 O |
| ATOM | 3235 | N | VAL | A | 451 | 99.305 | 88.576 | 32.010 | 1.00 | 24.89 N |
| ATOM | 3236 | CA | VAL | A | 451 | 99.098 | 88.121 | 33.376 | 1.00 | 25.62 C |
| ATOM | 3237 | C | VAL | A | 451 | 100.316 | 88.418 | 34.251 | 1.00 | 26.97 C |
| ATOM | 3238 | O | VAL | A | 451 | 100.343 | 88.080 | 35.434 | 1.00 | 27.47 O |
| ATOM | 3239 | CB | VAL | A | 451 | 98.758 | 86.605 | 33.417 | 1.00 | 24.80 C |
| ATOM | 3240 | CG1 | VAL | A | 451 | 97.465 | 86.346 | 32.657 | 1.00 | 22.49 C |
| ATOM | 3241 | CG2 | VAL | A | 451 | 99.884 | 85.787 | 32.822 | 1.00 | 24.04 C |
| ATOM | 3242 | N | GLY | A | 452 | 101.318 | 89.061 | 33.655 | 1.00 | 28.11 N |
| ATOM | 3243 | CA | GLY | A | 452 | 102.518 | 89.425 | 34.384 | 1.00 | 28.84 C |
| ATOM | 3244 | C | GLY | A | 452 | 103.396 | 88.273 | 34.816 | 1.00 | 30.29 C |
| ATOM | 3245 | O | GLY | A | 452 | 104.016 | 88.325 | 35.873 | 1.00 | 30.53 O |
| ATOM | 3246 | N | ALA | A | 453 | 103.461 | 87.231 | 33.998 | 1.00 | 30.98 N |
| ATOM | 3247 | CA | ALA | A | 453 | 104.278 | 86.065 | 34.312 | 1.00 | 31.22 C |
| ATOM | 3248 | C | ALA | A | 453 | 105.623 | 86.177 | 33.612 | 1.00 | 31.80 C |
| ATOM | 3249 | O | ALA | A | 453 | 105.694 | 86.079 | 32.386 | 1.00 | 32.94 O |
| ATOM | 3250 | CB | ALA | A | 453 | 103.567 | 84.800 | 33.862 | 1.00 | 30.42 C |
| ATOM | 3251 | N | GLY | A | 454 | 106.686 | 86.380 | 4.387 | 1.00 | 31.10 N |
| ATOM | 3252 | CA | GLY | A | 454 | 108.015 | 86.497 | 33.806 | 1.00 | 30.70 C |
| ATOM | 3253 | C | GLY | A | 454 | 108.595 | 85.166 | 33.359 | 1.00 | 30.23 C |
| ATOM | 3254 | O | GLY | A | 454 | 109.509 | 85.117 | 32.534 | 1.00 | 29.71 O |
| ATOM | 3255 | N | ASP | A | 455 | 108.076 | 84.086 | 33.930 | 1.00 | 30.07 N |
| ATOM | 3256 | CA | ASP | A | 455 | 108.504 | 82.742 | 33.583 | 1.00 | 30.58 C |
| ATOM | 3257 | C | ASP | A | 455 | 107.326 | 81.825 | 33.830 | 1.00 | 30.31 C |
| ATOM | 3258 | O | ASP | A | 455 | 106.353 | 82.228 | 34.463 | 1.00 | 30.69 O |
| ATOM | 3259 | CB | ASP | A | 455 | 109.701 | 82.290 | 34.426 | 1.00 | 32.56 C |
| ATOM | 3260 | CG | ASP | A | 455 | 109.415 | 82.301 | 35.919 | 1.00 | 34.66 C |
| ATOM | 3261 | OD1 | ASP | A | 455 | 108.311 | 81.896 | 36.331 | 1.00 | 36.16 O |
| ATOM | 3262 | OD2 | ASP | A | 455 | 110.313 | 82.688 | 36.694 | 1.00 | 38.54 O |
| ATOM | 3263 | N | ILE | A | 456 | 107.412 | 80.593 | 33.343 | 1.00 | 29.95 N |
| ATOM | 3264 | CA | ILE | A | 456 | 106.326 | 79.634 | 33.502 | 1.00 | 30.50 C |
| ATOM | 3265 | C | ILE | A | 456 | 105.976 | 79.367 | 34.957 | 1.00 | 31.87 C |
| ATOM | 3266 | O | ILE | A | 456 | 104.820 | 79.103 | 35.274 | 1.00 | 32.52 O |
| ATOM | 3267 | CB | ILE | A | 456 | 106.657 | 78.302 | 32.791 | 1.00 | 29.40 C |
| ATOM | 3268 | CG1 | ILE | A | 456 | 106.775 | 78.555 | 31.287 | 1.00 | 29.89 C |
| ATOM | 3269 | CG2 | ILE | A | 456 | 105.589 | 77.259 | 33.082 | 1.00 | 28.25 C |
| ATOM | 3270 | CD1 | ILE | A | 456 | 107.179 | 77.342 | 30.477 | 1.00 | 31.58 C |
| ATOM | 3271 | N | GLN | A | 457 | 106.964 | 79.445 | 35.844 | 1.00 | 32.73 N |
| ATOM | 3272 | CA | GLN | A | 457 | 106.718 | 79.207 | 37.264 | 1.00 | 33.99 C |
| ATOM | 3273 | C | GLN | A | 457 | 105.672 | 80.193 | 37.801 | 1.00 | 33.89 C |
| ATOM | 3274 | O | GLN | A | 457 | 104.718 | 79.800 | 38.477 | 1.00 | 33.85 C |
| ATOM | 3275 | CB | GLN | A | 457 | 108.021 | 79.349 | 38.049 | 1.00 | 36.03 C |
| ATOM | 3276 | CG | GLN | A | 457 | 107.883 | 79.030 | 39.528 | 1.00 | 41.19 C |
| ATOM | 3277 | CD | GLN | A | 457 | 109.173 | 79.257 | 40.300 | 1.00 | 44.64 C |
| ATOM | 3278 | OE1 | GLN | A | 457 | 110.235 | 78.745 | 39.930 | 1.00 | 46.35 O |
| ATOM | 3279 | NE2 | GLN | A | 457 | 109.084 | 80.019 | 41.386 | 1.00 | 46.46 N |
| ATOM | 3280 | N | GLU | A | 458 | 105.860 | 81.475 | 37.494 | 1.00 | 33.67 N |
| ATOM | 3281 | CA | GLU | A | 458 | 104.937 | 82.523 | 37.925 | 1.00 | 32.88 C |
| ATOM | 3282 | C | GLU | A | 458 | 103.574 | 82.270 | 37.315 | 1.00 | 30.94 C |

-continued

| | | | | | | | | | | |
|---|---|---|---|---|---|---|---|---|---|---|
| ATOM | 3283 | O | GLU | A | 458 | 102.542 | 82.607 | 37.889 | 1.00 | 30.37 O |
| ATOM | 3284 | CB | GLU | A | 458 | 105.436 | 83.899 | 37.478 | 1.00 | 33.84 C |
| ATOM | 3285 | CG | GLU | A | 458 | 106.617 | 84.441 | 38.255 | 1.00 | 36.71 C |
| ATOM | 3286 | CD | GLU | A | 458 | 107.151 | 85.736 | 37.661 | 1.00 | 39.24 C |
| ATOM | 3287 | OE1 | GLU | A | 458 | 106.336 | 86.630 | 37.337 | 1.00 | 39.29 O |
| ATOM | 3288 | OE2 | GLU | A | 458 | 108.390 | 85.867 | 37.532 | 1.00 | 41.42 O |
| ATOM | 3289 | N | LEU | A | 459 | 103.587 | 81.673 | 36.137 | 1.00 | 30.11 N |
| ATOM | 3290 | CA | LEU | A | 459 | 102.365 | 81.363 | 35.424 | 1.00 | 29.90 C |
| ATOM | 3291 | C | LEU | A | 459 | 101.543 | 80.371 | 36.251 | 1.00 | 30.10 C |
| ATOM | 3292 | O | LEU | A | 459 | 100.340 | 80.560 | 36.446 | 1.00 | 30.22 O |
| ATOM | 3293 | CB | LEU | A | 459 | 102.725 | 80.779 | 34.056 | 1.00 | 29.44 C |
| ATOM | 3294 | CG | LEU | A | 459 | 101.699 | 80.716 | 32.938 | 1.00 | 28.07 C |
| ATOM | 3295 | CD1 | LEU | A | 459 | 101.087 | 82.092 | 32.708 | 1.00 | 27.42 C |
| ATOM | 3296 | CD2 | LEU | A | 459 | 102.404 | 80.226 | 31.689 | 1.00 | 26.36 C |
| ATOM | 3297 | N | HIS | A | 460 | 102.190 | 79.322 | 36.754 | 1.00 | 30.22 N |
| ATOM | 3298 | CA | HIS | A | 460 | 101.483 | 78.337 | 37.561 | 1.00 | 30.19 C |
| ATOM | 3299 | C | HIS | A | 460 | 100.980 | 78.973 | 38.850 | 1.00 | 30.56 C |
| ATOM | 3300 | O | MIS | A | 460 | 99.824 | 78.792 | 39.228 | 1.00 | 30.63 O |
| ATOM | 3301 | CB | HIS | A | 460 | 102.378 | 77.138 | 37.927 | 1.00 | 30.63 C |
| ATOM | 3302 | CC | MIS | A | 460 | 102.860 | 76.337 | 36.753 | 1.00 | 31.06 C |
| ATOM | 3303 | ND1 | HIS | A | 460 | 102.178 | 76.270 | 35.558 | 1.00 | 31.79 N |
| ATOM | 3304 | CD2 | HIS | A | 460 | 103.925 | 75.507 | 36.620 | 1.00 | 31.34 C |
| ATOM | 3305 | CE1 | HIS | A | 460 | 102.802 | 75.437 | 34.742 | 1.00 | 31.58 C |
| ATOM | 3306 | NE2 | HIS | A | 460 | 103.865 | 74.959 | 35.361 | 1.00 | 30.54 N |
| ATOM | 3307 | N | GLU | A | 461 | 101.853 | 79.733 | 39.509 | 1.00 | 31.26 N |
| ATOM | 3308 | CA | GLU | A | 461 | 101.538 | 80.387 | 40.789 | 1.00 | 32.15 C |
| ATOM | 3309 | C | GLU | A | 461 | 100.548 | 81.562 | 40.795 | 1.00 | 30.88 C |
| ATOM | 3310 | O | GLU | A | 461 | 99.740 | 81.687 | 41.715 | 1.00 | 29.77 O |
| ATOM | 3311 | CB | GLU | A | 461 | 102.833 | 80.887 | 41.457 | 1.00 | 33.27 C |
| ATOM | 3312 | CG | GLU | A | 461 | 103.899 | 79.832 | 41.728 | 1.00 | 35.31 C |
| ATOM | 3313 | CD | GLU | A | 461 | 103.422 | 78.711 | 42.633 | 1.00 | 36.84 C |
| ATOM | 3314 | OE1 | GLU | A | 461 | 102.952 | 78.986 | 43.758 | 1.00 | 37.87 O |
| ATOM | 3315 | OE2 | GLU | A | 461 | 103.533 | 77.543 | 42.214 | 1.00 | 40.15 O |
| ATOM | 3316 | N | ASN | A | 462 | 100.616 | 82.417 | 39.779 | 1.00 | 29.95 N |
| ATOM | 3317 | CA | ASN | A | 462 | 99.779 | 83.611 | 39.733 | 1.00 | 30.16 C |
| ATOM | 3318 | C | ASN | A | 462 | 98.589 | 83.674 | 38.774 | 1.00 | 29.60 C |
| ATOM | 3319 | O | ASN | A | 462 | 97.568 | 84.282 | 39.107 | 1.00 | 30.16 O |
| ATOM | 3320 | CB | ASN | A | 462 | 100.683 | 84.817 | 39.484 | 1.00 | 31.63 C |
| ATOM | 3321 | CG | ASN | A | 462 | 101.759 | 84.960 | 40.543 | 1.00 | 32.75 C |
| ATOM | 3322 | OD1 | ASN | A | 462 | 102.725 | 85.696 | 40.367 | 1.00 | 35.69 O |
| ATOM | 3323 | ND2 | ASN | A | 462 | 101.588 | 84.262 | 41.656 | 1.00 | 31.98 N |
| ATOM | 3324 | N | ALA | A | 463 | 98.711 | 83.066 | 37.598 | 1.00 | 27.52 N |
| ATOM | 3325 | CA | ALA | A | 463 | 97.634 | 83.103 | 36.610 | 1.00 | 26.51 C |
| ATOM | 3326 | C | ALA | A | 463 | 96.338 | 82.451 | 37.076 | 1.00 | 25.73 C |
| ATOM | 3327 | O | ALA | A | 463 | 96.348 | 81.386 | 37.679 | 1.00 | 25.89 O |
| ATOM | 3328 | CB | ALA | A | 463 | 98.096 | 82.465 | 35.313 | 1.00 | 24.91 C |
| ATOM | 3329 | N | GLN | A | 464 | 95.222 | 83.113 | 36.785 | 1.00 | 25.80 N |
| ATOM | 3330 | CA | GLN | A | 464 | 93.888 | 82.619 | 37.136 | 1.00 | 25.60 C |
| ATOM | 3331 | C | GLN | A | 464 | 92.959 | 82.601 | 35.923 | 1.00 | 24.30 C |
| ATOM | 3332 | C | GLN | A | 464 | 93.147 | 83.369 | 34.977 | 1.00 | 23.88 O |
| ATOM | 3333 | CB | GLN | A | 464 | 93.270 | 83.492 | 38.214 | 1.00 | 25.18 C |
| ATOM | 3334 | CG | GLN | A | 464 | 93.996 | 83.413 | 39.517 | 1.00 | 28.22 C |
| ATOM | 3335 | CD | GLN | A | 464 | 93.378 | 84.314 | 40.545 | 1.00 | 29.41 C |
| ATOM | 3336 | OE1 | GLN | A | 464 | 93.378 | 85.539 | 40.395 | 1.00 | 30.21 O |
| ATOM | 3337 | NE2 | GLN | A | 464 | 92.829 | 83.716 | 41.596 | 1.00 | 30.03 N |
| ATOM | 3338 | N | PHE | A | 465 | 91.962 | 81.721 | 35.959 | 1.00 | 22.93 N |
| ATOM | 3339 | CA | PHE | A | 465 | 91.009 | 81.614 | 34.868 | 1.00 | 22.72 C |
| ATOM | 3340 | C | PHE | A | 465 | 89.627 | 82.121 | 35.246 | 1.00 | 23.14 C |
| ATOM | 3341 | O | PHE | A | 465 | 89.199 | 82.035 | 36.404 | 1.00 | 23.64 O |
| ATOM | 3342 | CB | PHE | A | 465 | 90.820 | 80.162 | 34.415 | 1.00 | 22.18 C |
| ATOM | 3343 | CG | PHE | A | 465 | 92.042 | 79.513 | 33.836 | 1.00 | 23.68 C |
| ATOM | 3344 | CD1 | PHE | A | 465 | 92.775 | 78.594 | 34.577 | 1.00 | 25.25 C |
| ATOM | 3345 | CD2 | PHE | A | 465 | 92.437 | 79.780 | 32.533 | 1.00 | 23.42 C |
| ATOM | 3346 | CE1 | PHE | A | 465 | 93.884 | 77.947 | 34.025 | 1.00 | 24.49 C |
| ATOM | 3347 | CE2 | PHE | A | 465 | 93.544 | 79.138 | 31.974 | 1.00 | 23.33 C |
| ATOM | 3348 | CZ | PHE | A | 465 | 94.265 | 78.220 | 32.724 | 1.00 | 24.38 C |
| ATOM | 3349 | N | VAL | A | 466 | 88.932 | 82.656 | 34.251 | 1.00 | 22.63 N |
| ATOM | 3350 | CA | VAL | A | 466 | 87.556 | 83.094 | 34.415 | 1.00 | 21.20 C |
| ATOM | 3351 | C | VAL | A | 466 | 86.828 | 82.188 | 33.423 | 1.00 | 21.50 C |
| ATOM | 3352 | O | VAL | A | 466 | 87.281 | 81.994 | 32.300 | 1.00 | 19.95 O |
| ATOM | 3353 | CB | VAL | A | 466 | 87.352 | 84.586 | 34.061 | 1.00 | 19.34 C |
| ATOM | 3354 | CG1 | VAL | A | 466 | 87.897 | 84.887 | 32.698 | 1.00 | 18.84 C |
| ATOM | 3355 | CG2 | VAL | A | 466 | 85.872 | 84.924 | 34.123 | 1.00 | 18.58 C |
| ATOM | 3356 | N | GLU | A | 467 | 85.726 | 81.601 | 33.854 | 1.00 | 22.06 N |
| ATOM | 3357 | CA | GLU | A | 467 | 84.979 | 80.698 | 33.005 | 1.00 | 24.06 C |
| ATOM | 3358 | C | GLU | A | 467 | 84.050 | 81.439 | 32.068 | 1.00 | 24.75 C |
| ATOM | 3359 | O | GLU | A | 467 | 83.415 | 82.413 | 32.465 | 1.00 | 25.25 O |
| ATOM | 3360 | CB | GLU | A | 467 | 84.151 | 79.763 | 33.858 | 1.00 | 24.21 C |
| ATOM | 3361 | CG | GLU | A | 467 | 83.546 | 78.653 | 33.077 | 1.00 | 28.44 C |

-continued

| | | | | | | | | | | |
|---|---|---|---|---|---|---|---|---|---|---|
| ATOM | 3362 | CD | GLU | A | 467 | 82.524 | 77.934 | 33.879 | 1.00 | 32.19 C |
| ATOM | 3363 | OE1 | GLU | A | 467 | 82.756 | 77.771 | 35.093 | 1.00 | 34.37 O |
| ATOM | 3364 | OE2 | GLU | A | 467 | 81.502 | 77.521 | 33.298 | 1.00 | 35.05 O |
| HETATM | 3365 | N | MSE | A | 468 | 83.956 | 80.981 | 30.826 | 1.00 | 24.94 N |
| HETATM | 3366 | CA | MSE | A | 468 | 83.066 | 81.631 | 29.878 | 1.00 | 26.54 C |
| HETATM | 3367 | C | MSE | A | 468 | 82.086 | 80.645 | 29.274 | 1.00 | 26.74 C |
| HETATM | 3368 | O | MSE | A | 468 | 82.353 | 79.444 | 29.218 | 1.00 | 26.45 O |
| HETATM | 3369 | CB | MSE | A | 468 | 83.858 | 82.322 | 28.763 | 1.00 | 28.88 C |
| HETATM | 3370 | CG | MSE | A | 468 | 84.730 | 81.421 | 27.918 | 1.00 | 31.63 C |
| HETATM | 3371 | SE | MSE | A | 468 | 85.425 | 82.387 | 26.542 | 1.00 | 39.89 SE |
| HETATM | 3372 | CE | MSE | A | 468 | 86.595 | 81.206 | 25.795 | 1.00 | 34.18 C |
| ATOM | 3373 | N | SER | A | 469 | 80.945 | 81.156 | 28.827 | 1.00 | 27.65 N |
| ATOM | 3374 | CA | SER | A | 469 | 79.919 | 80.314 | 28.212 | 1.00 | 28.52 C |
| ATOM | 3375 | C | SER | A | 469 | 80.148 | 80.275 | 26.705 | 1.00 | 29.26 C |
| ATOM | 3376 | O | SER | A | 469 | 81.093 | 80.886 | 26.197 | 1.00 | 28.60 O |
| ATOM | 3377 | CB | SER | A | 469 | 78.532 | 80.888 | 28.488 | 1.00 | 27.30 C |
| ATOM | 3378 | OG | SER | A | 469 | 78.385 | 82.148 | 27.847 | 1.00 | 27.56 O |
| ATOM | 3379 | N | GLY | A | 470 | 79.271 | 79.566 | 25.996 | 1.00 | 31.42 N |
| ATOM | 3380 | CA | GLY | A | 470 | 79.384 | 79.479 | 24.549 | 1.00 | 33.33 C |
| ATOM | 3381 | C | GLY | A | 470 | 79.362 | 80.860 | 23.920 | 1.00 | 35.22 |
| ATOM | 3382 | O | GLY | A | 470 | 80.083 | 81.131 | 22.956 | 1.00 | 36.54 O |
| ATOM | 3383 | N | ALA | A | 471 | 78.530 | 81.738 | 24.477 | 1.00 | 35.45 N |
| ATOM | 3384 | CA | ALA | A | 471 | 78.408 | 83.106 | 23.992 | 1.00 | 36.13 C |
| ATOM | 3385 | C | ALA | A | 471 | 79.720 | 83.867 | 24.206 | 1.00 | 36.97 C |
| ATOM | 3386 | O | ALA | A | 471 | 80.182 | 84.595 | 23.321 | 1.00 | 37.26 O |
| ATOM | 3387 | CB | ALA | A | 471 | 77.268 | 83.809 | 24.722 | 1.00 | 35.98 C |
| ATOM | 3388 | N | GLY | A | 472 | 80.311 | 83.701 | 25.388 | 1.00 | 37.72 N |
| ATOM | 3389 | CA | GLY | A | 472 | 81.565 | 84.369 | 25.691 | 1.00 | 38.01 C |
| ATOM | 3390 | C | GLY | A | 472 | 82.656 | 83.924 | 24.730 | 1.00 | 38.54 C |
| ATOM | 3391 | O | GLY | A | 472 | 83.558 | 84.695 | 24.385 | 1.00 | 38.01 O |
| ATOM | 3392 | N | LEU | A | 473 | 82.573 | 82.667 | 24.296 | 1.00 | 38.34 N |
| ATOM | 3393 | CA | LEU | A | 473 | 83.550 | 82.125 | 23.363 | 1.00 | 37.79 C |
| ATOM | 3394 | C | LEU | A | 473 | 83.349 | 82.890 | 22.050 | 1.00 | 37.07 C |
| ATOM | 3395 | O | LEU | A | 473 | 84.316 | 83.285 | 21.395 | 1.00 | 36.58 O |
| ATOM | 3396 | CB | LEU | A | 473 | 83.306 | 80.624 | 23.152 | 1.00 | 38.74 C |
| ATOM | 3397 | CG | LEU | A | 473 | 84.497 | 79.733 | 22.761 | 1.00 | 39.23 C |
| ATOM | 3398 | CD1 | LEU | A | 473 | 83.986 | 78.347 | 22.459 | 1.00 | 38.60 C |
| ATOM | 3399 | CD2 | LEU | A | 473 | 85.229 | 80.274 | 21.558 | 1.00 | 40.46 C |
| ATOM | 3400 | N | ILE | A | 474 | 82.084 | 83.108 | 21.687 | 1.00 | 36.82 N |
| ATOM | 3401 | CA | ILE | A | 474 | 81.737 | 83.841 | 20.463 | 1.00 | 36.70 C |
| ATOM | 3402 | C | ILE | A | 474 | 82.348 | 85.238 | 20.536 | 1.00 | 36.56 C |
| ATOM | 3403 | O | ILE | A | 474 | 82.968 | 85.707 | 19.582 | 1.00 | 36.03 O |
| ATOM | 3404 | CB | ILE | A | 474 | 80.198 | 84.001 | 20.294 | 1.00 | 36.35 C |
| ATOM | 3405 | CG1 | ILE | A | 474 | 79.516 | 82.630 | 20.276 | 1.00 | 36.33 C |
| ATOM | 3406 | CG2 | ILE | A | 474 | 79.889 | 84.760 | 19.006 | 1.00 | 35.09 C |
| ATOM | 3407 | CD1 | ILE | A | 474 | 79.989 | 81.719 | 19.171 | 1.00 | 35.80 C |
| ATOM | 3408 | N | GLU | A | 475 | 82.159 | 85.899 | 21.674 | 1.00 | 35.95 & |
| ATOM | 3409 | CA | GLU | A | 475 | 82.700 | 87.233 | 21.880 | 1.00 | 36.17 C |
| ATOM | 3410 | C | GLU | A | 475 | 84.216 | 87.235 | 21.791 | 1.00 | 36.53 C |
| ATOM | 3411 | O | GLU | A | 475 | 84.807 | 88.209 | 21.327 | 1.00 | 36.42 O |
| ATOM | 3412 | CB | GLU | A | 475 | 82.263 | 87.776 | 23.254 | 1.00 | 37.61 C |
| ATOM | 3413 | CG | GLU | A | 475 | 83.143 | 88.914 | 23.827 | 1.00 | 37.08 C |
| ATOM | 3414 | CD | GLU | A | 475 | 82.626 | 89.458 | 25.164 | 1.00 | 37.58 C |
| ATOM | 3415 | OE1 | GLU | A | 475 | 81.614 | 90.188 | 25.161 | 1.00 | 38.57 O |
| ATOM | 2416 | OE2 | GLU | A | 475 | 83.216 | 89.146 | 26.221 | 1.00 | 33.85 O |
| ATOM | 2417 | N | SER | A | 476 | 84.841 | 86.145 | 22.237 | 1.00 | 37.04 N |
| ATOM | 2418 | CA | SER | A | 476 | 86.300 | 86.039 | 22.242 | 1.00 | 37.27 C |
| ATOM | 2419 | C | SER | A | 476 | 86.924 | 85.973 | 20.851 | 1.00 | 37.06 C |
| ATOM | 2420 | O | SER | A | 476 | 88.046 | 86.442 | 20.638 | 1.00 | 37.30 O |
| ATOM | 3421 | CB | SER | A | 476 | 86.728 | 84.830 | 23.068 | 1.00 | 36.80 C |
| ATOM | 3422 | OG | SER | A | 476 | 86.251 | 84.963 | 24.391 | 1.00 | 36.30 O |
| ATOM | 3423 | N | HIS | A | 477 | 86.197 | 85.391 | 19.908 | 1.00 | 36.25 N |
| ATOM | 3424 | CA | HIS | A | 477 | 86.667 | 85.288 | 18.533 | 1.00 | 36.22 C |
| ATOM | 3425 | C | HIS | A | 477 | 86.181 | 86.477 | 17.724 | 1.00 | 36.09 C |
| ATOM | 3426 | O | HIS | A | 477 | 85.207 | 87.141 | 18.100 | 1.00 | 34.72 O |
| ATOM | 3427 | CB | HIS | A | 477 | 86.132 | 84.008 | 17.897 | 1.00 | 36.36 C |
| ATOM | 3428 | CG | HIS | A | 477 | 86.901 | 82.789 | 18.267 | 1.00 | 36.15 C |
| ATOM | 3429 | ND1 | HIS | A | 477 | 88.077 | 82.440 | 17.644 | 1.00 | 37.86 N |
| ATOM | 3430 | CD2 | HIS | A | 477 | 86.690 | 81.858 | 19.224 | 1.00 | 37.82 C |
| ATOM | 3431 | CE1 | HIS | A | 477 | 88.559 | 81.343 | 18.200 | 1.00 | 38.68 C |
| ATOM | 3432 | NE2 | HIS | A | 477 | 87.736 | 80.969 | 19.162 | 1.00 | 38.42 N |
| ATOM | 3433 | N | PRO | A | 478 | 86.865 | 86.778 | 16.606 | 1.00 | 36.62 N |
| ATOM | 3434 | CA | PRO | A | 478 | 86.409 | 87.910 | 15.801 | 1.00 | 37.52 C |
| ATOM | 3435 | C | PRO | A | 478 | 84.974 | 87.589 | 15.387 | 1.00 | 38.47 C |
| ATOM | 3436 | O | PRO | A | 478 | 84.626 | 86.417 | 15.192 | 1.00 | 37.19 O |
| ATOM | 3437 | CB | PRO | A | 478 | 87.391 | 87.901 | 14.624 | 1.00 | 36.75 C |
| ATOM | 3438 | CG | PRO | A | 478 | 88.651 | 87.370 | 15.266 | 1.00 | 36.00 C |
| ATOM | 3439 | CD | PRO | A | 478 | 88.056 | 86.173 | 15.987 | 1.00 | 36.59 C |
| ATOM | 3440 | N | RIS | A | 479 | 84.141 | 88.617 | 15.271 | 1.00 | 40.10 N |

-continued

| | | | | | | | | | |
|---|---|---|---|---|---|---|---|---|---|
| ATOM | 3441 | CA | HIS | A | 479 | 82.749 | 88.409 | 14.898 | 1.00 | 41.71 C |
| ATOM | 3442 | C | HIS | A | 479 | 82.163 | 89.607 | 14.178 | 1.00 | 43.00 C |
| ATOM | 3443 | O | HIS | A | 479 | 82.691 | 90.723 | 14.263 | 1.00 | 42.96 O |
| ATOM | 3444 | CB | HIS | A | 479 | 81.906 | 88.138 | 16.142 | 1.00 | 42.19 C |
| ATOM | 3445 | CG | HIS | A | 479 | 82.004 | 89.217 | 17.175 | 1.00 | 42.96 C |
| ATOM | 3446 | ND1 | HIS | A | 479 | 83.105 | 89.373 | 17.989 | 1.00 | 44.02 N |
| ATOM | 3447 | CD2 | HIS | A | 479 | 81.154 | 90.221 | 17.499 | 1.00 | 44.12 C |
| ATOM | 3448 | CE1 | HIS | A | 479 | 82.929 | 90.423 | 18.773 | 1.00 | 43.65 C |
| ATOM | 3449 | NE2 | HIS | A | 479 | 81.753 | 90.956 | 18.495 | 1.00 | 44.04 N |
| ATOM | 3450 | N | ASP | A | 480 | 81.055 | 89.355 | 13.482 | 1.00 | 44.35 N |
| ATOM | 3451 | CA | ASP | A | 480 | 80.321 | 90.373 | 12.741 | 1.00 | 45.86 C |
| ATOM | 3452 | C | ASP | A | 480 | 81.196 | 91.161 | 11.787 | 1.00 | 45.95 C |
| ATOM | 3453 | O | ASP | A | 480 | 81.074 | 92.381 | 11.676 | 1.00 | 46.64 O |
| ATOM | 3454 | CB | ASP | A | 480 | 79.631 | 91.326 | 13.716 | 1.00 | 47.55 C |
| ATOM | 3455 | CG | ASP | A | 480 | 78.698 | 90.601 | 14.672 | 1.00 | 50.07 C |
| ATOM | 3456 | OD1 | ASP | A | 480 | 77.750 | 89.935 | 14.191 | 1.00 | 50.68 O |
| ATOM | 3457 | OD2 | ASP | A | 480 | 78.912 | 90.698 | 15.904 | 1.00 | 52.11 O |
| ATOM | 3458 | N | VAL | A | 481 | 82.083 | 90.457 | 11.099 | 1.00 | 46.00 N |
| ATOM | 3459 | CA | VAL | A | 481 | 82.975 | 91.093 | 10.141 | 1.00 | 45.97 C |
| ATOM | 3460 | C | VAL | A | 481 | 83.437 | 90.069 | 9.105 | 1.00 | 45.58 C |
| ATOM | 3461 | O | VAL | A | 481 | 83.781 | 88.934 | 9.438 | 1.00 | 44.87 O |
| ATOM | 3462 | CB | VAL | A | 481 | 84.199 | 91.748 | 10.861 | 1.00 | 46.24 C |
| ATOM | 3463 | CG1 | VAL | A | 481 | 84.888 | 90.733 | 11.769 | 1.00 | 46.53 C |
| ATOM | 3464 | CG2 | VAL | A | 481 | 85.177 | 92.301 | 9.834 | 1.00 | 45.43 C |
| ATOM | 3465 | N | GLN | A | 482 | 83.416 | 90.475 | 7.842 | 1.00 | 45.62 N |
| ATOM | 3466 | CA | GLN | A | 482 | 83.822 | 89.600 | 6.756 | 1.00 | 45.66 C |
| ATOM | 3467 | C | GLN | A | 482 | 85.331 | 89.650 | 6.600 | 1.00 | 45.00 C |
| ATOM | 3468 | O | GLN | A | 482 | 85.898 | 90.706 | 6.353 | 1.00 | 44.56 O |
| ATOM | 3469 | CB | GLN | A | 482 | 83.129 | 90.035 | 5.466 | 1.00 | 46.54 C |
| ATOM | 3470 | CG | GLN | A | 482 | 83.384 | 89.130 | 4.279 | 1.00 | 49.29 C |
| ATOM | 3471 | CD | GLN | A | 482 | 82.506 | 89.489 | 3.095 | 1.00 | 51.02 C |
| ATOM | 3472 | OE1 | GLN | A | 482 | 81.280 | 89.447 | 3.190 | 1.00 | 53.04 O |
| ATOM | 3473 | NE2 | GLN | A | 482 | 83.126 | 89.847 | 1.976 | 1.00 | 50.81 N |
| ATOM | 3474 | N | ILE | A | 483 | 85.977 | 88.500 | 6.760 | 1.00 | 45.70 N |
| ATOM | 3475 | CA | ILE | A | 483 | 87.431 | 88.406 | 6.643 | 1.00 | 46.40 C |
| ATOM | 3476 | C | ILE | A | 483 | 87.797 | 87.626 | 5.378 | 1.00 | 46.80 C |
| ATOM | 3477 | O | ILE | A | 483 | 87.378 | 86.479 | 5.209 | 1.00 | 47.10 O |
| ATOM | 3478 | CB | ILE | A | 483 | 88.045 | 87.668 | 7.870 | 1.00 | 46.86 C |
| ATOM | 3479 | CG1 | ILE | A | 483 | 87.565 | 88.314 | 9.172 | 1.00 | 47.22 C |
| ATOM | 3480 | CG2 | ILE | A | 483 | 89.566 | 87.721 | 7.804 | 1.00 | 46.15 C |
| ATOM | 3481 | CD1 | ILE | A | 483 | 88.107 | 87.641 | 10.430 | 1.00 | 47.26 C |
| ATOM | 3482 | N | THR | A | 484 | 88.573 | 88.240 | 4.491 | 1.00 | 47.02 N |
| ATOM | 3483 | CA | THR | A | 484 | 88.970 | 87.565 | 3.258 | 1.00 | 47.69 C |
| ATOM | 3484 | C | THR | A | 484 | 90.448 | 87.182 | 3.316 | 1.00 | 47.46 C |
| ATOM | 3485 | O | THR | A | 484 | 90.908 | 86.296 | 2.599 | 1.00 | 46.97 O |
| ATOM | 3486 | CB | THR | A | 484 | 88.710 | 98.453 | 2.002 | 1.00 | 48.12 C |
| ATOM | 3487 | CG1 | THR | A | 484 | 89.451 | 89.676 | 2.114 | 1.00 | 49.12 O |
| ATOM | 3488 | CG2 | THR | A | 484 | 87.219 | 88.767 | 1.861 | 1.00 | 47.18 C |
| ATOM | 3489 | N | ASN | A | 485 | 91.184 | 87.894 | 4.171 | 1.00 | 47.14 N |
| ATOM | 3490 | CA | ASN | A | 485 | 92.605 | 87.644 | 4.356 | 1.00 | 47.75 C |
| ATOM | 3491 | C | ASN | A | 485 | 92.864 | 87.515 | 5.854 | 1.00 | 47.58 C |
| ATOM | 3492 | 0 | ASN | A | 485 | 92.851 | 88.507 | 6.594 | 1.00 | 47.74 O |
| ATOM | 3493 | CB | ASN | A | 485 | 93.436 | 88.785 | 3.767 | 1.00 | 48.75 C |
| ATOM | 3494 | CG | ASN | A | 485 | 94.934 | 88.540 | 3.890 | 1.00 | 50.65 C |
| ATOM | 3495 | OD1 | ASN | A | 485 | 95.453 | 87.518 | 3.429 | 1.00 | 50.94 O |
| ATOM | 3496 | ND2 | ASN | A | 485 | 95.636 | 89.483 | 4.508 | 1.00 | 51.72 N |
| ATOM | 3497 | N | GLU | A | 486 | 93.099 | 86.276 | 6.281 | 1.00 | 46.65 N |
| ATOM | 3498 | CA | GLU | A | 486 | 93.332 | 85.930 | 7.680 | 1.00 | 45.73 C |
| ATOM | 3499 | C | GLU | A | 486 | 94.720 | 86.252 | 8.207 | 1.00 | 45.11 C |
| ATOM | 3500 | 0 | GLU | A | 486 | 95.660 | 86.465 | 7.443 | 1.00 | 45.20 O |
| ATOM | 3501 | CB | GLU | A | 486 | 93.057 | 84.441 | 7.867 | 1.00 | 46.18 C |
| ATOM | 3502 | CG | GLU | A | 486 | 91.649 | 84.047 | 7.462 | 1.00 | 46.84 C |
| ATOM | 3503 | CD | GLU | A | 486 | 91.503 | 82.556 | 7.259 | 1.00 | 47.48 C |
| ATOM | 3504 | OE1 | GLU | A | 486 | 90.380 | 82.105 | 6.946 | 1.00 | 47.47 O |
| ATOM | 3505 | OE2 | GLU | A | 486 | 92.518 | 81.838 | 7.402 | 1.00 | 47.64 O |
| ATOM | 3506 | N | ALA | A | 487 | 94.835 | 86.284 | 9.530 | 1.00 | 44.77 N |
| ATOM | 3507 | CA | ALA | A | 487 | 96.106 | 86.563 | 10.187 | 1.00 | 44.41 C |
| ATOM | 3508 | C | ALA | A | 487 | 96.892 | 85.264 | 10.290 | 1.00 | 44.54 C |
| ATOM | 3509 | 0 | ALA | A | 487 | 96.314 | 84.184 | 10.407 | 1.00 | 43.71 O |
| ATOM | 3510 | CB | ALA | A | 487 | 95.867 | 87.143 | 11.563 | 1.00 | 44.17 C |
| ATOM | 3511 | N | PRO | A | 488 | 98.227 | 85.350 | 10.227 | 1.00 | 45.67 N |
| ATOM | 3512 | CA | PRO | A | 488 | 99.083 | 84.168 | 10.317 | 1.00 | 46.18 C |
| ATOM | 3513 | C | PRO | A | 488 | 98.978 | 83.485 | 11.675 | 1.00 | 46.38 C |
| ATOM | 3514 | O | PRO | A | 488 | 99.572 | 82.434 | 11.892 | 1.00 | 47.49 O |
| ATOM | 3515 | CB | PRO | A | 488 | 100.474 | 84.751 | 10.064 | 1.00 | 46.01 C |
| ATOM | 3516 | CG | PRO | A | 488 | 100.351 | 66.122 | 10.696 | 1.00 | 46.03 C |
| ATOM | 3517 | CD | PRO | A | 488 | 99.059 | 86.551 | 10.034 | 1.00 | 46.59 C |
| ATOM | 3518 | N | ASN | A | 489 | 98.218 | 84.075 | 12.587 | 1.00 | 46.12 N |
| ATOM | 3519 | CA | ASN | A | 489 | 98.073 | 83.499 | 13.918 | 1.00 | 46.19 C |

-continued

| | | | | | | | | | |
|---|---|---|---|---|---|---|---|---|---|
| ATOM | 3520 | C | ASN | A | 489 | 96.604 | 83.237 | 14.261 | 1.00 45.99 C |
| ATOM | 3521 | O | ASN | A | 489 | 96.258 | 82.970 | 15.415 | 1.00 45.30 O |
| ATOM | 3522 | CB | ASN | A | 489 | 98.712 | 84.433 | 14.948 | 1.00 45.82 C |
| ATOM | 3523 | CG | ASN | A | 489 | 97.953 | 85.736 | 15.101 | 1.00 47.05 C |
| ATOM | 3524 | OD1 | ASN | A | 489 | 97.335 | 86.229 | 14.152 | 1.00 47.80 O |
| ATOM | 3525 | ND2 | ASN | A | 489 | 98.019 | 86.320 | 16.293 | 1.00 47.88 N |
| ATOM | 3526 | N | TYR | A | 490 | 95.741 | 83.327 | 13.253 | 1.00 45.80 N |
| ATOM | 3527 | CA | TYR | A | 490 | 94.319 | 83.069 | 13.447 | 1.00 45.86 C |
| ATOM | 3528 | C | TYR | A | 490 | 93.669 | 82.536 | 12.168 | 1.00 46.13 C |
| ATOM | 3529 | C | TYR | A | 490 | 93.361 | 83.295 | 11.246 | 1.00 45.86 O |
| ATOM | 3530 | CB | TYR | A | 490 | 93.576 | 84.328 | 13.916 | 1.00 44.08 C |
| ATOM | 3531 | CG | TYR | A | 490 | 92.148 | 84.013 | 14.302 | 1.00 42.82 C |
| ATOM | 3532 | CD1 | TYR | A | 490 | 91.871 | 83.222 | 15.419 | 1.00 41.48 C |
| ATOM | 3533 | CD2 | TYR | A | 490 | 91.080 | 84.402 | 13.489 | 1.00 42.13 C |
| ATOM | 3534 | CE1 | TYR | A | 490 | 90.570 | 82.816 | 15.709 | 1.00 41.83 C |
| ATOM | 3535 | CE2 | TYR | A | 490 | 89.776 | 84.001 | 13.772 | 1.00 41.77 C |
| ATOM | 3536 | CZ | TYR | A | 490 | 89.529 | 83.204 | 14.881 | 1.00 41.35 C |
| ATOM | 3537 | OH | TYR | A | 490 | 88.248 | 82.771 | 15.141 | 1.00 40.05 O |
| ATOM | 3536 | N | SER | A | 491 | 93.475 | 81.220 | 12.135 | 1.00 47.86 N |
| ATOM | 3539 | CA | SER | A | 491 | 92.880 | 80.512 | 11.005 | 1.00 49.91 C |
| ATOM | 3540 | C | SER | A | 491 | 93.583 | 80.739 | 9.661 | 1.00 51.25 C |
| ATOM | 3541 | O | SER | A | 491 | 94.408 | 81.674 | 9.551 | 1.00 53.12 O |
| ATOM | 3542 | CB | SER | A | 491 | 91.402 | 80.881 | 10.887 | 1.00 50.03 C |
| ATOM | 3543 | OG | SER | A | 491 | 90.700 | 80.462 | 12.043 | 1.00 51.19 O |
| ATOM | 3544 | N | VAL | A | 492 | 93.288 | 79.975 | 8.714 | 1.00 52.00 N |
| TER | 3545 | | VAL | A | 492 | | | | |
| HETATM | 3546 | P | IMP | | 500 | 96.855 | 67.484 | 18.145 | 1.00 36.20 P |
| HETATM | 3547 | O1P | IMP | | 500 | 96.567 | 66.958 | 16.764 | 1.00 35.78 O |
| HETATM | 3548 | O2P | IMP | | 500 | 97.831 | 68.643 | 18.107 | 1.00 37.27 O |
| HETATM | 3549 | O3P | IMP | | 500 | 95.630 | 67.848 | 18.926 | 1.00 37.73 O |
| HETATM | 3550 | O5* | IMP | | 500 | 97.576 | 66.348 | 19.098 | 1.00 39.55 C |
| HETATM | 3551 | C5* | IMP | | 500 | 96.906 | 65.102 | 19.379 | 1.00 43.52 C |
| HETATM | 3552 | C4* | IMP | | 500 | 97.725 | 64.188 | 20.314 | 1.00 46.38 C |
| HETATM | 3553 | O4* | IMP | | 500 | 96.849 | 63.056 | 20.510 | 1.00 47.93 O |
| HETATM | 3554 | C3* | IMP | | 500 | 99.128 | 63.615 | 19.896 | 1.00 47.80 C |
| HETATM | 3555 | O3* | IMP | | 500 | 100.283 | 64.165 | 20.566 | 1.00 48.27 O |
| HETATM | 3556 | C2* | IMP | | 500 | 99.063 | 62.138 | 20.401 | 1.00 48.14 C |
| HETATM | 3557 | O2* | IMP | | 500 | 99.459 | 61.962 | 21.777 | 1.00 47.86 O |
| HETATM | 3558 | C1* | IMP | | 500 | 97.568 | 61.820 | 20.391 | 1.00 48.84 C |
| HETATM | 3559 | N9 | IMP | | 500 | 97.172 | 60.952 | 19.187 | 1.00 49.35 N |
| HETATM | 3560 | C8 | IMP | | 500 | 97.769 | 60.762 | 17.934 | 1.00 49.94 C |
| HETATM | 3561 | N7 | IMP | | 500 | 96.960 | 59.811 | 17.195 | 1.00 49.47 N |
| HETATM | 3562 | C5 | IMP | | 500 | 95.903 | 59.489 | 18.092 | 1.00 49.72 C |
| HETATM | 3563 | C6 | IMP | | 500 | 94.774 | 58.548 | 17.851 | 1.00 49.49 C |
| HETATM | 3564 | O6 | IMP | | 500 | 94.520 | 57.868 | 16.852 | 1.00 49.17 O |
| HETATM | 3565 | N1 | IMP | | 500 | 93.959 | 58.521 | 15.994 | 1.00 50.36 N |
| HETATM | 3566 | C2 | IMP | | 500 | 94.155 | 59.256 | 20.190 | 1.00 50.39 C |
| HETATM | 3567 | N3 | IMP | | 500 | 95.182 | 60.067 | 20.313 | 1.00 49.12 N |
| HETATM | 3568 | C4 | IMP | | 500 | 96.016 | 60.150 | 19.259 | 1.00 49.43 C |
| HETATM | 3569 | O | HOH | | 501 | 100.576 | 78.275 | 17.774 | 1.00 32.86 O |
| HETATM | 3570 | O | HOH | | 503 | 91.095 | 64.490 | 36.206 | 1.00 28.90 O |
| HETATM | 3571 | O | HOH | | 504 | 94.498 | 58.629 | 33.377 | 1.00 29.01 O |
| HETATM | 3572 | O | HOH | | 505 | 121.994 | 54.382 | 32.283 | 1.00 29.34 O |
| HETATM | 3573 | O | HOH | | 506 | 103.325 | 52.600 | 39.850 | 1.00 30.92 O |
| HETATM | 3574 | O | HOH | | 506 | 114.082 | 79.200 | 14.020 | 1.00 31.09 O |
| HETATM | 3575 | O | HOH | | 509 | 111.782 | 75.357 | 9.474 | 1.00 41.74 O |
| HETATM | 3576 | O | HOH | | 510 | 130.431 | 69.550 | 6.520 | 1.00 33.07 O |
| HETATM | 3577 | O | HOH | | 511 | 139.704 | 72.872 | 5.502 | 1.00 28.29 O |
| HETATM | 3578 | O | HOH | | 512 | 138.165 | 79.843 | 7.558 | 1.00 37.74 O |
| HETATM | 3579 | O | HOH | | 513 | 110.012 | 65.496 | 9.942 | 1.00 27.19 O |
| HETATM | 3580 | O | HOH | | 514 | 95.709 | 85.791 | 36.220 | 1.00 26.84 O |
| HETATM | 3581 | O | HOH | | 515 | 97.359 | 70.230 | 25.703 | 1.00 26.44 O |
| HETATM | 3582 | O | HOH | | 516 | 111.343 | 65.984 | 36.009 | 1.00 27.68 O |
| HETATM | 3583 | O | HOH | | 517 | 92.610 | 64.734 | 28.562 | 1.00 25.19 O |
| HETATM | 3584 | O | HOH | | 518 | 136.337 | 83.402 | 18.230 | 1.00 44.74 O |
| HETATM | 3585 | O | HOH | | 519 | 125.872 | 72.828 | 24.786 | 1.00 56.58 O |
| HETATM | 3586 | O | HOH | | 520 | 123.394 | 85.143 | 17.982 | 1.00 44.83 O |
| HETATM | 3587 | O | HOH | | 521 | 114.051 | 75.607 | 10.822 | 1.00 28.33 O |
| HETATM | 3588 | O | HOH | | 522 | 95.439 | 56.751 | 21.398 | 1.00 35.18 O |
| HETATM | 3589 | O | HOH | | 523 | 126.131 | 73.771 | 18.625 | 1.00 28.52 O |
| HETATM | 3590 | O | HOH | | 524 | 88.573 | 61.550 | 21.356 | 1.00 35.43 O |
| HETATM | 3591 | O | HOH | | 525 | 84.159 | 71.151 | 29.206 | 1.00 24.40 O |
| HETATM | 3592 | O | HOH | | 526 | 133.284 | 55.863 | 10.735 | 1.00 36.12 O |
| HETATM | 3593 | O | HOH | | 527 | 127.221 | 75.361 | 20.788 | 1.00 31.12 O |
| HETATM | 3594 | O | HOH | | 528 | 144.500 | 73.437 | 21.138 | 1.00 37.89 O |
| HETATM | 3595 | O | HOH | | 529 | 104.651 | 89.119 | 21.108 | 1.00 45.21 O |
| HETATM | 3596 | O | HOH | | 530 | 97.113 | 80.827 | 16.767 | 1.00 29.31 O |
| HETATM | 3597 | O | HOH | | 531 | 115.587 | 76.287 | 34.279 | 1.00 41.57 O |
| HETATM | 3598 | O | HOH | | 532 | 110.085 | 78.952 | 34.960 | 1.00 36.98 O |

-continued

| | | | | | | | | | | |
|---|---|---|---|---|---|---|---|---|---|---|
| HETATM | 3599 | O | HOH | 533 | 113.576 | 64.235 | 37.324 | 1.00 | 44.04 | O |
| HETATM | 3600 | O | HOH | 536 | 113.308 | 82.910 | 26.870 | 1.00 | 35.47 | O |
| HETATM | 3601 | O | HOH | 537 | 135.913 | 65.420 | 20.988 | 1.00 | 42.04 | O |
| HETATM | 3602 | O | HOH | 538 | 81.878 | 61.168 | 23.889 | 1.00 | 37.18 | O |
| HETATM | 3603 | O | HOH | 539 | 112.973 | 80.799 | 18.829 | 1.00 | 46.80 | O |
| HETATM | 3604 | O | HOH | 540 | 114.422 | 67.736 | 18.471 | 1.00 | 21.38 | O |
| HETATM | 3605 | O | HOH | 541 | 149.015 | 73.669 | 7.625 | 1.00 | 31.27 | O |
| HETATM | 3606 | O | HOH | 542 | 94.881 | 66.686 | 41.661 | 1.00 | 28.69 | O |
| HETATM | 3607 | O | HOH | 544 | 100.410 | 54.930 | 42.976 | 1.00 | 40.88 | O |
| HETATM | 3608 | O | HOH | 546 | 123.513 | 59.702 | 10.409 | 1.00 | 32.15 | O |
| HETATM | 3609 | O | HOH | 547 | 146.434 | 72.633 | 24.076 | 1.00 | 36.35 | O |
| HETATM | 3610 | O | HOH | 548 | 88.886 | 71.737 | 36.970 | 1.00 | 30.08 | O |
| HETATM | 3611 | O | HOH | 549 | 107.710 | 87.920 | 18.571 | 1.00 | 46.77 | O |
| HETATM | 3612 | O | HOH | 550 | 89.670 | 63.104 | 37.776 | 1.00 | 47.36 | O |
| HETATM | 3613 | O | HOH | 552 | 122.692 | 77.602 | 19.074 | 1.00 | 36.80 | O |
| HETATM | 3614 | O | HOH | 553 | 98.993 | 52.226 | 5.651 | 1.00 | 57.87 | O |
| HETATM | 3615 | O | HOH | 554 | 113.536 | 82.903 | 22.647 | 1.00 | 41.61 | O |
| HETATM | 3616 | O | HOH | 555 | 115.587 | 74.041 | 10.297 | 1.00 | 38.20 | O |
| HETATM | 3617 | O | HOH | 557 | 98.458 | 49.507 | 39.120 | 1.00 | 62.44 | O |
| HETATM | 3618 | O | HOH | 558 | 112.138 | 63.863 | 8.254 | 1.00 | 24.96 | O |
| HETATM | 3619 | O | HOH | 560 | 118.847 | 70.191 | 28.617 | 1.00 | 45.38 | O |
| HETATM | 3620 | O | HOH | 561 | 146.469 | 68.284 | 24.114 | 1.00 | 37.59 | O |
| HETATM | 3621 | O | HOH | 562 | 128.262 | 63.501 | 17.485 | 1.00 | 38.06 | O |
| HETATM | 3622 | O | HOH | 563 | 119.639 | 64.695 | 7.607 | 1.00 | 46.90 | O |
| HETATM | 3623 | O | HOH | 564 | 103.490 | 70.881 | 36.574 | 1.00 | 31.68 | O |
| HETATM | 3624 | O | HOH | 565 | 98.314 | 86.799 | 37.005 | 1.00 | 30.76 | O |
| HETATM | 3625 | O | HOH | 567 | 131.484 | 71.418 | 23.548 | 1.00 | 36.31 | O |
| HETATM | 3626 | O | HOH | 568 | 76.343 | 60.795 | 41.874 | 1.00 | 35.52 | O |
| HETATM | 3627 | O | HOH | 569 | 126.027 | 59.075 | 12.269 | 1.00 | 43.45 | O |
| HETATM | 3628 | O | HOH | 570 | 109.042 | 74.363 | 33.675 | 1.00 | 39.31 | O |
| HETATM | 3629 | O | HOM | 573 | 80.409 | 90.280 | 22.579 | 1.00 | 34.21 | O |
| HETATM | 3630 | O | HOH | 574 | 132.441 | 66.786 | 9.212 | 1.00 | 43.87 | O |
| HETATM | 3631 | O | HOH | 575 | 109.944 | 79.697 | 32.230 | 1.00 | 32.32 | O |
| HETATM | 3632 | O | HOH | 577 | 144.216 | 66.858 | 24.156 | 1.00 | 40.46 | O |
| HETATM | 3633 | O | HOH | 578 | 129.414 | 81.484 | 16.530 | 1.00 | 61.51 | O |
| HETATM | 3634 | O | HOH | 579 | 96.972 | 92.020 | 39.467 | 1.00 | 39.03 | O |
| HETATM | 3635 | O | HOH | 580 | 94.372 | 70.562 | 18.189 | 1.00 | 26.74 | O |
| HETATM | 3636 | O | HOH | 581 | 88.506 | 73.637 | 23.695 | 1.00 | 31.00 | O |
| HETATM | 3637 | O | HOH | 584 | 100.007 | 84.003 | 17.987 | 1.00 | 28.74 | O |
| HETATM | 3638 | O | HOH | 585 | 121.405 | 52.600 | 17.537 | 1.00 | 40.20 | O |
| HETATM | 3639 | O | HOH | 588 | 119.167 | 48.434 | 16.339 | 1.00 | 65.21 | O |
| HETATM | 3640 | O | HOH | 589 | 102.348 | 55.052 | 4.902 | 1.00 | 39.64 | O |
| HETATM | 3641 | O | HOH | 595 | 97.908 | 70.027 | 21.031 | 1.00 | 34.06 | O |
| HETATM | 3642 | O | HOH | 596 | 146.572 | 53.248 | 20.725 | 1.00 | 45.62 | O |
| HETATM | 3643 | O | HOH | 598 | 90.443 | 55.094 | 8.608 | 1.00 | 49.49 | O |
| HETATM | 3644 | O | HOH | 599 | 109.411 | 77.677 | 2.747 | 1.00 | 53.11 | O |
| HETATM | 3645 | O | HOH | 600 | 107.764 | 45.882 | 37.351 | 1.00 | 45.02 | O |
| HETATM | 3646 | O | HOH | 601 | 87.454 | 73.205 | 28.703 | 1.00 | 45.44 | O |
| HETATM | 3647 | O | HOH | 602 | 80.069 | 88.678 | 20.249 | 1.00 | 42.72 | O |
| HETATM | 3648 | O | HOH | 603 | 117.159 | 79.599 | 17.309 | 1.00 | 30.98 | O |
| HETATM | 3649 | O | HOH | 604 | 84.446 | 85.847 | 6.609 | 1.00 | 66.35 | O |
| HETATM | 3650 | O | HOH | 605 | 142.262 | 74.880 | 21.888 | 1.00 | 42.69 | O |
| HETATM | 3651 | O | HOH | 606 | 133.945 | 64.662 | 5.678 | 1.00 | 39.03 | O |
| HETATM | 3652 | O | HOH | 607 | 110.322 | 88.556 | 20.860 | 1.00 | 51.80 | O |
| HETATM | 3653 | O | HOH | 608 | 118.514 | 60.464 | 29.384 | 1.00 | 33.39 | O |
| HETATM | 3654 | O | HOH | 609 | 82.950 | 78.301 | 25.302 | 1.00 | 33.55 | O |
| HETATM | 3655 | O | HOH | 610 | 111.407 | 75.421 | 34.632 | 1.00 | 44.58 | O |
| HETATM | 3656 | O | HOH | 612 | 96.558 | 63.438 | 23.644 | 1.00 | 34.09 | O |
| HETATM | 3657 | O | HOH | 613 | 122.627 | 63.063 | 23.597 | 1.00 | 26.90 | O |
| HETATM | 3658 | O | HOH | 614 | 131.169 | 69.077 | 14.358 | 1.00 | 34.02 | O |
| HETATM | 3659 | O | HOH | 618 | 96.690 | 54.179 | 40.860 | 1.00 | 32.89 | O |
| HETATM | 3660 | O | HOH | 619 | 126.711 | 73.763 | 15.905 | 1.00 | 32.41 | O |
| HETATM | 3661 | O | HOH | 621 | 92.253 | 63.599 | 39.103 | 1.00 | 25.94 | O |
| HETATM | 3662 | O | HOH | 622 | 97.813 | 87.700 | 39.424 | 1.00 | 55.96 | O |
| HETATM | 3663 | O | HOH | 623 | 95.535 | 56.002 | 20.767 | 1.00 | 65.87 | O |
| HETATM | 3664 | O | HOH | 624 | 129.489 | 78.975 | 20.616 | 1.00 | 46.43 | O |
| HETATM | 3665 | O | HOH | 625 | 119.866 | 48.017 | 8.457 | 1.00 | 69.76 | O |
| HETATM | 3666 | O | HOH | 627 | 134.345 | 53.135 | 10.168 | 1.00 | 47.96 | O |
| HETATM | 3667 | O | HOH | 628 | 96.130 | 73.007 | 12.133 | 1.00 | 65.41 | O |
| HETATM | 3668 | O | HOH | 629 | 87.800 | 55.819 | 15.251 | 1.00 | 45.94 | O |
| HETATM | 3669 | O | HOH | 630 | 112.422 | 70.233 | 37.715 | 1.00 | 55.93 | O |
| HETATM | 3670 | O | HOH | 632 | 121.366 | 74.739 | 24.939 | 1.00 | 57.43 | O |
| HETATM | 3671 | O | HOH | 633 | 101.115 | 80.540 | 12.424 | 1.00 | 53.67 | O |
| HETATM | 3672 | O | HOH | 634 | 124.882 | 64.152 | 26.715 | 1.00 | 65.56 | O |
| HETATM | 3673 | O | HOH | 635 | 97.480 | 87.029 | 5.748 | 1.00 | 41.53 | O |
| HETATM | 3674 | O | HOH | 636 | 98.153 | 71.085 | 17.480 | 1.00 | 23.05 | O |
| HETATM | 3675 | O | HOH | 638 | 109.916 | 53.593 | 7.340 | 1.00 | 60.03 | O |
| HETATM | 3676 | O | HOH | 639 | 109.356 | 46.219 | 43.098 | 1.00 | 74.41 | O |
| HETATM | 3677 | O | HOH | 640 | 123.090 | 65.562 | 2.087 | 1.00 | 64.16 | O |

-continued

| | | | | | | | | | | |
|---|---|---|---|---|---|---|---|---|---|---|
| HETATM | 3678 | O | HOH | 641 | 121.091 | 58.113 | 37.981 | 1.00 | 53.09 | O |
| HETATM | 3679 | O | HOH | 642 | 106.879 | 71.024 | 39.823 | 1.00 | 49.73 | O |
| HETATM | 3680 | O | HOH | 644 | 125.842 | 60.086 | 22.102 | 1.00 | 57.75 | O |
| HETATM | 3681 | O | HOH | 645 | 89.792 | 80.261 | 21.919 | 1.00 | 65.49 | O |
| HETATM | 3682 | O | HOH | 646 | 127.581 | 71.494 | 10.877 | 1.00 | 41.56 | O |
| HETATM | 3683 | O | HOH | 647 | 116.711 | 52.692 | 38.666 | 1.00 | 55.88 | O |
| HETATM | 3684 | O | HOH | 648 | 137.352 | 49.806 | 16.559 | 1.00 | 67.37 | O |
| HETATM | 3685 | O | HOH | 649 | 93.707 | 89.594 | 38.028 | 1.00 | 28.70 | O |
| HETATM | 3686 | O | HOH | 650 | 102.722 | 58.313 | 7.082 | 1.00 | 52.26 | O |
| HETATM | 3687 | O | HOH | 651 | 99.494 | 73.756 | −9.807 | 1.00 | 57.10 | O |
| HETATM | 3688 | O | HOH | 652 | 100.369 | 60.404 | 12.181 | 1.00 | 24.56 | O |
| HETATM | 3689 | O | HOH | 653 | 86.387 | 73.114 | 22.271 | 1.00 | 36.14 | O |
| HETATM | 3690 | O | HOH | 655 | 82.774 | 85.056 | 16.980 | 1.00 | 29.50 | O |
| HETATM | 3691 | O | HOH | 656 | 138.719 | 75.750 | 24.731 | 1.00 | 43.44 | O |
| HETATM | 3692 | O | HOH | 657 | 135.443 | 63.373 | 23.553 | 1.00 | 62.79 | O |
| HETATM | 3693 | O | HOH | 658 | 136.532 | 59.341 | 22.164 | 1.00 | 61.51 | O |
| HETATM | 3694 | O | HOH | 659 | 112.228 | 46.754 | 14.166 | 1.00 | 44.56 | O |
| HETATM | 3695 | O | HOH | 661 | 85.056 | 77.737 | 37.011 | 1.00 | 51.97 | O |
| HETATM | 3696 | O | HOH | 664 | 93.862 | 94.123 | 24.058 | 1.00 | 44.59 | O |
| HETATM | 3697 | O | HOH | 665 | 125.115 | 50.268 | 16.057 | 1.00 | 50.48 | O |
| HETATM | 3698 | O | HOH | 666 | 109.792 | 82.218 | 39.304 | 1.00 | 41.41 | O |
| HETATM | 3699 | O | HOH | 667 | 81.419 | 71.538 | 32.800 | 1.00 | 43.84 | O |
| HETATM | 3700 | O | HOH | 671 | 100.872 | 91.979 | 23.613 | 1.00 | 64.05 | O |
| HETATM | 3701 | O | HOH | 672 | 121.924 | 64.730 | 9.693 | 1.00 | 40.99 | O |
| HETATM | 3702 | O | HOH | 673 | 103.164 | 53.450 | 45.794 | 1.00 | 46.76 | O |
| HETATM | 3703 | O | HOH | 674 | 112.887 | 44.758 | 35.892 | 1.00 | 60.15 | O |
| HETATM | 3704 | O | HOH | 675 | 121.226 | 52.298 | 40.410 | 1.00 | 59.96 | O |
| HETATM | 3705 | O | HOH | 676 | 114.778 | 79.883 | 12.588 | 1.00 | 53.72 | O |
| HETATM | 3706 | O | HOH | 677 | 111.493 | 44.375 | 26.336 | 1.00 | 44.91 | O |
| HETATM | 3707 | O | HOH | 680 | 125.672 | 77.196 | 7.641 | 1.00 | 62.63 | O |
| HETATM | 3708 | O | HOH | 681 | 149.427 | 68.734 | 21.594 | 1.00 | 69.45 | O |
| HETATM | 3709 | O | HOH | 682 | 130.498 | 68.890 | 11.409 | 1.00 | 43.07 | O |
| HETATM | 3710 | O | HOH | 684 | 97.027 | 74.301 | −8.091 | 1.00 | 51.74 | O |
| HETATM | 3711 | O | HOH | 685 | 93.468 | 57.644 | 35.310 | 1.00 | 25.70 | O |
| HETATM | 3712 | O | HOH | 687 | 120.082 | 63.118 | 33.794 | 1.00 | 66.97 | O |
| HETATM | 3713 | O | HOH | 688 | 91.794 | 50.180 | 5.365 | 1.00 | 61.88 | O |
| HETATM | 3714 | O | HOH | 691 | 120.955 | 66.509 | 26.956 | 1.00 | 57.92 | O |
| HETATM | 3715 | O | HOH | 692 | 147.976 | 65.172 | 14.279 | 1.00 | 58.48 | O |
| HETATM | 3716 | O | HOH | 693 | 90.415 | 78.310 | 23.880 | 1.00 | 38.31 | O |
| HETATM | 3717 | O | HOH | 694 | 113.372 | 43.333 | 17.881 | 1.00 | 68.93 | O |
| HETATM | 3718 | O | HOH | 695 | 101.223 | 90.113 | 38.606 | 1.00 | 45.49 | O |
| HETATM | 3719 | O | HOH | 696 | 108.151 | 50.895 | 41.168 | 1.00 | 59.49 | O |
| HETATM | 3720 | O | HOH | 697 | 90.431 | 44.244 | 14.620 | 1.00 | 43.55 | O |
| HETATM | 3721 | O | HOH | 698 | 146.554 | 70.443 | 18.977 | 1.00 | 32.63 | O |
| HETATM | 3722 | O | HOH | 702 | 107.324 | 89.479 | 37.117 | 1.00 | 65.35 | O |
| HETATM | 3723 | O | HOH | 706 | 181.406 | 55.047 | 15.937 | 1.00 | 56.70 | C |
| HETATM | 3724 | O | HOH | 707 | 101.778 | 67.697 | −5.655 | 1.00 | 34.92 | O |
| HETATM | 3725 | O | HOH | 709 | 136.699 | 62.881 | −10.241 | 1.00 | 53.86 | O |
| HETATM | 3726 | O | HOH | 710 | 115.523 | 70.686 | 9.393 | 1.00 | 35.01 | O |
| HETATM | 3727 | O | HOH | 714 | 140.987 | 80.163 | 24.272 | 1.00 | 65.37 | O |
| HETATM | 3728 | O | HOH | 715 | 144.845 | 70.181 | 8.359 | 1.00 | 45.96 | O |
| HETATM | 3729 | O | HOH | 716 | 127.420 | 64.712 | 10.814 | 1.00 | 50.93 | O |
| HETATM | 3730 | O | HbH | 717 | 112.586 | 85.955 | 35.733 | 1.00 | 63.37 | O |
| HETATM | 3731 | O | HOH | 718 | 96.397 | 65.225 | 43.866 | 1.00 | 54.78 | O |
| HETATM | 3732 | O | HOH | 719 | 149.381 | 55.765 | 8.190 | 1.00 | 46.95 | O |
| HETATM | 3733 | O | HOH | 723 | 115.502 | 77.990 | 9.376 | 1.00 | 46.76 | O |
| HETATM | 3734 | O | HOH | 725 | 76.437 | 79.568 | 26.459 | 1.00 | 59.19 | O |
| HETATM | 3735 | O | HOH | 726 | 95.324 | 49.183 | 27.259 | 1.00 | 51.94 | O |
| HETATM | 3736 | O | HOH | 727 | 111.936 | 82.375 | 12.461 | 1.00 | 38.86 | O |
| HETATM | 3737 | O | HOH | 728 | 133.312 | 81.928 | 11.453 | 1.00 | 51.26 | O |
| HETATM | 3738 | O | HOH | 729 | 107.996 | 85.280 | 18.442 | 1.00 | 39.71 | O |
| HETATM | 3739 | O | HOH | 730 | 148.848 | 63.651 | −10.490 | 1.00 | 48.09 | O |
| HETATM | 3740 | O | HOH | 733 | 134.306 | 63.018 | 10.766 | 1.00 | 31.65 | O |
| HETATM | 3741 | O | HOH | 735 | 124.671 | 60.360 | 17.610 | 1.00 | 52.69 | O |
| HETATM | 3742 | O | HOH | 736 | 111.727 | 60.489 | 42.963 | 1.00 | 62.15 | O |
| HETATM | 3743 | O | HOH | 737 | 134.980 | 50.157 | 7.477 | 1.00 | 60.92 | O |
| HETATM | 3744 | O | HOH | 738 | 146.654 | 76.277 | 6.833 | 1.00 | 40.87 | O |
| HETATM | 3745 | O | HOH | 739 | 89.251 | 64.149 | 19.814 | 1.00 | 33.88 | O |
| HETATM | 3746 | O | HOH | 741 | 105.433 | 55.341 | 8.828 | 1.00 | 58.55 | O |
| HETATM | 3747 | O | HOH | 749 | 88.458 | 78.199 | 19.817 | 1.00 | 66.31 | O |
| HETATM | 3748 | O | HOH | 750 | 106.898 | 44.639 | 18.376 | 1.00 | 56.87 | O |
| HETATM | 3749 | O | HOH | 751 | 105.309 | 68.078 | 49.132 | 1.00 | 66.24 | O |
| HETATM | 3750 | O | HOH | 752 | 92.980 | 48.934 | 17.873 | 1.00 | 42.58 | O |
| HETATM | 3751 | O | HOH | 753 | 100.420 | 53.758 | 15.446 | 1.00 | 60.31 | O |
| HETATM | 3752 | O | HOH | 754 | 120.798 | 66.196 | 40.717 | 1.00 | 66.93 | O |
| HETATM | 3753 | O | HOH | 755 | 108.406 | 89.679 | 12.448 | 1.00 | 61.48 | O |
| HETATM | 3754 | O | HOH | 757 | 132.463 | 72.528 | 4.509 | 1.00 | 59.31 | O |
| HETATM | 3755 | O | HOH | 761 | 127.038 | 77.545 | 21.661 | 1.00 | 47.91 | O |
| HETATM | 3756 | O | HOH | 762 | 106.459 | 50.413 | 17.617 | 1.00 | 59.90 | O |

-continued

| | | | | | | | | | | |
|---|---|---|---|---|---|---|---|---|---|---|
| HETATM | 3757 | O | HOH | 765 | 119.622 | 72.534 | 26.691 | 1.00 | 51.38 | O |
| HETATM | 3758 | O | HOH | 766 | 11s.174 | 72.450 | 5.241 | 1.00 | 68.42 | O |
| HETATM | 3759 | O | HOH | 768 | 105.322 | 87.067 | 41.471 | 1.00 | 68.21 | O |
| HETATM | 3760 | O | HOH | 770 | 105.218 | 41.445 | 29.836 | 1.00 | 63.03 | O |
| HETATM | 3761 | O | HOH | 771 | 83.989 | 78.004 | 39.580 | 1.00 | 67.38 | O |
| HETATM | 3762 | O | HOH | 772 | 148.829 | 67.245 | 20.069 | 1.00 | 44.56 | O |
| HETATM | 3763 | O | HOH | 773 | 106.544 | 84.270 | 11.229 | 1.00 | 40.15 | O |
| HETATM | 3764 | O | HOH | 775 | 105.699 | 39.006 | 23.992 | 1.00 | 68.38 | O |
| HETATM | 3765 | O | HOH | 778 | 114.007 | 85.900 | 33.916 | 1.00 | 42.88 | O |
| HETATM | 3766 | O | HOH | 780 | 93.889 | 60.095 | 23.291 | 1.00 | 62.44 | O |
| HETATM | 3767 | O | HOH | 781 | 129.215 | 73.681 | 21.887 | 1.00 | 37.93 | O |
| HETATM | 3768 | O | HOH | 787 | 81.781 | 76.779 | 28.784 | 1.00 | 61.15 | O |
| HETATN | 3769 | O | HOH | 788 | 147.918 | 62.639 | 14.966 | 1.00 | 39.80 | O |
| HETATM | 3770 | O | HOH | 789 | 79.084 | 63.731 | 35.792 | 1.00 | 60.46 | O |
| HETATM | 3771 | O | HOH | 791 | 106.162 | 72.361 | 37.935 | 1.00 | 51.27 | O |
| HETATM | 3772 | O | HOH | 793 | 113.985 | 72.209 | 7.836 | 1.00 | 54.33 | O |
| HETATM | 3773 | O | HOH | 794 | 147.561 | 84.941 | 11.984 | 1.00 | 59.95 | O |
| HETATM | 3774 | O | HOH | 796 | 117.356 | 86.976 | 18.333 | 1.00 | 57.65 | O |
| HETATM | 3775 | O | HOH | 797 | 96.398 | 58.891 | 24.526 | 1.00 | 48.25 | O |
| HETATM | 3776 | O | HOH | 799 | 113.947 | 81.311 | 24.929 | 1.00 | 48.99 | O |
| HETATM | 3777 | O | HOH | 800 | 130.861 | 56.862 | 14.557 | 1.00 | 67.81 | O |
| HETATM | 3778 | O | HOH | 803 | 136.966 | 56.000 | −10.559 | 1.00 | 66.93 | O |
| HETATM | 3779 | O | HOH | 807 | 120.744 | 54.584 | 40.505 | 1.00 | 65.23 | O |
| HETATM | 3780 | O | HOH | 809 | 111.191 | 79.767 | 14.798 | 1.00 | 39.00 | O |
| HETATM | 3781 | O | HOH | 810 | 100.504 | 80.761 | 16.287 | 1.00 | 40.40 | O |
| HETATM | 3782 | O | HOH | 812 | 119.309 | 46.953 | 19.630 | 1.00 | 58.74 | O |
| HETATM | 3783 | O | HOH | 817 | 79.924 | 78.741 | 21.466 | 1.00 | 62.43 | O |
| HETATM | 3784 | O | HOH | 819 | 114.995 | 48.374 | 8.804 | 1.00 | 68.51 | O |
| HETATM | 3785 | O | HOH | 823 | 121.219 | 69.376 | 9.088 | 1.00 | 61.14 | O |
| HETATM | 3786 | O | HOH | 824 | 83.259 | 52.990 | 49.620 | 1.00 | 42.61 | O |
| HETATM | 3787 | O | HOH | 826 | 73.121 | 53.007 | 46.366 | 1.00 | 51.95 | O |
| HETATM | 3788 | O | HOH | 829 | 125.131 | 57.072 | 24.888 | 1.00 | 43.39 | O |
| HETATM | 3789 | O | HOH | 830 | 117.478 | 81.142 | 25.399 | 1.00 | 63.97 | O |
| HETATM | 3790 | O | HOH | 832 | 118.060 | 80.843 | 9.442 | 1.00 | 68.90 | O |
| HETATM | 3791 | O | HOH | 833 | 125.309 | 81.768 | 10.259 | 1.00 | 36.71 | O |
| HETATM | 3792 | O | HOH | 834 | 106.669 | 69.383 | 1.728 | 1.00 | 62.38 | O |
| HETATM | 3793 | O | HOH | 836 | 134.415 | 57.557 | 20.513 | 1.00 | 51.26 | O |
| HETATM | 3794 | O | HOH | 837 | 138.774 | 48.063 | 14.052 | 1.00 | 62.75 | O |
| HETATM | 3795 | O | HOH | 838 | 105.034 | 90.698 | 36.793 | 1.00 | 43.22 | O |
| HETATM | 3796 | O | HOH | 839 | 94.179 | 62.599 | 22.253 | 1.00 | 39.73 | O |
| HETATM | 3797 | O | HOH | 840 | 102.012 | 56.721 | 46.229 | 1.00 | 49.59 | O |
| HETATM | 3798 | O | HOH | 842 | 129.445 | 55.023 | 4.305 | 1.00 | 44.96 | O |
| HETATM | 3799 | O | HOH | 843 | 95.363 | 50.937 | 5.969 | 1.00 | 60.45 | O |
| HETATM | 3800 | O | HOH | 847 | 148.499 | 52.780 | 8.080 | 1.00 | 60.01 | O |
| HETATM | 3801 | O | HOH | 852 | 90.466 | 70.795 | 38.792 | 1.00 | 60.50 | O |
| HETATM | 3802 | O | HOH | 853 | 138.576 | 76.612 | 2.592 | 1.00 | 62.24 | O |
| HETATM | 3803 | O | HOH | 855 | 116.588 | 74.760 | 7.223 | 1.00 | 60.72 | O |
| HETATM | 3804 | O | HOH | 860 | 113.703 | 91.874 | 24.531 | 1.00 | 68.47 | O |
| HETATM | 3805 | O | HOH | 861 | 130.923 | 52.830 | 6.921 | 1.00 | 62.84 | O |
| HETATM | 3806 | O | HOH | 862 | 142.316 | 48.653 | 13.579 | 1.00 | 50.41 | O |
| HETATM | 3807 | O | HOH | 863 | 132.567 | 53.947 | 3.095 | 1.00 | 68.97 | O |
| HETATM | 3808 | O | HOH | 865 | 100.473 | 47.680 | 26.060 | 1.00 | 65.28 | O |
| HETATM | 3809 | O | HOH | 866 | 133.655 | 75.864 | 1.041 | 1.00 | 69.12 | O |
| HETATM | 3810 | O | HOH | 867 | 122.519 | 76.254 | 7.931 | 1.00 | 61.12 | O |
| HETATM | 3811 | O | HOH | 868 | 84.905 | 74.842 | 20.730 | 1.00 | 46.62 | O |
| HETATM | 3812 | O | HOH | 869 | 148.011 | 52.884 | 0.797 | 1.00 | 66.79 | O |
| HETATM | 3813 | O | HOH | 872 | 94.647 | 87.503 | 38.810 | 1.00 | 38.25 | O |
| HETATM | 3814 | O | HOH | 873 | 101.350 | 92.083 | 26.520 | 1.00 | 62.62 | O |
| HETATM | 3815 | O | HOH | 875 | 126.984 | 55.912 | −0.651 | 1.00 | 69.71 | O |
| HETATM | 3816 | O | HOH | 878 | 127.346 | 68.643 | 12.063 | 1.00 | 33.35 | O |
| HETATM | 3817 | O | HOH | 879 | 117.590 | 70.113 | 8.367 | 1.00 | 32.01 | O |
| HETATM | 3818 | O | HOH | 884 | 94.685 | 91.830 | 3.118 | 1.00 | 53.98 | O |
| HETATM | 3819 | O | HOM | 886 | 94.421 | 91.554 | 39.231 | 1.00 | 35.13 | O |
| HETATM | 3820 | O | HOH | 887 | 90.370 | 90.226 | 5.222 | 1.00 | 36.45 | O |
| HETATM | 3821 | O | HOH | 888 | 138.171 | 82.094 | 23.696 | 1.00 | 43.62 | O |
| HETATM | 3822 | O | HOH | 890 | 145.344 | 74.873 | 18.144 | 1.00 | 52.45 | O |
| HETATM | 3823 | C | HOH | 891 | 86.699 | 56.553 | 44.193 | 1.00 | 59.80 | O |
| HETATM | 3824 | O | HOH | 895 | 110.253 | 51.388 | 39.073 | 1.00 | 64.37 | O |
| HETATM | 3825 | O | HOH | 899 | 142.548 | 59.418 | 25.624 | 1.00 | 68.03 | O |
| HETATM | 3826 | O | HOH | 902 | 96.309 | 63.463 | 47.551 | 1.00 | 68.27 | O |
| HETATM | 3827 | O | HOH | 904 | 103.052 | 43.719 | 26.788 | 1.00 | 64.56 | O |
| HETATM | 3828 | O | HOH | 905 | 148.314 | 72.538 | 19.514 | 1.00 | 53.02 | O |
| HETATM | 3829 | O | HOH | 906 | 115.081 | 80.764 | 15.768 | 1.00 | 37.40 | O |
| HETATM | 3830 | O | HOH | 907 | 111.660 | 74.882 | 5.430 | 1.00 | 36.15 | O |
| HETATM | 3831 | O | HOH | 908 | 91.410 | 88.940 | 39.058 | 1.00 | 40.21 | O |
| HETATM | 3832 | O | HOH | 909 | 92.100 | 65.397 | 41.837 | 1.00 | 42.61 | O |
| HETATM | 3833 | O | HOH | 910 | 135.015 | 70.210 | 22.164 | 1.00 | 32.10 | O |
| HETATM | 3834 | O | HOH | 911 | 124.196 | 60.165 | 24.502 | 1.00 | 68.95 | O |
| HETATM | 3835 | O | HOH | 912 | 104.972 | 48.595 | 38.399 | 1.00 | 50.34 | O |

-continued

| | | | | | | | | | | |
|---|---|---|---|---|---|---|---|---|---|---|
| HETATM | 3836 | O | HOH | 913 | 143.458 | 60.042 | 28.053 | 1.00 | 36.04 | O |
| HETATM | 3837 | O | HOH | 916 | 101.435 | 59.347 | 18.933 | 1.00 | 50.24 | O |
| HETATM | 3838 | O | HOH | 917 | 112.207 | 49.761 | 38.732 | 1.00 | 26.79 | O |
| HETATM | 3839 | O | HOH | 918 | 129.684 | 70.406 | 8.637 | 1.00 | 46.40 | O |
| HETATM | 3840 | O | HOH | 921 | 80.125 | 93.172 | 15.865 | 1.00 | 52.80 | O |
| HETATM | 3841 | O | HOH | 922 | 149.474 | 69.335 | 14.961 | 1.00 | 54.64 | O |
| HETATM | 3842 | O | HOH | 926 | 102.735 | 61.951 | 20.408 | 1.00 | 35.26 | O |
| HETATM | 3843 | O | HOH | 927 | 70.905 | 53.569 | 44.583 | 1.00 | 70.52 | O |
| HETATM | 3844 | O | HOH | 929 | 114.913 | 79.874 | 33.698 | 1.00 | 57.49 | O |
| HETATM | 3845 | O | HOH | 930 | 150.193 | 75.660 | 8.945 | 1.00 | 35.94 | O |
| HETATM | 3846 | O | HOH | 931 | 108.648 | 54.745 | 43.966 | 1.00 | 62.03 | O |
| HETATM | 3847 | O | HOH | 936 | 121.915 | 58.864 | 24.758 | 1.00 | 55.08 | O |
| HETATM | 3848 | O | HOH | 937 | 79.417 | 58.337 | 48.896 | 1.00 | 68.62 | O |
| HETATM | 3849 | O | HOH | 938 | 113.378 | 43.843 | 23.780 | 1.00 | 41.09 | O |
| HETATM | 3850 | O | HOH | 939 | 120.219 | 59.743 | 27.131 | 1.00 | 44.37 | O |
| HETATM | 3851 | O | HOH | 941 | 105.234 | 64.396 | −0.669 | 1.00 | 73.28 | O |
| HETATM | 3852 | O | HOH | 942 | 141.057 | 80.868 | −0.762 | 1.00 | 67.90 | O |
| HETATM | 3853 | O | HOH | 944 | 119.413 | 75.184 | 6.755 | 1.00 | 98.67 | O |
| HETATM | 3854 | O | HOH | 945 | 95.626 | 74.384 | 14.294 | 1.00 | 63.69 | O |
| HETATM | 3855 | O | HOH | 946 | 95.387 | 53.160 | 20.326 | 1.00 | 59.76 | O |
| HETATM | 3856 | O | HOH | 947 | 112.354 | 72.038 | 3.479 | 1.00 | 55.13 | O |
| HETATM | 3857 | O | HOH | 961 | 116.417 | 63.126 | 34.645 | 1.00 | 53.04 | O |
| HETATM | 3858 | O | HOH | 962 | 91.960 | 70.760 | 43.791 | 1.00 | 62.09 | O |
| HETATM | 3859 | O | HOH | 964 | 80.831 | 84.466 | 14.233 | 1.00 | 66.83 | O |
| HETATM | 3860 | O | HOH | 966 | 111.313 | 64.422 | 5.416 | 1.00 | 43.56 | O |
| HETATM | 3861 | O | HOH | 968 | 133.045 | 80.261 | 24.904 | 1.00 | 59.86 | O |
| HETATM | 3862 | O | HOH | 971 | 113.856 | 45.592 | 40.153 | 1.00 | 68.81 | O |
| HETATM | 3863 | O | HOH | 973 | 149.882 | 57.333 | 6.661 | 1.00 | 61.17 | O |
| HETATM | 3864 | O | HOH | 974 | 114.479 | 45.337 | 23.893 | 1.00 | 48.82 | O |
| HETATM | 3865 | O | HOH | 976 | 122.683 | 49.979 | 23.699 | 1.00 | 54.50 | O |
| HETATM | 3866 | O | HOH | 977 | 107.449 | 93.037 | 22.262 | 1.00 | 67.52 | O |
| HETATM | 3867 | O | HOH | 980 | 71.623 | 55.665 | 43.963 | 1.00 | 50.43 | O |
| HETATM | 3868 | O | HOH | 983 | 81.115 | 79.690 | 16.340 | 1.00 | 68.34 | O |
| HETATM | 3869 | O | HOH | 984 | 146.095 | 68.641 | 21.063 | 1.00 | 40.33 | O |
| HETATM | 3870 | O | HOH | 989 | 84.591 | 87.656 | 11.809 | 1.00 | 61.62 | O |
| HETATM | 3871 | O | HOH | 990 | 101.284 | 84.890 | 35.573 | 1.00 | 66.53 | O |
| HETATM | 3872 | O | HOH | 991 | 132.290 | 57.405 | 16.338 | 1.00 | 66.86 | O |
| HETATM | 3873 | O | HOH | 992 | 107.181 | 71.461 | 43.131 | 1.00 | 68.43 | O |
| HETATM | 3874 | O | HOH | 996 | 121.732 | 77.353 | 22.459 | 1.00 | 56.10 | O |
| HETATM | 3875 | O | HOH | 997 | 123.339 | 62.223 | 9.181 | 1.00 | 53.79 | O |
| HETATM | 3876 | O | HOH | 999 | 118.564 | 57.129 | 2.150 | 1.00 | 64.38 | O |
| HETATM | 3877 | O | HOH | 1002 | 113.406 | 85.261 | 25.792 | 1.00 | 54.44 | O |
| HETATM | 3876 | O | HOH | 1003 | 132.676 | 51.930 | 17.206 | 1.00 | 68.65 | O |
| HETATM | 3879 | O | HOH | 1006 | 82.100 | 75.518 | 31.280 | 1.00 | 51.37 | O |
| HETATM | 3880 | O | HOH | 1007 | 91.217 | 86.172 | 10.703 | 1.00 | 68.50 | O |
| HETATM | 3881 | O | HOH | 1011 | 148.150 | 63.664 | −4.949 | 1.00 | 66.39 | O |
| HETATM | 3882 | O | HOH | 1012 | 108.584 | 47.618 | 13.690 | 1.00 | 63.35 | O |
| HETATM | 3883 | O | HOH | 1014 | 104.916 | 54.259 | 6.694 | 1.00 | 66.63 | O |
| HETATM | 3884 | O | HOH | 1021 | 127.338 | 67.350 | −0.507 | 1.00 | 68.51 | O |
| HETATM | 3885 | O | HOH | 1024 | 100.255 | 43.755 | 35.224 | 1.00 | 49.55 | O |
| HETATM | 3886 | O | HOH | 1026 | 113.002 | 85.034 | 18.817 | 1.00 | 68.03 | O |
| HETATM | 3887 | O | HOH | 1027 | 74.446 | 56.955 | 41.184 | 1.00 | 34.26 | O |
| HETATM | 3888 | O | HOH | 1032 | 123.923 | 66.490 | 27.749 | 1.00 | 51.93 | O |
| HETATM | 3889 | O | HOH | 1037 | 105.661 | 94.018 | 14.310 | 1.00 | 48.05 | O |
| HETATM | 3890 | O | HOH | 1045 | 85.110 | 67.600 | 42.845 | 1.00 | 61.60 | O |
| HETATM | 3891 | O | HOH | 1049 | 72.485 | 57.802 | 45.989 | 1.00 | 68.63 | O |
| HETATM | 3892 | O | HOH | 1051 | 104.785 | 74.784 | 39.154 | 1.00 | 60.69 | C |
| HETATM | 3893 | O | HOH | 1053 | 104.639 | 40.347 | 24.518 | 1.00 | 61.31 | O |
| HETATM | 3894 | O | HOH | 1054 | 142.840 | 80.523 | 20.021 | 1.00 | 68.20 | O |
| HETATM | 3895 | O | HOH | 1056 | 123.658 | 55.426 | 39.072 | 1.00 | 68.01 | O |
| HETATM | 3896 | O | HOH | 1057 | 122.409 | 54.809 | 6.777 | 1.00 | 68.72 | O |
| HETATM | 3897 | O | HOH | 1060 | 148.405 | 75.478 | 20.015 | 1.00 | 68.99 | O |
| HETATM | 3898 | O | HOH | 1066 | 101.285 | 46.434 | 21.329 | 1.00 | 69.66 | O |
| HETATM | 3899 | O | HOH | 1068 | 101.265 | 47.738 | 38.183 | 1.00 | 52.34 | O |
| HETATM | 3900 | O | HOH | 1072 | 116.191 | 83.171 | 15.683 | 1.00 | 63.11 | O |
| HETATM | 3901 | O | HOH | 1076 | 124.162 | 83.118 | 19.379 | 1.00 | 65.19 | O |
| HETATM | 3902 | O | HOH | 1077 | 114.649 | 91.913 | 27.612 | 1.00 | 63.68 | O |
| HETATM | 3903 | O | HOH | 1078 | 131.138 | 72.022 | 1.639 | 1.00 | 65.80 | O |
| HETATM | 3904 | O | HOH | 1079 | 104.565 | 95.248 | 23.931 | 1.00 | 67.66 | O |
| HETATM | 3905 | O | HOH | 1080 | 130.600 | 83.061 | 14.460 | 1.00 | 68.73 | O |
| HETATM | 3906 | O | HOH | 1081 | 108.024 | 57.385 | 44.494 | 1.00 | 68.47 | O |
| HETATM | 3907 | O | HOH | 1089 | 98.180 | 52.040 | 22.425 | 1.00 | 57.82 | O |
| HETATM | 3908 | O | HOH | 1095 | 123.035 | 48.662 | 12.121 | 1.00 | 49.75 | O |
| HETATM | 3909 | O | HOH | 1100 | 116.951 | 82.153 | 13.434 | 1.00 | 47.33 | O |
| HETATM | 3910 | O | HOH | 1109 | 93.000 | 74.011 | 11.563 | 1.00 | 65.00 | O |
| HETATM | 3911 | O | HOH | 1110 | 84.826 | 60.423 | 43.980 | 1.00 | 68.47 | O |
| HETATM | 3912 | O | HOH | 1114 | 95.995 | 48.302 | 8.024 | 1.00 | 46.89 | O |
| HETATM | 3913 | O | HOH | 1115 | 146.331 | 50.245 | −5.119 | 1.00 | 55.03 | O |
| HETATM | 3914 | O | HOH | 1117 | 93.037 | 80.264 | 22.271 | 1.00 | 36.08 | O |

-continued

| | | | | | | | | | | |
|---|---|---|---|---|---|---|---|---|---|---|
| HETATM | 3915 | O | HOH | 1118 | 127.120 | 59.841 | 19.240 | 1.00 | 36.51 | O |
| HETATM | 3916 | O | HOH | 1123 | 130.326 | 80.122 | 18.283 | 1.00 | 54.14 | O |
| HETATM | 3917 | O | HOH | 1127 | 122.797 | 71.467 | 7.444 | 1.00 | 61.33 | O |
| HETATM | 3918 | O | HOH | 1128 | 86.326 | 63.775 | 40.835 | 1.00 | 65.83 | O |
| HETATM | 3919 | O | HOH | 1129 | 129.934 | 60.674 | 26.265 | 1.00 | 67.06 | O |
| HETATM | 3920 | O | HOH | 1132 | 91.126 | 55.593 | 11.580 | 1.00 | 55.91 | O |
| HETATM | 3921 | O | HOH | 1136 | 131.604 | 57.222 | −9.584 | 1.00 | 62.55 | O |
| HETATM | 3922 | O | HOH | 1137 | 122.963 | 68.163 | 16.106 | 1.00 | 33.32 | O |
| HETATM | 3923 | O | HOH | 1140 | 107.890 | 88.486 | 9.887 | 1.00 | 61.56 | C |
| HETATM | 3924 | O | HOH | 1142 | 143.969 | 58.642 | −10.289 | 1.00 | 69.08 | O |
| HETATM | 3925 | O | HOH | 1143 | 88.527 | 78.564 | −1.195 | 1.00 | 66.36 | O |
| HETATM | 3926 | O | HOH | 1146 | 109.850 | 50.598 | 43.199 | 1.00 | 64.27 | O |
| HETATM | 3927 | O | HOH | 1151 | 112.701 | 76.952 | 6.277 | 1.00 | 55.30 | O |
| HETATM | 3928 | O | HOH | 1154 | 102.564 | 50.394 | 12.484 | 1.00 | 59.53 | O |
| HETATM | 3929 | O | HOH | 1161 | 95.856 | 79.770 | 13.615 | 1.00 | 60.09 | O |
| HETATM | 3930 | O | HOH | 1162 | 149.220 | 72.694 | 15.463 | 1.00 | 36.11 | O |
| HETATM | 3931 | O | HOH | 1167 | 134.026 | 86.608 | 28.831 | 1.00 | 55.75 | O |
| HETATM | 3932 | O | HOH | 1168 | 137.288 | 47.676 | −0.383 | 1.00 | 58.53 | O |
| HETATM | 3933 | O | HOH | 1169 | 96.461 | 76.369 | −1.039 | 1.00 | 40.84 | O |
| HETATM | 3934 | O | HOH | 1170 | 146.839 | 76.924 | 18.226 | 1.00 | 62.40 | O |
| HETATM | 3935 | O | HOH | 1173 | 84.778 | 62.413 | 46.009 | 1.00 | 56.40 | O |
| HETATM | 3936 | O | HOH | 1174 | 104.665 | 61.328 | −0.147 | 1.00 | 68.18 | O |
| HETATM | 3937 | O | HOH | 1176 | 148.238 | 49.557 | 15.253 | 1.00 | 68.84 | O |
| HETATM | 3938 | O | HOH | 1180 | 96.826 | 57.686 | 5.466 | 1.00 | 68.82 | O |
| HETATM | 3939 | O | HOH | 1181 | 97.848 | 45.596 | 18.230 | 1.00 | 68.53 | O |
| HETATM | 3940 | O | HOH | 1183 | 105.561 | 78.152 | 46.280 | 1.00 | 55.13 | O |
| HETATM | 3941 | O | HOH | 1184 | 148.363 | 55.663 | 18.453 | 1.00 | 67.78 | O |
| HETATM | 3942 | O | HOH | 1188 | 117.761 | 72.763 | 3.201 | 1.00 | 49.39 | O |
| HETATM | 3943 | O | HOH | 1190 | 129.206 | 55.861 | −5.442 | 1.00 | 69.86 | O |
| HETATM | 3944 | O | HOH | 1195 | 107.481 | 76.284 | 39.087 | 1.00 | 57.19 | O |
| HETATM | 3945 | O | HOH | 1206 | 122.685 | 66.549 | 4.934 | 1.00 | 62.97 | O |
| HETATM | 3946 | O | HOH | 1207 | 150.879 | 41.867 | 5.427 | 1.00 | 67.80 | O |
| HETATM | 3947 | O | HOH | 1216 | 134.077 | 45.934 | 8.123 | 1.00 | 68.54 | O |
| HETATM | 3948 | O | HOH | 1217 | 92.702 | 54.498 | 4.335 | 1.00 | 68.29 | O |
| HETATM | 3949 | O | HOH | 1227 | 133.307 | 89.606 | 16.031 | 1.00 | 55.60 | O |
| HETATM | 3950 | O | HOH | 1228 | 145.314 | 58.907 | 23.524 | 1.00 | 57.48 | O |
| HETATM | 3951 | O | HOH | 1231 | 121.333 | 47.473 | 28.343 | 1.00 | 42.57 | O |
| HETATM | 3952 | O | HOH | 1237 | 80.672 | 64.102 | 43.307 | 1.00 | 62.67 | O |
| HETATM | 3953 | O | HOH | 1239 | 79.197 | 76.085 | 29.202 | 1.00 | 42.02 | O |
| HETATM | 3954 | O | HOH | 1240 | 147.532 | 79.940 | 6.435 | 1.00 | 49.20 | O |
| HETATM | 3955 | O | HOH | 1241 | 105.341 | 73.622 | 43.925 | 1.00 | 46.80 | O |
| HETATM | 3956 | O | HOH | 1242 | 108.748 | 84.315 | 11.317 | 1.00 | 43.50 | O |
| HETATM | 3957 | O | HOH | 1243 | 113.748 | 76.205 | 13.481 | 1.00 | 31.05 | O |
| HETATM | 3958 | O | HOH | 1244 | 106.486 | 82.249 | 41.211 | 1.00 | S3.73 | O |
| HETATM | 3959 | O | HOH | 1245 | 123.229 | 67.990 | 30.863 | 1.00 | 67.62 | O |
| HETATM | 3960 | O | HOH | 1246 | 97.244 | 56.293 | 3.245 | 1.00 | 59.53 | O |
| HETATM | 3961 | O | HOH | 1247 | 84.115 | 75.748 | 18.158 | 1.00 | 47.44 | O |
| HETATM | 3962 | O | HOH | 1248 | 92.641 | 62.480 | 43.494 | 1.00 | 56.54 | O |
| HETATM | 3963 | O | HOH | 1249 | 126.850 | 67.707 | 7.524 | 1.00 | 63.22 | O |
| HETATM | 3964 | O | HOH | 1250 | 116.737 | 46.525 | 9.414 | 1.00 | 60.31 | O |
| HETATM | 3965 | O | HOH | 1251 | 99.435 | 55.524 | 20.442 | 1.00 | 68.76 | O |
| HETATM | 3966 | O | HOH | 1252 | 93.533 | 48.432 | 11.284 | 1.00 | 64.31 | O |
| HETATM | 3967 | O | HOH | 1253 | 115.458 | 55.820 | 8.527 | 1.00 | 68.91 | O |
| HETATM | 3968 | O | HOH | 1254 | 94.383 | 48.132 | 30.166 | 1.00 | 55.54 | O |
| HETATM | 3969 | O | HOH | 1255 | 136.004 | 53.964 | 17.602 | 1.00 | 50.55 | O |
| HETATM | 3970 | O | HOH | 1256 | 97.765 | 60.337 | 0.278 | 1.00 | 67.66 | O |
| HETATM | 3971 | O | HOH | 1257 | 81.887 | 70.128 | 40.015 | 1.00 | 60.06 | O |
| HETATM | 3972 | O | HOH | 1258 | 98.568 | 43.853 | 36.969 | 1.00 | 60.96 | O |
| HETATM | 3973 | O | HOH | 1259 | 102.312 | 50.226 | 23.207 | 1.00 | 69.15 | O |
| HETATM | 3974 | O | HOH | 1260 | 93.845 | 73.542 | 7.463 | 1.00 | 62.17 | O |
| HETATM | 3975 | O | HOH | 1261 | 122.247 | 50.835 | 30.996 | 1.00 | 66.32 | O |
| HETATM | 3976 | O | HOH | 1262 | 137.839 | 46.740 | 1.638 | 1.00 | 44.22 | O |
| HETATM | 3977 | O | HOH | 1263 | 107.295 | 79.492 | 3.520 | 1.00 | 56.86 | O |
| HETATM | 3978 | O | HOH | 1264 | 108.339 | 49.640 | 21.504 | 1.00 | 48.82 | O |
| HETATM | 3979 | O | HOH | 1265 | 105.132 | 63.518 | 48.797 | 1.00 | 62.13 | O |
| HETATM | 3960 | O | HOH | 1266 | 139.420 | 62.113 | 23.787 | 1.00 | 50.94 | O |
| HETATM | 3981 | O | HOH | 1267 | 144.043 | 77.286 | 3.516 | 1.00 | 68.14 | O |
| HETATM | 3982 | O | HOH | 1268 | 149.733 | 53.900 | 4.381 | 1.00 | 56.17 | O |
| HETATM | 3983 | O | HOH | 1269 | 103.004 | 91.675 | 22.454 | 1.00 | 51.28 | O |
| HETATM | 3984 | O | HOH | 1270 | 102.342 | 79.977 | 8.282 | 1.00 | 60.86 | O |
| HETATM | 3985 | O | HOH | 1271 | 104.432 | 79.198 | 8.137 | 1.00 | 49.45 | O |
| HETATM | 3986 | O | HOH | 1272 | 96.642 | 78.325 | 15.154 | 1.00 | 49.69 | O |
| HETATM | 3987 | O | HOH | 1273 | 123.113 | 83.532 | 10.129 | 1.00 | 46.69 | O |
| HETATM | 3988 | O | HOH | 1274 | 108.924 | 75.712 | 35.457 | 1.00 | 44.24 | O |
| HETATM | 3989 | O | HOH | 1275 | 120.284 | 52.133 | 13.839 | 1.00 | 49.42 | O |
| HETATM | 3990 | O | HOH | 1276 | 153.804 | 67.675 | 3.008 | 1.00 | 68.53 | C |
| HETATM | 3991 | O | HOH | 1277 | 132.756 | 49.791 | 2.618 | 1.00 | 54.77 | O |
| HETATM | 3992 | O | HOH | 1278 | 123.687 | 61.097 | −1.686 | 1.00 | 66.47 | O |
| HETATM | 3993 | O | HOH | 1279 | 79.098 | 85.995 | 16.502 | 1.00 | 68.34 | O |

-continued

| | | | | | | | | | | |
|---|---|---|---|---|---|---|---|---|---|---|
| HETATM | 3994 | O | HOH | 1280 | 81.604 | 77.273 | 22.663 | 1.00 | 51.85 | O |
| HETATM | 3995 | O | HOH | 1281 | 97.665 | 46.523 | 21.377 | 1.00 | 66.98 | O |
| HETATM | 3996 | O | HOH | 1282 | 124.226 | 53.393 | 42.604 | 1.00 | 56.65 | O |
| HETATM | 3997 | O | HOH | 1283 | 70.053 | 51.433 | 45.374 | 1.00 | 31.76 | O |
| HETATM | 3998 | O | HOH | 1284 | 133.004 | 59.283 | 22.298 | 1.00 | 51.14 | O |
| HETATM | 3999 | O | HOH | 1285 | 110.435 | 58.745 | 9.141 | 1.00 | 66.24 | O |
| HETATM | 4000 | O | M0H | 1286 | 131.690 | 83.699 | 10.424 | 1.00 | 50.89 | O |
| HETATM | 4001 | O | HOH | 1287 | 87.121 | 83.954 | 6.897 | 1.00 | 61.10 | O |
| HETATM | 4002 | O | HOH | 1289 | 103.343 | 70.654 | 47.251 | 1.00 | 59.87 | O |
| HETATM | 4003 | O | HOH | 1290 | 151.878 | 57.545 | 4.368 | 1.00 | 68.93 | O |
| HETATM | 4004 | O | HOH | 1291 | 109.757 | 52.533 | 5.140 | 1.00 | 68.61 | O |
| HETATM | 4005 | O | HOH | 1292 | 137.500 | 85.244 | 14.713 | 1.00 | 48.53 | O |
| HETATM | 4006 | O | HOH | 1293 | 99.481 | 43.592 | 30.277 | 1.00 | 56.76 | O |
| HETATM | 4007 | O | HOH | 1294 | 79.393 | 66.499 | 44.205 | 1.00 | 51.03 | O |
| HETATM | 4008 | O | HOH | 1295 | 93.025 | 76.731 | 12.952 | 1.00 | 68.06 | O |
| HETATM | 4009 | O | HOH | 1296 | 104.177 | 39.636 | 37.064 | 1.00 | 66.28 | O |
| HETATM | 4010 | C | HOH | 1297 | 131.482 | 71.092 | 26.769 | 1.00 | 63.53 | O |
| HETATM | 4011 | O | HOH | 1299 | 108.732 | 64.733 | 46.862 | 1.00 | 59.61 | O |
| HETATM | 4012 | O | HOH | 1300 | 85.693 | 84.234 | 8.773 | 1.00 | 61.29 | O |
| HETATM | 4013 | O | HOH | 1301 | 130.439 | 55.137 | 19.928 | 1.00 | 68.52 | O |
| HETATM | 4014 | O | HOH | 1302 | 126.942 | 81.225 | 22.497 | 1.00 | 68.12 | O |
| HETATM | 4015 | O | HOH | 1303 | 85.867 | 53.208 | 45.199 | 1.00 | 54.32 | O |
| HETATM | 4016 | O | HOH | 1304 | 104.487 | 89.634 | 40.115 | 1.00 | 64.91 | O |
| HETATM | 4017 | O | HOH | 1305 | 106.217 | 68.163 | −1.625 | 1.00 | 55.54 | O |
| HETATM | 4018 | O | HOH | 1306 | 105.015 | 51.028 | 40.376 | 1.00 | 45.33 | O |
| HETATM | 4019 | O | HOH | 1307 | 120.170 | 70.835 | 39.052 | 1.00 | 58.73 | O |
| HETATM | 4020 | O | HOH | 1308 | 121.326 | 61.115 | 30.539 | 1.00 | 67.23 | O |
| HETATM | 4021 | O | HOH | 1309 | 107.923 | 60.643 | 46.488 | 1.00 | 69.06 | O |
| HETATM | 4022 | O | HOH | 1310 | 78.786 | 53.486 | 48.325 | 1.00 | 55.45 | O |
| HETATM | 4023 | O | HOH | 1311 | 130.804 | 55.401 | 22.465 | 1.00 | 59.73 | O |
| HETATM | 4024 | O | HOH | 1312 | 150.487 | 50.345 | 12.892 | 1.00 | 61.66 | O |
| HETATM | 4025 | O | HOH | 1313 | 100.834 | 38.834 | 32.531 | 1.00 | 62.67 | O |
| HETATM | 4026 | O | HOH | 1314 | 111.244 | 65.102 | 1.801 | 1.00 | 68.69 | O |
| HETATM | 4027 | O | HOH | 1315 | 132.117 | 79.062 | 22.385 | 1.00 | 40.28 | O |
| HETATM | 4025 | O | HOH | 1316 | 91.048 | 57.371 | 42.981 | 1.00 | 57.35 | O |
| HETATM | 4029 | O | HOH | 1317 | 144.712 | 49.327 | 0.134 | 1.00 | 49.54 | O |
| HETATM | 4030 | O | HOH | 1318 | 147.789 | 61.584 | −9.156 | 1.00 | 68.51 | C |
| HETATM | 4031 | O | HOH | 1319 | 123.090 | 61.674 | 6.437 | 1.00 | 69.05 | C |
| HETATM | 4032 | O | HOH | 1320 | 116.358 | 60.623 | 35.690 | 1.00 | 69.30 | O |
| HETATM | 4033 | O | HOH | 1321 | 113.530 | 91.177 | 21.954 | 1.00 | 52.62 | O |
| HETATM | 4034 | O | HOH | 1322 | 110.177 | 74.769 | 14.221 | 1.00 | 65.83 | O |
| HETATM | 4035 | O | HOH | 1323 | 135.219 | 50.902 | −6.112 | 1.00 | 68.00 | O |
| HETATM | 4036 | O | HOH | 1324 | 121.026 | 52.096 | 9.382 | 1.00 | 68.04 | O |
| HETATM | 4037 | O | HOH | 1325 | 86.410 | 84.214 | 10.939 | 1.00 | 54.69 | O |
| HETATM | 4036 | O | HOH | 1326 | 92.066 | 62.207 | −0.340 | 1.00 | 62.69 | O |
| HETATM | 4039 | O | HOH | 1327 | 108.159 | 72.272 | 1.047 | 1.00 | 69.41 | C |
| HETATM | 4040 | O | HOH | 1328 | 136.575 | 47.899 | 9.387 | 1.00 | 67.46 | O |
| HETATM | 4041 | O | HOH | 1329 | 112.693 | 55.745 | 39.945 | 1.00 | 50.31 | O |
| HETATM | 4042 | O | HOH | 1330 | 142.437 | 65.379 | −12.250 | 1.00 | 63.99 | O |
| HETATM | 4043 | O | HOH | 1331 | 97.845 | 53.121 | 3.695 | 1.00 | 68.33 | O |
| HETATM | 4044 | O | HOH | 1332 | 135.048 | 60.985 | 20.232 | 1.00 | 43.95 | O |
| HETATM | 4045 | O | HOH | 1334 | 131.683 | 75.485 | 22.258 | 1.00 | 35.53 | O |
| HETATM | 4046 | O | HOH | 1335 | 105.140 | 83.991 | 8.520 | 1.00 | 63.09 | O |
| HETATM | 4047 | C | HOH | 1336 | 119.421 | 70.763 | 31.673 | 1.00 | 42.24 | O |
| HETATM | 4048 | O | HOH | 1337 | 100.568 | 48.021 | 23.330 | 1.00 | 49.89 | O |
| HETATM | 4049 | O | HOH | 1338 | 133.982 | 54.355 | 16.339 | 1.00 | 62.13 | O |
| HETATM | 4050 | O | HOH | 1339 | 139.885 | 47.835 | 4.658 | 1.00 | 63.64 | O |
| HETATM | 4051 | O | HOH | 1340 | 150.581 | 62.937 | 15.908 | 1.00 | 63.60 | O |
| HETATM | 4052 | O | HOH | 1341 | 152.210 | 51.862 | 8.757 | 1.00 | 61.88 | O |
| HETATM | 4053 | C | HOH | 1342 | 92.864 | 62.277 | 3.434 | 1.00 | 57.80 | O |
| HETATM | 4054 | O | HOH | 1343 | 111.310 | 79.489 | 44.276 | 1.00 | 67.97 | O |
| HETATM | 4055 | O | HOH | 1344 | 149.427 | 48.324 | 7.299 | 1.00 | 59.90 | O |
| HETATM | 4056 | O | HOH | 1345 | 111.003 | 79.259 | 3.914 | 1.00 | 66.53 | O |
| HETATM | 4057 | O | HOH | 1346 | 116.893 | 54.202 | 7.477 | 1.00 | 47.23 | O |
| HETATM | 4058 | O | HOH | 1347 | 86.047 | 83.848 | 13.378 | 1.00 | 53.04 | O |
| HETATM | 4059 | O | HOH | 1348 | 117.820 | 76.586 | 7.356 | 1.00 | 57.31 | O |
| HETATM | 4060 | O | HOH | 1349 | 111.270 | 97.127 | 33.425 | 1.00 | 48.23 | O |
| HETATM | 4061 | O | HOH | 1350 | 129.000 | 77.928 | 24.673 | 1.00 | 44.60 | O |
| HETATM | 4062 | O | HOH | 1351 | 124.726 | 89.092 | 16.877 | 1.00 | 59.34 | O |
| HETATM | 4063 | O | HOH | 1352 | 93.181 | 64.700 | 49.080 | 1.00 | 52.82 | O |
| HETATM | 4064 | O | HOH | 1353 | 79.571 | 72.862 | 32.787 | 1.00 | 68.35 | O |
| HETATM | 4065 | O | HOH | 1354 | 115.741 | 90.948 | 32.009 | 1.00 | 48.04 | O |
| HETATM | 4066 | C | HOH | 1356 | 85.780 | 75.697 | 15.005 | 1.00 | 50.57 | O |
| HETATM | 4067 | O | HOH | 1357 | 112.933 | 95.254 | 27.038 | 1.00 | 44.69 | O |
| CONECT | 403 | 404 | | | | | | | | |
| CONECT | 404 | 403 | 405 | 407 | | | | | | |
| CONECT | 405 | 404 | 406 | | | | | | | |
| CONECT | 406 | 405 | | | | | | | | |
| CONECT | 407 | 404 | 408 | | | | | | | |

-continued

```
CONECT  408   407   409
CONECT  409   408   410
CONECT  410   409
CONECT  459   460
CONECT  460   459   461   463
CCNECT  461   460   462
CONECT  462   461
CONECT  463   460   464
CONECT  464   463   465
CONECT  465   464   466
CONECT  466   465
CONECT  576   577
CONECT  577   576   578   580
CONECT  578   577   579
CONECT  579   578
CONECT  580   577   581
CONECT  581   580   582
CONECT  582   581   583
CONECT  583   582
CONECT  882   883
CONECT  883   882   884   886
CONECT  884   883   885
CONECT  885   884
CONECT  886   883   887
CONECT  887   886   888
CONECT  888   887   889
CONECT  889   888
CONECT  1094  1095
CONECT  1095  1094  1096  1098
CONECT  1096  1095  1097
CONECT  1097  1096
CONECT  1098  1095  1099
CONECT  1099  1010  1100
CONECT  1100  1099  1101
CONECT  1101  1100
CONECT  1211  1212
CONECT  1212  1211  1213  1215
CONECT  1213  1212  1214
CONECT  1214  1213
CONECT  1215  1212  1216
CONECT  1216  1215  1217
CONECT  1217  1216  1218
CONECT  1218  1217
CONECT  2707  2708
CONECT  2708  2707  2709  2711
CONECT  2709  2708  2710
CONECT  2710  2709
CONECT  2711  2708  2712
CONECT  2712  2711  2713
CONECT  2713  2712  2714
CONECT  2714  2713
CONECT  2733  2734
CONECT  2734  2733  2735  2737
CONECT  2735  2734  2736
CONECT  2736  2735
CONECT  2737  2734  2738
CONECT  2738  2737  2739
CONECT  2739  2738  2740
CONECT  2740  2739
CONECT  2934  2935
CONECT  2935  2934  2936  2938
CONECT  2936  2935  2937
CONECT  2937  2936
CONECT  2938  2935  2939
CONECT  2939  2938  2940
CONECT  2940  2939  2941
CONECT  2941  2940
CONECT  2970  2971
CONECT  2971  2970  2972  2974
CONECT  2972  2971  2973
CONECT  2973  2972
CONECT  2974  2971  2975
CONECT  2975  2974  2976
CONECT  2976  2975  2977
CONECT  2977  2976
CONECT  3158  3159
CONECT  3159  3158  3160  3162
CONECT  3160  3159  3161
CONECT  3161  3160
```

-continued

```
CONECT  3162  3159  3163
CONECT  3163  3162  3164
CONECT  3164  3163  3165
CONECT  3165  3164
CONECT  3211  3212
CONECT  3212  3211  3213  3215
CONECT  3213  3212  3214
CONECT  3214  3213
CONECT  3215  3212  3216
CONECT  3216  3215  3217
CONECT  3217  3216  3218
CONECT  3218  3217
CONECT  3365  3366
CONECT  3366  3365  3367  3369
CONECT  3367  3366  3368
CONECT  3368  3367
CONECT  3369  3366  3370
CONECT  3370  3369  3371
CONECT  3371  3370  3372
CONECT  3372  3371
CONECT  3546  3547  3548  3549  3550
CONECT  3547  3546
CONECT  3548  3546
CONECT  3549  3546
CONECT  3550  3546  3551
CONECT  3551  3550  3552
CONECT  3552  3551  3553  3554
CONECT  3553  3552  3558
CONECT  3554  3552  3555  3556
CONECT  3555  3554
CONECT  3556  3554  3557  3558
CONECT  3557  3556
CONECT  3558  3553  3556  3559
CONECT  3559  3558  3560  3568
CONECT  3560  3559  3561
CONECT  3561  3560  3562
CONECT  3562  3561  3563  3568
CONECT  3563  3562  3564  3565
CONECT  3564  3563
CONECT  3565  3563  3566
CONECT  3566  3565  3567
CONECT  3567  3566  3568
CONECT  3568  3559  3562  3567
MASTER  437   0     14    18    16    0    1    64066  1   127  37
END
```

Documents Cited

Allison, A. C. & Eugui, E. M. Purine metabolism and immunosuppressive effects of mycophenolate mofetil. *Clin. Transplant.* 10, 77–84 (1996).

Andrei, G. & De Clercq, E. Molecular approaches for the treatment of hemorrhagic fever virus infections. *Antiviral Res.* 22, 45–75 (1993).

Antonino, L. C., Straub, K., & Wu, J. C. Probing the active site of human IMP dehydrogenase using halogenated purine riboside 5'-monophosphates and covalent modification reagents. *Biochemistry* 33, 1760–1765 (1994).

Antonino, L. C. and Wu, J. C. Human IMP dehydrogenase catalyzes the dehalogenation of 2-fluoro- and 2-chloroinosine 5'-monophosphate in the absence of NAD. *Biochemistry* 33, 1753–1759 (1994).

Ashbaugh, C. D. & Wessels, M. R. Cloning, sequence analysis and expression of the group A streptococcal guaB gene encoding inosine monophosphate dehydrogenase. *Gene* 165, 57–60 (1995).

Bairoch, A. Prosite Dictionary: Release 12.2, University of Geneva, Geneva, Switzerland (1995).

Bateman, A. The structure of a domain common to archaebaceria and the homocystinuria disease protein. *Trends Biochem. Sci.* 22, 12–13 (1997).

Brünger, A. T. et al. Crystallography and NMR system: A New Software Suite for Macromolecular Structure Determination, *Acta Crystallogr.* D, 54, 905–21 (1998).

Collart, F. R. and Huberman, E. Expression of IMP dehydrogenase in differentiating HL-60 cells *Blood* 75, 570–576 (1990).

Collart, F. R., Osipiuk, J., Trent, J., Olsen, G. J. & Huberman, E. Cloning, characterization, and sequence comparison of the gene coding for IMP dehydrogenase from *Pyrococcus furiosus. Gene*, 174, 206–216 (1996a).

Collart, F. R., Osipiuk, J., Trent, J., Olsen, G. J. & Huberman, E. Cloning and characterization of the gene encoding IMP dehydrogenase from *Arabidopsis thaliana. Gene*, 174, 217–220 (1996b).

Cowtan, K. D. 'DM': an automated procedure for phase improvement by density modification. *Joint CCP4 and ESF-EACBM Newsletter on Protein Crystallography.* 31, 34–38 (1994).

Hager, P. W., Collart, F. R., Huberman, E. & Mitchell, B. S. Recombinant human inosine monophosphate dehydrogenase Type I and Type II proteins. *Biochem. Pharm.* 49, 1323–1329 (1995).

Halloran, P. F. Molecular mechanisms of new immunosuppressants. *Clin. Transplant.* 10, 118–123 (1996).

Hendrickson, W. A. Determination of macromolecular structures from anomalous diffraction of synchrotron radiation. *Science* 254, 51–58 (1991).

Holbrook, J., Liljas, A., Steindel, S. J. & Rossman, M. G. Lactate Dehydrogenase. In *The Enzymes.* (Boyer, P. D., ed), pp 191–203, Academic Press, New York (1975).

Huete-Pérez, J. A., Wu, J. C., Whitby, F. G., & Wang, C. C. Identification of the IMP binding site in the IMP dehydrogenase from *Tritrichomonas foetus*. *Biochemistry* 34, 13889–13894 (1995).

Jayaram, H. N., Gearehbaghi, K, Jayaram, N. H., Rieser, J., Krohn, K. & Paull, K. D. Clinical pharmacokinetic study of tiazofurin administered as a 1-hr infusion. *Int. J. Cancer* 51, 182–188 (1992).

In. Jones, T. A. A graphics model building and refinement system for macromolecules. *J. Appl. Crystallogr.* 11, 268–272(1968).

Kabsch, W. & Saunder, C. Dictionary of protein secondary structure: pattern recognition of hydrogen-bonded and geometrical features. *Biopolymers* 22, 2577–2637 (1983).

Kerr, K. M. & Hedstrom, L. The role of conserved carboxylate residues in IMP dehydrogenase and identification of a transition state analog. *Biochemistry* 36, 13365–13373 (1997).

Kiguchi, K., Collart, F. R., Henning-Chubb, C., and Huberman, E. Induction of cell differentiation in melanoma cells by inhibitors of IMP dehydrogenase: altered patterns of IMP dehydrogenase expression and activity. *Cell Growth and Differen.* 1, 259–270 (1990).

Laskowski, R. A., Macarthur, M. W., Moss, D. S. & Thomton, J. M. PROCHECK—A program to check the stereochemical quality of protein structures. *J. Appl. Crystallogr.* 26, 283–291 (1993).

Link, J. O. & Straub, K. Trapping of an IMP dehydrogenase-substrate covalent intermediate by mycophenolic acid. *J. Am. Chem. Soc.* 118, 2091–2092 (1996).

Navaza, J. & Sludijan, P. AmoRe: An automated molecular replacement package. *Methods Enzymol.* 276, 581–594 (1997).

Nimmesgern, E., Fox, T., Fleming, M. A. & Thomson, J. A. Conformational changes and stabilization of inosine 5'-monophosphate dehydrogenase associated with ligand binding and inhibition by mycophenolic acid. J. Biol. Chem. 271, 9421–19427 (1996).

Otwinowski, Z & Minor, W. Processing of X-ray diffraction data collected in oscillation mode. *Methods Enzymol.* 276, 307–326 (1997).

Otwinowski, Z. MLPHARE-Maximum likelihood refinement of heavy atom parameters. In *Isomorphous Replacement and Anomalous Scattering*. (Wolf, W., Evans, P. R., & Leslie, A. G. W., eds), pp 80–86, Science and Engineering Research Council, Daresbury, England (1991).

Pankiewicz, K. W. Novel nicotinamide adenine dinucleotide analogues as potential anticancer agents: quest for specific inhibition of inosine monophosphate dehydrogenase. *Pharmacol. Ther.* 76, 89–100 (1997).

Pannu, N. S., Murshudov, G. N., Dodson, E. J. & Read, R. Incorporation of prior phase information strengthens maximum likelihood structural refinement. Acta Crystallogr. D, Acta Crystallogr D Biol Crystallogr. 54,1285–94 (1998).

Ramakrishnan, V. and Biou, V. Treatment of multiwavelength anomalous diffraction data as a special case of multiple isomorphous replacement. *Methods Enzymol.* 276, 538–557 (1997).

Read, R. J. SIGMAA—Improved fourier coefficients using calculated phases. *Acta Crystallogr.* A42, 140–149 (1986).

Rice, L. M. & Brlinger, A. T. Torsion angle-dynamics: Reduced variable conformational sampling enhances crystallographic structure refinement. *Proteins* 19, 277–290 (1994).

Sintchak, M. D., Fleming, M. A., Futer, O., Raybuck, S. A., Chambers, S. P., Caron, P. R., Murcko, M. A., & Wilson, K. P. Structure and mechanism of inosine monophosphate dehydrogenase in complex with the immunosuppressant mycophenolic acid. *Cell* 85, 921–930 (1996).

Smith, D. W., Frankel, L. R., Mathers, L. H., Tang, A. T., Atiagno, R. L. & Prober, C. G. A controlled trial of aerosolized ribavirin in infants receiving mechanical ventilation for severe respiratory syncytial virus infection. *N. Engl. J. Med.* 325, 24–29 (1991).

Wang, W., Papov, V. V., Minakawa, N., Matsuda, A., Biemann, & Hedstrom, L. Inactivation of Inosine 5'-monophosphate dehydrogenase by the antiviral agent 5-ethynyl-1-β-D-ribofuranosylimidazole-4-carboxamide 5'-monophosphate. *Biochemistry* 101 (1996) 35, 95–101.

Westbrook, E. M. & Naday, I. Charge-coupled device-based area detectors. *Methods Enzymol.* 276, 244–268 (1997).

Whitby, F. G., Luecke, H., Khun, P., Somoza, J. R., Huete-Perez, J. A., Phillips, J. D., Hill, C. P., Fletterick, R. J., & Wang, C. C. Crystal structure of *Tritrichomonas foetus* Inosine-5'-monophosphate dehydrogenase and the enzyme-product complex. *Biochemistry* 36, 10666–10674 (1997).

Xiang, B. & Markham, G. D. Probing the mechanism of inosine monophosphate dehydrogenase with kinetic isotope effects and NMR determination of the hydride transfer specificity. *Arch. Biochem. Biophys.* 388, 378–382 (1997).

Zhou, X., Cahoon, M., Rosa, P., and Hedstrom, L. Expression, purification and characterization of inosine 5'-monophosphate dehydrogenase from *Borrelia burgdorferi*. *J. Biol. Chem.* 272, 21977–21981 (1997).

We claim:

1. A crystal of bacterial IMPDH (inosine monophosphate dehydrogenase) produced from purified and enzymatically active IMPDH obtained from a bacterial preparation wherein the bacterial preparation is a pure culture of *Streptococcus pyogenes*.

2. The crystal of claim 1 further characterized by an ability to provide x-ray diffraction patterns useful to define molecular structures for functional bacterial IMPDH enzymes.

3. A crystalline molecule or molecular complex derived from IMPDH with enzymatic activity, the molecule or molecular complex comprising a binding pocket, wherein said binding pocket is defined by structure coordinates of IMPDH amino acids 50–56, 75–80, 229–235, 252–260, 283–286, 302–322, 343–345, 365–432 and 449–455, in the Protein Data Bank Accession Number 1ZFJ.

4. A crystalline molecule or molecular complex produced from bacterial IMPDH of claim 3, wherein the binding pocket has an amino acid sequence identity of 60% or greater relative to the *S. pyogenes* IMPDH binding pocket.

5. A method for developing lead compounds for an inhibitor of bacterial IMPDH (inosine monophosphate dehydrogenase), said method comprising:

(a) obtaining a crystal of bacterial IMPDH;

(b) recording x-ray diffraction data from said crystal;

(c) using said diffraction data to generate an electron density map consistent with a model for the molecular structure of a binding pocket of bacterial IMPDH; and (d) developing lead compounds for an inhibitor of the bacterial IMPDH based on the map of three dimensional structural information of the molecular structure of the binding pocket of bacterial IMPDH.

* * * * *

UNITED STATES PATENT AND TRADEMARK OFFICE
CERTIFICATE OF CORRECTION

PATENT NO. : 6,826,488 B1
DATED : November 30, 2004
INVENTOR(S) : Frank R. Collart et al.

It is certified that error appears in the above-identified patent and that said Letters Patent is hereby corrected as shown below:

<u>Title page,</u>
Item [75], Inventors, change "Andrezej Joachimiak" to -- Andrezej Joachimiak --.

Signed and Sealed this

Twelfth Day of April, 2005

JON W. DUDAS
*Director of the United States Patent and Trademark Office*

SEQUENCE LISTING

<160> NUMBER OF SEQ ID NOS: 23

<210> SEQ ID NO 1
<211> LENGTH: 15
<212> TYPE: PRT
<213> ORGANISM: Streptococcus pyogenes

<400> SEQUENCE: 1

Pro Gly Ser Ile Cys Thr Thr Arg Val Val Ala Gly Val Gly Val
 1               5                   10                  15

<210> SEQ ID NO 2
<211> LENGTH: 15

```
<212> TYPE: PRT
<213> ORGANISM: Bacillus subtilis

<400> SEQUENCE: 2

Pro Gly Ser Ile Cys Thr Thr Arg Val Val Ala Gly Val Gly Val
  1               5                  10                  15

<210> SEQ ID NO 3
<211> LENGTH: 15
<212> TYPE: PRT
<213> ORGANISM: Escherichia coli

<400> SEQUENCE: 3

Pro Gly Ser Ile Cys Thr Thr Arg Ile Val Thr Gly Val Gly Val
  1               5                  10                  15

<210> SEQ ID NO 4
<211> LENGTH: 15
<212> TYPE: PRT
<213> ORGANISM: Bacillus subtilis

<400> SEQUENCE: 4

Pro Gly Ser Ile Cys Thr Thr Arg Val Val Ala Gly Val Gly Val
  1               5                  10                  15

<210> SEQ ID NO 5
<211> LENGTH: 15
<212> TYPE: PRT
<213> ORGANISM: Mycobacterium tuberculosis

<400> SEQUENCE: 5

Pro Gly Ser Ile Cys Thr Thr Arg Val Val Ala Gly Val Gly Val
  1               5                  10                  15

<210> SEQ ID NO 6
<211> LENGTH: 15
<212> TYPE: PRT
<213> ORGANISM: Homo sapiens

<400> SEQUENCE: 6

Ser Gly Ser Ile Cys Ile Thr Gln Glu Val Leu Ala Cys Gly Arg
  1               5                  10                  15

<210> SEQ ID NO 7
<211> LENGTH: 15
<212> TYPE: PRT
<213> ORGANISM: Mus musculus

<400> SEQUENCE: 7

Ser Gly Ser Ile Cys Ile Thr Gln Glu Val Leu Ala Cys Gly Arg
  1               5                  10                  15

<210> SEQ ID NO 8
<211> LENGTH: 15
<212> TYPE: PRT
<213> ORGANISM: Arabidopsis thaliana

<400> SEQUENCE: 8

Ser Gly Ser Ile Cys Ile Thr Gln Glu Val Leu Ala Cys Gly Arg
  1               5                  10                  15

<210> SEQ ID NO 9
<211> LENGTH: 15
<212> TYPE: PRT
<213> ORGANISM: Leishmania donovani
```

```
<400> SEQUENCE: 9

Ser Gly Ser Ile Cys Ile Thr Gln Glu Val Leu Ala Cys Gly Arg
 1               5                  10                  15

<210> SEQ ID NO 10
<211> LENGTH: 15
<212> TYPE: PRT
<213> ORGANISM: Saccharomyces cerevisiae

<400> SEQUENCE: 10

Thr Gly Ser Ile Cys Ile Thr Gln Lys Val Met Ala Cys Gly Arg
 1               5                  10                  15

<210> SEQ ID NO 11
<211> LENGTH: 15
<212> TYPE: PRT
<213> ORGANISM: Drosophila melanogaster

<400> SEQUENCE: 11

Ser Gly Ser Ile Cys Ile Thr Gln Glu Val Met Ala Cys Gly Arg
 1               5                  10                  15

<210> SEQ ID NO 12
<211> LENGTH: 23
<212> TYPE: PRT
<213> ORGANISM: Streptococcus pyogenes

<400> SEQUENCE: 12

Met Ala Lys Gly Ser Ser Asp Arg Tyr Phe Gln Ser Asp Asn Ala Ala
 1               5                  10                  15

Asp Lys Leu Val Pro Glu Gly
            20

<210> SEQ ID NO 13
<211> LENGTH: 23
<212> TYPE: PRT
<213> ORGANISM: Bacillus subtilis

<400> SEQUENCE: 13

Met Ser Lys Gly Ser Ser Asp Arg Tyr Phe Gln Ser Asp Asn Ala Ala
 1               5                  10                  15

Asp Lys Leu Val Pro Glu Gly
            20

<210> SEQ ID NO 14
<211> LENGTH: 24
<212> TYPE: PRT
<213> ORGANISM: Escherichia coli

<400> SEQUENCE: 14

Met Lys Lys Gly Ser Ser Asp Arg Tyr Phe Gln Gly Ser Val Asn Glu
 1               5                  10                  15

Ala Asn Lys Leu Val Pro Glu Gly
            20

<210> SEQ ID NO 15
<211> LENGTH: 21
<212> TYPE: PRT
<213> ORGANISM: Bacillus subtilis

<400> SEQUENCE: 15

Met Glu Lys Gly Ser Lys Asp Arg Tyr Phe Gln Glu Glu Asn Lys Lys
```

```
                1               5                  10                 15
Phe Val Pro Glu Gly
                        20

<210> SEQ ID NO 16
<211> LENGTH: 30
<212> TYPE: PRT
<213> ORGANISM: Mycobacterium tuberculosis

<400> SEQUENCE: 16

Met Arg Gly Arg Gly Gly Ala Thr Ser Tyr Ser Lys Asp Arg Tyr Phe
 1               5                  10                 15

Ala Asp Asp Ala Leu Ser Glu Asp Lys Leu Val Pro Glu Gly
                20                  25                  30

<210> SEQ ID NO 17
<211> LENGTH: 23
<212> TYPE: PRT
<213> ORGANISM: Homo sapiens

<400> SEQUENCE: 17

Met Asp Lys His Leu Ser Ser Gln Asn Arg Tyr Phe Ser Glu Ala Asp
 1               5                  10                 15

Lys Ile Lys Val Ala Gln Gly
                20

<210> SEQ ID NO 18
<211> LENGTH: 23
<212> TYPE: PRT
<213> ORGANISM: Mus musculus

<400> SEQUENCE: 18

Met Asp Lys His Leu Ser Ser Gln Asn Arg Tyr Phe Ser Glu Ala Asp
 1               5                  10                 15

Lys Ile Lys Val Ala Gln Gly
                20

<210> SEQ ID NO 19
<211> LENGTH: 27
<212> TYPE: PRT
<213> ORGANISM: Arabidopsis thaliana

<400> SEQUENCE: 19

Met Glu Arg Gly Asp Ala Lys Gly Ala Ala Met Ser Arg Tyr Tyr His
 1               5                  10                 15

Asn Glu Met Asp Lys Met Lys Val Ala Gln Gly
                20                  25

<210> SEQ ID NO 20
<211> LENGTH: 27
<212> TYPE: PRT
<213> ORGANISM: Leishmania donovani

<400> SEQUENCE: 20

Met Gln Lys Thr Gly Thr Lys Gly Asn Ala Ser Thr Ser Arg Tyr Phe
 1               5                  10                 15

Ser Glu Ser Asp Ser Val Leu Val Ala Gln Gly
                20                  25

<210> SEQ ID NO 21
<211> LENGTH: 21
<212> TYPE: PRT
```

-continued

```
<213> ORGANISM: Drosophila melanogaster

<400> SEQUENCE: 21

Met Thr Lys Gly Ser Asp Gln Arg Tyr Leu Gly Asp Gln Thr Lys Leu
  1               5                  10                  15

Lys Ile Ala Gln Gly
            20

<210> SEQ ID NO 22
<211> LENGTH: 23
<212> TYPE: PRT
<213> ORGANISM: Saccharomyces cerevisiae

<400> SEQUENCE: 22

Met Ser Gln Gly Lys Glu Ser Gly Lys Arg Tyr Leu Ser Glu Asn Glu
  1               5                  10                  15

Ala Val Gln Val Ala Gln Gly
            20

<210> SEQ ID NO 23
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide
<221> NAME/KEY: MOD_RES
<222> LOCATION: (1)..(477)
<223> OTHER INFORMATION: "Xaa" represents selenomethionine

<400> SEQUENCE: 23

Ser Asn Trp Asp Thr Lys Phe Leu Lys Lys Gly Tyr Thr Phe Asp Asp
  1               5                  10                  15

Val Leu Leu Ile Pro Ala Glu Ser His Val Leu Pro Asn Glu Val Asp
                 20                  25                  30

Leu Lys Thr Lys Leu Ala Asp Asn Leu Thr Leu Asn Ile Pro Ile Ile
             35                  40                  45

Thr Ala Ala Xaa Asp Thr Val Thr Gly Ser Lys Xaa Ala Ile Ala Ile
         50                  55                  60

Ala Arg Ala Gly Gly Leu Gly Val Ile His Lys Asn Xaa Ser Ile Thr
 65                  70                  75                  80

Glu Gln Ala Glu Glu Val Arg Lys Val Lys Arg Ser Glu Asn Gly Val
                 85                  90                  95

Ile Ile Asp Pro Phe Phe Leu Thr Pro Glu His Lys Val Ser Glu Ala
                100                 105                 110

Glu Glu Leu Xaa Gln Arg Tyr Arg Ile Ser Gly Val Pro Ile Val Glu
            115                 120                 125

Thr Leu Ala Asn Arg Lys Leu Val Gly Ile Ile Thr Asn Arg Asp Xaa
        130                 135                 140

Arg Phe Ile Ser Asp Tyr Asn Ala Pro Ile Ser Glu His Xaa Thr Ser
145                 150                 155                 160

Glu His Leu Val Thr Ala Ala Val Gly Thr Asp Leu Glu Thr Ala Glu
                165                 170                 175

Arg Ile Leu His Glu His Arg Ile Glu Lys Leu Pro Leu Val Asp Asn
            180                 185                 190

Ser Gly Arg Leu Ser Gly Leu Ile Thr Ile Lys Asp Ile Glu Lys Val
        195                 200                 205

Ile Glu Phe Pro His Ala Ala Lys Asp Glu Phe Gly Arg Leu Leu Val
    210                 215                 220
```

-continued

```
Ala Ala Ala Val Gly Val Thr Ser Asp Thr Phe Glu Arg Ala Glu Ala
225                 230                 235                 240

Leu Phe Glu Ala Gly Ala Asp Ala Ile Val Ile Asp Thr Ala His Gly
            245                 250                 255

His Ser Ala Gly Val Leu Arg Lys Ile Ala Glu Ile Arg Ala His Phe
            260                 265                 270

Pro Asn Arg Thr Leu Ile Ala Gly Asn Ile Ala Thr Ala Glu Gly Ala
        275                 280                 285

Arg Ala Leu Tyr Asp Ala Gly Val Asp Val Val Lys Val Gly Ile Gly
    290                 295                 300

Pro Gly Ser Ile Cys Thr Thr Arg Val Val Ala Gly Val Gly Val Pro
305                 310                 315                 320

Gln Val Thr Ala Ile Tyr Asp Ala Ala Val Ala Arg Glu Tyr Gly
                325                 330                 335

Lys Thr Ile Ile Ala Asp Gly Gly Ile Lys Tyr Ser Gly Asp Ile Val
            340                 345                 350

Lys Ala Leu Ala Ala Gly Gly Asn Ala Val Xaa Leu Gly Ser Xaa Phe
        355                 360                 365

Ala Gly Thr Asp Glu Ala Pro Gly Glu Thr Glu Ile Tyr Gln Gly Arg
    370                 375                 380

Lys Tyr Lys Thr Tyr Arg Gly Xaa Gly Ser Ile Ala Ala Xaa Lys Lys
385                 390                 395                 400

Asn Lys Leu Val Pro Glu Gly Ile Glu Gly Arg Val Ala Tyr Lys Gly
            405                 410                 415

Ala Ala Ser Asp Ile Val Phe Gln Xaa Leu Gly Gly Ile Arg Ser Gly
            420                 425                 430

Xaa Gly Tyr Val Gly Ala Gly Asp Ile Gln Glu Leu His Glu Asn Ala
        435                 440                 445

Gln Phe Val Glu Xaa Ser Gly Ala Gly Leu Ile Glu Ser His Pro His
        450                 455                 460

Asp Val Gln Ile Thr Asn Glu Ala Pro Asn Tyr Ser Val
465                 470                 475
```